United States Patent
Ueng et al.

(10) Patent No.: US 10,544,113 B2
(45) Date of Patent: Jan. 28, 2020

(54) THIAZOLIDINONE COMPOUNDS AND USE THEREOF

(71) Applicant: National Health Research Institutes, Miaoli County (TW)

(72) Inventors: Shau-Hua Ueng, Miaoli County (TW); Shiu-Hwa Yeh, Miaoli County (TW); Shu-Yu Lin, Miaoli County (TW); Chuan Shih, Carmel, IN (US); Horace Loh, Little Canada, MN (US)

(73) Assignees: National Health Research Institute, Miaoli County (TW); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/449,406

(22) Filed: Mar. 3, 2017

(65) Prior Publication Data

US 2017/0253569 A1    Sep. 7, 2017

Related U.S. Application Data

(60) Provisional application No. 62/304,557, filed on Mar. 7, 2016.

(51) Int. Cl.

| | | |
|---|---|---|
| C07D 277/14 | (2006.01) | |
| A61K 31/426 | (2006.01) | |
| C07D 417/10 | (2006.01) | |
| A61K 31/427 | (2006.01) | |
| C07D 417/12 | (2006.01) | |
| A61K 31/4439 | (2006.01) | |
| A61K 31/454 | (2006.01) | |
| A61K 31/5377 | (2006.01) | |
| C07H 17/02 | (2006.01) | |
| C07D 417/04 | (2006.01) | |
| C07D 277/54 | (2006.01) | |
| C07D 249/08 | (2006.01) | |
| A61K 31/433 | (2006.01) | |
| C07D 417/14 | (2006.01) | |
| A61K 31/497 | (2006.01) | |
| A61K 31/506 | (2006.01) | |
| A61K 31/402 | (2006.01) | |
| C07D 207/27 | (2006.01) | |
| A61K 45/06 | (2006.01) | |

(52) U.S. Cl.
CPC .......... *C07D 277/14* (2013.01); *A61K 31/402* (2013.01); *A61K 31/426* (2013.01); *A61K 31/427* (2013.01); *A61K 31/433* (2013.01); *A61K 31/4439* (2013.01); *A61K 31/454* (2013.01); *A61K 31/497* (2013.01); *A61K 31/506* (2013.01); *A61K 31/5377* (2013.01); *A61K 45/06* (2013.01); *C07D 207/27* (2013.01); *C07D 249/08* (2013.01); *C07D 277/54* (2013.01); *C07D 417/04* (2013.01); *C07D 417/10* (2013.01); *C07D 417/12* (2013.01); *C07D 417/14* (2013.01); *C07H 17/02* (2013.01)

(58) Field of Classification Search
CPC .................................................... C07D 277/14
See application file for complete search history.

(56) References Cited

U.S. PATENT DOCUMENTS

| | | | |
|---|---|---|---|
| 6,777,434 B2 * | 8/2004 | Cho ..................... | C07D 277/14 514/369 |
| 2004/0024004 A1 | 2/2004 | Sherman et al. | |
| 2005/0113421 A1 | 5/2005 | Fraser et al. | |
| 2013/0040930 A1 | 2/2013 | Maeda et al. | |
| 2014/0275142 A1 * | 9/2014 | Toledano ............. | A61K 31/192 514/282 |

FOREIGN PATENT DOCUMENTS

| | | |
|---|---|---|
| CA | 1218071 | 2/1987 |
| CN | 102653526 A | 9/2012 |
| CN | 102786493 A * | 11/2012 |
| CN | 104016942 A | 9/2014 |
| GB | 1409898 A * | 9/1975 |
| JP | 57-88170 A * | 6/1982 |
| WO | WO-2008/112674 A1 | 9/2008 |
| WO | WO-2014/107344 A1 | 7/2014 |

OTHER PUBLICATIONS

Sugumaran et al., Research Journal of Pharmaceutical, Biological and Chemical Sciences, 2012, 3(2), pp. 625-631.*
Pardeshi et al., Indian Journal of Heterocyclic Chemistry, 24(3), Jan.-Mar. 2015, pp. 329-332.*
Shah et al., Journal of the Institution of Chemists (India), Mar. 1986, 58(2), pp. 49-51.*
Sriram et al., Journal of Pharmacy & Pharmaceutical Sciences, 2005, 8(3), pp. 426-429.*
Piscopo et al., Bollettino—Societa Italiana di Biologia Sperimentale, 1989, 65(6), pp. 535-541.*
Piscopo et al., Bollettino—Societa Italiana di Biologia Sperimentale, 1988, 64(2), pp. 153-158.*
Makki et al., Journal of Chemistry, 2013, pp. 1-8.*
PubChem SID 49671016, National Center for Biotechnology Information. PubChem Substance Database; SID=49671016, https://pubchem.ncbi.nlm.nih.gov/substance/49671016 (accessed Dec. 21, 2017), deposit date Apr. 7, 2008.*
PubChem AID 1996, National Center for Biotechnology Information. PubChem BioAssay Database; AID=1996, https://pubchem.ncbi.nlm.nih.gov/bioassay/1996 (accessed Dec. 21, 2017), deposit date Oct. 19, 2009.*

(Continued)

*Primary Examiner* — Laura L Stockton
(74) *Attorney, Agent, or Firm* — Cesari & McKenna, LLP

(57) ABSTRACT

A pharmaceutical composition containing a compound of Formula (I) for treating an opioid receptor-associated condition. Also disclosed is a method for treating an opioid receptor-associated condition using such a compound. Further disclosed are two sets of thiazolidinone compounds of formula (I): (i) compounds each having an enantiomeric excess greater than 90% and (ii) compounds each being substituted with deuterium.

23 Claims, 1 Drawing Sheet

(56) References Cited

OTHER PUBLICATIONS

PubChem CID 4519035, National Center for Biotechnology Information. PubChem Compound Database; CID=4519035, https://pubchem.ncbi.nlm.nih.gov/compound/4519035 (accessed Dec. 21, 2017, create Sep. 15, 2005.*

PubChem AID 422, National Center for Biotechnology Information. PubChem BioAssay Database; AID=422, https://pubchem.ncbi.nlm.nih.gov/bioassay/422 (accessed Dec. 22, 2017), deposit date Jun. 22, 2006.*

PubChem SID 24292872 {National Center for Biotechnology Information. PubChem Substance Database; SID=24292872, https://pubchem.ncbi.nlm.nih.gov /substance/24292872 (accessed Dec. 22, 2017), deposit date Mar. 30, 2007.*

PubChem CID 4195758, National Center for Biotechnology Information. PubChem Compound Database; CID=4195758, https://pubchem.ncbi.nlm.nih.gov/compound/4195758 (accessed Dec. 22, 2017, create date Sep. 13, 2005.*

Sugumaran et al. {Journal of Pharmaceutical and Biomedical Sciences, 2012, 16(16), 13, pp. 1-5. (Year: 2012).*

An English translation of CN-102786493-A (Yi et al.), 2012. (Year: 2012).*

An English translation of JP 57-88170 A (Hisamitsu Pharmaceutical Co., Inc.), 1982. (Year: 1982).*

Chemical Abstract 98:53872, 1983 (Hisamitsu Pharmaceutical Co., Inc., JP 57-88170 A). (Year: 1983).*

Sharma et al., Archiv der Pharmazie Chem. Life Sci., 2006, 339(3), pp. 145-152 (Year: 2006).*

Taranalli et al., Indian Journal of Pharmaceutical Sciences, Mar.-Apr. 2008, pp. 159-164 (Year: 2008).*

Doan et al., The Journal of Clinical Pharmacology, 2005, 45, pp. 751-762 (Year: 2005).*

Compound Summary for CID 4195758,,Pubchem. , National Center for Biotechnology Information. PubChem Compound Database; CID=4195758, https://pubchem.ncbi.nlm.nih.gov/compound/4195758 (accessed May 5, 2017), create date Sep. 13, 2005.

Mazzoni et al. "Synthesis and Pharmacological Activity of 2-(Substituted)-3-{2-[(4-Phenyl-4-Cyano)Piperidino]Ethyl}-1,3-Thiazolidin-4-Ones" Chemical Biology and Drug Design vol. 67, pp. 432-436, 2006.

Al-Khamees et al "Synthesis and Pharmacological Screening of a New Series of 3-(4-Anti-Pyryl)-2-Arylthiazolidin-4-Ones" European Journal of Medicinal Chemistry vol. 25, pp. 103-106, 1990.

Collina et al "Microwave Assisted Synthesis of Chiral Pyrrolines with Biological Activity" Tetrahedron Asymmetry vol. 15, pp. 3601-3608, 2004.

* cited by examiner

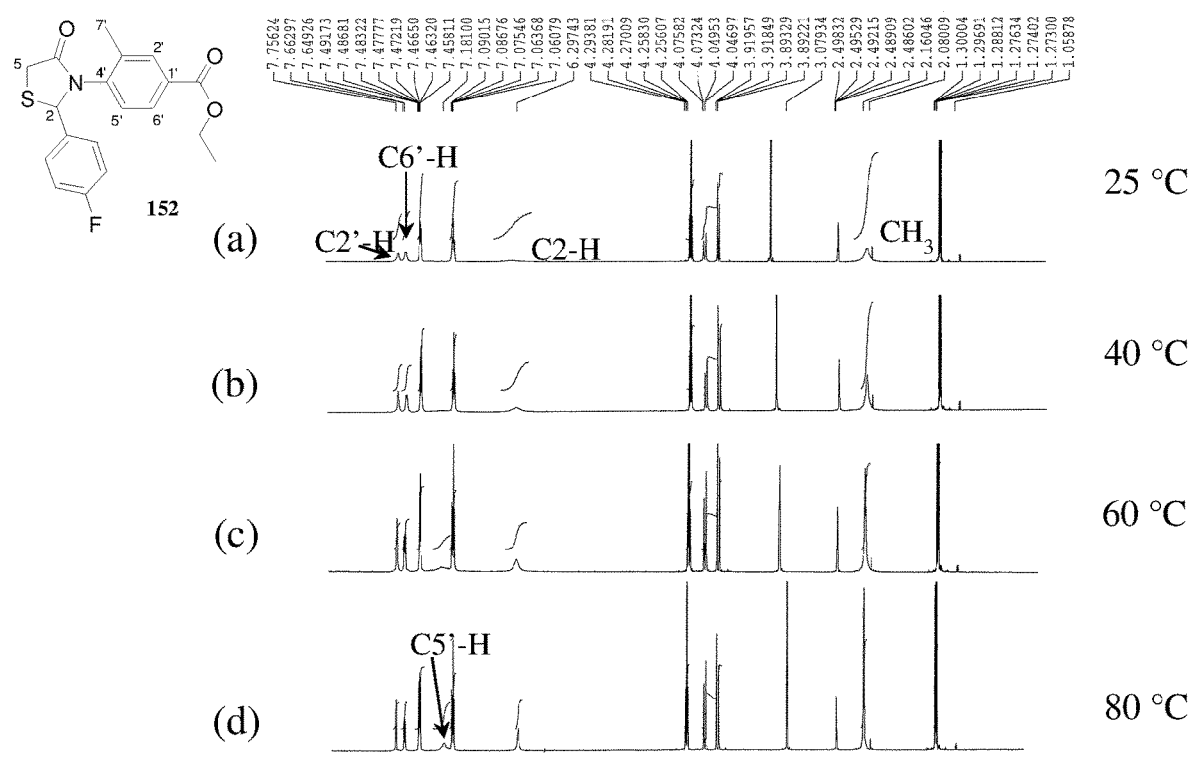

THIAZOLIDINONE COMPOUNDS AND USE THEREOF

CROSS-REFERENCE TO RELATED APPLICATIONS

The present application claims the priority of Provisional Application No. 62/304,557, filed on Mar. 7, 2016. The content of this prior application is hereby incorporated by reference in its entirety.

BACKGROUND

Opioids are classified as natural opioid (e.g., morphine and codeine noscopine), semi-synthetic opioid (e.g., heroin, oxymorphone, and hydromorphone), synthetic opioid (e.g., methadone, morphinians, and benzamorphans), and peptides opioid (e.g. endorphins, enkephalins and dynorphins).

It is well known in the art that opioids act in both the central and peripheral nervous systems to produce various pharmacological effects, including analgesia, drowsiness, mood changes, respiratory depression, dizziness, mental clouding, dysphoria pruritus, nausea, vomiting, increased pressure in the biliary tract, decreased gastrointestinal motility, and alteration of the endocrine or autonomic nervous systems. They have long been the most potent and effective analgesics available to treat acute pain (such as post-operative pain) and chronic and disabling pain (such as pain from cancer).

Opioids primarily activate three classic subtypes of opioid receptors, namely, mu-opioid receptor (MOR), delta-opioid receptor (DOR), and kappa-opioid receptor (KOR), to exert therapeutic effects. These opioid receptors are all G-protein-coupled receptors. Most opioids clinically used as analgesics produce undesired effects, e.g., respiratory depression. Furthermore, long-term use of opioids for controlling chronic pain develops severe side effects, e.g., tolerance, dependence, and addiction.

There is a need to develop new opioids that modulate opioid receptors with fewer side effects for the treatment of opioid receptor-associated conditions, e.g., pain, immune function, and esophageal reflux.

SUMMARY

The present invention relates to use of an antagonist-to-agonist allosteric modifier of a MOR for treating an opioid receptor-associated condition. Such a modifier combined with a MOR antagonist produces anti-nociceptive effects without developing severe side effects.

In one aspect, this invention relates to a method of treating an opioid receptor-associated condition. The method includes administering to a subject in need thereof a mu-opioid receptor antagonist and an effective amount of the compound of Formula (I):

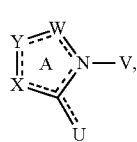

(I)

in which U is $C_{1-6}$ alkyl, $C_{3-8}$ cycloalkyl, $C_{2-8}$ heterocycloalkyl, $C_{6-14}$ aryl, or $C_{1-13}$ heteroaryl; V is $C_{1-6}$ alkyl, $C_{3-8}$ cycloalkyl, $C_{2-8}$ heterocycloalkyl, -L-$C_{6-14}$ aryl, or -L-$C_{1-13}$ heteroaryl, L being a bond, NR, or $S(O)_2$; X is S, $SO_2$, CRR', O, or N; Y is CRR', O, or N; and W is —C(O)—, —CH=, —CH$_2$—, N, or O, wherein each of the $C_{1-6}$ alkyl, $C_{3-8}$ cycloalkyl, $C_{2-8}$ heterocycloalkyl, $C_{6-14}$ aryl, and $C_{1-13}$ heteroaryl, independently, either is optionally mono-, di-, or tri-substituted with halo, OH, CN, $CF_3$, $NH_2$, $NO_2$, $SO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, $C_{6-14}$ aryl, $C_{1-13}$ heteroaryl, —C(O)OR, —C(O)NRR', —C(O)R, —C(O)NRS(O)$_2$R', —C(O)NRS(O)$_2$NR'R", —C(=NH)NRR', —S(O)$_2$R, —S(O)$_2$NRR', —NRR', —NRC(O)R', —NRS(O)$_2$R', or —NRS(O)$_2$NR'R"; or is optionally fused with $C_{3-8}$ cycloalkyl, $C_{2-8}$ heterocycloalkyl, $C_{6-14}$ aryl, or $C_{1-13}$ heteroaryl; each of R, R', and R", independently, being H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, or $C_{1-13}$ heteroaryl; and ⚌ is either a single bond or a double bond.

The above-described method for treating an opioid receptor-associated condition, in addition to administration of a compound of Formula (I), can further include administration of a MOR antagonist, e.g., naloxone, naltrexone, samidorphan, cyprodime, clocinnamox, and β-FNA. They can be administered jointly (i.e., in one pharmaceutical composition) or separately (i.e., in two pharmaceutical compositions).

This method works via a unique mechanism, namely, opioid antagonist-mediated activation of a MOR to produce anti-nociceptive effects. Unlike using a MOR agonist, the method of this invention uses an allosteric modifier combined with a MOR antagonist to produce anti-nociceptive effects without developing severe side effects, e.g., tolerance, dependence, and addiction.

In another aspect, this invention relates to a compound of formula (I):

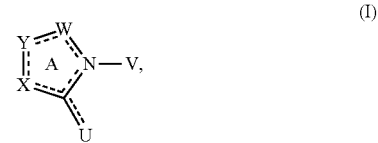

(I)

in which X is S, Y is —CH$_2$—, W is —C(O)—, ring A is

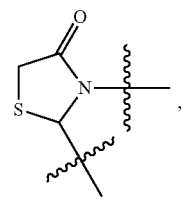 [SMILES: *C1SCC(=O)N1*]

U is $C_{14}$ aryl or $C_{1-3}$ heteroaryl, and V is

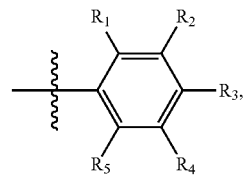

wherein $R_1$ is halo, $C_{1-6}$ alkyl, or $C_{2-6}$ alkenyl; each of $R_2$, $R_4$, and $R_5$, independently, is H, $C_{1-6}$ alkyl, $C_{3-8}$ cycloalkyl, $C_{2-8}$ heterocycloalkyl, $C_{1-6}$ alkoxy, $C_{6-14}$ aryl, or $C_{1-13}$ heteroaryl; and $R_3$ is halo, CN, $C_{1-6}$ alkyl, $C_{1-6}$ alkoxy, $C_{1-13}$ heteroaryl, —C(O)OR, —C(O)NRR', —C(O)R, —C(O)NRS(O)$_2$R', —C(O)NRS(O)$_2$NR'R", —C(=NH)NRR', —NRC(O)R', —NRR', or —NRS(O)$_2$R', each of R, R', and R", independently, being H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, or $C_{1-13}$ heteroaryl; and the compound has an enantiomeric excess of greater than 90%.

In a further aspect, this invention relates to a compound of formula (I):

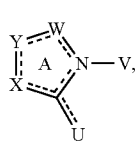

(I)

in which X is S, Y is —CH$_2$—, W is —C(O)—, ring A is

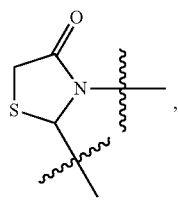 [SMILES: *C1SCC(=O)N1*]

U is $C_{6-14}$ aryl or $C_{1-3}$ heteroaryl, and V is

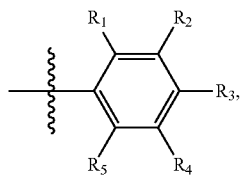

wherein $R_1$ is halo, $C_{1-6}$ alkyl, or $C_{2-6}$ alkenyl; each of $R_2$, $R_4$, and $R_5$, independently, is H, $C_{1-6}$ alkyl, $C_{3-8}$ cycloalkyl, $C_{2-8}$ heterocycloalkyl, $C_{1-6}$ alkoxy, $C_{6-14}$ aryl, or $C_{1-13}$ heteroaryl; $R_3$ is halo, CN, $C_{1-6}$ alkyl, $C_{1-6}$ alkoxy, $C_{1-13}$ heteroaryl, —C(O)OR, C(O)NRR', —C(O)R, —C(O)NRS(O)$_2$R', —C(O)NRS(O)$_2$NR'R", —C(=NH)NRR', —NRC(O)R', —NRR', or —NRS(O)$_2$R', each of R, R', and R", independently, being H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, or $C_{1-13}$ heteroaryl; and at least one of $R_1$, Y, and the carbon U attached to is mono-, di-, or tri-substituted with deuterium.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "haloalkyl" refers to alkyl substituted with one or more halogen (chloro, fluoro, bromo, or iodo) atoms. Examples include trifluoromethyl, bromomethyl, and 4,4,4-trifluorobutyl. The term "alkoxy" refers to an —O-alkyl group. Examples include methoxy, ethoxy, propoxy, and isopropoxy. The term "haloalkoxy" refers to alkoxy substituted with one or more halogen atoms. Examples include —O—CH$_2$Cl and —O—CHClCH$_2$Cl.

The term "cycloalkyl" refers to a saturated and partially unsaturated monocyclic, bicyclic, tricyclic, or tetracyclic hydrocarbon group having 3 to 12 carbons. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system, in which each ring may have 1 to 5 substituents. Examples of aryl groups include phenyl, naphthyl, and anthracenyl. The term "aralkyl" refers to alkyl substituted with an aryl group. Examples include benzyl and naphthylmethyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaralkyl" refers to an alkyl group substituted with a heteroaryl group. Examples include pyridylmethyl and furylmethyl.

The term "halo" refers to a fluoro, chloro, bromo, or iodo radical. The term "amino" refers to a radical derived from amine, which is unsunstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aralkyl, heteroaralkyl, haloalkyl, alkoxy, haloalkoxy, alkylamino, dialkylamino, aryl, and heteroaryl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further be substituted.

Herein, the term "compound" refers to the compounds of Formula (I) described above, as well as their salts and solvates, if applicable. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Also within the scope of this invention is a pharmaceutical composition for treating an opioid receptor-associated condition. The pharmaceutical composition contains a compound of Formula (I) as described above.

The pharmaceutical composition can further contain a MOR antagonist. Examples of the MOR antagonist include, but are not limited to naloxone, naltrexone, samidorphan, cyprodime, clocinnamox, and β-FNA. Such a composition can be used for treating an opioid receptor-associated condition, e.g., pain, via the above-described mechanism, i.e., an opioid antagonist-mediated activation of a MOR.

This invention also covers use of such a composition for the manufacture of a medicament for treating an opioid receptor-associated condition.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The above-described compounds or a pharmaceutical composition containing such a compound can be administered to a subject orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

BRIEF DESCRIPTION OF THE DRAWING

The FIGURE attached to the Specification is a variable-temperature $^1$HNMR spectra of compound 152 measured at four different temperatures: (a) 25° C.; (b) 40° C.; (c) 60° C.; and (d) 80° C.

DETAILED DESCRIPTION

Disclosed in detail herein is a pharmaceutical composition for treating an opioid receptor-associated condition. The pharmaceutical composition contains a compound of of Formula (I):

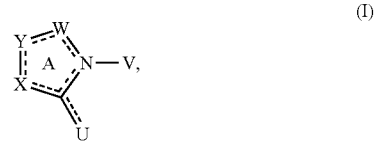

Referring to this formula, examples of ring A include, but are not limited to

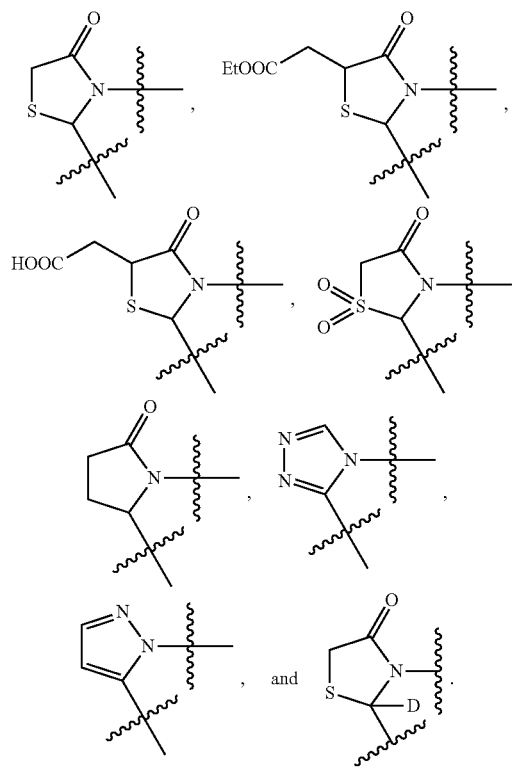

U can be one of the following moieties:
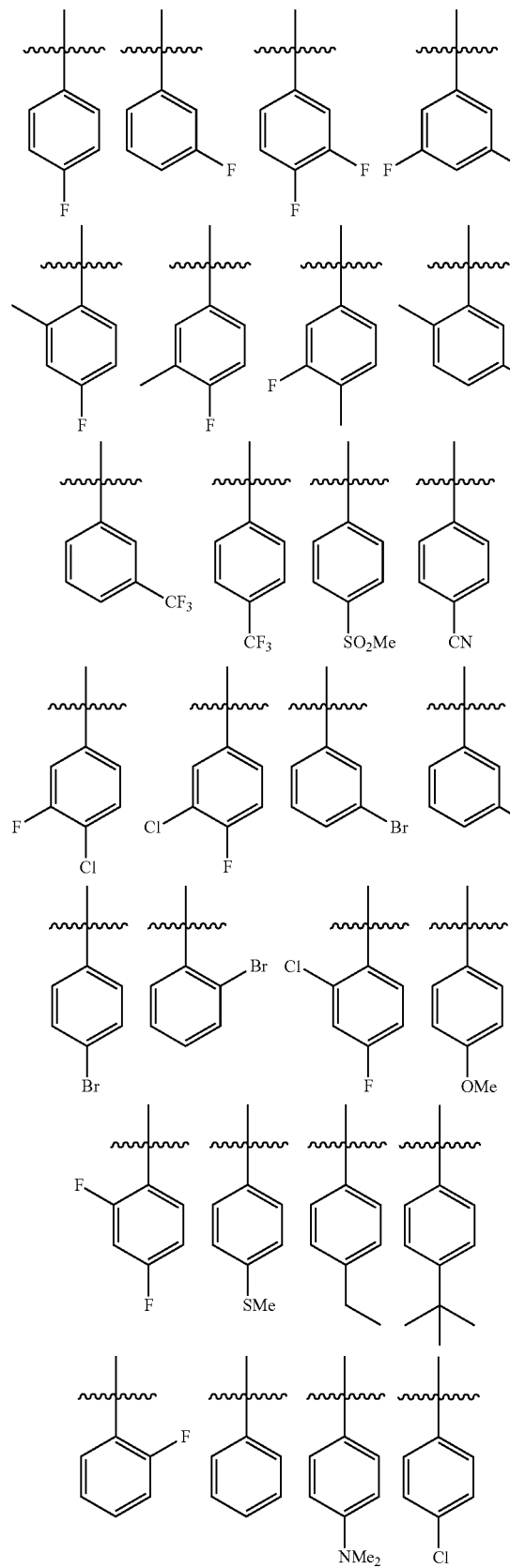
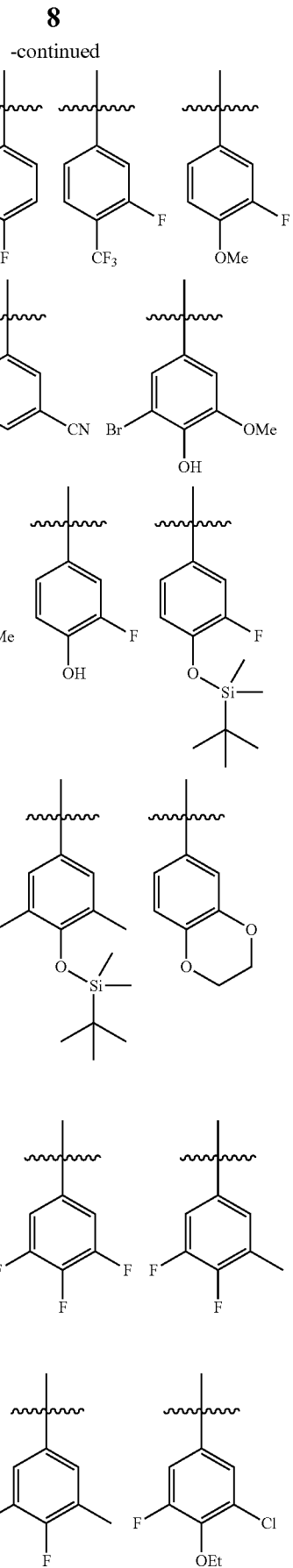

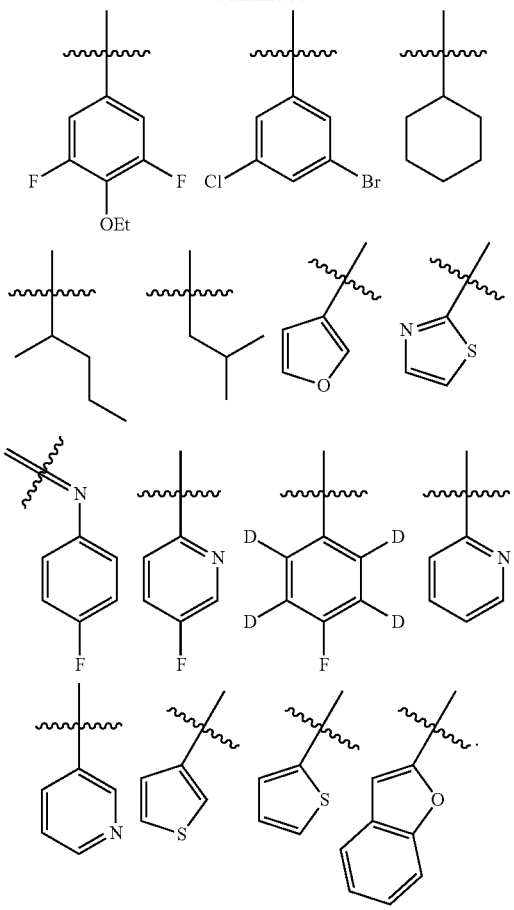
In one subset, compounds of formula (I) each have V as one of the following moieties:
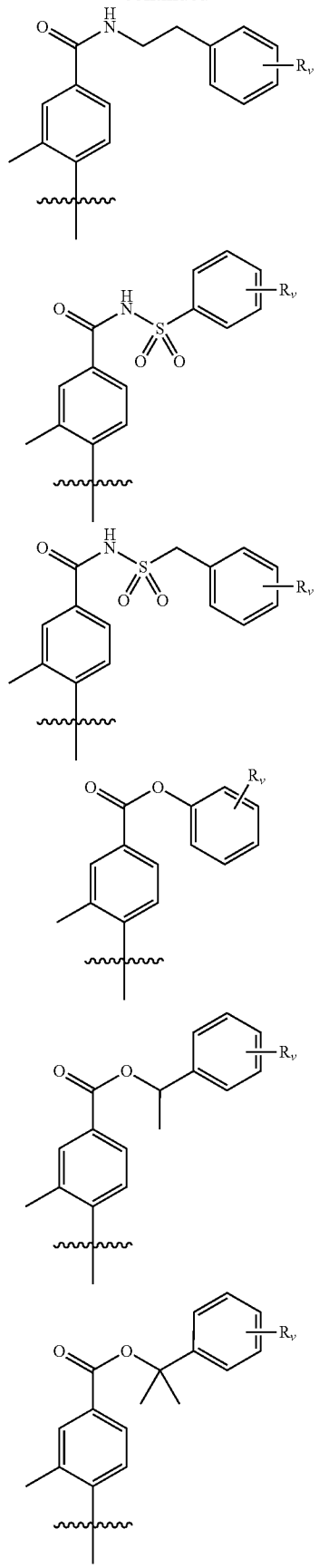

-continued

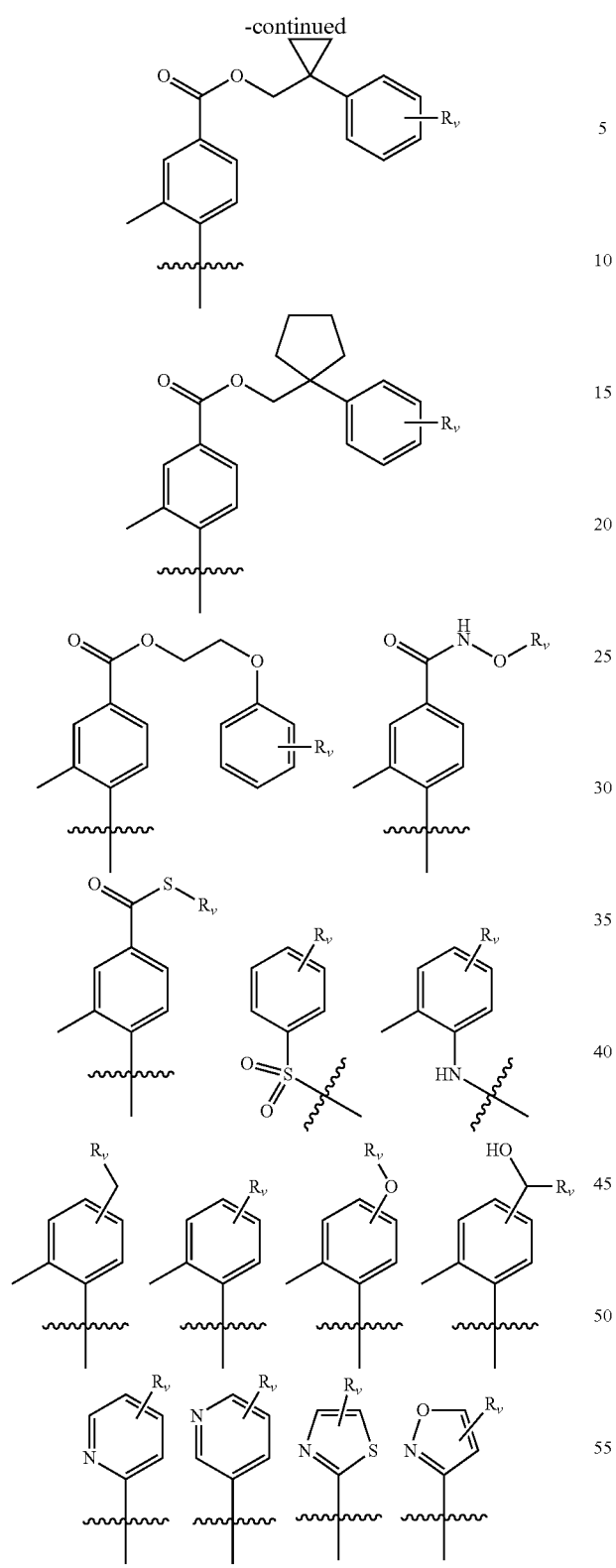

in which $R_v$ is mono-, di-, or tri-substituted moieties among H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, and $C_{1-13}$ heteroaryl.

In another subset, compounds of formula (I) each have V as one of the following moieties:

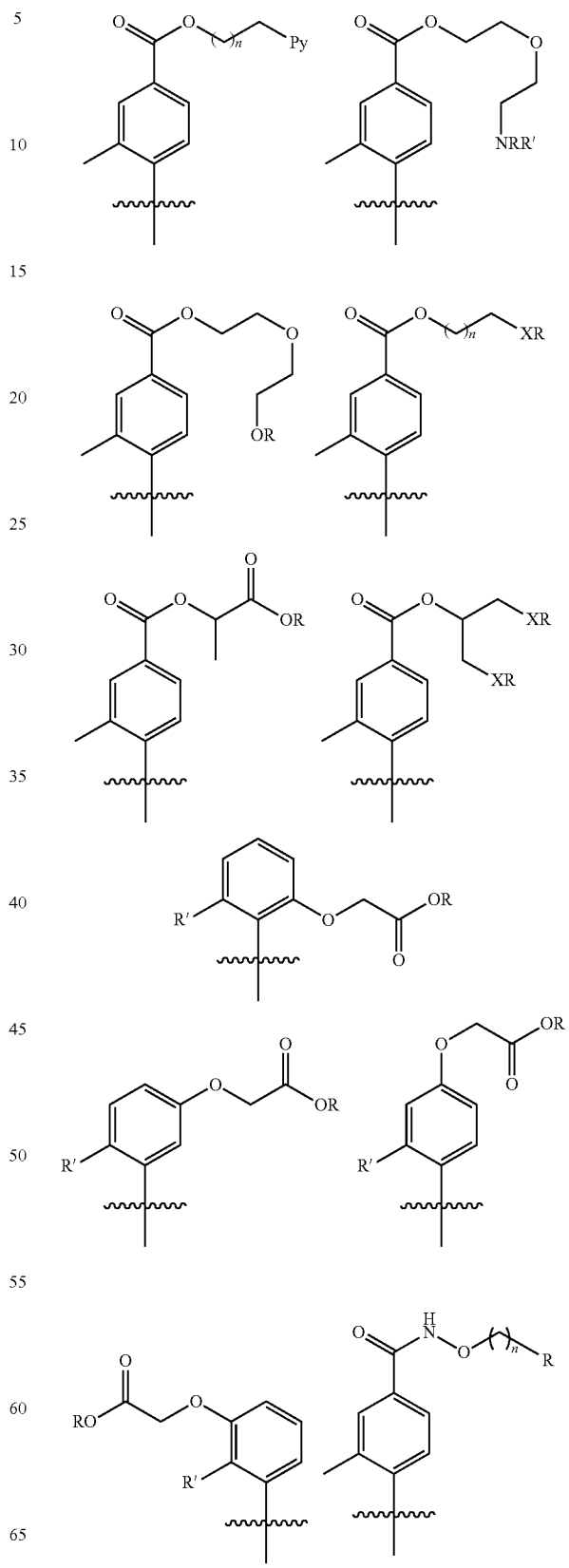

-continued
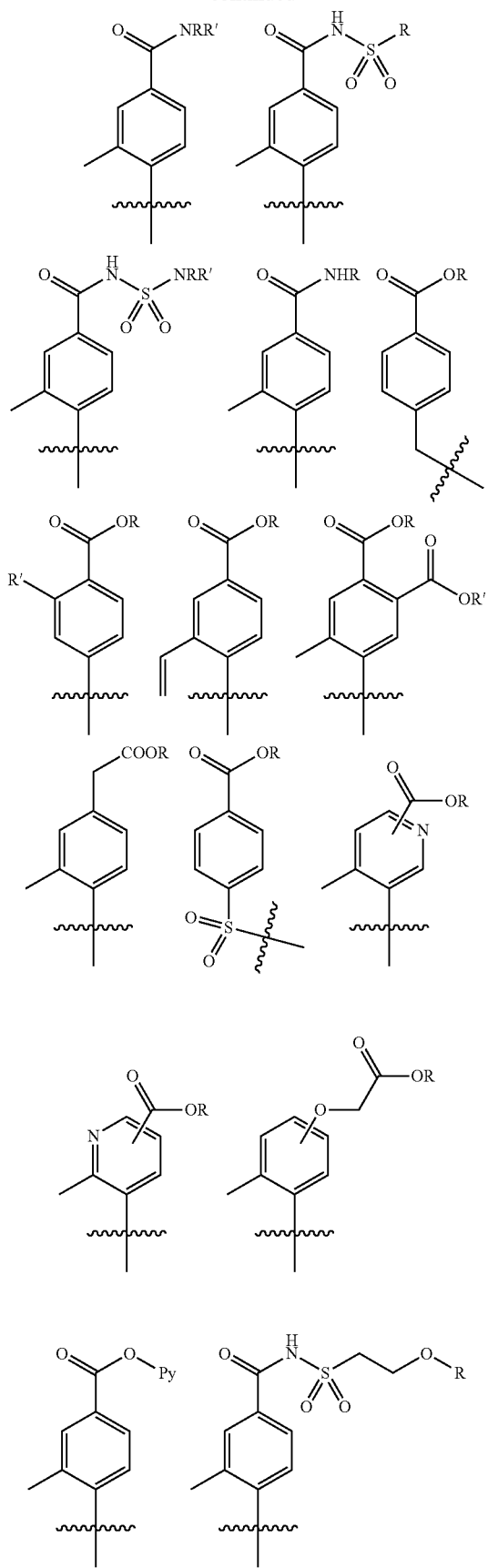
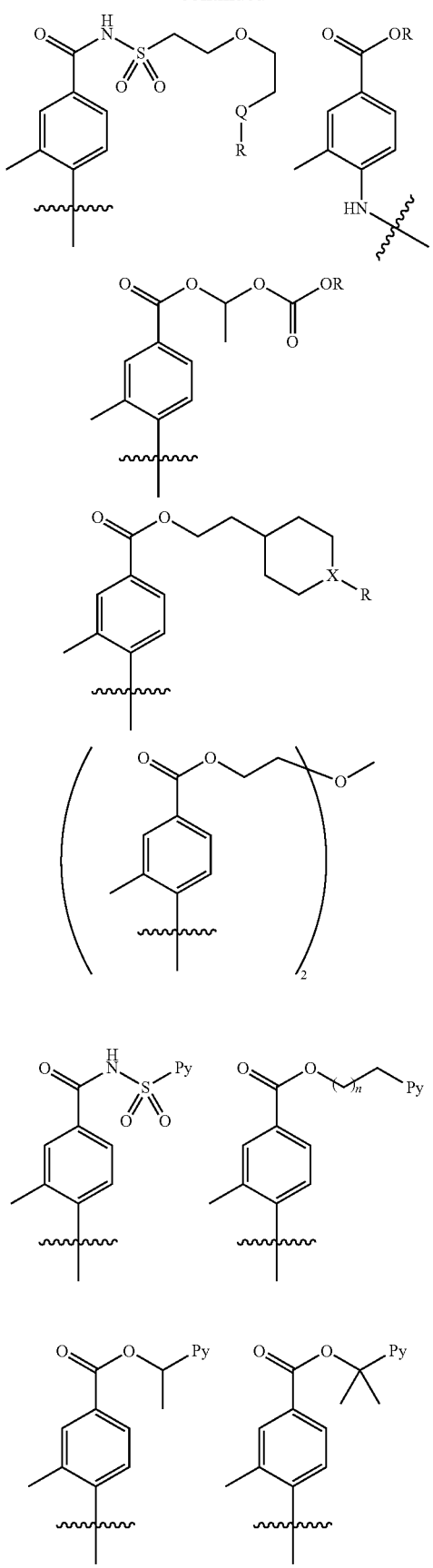

-continued

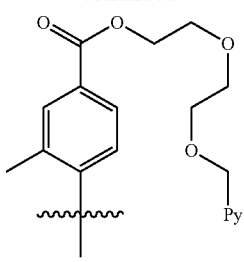

in which each of R and R', independently, is H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, or $C_{1-13}$ heteroaryl; n is 1 to 6; X is S, $SO_2$, CRR', O, or NR'; and Py is substituted or non-substituted ortho-, meta-, or para-pyridine.

Typically, V is

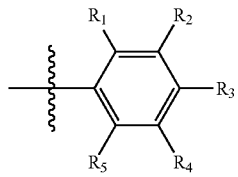

or $C_{1-13}$ heteroaryl, in which $R_1$ is halo, $C_{1-6}$ alkyl, or $C_{2-6}$ alkenyl; each of $R_2$, $R_4$, and $R_5$, independently, is H, $C_{1-6}$ alkyl, $C_{3-8}$ cycloalkyl, $C_{2-8}$ heterocycloalkyl, $C_{1-6}$ alkoxy, $C_{6-14}$ aryl, or $C_{1-13}$ heteroaryl; and $R_3$ is halo, CN, $C_{1-6}$ alkyl, $C_{1-6}$ alkoxy, $C_{1-13}$ heteroaryl, —C(O)OR, —C(O)NRR', —C(O)R, —C(O)NRS(O)$_2$R', —C(O)NRS(O)$_2$NR'R", —C(=NH)NRR', —NRC(O)R', —NRR', or —NRS(O)$_2$R', each of R, R', and R", independently, being H, halo, OH, CN, COOH, mono-, di-, or tri-alkylsubstitutes silyl, acetyl, acetamide, dialkylamino, alkylamino, $C_{1-6}$ alkyl, $C_{1-6}$ multihaloalkyl, $C_{1-6}$ alkoxy, $C_{1-6}$ multihaloalkoxy, $C_{3-8}$ cycloalkyl, $C_{2-8}$ heterocycloalkyl, $C_{6-14}$ aryl, or $C_{1-13}$ heteroaryl.

Examples of V include, but are not limited to, the following moieties:

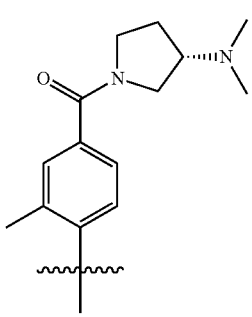
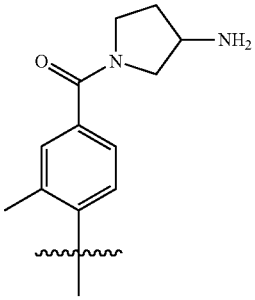

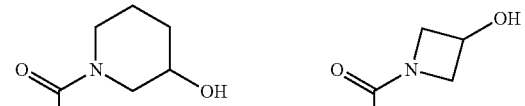
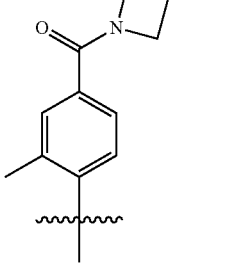
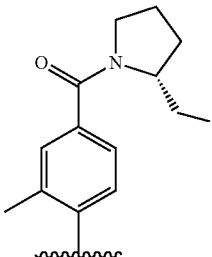
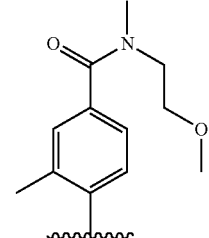
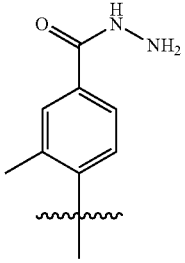
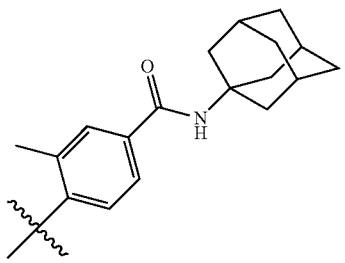
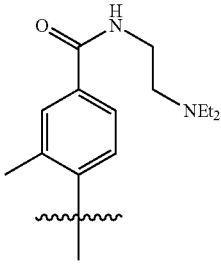
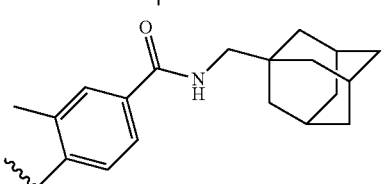
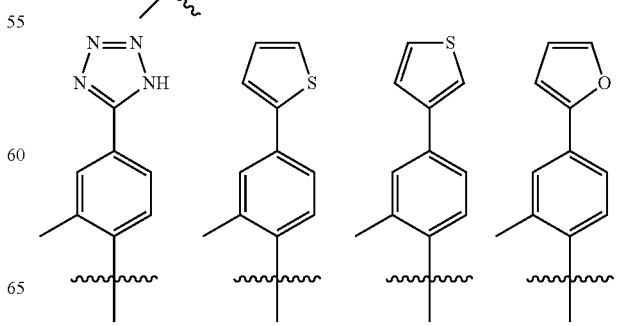

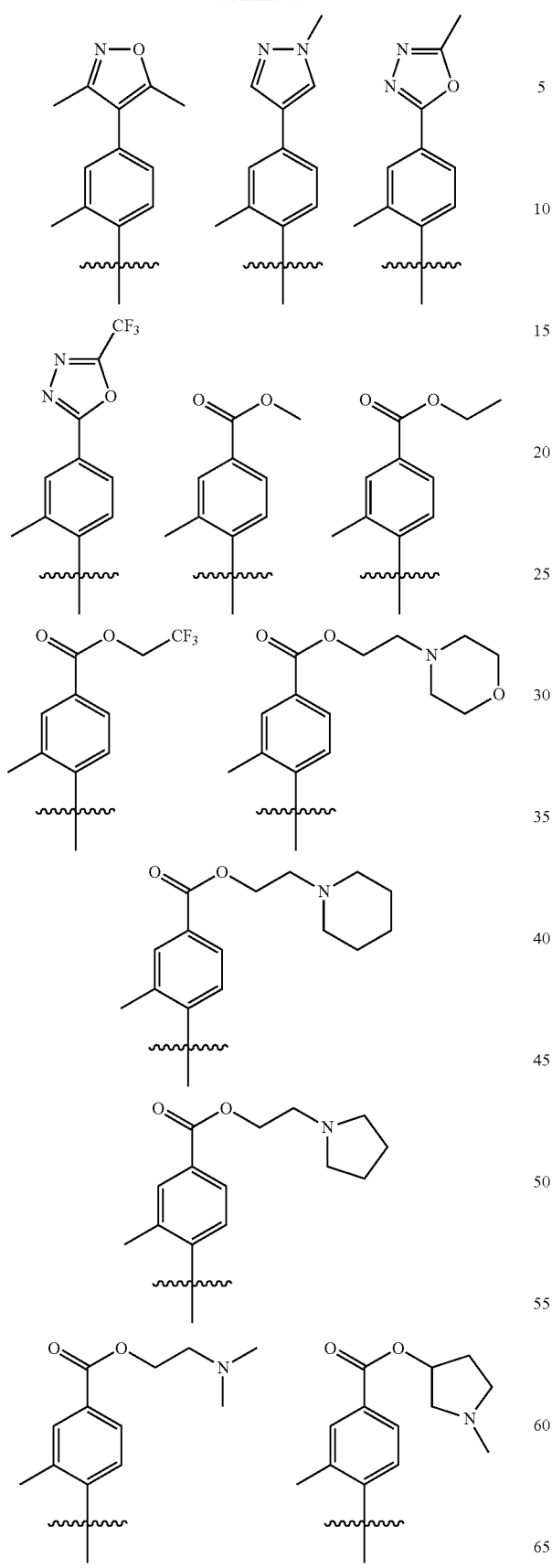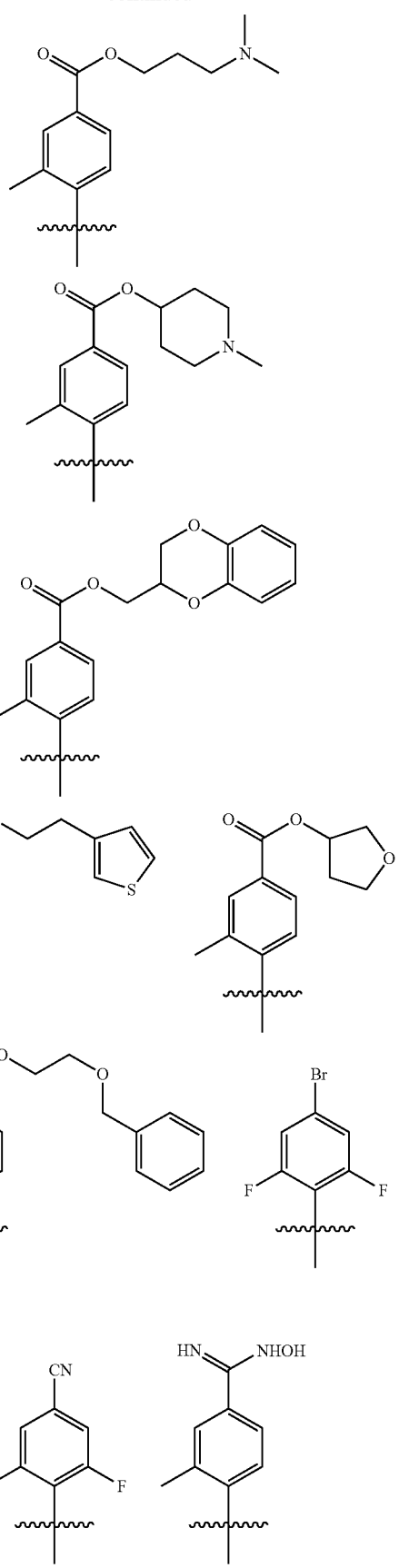

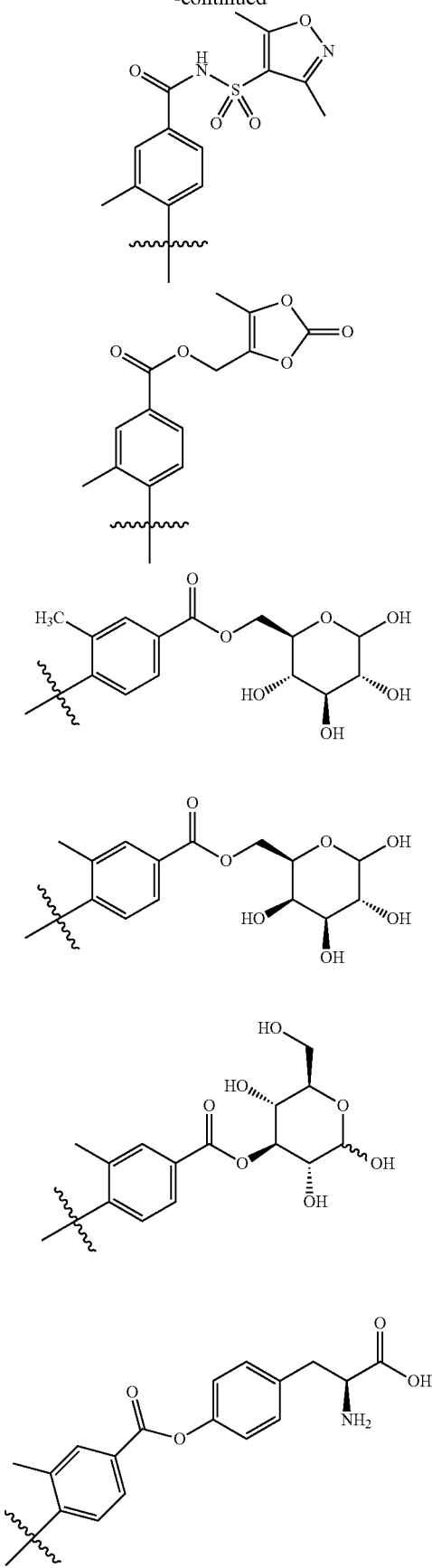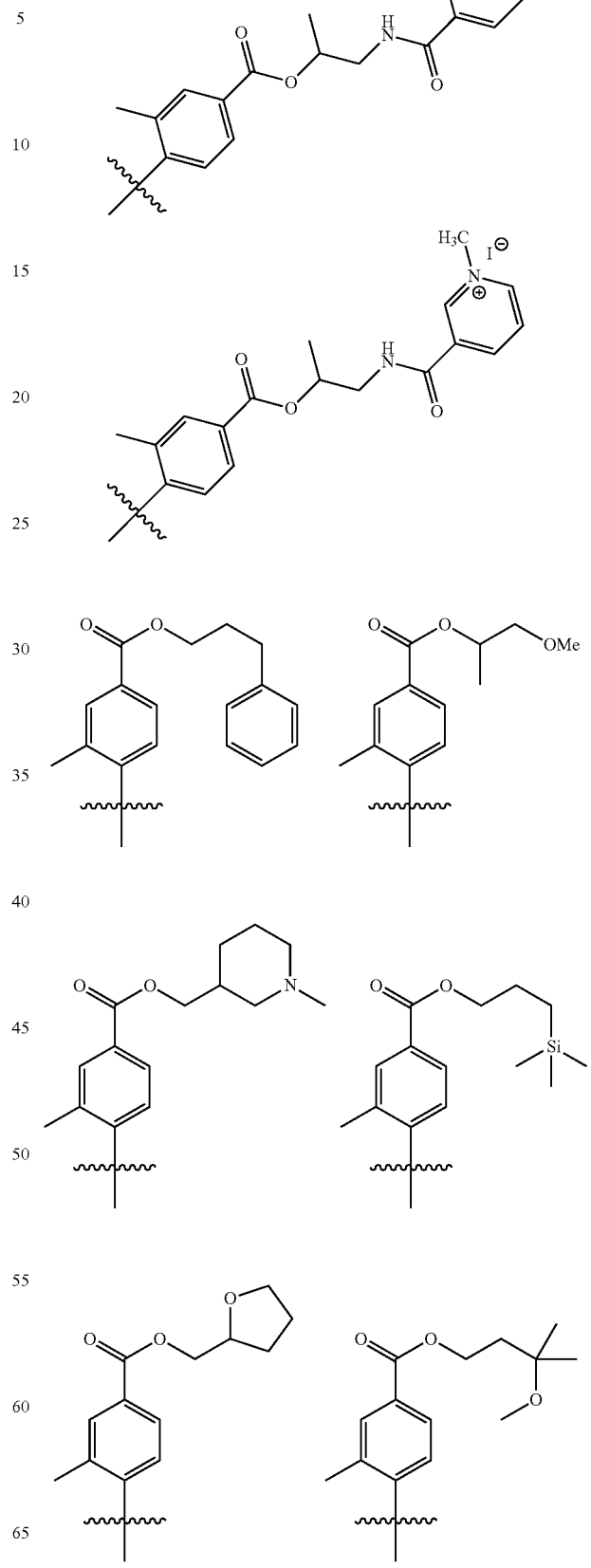

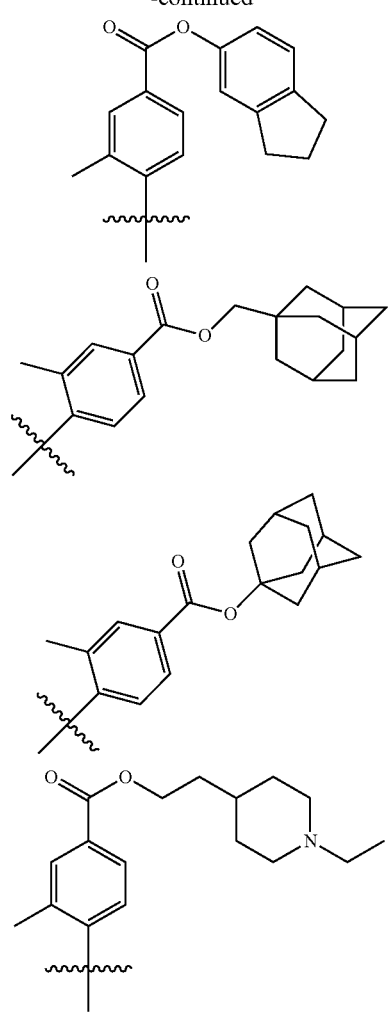
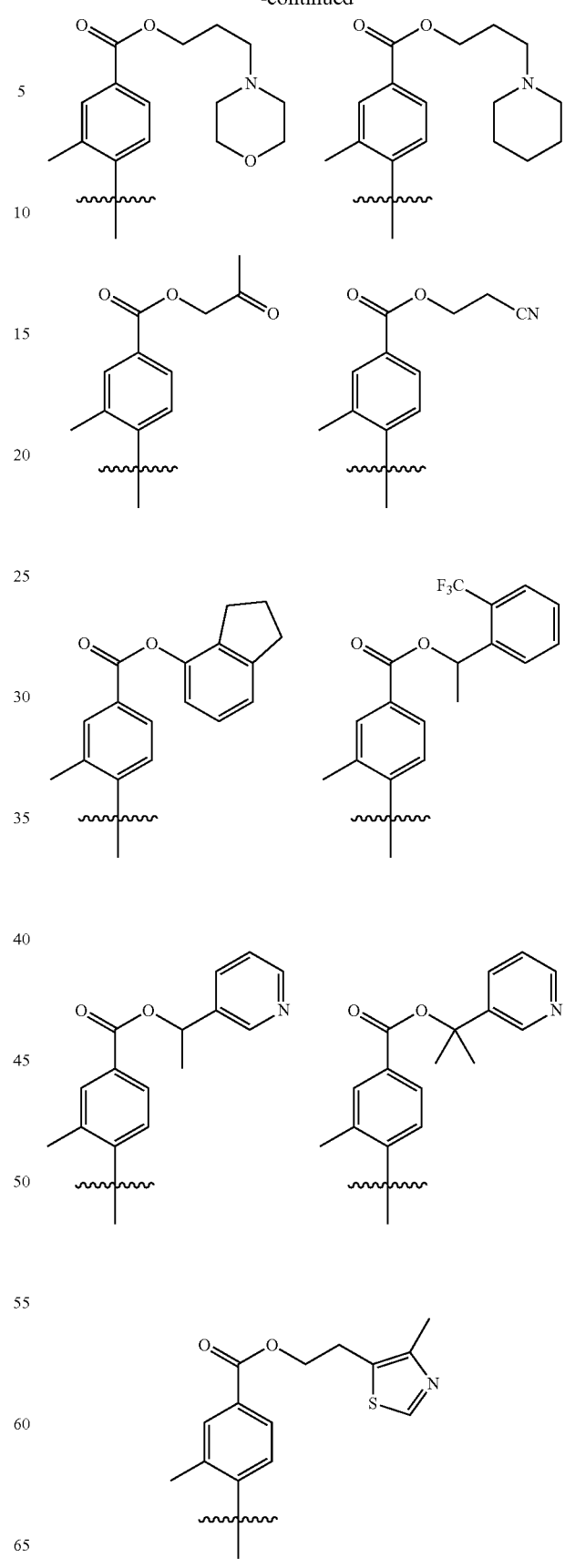

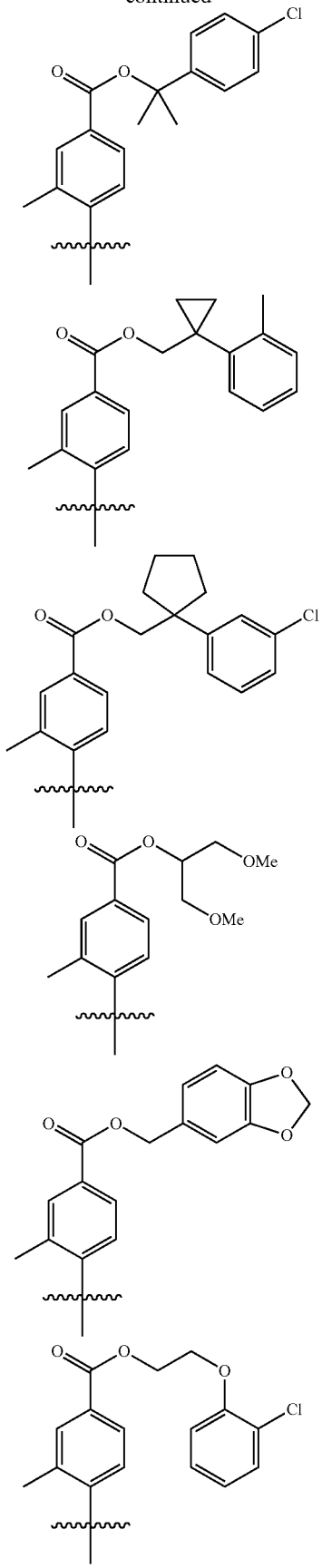
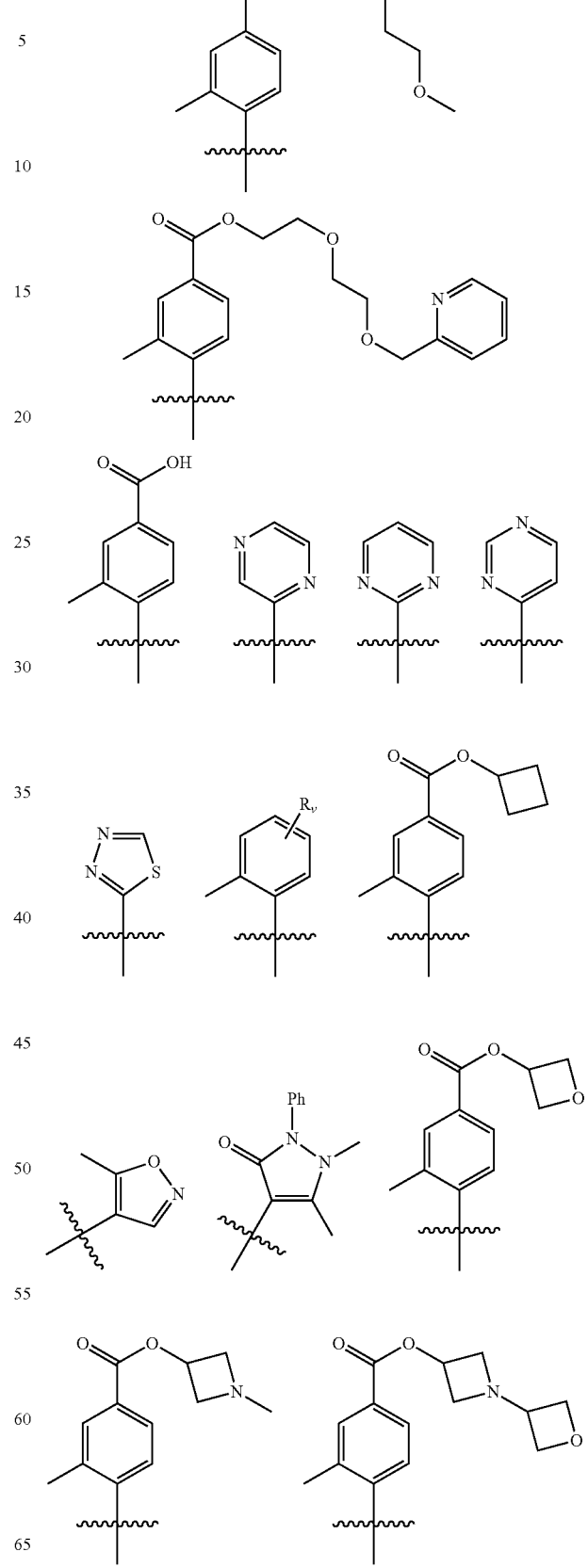

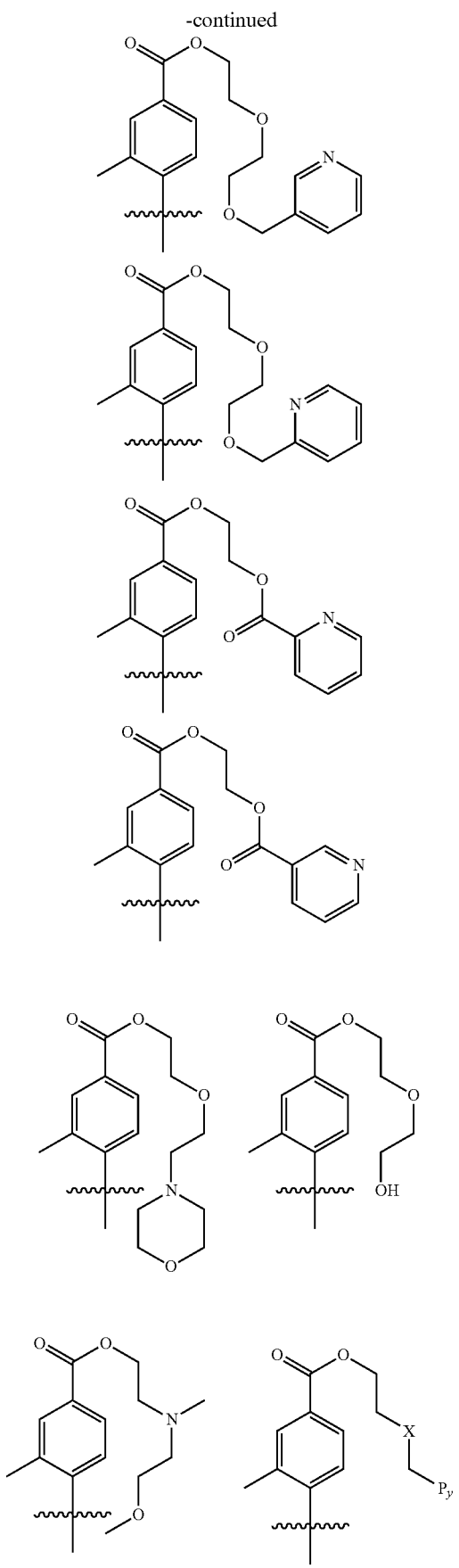
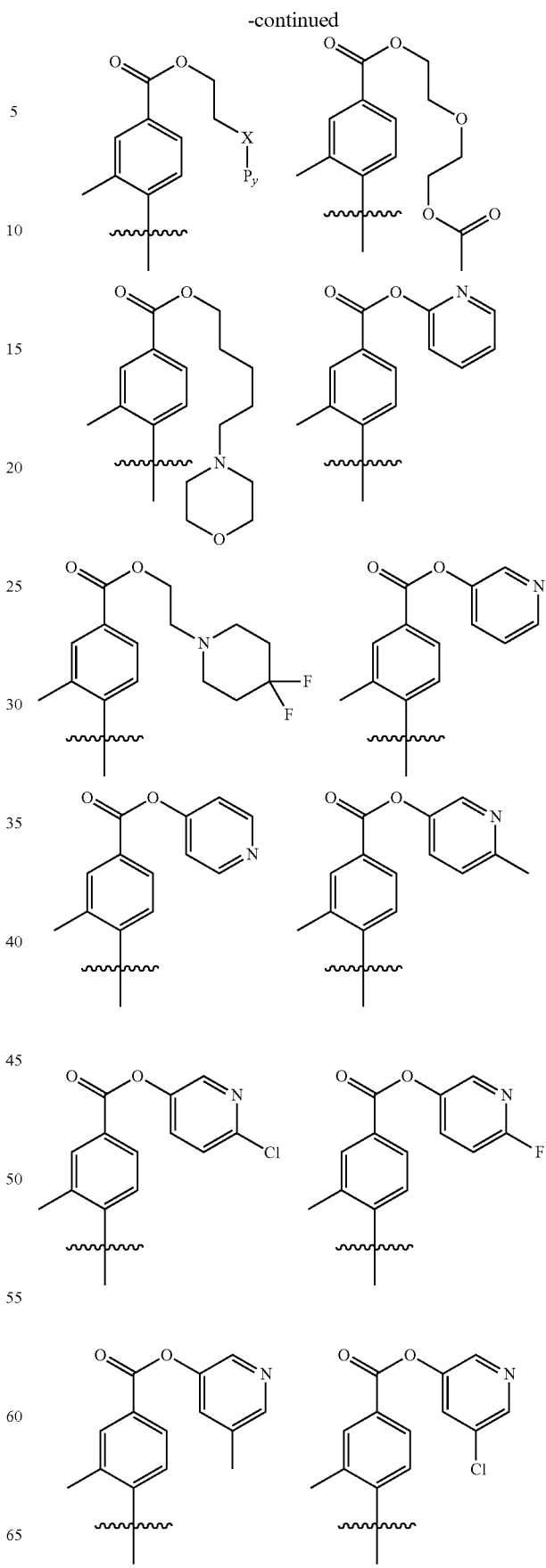

-continued

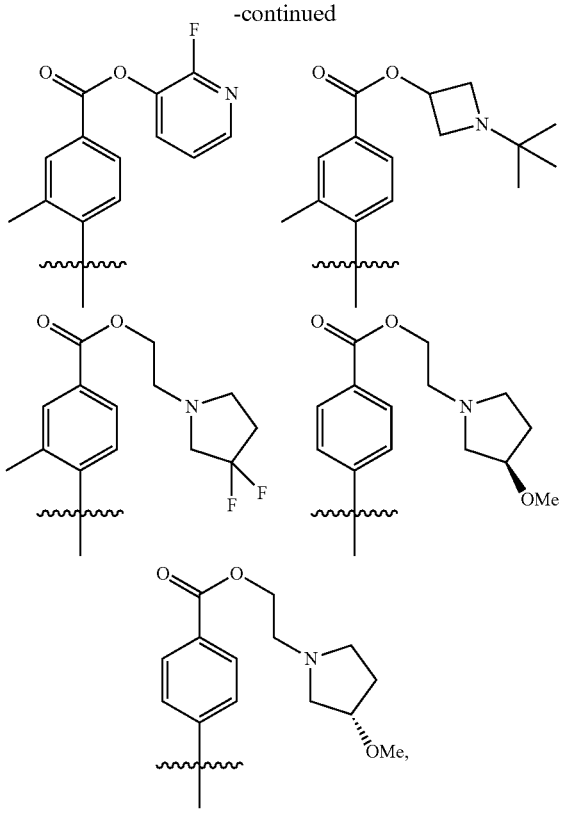

in which $R_v$ is

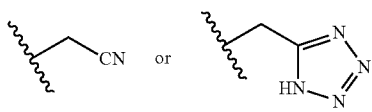

(at any position of the phenyl ring); X is O, S, or NH; and Py is substituted or non-substituted ortho-, meta-, or para-pyridine.

Also within this invention are two sets of thiazolidinone compound of Formula (I):

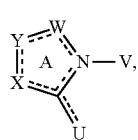

in which X is S, Y is —CH₂—, W is —C(O)—, ring A is

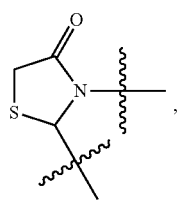 [SMILES: *C1SCC(=O)N1*]

U is $C_{6-14}$ aryl or $C_{1-13}$ heteroaryl, and V is

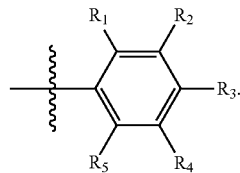

In one set, compounds of formula (I) each have an enantiomeric excess greater than 90%; and in the other set, compounds of formula (I) each have at least one of $R_1$, Y, and the carbon U attached to mono-, di-, or tri-substituted with deuterium. Typically, in both sets of compounds, $R_1$ is $CH_3$ and $R_3$ is —C(O)OR, —C(O)NRR', —C(O)R, —C(O)NRS(O)₂R', or —C(O)NRS(O)₂NR'R".

Further covered by this invention is a method of treating an opioid receptor-associated condition. The method includes administering to a subject in need thereof a mu-opioid receptor antagonist and an effective amount of the above-described compound of Formula (I).

Typically, the opioid receptor-associated condition is pain, immune disease, esophageal reflux, diarrhea, anxiety, or heroin addiction. The pain can be cancer pain, post operative pain, low back pain, rheumatoid arthritis pain, osteoarthritis pain, neuropathic pain, or fibromyalgia pain.

In an exemplary in vitro screening method for identifying antagonist-to-agonist allosteric modifiers of a MOR, cells that express a MOR are treated with a test compound and a MOR antagonist in a cellular calcium fluorescent assay and fluorescence intensity is then measured to determine whether the MOR is activated. A test compound is identified as an antagonist-to-agonist allosteric modifier of the MOR if the MOR is activated.

Two parameters, i.e., $EC_{50}$ and AUC, are typically used in such an assay to measure the degree of MOR activation exerted by the test compound. $EC_{50}$ herein refers to the concentration of a compound that induces a response halfway between the baseline and the maximum after a specified exposure time. AUC refers to the area under the response curve, an indication of the compound's capability of activating a MOR when combined with a MOR antagonist.

In an exemplary in vivo method, a test compound and a MOR antagonist are injected into a mouse pain model (for example, intravenous but not limited), basal latencies are recorded before the treatment and test latencies are recorded at various specified times after the injection, and a time-response curve is recorded and AUC values are calculated to determine whether an analgesic effect is exerted on the mouse. The test compound is confirmed to be an antagonist-to-agonist allosteric modifier of the MOR upon observation of an analgesic effect.

Methods for synthesizing the compounds of Formula (I) are well known in the art. See, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2nd ed., John Wiley and Sons 2009); S. Miyazawa et al., "Benzimidazole Compound" WO 2006112442; M. R. Mautino et al., "IDO Inhibitors" WO2009132238; T. Axenrod et al., "Synthesis and Characterization of 5-Substituted 1,3-Diazacyclohexane Derivatives" *J. Org. Chem.* 2000, 65, 1200-1206; C. D. Magnusson et al., "Chemoenzymatic Synthesis of Symmetrically Structured Triacylglycerols Possessing Short-chain Fatty Acids" *Tetrahedron,* 2010, 66, 2728-2731. T. D. Cushing et al., Heterocyclic compounds and their uses. WO 2010151791 A1, Dec. 29, 2010. M. D. H. Bhuiyan et al., "Synthesis of Symmetric Diester-Functionalised Tröger's Base Analogues." *Eur. J. Org. Chem.* 2010, 24, 4662-4670. Kelgtenrmans, H. et al., "A Fragment-Based Approach toward Substituted Trioxa[7]helicenes." *Org. Lett.* 2012, 14, 5200-5203. Persichetti, R. A.; Harbeson, S. L. Substituted morpholinyl compounds. US20080261983 A1, Oct. 23, 2008. Wang, J.-Z.; Zhou. J.; Xu, C.; Sun, H.; Kürti, L.; Xu, Q.-L. "Symmetry in Cascade Chirality-Transfer Processes: A Catalytic Atroposelective Direct Arylation Approach to BINOL Derivatives." *J. Am. Chem. Soc.* 2016, 138, 5202-5205. Plewe, M. B. et al., "Azaindole Hydroxamic Acids are Potent HIV-1 Integrase Inhibitors." *J. Med. Chem.* 2009, 52, 7211-7219.

The compounds of Formula (I) thus prepared can be initially screened using in vitro assays, e.g., the FLIPR® calcium assay described in Example 488 below, for their potency in activating a MOR in cells. They can be subsequently evaluated using in vivo assays, e.g., a tail-flick test assay described in Example 489 below, for their efficacy in modulating the conformation of intercellular opioid receptor in a mammal. The selected compounds can be further tested to verify their efficacy in treating an opioid receptor-associated condition. For example, a compound can be co-administered with a MOR antagonist (e.g., naltroxone, naltrexone, samidorphan, cyprodime, clocinnamox, β-FNA, naloxonazine, or nalmefene) to an animal (e.g., a mouse) having an opioid receptor-associated condition and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Shown in the Table 1 below are the structures and names of 486 exemplary compounds of Formula (I). The methods for preparing these compounds, as well as the analytical data for the compounds thus prepared, are set forth in Examples 1-486 below. The procedures for testing these compounds are described in Examples 488 and 489 also below.

All 486 compounds, when combined with a MOR antagonist, were found to activate a MOR to various degrees as indicated by their $EC_{50}$ and AUC values included in the following table. -: not available; TBD: to be determined.

TABLE 1

Exemplary compounds and their activities

| No. | Structure | Name | FLIPR $Ca^{2+}$ $EC_{50}$ (μM) | AUC |
|---|---|---|---|---|
| 1 | 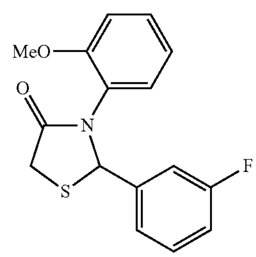 [SMILES: COc1ccccc1N1C(=O)CSC1c1cccc(F)c1] | 2-(3-Fluorophenyl)-3-(2-methoxyphenyl)thiazolidin-4-one | 12.4 | 4897 |
| 2 | 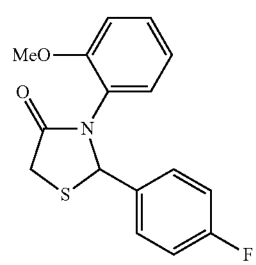 [SMILES: COc1ccccc1N1C(=O)CSC1c1ccc(F)cc1] | 2-(4-Fluorophenyl)-3-(2-methoxyphenyl)thiazolidin-4-one | 19.0 | 10472 |
| 3 | 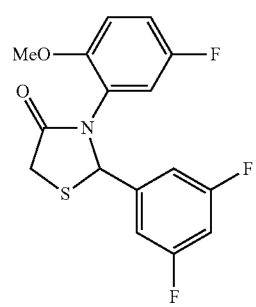 [SMILES: COc1ccc(F)cc1N1C(=O)CSC1c1cc(F)cc(F)c1] | 2-(3,5-Difluorophenyl)-3-(5-fluoro-2-methoxyphenyl)thiazolidin-4-one | — | — |

TABLE 1-continued

Exemplary compounds and their activities

| No. | Structure | Name | FLIPR Ca²⁺ EC$_{50}$ (μM) | AUC |
|---|---|---|---|---|
| 4 | 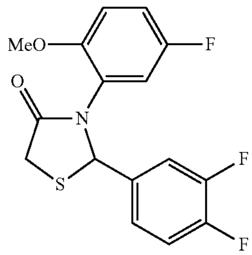 [SMILES: COc1ccc(F)cc1N1C(=O)CSC1c1ccc(F)c(F)c1] | 2-(3,4-Difluorophenyl)-3-(5-fluoro-2-methoxyphenyl)thiazolidin-4-one | 3.3 | 8199 |
| 5 | 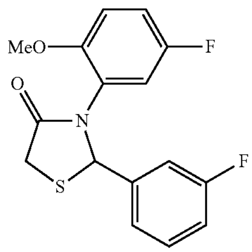 [SMILES: COc1ccc(F)cc1N1C(=O)CSC1c1cccc(F)c1] | 3-(5-Fluoro-2-methoxyphenyl)-2-(3-fluorophenyl)thiazolidin-4-one | 5.2 | 14312 |
| 6 | 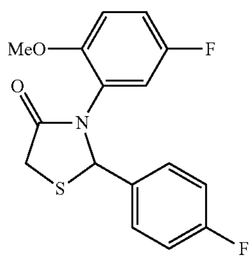 [SMILES: COc1ccc(F)cc1N1C(=O)CSC1c1ccc(F)cc1] | 3-(5-Fluoro-2-methoxyphenyl)-2-(4-fluorophenyl)thiazolidin-4-one | 3.9 | 9196 |
| 7 | 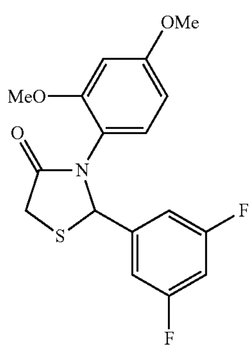 [SMILES: COc1ccc(N2C(=O)CSC2c2cc(F)cc(F)c2)c(OC)c1] | 2-(3,5-Difluorophenyl)-3-(2,4-dimethoxyphenyl)thiazolidin-4-one | — | — |
| 8 | 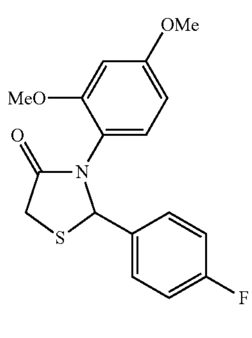 [SMILES: COc1ccc(N2C(=O)CSC2c2ccc(F)cc2)c(OC)c1] | 3-(2,4-Dimethoxyphenyl)-2-(4-fluorophenyl)thiazolidin-4-one | 0.3 | 3020 |

TABLE 1-continued

Exemplary compounds and their activities

| No. | Structure | Name | FLIPR Ca$^{2+}$ EC$_{50}$ (μM) | AUC |
|---|---|---|---|---|
| 9 | 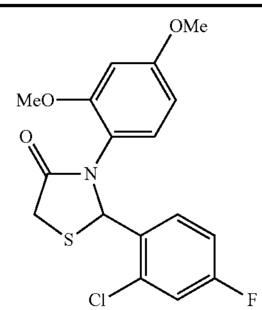 | 2-(2-Chloro-4-fluorophenyl)-3-(2,4-dimethoxyphenyl)thiazolidin-4-one | — | — |
| 10 | 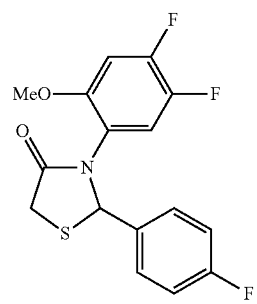 [SMILES: COc1cc(F)c(F)cc1N1C(=O)CSC1c1ccc(F)cc1] | 3-(4,5-Difluoro-2-methoxyphneyl)-2-(4-fluorophenyl)thiazolidin-4-one | 2.0 | 6152 |
| 11 | 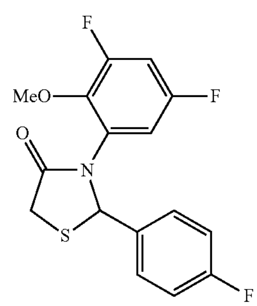 [SMILES: COc1c(F)cc(F)cc1N1C(=O)CSC1c1ccc(F)cc1] | 3-(3,5-Difluoro-2-methoxyphenyl)-2-(4-fluorophenyl)thiazolidin-4-one | 1.6 | 5451 |
| 12 | 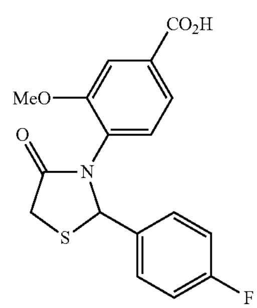 [SMILES: COc1cc(C(=O)O)ccc1N1C(=O)CSC1c1ccc(F)cc1] | 4-[2-(4-fluoro-phenyl)-4-oxo-thiazolidin-3-yl]-3-methoxy-benzoic acid | 10.6 | 12252 |
| 14 | 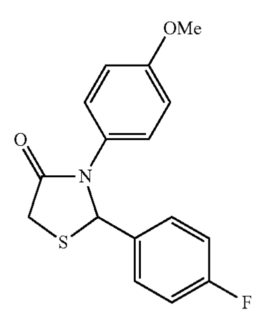 [SMILES: COc1ccc(N2C(=O)CSC2c2ccc(F)cc2)cc1] | 2-(4-Fluorophenyl)-3-(4-methoxyphenyl)thiazolidin-4-one | 3.9 | 5051 |

TABLE 1-continued

Exemplary compounds and their activities

| No. | Structure | Name | FLIPR Ca$^{2+}$ EC$_{50}$ (μM) | AUC |
|---|---|---|---|---|
| 15 | 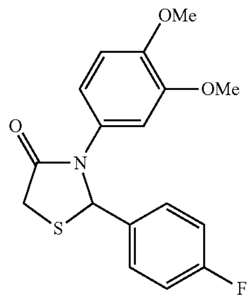 [SMILES: COc1ccc(N2C(=O)CSC2c2ccc(F)cc2)cc1OC] | 3-(3,4-Dimethoxyphenyl)-2-(4-fluorophenyl)thiazolidin-4-one | 10.0 | 10260 |
| 16 | 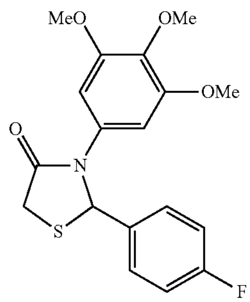 [SMILES: COc1cc(N2C(=O)CSC2c2ccc(F)cc2)cc(OC)c1OC] | 2-(4-Fluorophenyl)-3-(3,4,5-trimethoxyphenyl)thiazolidin-4-one | 8.3 | 10655 |
| 17 | 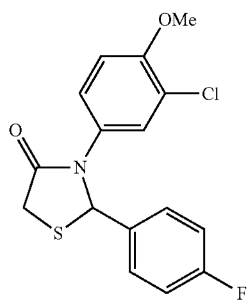 [SMILES: COc1ccc(N2C(=O)CSC2c2ccc(F)cc2)cc1Cl] | 3-(3-Chloro-4-methoxyphenyl)-2-(4-fluorophenyl)thiazolidin-4-one | — | — |
| 18 | 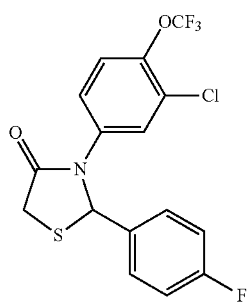 [SMILES: O=C1CSC(c2ccc(F)cc2)N1c1ccc(OC(F)(F)F)c(Cl)c1] | 3-(3-Chloro-4-(trifluoromethoxy)phenyl)-2-(4-fluorophenyl)thiazolidin-4-one | — | — |
| 19 | 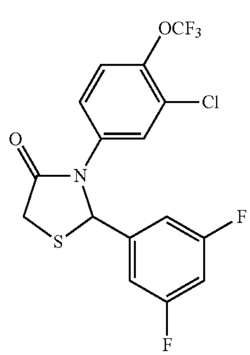 [SMILES: O=C1CSC(c2cc(F)cc(F)c2)N1c1ccc(OC(F)(F)F)c(Cl)c1] | 3-(3-Chloro-4-(trifluoromethoxy)phenyl)-2-(3,5-difluorophenyl)thiazolidin-4-one | — | — |

TABLE 1-continued

Exemplary compounds and their activities

| No. | Structure | Name | FLIPR Ca²⁺ EC$_{50}$ (μM) | AUC |
|---|---|---|---|---|
| 20 | 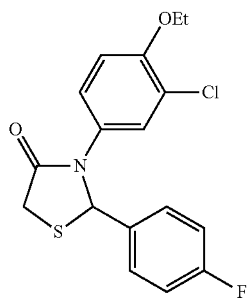 [SMILES: CCOc1ccc(N2C(=O)CSC2c2ccc(F)cc2)cc1Cl] | 3-(3-Chloro-4-ethoxyphenyl)-2-(4-fluorophenyl)thiazolidin-4-one | 7.3 | 4633 |
| 21 | 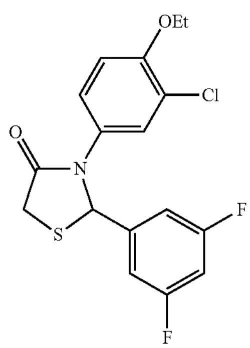 [SMILES: CCOc1ccc(N2C(=O)CSC2c2cc(F)cc(F)c2)cc1Cl] | 3-(3-Chloro-4-ethoxyphenyl)-2-(3,5-difluorophenyl)thiazolidin-4-one | — | — |
| 22 | 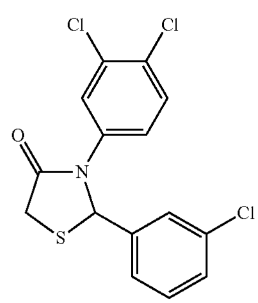 [SMILES: O=C1CSC(c2cccc(Cl)c2)N1c1ccc(Cl)c(Cl)c1] | 2-(3-Chlorophenyl)-3-(3,4-dichlorophenyl)thiazolidin-4-one | — | — |
| 23 | 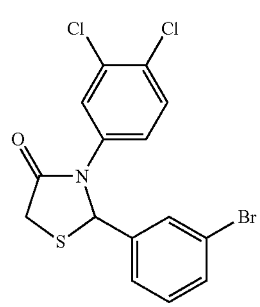 [SMILES: O=C1CSC(c2cccc(Br)c2)N1c1ccc(Cl)c(Cl)c1] | 2-(3-Bromophenyl)-3-(3,4-dichlorophenyl)thiazolidin-4-one | TBD | TBD |

TABLE 1-continued

Exemplary compounds and their activities

| No. | Structure | Name | FLIPR Ca²⁺ EC$_{50}$ (µM) | AUC |
|---|---|---|---|---|
| 24 | 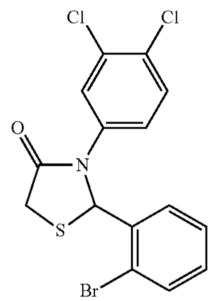 [SMILES: O=C1CSC(c2ccccc2Br)N1c1ccc(Cl)c(Cl)c1] | 2-(2-Bromophenyl)-3-(3,4-dichlorophenyl)thiazolidin-4-one | — | — |
| 25 | 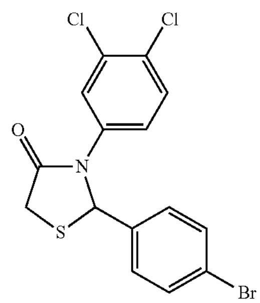 [SMILES: O=C1CSC(c2ccc(Br)cc2)N1c1ccc(Cl)c(Cl)c1] | 2-(4-Bromophenyl)-3-(3,4-dichlorophenyl)thiazolidin-4-one | — | — |
| 26 | 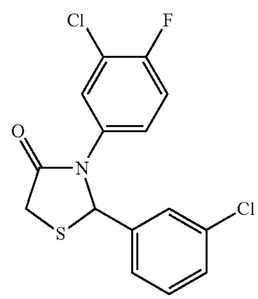 | 3-(3-Chloro-4-fluorophenyl)-2-(3-chlorophenyl)thiazolidin-4-one | — | — |
| 27 | 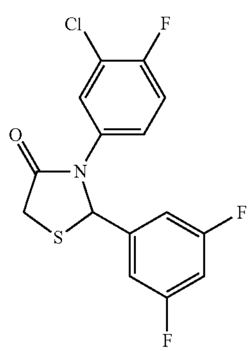 | 3-(3-Chloro-4-fluorophenyl)-2-(3,5-difluorophenyl)thiazolidin-4-one | — | — |
| 28 | 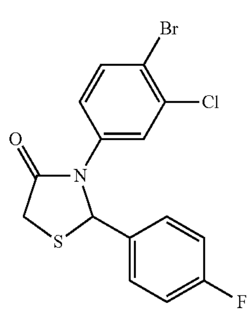 [SMILES: O=C1CSC(c2ccc(F)cc2)N1c1ccc(Br)c(Cl)c1] | 3-(4-Bromo-3-chlorophenyl)-2-(4-fluorophenyl)thiazolidin-4-one | — | — |

TABLE 1-continued

Exemplary compounds and their activities

| No. | Structure | Name | FLIPR Ca²⁺ EC$_{50}$ (µM) | AUC |
|---|---|---|---|---|
| 29 | 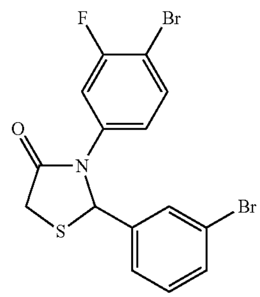 [SMILES: O=C1CSC(c2cccc(Br)c2)N1c1ccc(Br)c(F)c1] | 3-(4-Bromo-3-fluorophenyl)-2-(3-bromophenyl)thiazolidin-4-one | — | — |
| 30 | 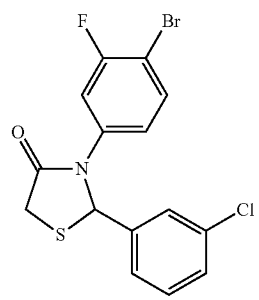 [SMILES: O=C1CSC(c2cccc(Cl)c2)N1c1ccc(Br)c(F)c1] | 3-(4-Bromo-3-fluorophenyl)-2-(3-chlorophenyl)thiazolidin-4-one | — | — |
| 31 | 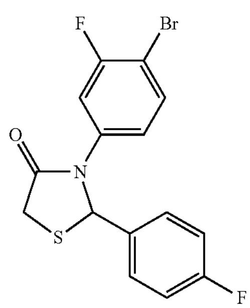 [SMILES: O=C1CSC(c2ccc(F)cc2)N1c1ccc(Br)c(F)c1] | 3-(4-Bromo-3-fluorophenyl)-2-(4-fluorophenyl)thiazolidin-4-one | — | — |
| 32 | 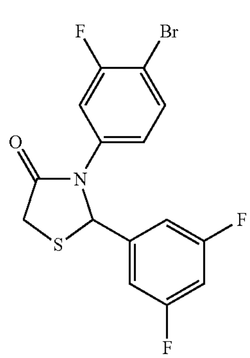 [SMILES: O=C1CSC(c2cc(F)cc(F)c2)N1c1ccc(Br)c(F)c1] | 3-(4-Bromo-3-fluorophenyl)-2-(3,5-difluorophenyl)thiazolidin-4-one | — | — |

TABLE 1-continued

Exemplary compounds and their activities

| No. | Structure | Name | FLIPR Ca$^{2+}$ EC$_{50}$ (µM) | AUC |
|---|---|---|---|---|
| 33 | 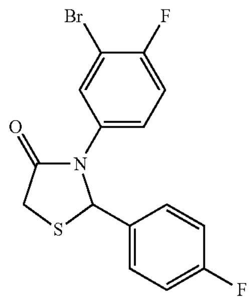 [SMILES: O=C1CSC(c2ccc(F)cc2)N1c1ccc(F)c(Br)c1] | 3-(3-Bromo-4-fluorophenyl)-2-(4-fluorophenyl)thiazolidin-4-one | — | — |
| 34 | 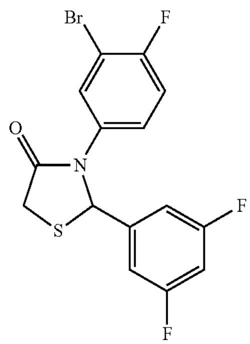 [SMILES: O=C1CSC(c2cc(F)cc(F)c2)N1c1ccc(F)c(Br)c1] | 3-(3-Bromo-4-fluorophenyl)-2-(3,5-difluorophenyl)thiazolidin-4-one | — | — |
| 35 | 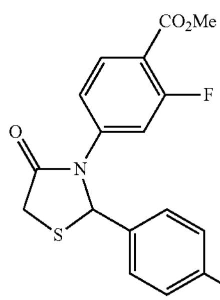 | 2-fluoro-4-[2-(4-fluoro-phenyl)-4-oxo-thiazolidin-3-yl]-benzoic acid methyl ester | — | — |
| 37 | 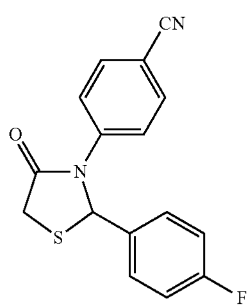 [SMILES: N#Cc1ccc(N2C(=O)CSC2c2ccc(F)cc2)cc1] | 4-(2-(4-Fluorophenyl)-4-oxothiazolidin-3-yl)benzonitrile | 8.2 | 3288 |
| 38 | 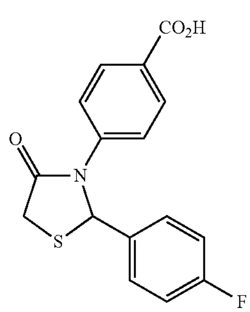 [SMILES: O=C(O)c1ccc(N2C(=O)CSC2c2ccc(F)cc2)cc1] | 4-(2-(4-Fluorophenyl)-4-oxothiazolidin-3-yl)benzoic acid | 5.4 | 5620 |

TABLE 1-continued

Exemplary compounds and their activities

| No. | Structure | Name | FLIPR Ca$^{2+}$ EC$_{50}$ (μM) | AUC |
|---|---|---|---|---|
| 39 | 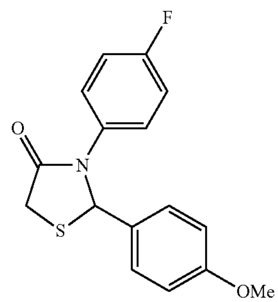 [SMILES: COc1ccc(C2SCC(=O)N2c2ccc(F)cc2)cc1] | 3-(4-Fluorophenyl)-2-(4-methoxyphenyl)thiazolidin-4-one | — | — |
| 40 | 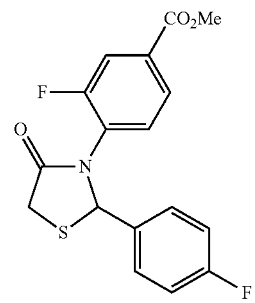 [SMILES: COC(=O)c1ccc(N2C(=O)CSC2c2ccc(F)cc2)c(F)c1] | Methyl 3-fluoro-4-[2-(4-fluorophenyl)-4-oxo-1,3-thiazolidin-3-yl]benzoate | — | — |
| 41 | 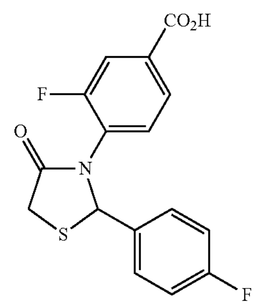 [SMILES: O=C(O)c1ccc(N2C(=O)CSC2c2ccc(F)cc2)c(F)c1] | 3-Fluoro-4-[2-(4-fluorophenyl)-4-oxo-1,3-thiazolidin-3-yl]benzoic acid | — | — |
| 42 | 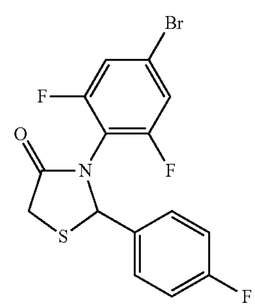 [SMILES: O=C1CSC(c2ccc(F)cc2)N1c1c(F)cc(Br)cc1F] | 3-(4-Bromo-2,6-difluorophenyl)-2-(4-fluorophenyl)-1,3-thiazolidin-4-one | — | — |
| 43 | 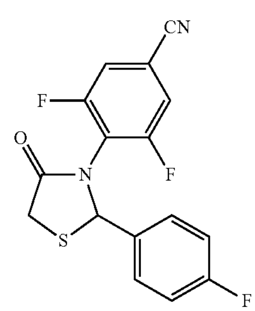 [SMILES: N#Cc1cc(F)c(N2C(=O)CSC2c2ccc(F)cc2)c(F)c1] | 3,5-Difluoro-4-[2-(4-fluorophenyl)-4-oxo-1,3-thiazolidin-3-yl]benzonitrile | 11.2 | 12926 |

TABLE 1-continued

Exemplary compounds and their activities

| No. | Structure | Name | FLIPR Ca$^{2+}$ EC$_{50}$ (μM) | AUC |
|---|---|---|---|---|
| 44 | 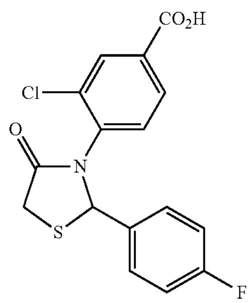 [SMILES: O=C(O)c1ccc(N2C(=O)CSC2c2ccc(F)cc2)c(Cl)c1] | 3-Chloro-4-[2-(4-fluorophenyl)-4-oxo-1,3-thiazolidin-3-yl]benzoic acid | 3.3 | 13250 |
| 46 | 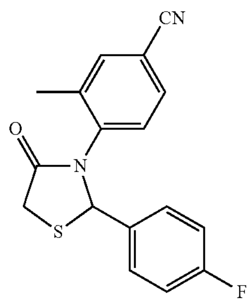 [SMILES: Cc1cc(C#N)ccc1N1C(=O)CSC1c1ccc(F)cc1] | 4-(2-(4-Fluorophenyl)-4-oxothiazolidin-3-yl)-3-methylbenzonitrile | 10 | 15394 |
| 47 | 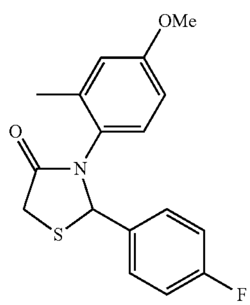 [SMILES: COc1ccc(N2C(=O)CSC2c2ccc(F)cc2)c(C)c1] | 2-(4-Fluorophenyl)-3-(4-methoxy-2-methylphenyl)thiazolidin-4-one | 3.3 | 12268 |
| 48 | 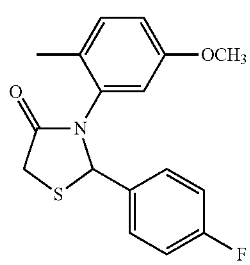 [SMILES: COc1ccc(C)c(N2C(=O)CSC2c2ccc(F)cc2)c1] | 2-(4-Fluorophenyl)-3-(5-methoxy-2-methylphenyl)-1,3-thiazolidin-4-one | — | — |
| 49 | 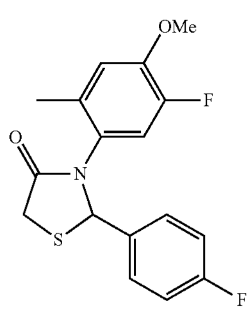 [SMILES: COc1cc(C)c(N2C(=O)CSC2c2ccc(F)cc2)cc1F] | 3-(5-Fluoro-4-methoxy-2-methylphenyl)-2-(4-fluorophenyl)thiazolidin-4-one | 1.8 | 13102 |

TABLE 1-continued

Exemplary compounds and their activities

| No. | Structure | Name | FLIPR Ca²⁺ EC$_{50}$ (μM) | AUC |
|---|---|---|---|---|
| 52 | 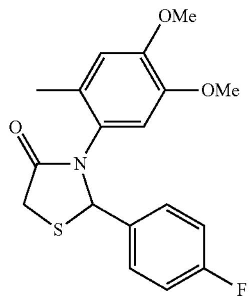 [SMILES: COc1cc(C)c(N2C(=O)CSC2c2ccc(F)cc2)cc1OC] | 3-(4,5-Dimethoxy-2-methylphenyl)-2-(4-fluorophenyl)thiazolidin-4-one | 3.6 | 7780 |
| 53 | 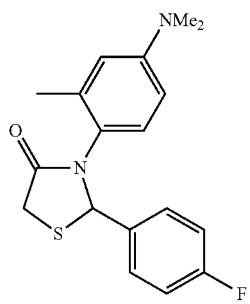 [SMILES: Cc1cc(N(C)C)ccc1N1C(=O)CSC1c1ccc(F)cc1] | 3-(4-(Dimethylamino)-2-methylphenyl)-2-(4-fluorophenyl)thiazolidin-4-one | 0.5 | 6407 |
| 54 | 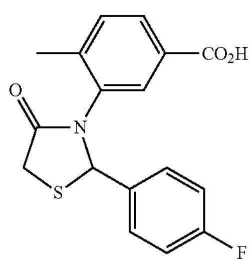 [SMILES: Cc1ccc(C(=O)O)cc1N1C(=O)CSC1c1ccc(F)cc1] | 3-(2-(4-Fluorophenyl)-4-oxothiazolidin-3-yl)-4-methylbenzoic acid | 3.3 | 8906 |
| 55 | 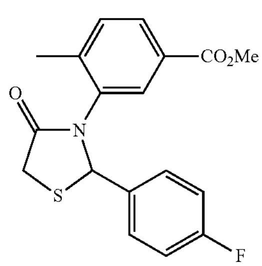 [SMILES: COC(=O)c1ccc(C)c(N2C(=O)CSC2c2ccc(F)cc2)c1] | 3-(2-(4-Fluorophenyl)-4-oxothiazolidin-3-yl)-4-methylbenzoic acid methyl ester | TBD | TBD |
| 56 | 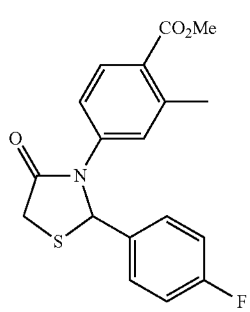 [SMILES: COC(=O)c1ccc(N2C(=O)CSC2c2ccc(F)cc2)cc1C] | 4-[2-(4-fluoro-phenyl)-4-oxo-thiazolidin-3-yl]-2-methyl-benzoic acid methyl acid | — | — |

TABLE 1-continued

Exemplary compounds and their activities

| No. | Structure | Name | FLIPR $Ca^{2+}$ $EC_{50}$ (μM) | AUC |
|---|---|---|---|---|
| 58 | 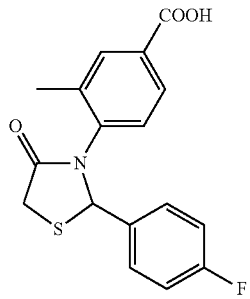 [SMILES: Cc1cc(C(=O)O)ccc1N1C(=O)CSC1c1ccc(F)cc1] | 4-(2-(4-Fluorophenyl)-4-oxothiazolidin-3-yl)-3-methylbenzoic acid | 1.1 | 16361 |
| 59 | 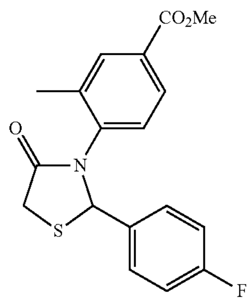 [SMILES: COC(=O)c1ccc(N2C(=O)CSC2c2ccc(F)cc2)c(C)c1] | Methyl 4-(2-(4-fluorophenyl)-4-oxothiazolidin-3-yl)-3-methylbenzoate | 2.6 | 11534 |
| 60 | 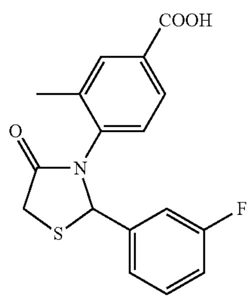 [SMILES: Cc1cc(C(=O)O)ccc1N1C(=O)CSC1c1cccc(F)c1] | 4-(2-(3-Fluorophenyl)-4-oxothiazolidin-3-yl)-3-methylbenzoic acid | 1.1 | 20700 |
| 62 | 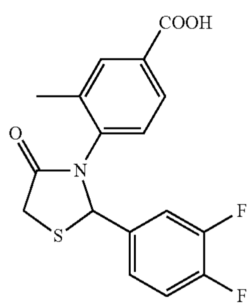 [SMILES: Cc1cc(C(=O)O)ccc1N1C(=O)CSC1c1ccc(F)c(F)c1] | 4-(2-(3,4-Difluorophenyl)-4-oxothiazolidin-3-yl)-3-methylbenzoic acid | 1.6 | 21586 |
| 64 | 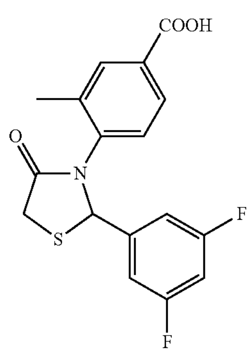 [SMILES: Cc1cc(C(=O)O)ccc1N1C(=O)CSC1c1cc(F)cc(F)c1] | 4-(2-(3,5-Difluorophenyl)-4-oxothiazolidin-3-yl)-3-methylbenzoic acid | 6.0 | 9368 |

TABLE 1-continued

Exemplary compounds and their activities

| No. | Structure | Name | FLIPR Ca²⁺ EC$_{50}$ (μM) | AUC |
|---|---|---|---|---|
| 66 | 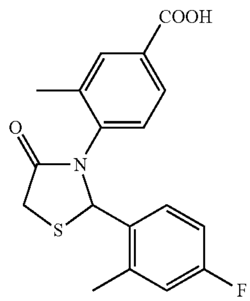 [SMILES: Cc1cc(F)ccc1C1SCC(=O)N1c1ccc(C(=O)O)cc1C] | 4-(2-(4-Fluoro-2-methylphenyl)-4-oxothiazolidin-3-yl)-3-methylbenzoic acid | — | — |
| 68 | 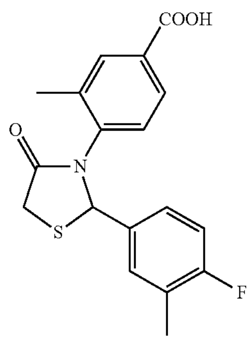 [SMILES: Cc1cc(C2SCC(=O)N2c2ccc(C(=O)O)cc2C)ccc1F] | 4-(2-(4-Fluoro-3-methylphenyl)-4-oxothiazolidin-3-yl)-3-methylbenzoic acid | 6.4 | 7951 |
| 70 | 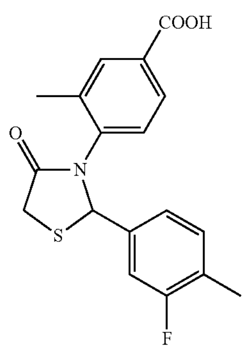 [SMILES: Cc1ccc(C2SCC(=O)N2c2ccc(C(=O)O)cc2C)cc1F] | 4-(2-(3-Fluoro-4-methylphenyl)-4-oxothiazolidin-3-yl)-3-methylbenzoic acid | — | — |
| 72 | 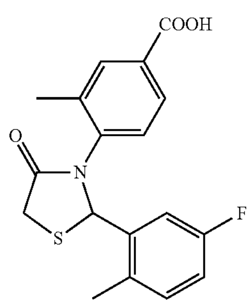 [SMILES: Cc1ccc(F)cc1C1SCC(=O)N1c1ccc(C(=O)O)cc1C] | 4-(2-(5-Fluoro-2-methylphenyl)-4-oxothiazolidin-3-yl)-3-methylbenzoic acid | 0.4 | 3237 |

TABLE 1-continued

Exemplary compounds and their activities

| No. | Structure | Name | FLIPR $Ca^{2+}$ $EC_{50}$ (µM) | AUC |
|---|---|---|---|---|
| 74 | 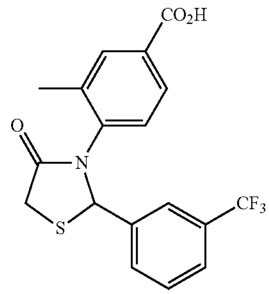 [SMILES: Cc1cc(C(=O)O)ccc1N1C(=O)CSC1c1cccc(C(F)(F)F)c1] | 3-Methyl-4-(4-oxo-2-(3-(trifluoromethyl)phenyl)thiazolidin-3-yl)benzoic acid | 4.9 | 13835 |
| 76 | 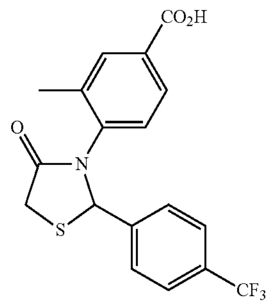 [SMILES: Cc1cc(C(=O)O)ccc1N1C(=O)CSC1c1ccc(C(F)(F)F)cc1] | 3-Methyl-4-(4-oxo-2-(4-(trifluoromethyl)phenyl)thiazolidin-3-yl)benzoic acid | — | — |
| 78 | 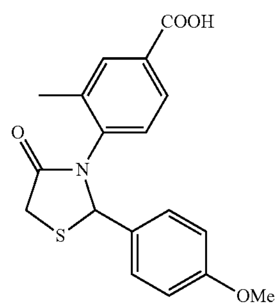 [SMILES: COc1ccc(C2SCC(=O)N2c2ccc(C(=O)O)cc2C)cc1] | 4-[2-(4-methoxy-phenyl)-4-oxo-thiazolidin-3-yl]-3-methyl-benzoic acid | 6.0 | 9368 |
| 80 | 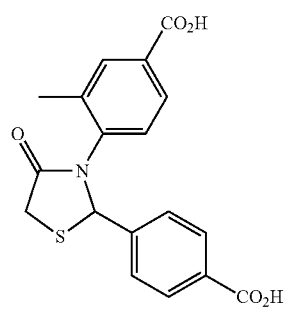 [SMILES: Cc1cc(C(=O)O)ccc1N1C(=O)CSC1c1ccc(C(=O)O)cc1] | 4-[2-(4-carboxy-phenyl)-4-oxo-thiazolidin-3-yl]-3-methyl-benzoic acid | — | — |
| 82 | 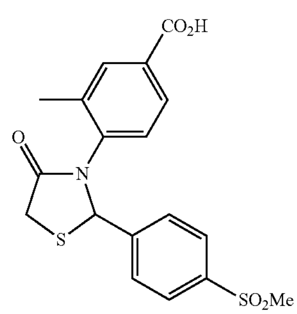 [SMILES: Cc1cc(C(=O)O)ccc1N1C(=O)CSC1c1ccc(S(C)(=O)=O)cc1] | 4-[2-(4-methanesulfonyl-phenyl)-4-oxo-thiazolidin-3-yl]-3-methyl-benzoic acid | — | — |

TABLE 1-continued

Exemplary compounds and their activities

| No. | Structure | Name | FLIPR Ca$^{2+}$ EC$_{50}$ (µM) | AUC |
|---|---|---|---|---|
| 84 | 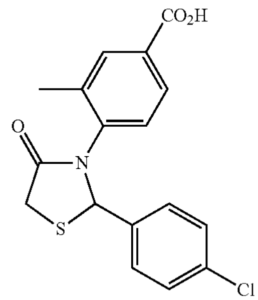 [SMILES: Cc1cc(C(=O)O)ccc1N1C(=O)CSC1c1ccc(Cl)cc1] | 4-[2-(4-chloro-phenyl)-4-oxo-thiazolidin-3-yl]-3-methyl-benzoic acid | 7.2 | 5509 |
| 86 | 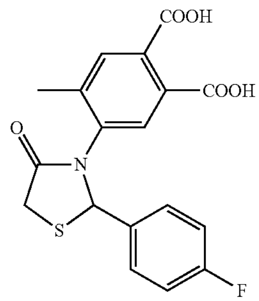 [SMILES: Cc1cc(C(=O)O)c(C(=O)O)cc1N1C(=O)CSC1c1ccc(F)cc1] | 4-(2-(4-Fluorophenyl)-4-oxothiazolidin-3-yl)-5-methylphthalic acid | 6.6 | 9544 |
| 90 | 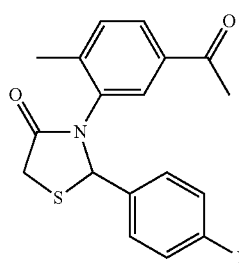 | 3-(5-Acetyl-2-methylphenyl)-2-(4-fluorophenyl)-1,3-thiazolidin-4-one | 8.4 | 9401 |
| 92 | 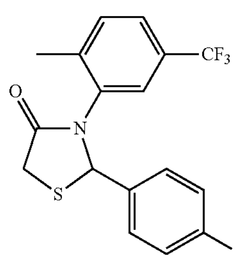 | 2-(4-Fluorophenyl)-3-[2-methyl-5-(trifluoromethyl)phenyl]-1,3-thiazolidin-4-one | 10.0 | 12278 |
| 93 | 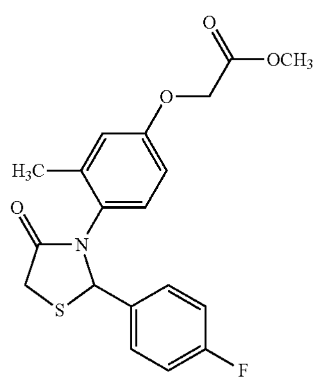 [SMILES: COC(=O)COc1ccc(N2C(=O)CSC2c2ccc(F)cc2)c(C)c1] | Methyl {4-[2-(4-fluorophenyl)-4-oxo-1,3-thiazolidin-3-yl]-3-methylphenoxy}acetate | 6.4 | 11009 |

TABLE 1-continued

Exemplary compounds and their activities

| No. | Structure | Name | FLIPR Ca$^{2+}$ EC$_{50}$ (μM) | AUC |
|---|---|---|---|---|
| 95 | 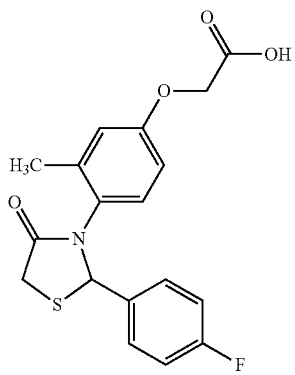 [SMILES: Cc1cc(OCC(=O)O)ccc1N1C(=O)CSC1c1ccc(F)cc1] | {4-[2-(4-Fluorophenyl)-4-oxo-1,3-thiazolidin-3-yl]-3-methylphenoxy}acetic acid | — | — |
| 96 | 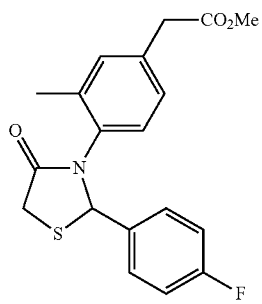 [SMILES: COC(=O)Cc1ccc(N2C(=O)CSC2c2ccc(F)cc2)c(C)c1] | Methyl {4-[2-(4-fluorophenyl)-4-oxo-1,3-thiazolidin-3-yl]-3-methylphenyl}acetate | 10.0 | 9657 |
| 101 | 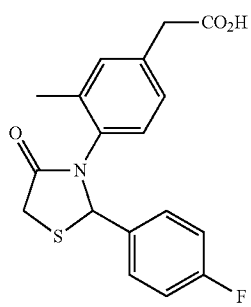 [SMILES: Cc1cc(CC(=O)O)ccc1N1C(=O)CSC1c1ccc(F)cc1] | {4-[2-(4-Fluorophenyl)-4-oxo-1,3-thiazolidin-3-yl]-3-methylphenyl}acetic acid | 7.2 | 10302 |
| 102 | 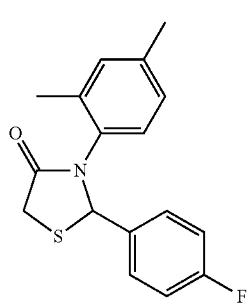 [SMILES: Cc1ccc(N2C(=O)CSC2c2ccc(F)cc2)c(C)c1] | 3-(2,4-Dimethylphenyl)-2-(4-fluorophenyl)thiazolidin-4-one | 5.3 | 9439 |

TABLE 1-continued

Exemplary compounds and their activities

| No. | Structure | Name | FLIPR Ca$^{2+}$ EC$_{50}$ (μM) | AUC |
|---|---|---|---|---|
| 103 | 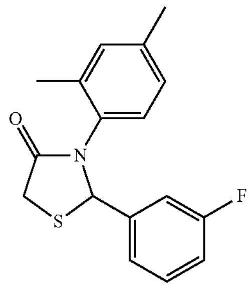 [SMILES: Cc1ccc(N2C(=O)CSC2c2cccc(F)c2)c(C)c1] | 3-(2,4-Dimethylphenyl)-2-(3-fluorophenyl)thiazolidin-4-one | — | — |
| 104 | 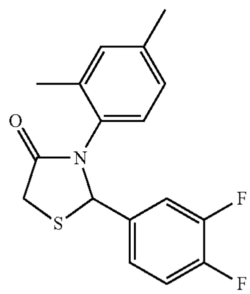 [SMILES: Cc1ccc(N2C(=O)CSC2c2ccc(F)c(F)c2)c(C)c1] | 2-(3,4-Difluorophenyl)-3-(2,4-dimethylphenyl)thiazolidin-4-one | — | — |
| 105 | 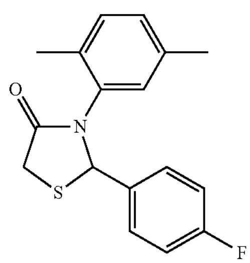 | 3-(2,5-Dimethylphenyl)-2-(4-fluorophenyl)thiazolidin-4-one | TBD | TBD |
| 106 | 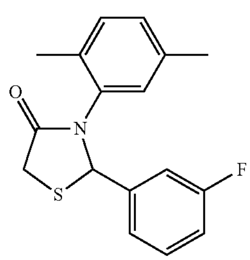 [SMILES: Cc1ccc(C)c(N2C(=O)CSC2c2cccc(F)c2)c1] | 3-(2,5-Dimethylphenyl)-2-(3-fluorophenyl)thiazolidin-4-one | — | — |
| 107 | 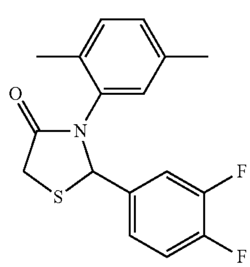 [SMILES: Cc1ccc(C)c(N2C(=O)CSC2c2ccc(F)c(F)c2)c1] | 2-(3,4-Difluorophenyl)-3-(2,5-dimethylphenyl)thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 108 | 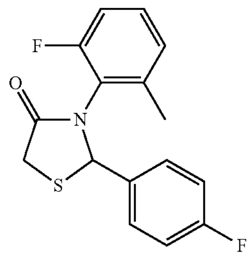 [SMILES: Cc1cccc(F)c1N1C(=O)CSC1c1ccc(F)cc1] | 3-(2-Fluoro-6-methylphenyl)-2-(4-fluorophenyl)thiazolidin-4-one | 3.3 | 15782 |
| 109 | 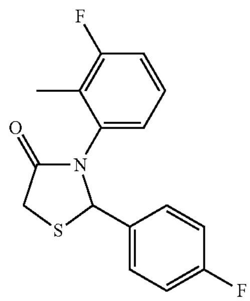 [SMILES: Cc1c(F)cccc1N1C(=O)CSC1c1ccc(F)cc1] | 3-(3-Fluoro-2-methylphenyl)-2-(4-fluorophenyl)thiazolidin-4-one | 2.6 | 9614 |
| 110 | 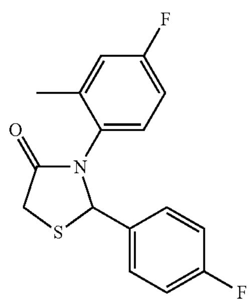 [SMILES: Cc1cc(F)ccc1N1C(=O)CSC1c1ccc(F)cc1] | 3-(4-Fluoro-2-methylphenyl)-2-(4-fluorophenyl)thiazolidin-4-one | 3.8 | 6308 |
| 111 | 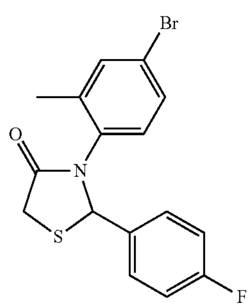 [SMILES: Cc1cc(Br)ccc1N1C(=O)CSC1c1ccc(F)cc1] | 3-(4-Bromo-2-methylphenyl)-2-(4-fluorophenyl)-1,3-thiazolidin-4-one | 11.0 | 20920 |
| 112 | 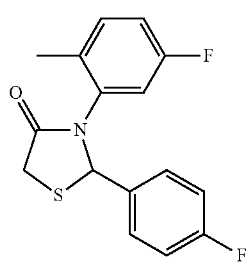 [SMILES: Cc1ccc(F)cc1N1C(=O)CSC1c1ccc(F)cc1] | 3-(5-Fluoro-2-methylphenyl)-2-(4-fluorophenyl)thiazolidin-4-one | 1.1 | 8847 |

TABLE 1-continued

Exemplary compounds and their activities

| No. | Structure | Name | FLIPR Ca²⁺ EC$_{50}$ (µM) | AUC |
|---|---|---|---|---|
| 113 | 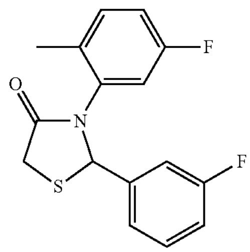 | 3-(5-Fluoro-2-methylphenyl)-2-(3-fluorophenyl)thiazolidin-4-one | 1.3 | 6998 |
| 114 | 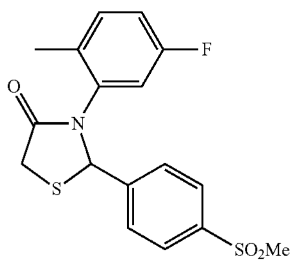 [SMILES: Cc1ccc(F)cc1N1C(=O)CSC1c1ccc(S(C)(=O)=O)cc1] | 3-(5-Fluoro-2-methylphenyl)-2-(4-(methylsulfonyl)phenyl)thiazolidin-4-one | — | — |
| 115 | 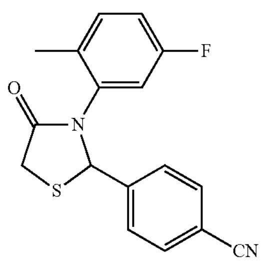 [SMILES: Cc1ccc(F)cc1N1C(=O)CSC1c1ccc(C#N)cc1] | 4-(3-(5-Fluoro-2-methylphenyl)-4-oxothiazolidin-2-yl)benzonitrile | — | — |
| 116 | 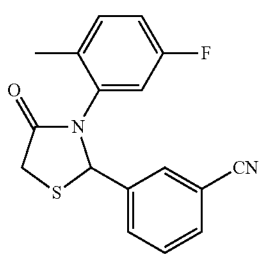 [SMILES: Cc1ccc(F)cc1N1C(=O)CSC1c1cccc(C#N)c1] | 3-[3-(5-fluoro-2-methyl-phenyl)-4-oxo-thiazolidin-2-yl]-benzonitrile | — | — |
| 117 | 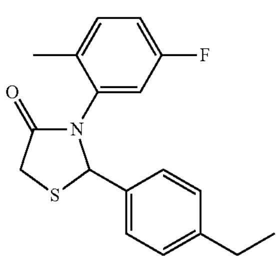 [SMILES: CCc1ccc(C2SCC(=O)N2c2cc(F)ccc2C)cc1] | 2-(4-ethyl-phenyl)-3-(5-fluoro-2-methyl-phenyl)-thiazolidin-4-one | 13.5 | 7880 |

TABLE 1-continued

| | | | FLIPR Ca²⁺ | |
|---|---|---|---|---|
| No. | Structure | Name | $EC_{50}$ (µM) | AUC |
| 118 | | 3-(5-fluoro-2-methyl-phenyl)-2-(4-methylsulfanyl-phenyl)-thiazolidin-4-one | — | — |
| 119 | | 3-(5-Fluoro-2-methylphenyl)-2-(3-fluoro-4-methylphenyl)thiazolidin-4-one | — | — |
| 120 | | 3-(5-Fluoro-2-methylphenyl)-2-(4-fluoro-3-methylphenyl)thiazolidin-4-one | — | — |
| 121 | | 2-(3,4-Difluorophenyl)-3-(5-fluoro-2-methylphenyl)thiazolidin-4-one | — | — |
| 122 | | 2-(3,5-Difluorophenyl)-3-(5-fluoro-2-methylphenyl)thiazolidin-4-one | 3.6 | 7010 |

TABLE 1-continued

Exemplary compounds and their activities

| No. | Structure | Name | FLIPR Ca$^{2+}$ EC$_{50}$ (μM) | AUC |
|---|---|---|---|---|
| 123 | 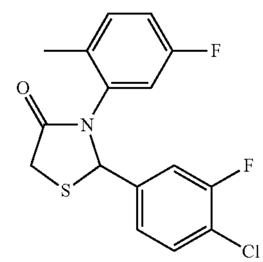 [SMILES: Cc1ccc(F)cc1N1C(=O)CSC1c1ccc(Cl)c(F)c1] | 2-(4-Chloro-3-fluorophenyl)-3-(5-fluoro-2-methylphenyl)thiazolidin-4-one | 0.5 | 4228 |
| 124 | 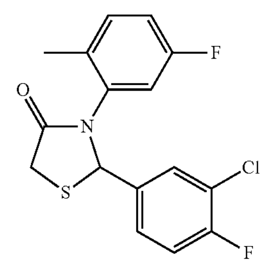 [SMILES: Cc1ccc(F)cc1N1C(=O)CSC1c1ccc(F)c(Cl)c1] | 2-(3-Chloro-4-fluorophenyl)-3-(5-fluoro-2-methylphenyl)thiazolidin-4-one | 3.8 | 8532 |
| 125 | 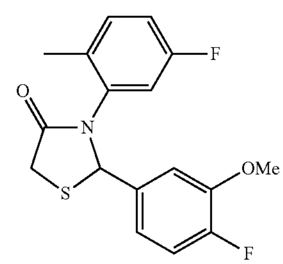 [SMILES: COc1cc(C2SCC(=O)N2c2cc(F)ccc2C)ccc1F] | 2-(4-Fluoro-3-methoxy-phenyl)-3-(5-fluoro-2-methyl-phenyl)-thiazolidin-4-one | — | — |
| 126 | 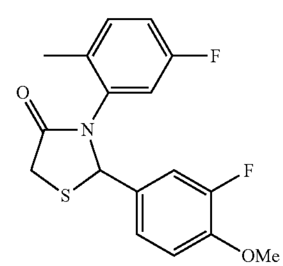 [SMILES: COc1ccc(C2SCC(=O)N2c2cc(F)ccc2C)cc1F] | 2-(3-Fluoro-4-methoxy-phenyl)-3-(5-fluoro-2-methyl-phenyl)-thiazolidin-4-one | — | — |
| 127 | 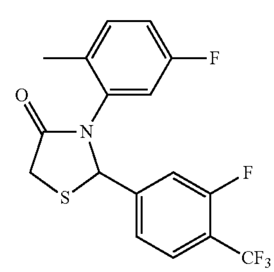 [SMILES: Cc1ccc(F)cc1N1C(=O)CSC1c1ccc(C(F)(F)F)c(F)c1] | 3-(5-Fluoro-2-methyl-phenyl)-2-(3-fluoro-4-trifluoromethyl-phenyl)-thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 128 | 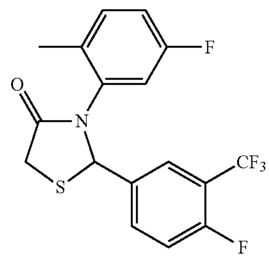 [SMILES: Cc1ccc(F)cc1N1C(=O)CSC1c1ccc(F)c(C(F)(F)F)c1] | 3-(5-Fluoro-2-methyl-phenyl)-2-(4-fluoro-3-trifluoromethyl-phenyl)-thiazolidin-4-one | — | — |
| 129 | 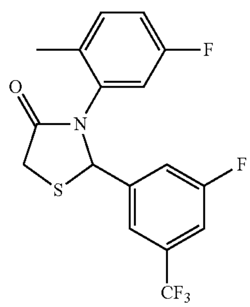 [SMILES: Cc1ccc(F)cc1N1C(=O)CSC1c1cc(F)cc(C(F)(F)F)c1] | 3-(5-Fluoro-2-methyl-phenyl)-2-(3-fluoro-5-trifluoromethyl-phenyl)-thiazolidin-4-one | — | — |
| 130 | 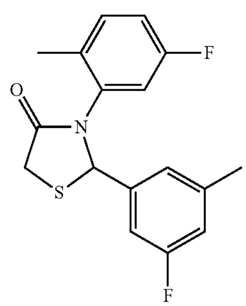 [SMILES: Cc1cc(F)cc(C2SCC(=O)N2c2cc(F)ccc2C)c1] | 3-(5-Fluoro-2-methyl-phenyl)-2-(3-fluoro-5-methyl-phenyl)-thiazolidin-4-one | — | — |
| 131 | 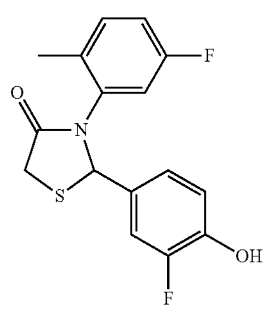 [SMILES: Cc1ccc(F)cc1N1C(=O)CSC1c1ccc(O)c(F)c1] | 2-(3-Fluoro-4-hydroxy-phenyl)-3-(5-fluoro-2-methyl-phenyl)-thiazolidin-4-one | — | — |
| 134 | 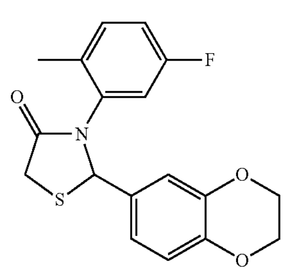 [SMILES: Cc1ccc(F)cc1N1C(=O)CSC1c1ccc2c(c1)OCCO2] | 2-(2,3-Dihydro-benzo[1,4]dioxin-6-yl)-3-(5-fluoro-2-methyl-phenyl)-thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 135 | 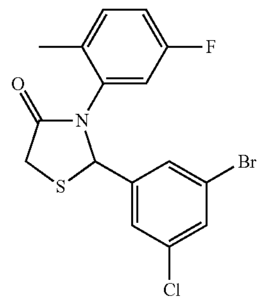 [SMILES: Cc1ccc(F)cc1N1C(=O)CSC1c1cc(Cl)cc(Br)c1] | 2-(3-Bromo-5-chloro-phenyl)-3-(5-fluoro-2-methyl-phenyl)-thiazolidin-4-one | — | — |
| 136 | 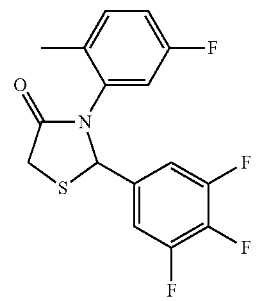 [SMILES: Cc1ccc(F)cc1N1C(=O)CSC1c1cc(F)c(F)c(F)c1] | 3-(5-Fluoro-2-methyl-phenyl)-2-(3,4,5-trifluoro-phenyl)-thiazolidin-4-one | — | — |
| 137 | 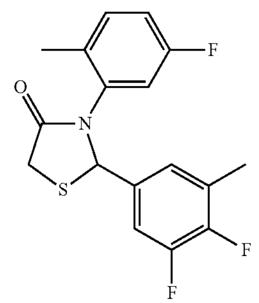 [SMILES: Cc1ccc(F)cc1N1C(=O)CSC1c1cc(C)c(F)c(F)c1] | 2-(3,4-Difluoro-5-methyl-phenyl)-3-(5-fluoro-2-methyl-phenyl)-thiazolidin-4-one | — | — |
| 138 | 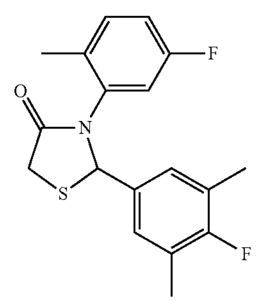 [SMILES: Cc1ccc(F)cc1N1C(=O)CSC1c1cc(C)c(F)c(C)c1] | 2-(4-Fluoro-3,5-dimethyl-phenyl)-3-(5-fluoro-2-methyl-phenyl)-thiazolidin-4-one | — | — |
| 139 | 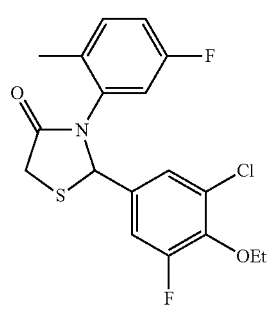 [SMILES: CCOc1c(F)cc(C2SCC(=O)N2c2cc(F)ccc2C)cc1Cl] | 2-(3-Vhloro-4-ethoxy-5-fluoro-phenyl)-3-(5-fluoro-2-methyl-phenyl)-thiazolidin-4-one | — | — |

TABLE 1-continued

Exemplary compounds and their activities

| No. | Structure | Name | FLIPR Ca²⁺ EC$_{50}$ (µM) | AUC |
|---|---|---|---|---|
| 140 | 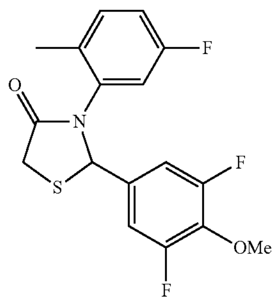 [SMILES: COc1c(F)cc(C2SCC(=O)N2c2cc(F)ccc2C)cc1F] | 2-(3,5-Difluoro-4-methoxy-phenyl)-3-(5-fluoro-2-methyl-phenyl)-thiazolidin-4-one | — | — |
| 141 | 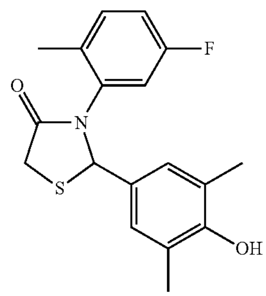 [SMILES: Cc1ccc(F)cc1N1C(=O)CSC1c1cc(C)c(O)c(C)c1] | 3-(5-Fluoro-2-methyl-phenyl)-2-(4-hydroxy-3,5-dimethyl-phenyl)-thiazolidin-4-one | — | — |
| 144 | 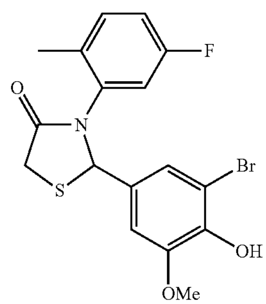 [SMILES: COc1cc(C2SCC(=O)N2c2cc(F)ccc2C)cc(Br)c1O] | 2-(3-Bromo-4-hydroxy-5-methoxy-phenyl)-3-(5-fluoro-2-methyl-phenyl)-thiazolidin-4-one | — | — |
| 147 | 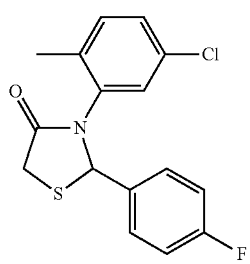 [SMILES: Cc1ccc(Cl)cc1N1C(=O)CSC1c1ccc(F)cc1] | 3-(5-Chloro-2-methylphenyl)-2-(4-fluorophenyl)thiazolidin-4-one | 3.2 | 11516 |
| 148 | 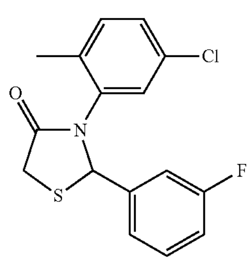 [SMILES: Cc1ccc(Cl)cc1N1C(=O)CSC1c1cccc(F)c1] | 3-(5-Chloro-2-methylphenyl)-2-(3-fluorophenyl)thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 149 | 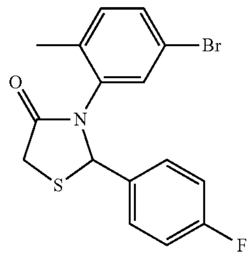 [SMILES: Cc1ccc(Br)cc1N1C(=O)CSC1c1ccc(F)cc1] | 3-(5-Bromo-2-methylphenyl)-2-(4-fluorophenyl)thiazolidin-4-one | 4.4 | 4427 |
| 150 | 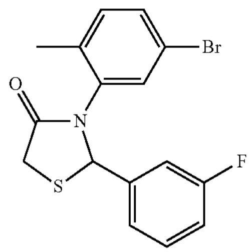 | 3-(5-Bromo-2-methylphenyl)-2-(3-fluorophenyl)thiazolidin-4-one | — | — |
| 151 | 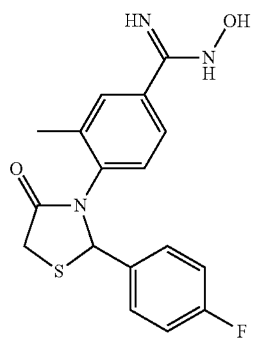 [SMILES: Cc1cc(C(=N)NO)ccc1N1C(=O)CSC1c1ccc(F)cc1] | 4-[2-(4-Fluorophenyl)-4-oxo-1,3-thiazolidin-3-yl]-N-hydroxy-3-methylbenzene carboximidamide | 3.4 | 10591 |
| 152 | 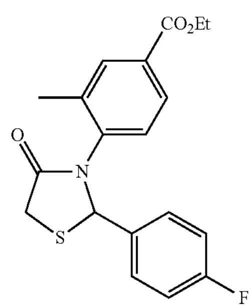 [SMILES: CCOC(=O)c1ccc(N2C(=O)CSC2c2ccc(F)cc2)c(C)c1] | 4-[2-(4-Fluoro-phenyl)-4-oxo-thiazolidin-3-yl]-3-methyl-benzoic acid ethyl ester | 6.3 | 14743 |
| 154 | 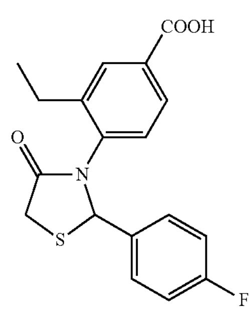 [SMILES: CCc1cc(C(=O)O)ccc1N1C(=O)CSC1c1ccc(F)cc1] | 4-(2-(4-Fluorophenyl)-4-oxothiazolidin-3-yl)-3-methylbenzoic acid | 3.7 | 15447 |

TABLE 1-continued

Exemplary compounds and their activities

| No. | Name | FLIPR Ca²⁺ EC$_{50}$ (μM) | AUC |
|---|---|---|---|
| 156 | 3-Ethyl-4-[2-(4-fluorophenyl)-4-oxo-thiazolidin-3-yl]-benzoic acid ethyl ester | 6.2 | 11998 |
| 157 | 3-Ethenyl-4-[2-(4-fluorophenyl)-4-oxo-1,3-thiazolidin-3-yl]benzoic acid | 10.0 | 5903 |
| 159 | 4-[2-(4-Fluorophenyl)-4-oxo-1,3-thiazolidin-3-yl]-3-methyl-N-(methylsulfonyl)-benzamide | 1.7 | 10396 |
| 160 | 4-[2-(4-Fluorophenyl)-4-oxo-1,3-thiazolidin-3-yl]-3-methyl-N-(propylsulfonyl)-benzamide | 4.3 | 13549 |

TABLE 1-continued

Exemplary compounds and their activities

| No. | Structure | Name | FLIPR Ca$^{2+}$ EC$_{50}$ (μM) | AUC |
|---|---|---|---|---|
| 162 | 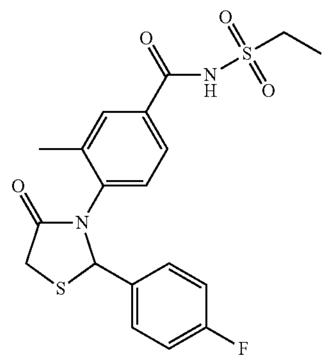 [SMILES: CCS(=O)(=O)NC(=O)c1ccc(N2C(=O)CSC2c2ccc(F)cc2)c(C)c1] | N-(Ethylsulfonyl)-4-[2-(4-fluorophenyl)-4-oxo-1,3-thiazolidin-3-yl]-3-methylbenzamide | 9.1 | 13767 |
| 163 | 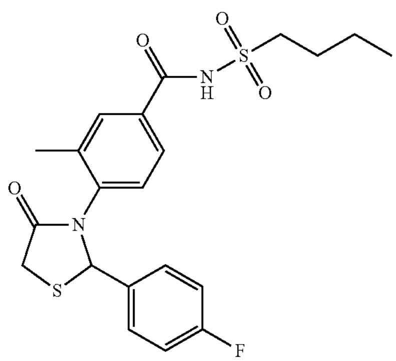 [SMILES: CCCCS(=O)(=O)NC(=O)c1ccc(N2C(=O)CSC2c2ccc(F)cc2)c(C)c1] | N-(Butylsulfonyl)-4-[2-(4-fluorophenyl)-4-oxo-1,3-thiazolidin-3-yl]-3-methylbenzamide | 1.2 | 11389 |
| 165 | 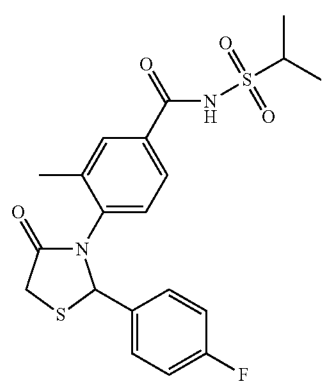 [SMILES: Cc1cc(C(=O)NS(=O)(=O)C(C)C)ccc1N1C(=O)CSC1c1ccc(F)cc1] | 4-[2-(4-Fluorophenyl)-4-oxo-1,3-thiazolidin-3-yl]-3-methyl-N-(2-propanylsulfonyl)-benzamide | 22.6 | 11927 |
| 167 | 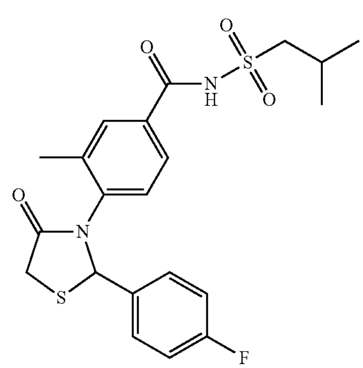 [SMILES: Cc1cc(C(=O)NS(=O)(=O)CC(C)C)ccc1N1C(=O)CSC1c1ccc(F)cc1] | 4-[2-(4-Fluorophenyl)-4-oxo-1,3-thiazolidin-3-yl]-3-methyl-N-[(2-methylpropyl)sulfonyl]benzamide | 3.4 | 9905 |

TABLE 1-continued

Exemplary compounds and their activities

| No. | Structure | Name | FLIPR Ca$^{2+}$ EC$_{50}$ (µM) | AUC |
|---|---|---|---|---|
| 169 | 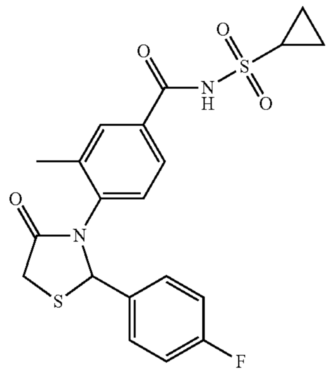 [SMILES: Cc1cc(C(=O)NS(=O)(=O)C2CC2)ccc1N1C(=O)CSC1c1ccc(F)cc1] | N-(Cyclopropylsulfonyl)-4-[2-(4-fluorophenyl)-4-oxo-1,3-thiazolidin-3-yl]-3-methylbenzamide | 3.0 | 13189 |
| 171 | 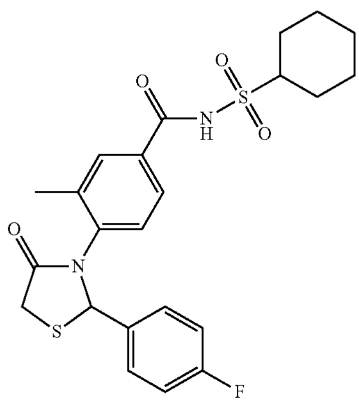 [SMILES: Cc1cc(C(=O)NS(=O)(=O)C2CCCCC2)ccc1N1C(=O)CSC1c1ccc(F)cc1] | N-(Cyclohexylsulfonyl)-4-[2-(4-fluorophenyl)-4-oxo-1,3-thiazolidin-3-yl]-3-methylbenzamide | 3.7 | 10272 |
| 173 | 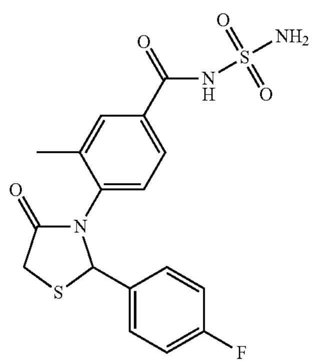 [SMILES: Cc1cc(C(=O)NS(N)(=O)=O)ccc1N1C(=O)CSC1c1ccc(F)cc1] | 4-[2-(4-Fluorophenyl)-4-oxo-1,3-thiazolidin-3-yl]-3-methyl-N-sulfamoylbenzamide | 5.3 | 14841 |
| 174 | 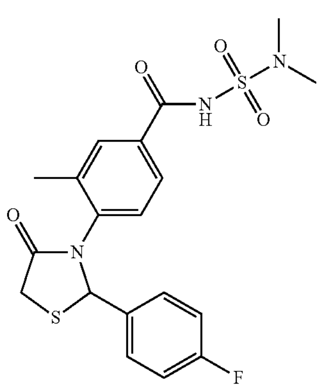 | N-(Dimethylsulfamoyl)-4-[2-(4-fluorophenyl)-4-oxo-1,3-thiazolidin-3-yl]-3-methylbenzamide | 3.8 | 12074 |

TABLE 1-continued

Exemplary compounds and their activities

| No. | Structure | Name | FLIPR Ca$^{2+}$ EC$_{50}$ (μM) | AUC |
|---|---|---|---|---|
| 175 | 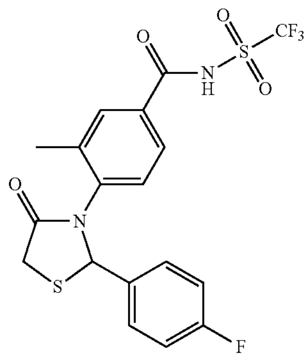 [SMILES: Cc1cc(C(=O)NS(=O)(=O)C(F)(F)F)ccc1N1C(=O)CSC1c1ccc(F)cc1] | 4-[2-(4-Fluorophenyl)-4-oxo-1,3-thiazolidin-3-yl]-3-methyl-N-[(trifluoromethyl)sulfonyl]benzamide | 1.6 | 13866 |
| 176 | 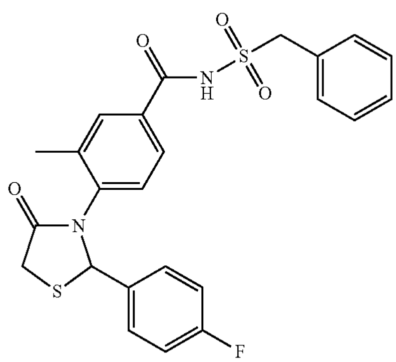 [SMILES: Cc1cc(C(=O)NS(=O)(=O)Cc2ccccc2)ccc1N1C(=O)CSC1c1ccc(F)cc1] | N-(Benzylsulfonyl)-4-[2-(4-fluorophenyl)-4-oxo-1,3-thiazolidin-3-yl]-3-methylbenzamide | 2.0 | 10601 |
| 177 | 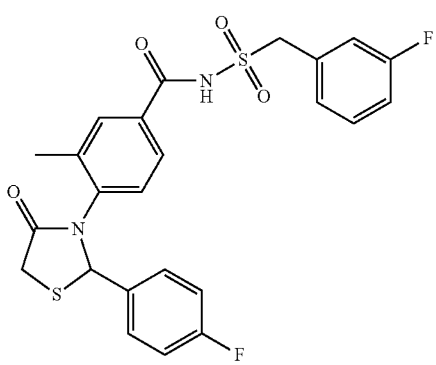 [SMILES: Cc1cc(C(=O)NS(=O)(=O)Cc2cccc(F)c2)ccc1N1C(=O)CSC1c1ccc(F)cc1] | N-[(3-Fluorobenzyl)sulfonyl]-4-[2-(4-fluorophenyl)-4-oxo-1,3-thiazolidin-3-yl]-3-methylbenzamide | 2.2 | 16276 |
| 179 | 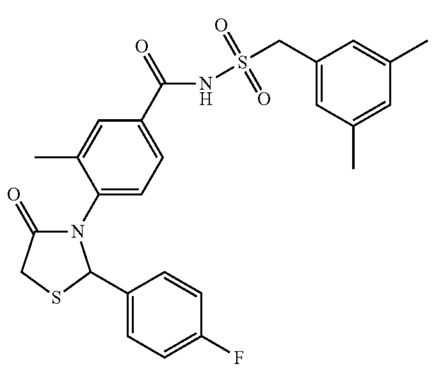 [SMILES: Cc1cc(C)cc(CS(=O)(=O)NC(=O)c2ccc(N3C(=O)CSC3c3ccc(F)cc3)c(C)c2)c1] | N-[(3,5-Dimethylbenzyl)sulfonyl]-4-[2-(4-fluorophenyl)-4-oxo-1,3-thiazolidin-3-yl]-3-methylbenzamide | 1.1 | 14442 |

TABLE 1-continued
Exemplary compounds and their activities
| No. | Structure | Name | FLIPR Ca$^{2+}$ EC$_{50}$ (μM) | AUC |
|---|---|---|---|---|
| 183 | 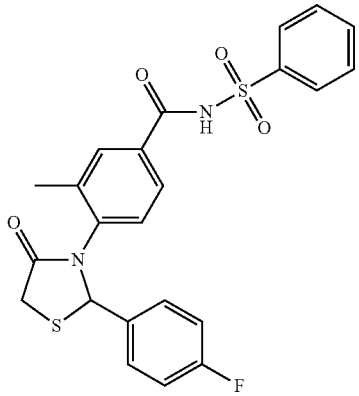 [SMILES: Cc1cc(C(=O)NS(=O)(=O)c2ccccc2)ccc1N1C(=O)CSC1c1ccc(F)cc1] | 4-[2-(4-Fluorophenyl)-4-oxo-1,3-thiazolidin-3-yl]-3-methyl-N-(phenylsulfonyl)-benzamide | 1.9 | 12230 |
| 185 | 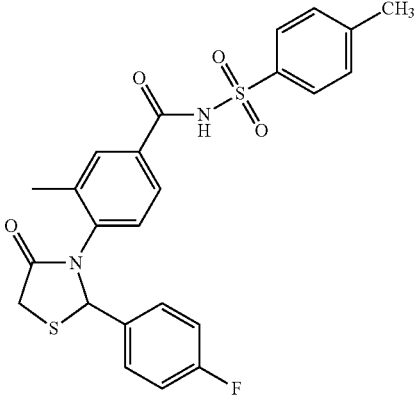 [SMILES: Cc1ccc(S(=O)(=O)NC(=O)c2ccc(N3C(=O)CSC3c3ccc(F)cc3)c(C)c2)cc1] | 4-[2-(4-Fluorophenyl)-4-oxo-1,3-thiazolidin-3-yl]-3-methyl-N-[(4-methylphenyl)sulfonyl]benzamide | 0.6 | 18048 |
| 186 | 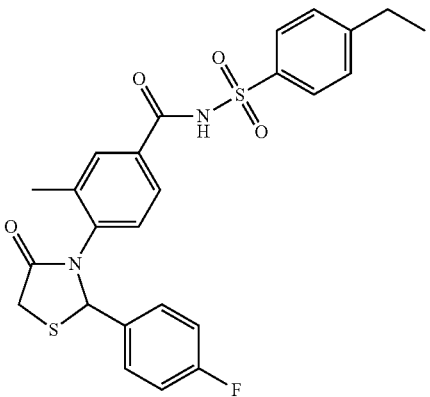 [SMILES: CCc1ccc(S(=O)(=O)NC(=O)c2ccc(N3C(=O)CSC3c3ccc(F)cc3)c(C)c2)cc1] | N-[(4-Ethylphenyl)sulfonyl]-4-[2-(4-fluorophenyl)-4-oxo-1,3-thiazolidin-3-yl]-3-methylbenzamide | 0.6 | 18048 |

TABLE 1-continued

Exemplary compounds and their activities

| No. | Structure | Name | FLIPR Ca$^{2+}$ EC$_{50}$ (μM) | AUC |
|---|---|---|---|---|
| 187 | 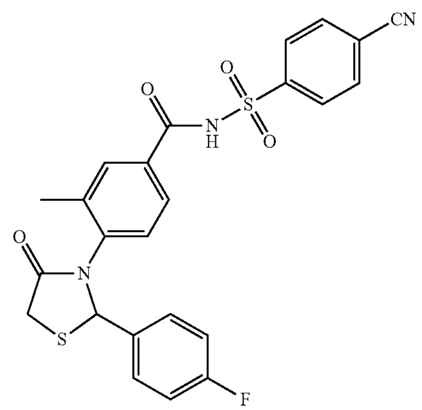 [SMILES: Cc1cc(C(=O)NS(=O)(=O)c2ccc(C#N)cc2)ccc1N1C(=O)CSC1c1ccc(F)cc1] | N-[(4-Cyanophenyl)sulfonyl]-4-[2-(4-fluorophenyl)-4-oxo-1,3-thiazolidin-3-yl]-3-methylbenzamide | 3.3 | 12927 |
| 188 | 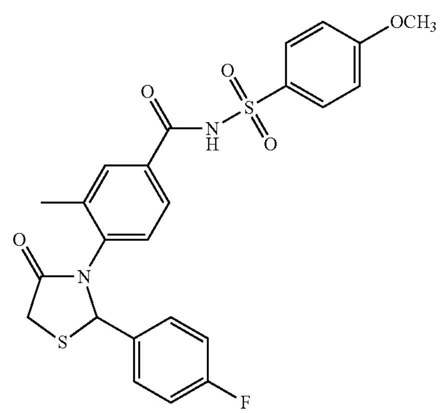 [SMILES: COc1ccc(S(=O)(=O)NC(=O)c2ccc(N3C(=O)CSC3c3ccc(F)cc3)c(C)c2)cc1] | 4-[2-(4-Fluorophenyl)-4-oxo-1,3-thiazolidin-3-yl]-N-[(4-methoxyphenyl)sulfonyl]-3-methylbenzamide | 0.7 | 21983 |
| 189 | 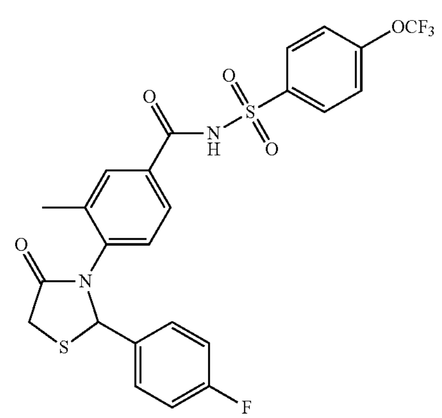 [SMILES: Cc1cc(C(=O)NS(=O)(=O)c2ccc(OC(F)(F)F)cc2)ccc1N1C(=O)CSC1c1ccc(F)cc1] | 4-[2-(4-Fluorophenyl)-4-oxo-1,3-thiazolidin-3-yl]-3-methyl-N-{[4-(trifluoromethoxy)phenyl]sulfonyl}benzamide | 1.1 | 9544 |

TABLE 1-continued

Exemplary compounds and their activities

| No. | Structure | Name | FLIPR Ca$^{2+}$ EC$_{50}$ (μM) | AUC |
|---|---|---|---|---|
| 190 | 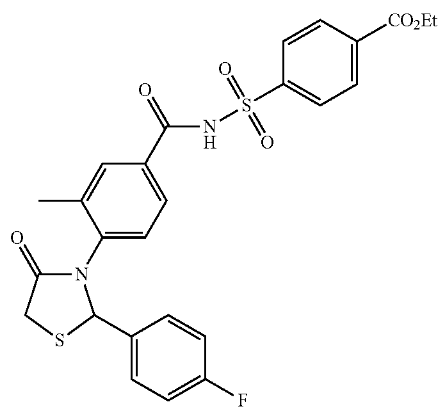 [SMILES: CCOC(=O)c1ccc(S(=O)(=O)NC(=O)c2ccc(N3C(=O)CSC3c3ccc(F)cc3)c(C)c2)cc1] | Ethyl 4-({4-[2-(4-fluorophenyl)-4-oxo-1,3-thiazolidin-3-yl]-3-methylbenzoyl}sulfamoyl)benzoate | 2.4 | 16512 |
| 192 | 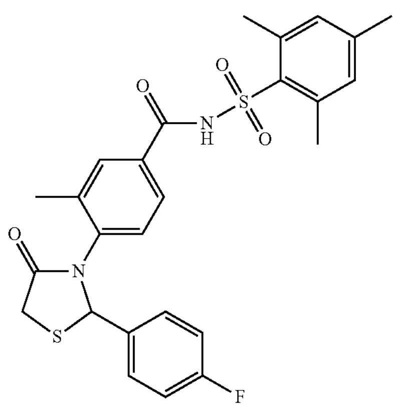 [SMILES: Cc1cc(C)c(S(=O)(=O)NC(=O)c2ccc(N3C(=O)CSC3c3ccc(F)cc3)c(C)c2)c(C)c1] | 4-[2-(4-Fluorophenyl)-4-oxo-1,3-thiazolidin-3-yl]-3-methyl-N-[(2,4,6-trimethylphenyl)sulfonyl]benzamide | 1.4 | 11866 |
| 194 | 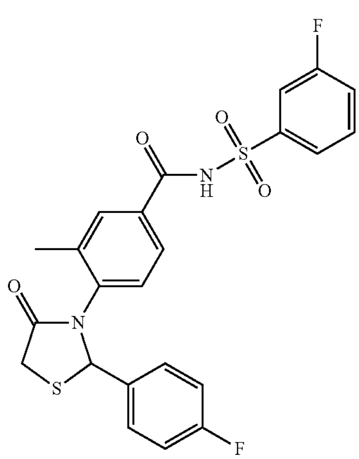 [SMILES: Cc1cc(C(=O)NS(=O)(=O)c2cccc(F)c2)ccc1N1C(=O)CSC1c1ccc(F)cc1] | 4-[2-(4-Fluorophenyl)-4-oxo-1,3-thiazolidin-3-yl]-N-[(3-fluorophenyl)sulfonyl]-3-methylbenzamide | 0.2 | 19019 |

TABLE 1-continued

Exemplary compounds and their activities

| No. | Structure | Name | FLIPR Ca²⁺ EC$_{50}$ (μM) | AUC |
|---|---|---|---|---|
| 196 | 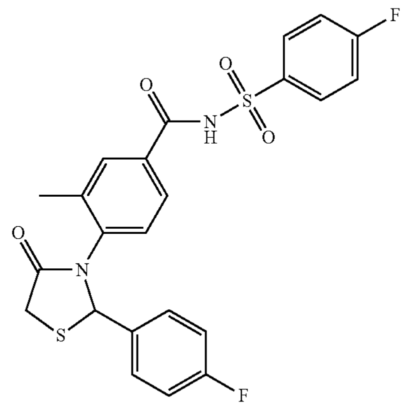 [SMILES: Cc1cc(C(=O)NS(=O)(=O)c2ccc(F)cc2)ccc1N1C(=O)CSC1c1ccc(F)cc1] | 4-[2-(4-Fluorophenyl)-4-oxo-1,3-thiazolidin-3-yl]-N-[(4-fluorophenyl)sulfonyl]-3-methylbenzamide | 1.1 | 15620 |
| 198 | 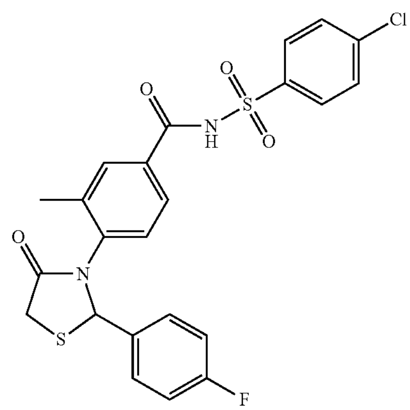 [SMILES: Cc1cc(C(=O)NS(=O)(=O)c2ccc(Cl)cc2)ccc1N1C(=O)CSC1c1ccc(F)cc1] | N-[(4-Chlorophenyl)sulfonyl]-4-[2-(4-fluorophenyl)-4-oxo-1,3-thiazolidin-3-yl]-3-methylbenzamide | 0.5 | 13313 |
| 200 | 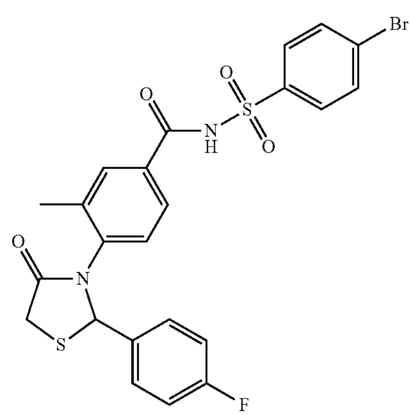 [SMILES: Cc1cc(C(=O)NS(=O)(=O)c2ccc(Br)cc2)ccc1N1C(=O)CSC1c1ccc(F)cc1] | N-[(4-Bromophenyl)sulfonyl]-4-[2-(4-fluorophenyl)-4-oxo-1,3-thiazolidin-3-yl]-3-methylbenzamide | 0.2 | 12340 |

TABLE 1-continued

Exemplary compounds and their activities

| No. | Structure | Name | FLIPR Ca$^{2+}$ EC$_{50}$ (μM) | AUC |
|---|---|---|---|---|
| 202 | 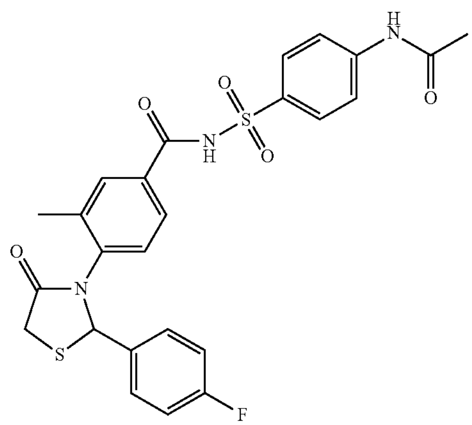 [SMILES: CC(=O)Nc1ccc(S(=O)(=O)NC(=O)c2ccc(N3C(=O)CSC3c3ccc(F)cc3)c(C)c2)cc1] | N-{[4-(Acetylamino)phenyl]sulfonyl}-4-[2-(4-fluorophenyl)-4-oxo-1,3-thiazolidin-3-yl]-3-methylbenzamide | 0.6 | 17087 |
| 204 | 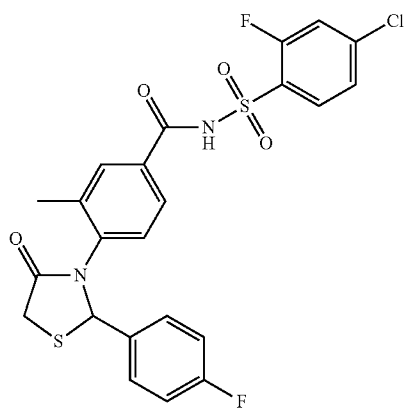 [SMILES: Cc1cc(C(=O)NS(=O)(=O)c2ccc(Cl)cc2F)ccc1N1C(=O)CSC1c1ccc(F)cc1] | N-[(4-Chloro-2-fluorophenyl)sulfonyl]-4-[2-(4-fluorophenyl)-4-oxo-1,3-thiazolidin-3-yl]-3-methylbenzamide | 0.1 | 15287 |
| 206 | 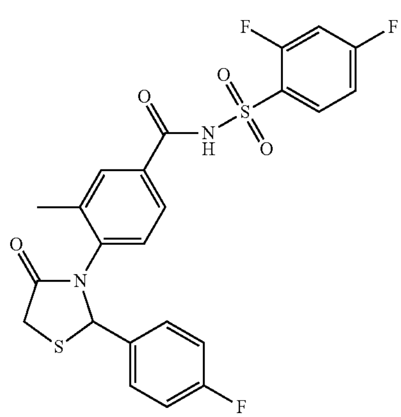 [SMILES: Cc1cc(C(=O)NS(=O)(=O)c2ccc(F)cc2F)ccc1N1C(=O)CSC1c1ccc(F)cc1] | N-[(2,4-Difluorophenyl)sulfonyl]-4-[2-(4-fluorophenyl)-4-oxo-1,3-thiazolidin-3-yl]-3-methylbenzamide | 0.2 | 9637 |

TABLE 1-continued

Exemplary compounds and their activities

| No. | Structure | Name | FLIPR Ca²⁺ EC$_{50}$ (μM) | AUC |
|---|---|---|---|---|
| 208 | 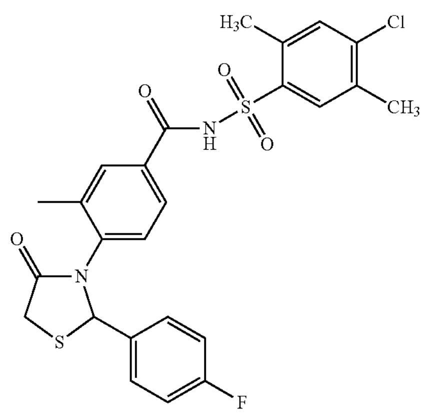 [SMILES: Cc1cc(S(=O)(=O)NC(=O)c2ccc(N3C(=O)CSC3c3ccc(F)cc3)c(C)c2)c(C)cc1Cl] | N-[(4-Chloro-2,5-dimethylphenyl)sulfonyl]-4-[2-(4-fluorophenyl)-4-oxo-1,3-thiazolidin-3-yl]-3-methylbenzamide | 0.4 | 13512 |
| 210 | 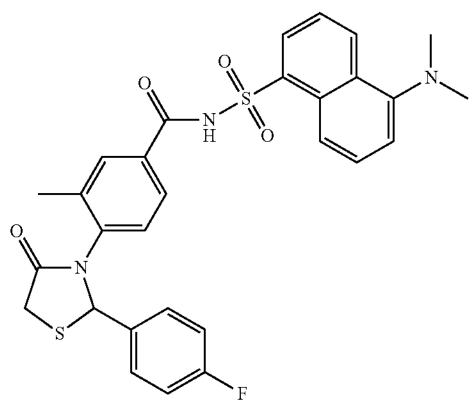 [SMILES: Cc1cc(C(=O)NS(=O)(=O)c2cccc3c(N(C)C)cccc23)ccc1N1C(=O)CSC1c1ccc(F)cc1] | N-{[5-(Dimethylamino)-1-naphthalenyl]sulfonyl}-4-[2-(4-fluorophenyl)-4-oxo-1,3-thiazolidin-3-yl]-3-methylbenzamide | 0.7 | 9425 |
| 211 | 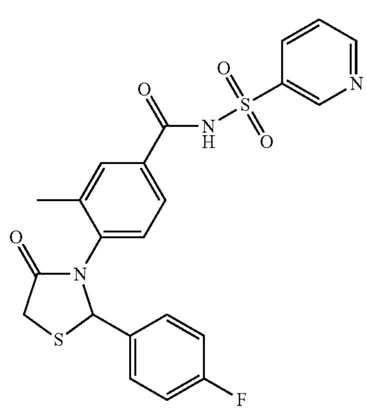 [SMILES: Cc1cc(C(=O)NS(=O)(=O)c2cccnc2)ccc1N1C(=O)CSC1c1ccc(F)cc1] | 4-[2-(4-Fluorophenyl)-4-oxo-1,3-thiazolidin-3-yl]-3-methyl-N-(3-pyridinylsulfonyl)-benzamide | 0.3 | 8779 |

TABLE 1-continued

Exemplary compounds and their activities

| No. | Structure | Name | FLIPR Ca$^{2+}$ EC$_{50}$ (μM) | AUC |
|---|---|---|---|---|
| 213 | 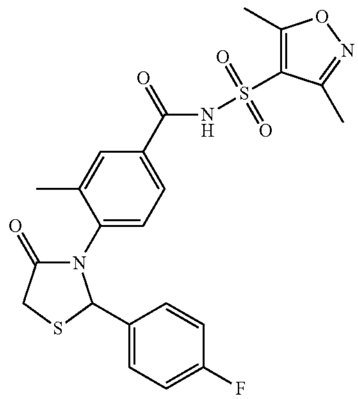 [SMILES: Cc1cc(C(=O)NS(=O)(=O)c2c(C)noc2C)ccc1N1C(=O)CSC1c1ccc(F)cc1] | N-[(3,5-Dimethyl-1,2-oxazol-4-yl)sulfonyl]-4-[2-(4-fluorophenyl)-4-oxo-1,3-thiazolidin-3-yl]-3-methylbenzamide | 0.9 | 9005 |
| 215 | 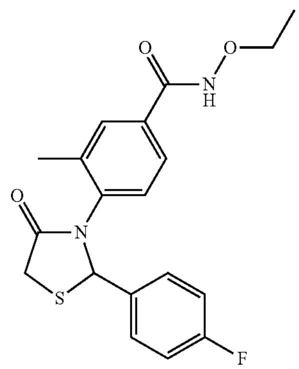 | N-Ethoxy-4-[2-(4-fluorophenyl)-4-oxo-1,3-thiazolidin-3-yl]-3-methylbenzamide | 4.1 | 10945 |
| 216 | 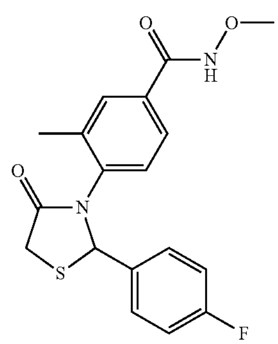 | 4-[2-(4-Fluorophenyl)-4-oxo-1,3-thiazolidin-3-yl]-N-methoxy-3-methylbenzamide | 4.2 | 14236 |
| 217 | 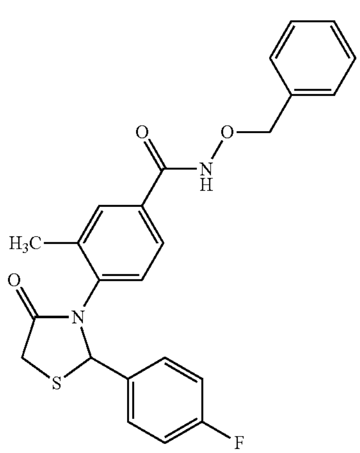 [SMILES: Cc1cc(C(=O)NOCc2ccccc2)ccc1N1C(=O)CSC1c1ccc(F)cc1] | N-(Benzyloxy)-4-[2-(4-fluorophenyl)-4-oxo-1,3-thiazolidin-3-yl]-3-methylbenzamide | 4.1 | 9543 |

TABLE 1-continued

Exemplary compounds and their activities

| No. | Structure | Name | FLIPR Ca²⁺ EC$_{50}$ (μM) | AUC |
|---|---|---|---|---|
| 218 | 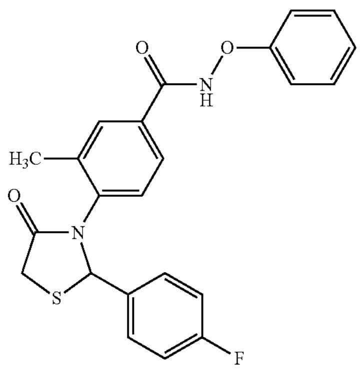 [SMILES: Cc1cc(C(=O)NOc2ccccc2)ccc1N1C(=O)CSC1c1ccc(F)cc1] | 4-[2-(4-Fluorophenyl)-4-oxo-1,3-thiazolidin-3-yl]-3-methyl-N-phenoxybenzamide | 3.6 | 12768 |
| 219 | 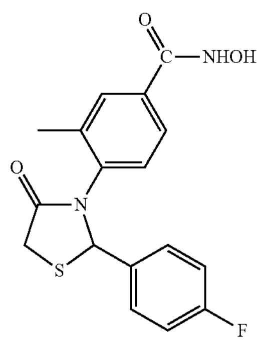 | 4-[2-(4-Fluorophenyl)-4-oxo-1,3-thiazolidin-3-yl]-N-hydroxy-3-methylbenzamide | 6.4 | 14222 |
| 220 | 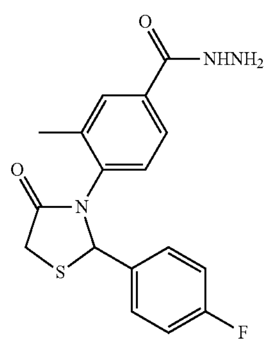 [SMILES: Cc1cc(C(=O)NN)ccc1N1C(=O)CSC1c1ccc(F)cc1] | 4-[2-(4-Fluorophenyl)-4-oxo-1,3-thiazolidin-3-yl]-3-methylbenzohydrazide | 4.9 | 13871 |
| 221 | 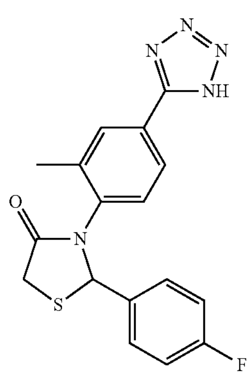 [SMILES: Cc1cc(-c2nnn[nH]2)ccc1N1C(=O)CSC1c1ccc(F)cc1] | 2-(4-Fluorophenyl)-3-[2-methyl-4-(1H-tetrazol-5-yl)phenyl]-1,3-thiazolidin-4-one | 0.2 | 8284 |

TABLE 1-continued
Exemplary compounds and their activities
| No. | Structure | Name | FLIPR Ca²⁺ EC$_{50}$ (μM) | AUC |
|---|---|---|---|---|
| 222 | 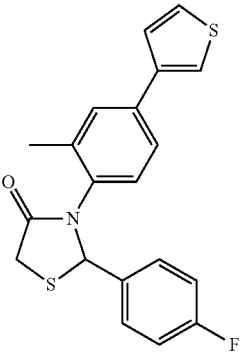 [SMILES: Cc1cc(-c2ccsc2)ccc1N1C(=O)CSC1c1ccc(F)cc1] | 2-(4-Fluorophenyl)-3-[2-methyl-4-(3-thiophenyl)phenyl]-1,3-thiazolidin-4-one | — | — |
| 223 | 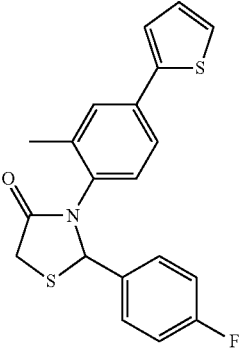 [SMILES: Cc1cc(-c2cccs2)ccc1N1C(=O)CSC1c1ccc(F)cc1] | 2-(4-Fluorophenyl)-3-[2-methyl-4-(2-thiophenyl)phenyl]-1,3-thiazolidin-4-one | — | — |
| 224 | 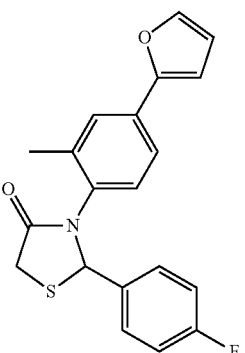 | 2-(4-Fluorophenyl)-3-[4-(2-furanyl)-2-methylphenyl]-1,3-thiazolidin-4-one | 11.7 | 7384 |
| 225 | 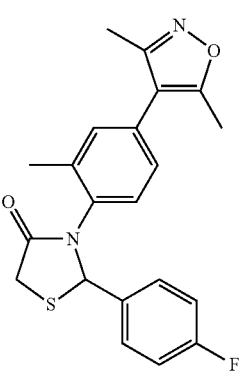 [SMILES: Cc1cc(-c2c(C)noc2C)ccc1N1C(=O)CSC1c1ccc(F)cc1] | 3-[4-(3,5-Dimethyl-1,2-oxazol-4-yl)-2-methylphenyl]-2-(4-fluorophenyl)-1,3-thiazolidin-4-one | — | — |

TABLE 1-continued

Exemplary compounds and their activities

| No. | Structure | Name | FLIPR Ca²⁺ EC$_{50}$ (μM) | AUC |
|---|---|---|---|---|
| 226 | 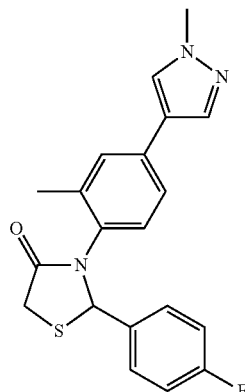 | 2-(4-Fluorophenyl)-3-[2-methyl-4-(1-methyl-1H-pyrazol-4-yl)phenyl]-1,3-thiazolidin-4-one | — | — |
| 227 | 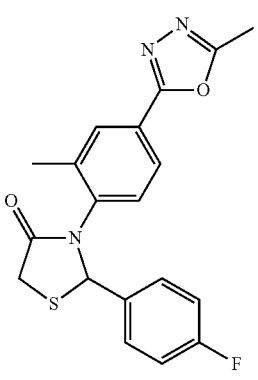 [SMILES: Cc1nnc(-c2ccc(N3C(=O)CSC3c3ccc(F)cc3)c(C)c2)o1] | 2-(4-Fluorophenyl)-3-[2-methyl-4-(5-methyl-1,3,4-oxadiazol-2-yl)phenyl]-1,3-thiazolidin-4-one | 5.5 | 15410 |
| 228 | 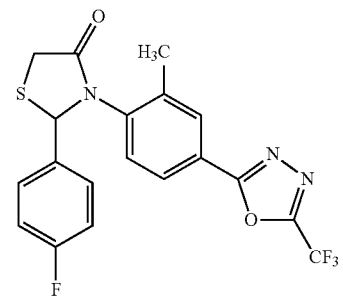 [SMILES: Cc1cc(-c2nnc(C(F)(F)F)o2)ccc1N1C(=O)CSC1c1ccc(F)cc1] | 2-(4-Fluorophenyl)-3-{2-methyl-4-[5-(trifluoromethyl)-1,3,4-oxadiazol-2-yl]phenyl}-1,3-thiazolidin-4-one | 8.6 | 7035 |
| 229 | 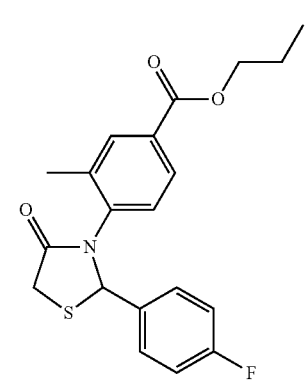 [SMILES: CCCOC(=O)c1ccc(N2C(=O)CSC2c2ccc(F)cc2)c(C)c1] | 4-[2-(4-Fluoro-phenyl)-4-oxo-thiazolidin-3-yl]-3-methyl-benzoic acid propyl ester | 9.7 | 13237 |

TABLE 1-continued

Exemplary compounds and their activities

| No. | Structure | Name | FLIPR Ca$^{2+}$ EC$_{50}$ (μM) | AUC |
|---|---|---|---|---|
| 230 | 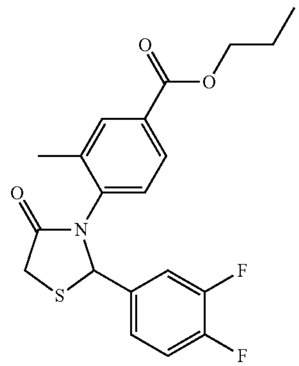 [SMILES: CCCOC(=O)c1ccc(N2C(=O)CSC2c2ccc(F)c(F)c2)c(C)c1] | 4-[2-(3,4-Difluoro-phenyl)-4-oxo-thiazolidin-3-yl]-3-methyl-benzoic acid propyl ester | — | — |
| 231 | 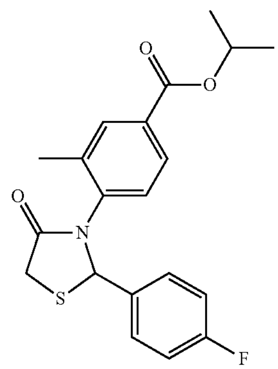 [SMILES: Cc1cc(C(=O)OC(C)C)ccc1N1C(=O)CSC1c1ccc(F)cc1] | 4-[2-(4-Fluoro-phenyl)-4-oxo-thiazolidin-3-yl]-3-methyl-benzoic acid isopropyl ester | 2.7 | 15328 |
| 234 | 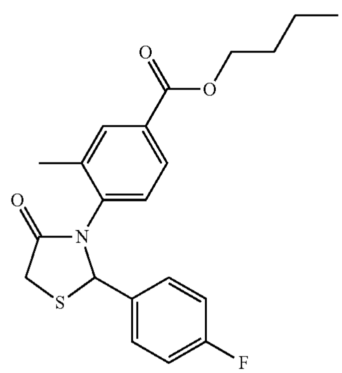 [SMILES: CCCCOC(=O)c1ccc(N2C(=O)CSC2c2ccc(F)cc2)c(C)c1] | 4-[2-(4-Fluoro-phenyl)-4-oxo-thiazolidin-3-yl]-3-methyl-benzoic acid butyl ester | 9.0 | 10062 |
| 235 | 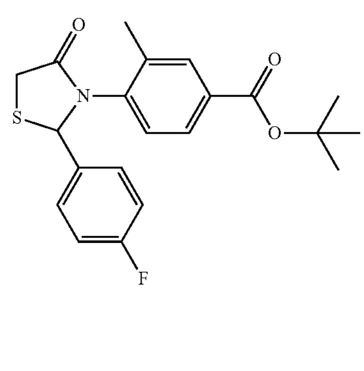 [SMILES: Cc1cc(C(=O)OC(C)(C)C)ccc1N1C(=O)CSC1c1ccc(F)cc1] | 2-Methyl-2-propanyl 4-[2-(4-fluorophenyl)-4-oxo-1,3-thiazolidin-3-yl]-3-methylbenzoate | 6.8 | 15203 |

TABLE 1-continued

Exemplary compounds and their activities

| No. | Name | FLIPR Ca$^{2+}$ EC$_{50}$ (μM) | AUC |
|---|---|---|---|
| 236 | 1-Methylcyclopropyl 4-[2-(4-fluorophenyl)-4-oxo-1,3-thiazolidin-3-yl]-3-methylbenzoate | 4.7 | 13348 |
| 237 | 3,3-Dimethylbutyl 4-[2-(4-fluorophenyl)-4-oxo-1,3-thiazolidin-3-yl]-3-methylbenzoate | — | — |
| 238 | 2-Cyclopropylethyl 4-[2-(4-fluorophenyl)-4-oxo-1,3-thiazolidin-3-yl]-3-methylbenzoate | 12.3 | 15409 |
| 239 | Cyclopentylmethyl 4-[2-(4-fluorophenyl)-4-oxo-1,3-thiazolidin-3-yl]-3-methylbenzoate | 9.4 | 4342 |
| 240 | Cyclohexylmethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 241 | 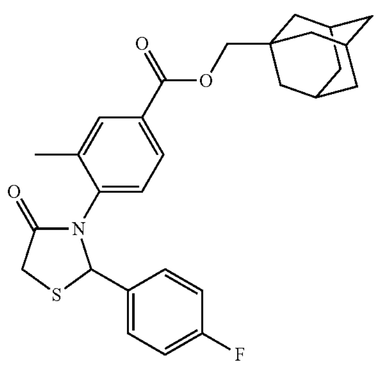 [SMILES: Cc1cc(C(=O)OCC23CC4CC(CC(C4)C2)C3)ccc1N1C(=O)CSC1c1ccc(F)cc1] | 4-[2-(4-Fluoro-phenyl)-4-oxo-thiazolidin-3-yl]-3-methyl-benzoic acid adamantan-1-ylmethyl ester | — | — |
| 242 | 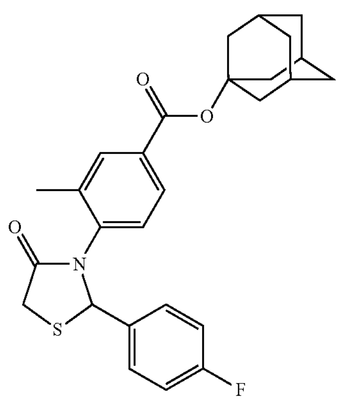 [SMILES: Cc1cc(C(=O)OC23CC4CC(CC(C4)C2)C3)ccc1N1C(=O)CSC1c1ccc(F)cc1] | 4-[2-(4-Fluoro-phenyl)-4-oxo-thiazolidin-3-yl]-3-methyl-benzoic acid adamantan-1-yl ester | — | — |
| 245 | 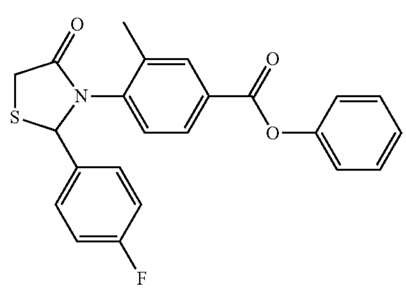 | Phenyl 4-[2-(4-fluorophenyl)-4-oxo-1,3-thiazolidin-3-yl]-3-methylbenzoate | — | — |
| 246 | 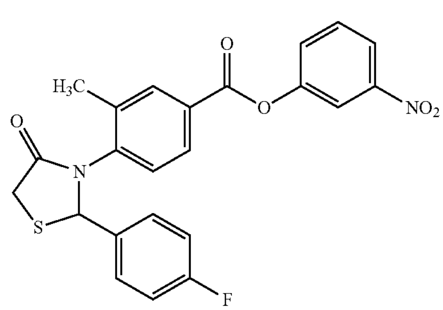 [SMILES: Cc1cc(C(=O)Oc2cccc([N+](=O)[O-])c2)ccc1N1C(=O)CSC1c1ccc(F)cc1] | 3-Nitrophenyl 4-[2-(4-fluorophenyl)-4-oxo-1,3-thiazolidin-3-yl]-3-methylbenzoate | TBD | TBD |

TABLE 1-continued

Exemplary compounds and their activities

| No. | Structure | Name | FLIPR Ca$^{2+}$ EC$_{50}$ (μM) | AUC |
|---|---|---|---|---|
| 247 | 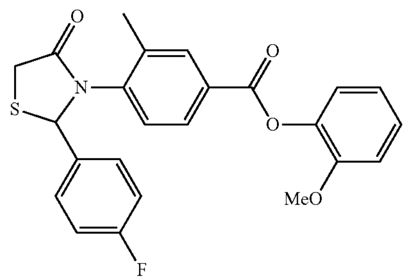 [SMILES: COc1ccccc1OC(=O)c1ccc(N2C(=O)CSC2c2ccc(F)cc2)c(C)c1] | 2-Methoxyphenyl 4-[2-(4-fluorophenyl)-4-oxo-1,3-thiazolidin-3-yl]-3-methylbenzoate | — | — |
| 248 | 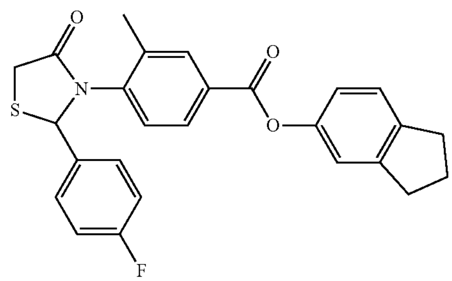 [SMILES: Cc1cc(C(=O)Oc2ccc3c(c2)CCC3)ccc1N1C(=O)CSC1c1ccc(F)cc1] | 2,3-Dihydro-1H-inden-5-yl 4-[2-(4-fluorophenyl)-4-oxo-1,3-thiazolidin-3-yl]-3-methylbenzoate | — | — |
| 249 | 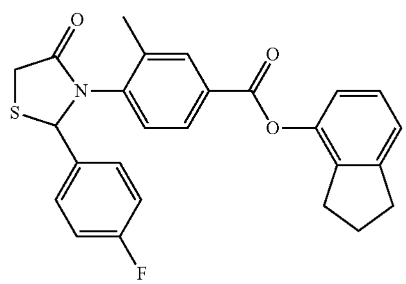 [SMILES: Cc1cc(C(=O)Oc2cccc3c2CCC3)ccc1N1C(=O)CSC1c1ccc(F)cc1] | 2,3-Dihydro-1H-inden-4-yl 4-[2-(4-fluorophenyl)-4-oxo-1,3-thiazolidin-3-yl]-3-methylbenzoate | — | — |
| 250 | 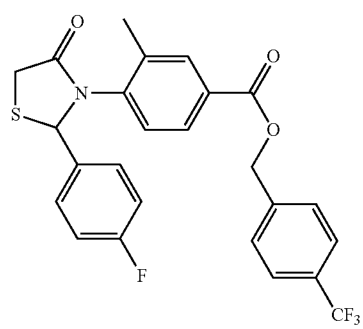 [SMILES: Cc1cc(C(=O)OCc2ccc(C(F)(F)F)cc2)ccc1N1C(=O)CSC1c1ccc(F)cc1] | 4-(Trifluoromethyl)benzyl 4-[2-(4-fluorophenyl)-4-oxo-1,3-thiazolidin-3-yl]-3-methylbenzoate | — | — |
| 251 | 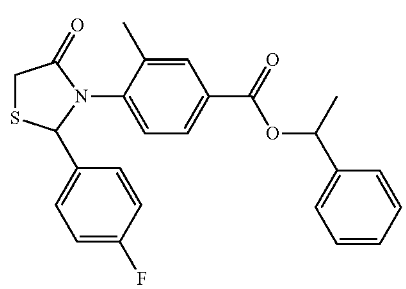 | 1-Phenylethyl 4-[2-(4-fluorophenyl)-4-oxo-1,3-thiazolidin-3-yl]-3-methylbenzoate | TBD | TBD |

TABLE 1-continued

Exemplary compounds and their activities

| No. | Structure | Name | FLIPR Ca$^{2+}$ EC$_{50}$ (μM) | AUC |
|---|---|---|---|---|
| 252 | 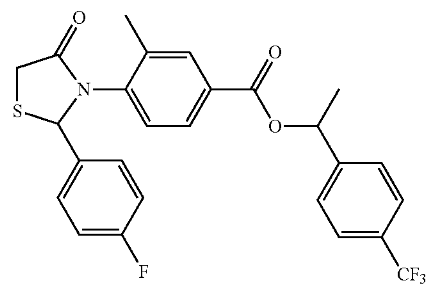 [SMILES: Cc1cc(C(=O)OC(C)c2ccc(C(F)(F)F)cc2)ccc1N1C(=O)CSC1c1ccc(F)cc1] | 1-[4-(Trifluoromethyl)phenyl]ethyl 4-[2-(4-fluorophenyl)-4-oxo-1,3-thiazolidin-3-yl]-3-methylbenzoate | TBD | TBD |
| 253 | 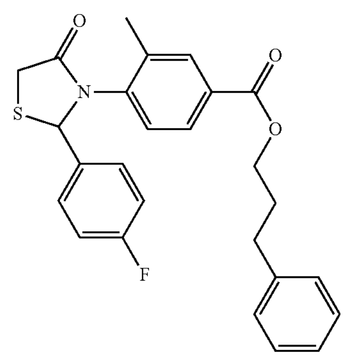 [SMILES: Cc1cc(C(=O)OCCCc2ccccc2)ccc1N1C(=O)CSC1c1ccc(F)cc1] | 3-Phenylpropyl 4-[2-(4-fluorophenyl)-4-oxo-1,3-thiazolidin-3-yl]-3-methylbenzoate | 11.2 | 6717 |
| 254 | 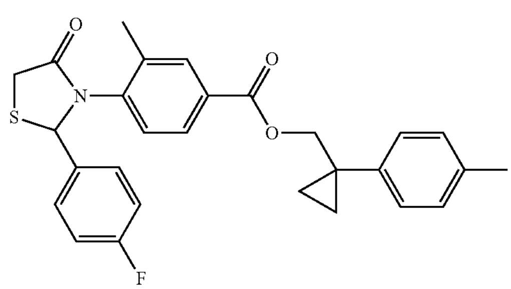 [SMILES: Cc1ccc(C2(COC(=O)c3ccc(N4C(=O)CSC4c4ccc(F)cc4)c(C)c3)CC2)cc1] | [1-(4-Chlorophenyl)cyclopropyl]methyl 4-[2-(4-fluorophenyl)-4-oxo-1,3-thiazolidin-3-yl]-3-methylbenzoate | — | — |
| 255 | 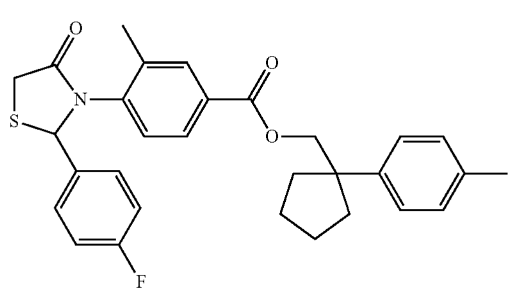 [SMILES: Cc1ccc(C2(COC(=O)c3ccc(N4C(=O)CSC4c4ccc(F)cc4)c(C)c3)CCCC2)cc1] | [1-(4-Chlorophenyl)cyclopentyl]methyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (µM) | AUC |
|---|---|---|---|---|
| 258 | 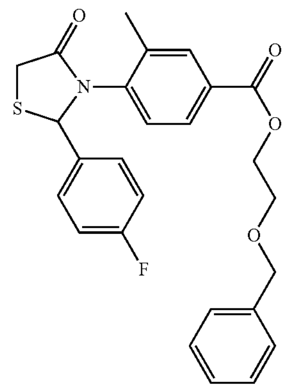 [SMILES: Cc1cc(C(=O)OCCOCc2ccccc2)ccc1N1C(=O)CSC1c1ccc(F)cc1] | 2-(Benzyloxy)ethyl 4-[2-(4-fluorophenyl)-4-oxo-1,3-thiazolidin-3-yl]-3-methylbenzoate | 3.3 | 6353 |
| 259 | 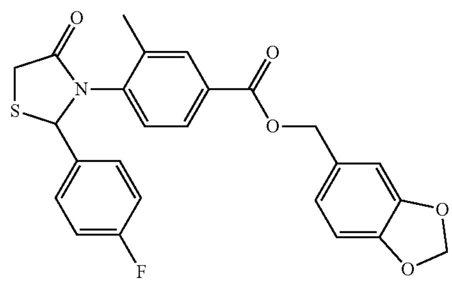 [SMILES: Cc1cc(C(=O)OCc2ccc3c(c2)OCO3)ccc1N1C(=O)CSC1c1ccc(F)cc1] | 1,3-Benzodioxol-5-ylmethyl 4-[2-(4-fluorophenyl)-4-oxo-1,3-thiazolidin-3-yl]-3-methylbenzoate | — | — |
| 260 | 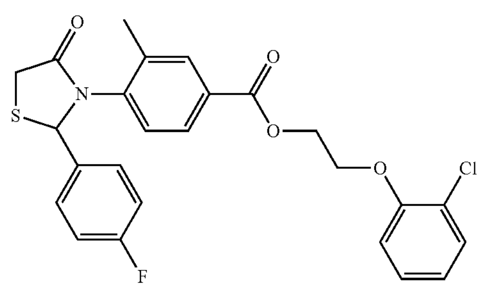 [SMILES: Cc1cc(C(=O)OCCOc2ccccc2Cl)ccc1N1C(=O)CSC1c1ccc(F)cc1] | 2-(2-Chlorophenoxy)ethyl 4-[2-(4-fluorophenyl)-4-oxo-1,3-thiazolidin-3-yl]-3-methylbenzoate | — | — |
| 261 | 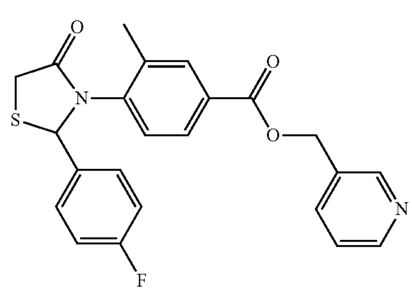 [SMILES: Cc1cc(C(=O)OCc2cccnc2)ccc1N1C(=O)CSC1c1ccc(F)cc1] | 3-Pyridinylmethyl 4-[2-(4-fluorophenyl)-4-oxo-1,3-thiazolidin-3-yl]-3-methylbenzoate | 2.9 | 11434 |

TABLE 1-continued

Exemplary compounds and their activities

| No. | Structure | Name | FLIPR Ca$^{2+}$ EC$_{50}$ (μM) | AUC |
|---|---|---|---|---|
| 262 | 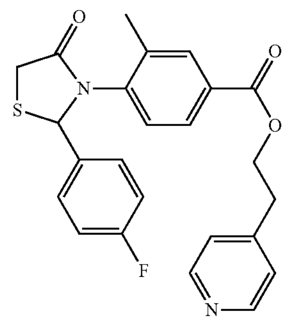 [SMILES: Cc1cc(C(=O)OCCc2ccncc2)ccc1N1C(=O)CSC1c1ccc(F)cc1] | 2-(4-Pyridinyl)ethyl 4-[2-(4-fluorophenyl)-4-oxo-1,3-thiazolidin-3-yl]-3-methylbenzoate | TBD | TBD |
| 263 | 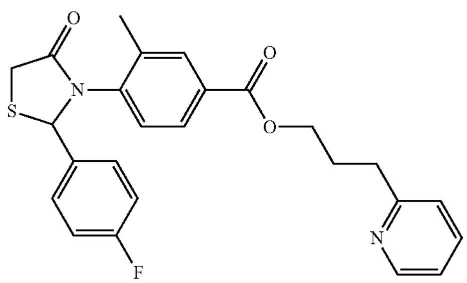 [SMILES: Cc1cc(C(=O)OCCCc2ccccn2)ccc1N1C(=O)CSC1c1ccc(F)cc1] | 3-(2-Pyridinyl)propyl 4-[2-(4-fluorophenyl)-4-oxo-1,3-thiazolidin-3-yl]-3-methylbenzoate | 9.2 | 14918 |
| 264 | 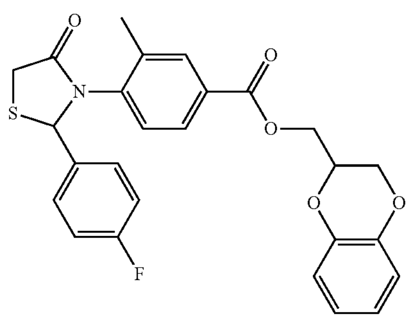 [SMILES: Cc1cc(C(=O)OCC2COc3ccccc3O2)ccc1N1C(=O)CSC1c1ccc(F)cc1] | 2,3-Dihydro-1,4-benzodioxin-2-ylmethyl 4-[2-(4-fluorophenyl)-4-oxo-1,3-thiazolidin-3-yl]-3-methylbenzoate | — | — |
| 265 | 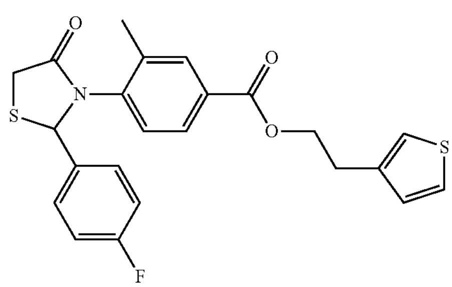 [SMILES: Cc1cc(C(=O)OCCc2ccsc2)ccc1N1C(=O)CSC1c1ccc(F)cc1] | 2-(3-Thiophenyl)ethyl 4-[2-(4-fluorophenyl)-4-oxo-1,3-thiazolidin-3-yl]-3-methylbenzoate | — | — |
| 266 | 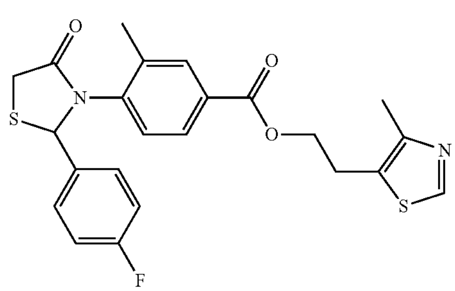 [SMILES: Cc1cc(C(=O)OCCc2scnc2C)ccc1N1C(=O)CSC1c1ccc(F)cc1] | 2-(4-Methyl-1,3-thiazol-5-yl)ethyl 4-[2-(4-fluorophenyl)-4-oxo-1,3-thiazolidin-3-yl]-3-methylbenzoate | 4.6 | 12653 |

TABLE 1-continued

Exemplary compounds and their activities

| No. | Structure | Name | FLIPR Ca$^{2+}$ EC$_{50}$ (μM) | AUC |
|---|---|---|---|---|
| 267 | 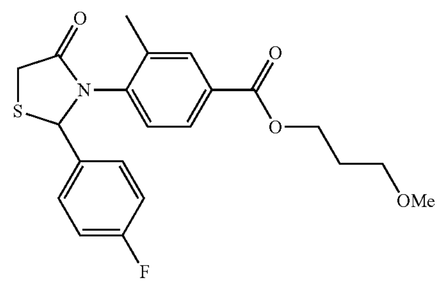 [SMILES: COCCCOC(=O)c1ccc(N2C(=O)CSC2c2ccc(F)cc2)c(C)c1] | 3-Methoxypropyl 4-[2-(4-fluorophenyl)-4-oxo-1,3-thiazolidin-3-yl]-3-methylbenzoate | 6.4 | 15960 |
| 268 | 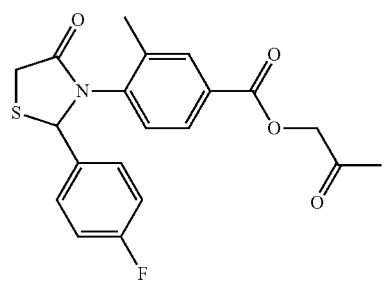 [SMILES: CC(=O)COC(=O)c1ccc(N2C(=O)CSC2c2ccc(F)cc2)c(C)c1] | 2-Oxopropyl 4-[2-(4-fluorophenyl)-4-oxo-1,3-thiazolidin-3-yl]-3-methylbenzoate | 3.8 | 12787 |
| 269 | 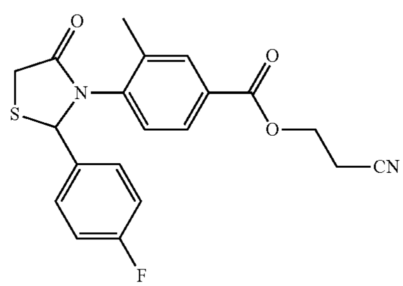 [SMILES: Cc1cc(C(=O)OCCC#N)ccc1N1C(=O)CSC1c1ccc(F)cc1] | 2-Cyanoethyl 4-[2-(4-fluorophenyl)-4-oxo-1,3-thiazolidin-3-yl]-3-methylbenzoate | 12.3 | 14183 |
| 270 | 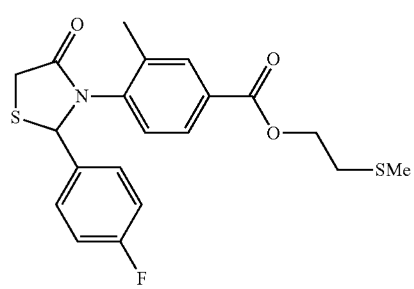 [SMILES: CSCCOC(=O)c1ccc(N2C(=O)CSC2c2ccc(F)cc2)c(C)c1] | 2-(Methylsulfanyl)ethyl 4-[2-(4-fluorophenyl)-4-oxo-1,3-thiazolidin-3-yl]-3-methylbenzoate | 6.4 | 18775 |
| 271 | 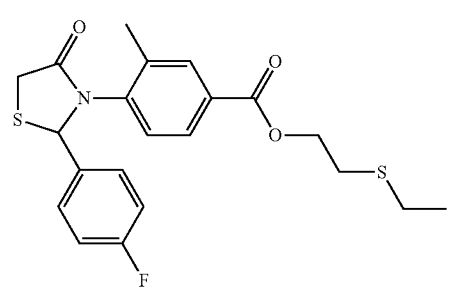 [SMILES: CCSCCOC(=O)c1ccc(N2C(=O)CSC2c2ccc(F)cc2)c(C)c1] | 2-(Ethylsulfanyl)ethyl 4-[2-(4-fluorophenyl)-4-oxo-1,3-thiazolidin-3-yl]-3-methylbenzoate | 14.0 | 11997 |

TABLE 1-continued

Exemplary compounds and their activities

| No. | Structure | Name | FLIPR Ca$^{2+}$ EC$_{50}$ (μM) | AUC |
|---|---|---|---|---|
| 272 | 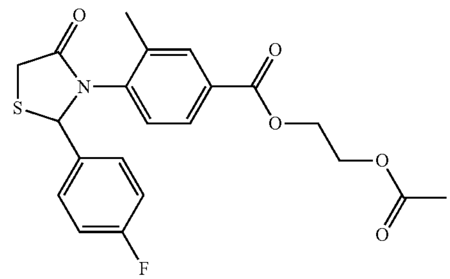 [SMILES: CC(=O)OCCOC(=O)c1ccc(N2C(=O)CSC2c2ccc(F)cc2)c(C)c1] | 2-(Acetyloxy)ethyl 4-[2-(4-fluorophenyl)-4-oxo-1,3-thiazolidin-3-yl]-3-methylbenzoate | 2.8 | 12131 |
| 273 | 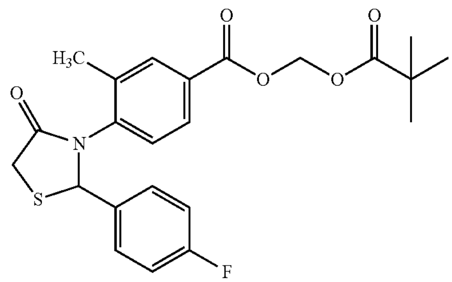 [SMILES: Cc1cc(C(=O)OCOC(=O)C(C)(C)C)ccc1N1C(=O)CSC1c1ccc(F)cc1] | [(2,2-Dimethylpropanoyl)oxy]methyl 4-[2-(4-fluorophenyl)-4-oxo-1,3-thiazolidin-3-yl]-3-methylbenzoate | 5.7 | 12265 |
| 274 | 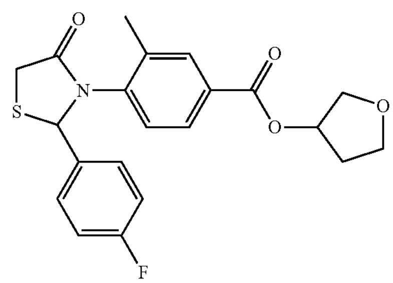 [SMILES: Cc1cc(C(=O)OC2CCOC2)ccc1N1C(=O)CSC1c1ccc(F)cc1] | Tetrahydro-3-furanyl 4-[2-(4-fluorophenyl)-4-oxo-1,3-thiazolidin-3-yl]-3-methylbenzoate | TBD | TBD |
| 275 | 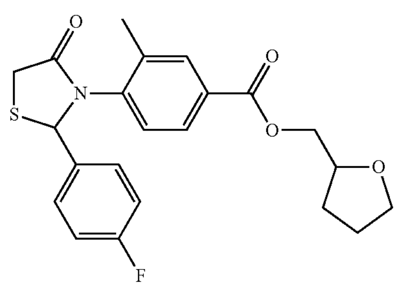 [SMILES: Cc1cc(C(=O)OCC2CCCO2)ccc1N1C(=O)CSC1c1ccc(F)cc1] | Tetrahydro-2-furanylmethyl 4-[2-(4-fluorophenyl)-4-oxo-1,3-thiazolidin-3-yl]-3-methylbenzoate | 26.9 | 11236 |
| 276 | 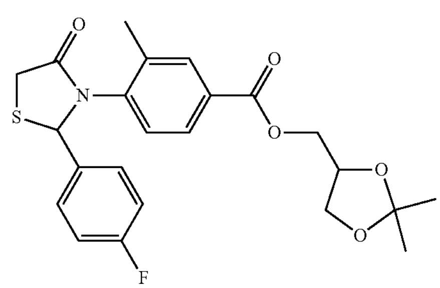 [SMILES: Cc1cc(C(=O)OCC2COC(C)(C)O2)ccc1N1C(=O)CSC1c1ccc(F)cc1] | (2,2-Dimethyl-1,3-dioxolan-4-yl)methyl 4-[2-(4-fluorophenyl)-4-oxo-1,3-thiazolidin-3-yl]-3-methylbenzoate | 6.3 | 15090 |

TABLE 1-continued

Exemplary compounds and their activities

| No. | Structure | Name | FLIPR Ca$^{2+}$ EC$_{50}$ (μM) | AUC |
|---|---|---|---|---|
| 277 | 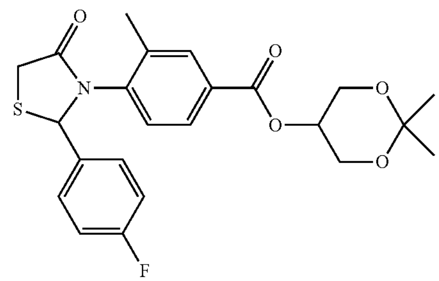 [SMILES: Cc1cc(C(=O)OC2COC(C)(C)OC2)ccc1N1C(=O)CSC1c1ccc(F)cc1] | 2,2-Dimethyl-1,3-dioxan-5-yl 4-[2-(4-fluorophenyl)-4-oxo-1,3-thiazolidin-3-yl]-3-methylbenzoate | 6.1 | 14634 |
| 278 | 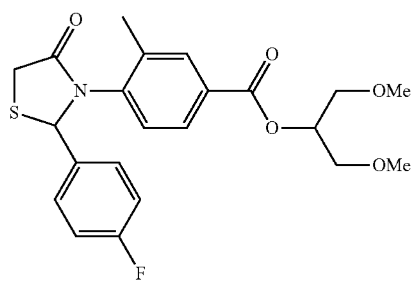 [SMILES: COCC(COC)OC(=O)c1ccc(N2C(=O)CSC2c2ccc(F)cc2)c(C)c1] | 1,3-Dimethoxy-2-propanyl 4-[2-(4-fluorophenyl)-4-oxo-1,3-thiazolidin-3-yl]-3-methylbenzoate | TBD | TBD |
| 279 | 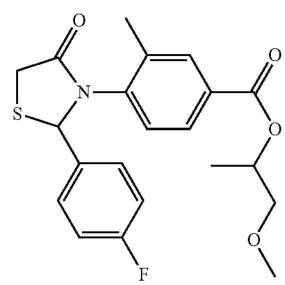 [SMILES: COCC(C)OC(=O)c1ccc(N2C(=O)CSC2c2ccc(F)cc2)c(C)c1] | 1-Methoxy-2-propanyl 4-[2-(4-fluorophenyl)-4-oxo-1,3-thiazolidin-3-yl]-3-methylbenzoate | 4.1 | 10883 |
| 280 | 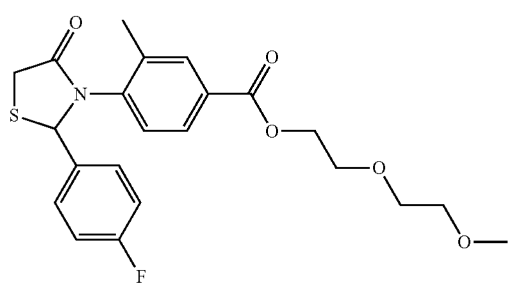 [SMILES: COCCOCCOC(=O)c1ccc(N2C(=O)CSC2c2ccc(F)cc2)c(C)c1] | 2-(2-Methoxyethoxy)ethyl 4-[2-(4-fluorophenyl)-4-oxo-1,3-thiazolidin-3-yl]-3-methylbenzoate | 7.1 | 15386 |
| 281 | 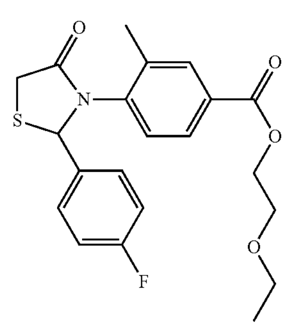 [SMILES: CCOCCOC(=O)c1ccc(N2C(=O)CSC2c2ccc(F)cc2)c(C)c1] | 2-Ethoxyethyl 4-[2-(4-fluorophenyl)-4-oxo-1,3-thiazolidin-3-yl]-3-methylbenzoate | 4.5 | 9792 |

TABLE 1-continued

Exemplary compounds and their activities

| No. | Structure | Name | FLIPR Ca$^{2+}$ EC$_{50}$ (μM) | AUC |
|---|---|---|---|---|
| 282 | 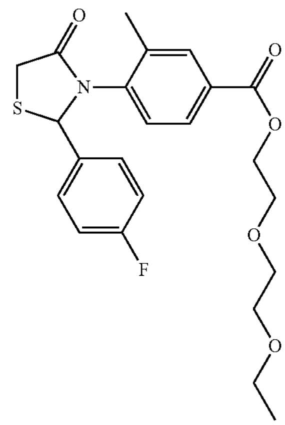 [SMILES: CCOCCOCCOC(=O)c1ccc(N2C(=O)CSC2c2ccc(F)cc2)c(C)c1] | 2-(2-Ethoxyethoxy)ethyl 4-[2-(4-fluorophenyl)-4-oxo-1,3-thiazolidin-3-yl]-3-methylbenzoate | TBD | TBD |
| 283 | 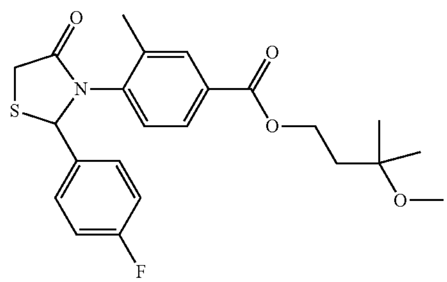 [SMILES: COC(C)(C)CCOC(=O)c1ccc(N2C(=O)CSC2c2ccc(F)cc2)c(C)c1] | 3-Methoxy-3-methylbutyl 4-[2-(4-fluorophenyl)-4-oxo-1,3-thiazolidin-3-yl]-3-methylbenzoate | TBD | TBD |
| 284 | 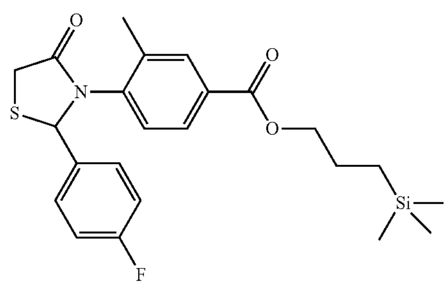 [SMILES: Cc1cc(C(=O)OCCC[Si](C)(C)C)ccc1N1C(=O)CSC1c1ccc(F)cc1] | 3-(Trimethylsilyl)propyl 4-[2-(4-fluorophenyl)-4-oxo-1,3-thiazolidin-3-yl]-3-methylbenzoate | TBD | TBD |
| 285 | 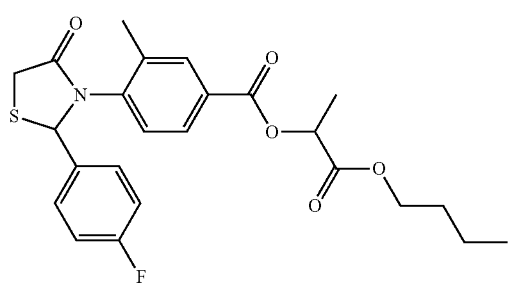 [SMILES: CCCCOC(=O)C(C)OC(=O)c1ccc(N2C(=O)CSC2c2ccc(F)cc2)c(C)c1] | 1-Butoxy-1-oxo-2-propanyl 4-[2-(4-fluorophenyl)-4-oxo-1,3-thiazolidin-3-yl]-3-methylbenzoate | TBD | TBD |
| 286 | 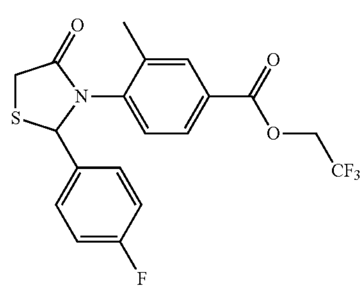 [SMILES: Cc1cc(C(=O)OCC(F)(F)F)ccc1N1C(=O)CSC1c1ccc(F)cc1] | 2,2,2-Trifluoroethyl 4-[2-(4-fluorophenyl)-4-oxo-1,3-thiazolidin-3-yl]-3-methylbenzoate | 9.2 | 13001 |

TABLE 1-continued

Exemplary compounds and their activities

| No. | Structure | Name | FLIPR Ca²⁺ EC$_{50}$ (μM) | AUC |
|---|---|---|---|---|
| 287 | 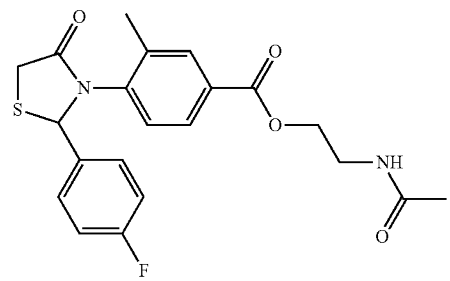 [SMILES: CC(=O)NCCOC(=O)c1ccc(N2C(=O)CSC2c2ccc(F)cc2)c(C)c1] | 2-(Acetylamino)ethyl 4-[2-(4-fluorophenyl)-4-oxo-1,3-thiazolidin-3-yl]-3-methylbenzoate | TBD | TBD |
| 288 | 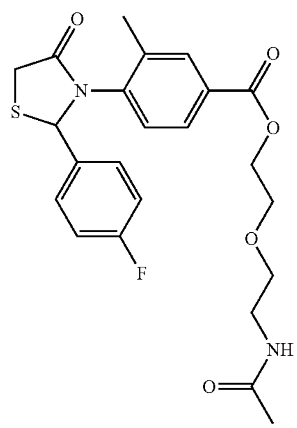 [SMILES: CC(=O)NCCOCCOC(=O)c1ccc(N2C(=O)CSC2c2ccc(F)cc2)c(C)c1] | 2-[2-(Acetylamino)ethoxy]ethyl 4-[2-(4-fluorophenyl)-4-oxo-1,3-thiazolidin-3-yl]-3-methylbenzoate | TBD | TBD |
| 290 | 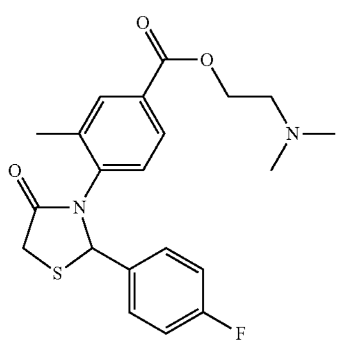 [SMILES: Cc1cc(C(=O)OCCN(C)C)ccc1N1C(=O)CSC1c1ccc(F)cc1] | 2-(Dimethylamino)ethyl 4-[2-(4-fluorophenyl)-4-oxo-1,3-thiazolidin-3-yl]-3-methylbenzoate | 10.0 | 14778 |
| 291 | 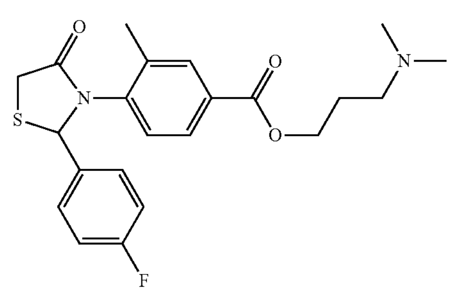 [SMILES: Cc1cc(C(=O)OCCCN(C)C)ccc1N1C(=O)CSC1c1ccc(F)cc1] | 3-(Dimethylamino)propyl 4-[2-(4-fluorophenyl)-4-oxo-1,3-thiazolidin-3-yl]-3-methylbenzoate | 1.9 | 8913 |

TABLE 1-continued

Exemplary compounds and their activities

| No. | Structure | Name | FLIPR Ca²⁺ EC$_{50}$ (μM) | AUC |
|---|---|---|---|---|
| 292 | 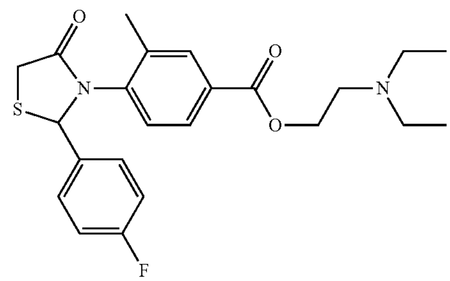 [SMILES: CCN(CC)CCOC(=O)c1ccc(N2C(=O)CSC2c2ccc(F)cc2)c(C)c1] | 2-(Diethylamino)ethyl 4-[2-(4-fluorophenyl)-4-oxo-1,3-thiazolidin-3-yl]-3-methylbenzoate | 3.1 | 10056 |
| 293 | 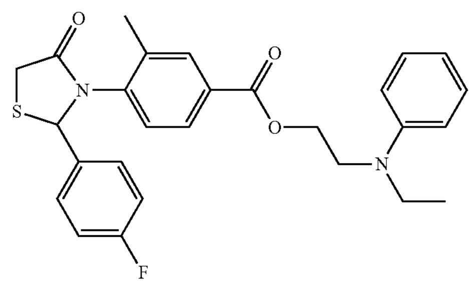 [SMILES: CCN(CCOC(=O)c1ccc(N2C(=O)CSC2c2ccc(F)cc2)c(C)c1)c1ccccc1] | 2-[Ethyl(phenyl)amino]ethyl 4-[2-(4-fluorophenyl)-4-oxo-1,3-thiazolidin-3-yl]-3-methylbenzoate | TBD | TBD |
| 294 | 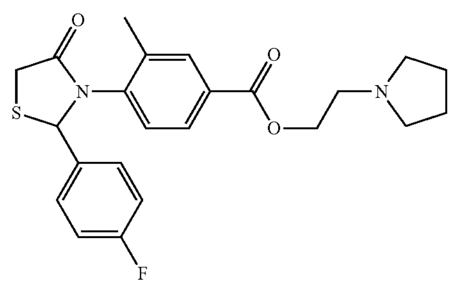 [SMILES: Cc1cc(C(=O)OCCN2CCCC2)ccc1N1C(=O)CSC1c1ccc(F)cc1] | 2-(1-Pyrrolidinyl)ethyl 4-[2-(4-fluorophenyl)-4-oxo-1,3-thiazolidin-3-yl]-3-methylbenzoate | 2.9 | 14394 |
| 295 | 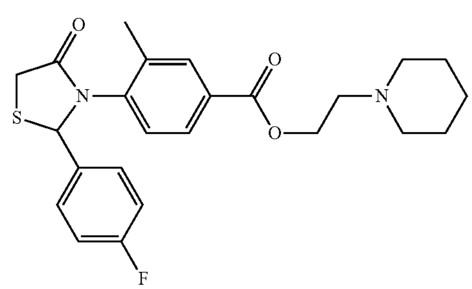 [SMILES: Cc1cc(C(=O)OCCN2CCCCC2)ccc1N1C(=O)CSC1c1ccc(F)cc1] | 2-(1-Piperidinyl)ethyl 4-[2-(4-fluorophenyl)-4-oxo-1,3-thiazolidin-3-yl]-3-methylbenzoate | 2.8 | 10426 |
| 296 | 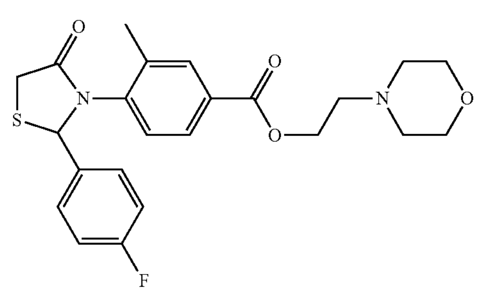 [SMILES: Cc1cc(C(=O)OCCN2CCOCC2)ccc1N1C(=O)CSC1c1ccc(F)cc1] | 2-(4-Morpholinyl)ethyl 4-[2-(4-fluorophenyl)-4-oxo-1,3-thiazolidin-3-yl]-3-methylbenzoate | 2.3 | 14052 |

TABLE 1-continued

Exemplary compounds and their activities

| No. | Structure | Name | FLIPR Ca$^{2+}$ EC$_{50}$ (μM) | AUC |
|---|---|---|---|---|
| 297 | 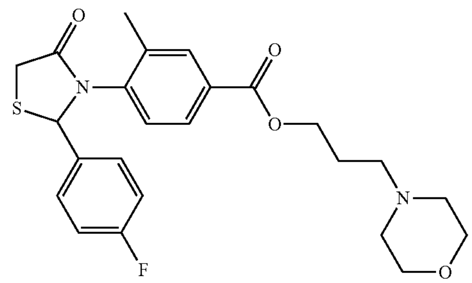 [SMILES: Cc1cc(C(=O)OCCCN2CCOCC2)ccc1N1C(=O)CSC1c1ccc(F)cc1] | 3-(4-Morpholinyl)propyl 4-[2-(4-fluorophenyl)-4-oxo-1,3-thiazolidin-3-yl]-3-methylbenzoate | 8.1 | 13753 |
| 298 | 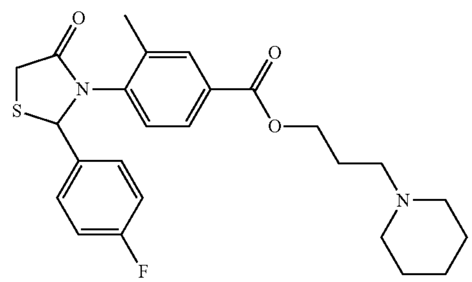 [SMILES: Cc1cc(C(=O)OCCCN2CCCCC2)ccc1N1C(=O)CSC1c1ccc(F)cc1] | 3-(1-Piperidinyl)propyl 4-[2-(4-fluorophenyl)-4-oxo-1,3-thiazolidin-3-yl]-3-methylbenzoate | 1.7 | 9283 |
| 299 | 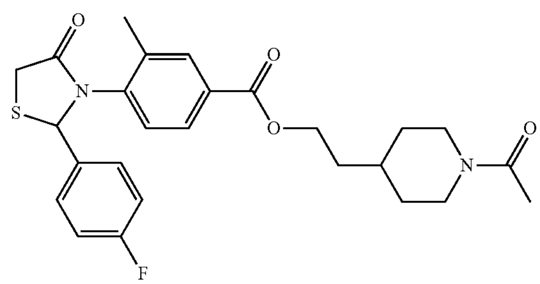 [SMILES: CC(=O)N1CCC(CCOC(=O)c2ccc(N3C(=O)CSC3c3ccc(F)cc3)c(C)c2)CC1] | 2-(1-Acetyl-4-piperidinyl)ethyl 4-[2-(4-fluorophenyl)-4-oxo-1,3-thiazolidin-3-yl]-3-methylbenzoate | 5.0 | 10053 |
| 300 | 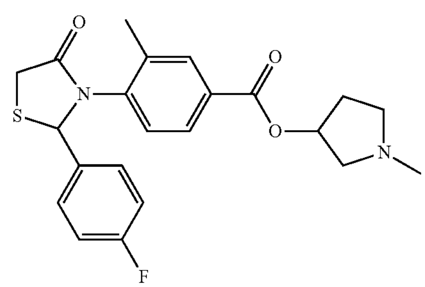 [SMILES: Cc1cc(C(=O)OC2CCN(C)C2)ccc1N1C(=O)CSC1c1ccc(F)cc1] | 1-Methyl-3-pyrrolidinyl 4-[2-(4-fluorophenyl)-4-oxo-1,3-thiazolidin-3-yl]-3-methylbenzoate | 1.6 | 12918 |
| 301 | 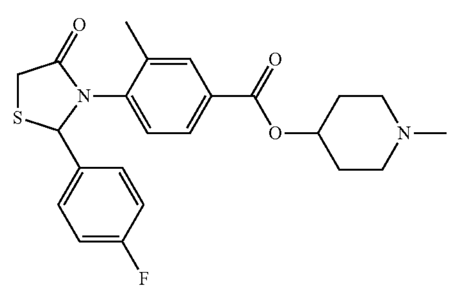 [SMILES: Cc1cc(C(=O)OC2CCN(C)CC2)ccc1N1C(=O)CSC1c1ccc(F)cc1] | 1-Methyl-4-piperidinyl 4-[2-(4-fluorophenyl)-4-oxo-1,3-thiazolidin-3-yl]-3-methylbenzoate | 0.9 | 9593 |

TABLE 1-continued

Exemplary compounds and their activities

| No. | Structure | Name | FLIPR Ca²⁺ EC$_{50}$ (μM) | AUC |
|---|---|---|---|---|
| 302 | 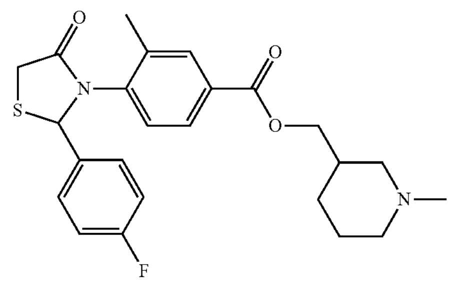 [SMILES: Cc1cc(C(=O)OCC2CCCN(C)C2)ccc1N1C(=O)CSC1c1ccc(F)cc1] | (1-Methyl-3-piperidinyl)methyl 4-[2-(4-fluorophenyl)-4-oxo-1,3-thiazolidin-3-yl]-3-methylbenzoate | TBD | TBD |
| 303 | 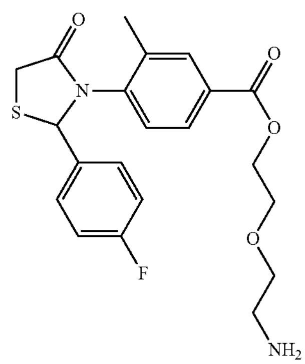 [SMILES: Cc1cc(C(=O)OCCOCCN)ccc1N1C(=O)CSC1c1ccc(F)cc1] | 2-(2-Aminoethoxy)ethyl 4-[2-(4-fluorophenyl)-4-oxo-1,3-thiazolidin-3-yl]-3-methylbenzoate | 7.0 | 9530 |
| 306 | 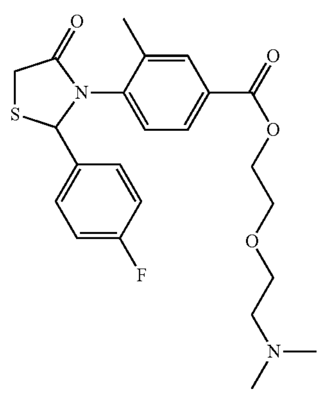 [SMILES: Cc1cc(C(=O)OCCOCCN(C)C)ccc1N1C(=O)CSC1c1ccc(F)cc1] | 2-[2-(Dimethylamino)ethoxy]ethyl 4-[2-(4-fluorophenyl)-4-oxo-1,3-thiazolidin-3-yl]-3-methylbenzoate | 6.2 | 7531 |
| 307 | 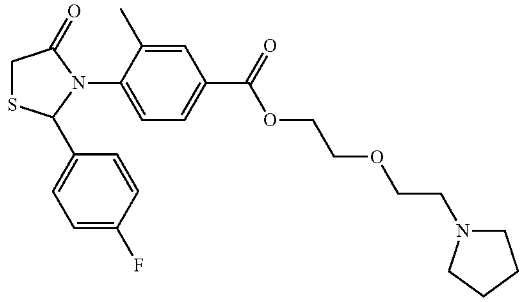 [SMILES: Cc1cc(C(=O)OCCOCCN2CCCC2)ccc1N1C(=O)CSC1c1ccc(F)cc1] | 2-[2-(1-Pyrrolidinyl)ethoxy]ethyl 4-[2-(4-fluorophenyl)-4-oxo-1,3-thiazolidin-3-yl]-3-methylbenzoate | 8.7 | 14731 |

TABLE 1-continued

Exemplary compounds and their activities

| No. | Structure | Name | FLIPR Ca²⁺ EC$_{50}$ (µM) | AUC |
|---|---|---|---|---|
| 309 | 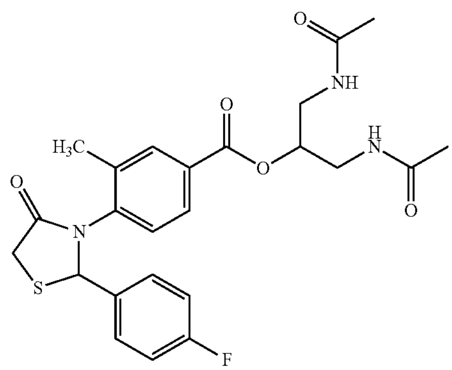 [SMILES: CC(=O)NCC(CNC(C)=O)OC(=O)c1ccc(N2C(=O)CSC2c2ccc(F)cc2)c(C)c1] | 1,3-Bis(acetylamino)-2-propanyl 4-[2-(4-fluorophenyl)-4-oxo-1,3-thiazolidin-3-yl]-3-methylbenzoate | TBD | TBD |
| 310 | 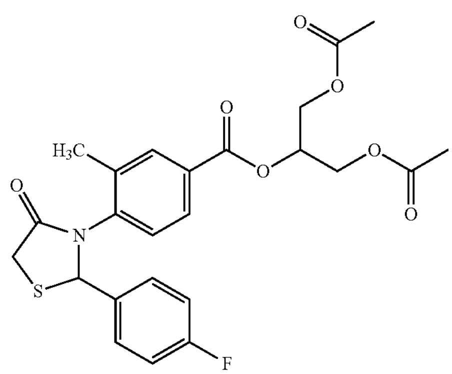 [SMILES: CC(=O)OCC(COC(C)=O)OC(=O)c1ccc(N2C(=O)CSC2c2ccc(F)cc2)c(C)c1] | 1,3-Bis(acetyloxy)-2-propanyl 4-[2-(4-fluorophenyl)-4-oxo-1,3-thiazolidin-3-yl]-3-methylbenzoate | 3.3 | 12428 |
| 311 | 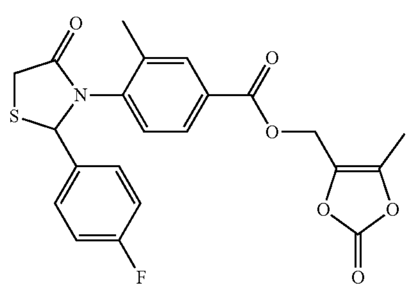 [SMILES: Cc1cc(C(=O)OCc2oc(=O)oc2C)ccc1N1C(=O)CSC1c1ccc(F)cc1] | (5-Methyl-2-oxo-1,3-dioxol-4-yl)methyl 4-[2-(4-fluorophenyl)-4-oxo-1,3-thiazolidin-3-yl]-3-methylbenzoate | 4.0 | 12968 |
| 312 | 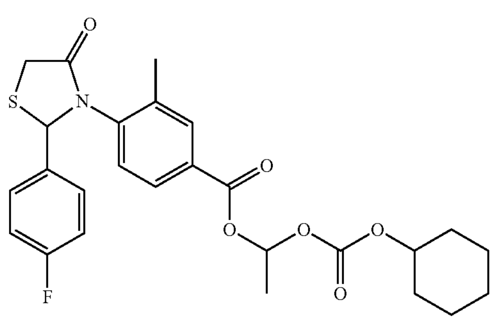 [SMILES: Cc1cc(C(=O)OC(C)OC(=O)OC2CCCCC2)ccc1N1C(=O)CSC1c1ccc(F)cc1] | 1-{[(Cyclohexyloxy)carbonyl]oxy}ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 313 | 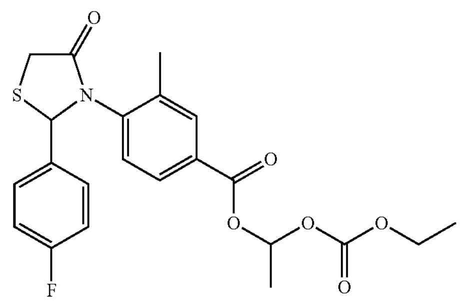 [SMILES: CCOC(=O)OC(C)OC(=O)c1ccc(N2C(=O)CSC2c2ccc(F)cc2)c(C)c1] | 1-[(Ethoxycarbonyl)oxy]ethyl 4-[2-(4-fluorophenyl)-4-oxo-1,3-thiazolidin-3-yl]-3-methylbenzoate | 5.1 | 18341 |
| 314 | 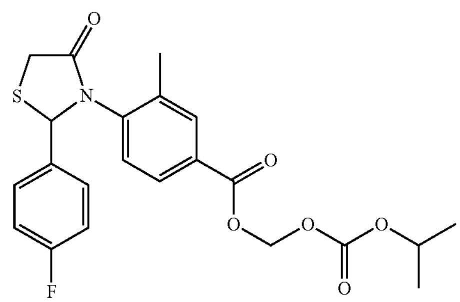 [SMILES: Cc1cc(C(=O)OCOC(=O)OC(C)C)ccc1N1C(=O)CSC1c1ccc(F)cc1] | {[(2-Propanyloxy)carbonyl]oxy}methyl 4-[2-(4-fluorophenyl)-4-oxo-1,3-thiazolidin-3-yl]-3-methylbenzoate | 4.5 | 10852 |
| 315 | 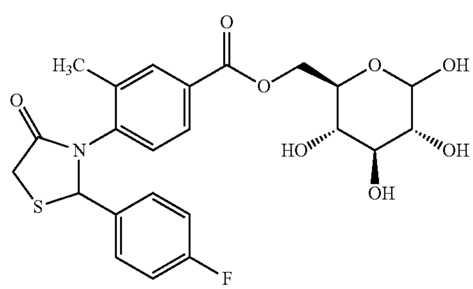 [SMILES: Cc1cc(C(=O)OC[C@H]2OC(O)[C@H](O)[C@@H](O)[C@@H]2O)ccc1N1C(=O)CSC1c1ccc(F)cc1] | 6-O-{4-[2-(4-Fluorophenyl)-4-oxo-1,3-thiazolidin-3-yl]-3-methylbenzoyl}-D-glucopyranose | TBD | TBD |
| 319 | 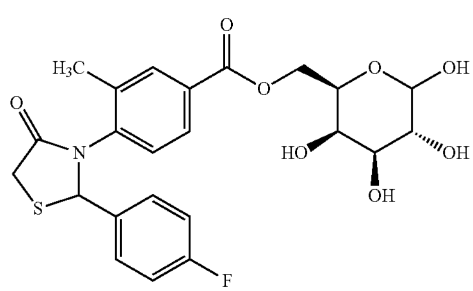 [SMILES: Cc1cc(C(=O)OC[C@H]2OC(O)[C@H](O)[C@@H](O)[C@H]2O)ccc1N1C(=O)CSC1c1ccc(F)cc1] | 6-O-{4-[2-(4-Fluorophenyl)-4-oxo-1,3-thiazolidin-3-yl]-3-methylbenzoyl}-D-galactopyranose | TBD | TBD |
| 321 | 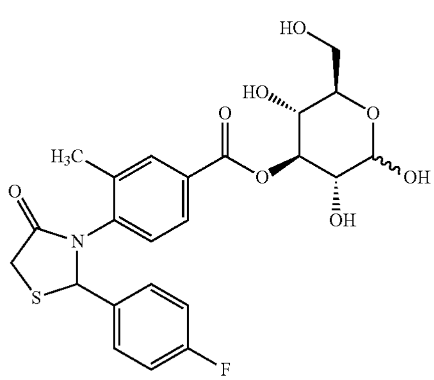 [SMILES: Cc1cc(C(=O)O[C@H]2[C@H](O)[C@@H](CO)OC(O)[C@@H]2O)ccc1N1C(=O)CSC1c1ccc(F)cc1] | 3-O-{4-[2-(4-Fluorophenyl)-4-oxo-1,3-thiazolidin-3-yl]-3-methylbenzoyl}-D-glucopyranose | TBD | TBD |

TABLE 1-continued

Exemplary compounds and their activities

| No. | Structure | Name | FLIPR Ca$^{2+}$ EC$_{50}$ (µM) | AUC |
|---|---|---|---|---|
| 323 | 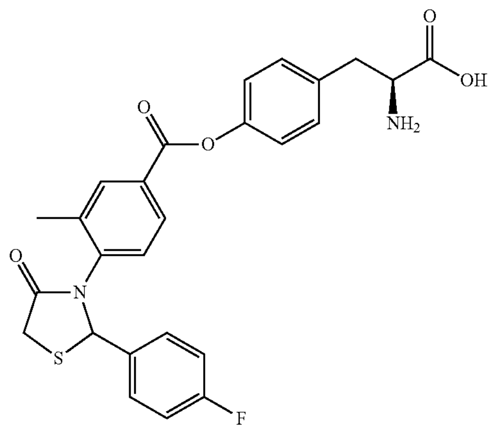 [SMILES: Cc1cc(C(=O)Oc2ccc(C[C@H](N)C(=O)O)cc2)ccc1N1C(=O)CSC1c1ccc(F)cc1] | O-{4-[2-(4-Fluorophenyl)-4-oxo-1,3-thiazolidin-3-yl]-3-methylbenzoyl}-L-tyrosine | TBD | TBD |
| 326 | 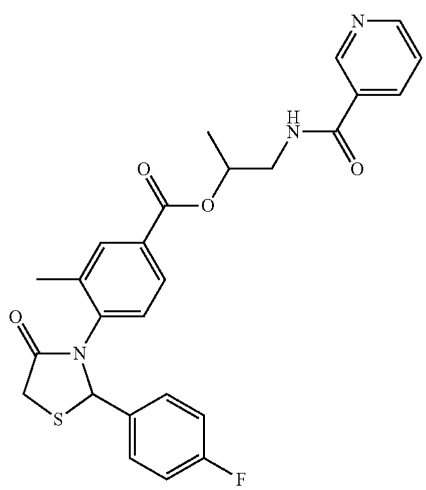 [SMILES: Cc1cc(C(=O)OC(C)CNC(=O)c2cccnc2)ccc1N1C(=O)CSC1c1ccc(F)cc1] | 1-[(3-Pyridinylcarbonyl)amino]-2-propanyl 4-[2-(4-fluorophenyl)-4-oxo-1,3-thiazolidin-3-yl]-3-methylbenzoate | 2.4 | 12342 |
| 328 | 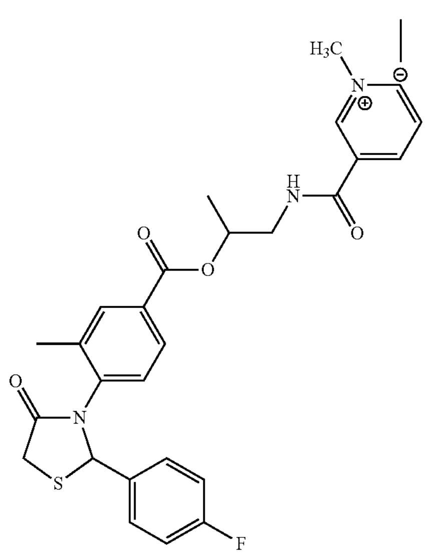 | 3-{[2-({4-[2-(4-Fluorophenyl)-4-oxo-1,3-thiazolidin-3-yl]-3-methylbenzoyl}oxy)propyl]carbamoyl}-1-methylpyridinium iodide | 11.8 | 9505 |

TABLE 1-continued

Exemplary compounds and their activities

| No. | Structure | Name | FLIPR Ca$^{2+}$ EC$_{50}$ (μM) | AUC |
|---|---|---|---|---|
| 329 | 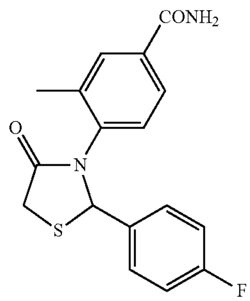 [SMILES: Cc1cc(C(N)=O)ccc1N1C(=O)CSC1c1ccc(F)cc1] | 4-(2-(4-Fluorophenyl)-4-oxothiazolidin-3-yl)-3-methylbenzamide | 1.7 | 13749 |
| 331 | 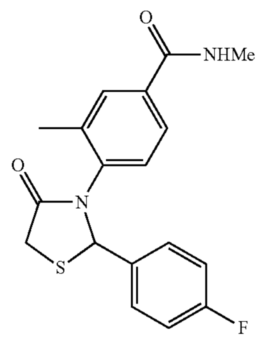 [SMILES: CNC(=O)c1ccc(N2C(=O)CSC2c2ccc(F)cc2)c(C)c1] | N-Methyl-4-(2-(4-fluorophenyl)-4-oxothiazolidin-3-yl)-3-methylbenzamide | 5.7 | 10998 |
| 332 | 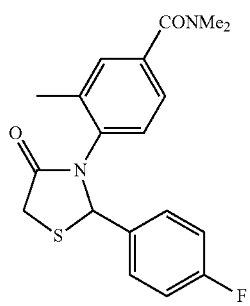 | 4-(2-(4-Fluorophenyl)-4-oxothiazolidin-3-yl)-N,N,3-trimethylbenzamide | 10.0 | 14442 |
| 334 | 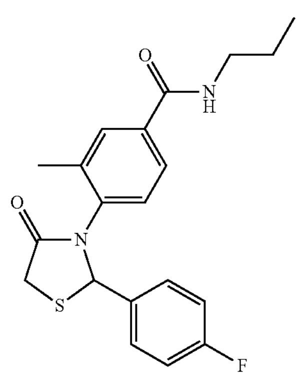 [SMILES: CCCNC(=O)c1ccc(N2C(=O)CSC2c2ccc(F)cc2)c(C)c1] | 4-[2-(4-Fluoro-phenyl)-4-oxo-thiazolidin-3-yl]-3-methyl-N-propyl-benzamide | 5.7 | 9672 |

TABLE 1-continued

Exemplary compounds and their activities

| No. | Structure | Name | FLIPR Ca$^{2+}$ EC$_{50}$ (μM) | AUC |
|---|---|---|---|---|
| 335 | 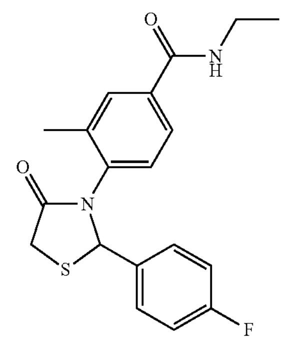 [SMILES: CCNC(=O)c1ccc(N2C(=O)CSC2c2ccc(F)cc2)c(C)c1] | N-ethyl-4-[2-(4-Fluoro-phenyl)-4-oxo-thiazolidin-3-yl]-3-methyl-benzamide | 4.2 | 11180 |
| 336 | 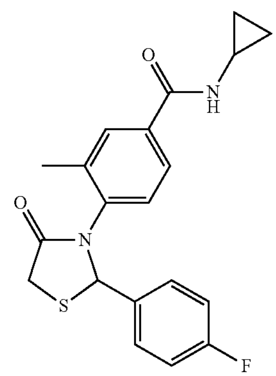 [SMILES: Cc1cc(C(=O)NC2CC2)ccc1N1C(=O)CSC1c1ccc(F)cc1] | N-Cyclopropyl-4-[2-(4-fluoro-phenyl)-4-oxo-thiazolidin-3-yl]-3-methyl-benzamide | 11.0 | 11347 |
| 337 | 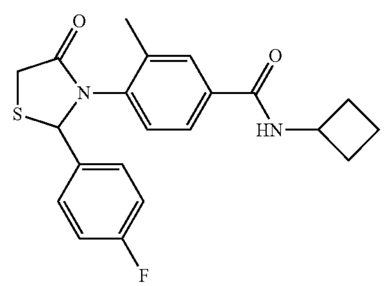 [SMILES: Cc1cc(C(=O)NC2CCC2)ccc1N1C(=O)CSC1c1ccc(F)cc1] | N-Cyclobutyl-4-[2-(4-fluorophenyl)-4-oxo-1,3-thiazolidin-3-yl]-3-methylbenzamide | 0.3 | 8936 |
| 338 | 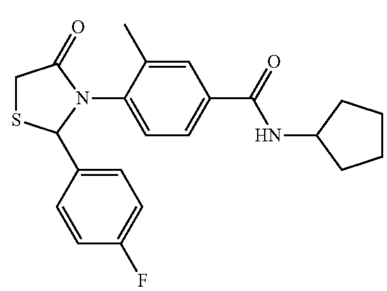 [SMILES: Cc1cc(C(=O)NC2CCCC2)ccc1N1C(=O)CSC1c1ccc(F)cc1] | N-Cyclopentyl-4-[2-(4-fluorophenyl)-4-oxo-1,3-thiazolidin-3-yl]-3-methylbenzamide | 4.4 | 9215 |

TABLE 1-continued

Exemplary compounds and their activities

| No. | Structure | Name | FLIPR Ca²⁺ EC$_{50}$ (μM) | AUC |
|---|---|---|---|---|
| 339 | 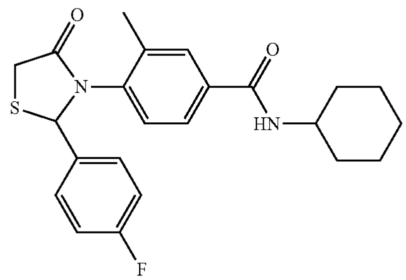 [SMILES: Cc1cc(C(=O)NC2CCCCC2)ccc1N1C(=O)CSC1c1ccc(F)cc1] | N-Cyclohexyl-4-[2-(4-fluorophenyl)-4-oxo-1,3-thiazolidin-3-yl]-3-methylbenzamide | 10.0 | 7164 |
| 340 | 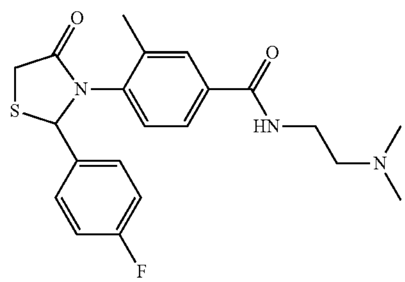 [SMILES: Cc1cc(C(=O)NCCN(C)C)ccc1N1C(=O)CSC1c1ccc(F)cc1] | N-[2-(Dimethylamino)ethyl]-4-[2-(4-fluorophenyl)-4-oxo-1,3-thiazolidin-3-yl]-3-methylbenzamide | 10.0 | 9445 |
| 341 | 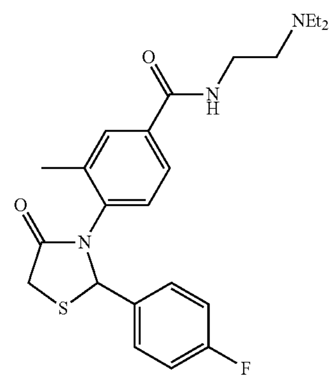 | N-(2-(Diethylamino)ethyl)-4-(2-(4-fluorophenyl)-4-oxothiazolidin-3-yl)-3-methylbenzamide | 3.3 | 9983 |
| 342 | 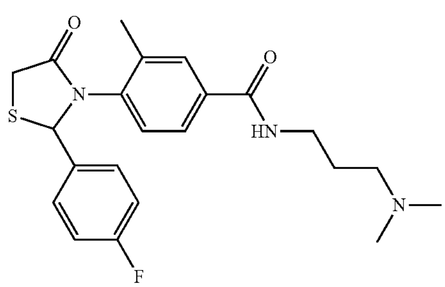 [SMILES: Cc1cc(C(=O)NCCCN(C)C)ccc1N1C(=O)CSC1c1ccc(F)cc1] | N-[3-(Dimethylamino)propyl]-4-[2-(4-fluorophenyl)-4-oxo-1,3-thiazolidin-3-yl]-3-methylbenzamide | 3.3 | 16741 |
| 343 | 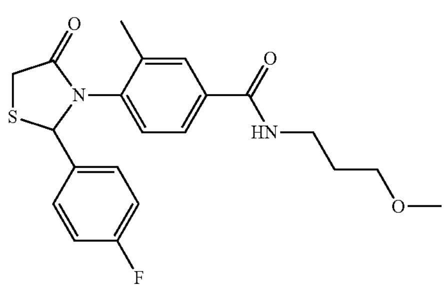 [SMILES: COCCCNC(=O)c1ccc(N2C(=O)CSC2c2ccc(F)cc2)c(C)c1] | 4-[2-(4-Fluorophenyl)-4-oxo-1,3-thiazolidin-3-yl]-N-(3-methoxypropyl)-3-methylbenzamide | 3.7 | 11934 |

TABLE 1-continued

Exemplary compounds and their activities

| No. | Structure | Name | FLIPR Ca$^{2+}$ EC$_{50}$ (µM) | AUC |
|---|---|---|---|---|
| 344 | 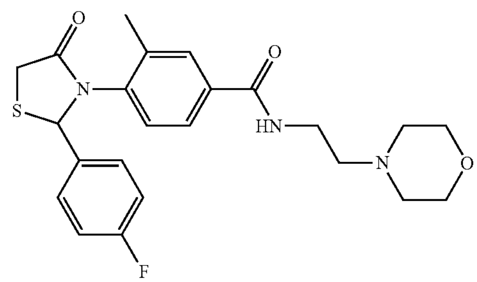 [SMILES: Cc1cc(C(=O)NCCN2CCOCC2)ccc1N1C(=O)CSC1c1ccc(F)cc1] | 4-[2-(4-Fluorophenyl)-4-oxo-1,3-thiazolidin-3-yl]-3-methyl-N-[2-(4-morpholinyl)ethyl]benzamide | 7.0 | 12329 |
| 345 | 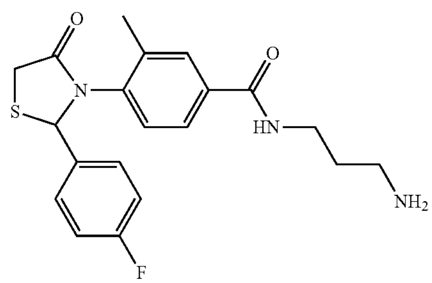 [SMILES: Cc1cc(C(=O)NCCCN)ccc1N1C(=O)CSC1c1ccc(F)cc1] | N-(3-Aminopropyl)-4-[2-(4-fluorophenyl)-4-oxo-1,3-thiazolidin-3-yl]-3-methylbenzamide | — | — |
| 347 | 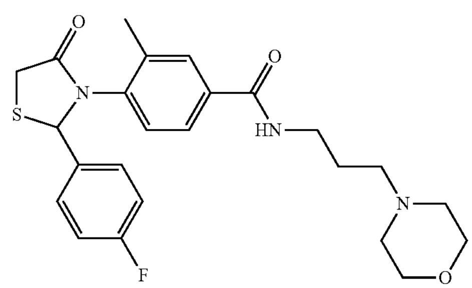 [SMILES: Cc1cc(C(=O)NCCCN2CCOCC2)ccc1N1C(=O)CSC1c1ccc(F)cc1] | 4-[2-(4-Fluorophenyl)-4-oxo-1,3-thiazolidin-3-yl]-3-methyl-N-[3-(4-morpholinyl)propyl]benzamide | 8.2 | 12967 |
| 348 | 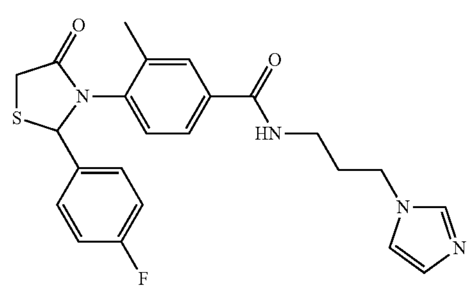 [SMILES: Cc1cc(C(=O)NCCCn2ccnc2)ccc1N1C(=O)CSC1c1ccc(F)cc1] | 4-[2-(4-Fluorophenyl)-4-oxo-1,3-thiazolidin-3-yl]-N-[3-(1H-imidazol-1-yl)propyl]-3-methylbenzamide | 8.8 | 13641 |
| 349 | 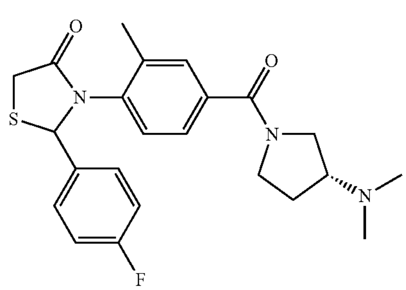 [SMILES: Cc1cc(C(=O)N2CC[C@@H](N(C)C)C2)ccc1N1C(=O)CSC1c1ccc(F)cc1] | 3-(4-{[(3R)-3-(Dimethylamino)-1-pyrrolidinyl]carbonyl}-2-methylphenyl)-2-(4-fluorophenyl)-1,3-thiazolidin-4-one | 10.0 | 11923 |

TABLE 1-continued

Exemplary compounds and their activities

| No. | Structure | Name | FLIPR Ca²⁺ EC$_{50}$ (μM) | AUC |
|---|---|---|---|---|
| 350 | 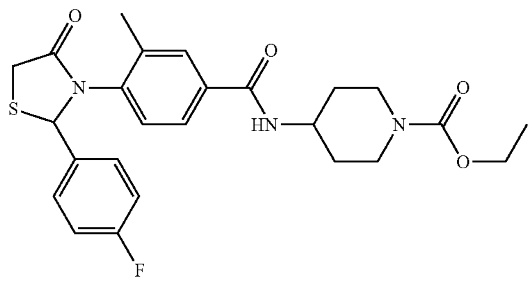 [SMILES: CCOC(=O)N1CCC(NC(=O)c2ccc(N3C(=O)CSC3c3ccc(F)cc3)c(C)c2)CC1] | 4-({4-[2-(4-fluorophenyl)-4-oxo-1,3-thiazolidin-3-yl]-3-methylbenzoyl}amino)-1-piperidinecarboxylate | 4.4 | 12979 |
| 351 | 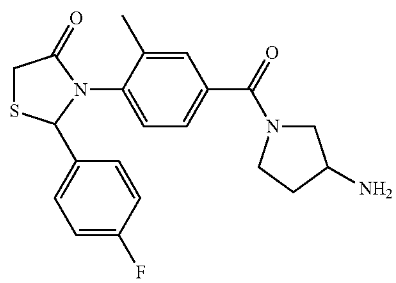 [SMILES: Cc1cc(C(=O)N2CCC(N)C2)ccc1N1C(=O)CSC1c1ccc(F)cc1] | 3-{4-[(3-Amino-1-pyrrolidinyl)carbonyl]-2-methylphenyl}-2-(4-fluorophenyl)-1,3-thiazolidin-4-one | 10.0 | 11205 |
| 353 | 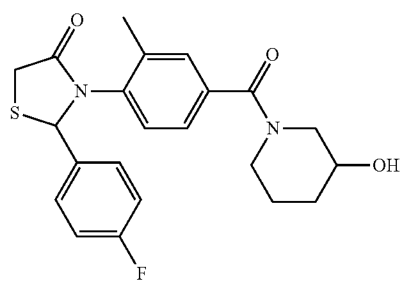 [SMILES: Cc1cc(C(=O)N2CCCC(O)C2)ccc1N1C(=O)CSC1c1ccc(F)cc1] | 2-(4-Fluorophenyl)-3-{4-[(3-hydroxy-1-piperidinyl)carbonyl]-2-methylphenyl}-1,3-thiazolidin-4-one | 7.3 | 11991 |
| 354 | 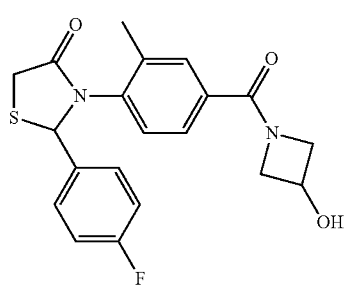 [SMILES: Cc1cc(C(=O)N2CC(O)C2)ccc1N1C(=O)CSC1c1ccc(F)cc1] | 2-(4-Fluorophenyl)-3-{4-[(3-hydroxy-1-azetidinyl)carbonyl]-2-methylphenyl}-1,3-thiazolidin-4-one | 3.6 | 14863 |
| 355 | 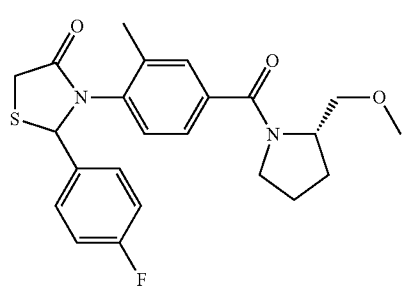 [SMILES: COC[C@@H]1CCCN1C(=O)c1ccc(N2C(=O)CSC2c2ccc(F)cc2)c(C)c1] | 2-(4-Fluorophenyl)-3-(4-{[(2S)-2-(methoxymethyl)-1-pyrrolidinyl]carbonyl}-2-methylphenyl)-1,3-thiazolidin-4-one | 10.0 | 12691 |

TABLE 1-continued

Exemplary compounds and their activities

| No. | Structure | Name | FLIPR Ca$^{2+}$ EC$_{50}$ (μM) | AUC |
|---|---|---|---|---|
| 356 | 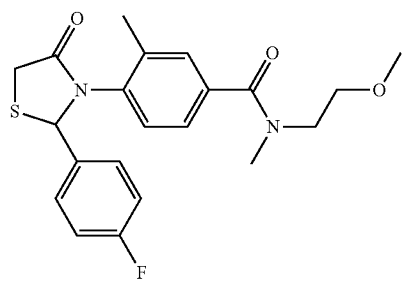 [SMILES: COCCN(C)C(=O)c1ccc(N2C(=O)CSC2c2ccc(F)cc2)c(C)c1] | 4-[2-(4-Fluorophenyl)-4-oxo-1,3-thiazolidin-3-yl]-N-(2-methoxyethyl)-N,3-dimethylbenzamide | 11.8 | 9505 |
| 357 | 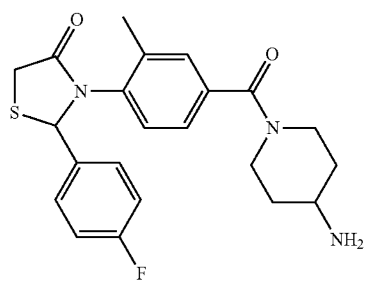 [SMILES: Cc1cc(C(=O)N2CCC(N)CC2)ccc1N1C(=O)CSC1c1ccc(F)cc1] | 3-{4-[(4-Amino-1-piperidinyl)carbonyl]-2-methylphenyl}-2-(4-fluorophenyl)-1,3-thiazolidin-4-one | 10.0 | 12663 |
| 359 | 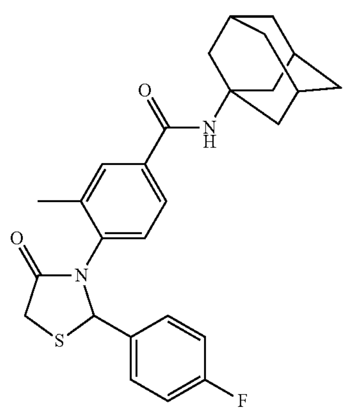 [SMILES: Cc1cc(C(=O)NC23CC4CC(CC(C4)C2)C3)ccc1N1C(=O)CSC1c1ccc(F)cc1] | N-(Adamantan-1-yl)-4-(2-(4-fluorophenyl)-4-oxothiazolidin-3-yl)-3-methylbenzamide | — | — |
| 360 | 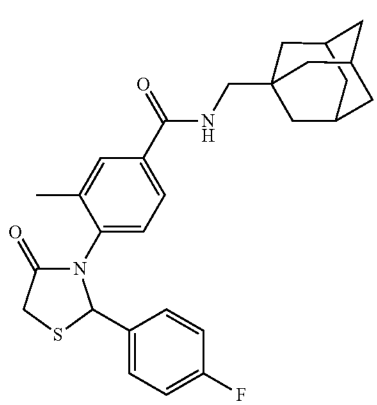 [SMILES: Cc1cc(C(=O)NCC23CC4CC(CC(C4)C2)C3)ccc1N1C(=O)CSC1c1ccc(F)cc1] | N-(Adamantan-1-ylmethyl)-4-(2-(4-fluorophenyl)-4-oxothiazolidin-3-yl)-3-methylbenzamide | — | — |

TABLE 1-continued

Exemplary compounds and their activities

| No. | Structure | Name | FLIPR Ca$^{2+}$ EC$_{50}$ (µM) | AUC |
|---|---|---|---|---|
| 361 | 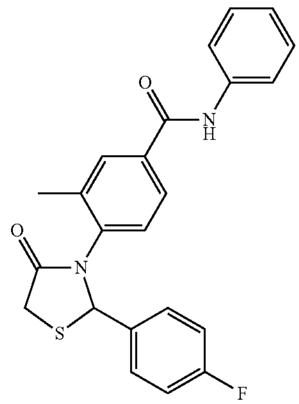 [SMILES: Cc1cc(C(=O)Nc2ccccc2)ccc1N1C(=O)CSC1c1ccc(F)cc1] | 4-[2-(4-Fluorophenyl)-4-oxo-1,3-thiazolidin-3-yl]-3-methyl-N-phenylbenzamide | 8.8 | 6128 |
| 362 | 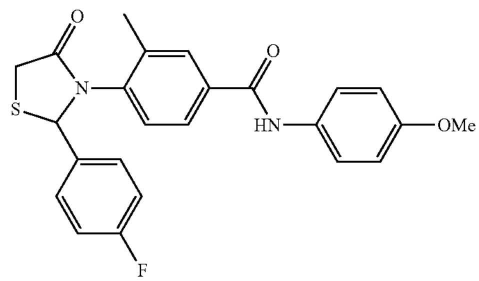 [SMILES: COc1ccc(NC(=O)c2ccc(N3C(=O)CSC3c3ccc(F)cc3)c(C)c2)cc1] | 4-[2-(4-Fluorophenyl)-4-oxo-1,3-thiazolidin-3-yl]-N-(4-methoxyphenyl)-3-methylbenzamide | — | — |
| 363 | 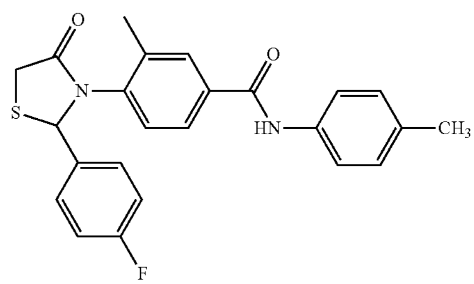 [SMILES: Cc1ccc(NC(=O)c2ccc(N3C(=O)CSC3c3ccc(F)cc3)c(C)c2)cc1] | 4-[2-(4-Fluorophenyl)-4-oxo-1,3-thiazolidin-3-yl]-3-methyl-N-(4-methylphenyl)benzamide | — | — |
| 364 | 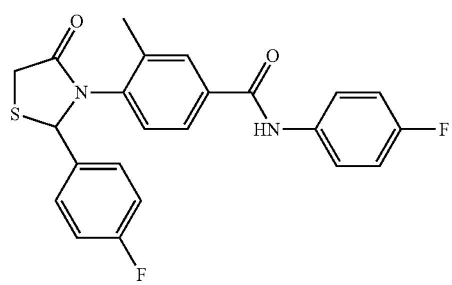 [SMILES: Cc1cc(C(=O)Nc2ccc(F)cc2)ccc1N1C(=O)CSC1c1ccc(F)cc1] | N-(4-Fluorophenyl)-4-[2-(4-fluorophenyl)-4-oxo-1,3-thiazolidin-3-yl]-3-methylbenzamide | — | — |
| 365 | 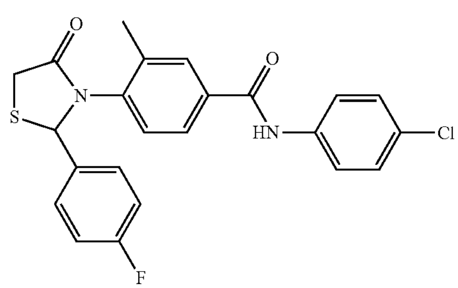 [SMILES: Cc1cc(C(=O)Nc2ccc(Cl)cc2)ccc1N1C(=O)CSC1c1ccc(F)cc1] | N-(4-Chlorophenyl)-4-[2-(4-fluorophenyl)-4-oxo-1,3-thiazolidin-3-yl]-3-methylbenzamide | — | — |

TABLE 1-continued

Exemplary compounds and their activities

| No. | Structure | Name | FLIPR Ca²⁺ $EC_{50}$ (µM) | AUC |
|---|---|---|---|---|
| 366 | 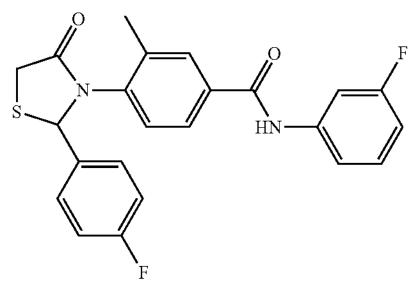 [SMILES: Cc1cc(C(=O)Nc2cccc(F)c2)ccc1N1C(=O)CSC1c1ccc(F)cc1] | N-(3-Fluorophenyl)-4-[2-(4-fluorophenyl)-4-oxo-1,3-thiazolidin-3-yl]-3-methylbenzamide | — | — |
| 367 | 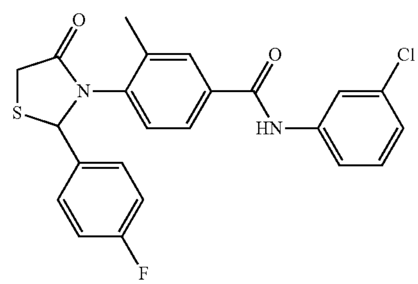 [SMILES: Cc1cc(C(=O)Nc2cccc(Cl)c2)ccc1N1C(=O)CSC1c1ccc(F)cc1] | N-(3-Chlorophenyl)-4-[2-(4-fluorophenyl)-4-oxo-1,3-thiazolidin-3-yl]-3-methylbenzamide | — | — |
| 368 | 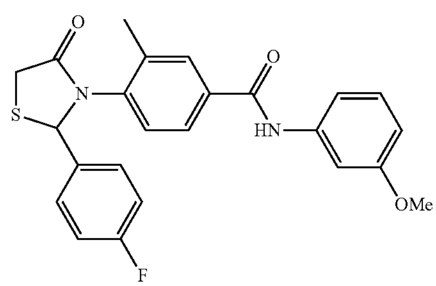 [SMILES: COc1cccc(NC(=O)c2ccc(N3C(=O)CSC3c3ccc(F)cc3)c(C)c2)c1] | 4-[2-(4-Fluorophenyl)-4-oxo-1,3-thiazolidin-3-yl]-N-(3-methoxyphenyl)-3-methylbenzamide | 6.7 | 8915 |
| 369 | 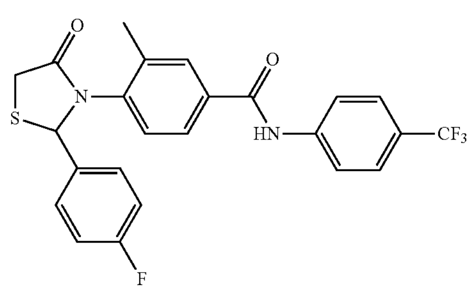 [SMILES: Cc1cc(C(=O)Nc2ccc(C(F)(F)F)cc2)ccc1N1C(=O)CSC1c1ccc(F)cc1] | 4-[2-(4-Fluorophenyl)-4-oxo-1,3-thiazolidin-3-yl]-3-methyl-N-[4-(trifluoromethyl)phenyl]benzamide | — | — |
| 370 | 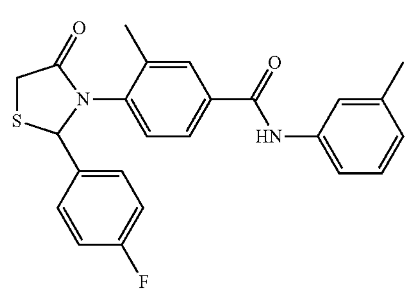 [SMILES: Cc1cccc(NC(=O)c2ccc(N3C(=O)CSC3c3ccc(F)cc3)c(C)c2)c1] | 4-[2-(4-Fluorophenyl)-4-oxo-1,3-thiazolidin-3-yl]-3-methyl-N-(3-methylphenyl)benzamide | — | — |

TABLE 1-continued

Exemplary compounds and their activities

| No. | Structure | Name | FLIPR Ca$^{2+}$ EC$_{50}$ (µM) | AUC |
|---|---|---|---|---|
| 371 | 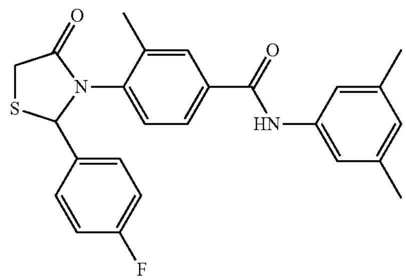 [SMILES: Cc1cc(C)cc(NC(=O)c2ccc(N3C(=O)CSC3c3ccc(F)cc3)c(C)c2)c1] | N-(3,5-Dimethylphenyl)-4-[2-(4-fluorophenyl)-4-oxo-1,3-thiazolidin-3-yl]-3-methylbenzamide | — | — |
| 372 | 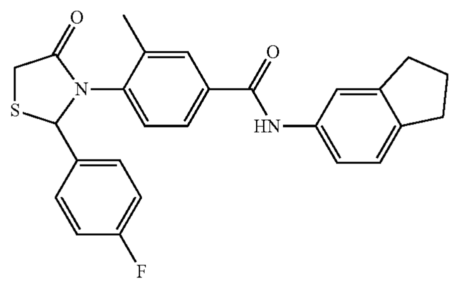 [SMILES: Cc1cc(C(=O)Nc2ccc3c(c2)CCC3)ccc1N1C(=O)CSC1c1ccc(F)cc1] | N-(2,3-Dihydro-1H-inden-5-yl)-4-[2-(4-fluorophenyl)-4-oxo-1,3-thiazolidin-3-yl]-3-methylbenzamide | — | — |
| 373 | 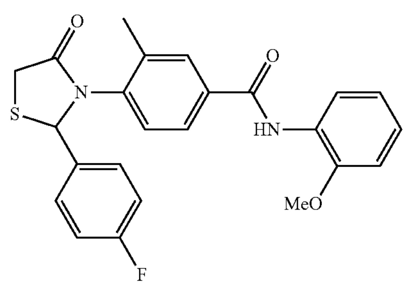 [SMILES: COc1ccccc1NC(=O)c1ccc(N2C(=O)CSC2c2ccc(F)cc2)c(C)c1] | 4-[2-(4-Fluorophenyl)-4-oxo-1,3-thiazolidin-3-yl]-N-(2-methoxyphenyl)-3-methylbenzamide | 13.6 | 12223 |
| 374 | 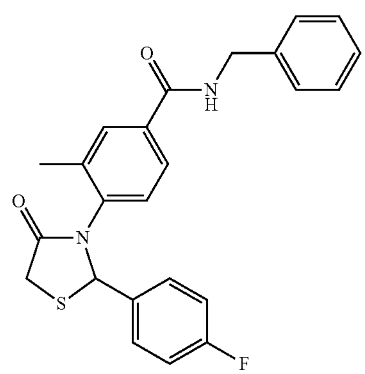 [SMILES: Cc1cc(C(=O)NCc2ccccc2)ccc1N1C(=O)CSC1c1ccc(F)cc1] | N-Benzyl-4-[2-(4-fluorophenyl)-4-oxo-1,3-thiazolidin-3-yl]-3-methylbenzamide | 5.1 | 6726 |
| 375 | 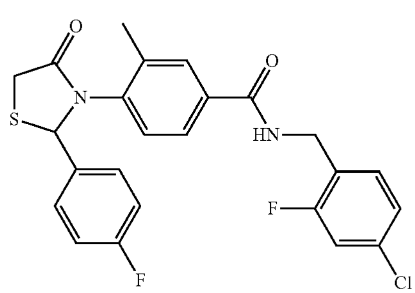 [SMILES: Cc1cc(C(=O)NCc2ccc(Cl)cc2F)ccc1N1C(=O)CSC1c1ccc(F)cc1] | N-(4-Chloro-2-fluorobenzyl)-4-[2-(4-fluorophenyl)-4-oxo-1,3-thiazolidin-3-yl]-3-methylbenzamide | 3.8 | 4172 |

TABLE 1-continued

Exemplary compounds and their activities

| No. | Structure | Name | FLIPR Ca²⁺ EC$_{50}$ (µM) | AUC |
|---|---|---|---|---|
| 376 | 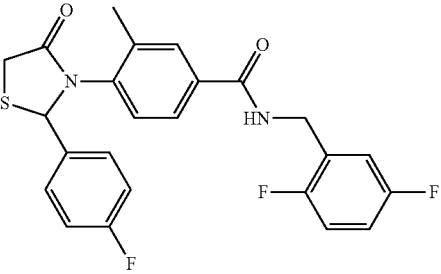 [SMILES: Cc1cc(C(=O)NCc2cc(F)ccc2F)ccc1N1C(=O)CSC1c1ccc(F)cc1] | N-(2,5-Difluorobenzyl)-4-[2-(4-fluorophenyl)-4-oxo-1,3-thiazolidin-3-yl]-3-methylbenzamide | 1.0 | 8823 |
| 377 | 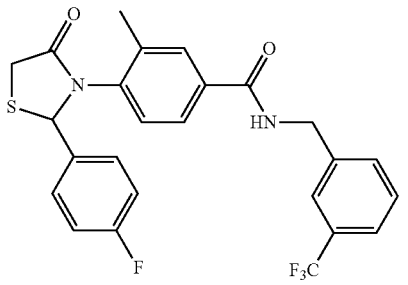 [SMILES: Cc1cc(C(=O)NCc2cccc(C(F)(F)F)c2)ccc1N1C(=O)CSC1c1ccc(F)cc1] | 4-[2-(4-Fluorophenyl)-4-oxo-1,3-thiazolidin-3-yl]-3-methyl-N-[3-(trifluoromethyl)benzyl]benzamide | 12.5 | 12637 |
| 378 | 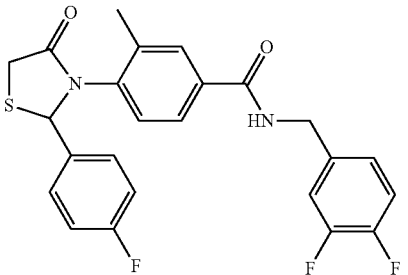 [SMILES: Cc1cc(C(=O)NCc2ccc(F)c(F)c2)ccc1N1C(=O)CSC1c1ccc(F)cc1] | N-(3,4-Difluorobenzyl)-4-[2-(4-fluorophenyl)-4-oxo-1,3-thiazolidin-3-yl]-3-methylbenzamide | 6.3 | 15891 |
| 379 | 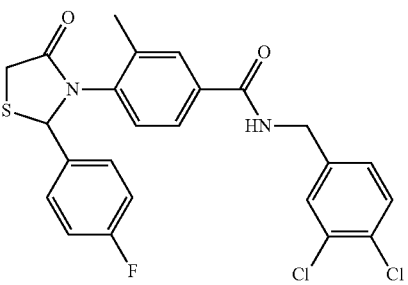 [SMILES: Cc1cc(C(=O)NCc2ccc(Cl)c(Cl)c2)ccc1N1C(=O)CSC1c1ccc(F)cc1] | N-(3,4-Dichlorobenzyl)-4-[2-(4-fluorophenyl)-4-oxo-1,3-thiazolidin-3-yl]-3-methylbenzamide | — | — |
| 380 | 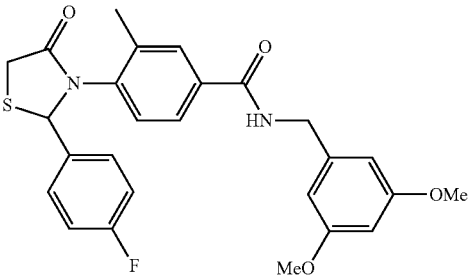 [SMILES: COc1cc(CNC(=O)c2ccc(N3C(=O)CSC3c3ccc(F)cc3)c(C)c2)cc(OC)c1] | N-(3,5-Dimethoxybenzyl)-4-[2-(4-fluorophenyl)-4-oxo-1,3-thiazolidin-3-yl]-3-methylbenzamide | 8.2 | 10013 |

TABLE 1-continued

Exemplary compounds and their activities

| No. | Structure | Name | FLIPR Ca$^{2+}$ EC$_{50}$ (μM) | AUC |
|---|---|---|---|---|
| 381 | 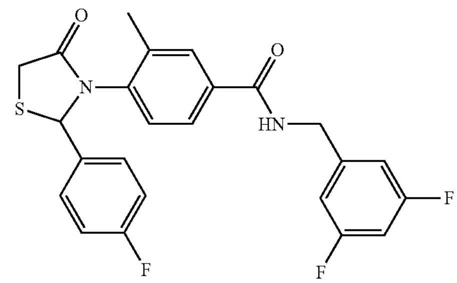 [SMILES: Cc1cc(C(=O)NCc2cc(F)cc(F)c2)ccc1N1C(=O)CSC1c1ccc(F)cc1] | N-(3,5-Difluorobenzyl)-4-[2-(4-fluorophenyl)-4-oxo-1,3-thiazolidin-3-yl]-3-methylbenzamide | 8.2 | 6035 |
| 382 | 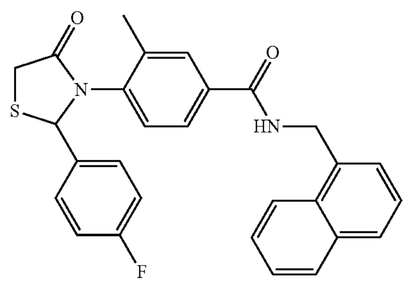 [SMILES: Cc1cc(C(=O)NCc2cccc3ccccc23)ccc1N1C(=O)CSC1c1ccc(F)cc1] | 4-[2-(4-Fluorophenyl)-4-oxo-1,3-thiazolidin-3-yl]-3-methyl-N-(1-naphthalenylmethyl)benzamide | — | — |
| 383 | 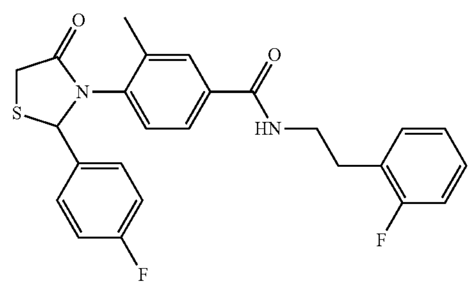 [SMILES: Cc1cc(C(=O)NCCc2ccccc2F)ccc1N1C(=O)CSC1c1ccc(F)cc1] | N-[2-(2-Fluorophenyl)ethyl]-4-[2-(4-fluorophenyl)-4-oxo-1,3-thiazolidin-3-yl]-3-methylbenzamide | 6.9 | 5504 |
| 384 | 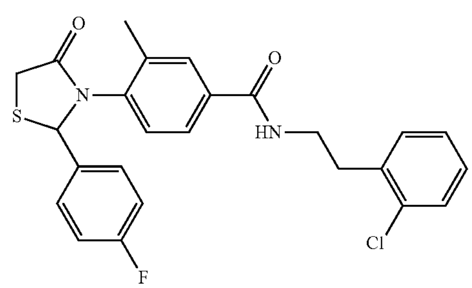 [SMILES: Cc1cc(C(=O)NCCc2ccccc2Cl)ccc1N1C(=O)CSC1c1ccc(F)cc1] | N-[2-(2-Chlorophenyl)ethyl]-4-[2-(4-fluorophenyl)-4-oxo-1,3-thiazolidin-3-yl]-3-methylbenzamide | 6.6 | 5742 |
| 385 | 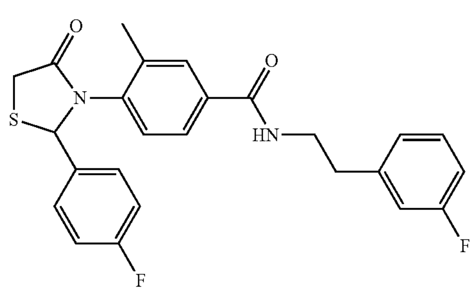 [SMILES: Cc1cc(C(=O)NCCc2cccc(F)c2)ccc1N1C(=O)CSC1c1ccc(F)cc1] | N-[2-(3-Fluorophenyl)ethyl]-4-[2-(4-fluorophenyl)-4-oxo-1,3-thiazolidin-3-yl]-3-methylbenzamide | 3.9 | 7501 |

TABLE 1-continued

Exemplary compounds and their activities

| No. | Structure | Name | FLIPR Ca$^{2+}$ EC$_{50}$ (μM) | AUC |
|---|---|---|---|---|
| 386 | 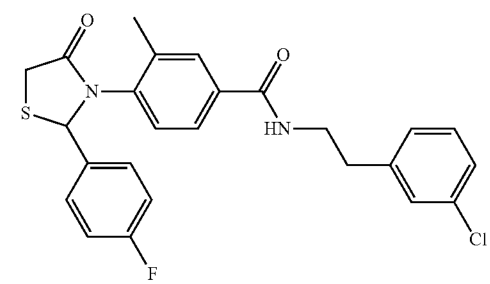 [SMILES: Cc1cc(C(=O)NCCc2cccc(Cl)c2)ccc1N1C(=O)CSC1c1ccc(F)cc1] | N-[2-(3-Chlorophenyl)ethyl]-4-[2-(4-fluorophenyl)-4-oxo-1,3-thiazolidin-3-yl]-3-methylbenzamide | 4.2 | 5727 |
| 387 | 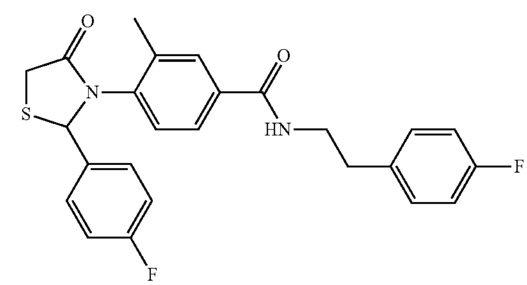 [SMILES: Cc1cc(C(=O)NCCc2ccc(F)cc2)ccc1N1C(=O)CSC1c1ccc(F)cc1] | N-[2-(4-Fluorophenyl)ethyl]-4-[2-(4-fluorophenyl)-4-oxo-1,3-thiazolidin-3-yl]-3-methylbenzamide | 4.0 | 5770 |
| 388 | 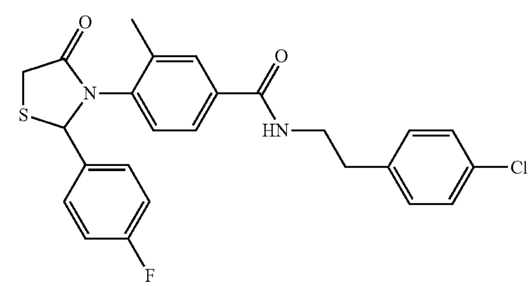 [SMILES: Cc1cc(C(=O)NCCc2ccc(Cl)cc2)ccc1N1C(=O)CSC1c1ccc(F)cc1] | N-[2-(4-Chlorophenyl)ethyl]-4-[2-(4-fluorophenyl)-4-oxo-1,3-thiazolidin-3-yl]-3-methybenzamide | 2.0 | 2951 |
| 389 | 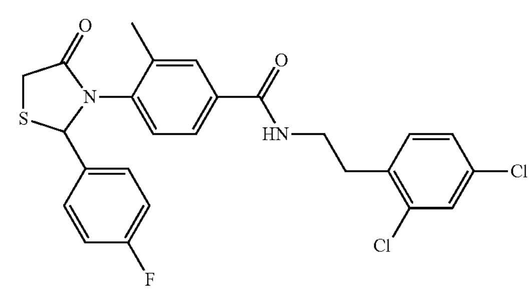 [SMILES: Cc1cc(C(=O)NCCc2ccc(Cl)cc2Cl)ccc1N1C(=O)CSC1c1ccc(F)cc1] | N-[2-(2,4-Dichlorophenyl)ethyl]-4-[2-(4-fluorophenyl)-4-oxo-1,3-thiazolidin-3-yl]-3-methylbenzamide | — | — |
| 390 | 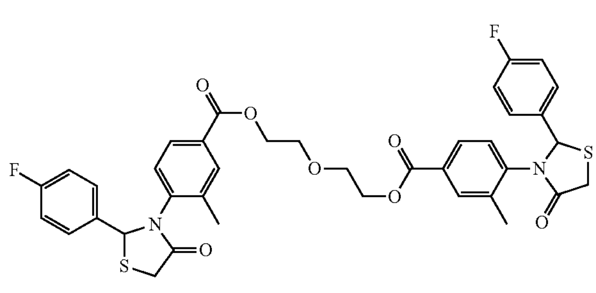 [SMILES: Cc1cc(C(=O)OCCOCCOC(=O)c2ccc(N3C(=O)CSC3c3ccc(F)cc3)c(C)c2)ccc1N1C(=O)CSC1c1ccc(F)cc1] | Oxydi-2,1-ethanediyl bis{4-[2-(4-fluorophenyl)-4-oxo-1,3-thiazolidin-3-yl]-3-methylbenzoate} | 13.9 | 7399 |

TABLE 1-continued

Exemplary compounds and their activities

| No. | Structure | Name | FLIPR Ca²⁺ EC$_{50}$ (μM) | AUC |
|---|---|---|---|---|
| 391 | 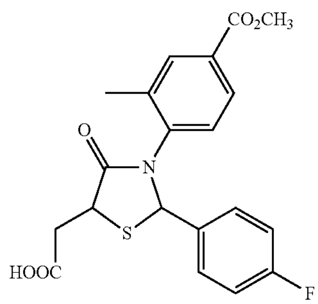 [SMILES: COC(=O)c1ccc(N2C(=O)C(CC(=O)O)SC2c2ccc(F)cc2)c(C)c1] | {2-(4-Fluorophenyl)-3-[4-(methoxycarbonyl)-2-methylphenyl]-4-oxo-1,3-thiazolidin-5-yl}acetic acid | — | — |
| 393 | 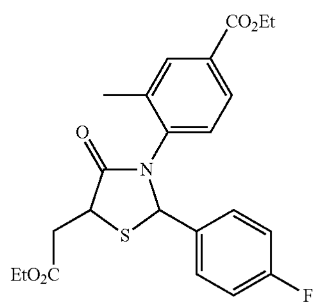 [SMILES: CCOC(=O)CC1SC(c2ccc(F)cc2)N(c2ccc(C(=O)OCC)cc2C)C1=O] | Ethyl 4-[5-(2-ethoxy-2-oxoethyl)-2-(4-fluorophenyl)-4-oxo-1,3-thiazolidin-3-yl]-3-methylbenzoate | — | — |
| 394 | 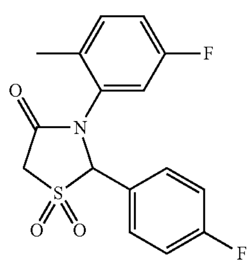 [SMILES: Cc1ccc(F)cc1N1C(=O)CS(=O)(=O)C1c1ccc(F)cc1] | 3-(5-Fluoro-2-methylphenyl)-2-(4-fluorophenyl)thiazolidin-4-one 1,1-dioxide | — | — |
| 395 | 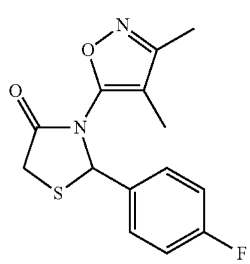 [SMILES: Cc1noc(N2C(=O)CSC2c2ccc(F)cc2)c1C] | 3-(3,4-Dimethyl-1,2-oxazol-5-yl)-2-(4-fluorophenyl)-1,3-thiazolidin-4-one | 12.0 | 7107 |
| 396 | 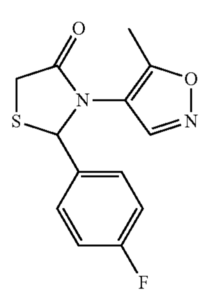 [SMILES: Cc1oncc1N1C(=O)CSC1c1ccc(F)cc1] | 2-(4-Fluorophenyl)-3-(5-methyl-1,2-oxazol-4-yl)-1,3-thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 397 | 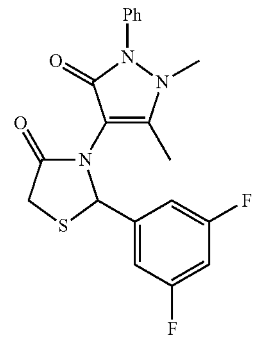 [SMILES: Cc1c(N2C(=O)CSC2c2cc(F)cc(F)c2)c(=O)n(-c2ccccc2)n1C] | 2-(3,5-Difluorophenyl)-3-(1,5-dimethyl-3-oxo-2-phenyl-2,3-dihydro-1H-pyrazol-4-yl)thiazolidin-4-one | — | — |
| 398 | 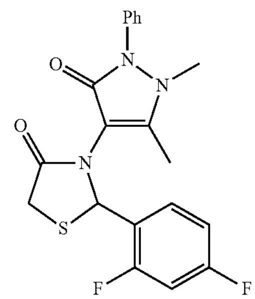 [SMILES: Cc1c(N2C(=O)CSC2c2ccc(F)cc2F)c(=O)n(-c2ccccc2)n1C] | 2-(2,4-Difluorophenyl)-3-(1,5-dimethyl-3-oxo-2-phenyl-2,3-dihydro-1H-pyrazol-4-yl)thiazolidin-4-one\ | — | — |
| 399 | 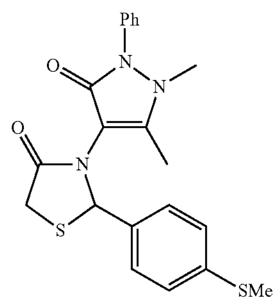 [SMILES: CSc1ccc(C2SCC(=O)N2c2c(C)n(C)n(-c3ccccc3)c2=O)cc1] | 3-(1,5-Dimethyl-3-oxo-2-phenyl-2,3-dihydro-1H-pyrazol-4-yl)-2-(4-(methylthio)phenyl)thiazolidin-4-one | — | — |
| 400 | 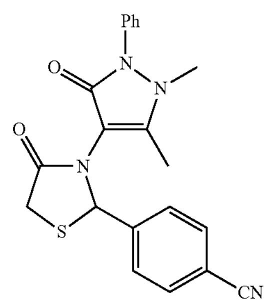 [SMILES: Cc1c(N2C(=O)CSC2c2ccc(C#N)cc2)c(=O)n(-c2ccccc2)n1C] | 4-(3-(1,5-Dimethyl-3-oxo-2-phenyl-2,3-dihydro-1H-pyrazol-4-yl)-4-oxothiazolidin-2-yl)benzonitrile | — | — |
| 401 | 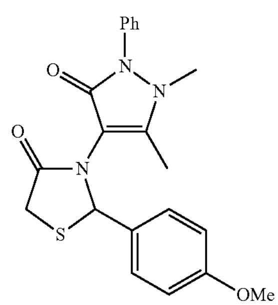 [SMILES: COc1ccc(C2SCC(=O)N2c2c(C)n(C)n(-c3ccccc3)c2=O)cc1] | 3-(1,5-Dimethyl-3-oxo-2-phenyl-2,3-dihydro-1H-pyrazol-4-yl)-2-(4-methoxyphenyl)thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 402 | 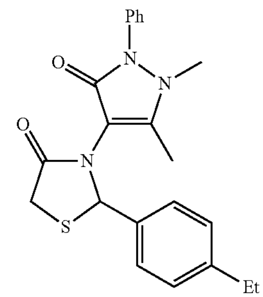 [SMILES: CCc1ccc(C2SCC(=O)N2c2c(C)n(C)n(-c3ccccc3)c2=O)cc1] | 3-(1,5-Dimethyl-3-oxo-2-phenyl-2,3-dihydro-1H-pyrazol-4-yl)-2-(4-ethylphenyl)thiazolidin-4-one | — | — |
| 403 | 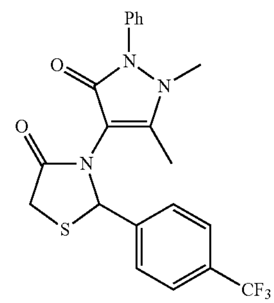 [SMILES: Cc1c(N2C(=O)CSC2c2ccc(C(F)(F)F)cc2)c(=O)n(-c2ccccc2)n1C] | 3-(1,5-Dimethyl-3-oxo-2-phenyl-2,3-dihydro-1H-pyrazol-4-yl)-2-(4-(trifluoromethyl)phenyl)thiazolidin-4-one | — | — |
| 404 | 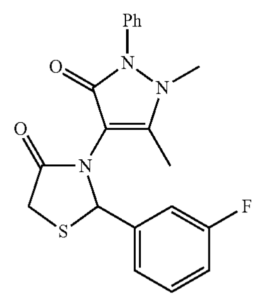 [SMILES: Cc1c(N2C(=O)CSC2c2cccc(F)c2)c(=O)n(-c2ccccc2)n1C] | 3-(1,5-Dimethyl-3-oxo-2-phenyl-2,3-dihydro-1H-pyrazol-4-yl)-2-(3-fluorophenyl)thiazolidin-4-one | 21.8 | 7127 |
| 405 | 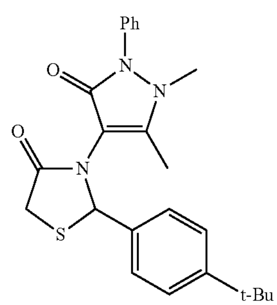 [SMILES: Cc1c(N2C(=O)CSC2c2ccc(C(C)(C)C)cc2)c(=O)n(-c2ccccc2)n1C] | 2-(4-(tert-Butyl)phenyl)-3-(1,5-dimethyl-3-oxo-2-phenyl-2,3-dihydro-1H-pyrazol-4-yl)thiazolidin-4-one | — | — |
| 406 | 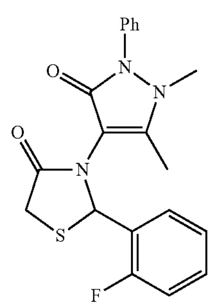 [SMILES: Cc1c(N2C(=O)CSC2c2ccccc2F)c(=O)n(-c2ccccc2)n1C] | 3-(1,5-Dimethyl-3-oxo-2-phenyl-2,3-dihydro-1H-pyrazol-4-yl)-2-(2-fluorophenyl)thiazolidin-4-one | 31.2 | 9974 |

TABLE 1-continued

Exemplary compounds and their activities

| No. | Structure | Name | FLIPR Ca$^{2+}$ EC$_{50}$ (μM) | AUC |
|---|---|---|---|---|
| 407 | 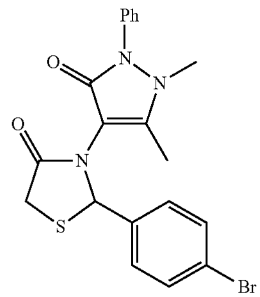 [SMILES: Cc1c(N2C(=O)CSC2c2ccc(Br)cc2)c(=O)n(-c2ccccc2)n1C] | 2-(4-Bromophenyl)-3-(1,5-dimethyl-3-oxo-2-phenyl-2,3-dihydro-1H-pyrazol-4-yl)thiazolidin-4-one | — | — |
| 408 | 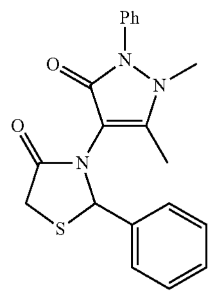 [SMILES: Cc1c(N2C(=O)CSC2c2ccccc2)c(=O)n(-c2ccccc2)n1C] | 3-(1,5-Dimethyl-3-oxo-2-phenyl-2,3-dihydro-1H-pyrazol-4-yl)-2-phenylthiazolidin-4-one | 12.7 | 9281 |
| 409 | 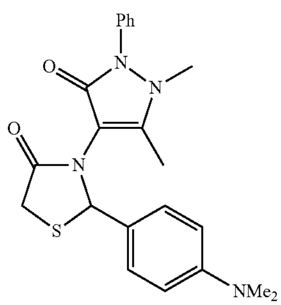 [SMILES: Cc1c(N2C(=O)CSC2c2ccc(N(C)C)cc2)c(=O)n(-c2ccccc2)n1C] | 3-(1,5-Dimethyl-3-oxo-2-phenyl-2,3-dihydro-1H-pyrazol-4-yl)-2-(4-(dimethylamino)phenyl)thiazolidin-4-one | — | — |
| 410 | 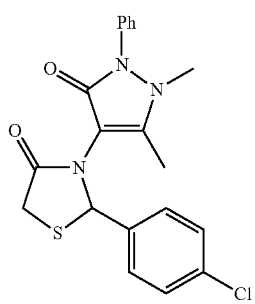 [SMILES: Cc1c(N2C(=O)CSC2c2ccc(Cl)cc2)c(=O)n(-c2ccccc2)n1C] | 2-(4-Chlorophenyl)-3-(1,5-dimethyl-3-oxo-2-phenyl-2,3-dihydro-1H-pyrazol-4-yl)thiazolidin-4-one | — | — |
| 411 | 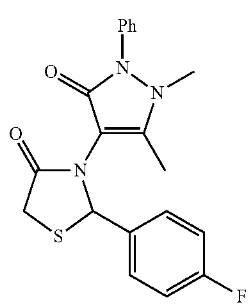 [SMILES: Cc1c(N2C(=O)CSC2c2ccc(F)cc2)c(=O)n(-c2ccccc2)n1C] | 3-(1,5-Dimethyl-3-oxo-2-phenyl-2,3-dihydro-1H-pyrazol-4-yl)-2-(4-fluorophenyl)thiazolidin-4-one | 20.0 | 8099 |

TABLE 1-continued

Exemplary compounds and their activities

| No. | Structure | Name | FLIPR Ca$^{2+}$ EC$_{50}$ (μM) | AUC |
|---|---|---|---|---|
| 412 | 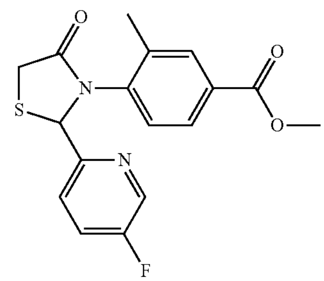 [SMILES: COC(=O)c1ccc(N2C(=O)CSC2c2ccc(F)cn2)c(C)c1] | Methyl 4-[2-(5-fluoro-2-pyridinyl)-4-oxo-1,3-thiazolidin-3-yl]-3-methylbenzoate | — | — |
| 413 | 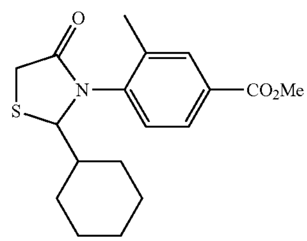 [SMILES: COC(=O)c1ccc(N2C(=O)CSC2C2CCCCC2)c(C)c1] | Methyl 4-(2-cyclohexyl-4-oxo-1,3-thiazolidin-3-yl)-3-methylbenzoate | — | — |
| 414 | 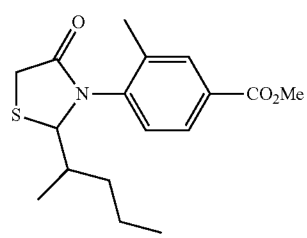 [SMILES: CCCC(C)C1SCC(=O)N1c1ccc(C(=O)OC)cc1C] | Methyl 3-methyl-4-[4-oxo-2-(2-pentanyl)-1,3-thiazolidin-3-yl]benzoate | — | — |
| 415 | 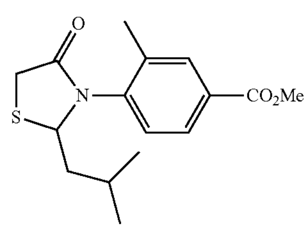 [SMILES: COC(=O)c1ccc(N2C(=O)CSC2CC(C)C)c(C)c1] | Methyl 3-methyl-4-[2-(2-methylpropyl)-4-oxo-1,3-thiazolidin-3-yl]benzoate | — | — |
| 416 | 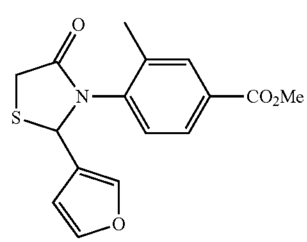 [SMILES: COC(=O)c1ccc(N2C(=O)CSC2c2ccoc2)c(C)c1] | Methyl 4-[2-(3-furanyl)-4-oxo-1,3-thiazolidin-3-yl]-3-methylbenzoate | 11.7 | 6514 |
| 417 | 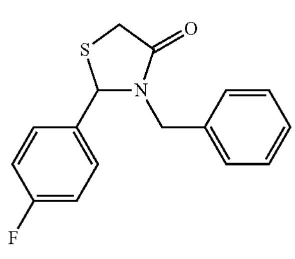 [SMILES: O=C1CSC(c2ccc(F)cc2)N1Cc1ccccc1] | 3-Benzyl-2-(4-fluorophenyl)-1,3-thiazolidin-4-one | — | — |

TABLE 1-continued

Exemplary compounds and their activities

| No. | Structure | Name | FLIPR Ca$^{2+}$ EC$_{50}$ (µM) | AUC |
|---|---|---|---|---|
| 418 | 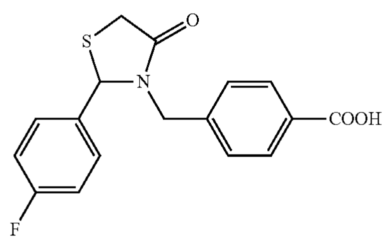 [SMILES: O=C(O)c1ccc(CN2C(=O)CSC2c2ccc(F)cc2)cc1] | 4-{[2-(4-Fluorophenyl)-4-oxo-1,3-thiazolidin-3-yl]methyl}benzoic acid | — | — |
| 421 | 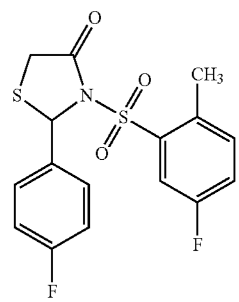 [SMILES: Cc1ccc(F)cc1S(=O)(=O)N1C(=O)CSC1c1ccc(F)cc1] | 3-[(5-Fluoro-2-methylphenyl)sulfonyl]-2-(4-fluorophenyl)-1,3-thiazolidin-4-one | — | — |
| 423 | 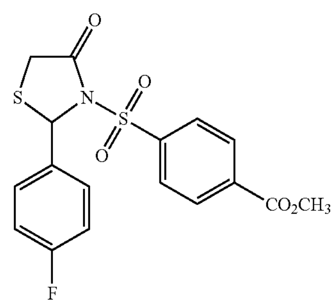 [SMILES: COC(=O)c1ccc(S(=O)(=O)N2C(=O)CSC2c2ccc(F)cc2)cc1] | Methyl 4-{[2-(4-fluorophenyl)-4-oxo-1,3-thiazolidin-3-yl]sulfonyl}benzoate | — | — |
| 424 | 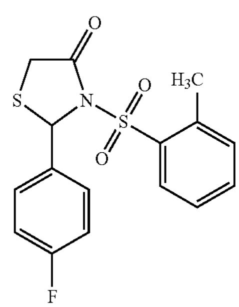 [SMILES: Cc1ccccc1S(=O)(=O)N1C(=O)CSC1c1ccc(F)cc1] | 2-(4-Fluorophenyl)-3-[(2-methylphenyl)sulfonyl]-1,3-thiazolidin-4-one | — | — |
| 425 | 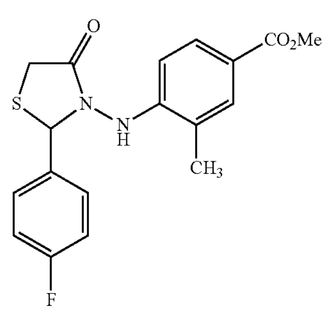 [SMILES: COC(=O)c1ccc(NN2C(=O)CSC2c2ccc(F)cc2)c(C)c1] | Methyl 4-{[2-(4-fluorophenyl)-4-oxo-1,3-thiazolidin-3-yl]amino}-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 427 | 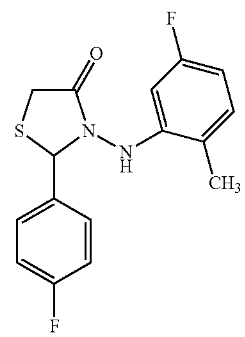 [SMILES: Cc1ccc(F)cc1NN1C(=O)CSC1c1ccc(F)cc1] | 3-[(5-Fluoro-2-methylphenyl)amino]-2-(4-fluorophenyl)-1,3-thiazolidin-4-one | — | — |
| 429 | 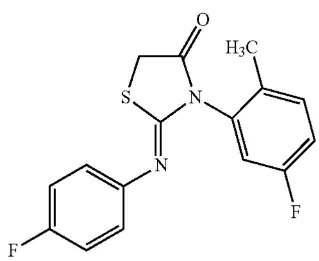 [SMILES: Cc1ccc(F)cc1N1C(=O)CS/C1=N\c1ccc(F)cc1] | (2Z)-3-(5-Fluoro-2-methylphenyl)-2-[(4-fluorophenyl)imino]-1,3-thiazolidin-4-one | — | — |
| 431 | 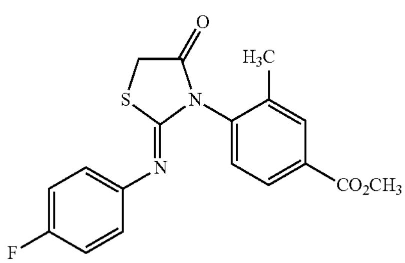 [SMILES: COC(=O)c1ccc(N2C(=O)CS/C2=N\c2ccc(F)cc2)c(C)c1] | Methyl 4-{(2Z)-2-[(4-fluorophenyl)imino]-4-oxo-1,3-thiazolidin-3-yl}-3-methylbenzoate | — | — |
| 433 | 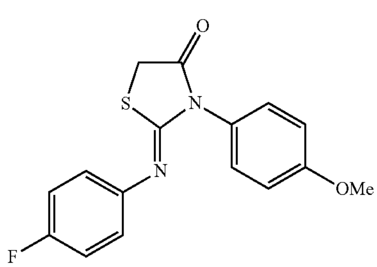 [SMILES: COc1ccc(N2C(=O)CS/C2=N\c2ccc(F)cc2)cc1] | (2Z)-2-[(4-Fluorophenyl)imino]-3-(4-methoxyphenyl)-1,3-thiazolidin-4-one | — | — |
| 435 | 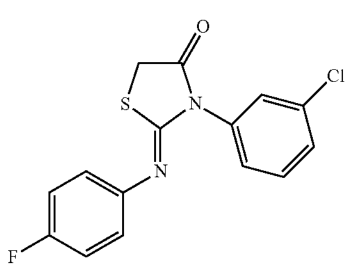 [SMILES: O=C1CS/C(=N\c2ccc(F)cc2)N1c1cccc(Cl)c1] | (2Z)-3-(3-Chlorophenyl)-2-[(4-fluorophenyl)imino]-1,3-thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 437 | 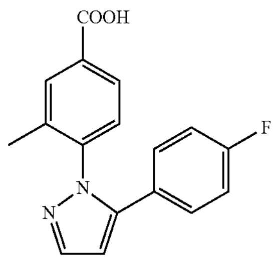 [SMILES: Cc1cc(C(=O)O)ccc1-n1nccc1-c1ccc(F)cc1] | 4-[5-(4-Fluorophenyl)-1H-pyrazol-1-yl]-3-methylbenzoic acid | — | — |
| 442 | 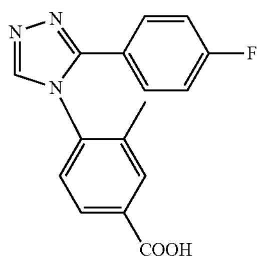 [SMILES: Cc1cc(C(=O)O)ccc1-n1cnnc1-c1ccc(F)cc1] | 4-[3-(4-Fluorophenyl)-4H-1,2,4-triazol-4-yl]-3-methylbenzoic acid | — | — |
| 446 | 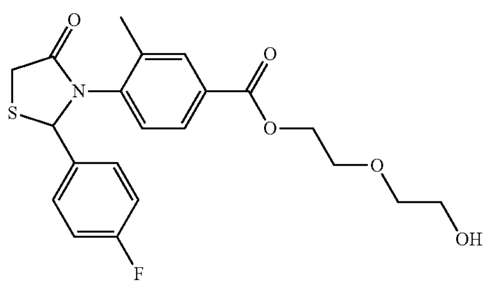 [SMILES: Cc1cc(C(=O)OCCOCCO)ccc1N1C(=O)CSC1c1ccc(F)cc1] | 2-(2-Hydroxyethoxy)ethyl 4-[2-(4-fluorophenyl)-4-oxo-1,3-thiazolidin-3-yl]-3-methylbenzoate | — | — |
| 449 | 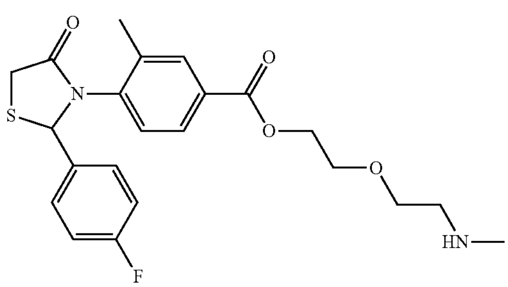 [SMILES: CNCCOCCOC(=O)c1ccc(N2C(=O)CSC2c2ccc(F)cc2)c(C)c1] | 2-[2-(Methylamino)ethoxy]ethyl 4-[2-(4-fluorophenyl)-4-oxo-1,3-thiazolidin-3-yl]-3-methylbenzoate | — | — |
| 453 | 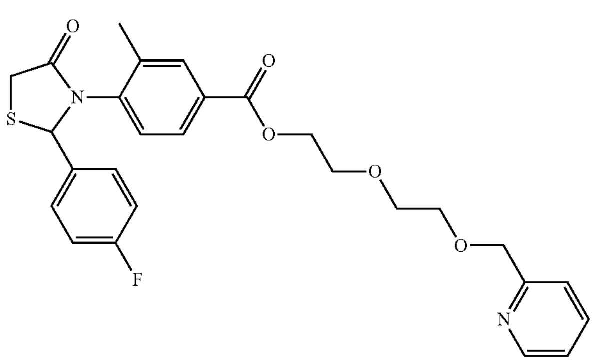 [SMILES: Cc1cc(C(=O)OCCOCCOCc2ccccn2)ccc1N1C(=O)CSC1c1ccc(F)cc1] | 2-[2-(Pyridin-2-ylmethoxy)ethoxy]ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 456 | 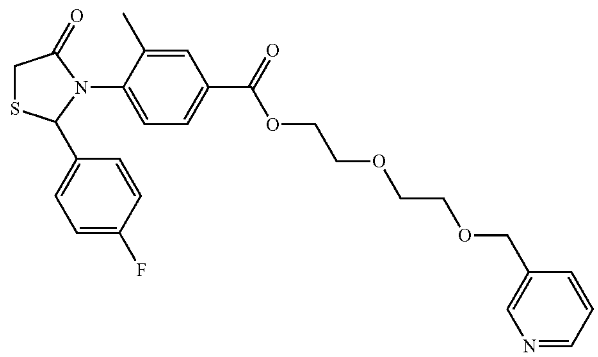 [SMILES: Cc1cc(C(=O)OCCOCCOCc2ccncc2)ccc1N1C(=O)CSC1c1ccc(F)cc1] | 2-[2-(Pyridin-3-ylmethoxy)ethoxy]ethyl 4-[2-(4-fluorophenyl)-4-oxo-1,3-thiazolidin-3-yl]-3-methylbenzoate | — | — |
| 458 | 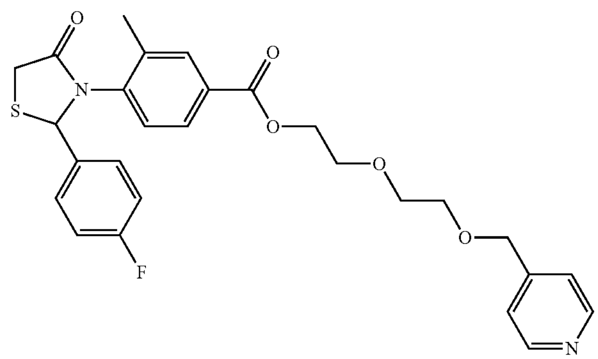 | 2-[2-(Pyridin-4-ylmethoxy)ethoxy]ethyl 4-[2-(4-fluorophenyl)-4-oxo-1,3-thiazolidin-3-yl]-3-methylbenzoate | — | — |
| 460 | 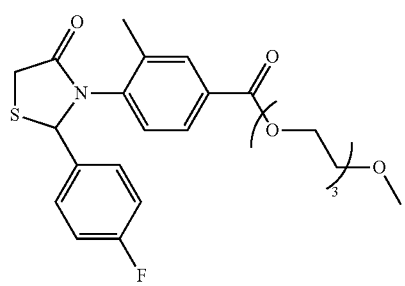 | 2-[2-(2-Methoxyethoxy)ethoxy]ethyl 4-[2-(4-fluorophenyl)-4-oxo-1,3-thiazolidin-3-yl]-3-methylbenzoate | — | — |
| 461 | 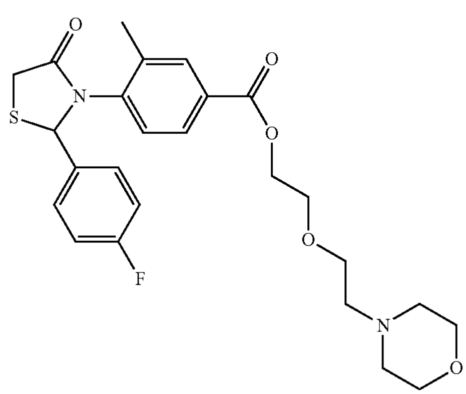 [SMILES: Cc1cc(C(=O)OCCOCCN2CCOCC2)ccc1N1C(=O)CSC1c1ccc(F)cc1] | 2-[2-(Morpholin-4-yl)ethoxy]ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (µM) | AUC |
|---|---|---|---|---|
| 463 | 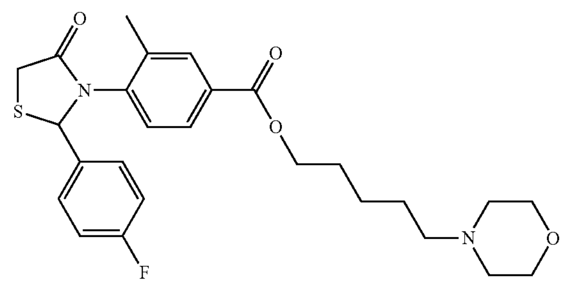 [SMILES: Cc1cc(C(=O)OCCCCCN2CCOCC2)ccc1N1C(=O)CSC1c1ccc(F)cc1] | 5-(Morpholin-4-yl)pentyl 4-[2-(4-fluorophenyl)-4-oxo-1,3-thiazolidin-3-yl]-3-methylbenzoate | — | — |
| 465 | 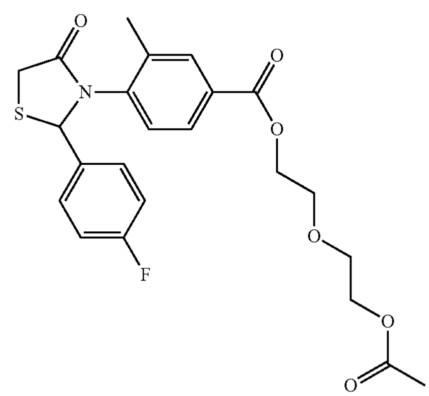 [SMILES: CC(=O)OCCOCCOC(=O)c1ccc(N2C(=O)CSC2c2ccc(F)cc2)c(C)c1] | 2-[2-(Acetyloxy)ethoxy]ethyl 4-[2-(4-fluorophenyl)-4-oxo-1,3-thiazolidin-3-yl]-3-methylbenzoate | — | — |
| 467 | 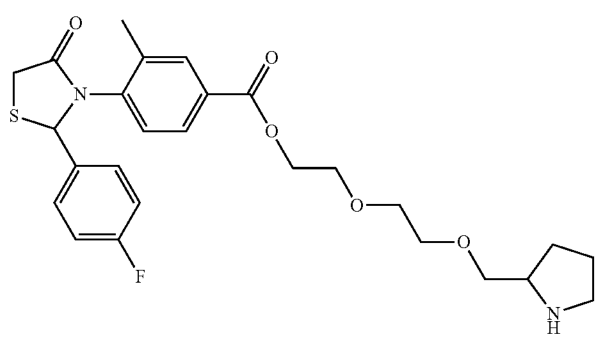 [SMILES: Cc1cc(C(=O)OCCOCCOCC2CCCN2)ccc1N1C(=O)CSC1c1ccc(F)cc1] | 2-[2-(Pyrrolidin-2-ylmethoxy)ethoxy]ethyl 4-[2-(4-fluorophenyl)-4-oxo-1,3-thiazolidin-3-yl]-3-methylbenzoate | — | — |
| 471 | 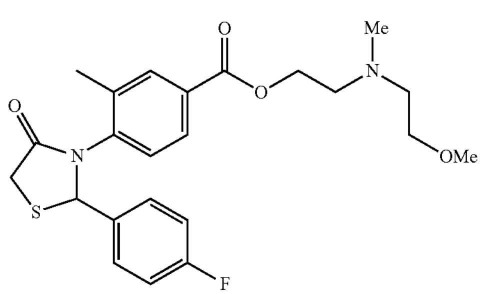 [SMILES: COCCN(C)CCOC(=O)c1ccc(N2C(=O)CSC2c2ccc(F)cc2)c(C)c1] | 2-[(2-Methoxyethyl)(methyl)amino]ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 474 | 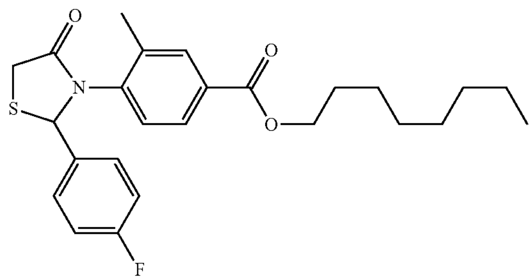 [SMILES: CCCCCCCCOC(=O)c1ccc(N2C(=O)CSC2c2ccc(F)cc2)c(C)c1] | Octyl 4-[2-(4-fluorophenyl)-4-oxo-1,3-thiazolidin-3-yl]-3-methylbenzoate | — | — |
| 475 | 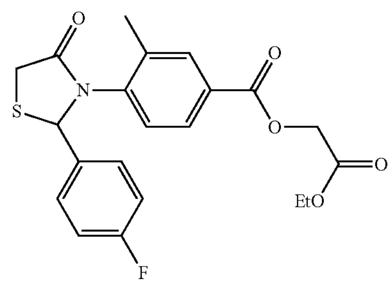 [SMILES: CCOC(=O)COC(=O)c1ccc(N2C(=O)CSC2c2ccc(F)cc2)c(C)c1] | 2-Ethoxy-2-oxoethyl 4-[2-(4-fluorophenyl)-4-oxo-1,3-thiazolidin-3-yl]-3-methylbenzoate | — | — |
| 476 | 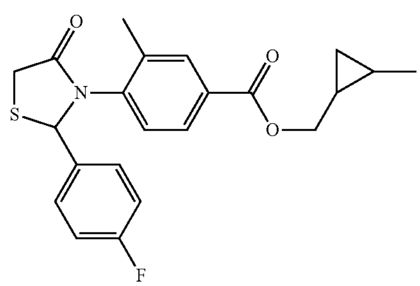 [SMILES: Cc1cc(C(=O)OCC2CC2C)ccc1N1C(=O)CSC1c1ccc(F)cc1] | (2-Methylcyclopropyl)methyl 4-[2-(4-fluorophenyl)-4-oxo-1,3-thiazolidin-3-yl]-3-methylbenzoate | — | — |
| 477 | 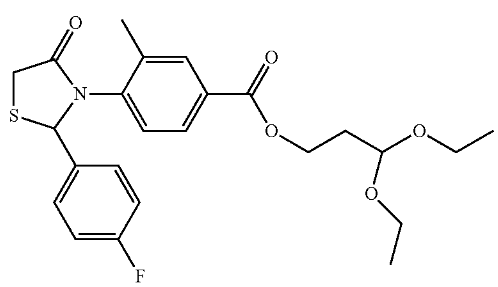 [SMILES: CCOC(CCOC(=O)c1ccc(N2C(=O)CSC2c2ccc(F)cc2)c(C)c1)OCC] | 3,3-Diethoxypropyl 4-[2-(4-fluorophenyl)-4-oxo-1,3-thiazolidin-3-yl]-3-methylbenzoate | — | — |
| 478 | 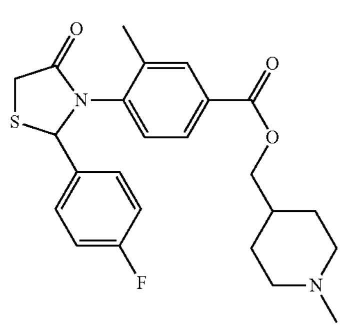 [SMILES: Cc1cc(C(=O)OCC2CCN(C)CC2)ccc1N1C(=O)CSC1c1ccc(F)cc1] | (1-Methylpiperidin-4-yl)methyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 479 | 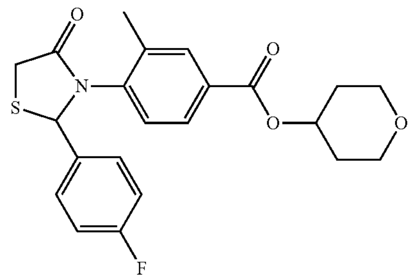 [SMILES: Cc1cc(C(=O)OC2CCOCC2)ccc1N1C(=O)CSC1c1ccc(F)cc1] | Tetrahydro-2H-pyran-4-yl 4-[2-(4-fluorophenyl)-4-oxo-1,3-thiazolidin-3-yl]-3-methylbenzoate | — | — |
| 480 | 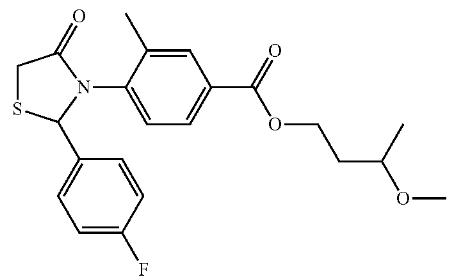 [SMILES: COC(C)CCOC(=O)c1ccc(N2C(=O)CSC2c2ccc(F)cc2)c(C)c1] | 3-Methoxybutyl 4-[2-(4-fluorophenyl)-4-oxo-1,3-thiazolidin-3-yl]-3-methylbenzoate | — | — |
| 481 | 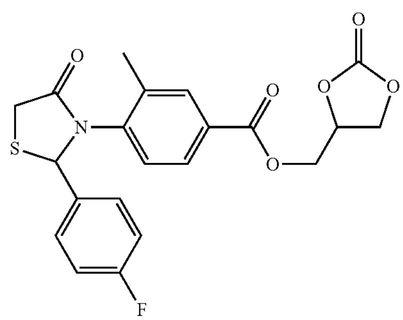 [SMILES: Cc1cc(C(=O)OCC2COC(=O)O2)ccc1N1C(=O)CSC1c1ccc(F)cc1] | (2-Oxo-1,3-dioxolan-4-yl)methyl 4-[2-(4-fluorophenyl)-4-oxo-1,3-thiazolidin-3-yl]-3-methylbenzoate | — | — |
| 482 | 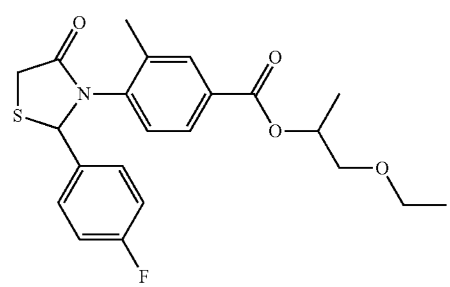 [SMILES: CCOCC(C)OC(=O)c1ccc(N2C(=O)CSC2c2ccc(F)cc2)c(C)c1] | 1-Ethoxypropan-2-yl 4-[2-(4-fluorophenyl)-4-oxo-1,3-thiazolidin-3-yl]-3-methylbenzoate | — | — |
| 483 | 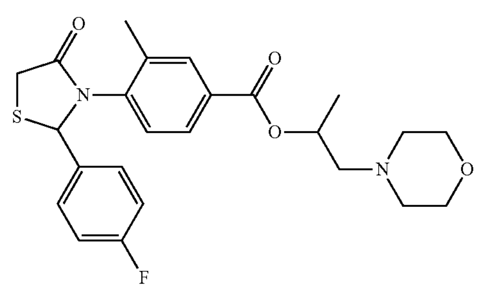 [SMILES: Cc1cc(C(=O)OC(C)CN2CCOCC2)ccc1N1C(=O)CSC1c1ccc(F)cc1] | 1-(Morpholin-4-yl)propan-2-yl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (µM) | AUC |
|---|---|---|---|---|
| 484 | 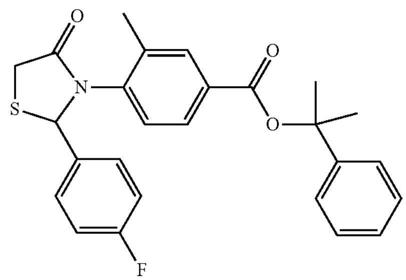 | 2-Phenylpropan-2-yl 4-[2-(4-fluorophenyl)-4-oxo-1,3-thiazolidin-3-yl]-3-methylbenzoate | — | — |
| 485 | 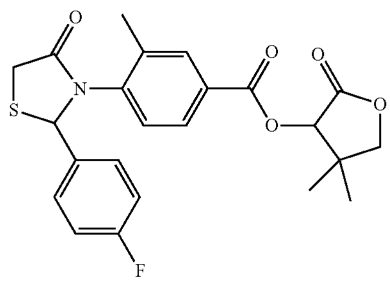 [SMILES: Cc1cc(C(=O)OC2C(=O)OCC2(C)C)ccc1N1C(=O)CSC1c1ccc(F)cc1] | 4,4-Dimethyl-2-oxotetrahydrofuran-3-yl 4-[2-(4-fluorophenyl)-4-oxo-1,3-thiazolidin-3-yl]-3-methylbenzoate | — | — |
| 486 | 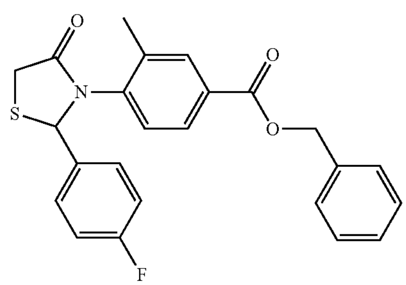 [SMILES: Cc1cc(C(=O)OCc2ccccc2)ccc1N1C(=O)CSC1c1ccc(F)cc1] | Benzyl 4-[2-(4-fluorophenyl)-4-oxo-1,3-thiazolidin-3-yl]-3-methylbenzoate | — | — |
| 487 | 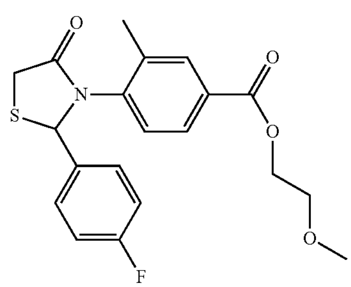 [SMILES: COCCOC(=O)c1ccc(N2C(=O)CSC2c2ccc(F)cc2)c(C)c1] | 2-Methoxyethyl 4-[2-(4-fluorophenyl)-4-oxo-1,3-thiazolidin-3-yl]-3-methylbenzoate | — | — |
| 488 | 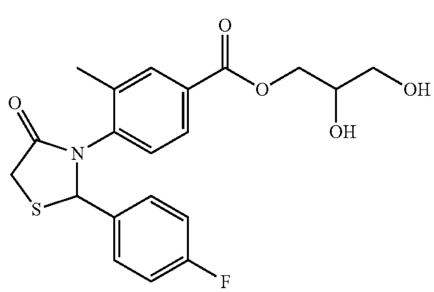 [SMILES: Cc1cc(C(=O)OCC(O)CO)ccc1N1C(=O)CSC1c1ccc(F)cc1] | 2,3-Dihydroxypropyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 489 | 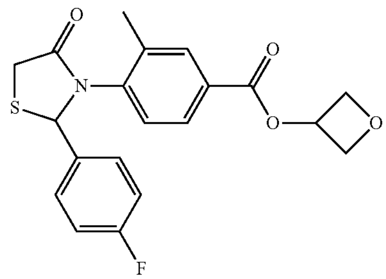 [SMILES: Cc1cc(C(=O)OC2COC2)ccc1N1C(=O)CSC1c1ccc(F)cc1] | Oxetan-3-yl 4-[2-(4-fluorophenyl)-4-oxo-1,3-thiazolidin-3-yl]-3-methylbenzoate | — | — |
| 490 | 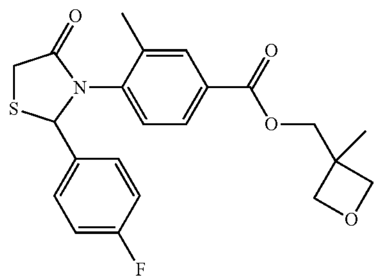 [SMILES: Cc1cc(C(=O)OCC2(C)COC2)ccc1N1C(=O)CSC1c1ccc(F)cc1] | (3-Methyloxetan-3-yl)methyl 4-[2-(4-fluorophenyl)-4-oxo-1,3-thiazolidin-3-yl]-3-methylbenzoate | — | — |
| 491 | 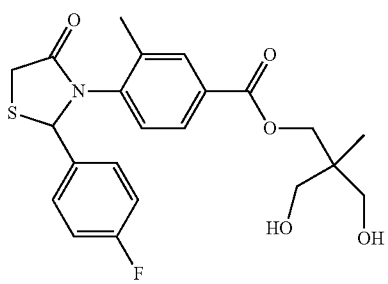 [SMILES: Cc1cc(C(=O)OCC(C)(CO)CO)ccc1N1C(=O)CSC1c1ccc(F)cc1] | 3-Hydroxy-2-(hydroxymethyl)-2-methylpropyl 4-[2-(4-fluorophenyl)-4-oxo-1,3-thiazolidin-3-yl]-3-methylbenzoate | — | — |
| 492 | 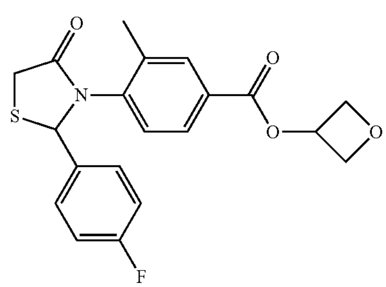 [SMILES: Cc1cc(C(=O)OC2COC2)ccc1N1C(=O)CSC1c1ccc(F)cc1] | Cyclobutyl 4-[2-(4-fluorophenyl)-4-oxo-1,3-thiazolidin-3-yl]-3-methylbenzoate | — | — |
| 493 | 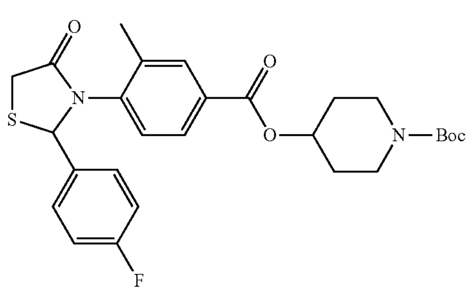 [SMILES: Cc1cc(C(=O)OC2CCN(C(=O)OC(C)(C)C)CC2)ccc1N1C(=O)CSC1c1ccc(F)cc1] | tert-Butyl 4-({4-[2-(4-fluorophenyl)-4-oxo-1,3-thiazolidin-3-yl]-3-methylbenzoyl}oxy)piperidine-1-carboxylate | — | — |

TABLE 1-continued

Exemplary compounds and their activities

| No. | Structure | Name | FLIPR Ca²⁺ EC$_{50}$ (μM) | AUC |
|---|---|---|---|---|
| 494 | 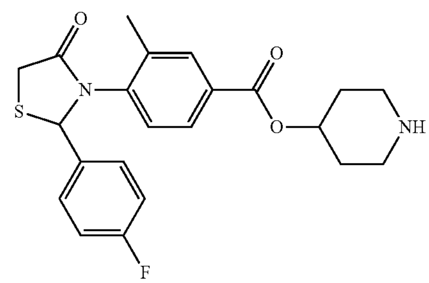 [SMILES: Cc1cc(C(=O)OC2CCNCC2)ccc1N1C(=O)CSC1c1ccc(F)cc1] | Piperidin-4-yl 4-[2-(4-fluorophenyl)-4-oxo-1,3-thiazolidin-3-yl]-3-methylbenzoate | — | — |
| 495 | 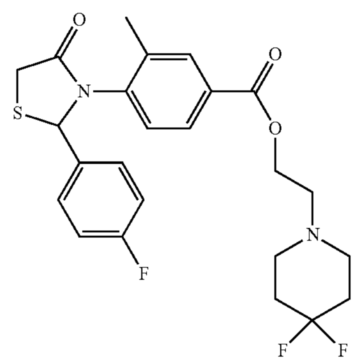 [SMILES: Cc1cc(C(=O)OCCN2CCC(F)(F)CC2)ccc1N1C(=O)CSC1c1ccc(F)cc1] | 2-(4,4-Difluoropiperidin-1-yl)ethyl 4-[2-(4-fluorophenyl)-4-oxo-1,3-thiazolidin-3-yl]-3-methylbenzoate | — | — |
| 497 | 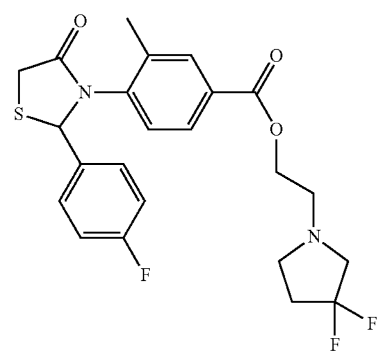 [SMILES: Cc1cc(C(=O)OCCN2CCC(F)(F)C2)ccc1N1C(=O)CSC1c1ccc(F)cc1] | 2-(3,3-Difluoropyrrolidin-1-yl)ethyl 4-[2-(4-fluorophenyl)-4-oxo-1,3-thiazolidin-3-yl]-3-methylbenzoate | — | — |
| 499 | 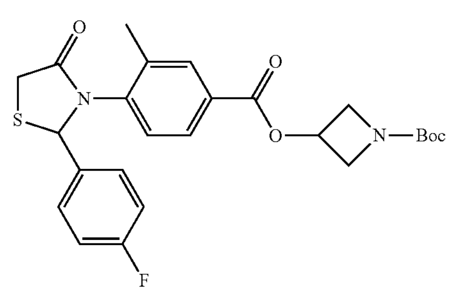 [SMILES: Cc1cc(C(=O)OC2CN(C(=O)OC(C)(C)C)C2)ccc1N1C(=O)CSC1c1ccc(F)cc1] | tert-Butyl 3-({4-[2-(4-fluorophenyl)-4-oxo-1,3-thiazolidin-3-yl]-3-methylbenzoyl}oxy)azetidine-1-carboxylate | — | — |

TABLE 1-continued

Exemplary compounds and their activities

| No. | Structure | Name | FLIPR Ca²⁺ EC$_{50}$ (μM) | AUC |
|---|---|---|---|---|
| 500 | 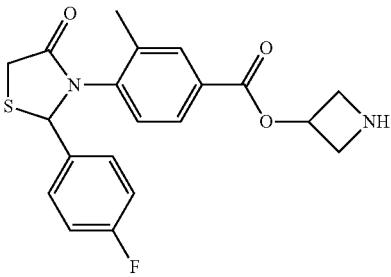 [SMILES: Cc1cc(C(=O)OC2CNC2)ccc1N1C(=O)CSC1c1ccc(F)cc1] | Azetidin-3-yl 4-[2-(4-fluorophenyl)-4-oxo-1,3-thiazolidin-3-yl]-3-methylbenzoate | — | — |
| 501 | 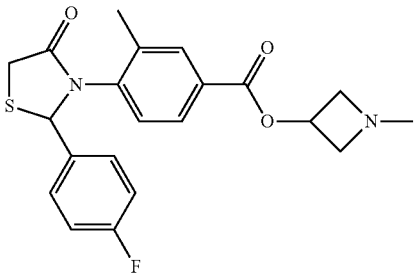 [SMILES: Cc1cc(C(=O)OC2CN(C)C2)ccc1N1C(=O)CSC1c1ccc(F)cc1] | 1-Methylazetidin-3-yl 4-[2-(4-fluorophenyl)-4-oxo-1,3-thiazolidin-3-yl]-3-methylbenzoate | — | — |
| 503 | 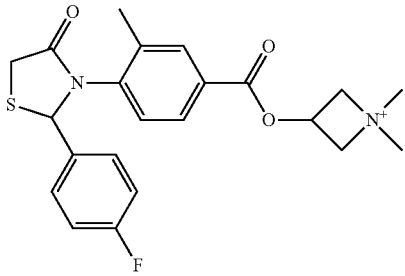 [SMILES: Cc1cc(C(=O)OC2C[N+](C)(C)C2)ccc1N1C(=O)CSC1c1ccc(F)cc1] | 3-{4-[2-(4-Fluorophenyl)-4-oxo-1,3-thiazolidin-3-yl]-3-methylbenzoyl}oxy)-1,1-dimethylazetidinium | — | — |
| 504 | 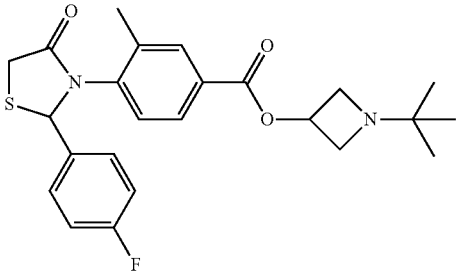 [SMILES: Cc1cc(C(=O)OC2CN(C(C)(C)C)C2)ccc1N1C(=O)CSC1c1ccc(F)cc1] | 1-tert-Butylazetidin-3-yl 4-[2-(4-fluorophenyl)-4-oxo-1,3-thiazolidin-3-yl]-3-methylbenzoate | — | — |
| 505 | 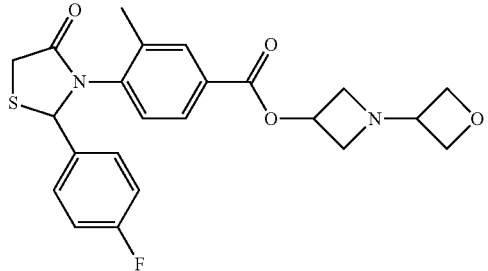 [SMILES: Cc1cc(C(=O)OC2CN(C3COC3)C2)ccc1N1C(=O)CSC1c1ccc(F)cc1] | 1-(Oxetan-3-yl)azetidin-3-yl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (µM) | AUC |
|---|---|---|---|---|
| 507 | 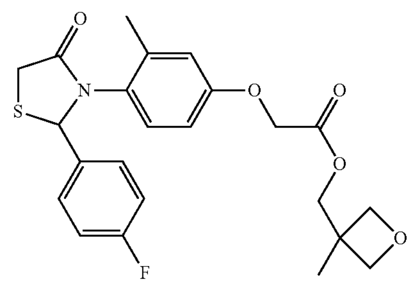 [SMILES: Cc1cc(OCC(=O)OCC2(C)COC2)ccc1N1C(=O)CSC1c1ccc(F)cc1] | 2-[(3-Methyloxetan-3-yl)methoxy]-2-oxoethyl 4-[2-(4-fluorophenyl)-4-oxo-1,3-thiazolidin-3-yl]-3-methylbenzoate | — | — |
| 508 | 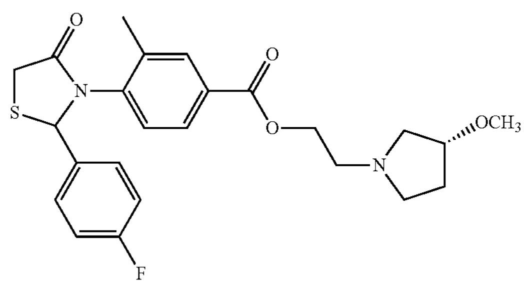 [SMILES: CO[C@@H]1CCN(CCOC(=O)c2ccc(N3C(=O)CSC3c3ccc(F)cc3)c(C)c2)C1] | 2-[(3R)-3-Methoxypyrrolidin-1-yl]ethyl 4-[2-(4-fluorophenyl)-4-oxo-1,3-thiazolidin-3-yl]-3-methylbenzoate | — | — |
| 510 | 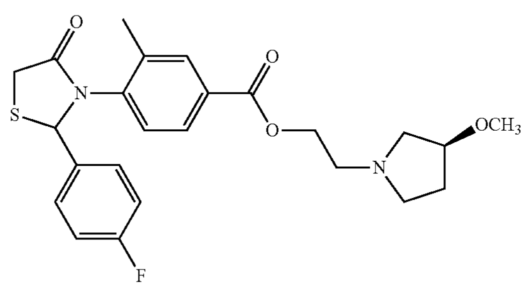 [SMILES: CO[C@H]1CCN(CCOC(=O)c2ccc(N3C(=O)CSC3c3ccc(F)cc3)c(C)c2)C1] | 2-[(3S)-3-Methoxypyrrolidin-1-yl]ethyl 4-[2-(4-fluorophenyl)-4-oxo-1,3-thiazolidin-3-yl]-3-methylbenzoate | — | — |
| 512 | 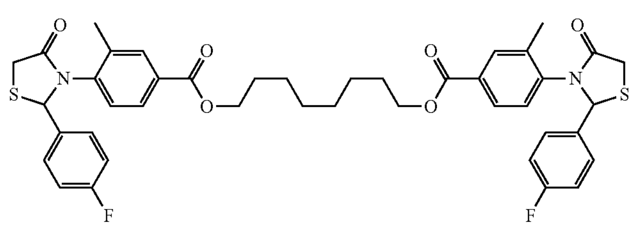 [SMILES: Cc1cc(C(=O)OCCCCCCCCOC(=O)c2ccc(N3C(=O)CSC3c3ccc(F)cc3)c(C)c2)ccc1N1C(=O)CSC1c1ccc(F)cc1] | Octane-1,8-diyl bis{4-[2-(4-fluorophenyl)-4-oxo-1,3-thiazolidin-3-yl]-3-methylbenzoate} | — | — |
| 513 | 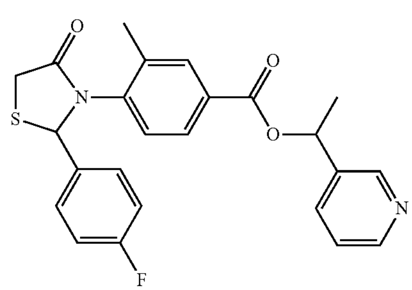 [SMILES: Cc1cc(C(=O)OC(C)c2cccnc2)ccc1N1C(=O)CSC1c1ccc(F)cc1] | 1-(Pyridin-3-yl)ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 514 | 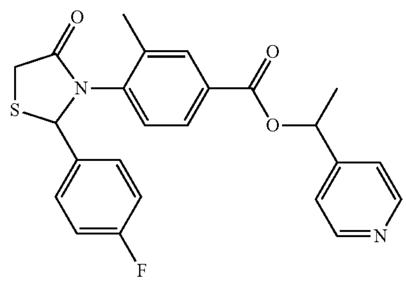 [SMILES: Cc1cc(C(=O)OC(C)c2ccncc2)ccc1N1C(=O)CSC1c1ccc(F)cc1] | 1-(Pyridin-4-yl)ethyl 4-[2-(4-fluorophenyl)-4-oxo-1,3-thiazolidin-3-yl]-3-methylbenzoate | — | — |
| 515 | 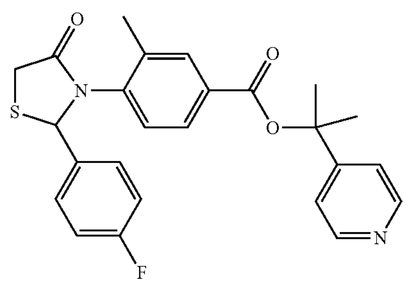 [SMILES: Cc1cc(C(=O)OC(C)(C)c2ccncc2)ccc1N1C(=O)CSC1c1ccc(F)cc1] | 2-(Pyridin-4-yl)propan-2-yl 4-[2-(4-fluorophenyl)-4-oxo-1,3-thiazolidin-3-yl]-3-methylbenzoate | — | — |
| 516 | 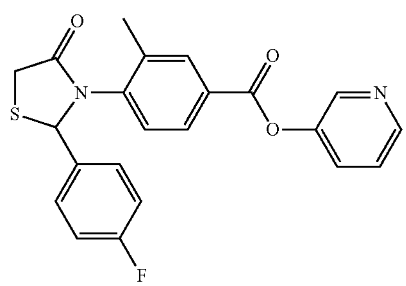 [SMILES: Cc1cc(C(=O)Oc2cccnc2)ccc1N1C(=O)CSC1c1ccc(F)cc1] | Pyridin-3-yl 4-[2-(4-fluorophenyl)-4-oxo-1,3-thiazolidin-3-yl]-3-methylbenzoate | — | — |
| 517 | 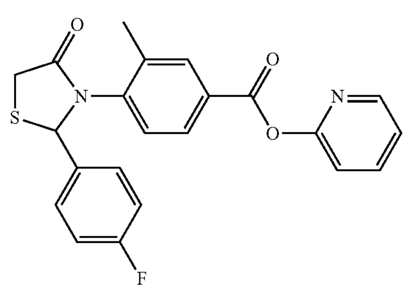 [SMILES: Cc1cc(C(=O)Oc2ccccn2)ccc1N1C(=O)CSC1c1ccc(F)cc1] | Pyridin-2-yl 4-[2-(4-fluorophenyl)-4-oxo-1,3-thiazolidin-3-yl]-3-methylbenzoate | — | — |
| 518 | 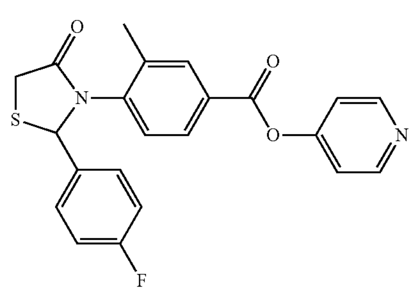 [SMILES: Cc1cc(C(=O)Oc2ccncc2)ccc1N1C(=O)CSC1c1ccc(F)cc1] | Pyridin-4-yl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 519 | 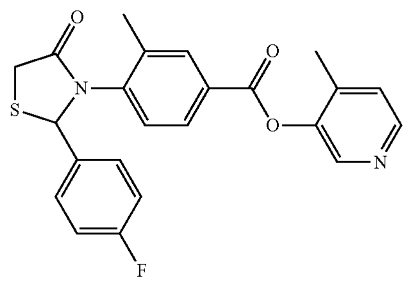 [SMILES: Cc1ccncc1OC(=O)c1ccc(N2C(=O)CSC2c2ccc(F)cc2)c(C)c1] | 4-Methylpyridin-3-yl 4-[2-(4-fluorophenyl)-4-oxo-1,3-thiazolidin-3-yl]-3-methylbenzoate | — | — |
| 520 | 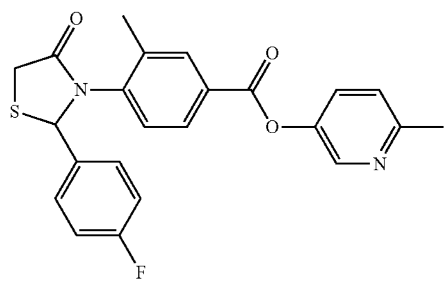 [SMILES: Cc1ccc(OC(=O)c2ccc(N3C(=O)CSC3c3ccc(F)cc3)c(C)c2)cn1] | 6-Methylpyridin-3-yl 4-[2-(4-fluorophenyl)-4-oxo-1,3-thiazolidin-3-yl]-3-methylbenzoate | — | — |
| 521 | 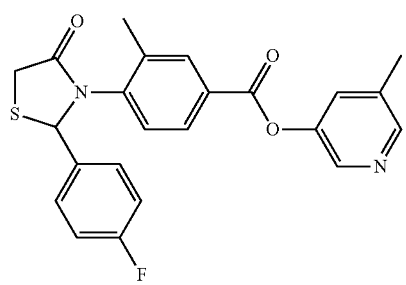 [SMILES: Cc1cncc(OC(=O)c2ccc(N3C(=O)CSC3c3ccc(F)cc3)c(C)c2)c1] | 5-Methylpyridin-3-yl 4-[2-(4-fluorophenyl)-4-oxo-1,3-thiazolidin-3-yl]-3-methylbenzoate | — | — |
| 522 | 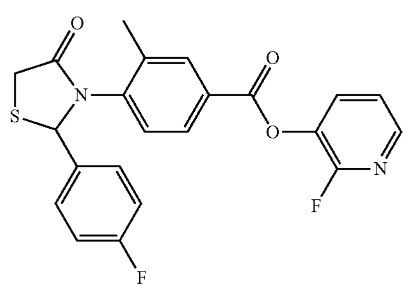 [SMILES: Cc1cc(C(=O)Oc2cccnc2F)ccc1N1C(=O)CSC1c1ccc(F)cc1] | 2-Fluoropyridin-3-yl 4-[2-(4-fluorophenyl)-4-oxo-1,3-thiazolidin-3-yl]-3-methylbenzoate | — | — |
| 523 | 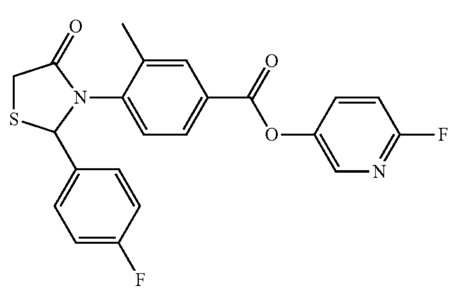 [SMILES: Cc1cc(C(=O)Oc2ccc(F)nc2)ccc1N1C(=O)CSC1c1ccc(F)cc1] | 6-Fluoropyridin-3-yl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (µM) | AUC |
|---|---|---|---|---|
| 524 | 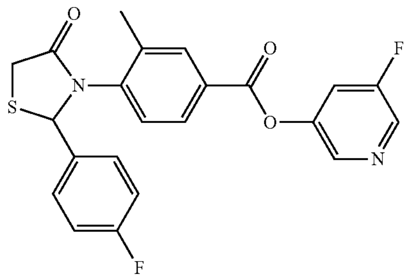 [SMILES: Cc1cc(C(=O)Oc2cncc(F)c2)ccc1N1C(=O)CSC1c1ccc(F)cc1] | 5-Fluoropyridin-3-yl 4-[2-(4-fluorophenyl)-4-oxo-1,3-thiazolidin-3-yl]-3-methylbenzoate | — | — |
| 525 | 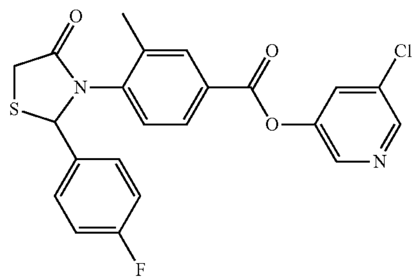 [SMILES: Cc1cc(C(=O)Oc2cncc(Cl)c2)ccc1N1C(=O)CSC1c1ccc(F)cc1] | 5-Chloropyridin-3-yl 4-[2-(4-fluorophenyl)-4-oxo-1,3-thiazolidin-3-yl]-3-methylbenzoate | — | — |
| 526 | 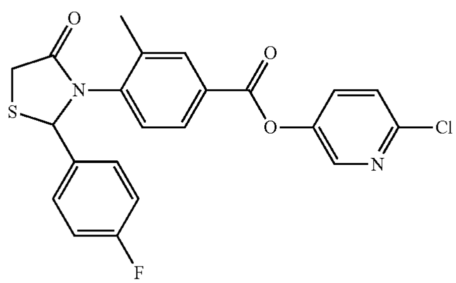 [SMILES: Cc1cc(C(=O)Oc2ccc(Cl)nc2)ccc1N1C(=O)CSC1c1ccc(F)cc1] | 6-Chloropyridin-3-yl 4-[2-(4-fluorophenyl)-4-oxo-1,3-thiazolidin-3-yl]-3-methylbenzoate | — | — |
| 527 | 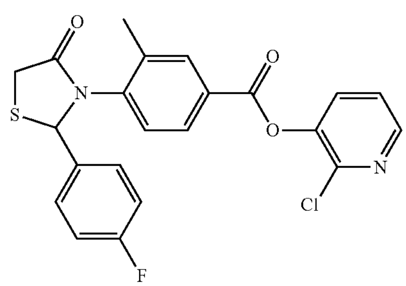 [SMILES: Cc1cc(C(=O)Oc2cccnc2Cl)ccc1N1C(=O)CSC1c1ccc(F)cc1] | 2-Chloropyridin-3-yl 4-[2-(4-fluorophenyl)-4-oxo-1,3-thiazolidin-3-yl]-3-methylbenzoate | — | — |
| 528 | 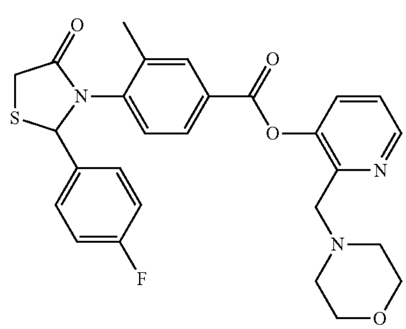 [SMILES: Cc1cc(C(=O)Oc2cccnc2CN2CCOCC2)ccc1N1C(=O)CSC1c1ccc(F)cc1] | 2-(Morpholin-4-ylmethyl)pyridin-3-yl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 530 | 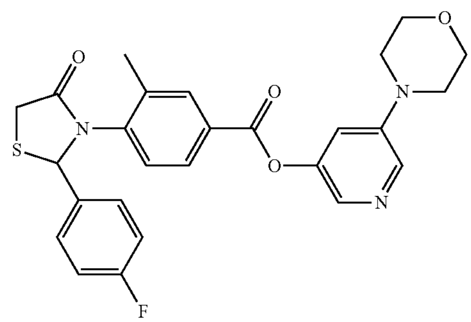 [SMILES: Cc1cc(C(=O)Oc2cncc(N3CCOCC3)c2)ccc1N1C(=O)CSC1c1ccc(F)cc1] | 5-(Morpholin-4-yl)pyridin-3-yl 4-[2-(4-fluorophenyl)-4-oxo-1,3-thiazolidin-3-yl]-3-methylbenzoate | — | — |
| 531 | 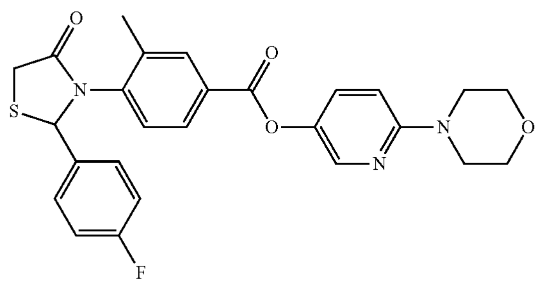 [SMILES: Cc1cc(C(=O)Oc2ccc(N3CCOCC3)nc2)ccc1N1C(=O)CSC1c1ccc(F)cc1] | 6-(Morpholin-4-yl)pyridin-3-yl 4-[2-(4-fluorophenyl)-4-oxo-1,3-thiazolidin-3-yl]-3-methylbenzoate | — | — |
| 532 | 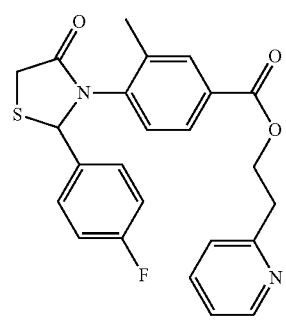 [SMILES: Cc1cc(C(=O)OCCc2ccccn2)ccc1N1C(=O)CSC1c1ccc(F)cc1] | 2-(Pyridin-2-yl)ethyl 4-[2-(4-fluorophenyl)-4-oxo-1,3-thiazolidin-3-yl]-3-methylbenzoate | — | — |
| 533 | 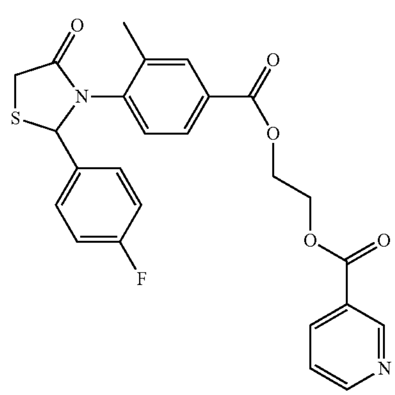 [SMILES: Cc1cc(C(=O)OCCOC(=O)c2cccnc2)ccc1N1C(=O)CSC1c1ccc(F)cc1] | 2-({4-[2-(4-Fluorophenyl)-4-oxo-1,3-thiazolidin-3-yl]-3-methylbenzoyl}oxy)ethyl pyridine-3-carboxylate | — | — |

TABLE 1-continued

Exemplary compounds and their activities

| No. | Structure | Name | FLIPR Ca²⁺ EC$_{50}$ (μM) | AUC |
|---|---|---|---|---|
| 536 | 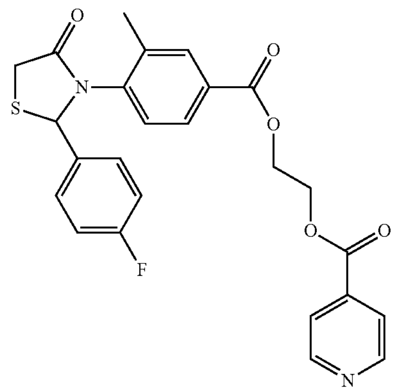 [SMILES: Cc1cc(C(=O)OCCOC(=O)c2ccncc2)ccc1N1C(=O)CSC1c1ccc(F)cc1] | 2-({4-[2-(4-Fluorophenyl)-4-oxo-1,3-thiazolidin-3-yl]-3-methylbenzoyl}oxy)ethyl pyridine-4-carboxylate | — | — |
| 538 | 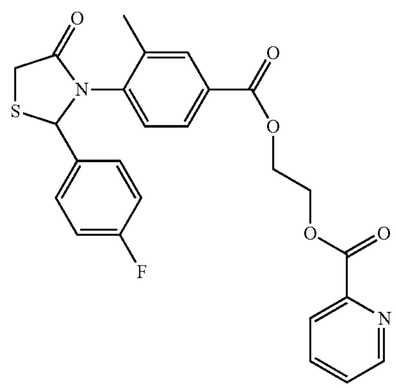 [SMILES: Cc1cc(C(=O)OCCOC(=O)c2ccccn2)ccc1N1C(=O)CSC1c1ccc(F)cc1] | 2-({4-[2-(4-Fluorophenyl)-4-oxo-1,3-thiazolidin-3-yl]-3-methylbenzoyl}oxy)ethyl pyridine-2-carboxylate | — | — |
| 540 | 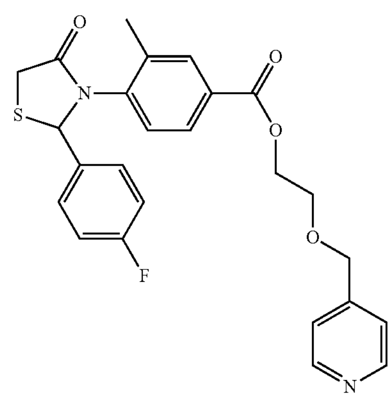 [SMILES: Cc1cc(C(=O)OCCOCc2ccncc2)ccc1N1C(=O)CSC1c1ccc(F)cc1] | 2-(Pyridin-4-ylmethoxy)ethyl 4-[2-(4-fluorophenyl)-4-oxo-1,3-thiazolidin-3-yl]-3-methylbenzoate | — | — |
| 542 | 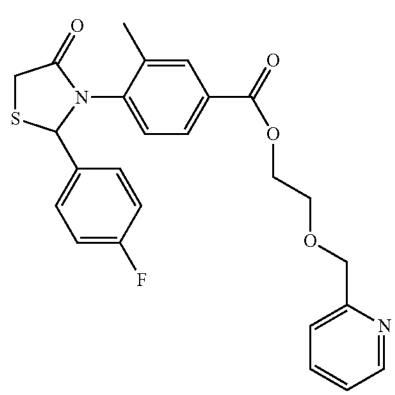 [SMILES: Cc1cc(C(=O)OCCOCc2ccccn2)ccc1N1C(=O)CSC1c1ccc(F)cc1] | 2-(Pyridin-2-ylmethoxy)ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 544 | 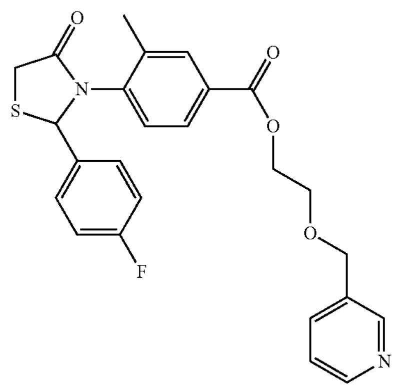 [SMILES: Cc1cc(C(=O)OCCOCc2cccnc2)ccc1N1C(=O)CSC1c1ccc(F)cc1] | 2-(Pyridin-3-ylmethoxy)ethyl 4-[2-(4-fluorophenyl)-4-oxo-1,3-thiazolidin-3-yl]-3-methylbenzoate | — | — |
| 546 | 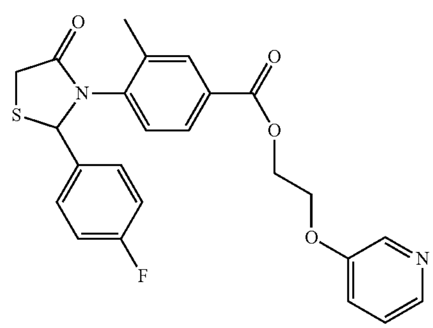 | 2-(Pyridin-3-yloxy)ethyl 4-[2-(4-fluorophenyl)-4-oxo-1,3-thiazolidin-3-yl]-3-methylbenzoate | — | — |
| 548 | 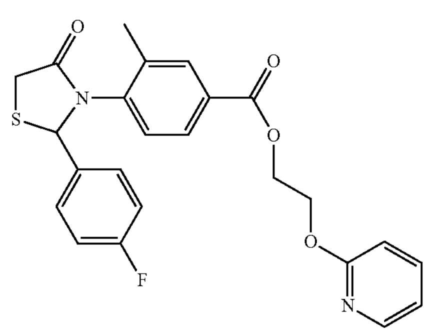 [SMILES: Cc1cc(C(=O)OCCOc2ccccn2)ccc1N1C(=O)CSC1c1ccc(F)cc1] | 2-(Pyridin-2-yloxy)ethyl 4-[2-(4-fluorophenyl)-4-oxo-1,3-thiazolidin-3-yl]-3-methylbenzoate | — | — |
| 550 | 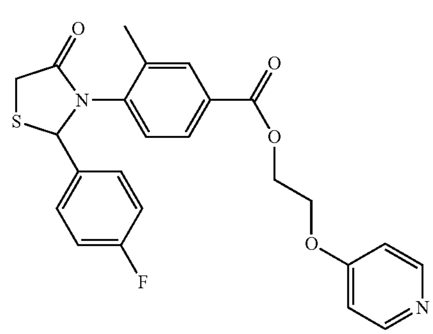 [SMILES: Cc1cc(C(=O)OCCOc2ccncc2)ccc1N1C(=O)CSC1c1ccc(F)cc1] | 2-(Pyridin-4-yloxy)ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (µM) | AUC |
|---|---|---|---|---|
| 552 | 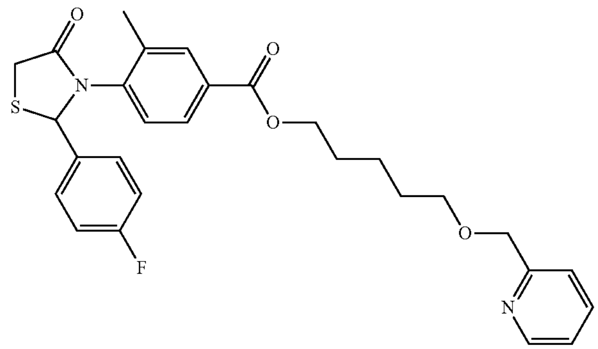 | 5-(Pyridin-2-ylmethoxy)pentyl 4-[2-(4-fluorophenyl)-4-oxo-1,3-thiazolidin-3-yl]-3-methylbenzoate | — | — |
| 556 | 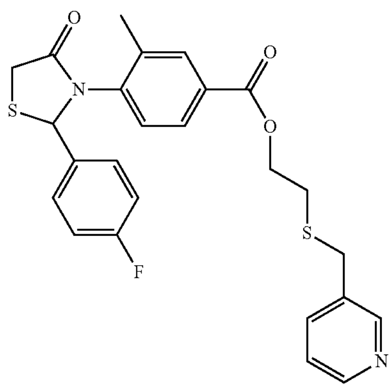 | 2-[(Pyridin-3-ylmethyl)sulfanyl]ethyl 4-[2-(4-fluorophenyl)-4-oxo-1,3-thiazolidin-3-yl]-3-methylbenzoate | — | — |
| 558 | 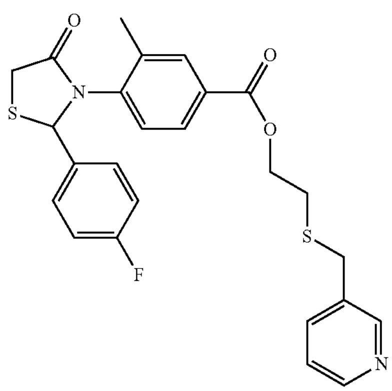 | 2-[(Pyridin-2-ylmethyl)sulfanyl]ethyl 4-[2-(4-fluorophenyl)-4-oxo-1,3-thiazolidin-3-yl]-3-methylbenzoate | — | — |
| 560 | 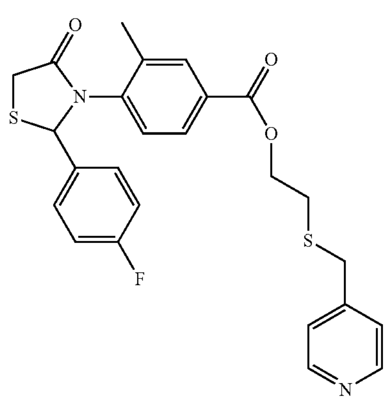 | 2-[(Pyridin-4-ylmethyl)sulfanyl]ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 562 | 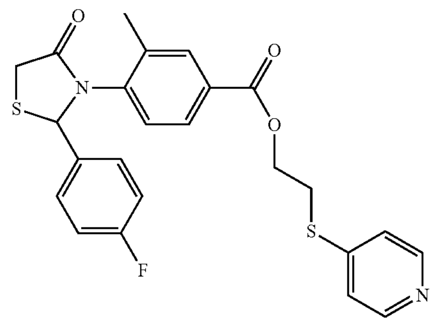 | 2-(Pyridin-4-ylsulfanyl)ethyl 4-[2-(4-fluorophenyl)-4-oxo-1,3-thiazolidin-3-yl]-3-methylbenzoate | — | — |
| 564 | 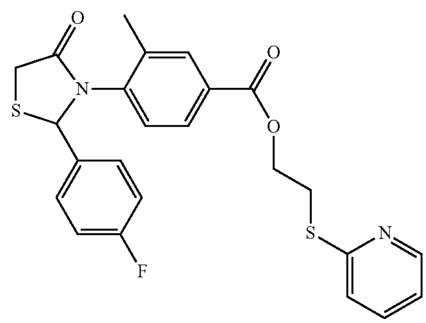 [SMILES: Cc1cc(C(=O)OCCSc2ccccn2)ccc1N1C(=O)CSC1c1ccc(F)cc1] | 2-(Pyridin-2-ylsulfanyl)ethyl 4-[2-(4-fluorophenyl)-4-oxo-1,3-thiazolidin-3-yl]-3-methylbenzoate | — | — |
| 566 | 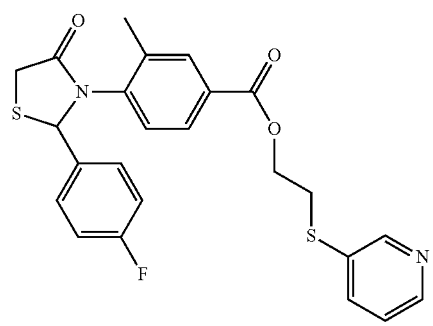 [SMILES: Cc1cc(C(=O)OCCSc2cccnc2)ccc1N1C(=O)CSC1c1ccc(F)cc1] | 2-(Pyridin-3-ylsulfanyl)ethyl 4-[2-(4-fluorophenyl)-4-oxo-1,3-thiazolidin-3-yl]-3-methylbenzoate | — | — |
| 568 | 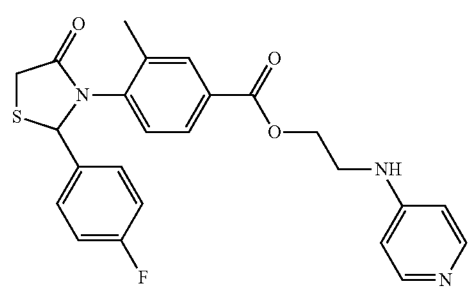 [SMILES: Cc1cc(C(=O)OCCNc2ccncc2)ccc1N1C(=O)CSC1c1ccc(F)cc1] | 2-(Pyridin-4-ylamino)ethyl 4-[2-(4-fluorophenyl)-4-oxo-1,3-thiazolidin-3-yl]-3-methylbenzoate | — | — |
| 571 | 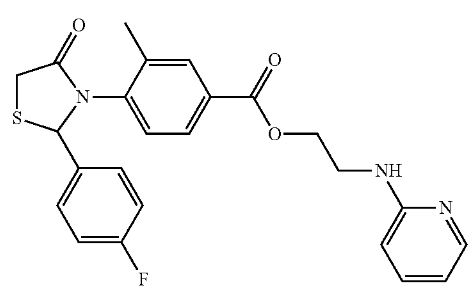 | 2-(Pyridin-2-ylamino)ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca²⁺ EC$_{50}$ (μM) | AUC |
|---|---|---|---|---|
| 574 | 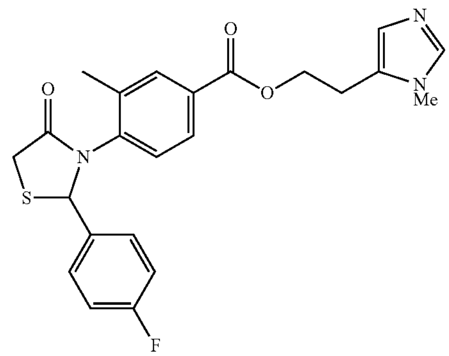 [SMILES: Cc1cc(C(=O)OCCc2cncn2C)ccc1N1C(=O)CSC1c1ccc(F)cc1] | 2-(1-Methyl-1H-imidazol-5-yl)ethyl 4-[2-(4-fluorophenyl)-4-oxo-1,3-thiazolidin-3-yl]-3-methylbenzoate | — | — |
| 575 | 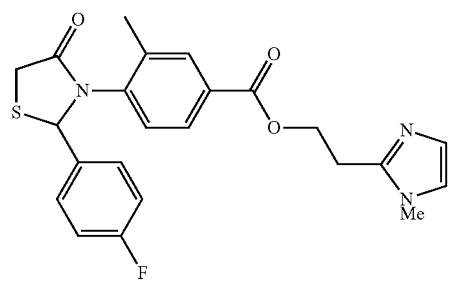 [SMILES: Cc1cc(C(=O)OCCc2nccn2C)ccc1N1C(=O)CSC1c1ccc(F)cc1] | 2-(1-Methyl-1H-imidazol-2-yl)ethyl 4-[2-(4-fluorophenyl)-4-oxo-1,3-thiazolidin-3-yl]-3-methylbenzoate | — | — |
| 576 | 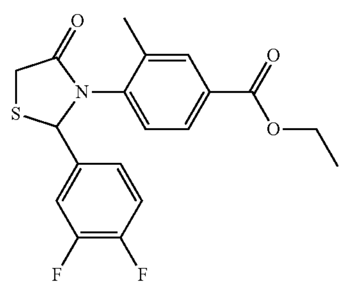 [SMILES: CCOC(=O)c1ccc(N2C(=O)CSC2c2ccc(F)c(F)c2)c(C)c1] | Ethyl 4-[2-(3,4-difluorophenyl)-4-oxo-1,3-thiazolidin-3-yl]-3-methylbenzoate | — | — |
| 578 | 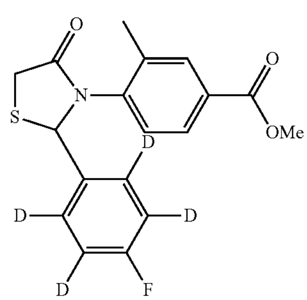 [SMILES: [2H]c1c([2H])c(C2SCC(=O)N2c2ccc(C(=O)OC)cc2C)c([2H])c([2H])c1F] | Methyl 4-{2-[4-fluoro-2,3,5,6-d$_4$-phenyl]-4-oxo-1,3-thiazolidin-3-yl}-3-methylbenzoate | — | — |
| 579 | 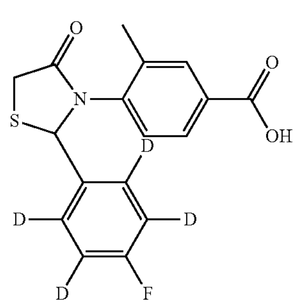 [SMILES: [2H]c1c([2H])c(C2SCC(=O)N2c2ccc(C(=O)O)cc2C)c([2H])c([2H])c1F] | 4-{2-[4-Fluoro-2,3,5,6-d$_4$-phenyl]-4-oxo-1,3-thiazolidin-3-yl}-3-methylbenzoic acid | 1.93 | 14761 |

TABLE 1-continued

Exemplary compounds and their activities

| No. | Structure | Name | FLIPR Ca$^{2+}$ EC$_{50}$ (μM) | AUC |
|---|---|---|---|---|
| 580 | 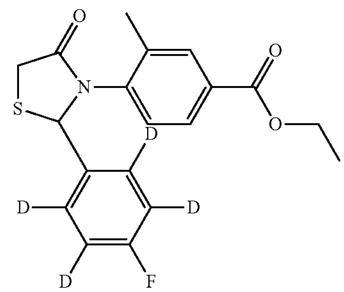 [SMILES: [2H]c1c([2H])c(C2SCC(=O)N2c2ccc(C(=O)OCC)cc2C)c([2H])c([2H])c1F] | Ethyl 4-{2-[4-fluoro-2,3,5,6-d$_4$-phenyl]-4-oxo-1,3-thiazolidin-3-yl}-3-methylbenzoate | 4.26 | 14441 |
| 581 | 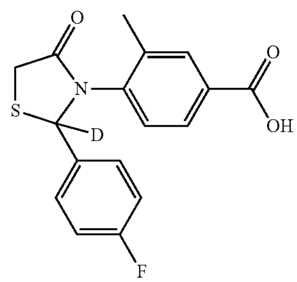 [SMILES: [2H]C1(c2ccc(F)cc2)SCC(=O)N1c1ccc(C(=O)O)cc1C] | 4-[2-(4-Fluorophenyl)-4-oxo-2-d$_1$-1,3-thiazolidin-3-yl]-3-methylbenzoic acid | 3.31 | 13703 |
| 583 | 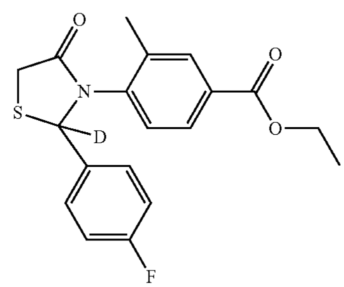 [SMILES: [2H]C1(c2ccc(F)cc2)SCC(=O)N1c1ccc(C(=O)OCC)cc1C] | Ethyl 4-[2-(4-fluorophenyl)-4-oxo-2-d$_1$-1,3-thiazolidin-3-yl]-3-methylbenzoate | 4.42 | 11275 |
| 584 | 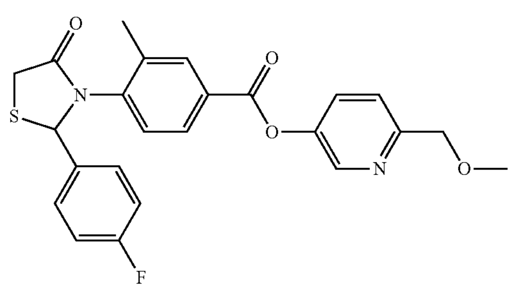 [SMILES: COCc1ccc(OC(=O)c2ccc(N3C(=O)CSC3c3ccc(F)cc3)c(C)c2)cn1] | 6-(Methoxymethyl)pyridin-3-yl 4-[2-(4-fluorophenyl)-4-oxo-1,3-thiazolidin-3-yl]-3-methylbenzoate | — | — |
| 587 | 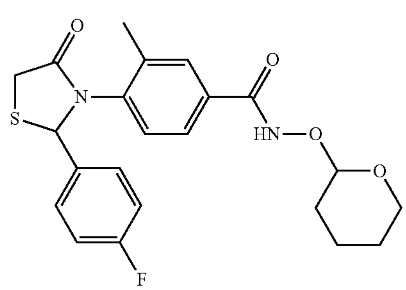 [SMILES: Cc1cc(C(=O)NOC2CCCCO2)ccc1N1C(=O)CSC1c1ccc(F)cc1] | 4-[2-(4-Fluorophenyl)-4-oxo-1,3-thiazolidin-3-yl]-3-methyl-N-(tetrahydro-2H-pyran-2-yloxy)benzamide | — | — |

TABLE 1-continued

Exemplary compounds and their activities

| No. | Structure | Name | FLIPR Ca²⁺ EC$_{50}$ (μM) | AUC |
|---|---|---|---|---|
| 588 | 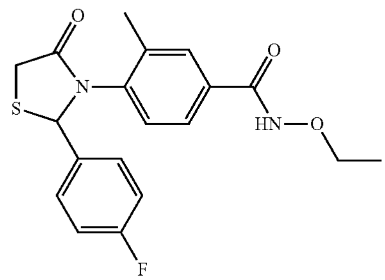 [SMILES: CCONC(=O)c1ccc(N2C(=O)CSC2c2ccc(F)cc2)c(C)c1] | N-Ethoxy-4-[2-(4-fluorophenyl)-4-oxo-1,3-thiazolidin-3-yl]-3-methylbenzamide | 9.27 | 9986 |
| 589 | 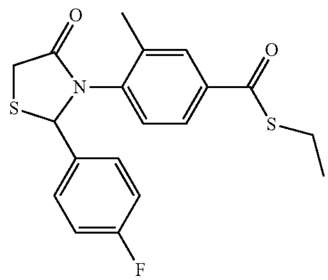 [SMILES: CCSC(=O)c1ccc(N2C(=O)CSC2c2ccc(F)cc2)c(C)c1] | S-Ethyl 4-[2-(4-fluorophenyl)-4-oxo-1,3-thiazolidin-3-yl]-3-methylbenzenecarbothioate | — | — |
| 591 | 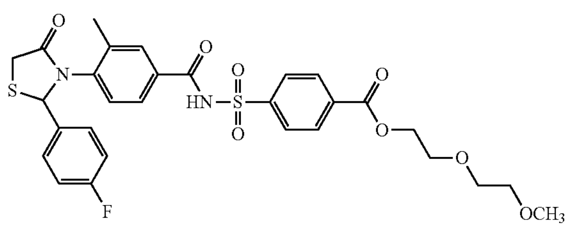 [SMILES: COCCOCCOC(=O)c1ccc(S(=O)(=O)NC(=O)c2ccc(N3C(=O)CSC3c3ccc(F)cc3)c(C)c2)cc1] | 2-(2-Methoxyethoxy)ethyl 4-({4-[2-(4-fluorophenyl)-4-oxo-1,3-thiazolidin-3-yl]-3-methylbenzoyl}sulfamoyl)benzoate | 10.3 | 13033 |
| 593 | 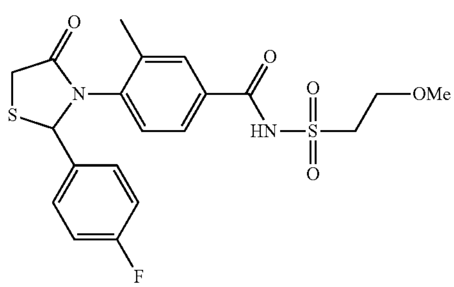 [SMILES: COCCS(=O)(=O)NC(=O)c1ccc(N2C(=O)CSC2c2ccc(F)cc2)c(C)c1] | 4-[2-(4-Fluorophenyl)-4-oxo-1,3-thiazolidin-3-yl]-N-[(2-methoxyethyl)sulfonyl]-3-methylbenzamide | 2.21 | 11543 |
| 597 | 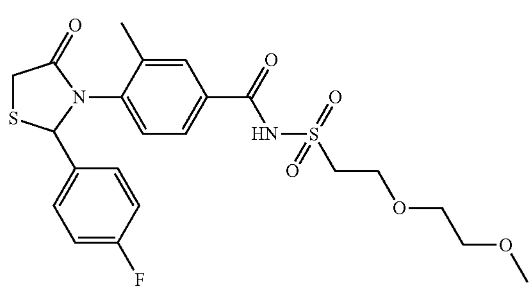 [SMILES: COCCOCCS(=O)(=O)NC(=O)c1ccc(N2C(=O)CSC2c2ccc(F)cc2)c(C)c1] | 4-[2-(4-Fluorophenyl)-4-oxo-1,3-thiazolidin-3-yl]-N-{[2-(2-methoxyethoxy)ethyl]sulfonyl}-3-methylbenzamide | 1.12 | 10720 |

TABLE 1-continued

Exemplary compounds and their activities

| No. | Structure | Name | FLIPR Ca$^{2+}$ EC$_{50}$ (μM) | AUC |
|-----|-----------|------|-------------------------------|-----|
| 600 | 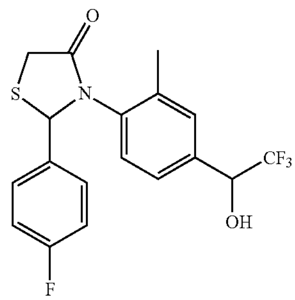 [SMILES: Cc1cc(C(O)C(F)(F)F)ccc1N1C(=O)CSC1c1ccc(F)cc1] | 2-(4-Fluorophenyl)-3-[2-methyl-4-(2,2,2-trifluoro-1-hydroxyethyl)phenyl]-1,3-thiazolidin-4-one | 6.75 | 13110 |
| 605 | 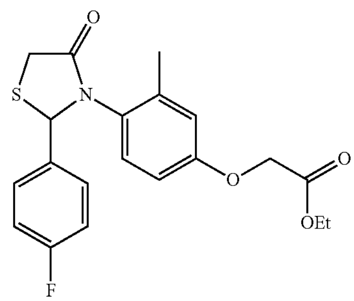 [SMILES: CCOC(=O)COc1ccc(N2C(=O)CSC2c2ccc(F)cc2)c(C)c1] | Ethyl {4-[2-(4-fluorophenyl)-4-oxo-1,3-thiazolidin-3-yl]-3-methylphenoxy}acetate | — | — |
| 607 | 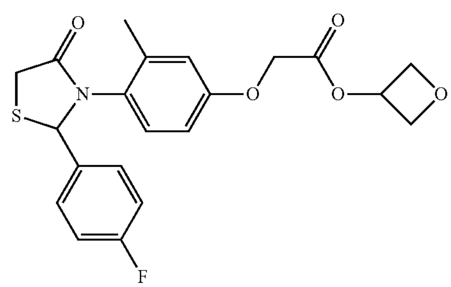 [SMILES: Cc1cc(OCC(=O)OC2COC2)ccc1N1C(=O)CSC1c1ccc(F)cc1] | Oxetan-3-yl {4-[2-(4-fluorophenyl)-4-oxo-1,3-thiazolidin-3-yl]-3-methylphenoxy}acetate | — | — |
| 608 | 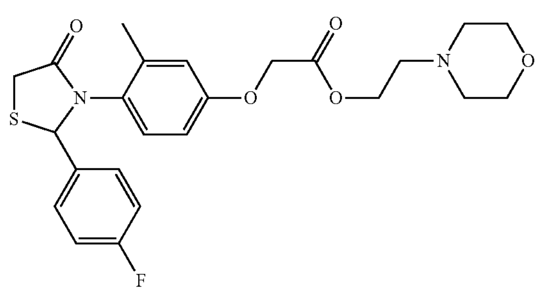 [SMILES: Cc1cc(OCC(=O)OCCN2CCOCC2)ccc1N1C(=O)CSC1c1ccc(F)cc1] | 2-(Morpholin-4-yl)ethyl {4-[2-(4-fluorophenyl)-4-oxo-1,3-thiazolidin-3-yl]-3-methylphenoxy}acetate | — | — |
| 609 | 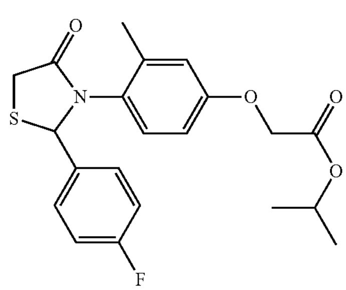 [SMILES: Cc1cc(OCC(=O)OC(C)C)ccc1N1C(=O)CSC1c1ccc(F)cc1] | Propan-2-yl {4-[2-(4-fluorophenyl)-4-oxo-1,3-thiazolidin-3-yl]-3-methylphenoxy}acetate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 610 | 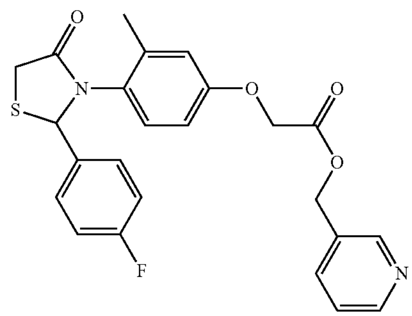 [SMILES: Cc1cc(OCC(=O)OCc2cccnc2)ccc1N1C(=O)CSC1c1ccc(F)cc1] | Pyridin-3-ylmethyl {4-[2-(4-fluorophenyl)-4-oxo-1,3-thiazolidin-3-yl]-3-methylphenoxy}acetate | — | — |
| 611 | 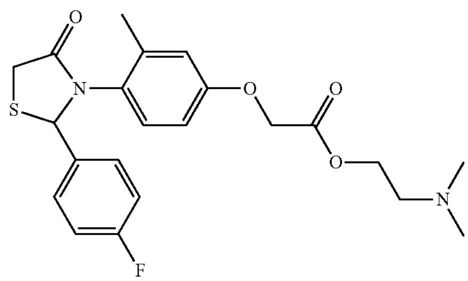 [SMILES: Cc1cc(OCC(=O)OCCN(C)C)ccc1N1C(=O)CSC1c1ccc(F)cc1] | 2-(Dimethylamino)ethyl {4-[2-(4-fluorophenyl)-4-oxo-1,3-thiazolidin-3-yl]-3-methylphenoxy}acetate | — | — |
| 612 | 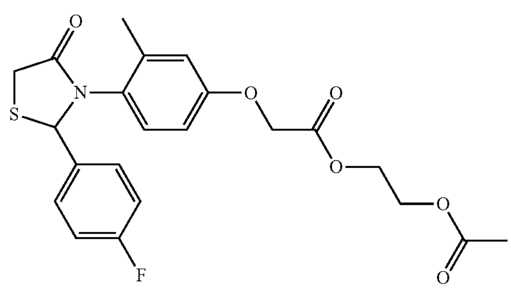 [SMILES: CC(=O)OCCOC(=O)COc1ccc(N2C(=O)CSC2c2ccc(F)cc2)c(C)c1] | 2-(Acetyloxy)ethyl {4-[2-(4-fluorophenyl)-4-oxo-1,3-thiazolidin-3-yl]-3-methylphenoxy}acetate | — | — |
| 614 | 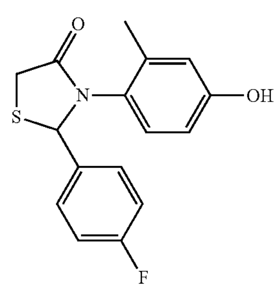 [SMILES: Cc1cc(O)ccc1N1C(=O)CSC1c1ccc(F)cc1] | 2-(4-Fluorophenyl)-3-(4-hydroxy-2-methylphenyl)-1,3-thiazolidin-4-one | — | — |
| 615 | 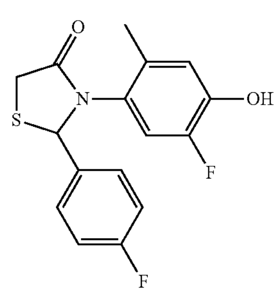 [SMILES: Cc1cc(O)c(F)cc1N1C(=O)CSC1c1ccc(F)cc1] | 3-(5-Fluoro-4-hydroxy-2-methylphenyl)-2-(4-fluorophenyl)-1,3-thiazolidin-4-one | — | — |

TABLE 1-continued

Exemplary compounds and their activities

| No. | Structure | Name | FLIPR Ca$^{2+}$ EC$_{50}$ (μM) | AUC |
|---|---|---|---|---|
| 616 | 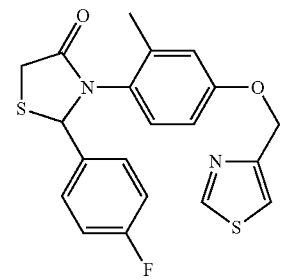 [SMILES: Cc1cc(OCc2cscn2)ccc1N1C(=O)CSC1c1ccc(F)cc1] | 2-(4-Fluorophenyl)-3-[2-methyl-4-(1,3-thiazol-4-ylmethoxy)phenyl]-1,3-thiazolidin-4-one | — | — |
| 617 | 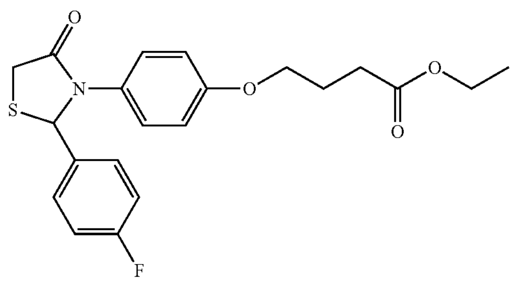 [SMILES: CCOC(=O)CCCOc1ccc(N2C(=O)CSC2c2ccc(F)cc2)cc1] | Ethyl 4-{4-[2-(4-fluorophenyl)-4-oxo-1,3-thiazolidin-3-yl]-3-methylphenoxy}butanoate | — | — |
| 618 | 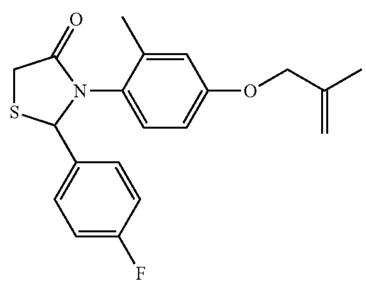 [SMILES: C=C(C)COc1ccc(N2C(=O)CSC2c2ccc(F)cc2)c(C)c1] | 2-(4-Fluorophenyl)-3-{2-methyl-4-[(2-methylprop-2-en-1-yl)oxy]phenyl}-1,3-thiazolidin-4-one | — | — |
| 619 | 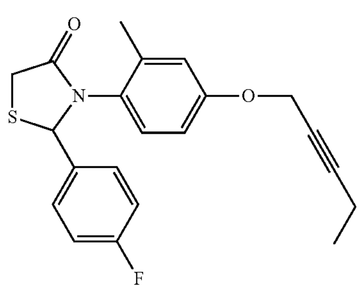 [SMILES: CCC#CCOc1ccc(N2C(=O)CSC2c2ccc(F)cc2)c(C)c1] | 2-(4-Fluorophenyl)-3-[2-methyl-4-(pent-2-yn-1-yloxy)phenyl]-1,3-thiazolidin-4-one | — | — |
| 620 | 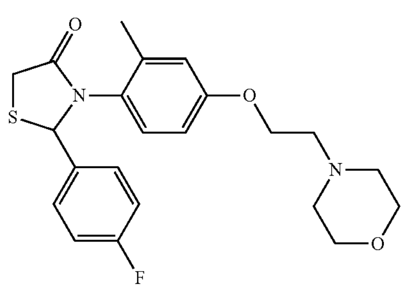 [SMILES: Cc1cc(OCCN2CCOCC2)ccc1N1C(=O)CSC1c1ccc(F)cc1] | 2-(4-Fluorophenyl)-3-{2-methyl-4-[2-(morpholin-4-yl)ethoxy]phenyl}-1,3-thiazolidin-4-one | — | — |

TABLE 1-continued

Exemplary compounds and their activities

| No. | Structure | Name | FLIPR Ca$^{2+}$ EC$_{50}$ (µM) | AUC |
|---|---|---|---|---|
| 621 | 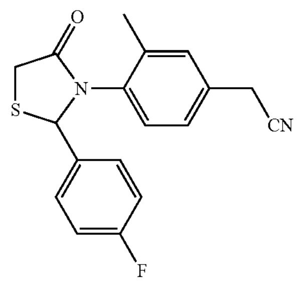 [SMILES: Cc1cc(CC#N)ccc1N1C(=O)CSC1c1ccc(F)cc1] | {4-[2-(4-Fluorophenyl)-4-oxo-1,3-thiazolidin-3-yl]-3-methylphenyl}acetonitrile | — | — |
| 624 | 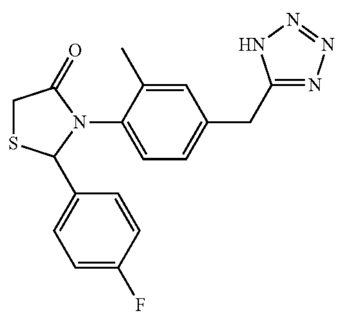 [SMILES: Cc1cc(Cc2nnn[nH]2)ccc1N1C(=O)CSC1c1ccc(F)cc1] | 2-(4-Fluorophenyl)-3-[2-methyl-4-(1H-tetrazol-5-ylmethyl)phenyl]-1,3-thiazolidin-4-one | — | — |
| 625 | 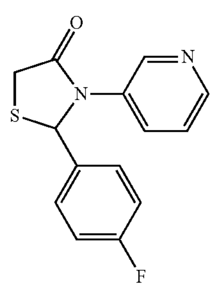 [SMILES: O=C1CSC(c2ccc(F)cc2)N1c1cccnc1] | 2-(4-Fluorophenyl)-3-(pyridin-3-yl)-1,3-thiazolidin-4-one | — | — |
| 626 | 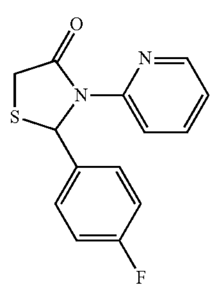 [SMILES: O=C1CSC(c2ccc(F)cc2)N1c1ccccn1] | 2-(4-Fluorophenyl)-3-(pyridin-2-yl)-1,3-thiazolidin-4-one | — | — |
| 627 | 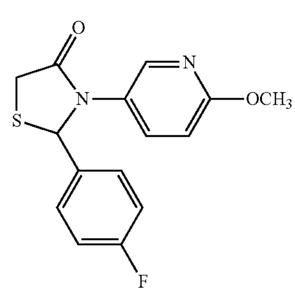 [SMILES: COc1ccc(N2C(=O)CSC2c2ccc(F)cc2)cn1] | 2-(4-Fluorophenyl)-3-(6-methoxypyridin-3-yl)-1,3-thiazolidin-4-one | — | — |

TABLE 1-continued

Exemplary compounds and their activities

| No. | Structure | Name | FLIPR Ca²⁺ EC$_{50}$ (µM) | AUC |
|---|---|---|---|---|
| 628 | 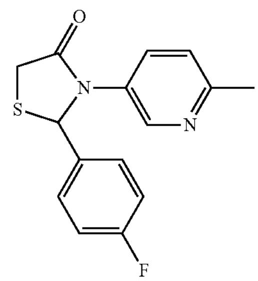 [SMILES: Cc1ccc(N2C(=O)CSC2c2ccc(F)cc2)cn1] | 2-(4-Fluorophenyl)-3-(6-methylpyridin-3-yl)-1,3-thiazolidin-4-one | — | — |
| 629 | 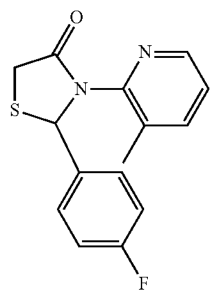 [SMILES: Cc1cccnc1N1C(=O)CSC1c1ccc(F)cc1] | 2-(4-Fluorophenyl)-3-(3-methylpyridin-2-yl)-1,3-thiazolidin-4-one | 10 | 4804 |
| 630 | 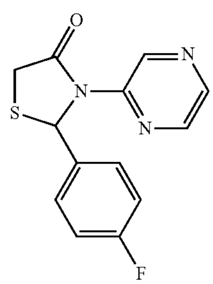 [SMILES: O=C1CSC(c2ccc(F)cc2)N1c1cnccn1] | 2-(4-Fluorophenyl)-3-(pyrazin-2-yl)-1,3-thiazolidin-4-one | — | — |
| 631 | 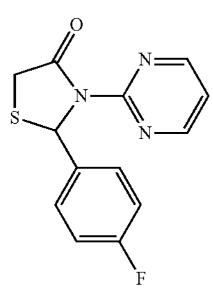 [SMILES: O=C1CSC(c2ccc(F)cc2)N1c1ncccn1] | 2-(4-Fluorophenyl)-3-(pyrimidin-2-yl)-1,3-thiazolidin-4-one | — | — |
| 632 | 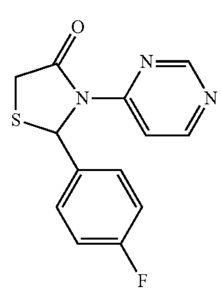 [SMILES: O=C1CSC(c2ccc(F)cc2)N1c1ccncn1] | 2-(4-Fluorophenyl)-3-(pyrimidin-4-yl)-1,3-thiazolidin-4-one | — | — |

TABLE 1-continued

Exemplary compounds and their activities

| No. | Structure | Name | FLIPR Ca²⁺ EC$_{50}$ (μM) | AUC |
|---|---|---|---|---|
| 633 | 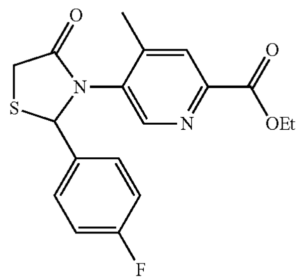 [SMILES: CCOC(=O)c1cc(C)c(N2C(=O)CSC2c2ccc(F)cc2)cn1] | Ethyl 5-[2-(4-fluorophenyl)-4-oxo-1,3-thiazolidin-3-yl]-4-methylpyridine-2-carboxylate | — | — |
| 635 | 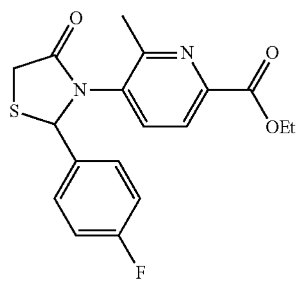 [SMILES: CCOC(=O)c1ccc(N2C(=O)CSC2c2ccc(F)cc2)c(C)n1] | Ethyl 5-[2-(4-fluorophenyl)-4-oxo-1,3-thiazolidin-3-yl]-6-methylpyridine-2-carboxylate | 10.9 | 9843 |
| 639 | 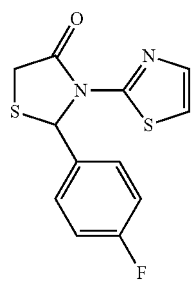 [SMILES: O=C1CSC(c2ccc(F)cc2)N1c1nccs1] | 2-(4-Fluorophenyl)-3-(1,3-thiazol-2-yl)-1,3-thiazolidin-4-one | — | — |
| 640 | 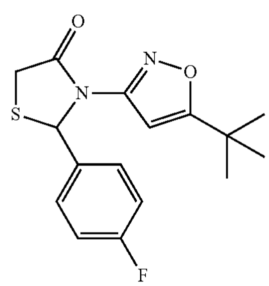 [SMILES: CC(C)(C)c1cc(N2C(=O)CSC2c2ccc(F)cc2)no1] | 3-(5-tert-Butyl-1,2-oxazol-3-yl)-2-(4-fluorophenyl)-1,3-thiazolidin-4-one | 14.2 | 9872 |
| 641 | 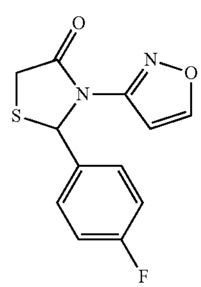 [SMILES: O=C1CSC(c2ccc(F)cc2)N1c1ccon1] | 2-(4-Fluorophenyl)-3-(1,2-oxazol-3-yl)-1,3-thiazolidin-4-one | — | — |

TABLE 1-continued

Exemplary compounds and their activities

| No. | Structure | Name | FLIPR Ca$^{2+}$ EC$_{50}$ (µM) | AUC |
|---|---|---|---|---|
| 642 | 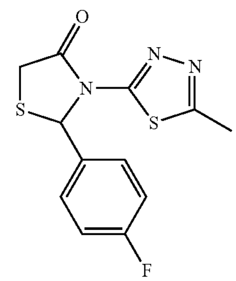 [SMILES: Cc1nnc(N2C(=O)CSC2c2ccc(F)cc2)s1] | 2-(4-Fluorophenyl)-3-(5-methyl-1,3,4-thiadiazol-2-yl)-1,3-thiazolidin-4-one | — | — |
| 643 | 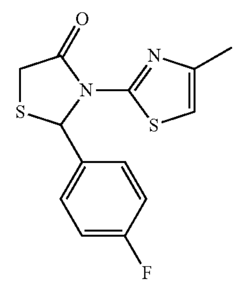 [SMILES: Cc1csc(N2C(=O)CSC2c2ccc(F)cc2)n1] | 2-(4-Fluorophenyl)-3-(4-methyl-1,3-thiazol-2-yl)-1,3-thiazolidin-4-one | — | — |
| 644 | 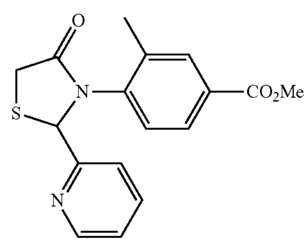 [SMILES: COC(=O)c1ccc(N2C(=O)CSC2c2ccccn2)c(C)c1] | Methyl 3-methyl-4-[4-oxo-2-(pyridin-2-yl)-1,3-thiazolidin-3-yl]benzoate | — | — |
| 645 | 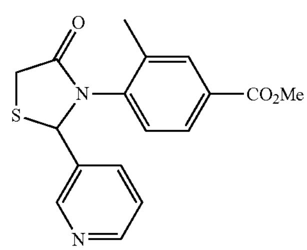 [SMILES: COC(=O)c1ccc(N2C(=O)CSC2c2cccnc2)c(C)c1] | Methyl 3-methyl-4-[4-oxo-2-(pyridin-3-yl)-1,3-thiazolidin-3-yl]benzoate | — | — |
| 646 | 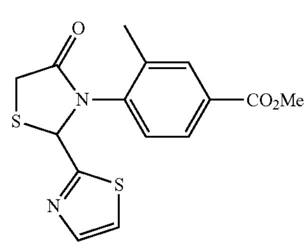 [SMILES: COC(=O)c1ccc(N2C(=O)CSC2c2nccs2)c(C)c1] | Methyl 3-methyl-4-[4-oxo-2-(1,3-thiazol-2-yl)-1,3-thiazolidin-3-yl]benzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 647 | 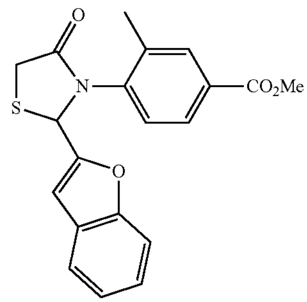 [SMILES: COC(=O)c1ccc(N2C(=O)CSC2c2cc3ccccc3o2)c(C)c1] | Methyl 4-[2-(1-benzofuran-2-yl)-4-oxo-1,3-thiazolidin-3-yl]-3-methylbenzoate | — | — |
| 648 | 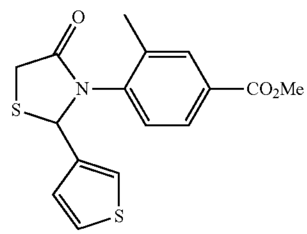 [SMILES: COC(=O)c1ccc(N2C(=O)CSC2c2ccsc2)c(C)c1] | Methyl 3-methyl-4-[4-oxo-2-(thiophen-3-yl)-1,3-thiazolidin-3-yl]benzoate | 2.01 | 9356 |
| 649 | 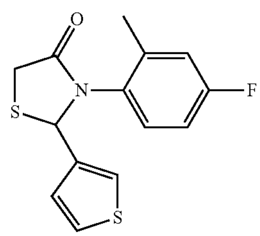 [SMILES: Cc1cc(F)ccc1N1C(=O)CSC1c1ccsc1] | 3-(4-Fluoro-2-methylphenyl)-2-(thiophen-3-yl)-1,3-thiazolidin-4-one | — | — |
| 650 | 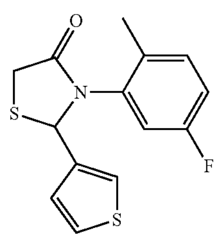 [SMILES: Cc1ccc(F)cc1N1C(=O)CSC1c1ccsc1] | 3-(5-Fluoro-2-methylphenyl)-2-(thiophen-3-yl)-1,3-thiazolidin-4-one | — | — |
| 651 | 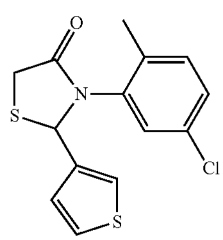 [SMILES: Cc1ccc(Cl)cc1N1C(=O)CSC1c1ccsc1] | 3-(5-Chloro-2-methylphenyl)-2-(thiophen-3-yl)-1,3-thiazolidin-4-one | — | — |
| 652 | 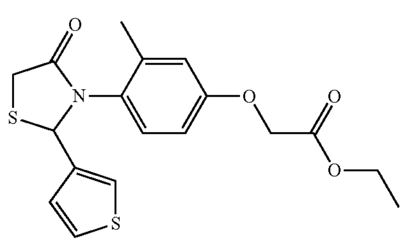 [SMILES: CCOC(=O)COc1ccc(N2C(=O)CSC2c2ccsc2)c(C)c1] | Ethyl {3-methyl-4-[4-oxo-2-(thiophen-3-yl)-1,3-thiazolidin-3-yl]phenoxy}acetate | — | — |

TABLE 1-continued

Exemplary compounds and their activities

| No. | Structure | Name | FLIPR Ca²⁺ EC$_{50}$ (μM) | AUC |
|---|---|---|---|---|
| 654 | 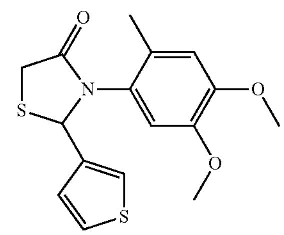 [SMILES: COc1cc(C)c(N2C(=O)CSC2c2ccsc2)cc1OC] | 3-(4,5-Dimethoxy-2-methylphenyl)-2-(thiophen-3-yl)-1,3-thiazolidin-4-one | — | — |
| 655 | 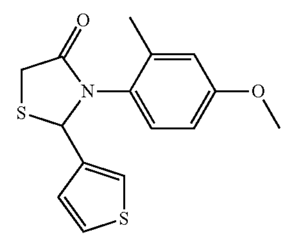 [SMILES: COc1ccc(N2C(=O)CSC2c2ccsc2)c(C)c1] | 3-(4-Methoxy-2-methylphenyl)-2-(thiophen-3-yl)-1,3-thiazolidin-4-one | — | — |
| 656 | 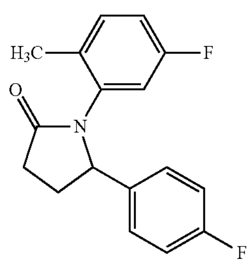 [SMILES: Cc1ccc(F)cc1N1C(=O)CCC1c1ccc(F)cc1] | 1-(5-Fluoro-2-methylphenyl)-5-(4-fluorophenyl)pyrrolidin-2-one | — | — |
| 658 | 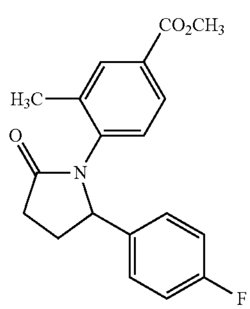 [SMILES: COC(=O)c1ccc(N2C(=O)CCC2c2ccc(F)cc2)c(C)c1] | Methyl 4-[2-(4-fluorophenyl)-5-oxopyrrolidin-1-yl]-3-methylbenzoate | — | — |
| 660 | 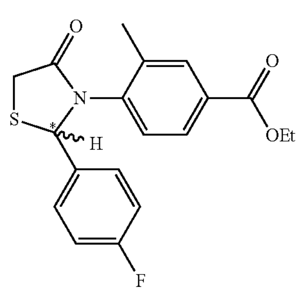 [SMILES: CCOC(=O)c1ccc(N2C(=O)CSC2c2ccc(F)cc2)c(C)c1] | (−)-Ethyl 4-[2-(4-fluorophenyl)-4-oxo-1,3-thiazolidin-3-yl]-3-methylbenzoate | — | — |

TABLE 1-continued

Exemplary compounds and their activities

| No. | Structure | Name | FLIPR Ca$^{2+}$ EC$_{50}$ (μM) | AUC |
|---|---|---|---|---|
| 661 | 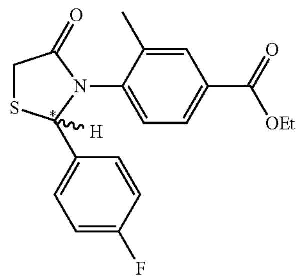 [SMILES: CCOC(=O)c1ccc(N2C(=O)CSC2c2ccc(F)cc2)c(C)c1] | (+)-Ethyl 4-[2-(4-fluorophenyl)-4-oxo-1,3-thiazolidin-3-yl]-3-methylbenzoate | — | — |

Shown in Table 2 below are activities of tail-flick test are presented in two ranges, i.e., ++: 25 mg/kg (intravenous) or 50 nmol (intrathecal) active; and +: 100 mg/kg (intravenous) active.

TABLE 2

Compounds' activities of tail-flick test

| No | Activity of tail-flick test |
|---|---|
| 58 | ++ |
| 152 | ++ |
| 160 | ++ |
| 169 | ++ |
| 174 | ++ |
| 175 | ++ |
| 187 | ++ |
| 196 | ++ |
| 204 | ++ |
| 236 | + |
| 239 | ++ |
| 255 | + |
| 258 | + |
| 260 | + |
| 263 | + |
| 264 | + |
| 265 | + |
| 269 | ++ |
| 270 | ++ |
| 272 | ++ |
| 276 | + |
| 280 | ++ |
| 281 | + |
| 282 | + |
| 286 | + |
| 290 | + |
| 294 | + |
| 296 | ++ |
| 297 | + |
| 299 | ++ |
| 303 | + |
| 310 | + |
| 311 | + |
| 313 | + |
| 446 | ++ |
| 453 | ++ |
| 456 | ++ |
| 458 | ++ |
| 461 | ++ |
| 463 | ++ |
| 465 | ++ |
| 471 | ++ |
| 489 | ++ |
| 495 | ++ |
| 497 | ++ |

TABLE 2-continued

Compounds' activities of tail-flick test

| No | Activity of tail-flick test |
|---|---|
| 499 | ++ |
| 504 | ++ |
| 505 | ++ |
| 508 | ++ |
| 510 | ++ |
| 516 | ++ |
| 517 | ++ |
| 519 | ++ |
| 520 | ++ |
| 521 | ++ |
| 522 | ++ |
| 523 | ++ |
| 525 | ++ |
| 526 | ++ |
| 532 | ++ |
| 533 | ++ |
| 538 | ++ |
| 540 | ++ |
| 542 | ++ |
| 546 | ++ |
| 548 | ++ |
| 550 | ++ |
| 556 | ++ |
| 560 | ++ |
| 562 | ++ |
| 564 | ++ |
| 571 | ++ |
| 589 | ++ |
| 605 | ++ |
| 607 | ++ |

Described below are eleven procedures used to synthesize intermediates of the above-described 661 compounds.

Standard procedure A for the preparation of thazolidinone derivatives. To a solution of aniline in toluene was added benzaldehyde and Na$_2$SO$_4$ anhydrous at room temperature, and it was stirred at room temperature or reflux for 5-20 h to obtain the imine intermediate. Then 2-mercaptoacetic acid was added to the reaction mixture, and it was reflux for 8-22 h. The reaction mixture was cooled to room temperature and diluted with ethyl acetate. The solution was washed with 10-20% NaOH$_{(aq)}$, HCl$_{(aq)}$ or brine. The organic layer was dried over MgSO$_{4(s)}$, filtered, and concentrated under reduced pressure to afford a residue. The residue was purified to give the desired product.

Standard procedure B for the hydrolysis of thazolidinone derivatives. A solution of thazolidinone in 20% NaOH$_{(aq)}$ and methanol or ethanol was stirred at room temperature for 2-4 h. Methanol or ethanol was removed under reduced pressure. The residue was acidified by 1 N or 2 N $HCl_{(aq)}$ and extracted with ethyl acetate or $CH_2Cl_2$. The combined organic layers were dried over $MgSO_{4(s)}$, filtered, and concentrated to afford a residue. The residue was purified to give the desired product.

Standard procedure C for the preparation of thiazolidinyl sulfonamides.

To a solution of 4-[2-(4-fluorophenyl)-4-oxo-1,3-thiazolidin-3-yl]-3-methylbenzoic acid in $CH_2Cl_2$ was added 4-(dimethylamino)pyridine (DMAP), sulfonamide, and N-ethyl-N'-(3-dimethylaminopropyl)carbodiimide hydrochloride (EDCI • HCl) at room temperature. After the reaction mixture was stirred for 16 h-20 h, it was diluted with $CH_2Cl_2$ and washed with 2 N $HCl_{(aq)}$ and brine. The organic layer was dried over $MgSO_{4(s)}$, filtered, and concentrated. The residue was purified to give the desired products.

Standard procedure D for the preparation of sulfonamides.

A solution of sulfonyl chloride in methanol and ammonium hydroxide solution was stirred at 0° C. or room temperature. After the reaction was complete, methanol was removed under reduced pressure. The solution was extracted with ethyl acetate. The combined organic layers were dried over $MgSO_{4(s)}$, filtered, and concentrated to give the desired products without further purification.

Standard procedure E for the amide formation of thazolidinone derivatives.

To a solution of 4-[2-(4-fluorophenyl)-4-oxo-1,3-thiazolidin-3-yl]-3-methylbenzoic acid in $CH_2Cl_2$ was added triethylamine and ethyl chloroformate at 0° C. After the reaction mixture was stirred at room temperature for 45 min to 1 h, a solution of potassium hydroxide and amine in methanol was added to the reaction mixture. The reaction was stirred for 3-6 h and then concentrated to afford a residue. The residue was purified to give the desired products.

Standard procedure F for the preparation of heteroaryl thazolidinone derivatives.

A solution of 3-(4-bromo-2-methylphenyl)-2-(4-fluorophenyl)-1,3-thiazolidin-4-one, sodium bicarbonate, and boronic acid in 1,2-dimethoxyethane (DME) and water was degassed with argon for 15 min. Tetrakis(triphenylphosphine)palladium ($Pd(PPh_3)_4$) was added and it was further degassed with argon for another 10 min. The reaction mixture was reflux for 3-4 h and cooled to room temperature. The solution was diluted with $CH_2Cl_2$ and washed with water and brine. The organic layer was dried over $MgSO_{4(s)}$, filtered, and concentrated. The residue was purified to give the desired products.

Standard procedure G for the esterification of 4-[2-(4-fluorophenyl)-4-oxo-1,3-thiazolidin-3-yl]-3-methylbenzoic acid.

To a solution of 4-[2-(4-fluorophenyl)-4-oxo-1,3-thiazolidin-3-yl]-3-methylbenzoic acid in $CH_2Cl_2$ was added 4-(dimethylamino)pyridine (DMAP), alcohol, and N-ethyl-N'-(3-dimethylaminopropyl)carbodiimide hydrochloride (EDCI • HCl) at room temperature. After the reaction mixture was stirred for 16-20 h, it was diluted with $CH_2Cl_2$ and washed with 2 N $HCl_{(aq)}$. The organic layer was dried over $MgSO_{4(s)}$, filtered, and concentrated. The residue was purified to give the desired products.

Standard procedure H for the alkylation of 4-[2-(4-fluorophenyl)-4-oxo-1,3-thiazolidin-3-yl]-3-methylbenzoic acid.

To a solution of 4-[2-(4-fluorophenyl)-4-oxo-1,3-thiazolidin-3-yl]-3-methylbenzoic acid in DMF was added $K_2CO_3$ and chloro-substituted derivative at room temperature. The reaction mixture was stirred for 18 h, and then DMF was removed under reduced pressure. The residue was purified by Isco Combi-Flash Companion column chromatography to give the desired products. In one of example, the desired compound was collected by vacuum filtered and washed with water and diethyl ether.

Standard procedure I for the sulfonylation of 2-(4-fluoro-phenyl)-thiazolidin-4-one.

To a solution of 2-(4-fluoro-phenyl)-thiazolidin-4-one in $CH_2Cl_2$ was added triethylamine, DMAP, and sulfonyl chloride derivative at room temperature. After the reaction mixture was stirred for 6-18 h, it was diluted with $CH_2Cl_2$ and washed with 2 N $HCl_{(aq)}$. The organic layer was dried over $MgSO_{4(s)}$, filtered, and concentrated. The residue was purified to give the desired products.

Standard procedure J for the preparation of phenylimino-thiazolidin-4-one derivatives.

To a solution of acetamide in THF (5.0 mL) was added 60% sodium hydride (NaH) in mineral oil at 0° C., and it was stirred for 30 min. Then 4-fluorophenyl isothiocyanate was added to the reaction. The reaction mixture was stirred for 16 h. The mixture was quenched with water and extracted with ethyl acetate. The combined organic layers were dried over $MgSO_{4(s)}$, filtered, and concentrated. The residue was purified to give the desired products.

Standard procedure K for the amide formation of thazolidinone derivatives.

To a solution of 4-[2-(4-fluorophenyl)-4-oxo-1,3-thiazolidin-3-yl]-3-methylbenzoic acid in $CH_2Cl_2$ was added O-(benzotriazol-1-yl)-N,N,N',N'-tetramethyluronium hexafluorophosphate (HBTU), various aniline, and triethyl amine at room temperature. After the reaction mixture was stirred for 16-20 h, water was added to the reaction. The reaction mixture was extracted with $CH_2Cl_2$ or ethyl acetate. The organic layer was dried over $MgSO_{4(s)}$, filtered, and concentrated. The residue was purified to give the desired products.

Standard procedure L for the alkylation of 4-[2-(4-fluorophenyl)-4-oxo-1,3-thiazolidin-3-yl]-3-methylbenzoic acid.

A solution of 4-[2-(4-fluorophenyl)-4-oxo-1,3-thiazolidin-3-yl]-3-methylbenzoic acid, chloro-substituted derivative, and $K_2CO_3$ in DMF was stirred at 80° C. for 18 h and cooled to room temperature. The reaction mixture was quenched with water and extracted with ethyl acetate. The combined organic layers were dried over $MgSO_{4(s)}$, filtered, and concentrated. The residue was purified by Isco Combi-Flash Companion column chromatography to give the desired products.

EXAMPLE 1

2-(3-Fluorophenyl)-3-(2-methoxyphenyl)thiazolidin-4-one

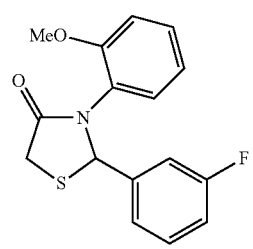

Compound 1

The compound was prepared by following the standard procedure A with 2-methoxyaniline (49.2 mg, 0.400 mmol), 3-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by recrystallization to give the desired product as a yellow solid (78.0 mg, 64%). $^1$H NMR (CDCl$_3$, 400 MHz) δ 7.23-7.18 (m, 2H), 7.08 (t, 2H), 6.95-6.87 (m, 3H), 6.82 (t, 1H), 6.07 (s, 1H), 3.95 (d, 1H), 3.88 (d, 1H), 3.84 (s, 3H); LC-MS (ESI) m/z 304.9 [M+H]$^+$.

EXAMPLE 2

2-(4-Fluorophenyl)-3-(2-methoxyphenyl)thiazolidin-4-one

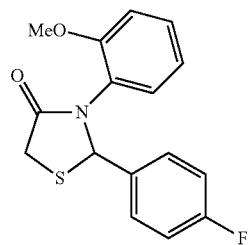

Compound 2

The compound was prepared by following the standard procedure A with 2-methoxylaniline (49.2 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (77.0 mg, 63%). $^1$H NMR (CDCl$_3$, 400 MHz) δ 7.31 (dd, 2H), 7.22-7.18 (m, 1H), 6.93 (t, 2H), 6.87 (d, 2H), 6.81 (t, 1H), 6.08 (s, 1H), 3.92 (s, 2H), 3.83 (s, 3H); LC-MS (ESI) m/z 304.9 [M+H]$^+$.

EXAMPLE 3

2-(3,5-Difluorophenyl)-3-(5-fluoro-2-methoxyphenyl)thiazolidin-4-one

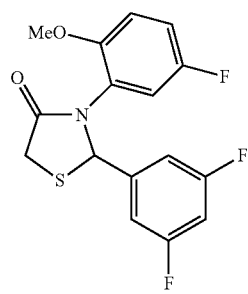

Compound 3

The compound was prepared by following the standard procedure A with 5-fluoro-2-methoxyaniline (56.4 mg, 0.400 mmol), 3,5-difluorobenzaldehyde (56.8 mg, 0.400 mmol), and 2-mercaptoacetic acid (0.670 mL, 86.5 mg, 0.940 mmol). It was reflux 6 h for the first step and 18 h for the second step. After work-up, the crude product was purified by recrystallization to give the desired product as a yellow solid (63.0 mg, 46%). $^1$H NMR (CDCl$_3$, 400 MHz) δ 6.95 (td, 1H), 6.89-6.82 (m, 3H), 6.75-6.68 (m, 2H), 6.05 (s, 1H), 3.93 (d, 1H), 3.87 (d, 1H), 3.83 (s, 3H); LC-MS (ESI) m/z 340.8 [M+H]$^+$.

EXAMPLE 4

2-(3,4-Difluorophenyl)-3-(5-fluoro-2-methoxyphenyl)thiazolidin-4-one

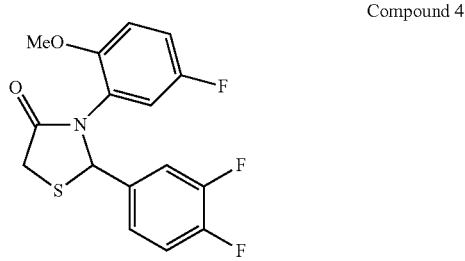 [SMILES: COc1ccc(F)cc1N1C(=O)CSC1c1ccc(F)c(F)c1]

Compound 4

The compound was prepared by following the standard procedure A with 5-fluoro-2-methoxyaniline (56.4 mg, 0.400 mmol), 3,4-difluorobenzaldehyde (56.8 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (82 mg, 61%). $^1$H NMR (CDCl$_3$, 400 MHz) δ 7.21 (t, 1H), 7.08-7.00 (m, 2H), 6.95-6.91 (m, 1H), 6.82 (dd, 1H), 6.69 (dd, 1H), 6.06 (s, 1H), 3.90 (s, 2H), 3.82 (s, 3H); LC-MS (ESI) m/z 340.8 [M+H]$^+$.

EXAMPLE 5

3-(5-Fluoro-2-methoxyphenyl)-2-(3-fluorophenyl)thiazolidin-4-one

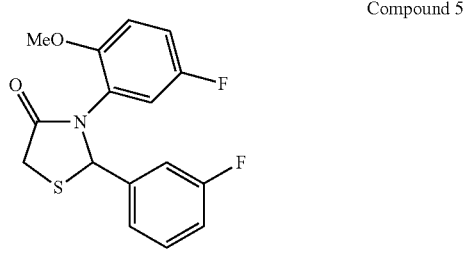 [SMILES: COc1ccc(F)cc1N1C(=O)CSC1c1cccc(F)c1]

Compound 5

The compound was prepared by following the standard procedure A with 5-fluoro-2-methoxyaniline (56.4 mg, 0.400 mmol), 3-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (83.0 mg, 64%). $^1$H NMR (CDCl$_3$, 400 MHz) δ 7.23 (dd, 1H), 7.07 (d, 2H), 6.97-6.89 (m, 2H), 6.80 (dd, 1H), 6.70 (dd, 1H), 6.08 (s, 1H), 3.93 (d, 1H), 3.87 (d, 1H), 3.81 (s, 3H); LC-MS (ESI) m/z 322.8 [M+H]$^+$.

EXAMPLE 6

3-(5-Fluoro-2-methoxyphenyl)-2-(4-fluorophenyl)thiazolidin-4-one

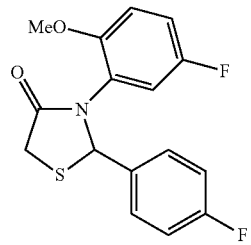

Compound 6

The compound was prepared by following the standard procedure A with 5-fluoro-2-methoxyaniline (56.4 mg, 0.400 mmol), 4-fluorobenzaldehyde (49.6 mg, 0.400 mmol), and 2-mercaptoacetic acid (0.67 mL, 86.5 mg, 0.94 mmol). It was reflux 6 h for the first step and 18 h for the second step. After work-up, the crude product was purified by recrystallized to give the desired product as a yellow solid (57.0 mg, 44%). $^1$H NMR (CDCl$_3$, 300 MHz) δ 7.30 (dd, 1H), 6.95 (t, 3H), 6.89 (dd, 1H), 6.79 (dd, 1H), 6.66 (dd, 1H), 6.09 (s, 1H), 3.90 (s, 2H), 3.80 (s, 3H); LC-MS (ESI) m/z 322.8 [M+H]$^+$.

EXAMPLE 7

2-(3,5-Difluorophenyl)-3-(2,4-dimethoxyphenyl)thiazolidin-4-one

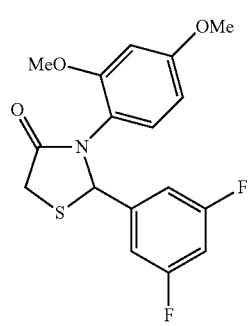

Compound 7

The compound was prepared by following the standard procedure A with 2,4-dimethoxyaniline (61.3 mg, 0.400 mmol), 3,5-difluorobenzaldehyde (56.8 mg, 0.400 mmol), and 2-mercaptoacetic acid (0.67 mL, 86.5 mg, 0.940 mmol). It was reflux 6 h for the first step and 18 h for the second step. After work-up, the crude product was purified by recrystallization to give the desired product as a yellow solid (60.0 mg, 43%). $^1$H NMR (CDCl$_3$, 400 MHz) δ 6.87 (dd, 2H), 6.83 (d, 1H), 6.69 (tt, 1H), 6.44 (d, 1H), 6.36 (dd, 1H), 5.95 (s, 1H), 3.90 (d, 1H), 3.85 (d, 1H), 3.81 (s, 3H), 3.74 (s, 3H); LC-MS (ESI) m/z 352.8 [M+H]$^+$.

EXAMPLE 8

3-(2,4-Dimethoxyphenyl)-2-(4-fluorophenyl)thiazolidin-4-one

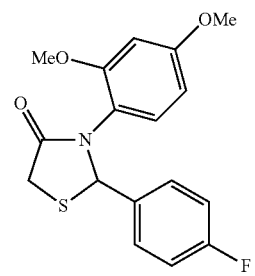

Compound 8

The compound was prepared by following the standard procedure A with 2,4-dimethoxyaniline (61.3 mg, 0.400 mmol), 4-fluorobenzaldehyde (49.6 mg, 0.400 mmol), and 2-mercaptoacetic acid (0.67 mL, 86.5 mg, 0.940 mmol). It was reflux 6 h for the first step and 18 h for the second step. After work-up, the crude product was purified by flash chromatography (ethyl acetate:hexane=3:4) to give the desired product as a yellow viscous liquid (103 mg, 77%). $^1$H NMR (CDCl$_3$, 400 MHz) δ 7.30 (dd, 2H), 6.95 (t, 2H), 6.73 (d, 1H), 6.41 (d, 1H), 6.31 (dd, 1H), 5.99 (s, 1H), 3.91-3.89 (m, 2H), 3.79 (s, 3H), 3.73 (s, 3H); LC-MS (ESI) m/z 334.9 [M+H]$^+$.

EXAMPLE 9

2-(2-Chloro-4-fluorophenyl)-3-(2,4-dimethoxyphenyl)thiazolidin-4-one

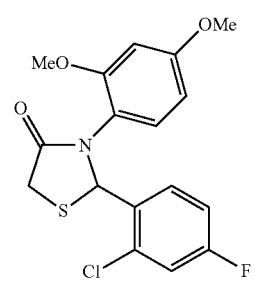

Compound 9

The compound was prepared by following the standard procedure A with 2,4-dimethoxyaniline (76.0 mg, 0.500 mmol), 2-chloro-4-fluorobenzaldehyde (79.0 mg, 0.500 mmol), and 2-mercaptoacetic acid (0.042 mL, 54.0 mg, 0.600 mmol). It was reflux 6 h for the first step and 18 h for the second step. After work-up, the crude product was purified by recrystallization to give the desired product as a yellow solid (129 mg, 70%). $^1$H NMR (CDCl$_3$) δ 7.63 (br s, 1H), 7.03-6.93 (br, 2H), 6.86 (d, 1H), 6.56 (br s, 1H), 6.42 (d, 1H), 6.33 (dd, 1H), 3.90 (d, 1H), 3.83 (d, 1H), 3.80 (s, 3H), 3.72 (s, 3H); LC-MS (ESI) m/z 368.8 [M+H]$^+$.

EXAMPLE 10

3-(4,5-Difluoro-2-methoxyphenyl)-2-(4-fluorophenyl)thiazolidin-4-one

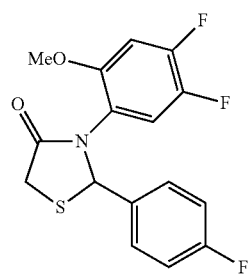

Compound 10

The compound was prepared by following the standard procedure A with 4,5-difluoro-2-methoxyaniline (63.7 mg, 0.400 mmol), 4-fluorobenzaldehyde (49.6 mg, 0.400 mmol), and 2-mercaptoacetic acid (0.500 mL, 64.7 mg, 0.700 mmol). It was reflux 6 h for the first step and 18 h for the second step. After work-up, the crude product was purified by flash chromatography (ethyl acetate:hexane=2:3) to give the desired product as a yellow viscous liquid (44.0 mg, 32%). $^1$H NMR (CDCl$_3$, 400 MHz) δ 7.30 (dd, 2H), 6.97 (t, 2H), 6.76-6.66 (m, 2H), 6.02 (s, 1H), 3.89 (s, 2H), 3.80 (s, 3H); LC-MS (ESI) m/z 339.9 [M+H]$^+$.

EXAMPLE 11

3-(3,5-Difluoro-2-methoxyphenyl)-2-(4-fluorophenyl)thiazolidin-4-one

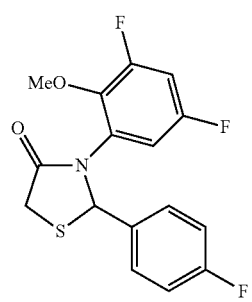

Compound 11

The compound was prepared by following the standard procedure A with 3,5-difluoro-2-methoxyaniline (63.7 mg, 0.400 mmol), 4-fluorobenzaldehyde (49.6 mg, 0.400 mmol), and 2-mercaptoacetic acid (0.500 mL, 64.7 mg, 0.700 mmol). It was reflux 6 h for the first step and 18 h for the second step. After work-up, the crude product was purified by flash chromatography (ethyl acetate:hexane=1:3) to give the desired product as a yellow viscous liquid (23.0 mg, 17%). $^1$H NMR (CDCl$_3$, 400 MHz) δ 7.32 (dd, 2H), 6.97 (t, 2H), 6.79-6.73 (m, 1H), 6.46 (dd, 1H), 6.06 (s, 1H), 3.87 (s, 5H); LC-MS (ESI) m/z 340.9 [M+H]$^+$.

EXAMPLE 12

4-[2-(4-Fluoro-phenyl)-4-oxo-thiazolidin-3-yl]-3-methoxy-benzoic acid

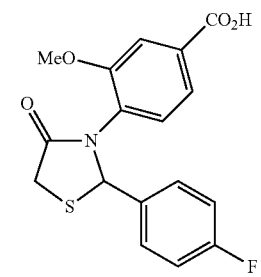

Compound 12

Step 1. Synthesis of 4-[2-(4-fluoro-phenyl)-4-oxo-thiazolidin-3-yl]-3-methoxy-benzoic acid methyl ester Compound 13

The compound was prepared by following the standard procedure A with methyl 4-amino-3-methoxybenzoate (181 mg, 1.00 mmol), 4-fluorobenzaldehyde (186 mg, 1.50 mmol), and 2-mercaptoacetic acid (0.130 ml, 168 mg, 1.80 mmol). It was stirred at room temperature 5 h for the first step and 16 h for the second step. After work-up, the crude product was purified by flash chromatography (ethyl acetate:hexane=2:3) to give the desired product as a yellow viscous liquid (91.0 mg, 25%). $^1$H NMR (CDCl$_3$, 300 MHz) δ 7.53-7.49 (m, 2H), 7.29 (dd, 2H), 6.99 (d, 1H), 6.92 (t, 1H), 6.16 (s, 1H), 3.92 (s, 2H), 3.89 (s, 3H), 3.87 (s, 3H); LC-MS (ESI) m/z 362.8 [M+H]$^+$.

Step 2. Synthesis of 4-[2-(4-fluoro-phenyl)-4-oxo-thiazolidin-3-yl]-3-methoxy-benzoic acid The compound was prepared by following the standard procedure B with 4-[2-(4-fluoro-phenyl)-4-oxo-thiazolidin-3-yl]-3-methoxy-benzoic acid methyl ester (70.0 mg, 0.190 mmol) and 20% NaOH$_{(aq)}$ (0.5 mL, 2.5 mmol) to give the desired product as a white solid (41.0 mg, 61%). $^1$H NMR (CDCl$_3$, 300 MHz) δ 7.60-7.50 (m, 2H), 7.30 (t, 2H), 7.00 (d, 1H), 6.93 (t, 2H), 6.17 (s, 1H), 3.94 (s, 2H), 3.89 (s, 3H); LC-MS (ESI) m/z 348.8 [M+H]$^+$.

EXAMPLE 13

2-(4-Fluorophenyl)-3-(4-methoxyphenyl)thiazolidin-4-one

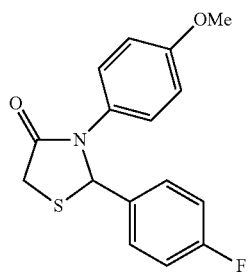

Compound 14

The compound was prepared by following the standard procedure A with 4-methoxyaniline (24.6 mg, 0.200 mmol), 4-fluorobenzaldehyde (24.8 mg, 0.200 mmol), and 2-mercaptoacetic acid (0.170 mL, 21.6 mg, 0.230 mmol). It was reflux 6 h for the first step and 18 h for the second step. After work-up, the crude product was purified by recrystallization to give the desired product as a white solid (55.0 mg, 90%). $^1$H NMR (CDCl$_3$, 300 MHz) δ 7.29 (dd, 2H), 7.01-6.95 (m, 4H), 6.79 (d, 2H), 5.98 (s, 1H), 3.97 (d, 1H), 3.88 (d, 1H), 3.73 (s, 3H); LC-MS (ESI) m/z 304.8 [M+H]$^+$.

EXAMPLE 14

3-(3,4-Dimethoxyphenyl)-2-(4-fluorophenyl)thiazolidin-4-one

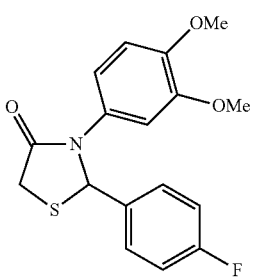

Compound 15

The compound was prepared by following the standard procedure A with 3,4-dimethoxylaniline (61.2 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=5:4) to give the desired product as a yellow viscous liquid (107 mg, 80%). $^1$H NMR (CDCl$_3$, 400 MHz) δ 7.29 (dd, 2H), 6.98 (t, 2H), 6.73 (d, 1H), 6.61-6.57 (m, 2H), 5.95 (s, 1H), 3.97 (d, 1H), 3.89 (d, 1H), 3.80 (s, 3H), 3.73 (s, 3H); LC-MS (ESI) m/z 334.9 [M+H]$^+$.

EXAMPLE 15

2-(4-Fluorophenyl)-3-(3,4,5-trimethoxyphenyl)thiazolidin-4-one

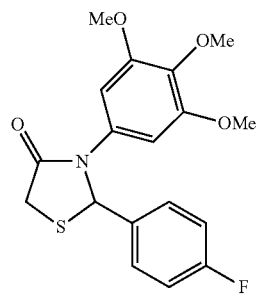

Compound 16

The compound was prepared by following the standard procedure A with 3,4,5-trimethoxyaniline (73.3 mg, 0.400 mmol), 4-fluorobenzaldehyde (49.6 mg, 0.400 mmol), and 2-mercaptoacetic acid (0.67 mL, 86.5 mg, 0.940 mmol). It was reflux 6 h for the first step and 18 h for the second step. After work-up, the crude product was purified by recrystallization to give the desired product as a yellow solid (52.0 mg, 36%). $^1$H NMR (CDCl$_3$, 400 MHz) δ 7.31 (dd, 2H), 7.01 (t, 2H), 6.25 (s, 2H), 5.94 (s, 1H), 3.98 (d, 1H), 3.89 (d, 1H), 3.77 (s, 3H), 3.70 (s, 6H); LC-MS (ESI) m/z 364.8 [M+H]$^+$.

EXAMPLE 16

3-(3-Chloro-4-methoxyphenyl)-2-(4-fluorophenyl)thiazolidin-4-one

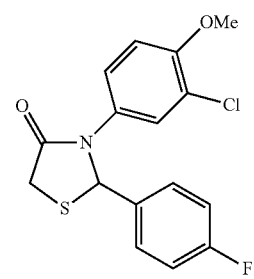

Compound 17

The compound was prepared by following the standard procedure A with 3-chloro-4-methoxyaniline (63 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (100 mg, 74%). $^1$H NMR (CDCl$_3$, 400 MHz) δ 7.28 (dd, 2H), 7.17 (s, 1H), 6.99 (t, 2H), 6.94 (dd, 1H), 6.80 (d, 1H), 5.98 (s, 1H), 3.96 (d, 1H), 3.87 (d, 1H), 3.83 (s, 3H); LC-MS (ESI) m/z 338.7 [M+H]$^+$.

EXAMPLE 17

3-(3-Chloro-4-(trifluoromethoxy)phenyl)-2-(4-fluorophenyl)thiazolidin-4-one

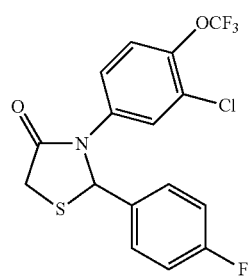

Compound 18

The compound was prepared by following the standard procedure A with 3-chloro-4-(trifluoromethoxy)aniline (42.3 mg, 0.200 mmol), 4-fluorobenzaldehyde (24.8 mg, 0.200 mmol), and 2-mercaptoacetic acid (0.170 mL, 21.6 mg, 0.230 mmol). It was reflux 6 h for the first step and 18 h for the second step. After work-up, the crude product was purified by flash chromatography (ethyl acetate:hexane=2:7) to give the desired product as a yellow viscous liquid (22.0 mg, 28%). $^1$H NMR (CDCl$_3$, 400 MHz) δ 7.38 (d, 1H), 7.28 (dd, 2H), 7.22 (d, 1H), 7.08 (dd, 1H), 7.02 (t, 2H), 6.07 (s, 1H), 3.96 (d, 1H), 3.87 (d, 1H); LC-MS (ESI) m/z 392.9 [M+H]$^+$.

EXAMPLE 18

3-(3-Chloro-4-(trifluoromethoxy)phenyl)-2-(3,5-difluorophenyl)thiazolidin-4-one

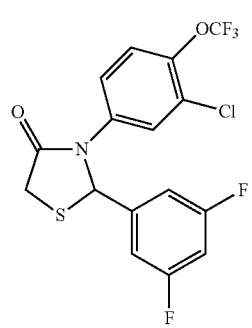

Compound 19

The compound was prepared by following the standard procedure A with 3-chloro-4-(trifluoromethoxy)aniline (42.3 mg, 0.200 mmol), 3,5-difluorobenzaldehyde (28.4 mg, 0.200 mmol), and 2-mercaptoacetic acid (0.170 mL, 21.6 mg, 0.230 mmol). It was reflux 6 h for the first step and 18 h for the second step. After work-up, the crude product was purified by flash chromatography (ethyl acetate:hexane=1:5) to give the desired product as a yellow viscous liquid (30.0 mg, 37%). $^1$H NMR (CDCl$_3$, 400 MHz) δ 7.44 (s, 1H), 7.28-7.25 (m, 1H), 7.15-7.11 (m, 1H), 6.82 (dd, 2H), 6.76 (tt, 1H), 6.01 (s, 1H), 3.97 (d, 1H), 3.85 (d, 1H); LC-MS (ESI) m/z 409.9 [M+H]$^+$.

EXAMPLE 19

3-(3-Chloro-4-ethoxyphenyl)-2-(4-fluorophenyl)thiazolidin-4-one

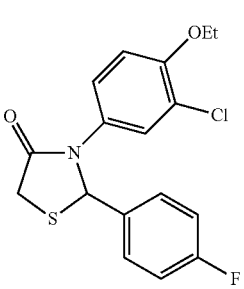

Compound 20

The compound was prepared by following the standard procedure A with 3-chloro-4-ethoxyaniline (34.3 mg, 0.200 mmol), 4-fluorobenzaldehyde (24.8 mg, 0.200 mmol), and 2-mercaptoacetic acid (0.017 mL, 20.3 mg, 0.220 mmol). It was reflux 6 h for the first step and 18 h for the second step. After work-up, the crude product was purified by flash chromatography (ethyl acetate:hexane=3:5) to give the desired product as a yellow viscous liquid (63.0 mg, 90%). $^1$H NMR (CDCl$_3$, 400 MHz) δ 7.29-7.26 (m, 2H), 7.15 (s, 1H), 6.99 (t, 2H), 6.91 (dd, 1H), 6.78 (d, 1H), 5.97 (s, 1H), 4.02 (q, 2H), 3.95 (d, 1H), 3.87 (d, 1H), 1.41 (t, 3H); LC-MS (ESI) m/z 352.8 [M+H]$^+$.

EXAMPLE 20

3-(3-Chloro-4-ethoxyphenyl)-2-(3,5-difluorophenyl)thiazolidin-4-one

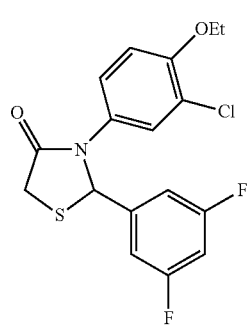

Compound 21

The compound was prepared by following the standard procedure A with 3-chloro-4-ethoxyaniline (34.3 mg, 0.200 mmol), 3,5-difluorobenzaldehyde (28.4 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a white solid (40.0 mg, 54%). $^1$H NMR (CDCl$_3$, 400 MHz) δ 7.19 (d, 1H), 6.96 (dd, 1H), 6.82-6.78 (m, 3H), 6.71 (tt, 1H), 5.91 (s, 1H), 4.03 (q, 2H), 3.95 (d, 1H), 3.84 (d, 1H), 1.41 (t, 3H); LC-MS (ESI) m/z 370.7 [M+H]$^+$.

EXAMPLE 21

2-(3-Chlorophenyl)-3-(3,4-dichlorophenyl)thiazolidin-4-one

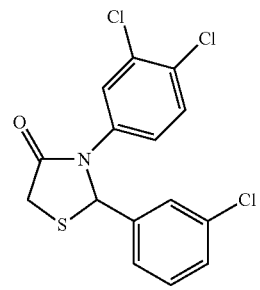

Compound 22

The compound was prepared by following the standard procedure A with 3,4-dichloroaniline (40.5 mg, 0.250 mmol), 3-chlorobenzaldehyde (35.0 mg, 0.250 mmol), and 2-mercaptoacetic acid (0.021 mL, 27.0 mg, 0.300 mmol). It was reflux 6 h for the first step and 18 h for the second step. After work-up, the crude product was purified by flash chromatography (ethyl acetate:hexane=1:4) to give the desired product as a yellow viscous liquid (33.0 mg, 37%). $^1$H NMR (CDCl$_3$, 400 MHz) δ 7.40 (d, 1H), 7.36 (d, 1H), 7.29-7.26 (m, 3H), 7.16-7.14 (m, 1H), 7.02 (dd, 1H), 6.01 (s, 1H), 3.97 (d, 1H), 3.85 (d, 1H); LC-MS (ESI) m/z 357.8 [M+H]$^+$.

EXAMPLE 22

2-(3-Bromophenyl)-3-(3,4-dichlorophenyl)thiazolidin-4-one

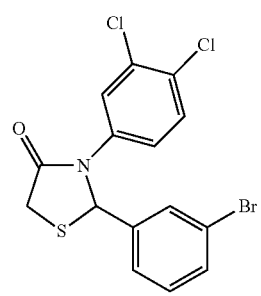

Compound 23

The compound was prepared by following the standard procedure A with 3,4-dichloroaniline (44.6 mg, 0.280 mmol), 3-bromobenzaldehyde (46.3 mg, 0.250 mmol), and 2-mercaptoacetic acid (0.021 mL, 27.0 mg, 0.300 mmol). It was reflux 6 h for the first step and 18 h for the second step. After work-up, the crude product was purified by flash chromatography (ethyl acetate:hexane=1:5) to give the desired product as a yellow viscous liquid (83.1 mg, 82%). $^1$H NMR (CDCl$_3$, 300 MHz) δ 7.42-7.34 (m, 3H), 7.20 (d, 2H), 7.02 (dd, 1H), 6.00 (s, 1H), 3.97 (d, 1H), 3.85 (d, 1H); LC-MS (ESI) m/z 404.7 [M+H]$^+$.

EXAMPLE 23

2-(2-Bromophenyl)-3-(3,4-dichlorophenyl)thiazolidin-4-one

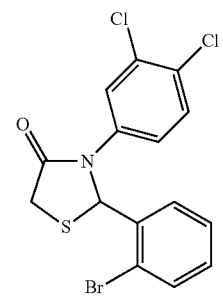

Compound 24

The compound was prepared by following the standard procedure A with 3,4-dichloroaniline (35.6 mg, 0.220 mmol), 2-bromobenzaldehyde (37.0 mg, 0.200 mmol), and 2-mercaptoacetic acid (0.017 mL, 20.3 mg, 0.220 mmol). It was reflux 6 h for the first step and 18 h for the second step. After work-up, the crude product was purified by flash chromatography (ethyl acetate:hexane=2:11) to give the desired product as a yellow viscous liquid (40.0 mg, 50%). $^1$H NMR (CDCl$_3$, 400 MHz) δ 7.60 (dd, 1H), 7.56 (d, 1H), 7.35 (d, 1H), 7.33-7.20 (m, 2H), 7.18 (td, 1H), 7.10 (dd, 1H), 6.49 (s, 1H), 3.91 (d, 1H), 3.80 (d, 1H); LC-MS (ESI) m/z 401.5 [M+H]$^+$.

EXAMPLE 24

2-(4-Bromophenyl)-3-(3,4-dichlorophenyl)thiazolidin-4-one

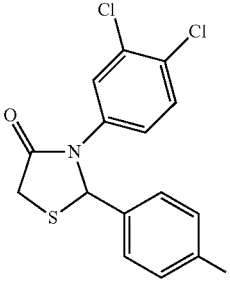

Compound 25

The compound was prepared by following the standard procedure A with 3,4-dichloroaniline (35.6 mg, 0.220 mmol), 4-bromobenzaldehyde (37.0 mg, 0.200 mmol), and thioglycolic acid (0.017 mL, 20.3 mg, 0.220 mmol). It was reflux 6 h for the first step and 18 h for the second step. After work-up, the crude product was purified by recrystallization to give the desired product as a yellow solid (49.7 mg, 60%). $^1$H NMR (CDCl$_3$, 400 MHz) δ 7.43 (d, 2H), 7.35 (d, 1H), 7.32 (d, 1H), 7.14 (d, 2H), 6.98 (dd, 1H), 6.01 (s, 1H), 3.93 (d, 1H), 3.84 (d, 1H); LC-MS (ESI) m/z 401.7 [M+H]$^+$.

EXAMPLE 25

3-(3-Chloro-4-fluorophenyl)-2-(3-chlorophenyl)thiazolidin-4-one

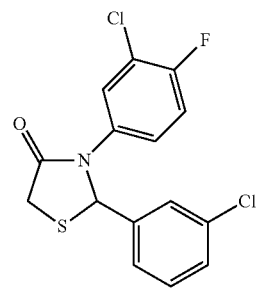

Compound 26

The compound was prepared by following the standard procedure A with 4-fluoro-3-chloroaniline (32.0 mg, 0.220 mmol), 3-chlorobenzaldehyde (28.1 mg, 0.200 mmol), and 2-mercaptoacetic acid (0.017 mL, 20.3 mg, 0.220 mmol). It was reflux 6 h for the first step and 18 h for the second step. After work-up, the crude product was purified by flash chromatography (ethyl acetate:hexane=1:3) to give the desired product as a yellow viscous liquid (41.6 mg, 60%). $^1$H NMR (CDCl$_3$, 300 MHz) δ 7.32-7.23 (m, 4H), 7.20-7.13 (m, 1H), 7.09-6.98 (m, 2H), 5.97 (s, 1H), 3.98 (d, 1H), 3.86 (d, 1H); LC-MS (ESI) m/z 341.8 [M+H]$^+$.

EXAMPLE 26

3-(3-Chloro-4-fluorophenyl)-2-(3,5-difluorophenyl)thiazolidin-4-one

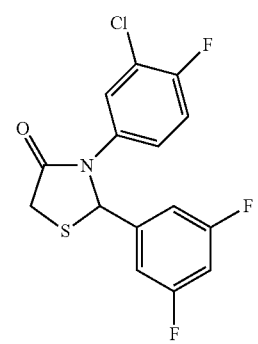

Compound 27

The compound was prepared by following the standard procedure A with 3-chloro-4-fluoroaniline (29.1 mg, 0.200 mmol), 3,5-difluorobenzaldehyde (28.4 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a yellow solid (28.0 mg, 41%). $^1$H NMR (CDCl$_3$, 400 MHz) δ 7.30 (dd, 1H), 7.07 (t, 1H), 7.03-6.99 (m, 1H), 6.83-6.75 (m, 2H), 6.73 (tt, 1H), 5.95 (s, 1H), 3.95 (d, 1H), 3.84 (d, 1H); LC-MS (ESI) m/z 344.7 [M+H]$^+$.

EXAMPLE 27

3-(4-Bromo-3-chlorophenyl)-2-(4-fluorophenyl)thiazolidin-4-one

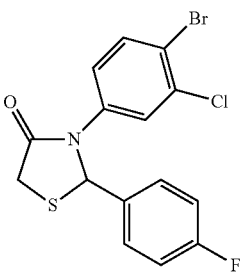

Compound 28

The compound was prepared by following the standard procedure A with 4-bromo-3-chloroaniline (41.3 mg, 0.200 mmol), 4-fluorobenzaldehyde (24.8 mg, 0.200 mmol), and 2-mercaptoacetic acid (0.17 mL, 21.6 mg, 0.230 mmol). It was reflux 6 h for the first step and 18 h for the second step. After work-up, the crude product was purified by flash chromatography (ethyl acetate:hexane=1:3) to give the desired product as a yellow viscous liquid (27.0 mg, 35%). $^1$H NMR (CDCl$_3$, 400 MHz) δ 7.50 (d, 1H), 7.35 (s, 1H), 7.26 (dd, 2H), 7.01 (t, 2H), 6.92 (dd, 1H), 6.06 (s, 1H), 3.94 (d, 1H), 3.86 (d, 1H); LC-MS (ESI) m/z 385.7 [M+H]$^+$.

EXAMPLE 28

3-4-Bromo-3-fluorophenyl)-2-(3-bromophenyl)thiazolidin-4-one

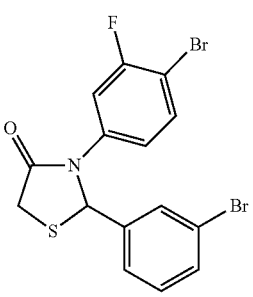

Compound 29

The compound was prepared by following the standard procedure A with 4-bromo-3-fluoroaniline (29.1 mg, 0.200 mmol), 3-bromobenzaldehyde (37.0 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a yellow solid (58.0 mg, 67%). $^1$H NMR (CDCl$_3$, 400 MHz) δ 7.50-7.40 (m, 3H), 7.22-7.18 (m, 2H), 7.13 (dd, 1H), 6.88 (d, 1H), 6.02 (s, 1H), 3.97 (d, 1H), 3.85 (d, 1H); LC-MS (ESI) m/z 429.6 [M+H]$^+$.

EXAMPLE 29

3-(4-Bromo-3-fluorophenyl)-2-(3-chlorophenyl)thiazolidin-4-one

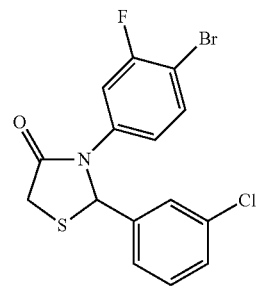

Compound 30

The compound was prepared by following the standard procedure A with 4-bromo-3-fluoroaniline (29.1 mg, 0.200 mmol), 3-chlorobenzaldehyde (28.1 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a yellow solid (40.0 mg, 50%). $^1$H NMR (CDCl$_3$, 300 MHz) δ 7.46 (t, 1H), 7.30-7.20 (m, 3H), 7.20-7.10 (m, 2H), 6.88 (dd, 1H), 6.03 (s, 1H), 3.97 (d, 1H), 3.84 (d, 1H); LC-MS (ESI) m/z 385.6 [M+H]$^+$.

EXAMPLE 30

3-(4-Bromo-3-fluorophenyl)-2-(4-fluorophenyl)thiazolidin-4-one

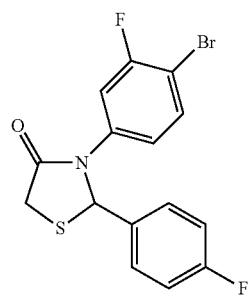

Compound 31

The compound was prepared by following the standard procedure A with 4-bromo-3-fluoroaniline (41.8 mg, 0.220 mmol), 4-fluorobenzaldehyde (24.8 mg, 0.200 mmol), and 2-mercaptoacetic acid (0.017 mL, 20.3 mg, 0.220 mmol). It was reflux 6 h for the first step and 18 h for the second step. After work-up, the crude product was purified by flash chromatography (ethyl acetate:hexane=1:3) to give the desired product as a yellow viscous liquid (30.0 mg, 41%). $^1$H NMR (CDCl$_3$, 300 MHz) δ 7.42 (t, 1H), 7.27-7.22 (m, 2H), 7.05 (dd, 1H), 6.99 (t, 2H), 6.83 (dd, 1H), 6.06 (s, 1H), 3.93 (d, 1H), 3.85 (d, 1H); LC-MS (ESI) m/z 369.7 [M+H]$^+$.

EXAMPLE 31

3-(4-Bromo-3-fluorophenyl)-2-(3,5-difluorophenyl)thiazolidin-4-one

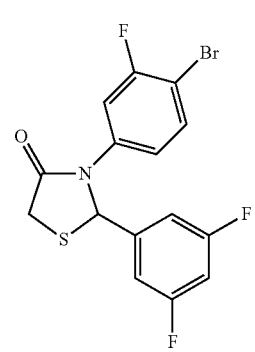

Compound 32

The compound was prepared by following the standard procedure A with 4-bromo-3-fluoroaniline (38.0 mg, 0.200 mmol), 3,5-difluorobenzaldehyde (28.4 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a yellow solid (46.0 mg, 60%). $^1$H NMR (CDCl$_3$, 300 MHz) δ 7.48 (dd, 1H), 7.14 (dt, 1H), 6.90 (dd, 1H), 6.84-6.71 (m, 3H), 6.02 (s, 1H), 3.96 (d, 1H), 3.84 (d, 1H); LC-MS (ESI) m/z 387.8 [M+H]$^+$.

EXAMPLE 32

3-(3-Bromo-4-fluorophenyl)-2-(4-fluorophenyl)thiazolidin-4-one

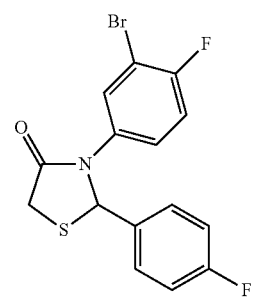

Compound 33

The compound was prepared by following the standard procedure A with 3-bromo-4-fluoroaniline (41.3 mg, 0.200 mmol), 4-fluorobenzaldehyde (21.4 mg, 0.200 mmol), and 2-mercaptoacetic acid (0.017 mL, 20.3 mg, 0.220 mmol). It was reflux 6 h for the first step and 18 h for the second step. After work-up, the crude product was purified by flash chromatography (ethyl acetate:hexane=2:5) to give the desired product as a yellow viscous liquid (50.0 mg, 70%). $^1$H NMR (CDCl$_3$, 300 MHz) δ 7.39 (d, 1H), 7.30-7.26 (m, 2H), 7.05-6.97 (m, 4H), 6.01 (s, 1H), 3.96 (d, 1H), 3.87 (d, 1H); LC-MS (ESI) m/z 369.8 [M+H]$^+$.

EXAMPLE 33

3-(3-Bromo-4-fluorophenyl)-2-(3,5-difluorophenyl)thiazolidin-4-one

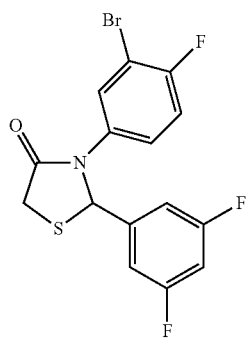

Compound 34

The compound was prepared by following the standard procedure A with 3-bromo-4-fluoroaniline (41.3 mg, 0.200 mmol), 3,5-difluorobenzaldehyde (28.4 mg, 0.200 mmol), and 2-mercaptoacetic acid (0.017 mL, 20.3 mg, 0.220 mmol). It was reflux 6 h for the first step and 18 h for the second step. After work-up, the crude product was purified by recrystallization to give the desired product as a yellow solid (60.0 mg, 77%). $^1$H NMR (CDCl$_3$, 300 MHz) δ 7.46 (d, 1H), 7.07 (d, 2H), 6.85-6.77 (m, 2H), 6.75 (tt, 1H), 5.97 (s, 1H), 3.97 (d, 1H), 3.85 (d, 1H); LC-MS (ESI) m/z 387.6 [M+H]$^+$.

EXAMPLE 34

2-Fluoro-4-[2-(4-fluoro-phenyl)-4-oxo-thiazolidin-3-yl]-benzoic acid methyl ester

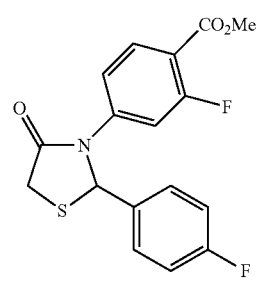

Compound 35

Step 1. Synthesis of methyl 4-amino-2-fluorobenzoate

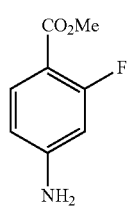

Compound 36

To a solution of 4-amino-2-fluorobenzoic acid (1.00 g, 6.40 mmol) in 15 mL of methanol was treated concentrated HCl (2.0 mL, 24.0 mmol) in one portion at r.t. The reaction mixture was refluxed overnight then directly concentrated to give a crude product, which was partitioned between ethyl acetate (50 mL) and saturated NaHCO$_{3(aq)}$ (20 mL). The organic layer was washed with brine (10 mL), dried over MgSO$_4$, and concentrated to give the desired product (932 mg, 85%). $^1$H NMR (CDCl$_3$, 400 MHz) δ 7.77 (t, 1H), 6.42 (d, 1H), 6.34 (d, 1H), 4.18 (br s, 2H), 3.87 (s, 3H).

Step 2. Synthesis of 2-fluoro-4-[2-(4-fluoro-phenyl)-4-oxo-thiazolidin-3-yl]-benzoic acid methyl ester The compound was prepared by following the standard procedure A with methyl 4-amino-2-fluorobenzoate (169 mg, 1.00 mmol), 4-fluorobenzaldehyde (186 mg, 1.50 mmol), and 2-mercaptoacetic acid (0.128 ml, 165 mg, 1.80 mmol). It was stirred at room temperature 5 h for the first step and 16 h for the second step. After work-up, the crude product was purified by flash chromatography (ethyl acetate: hexane=1:3) to give the desired product as a yellow viscous liquid (130 mg, 37%). $^1$H NMR (CDCl$_3$, 400 MHz) δ 7.85 (t, 1H), 7.27 (dd, 2H), 7.19 (d, 1H), 7.07 (d, 1H), 7.01 (t, 2H), 6.18 (s, 1H), 3.95 (d, 1H), 3.89 (s, 3H), 3.86 (d, 1H); LC-MS (ESI) m/z 349.7 [M+H]$^+$.

EXAMPLE 35

4-(2-(4-Fluorophenyl)-4-oxothiazolidin-3-yl)benzonitrile

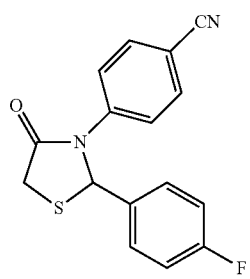

Compound 37

The compound was prepared by following the standard procedure A with 4-aminobenzonitrile (1.18 g, 10.0 mmol), 4-fluorobenzaldehyde (1.24 g, 10.0 mmol), and 2-mercaptoacetic acid (1.25 mL, 1.62 g, 17.5 mmol). It was reflux 6 h for the first step and 18 h for the second step. After work-up, the crude product was purified by recrystallization to give the desired product as a yellow solid (1.18 g, 40%). $^1$H NMR (CDCl$_3$, 400 MHz) δ 7.57 (d, 2H), 7.37 (d, 2H), 7.26 (dd, 2H), 7.00 (t, 2H), 6.18 (s, 1H), 3.95 (d, 1H), 3.87 (d, 1H); LC-MS (ESI) m/z 299.1 [M+H]$^+$.

263

EXAMPLE 36

4-(2-(4-Fluorophenyl)-4-oxothiazolidin-3-yl)benzoic acid

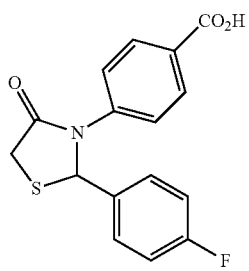

Compound 38

To a suspension of 4-(2-(4-fluorophenyl)-4-oxothiazolidin-3-yl)benzonitrile (100 mg, 0.340 mmol) in H$_2$O (2 mL) was added H$_2$SO$_{4(conc.)}$ (2 me) in one portion. The reaction mixture was refluxed for 3 h then partitioned between ethyl acetate (30 mL) and H$_2$O (20 mL). The organic layer was washed with brine, dried over MgSO$_4$ and concentrated to give a crude product which was purified by flash chromatography to give the desired product as a yellow liquid (3.50 mg, 3.2%). $^1$H NMR (CDCl$_3$, 400 MHz) δ 7.57 (dd, 2H), 7.36 (dd, 2H), 7.26 (dd, 2H), 7.00 (t, 2H), 6.18 (s, 1H), 3.95 (d, 1H), 3.87 (d, 1H).

EXAMPLE 37

3-(4-Fluorophenyl)-2-(4-methoxyphenyl)thiazolidin-4-one

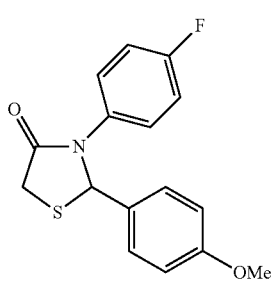

Compound 39

The compound was prepared by following the standard procedure A with 4-fluoroaniline (55.6 mg, 0.500 mmol), p-anisaldehyde (68.0 mg, 0.500 mmol), and 2-mercaptoacetic acid (0.042 mL, 54.0 mg, 0.600 mmol). It was reflux 6 h for the first step and 18 h for the second step. After work-up, the crude product was purified by flash chromatography (ethyl acetate:hexane=1:3) to give the desired product as a yellow viscous liquid (100 mg, 66%). $^1$H NMR (CDCl$_3$, 400 MHz) δ 7.19 (d, 2H), 7.07-7.04 (m, 2H), 6.94 (t, 2H), 6.78 (d, 2H), 5.97 (s, 1H), 3.95 (d, 1H), 3.85 (d, 1H), 3.75 (s, 3H); LC-MS (ESI) m/z 304.9 [M+H]$^+$.

264

EXAMPLE 38

Methyl 3-fluoro-4-[2-(4-fluorophenyl)-4-oxo-1,3-thiazolidin-3-yl]benzoate

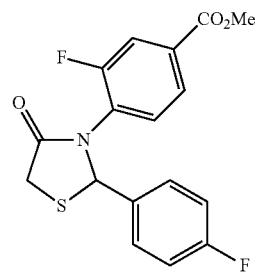

Compound 40

Following standard procedure A, methyl 4-amino-3-fluorobenzene carboxylate (0.680 g, 4.02 mmol), 4-fluorobenzaldehyde (1.00 g, 8.04 mmol), Na$_2$SO$_4$ (1.14 g, 8.04 mmol), 2-mercaptoacetic acid (0.500 mL, 7.20 mmol), and toluene (10 mL) were used to carry out the reaction. It was reflux 5 h for the first step and 20 h for the second step. After work-up, the residue was purified by Isco Combi-Flash Companion column chromatography (0-40% ethyl acetate in n-hexane) to give methyl 3-fluoro-4-[2-(4-fluorophenyl)-4-oxo-1,3-thiazolidin-3-yl]benzoate (0.340 g, 24%) as a yellow gum. 1H NMR (CDCl$_3$, 400 MHz) δ 7.74-7.69 (m, 2H), 7.33 (dd, 2H), 7.16 (dd, 1H), 6.95 (t, 2H), 6.17 (s, 1H), 3.94 (s, 2H), 3.88 (s, 3H); LC-MS (ESI) m/z 350.2 [M+H]$^+$.

EXAMPLE 39

3-Fluoro-4-[2-(4-fluorophenyl)-4-oxo-1,3-thiazolidin-3-yl]benzoic acid

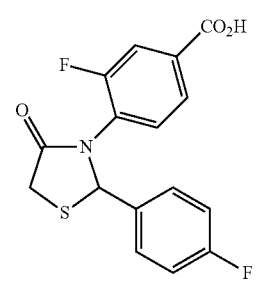

Compound 41

Following standard procedure B, methyl 3-fluoro-4-[2-(4-fluorophenyl)-4-oxo-1,3-thiazolidin-3-yl]benzoate (0.340 g, 0.973 mmol), 20% NaOH$_{(aq)}$ (0.90 mL), and methanol (8.0 mL) were used to carry out the reaction. After the reaction was stirred for 2 h and work-up, the residue was purified by Isco Combi-Flash Companion column chromatography (0-5% MeOH in CH$_2$Cl$_2$) to give 3-fluoro-4-[2-(4-fluorophenyl)-4-oxo-1,3-thiazolidin-3-yl]benzoic acid (0.213 g, 65%) as a white solid. 1H NMR (CDCl$_3$, 400 MHz) δ 7.78-7.72 (m, 2H), 7.34 (dd, 2H), 7.20 (dd, 1H), 6.96 (t, 2H), 6.18 (s, 1H), 3.95 (s, 2H); LC-MS (ESI) m/z 336.2 [M+H]$^+$.

EXAMPLE 40

3-(4-Bromo-2,6-difluorophenyl)-2-(4-fluorophenyl)-1,3-thiazolidin-4-one

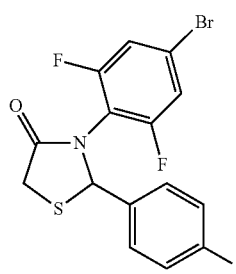

Compound 42

Following standard procedure A, 4-bromo-2,6-difluoroaniline (0.760 g, 3.65 mmol), 4-fluorobenzaldehyde (0.570 g, 4.59 mmol), $Na_2SO_4$ (0.520 g, 3.66 mmol), 2-mercaptoacetic acid (0.450 mL, 6.45 mmol), and toluene (11 mL) were used to carry out the reaction. It was reflux 7 h for the first step and 20 h for the second step. After work-up, the residue was purified by Isco Combi-Flash Companion column chromatography (0-20% ethyl acetate in n-hexane) to give 3-(4-bromo-2,6-difluorophenyl)-2-(4-fluorophenyl)-1,3-thiazolidin-4-one (358 mg, 25%) as a white solid. 1H NMR ($CDCl_3$, 400 MHz) δ 7.37 (dd, 2H), 7.05 (m, 2H), 6.97 (t, 2H), 6.08 (s, 1H), 3.92 (s, 2H); LC-MS (ESI) m/z 388.1 $[M+H]^+$.

EXAMPLE 41

3,5-Difluoro-4-[2-(4-fluorophenyl)-4-oxo-1,3-thiazolidin-3-yl]benzonitrile

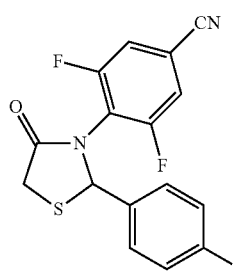

Compound 43

A solution of 3-(4-bromo-2,6-difluorophenyl)-2-(4-fluorophenyl)-1,3-thiazolidin-4-one (119 mg, 0.307 mmol) and copper(I) cyanide (82.5 mg, 0.921 mmol) in DMF (1.0 mL) was reflux for 8 h. After the reaction was cooled and quenched with $NH_4OH_{(aq)}$ (25 mL), the solution was extracted with ethyl acetate. The combined organic layers were dried over $MgSO_{4(s)}$, filtered, and concentrated under reduced pressure to afford a residue. The residue was purified by Isco Combi-Flash Companion column chromatography (0-30% ethyl acetate in n-hexane) and then recrystallized with $CH_2Cl_2$/diethyl ether to give 3,5-difluoro-4-[2-(4-fluorophenyl)-4-oxo-1,3-thiazolidin-3-yl]benzonitrile (12.8 mg, 12%) as a yellow solid. 1H NMR ($CDCl_3$, 400 MHz) δ 7.37 (dd, 2H), 7.18 (m, 2H,), 6.97 (t, 2H), 6.17 (s, 1H), 3.94 (s, 2H); LC-MS (ESI) m/z 335.1 $[M+H]^+$.

example 42

3-Chloro-4-[2-(4-fluorophenyl)-4-oxo-1,3-thiazolidin-3-yl]benzoic acid

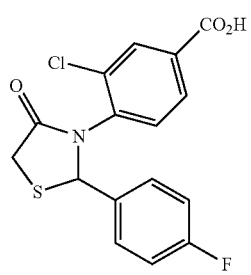

Compound 44

Step 1. Methyl 3-chloro-4-[2-(4-fluorophenyl)-4-oxo-1,3-thiazolidin-3-yl]benzoate

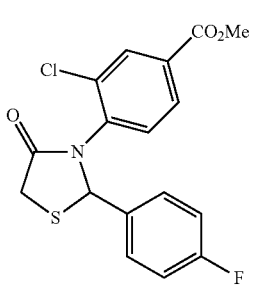

Compound 45

Following standard procedure A, methyl 4-amino-3-chlorobenzene carboxylate (0.522 g, 2.81 mmol), 4-fluorobenzaldehyde (0.999 g, 7.04 mmol), $Na_2SO_4$ (0.799 g, 5.63 mmol), 2-mercaptoacetic acid (0.400 mL, 5.73 mmol), and toluene (9.0 mL) were used to carry out the reaction. It was reflux 7 h for the first step and 20 h for the second step. After work-up, the residue was purified by Isco Combi-Flash Companion column chromatography (0-40% ethyl acetate in n-hexane) to give methyl 3-chloro-4-[2-(4-fluorophenyl)-4-oxo-1,3-thiazolidin-3-yl]benzoate (70.5 mg, 7%) as a brown foam. 1H NMR ($CDCl_3$, 400 MHz) δ 8.07 (s, 1H), 7.78 (dd, 1H), 7.35 (dd, 2H), 6.98-6.94 (m, 3H), 6.13 (s, 1H), 3.96 (s, 2H), 3.89 (s, 3H).

Step 2. 3-Chloro-4-[2-(4-fluorophenyl)-4-oxo-1,3-thiazolidin-3-yl]benzoic acid Following standard procedure B, methyl 3-chloro-4-[2-(4-fluorophenyl)-4-oxo-1,3-thiazolidin-3-yl]benzoate (0.340 g, 0.973 mmol), 20% $NaOH_{(aq)}$ (0.25 mL), and methanol (4.0 mL) were used to carry out the reaction. After the reaction was stirred for 2 h and work-up, the residue was purified by Isco Combi-Flash Companion column chromatography (0-10% MeOH in $CH_2Cl_2$) to give 3-chloro-4-[2-(4-fluorophenyl)-4-oxo-1,3-thiazolidin-3-yl]benzoic acid (35.2 mg, 37%) as a yellow gum. 1H NMR ($CDCl_3$, 400

MHz) δ 8.10 (s, 1H), 7.81 (d, 1H), 7.36 (dd, 2H), 6.99-6.94 (m, 3H), 6.15 (s, 1H), 3.97 (s, 2H); LC-MS (ESI) m/z 352.2 [M+H]⁺.

EXAMPLE 43

4-(2-(4-Fluorophenyl)-4-oxothiazolidin-3-yl)-3-methylbenzonitrile

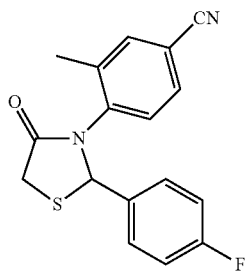

Compound 46

The compound was prepared by following the standard procedure A with 4-amino-3-methylbenzonitrile (200 mg, 1.50 mmol), 4-fluorobenzaldehyde (187 mg, 1.50 mmol), and 2-mercaptoacetic acid (0.190 mL, 246 mg, 2.67 mmol). It was reflux 6 h for the first step and 18 h for the second step. After work-up, the crude product was purified by flash chromatography (ethyl acetate:hexane=1:2) to give the desired product as a yellow viscous liquid (51.0 mg, 11%). ¹H NMR (CDCl₃, 300 MHz) δ 7.49 (br s, 1H), 7.38 (br d, 1H), 7.31 (dd, 2H), 6.98 (t, 2H), 5.93 (br s, 1H), 4.00 (d, 1H), 3.91 (d, 1H), 2.20 (br s, 3H); LC-MS (ESI) m/z 313.2 [M+H]⁺.

EXAMPLE 44

2-(4-Fluorophenyl)-3-(4-methoxy-2-methylphenyl) thiazolidin-4-one

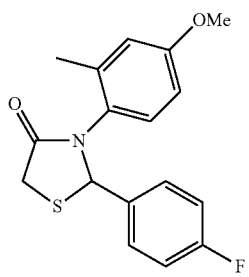

Compound 47

The compound was prepared by following the standard procedure A with 4-methoxy-2-methylaniline (4.00 g, 29.2 mmol), 4-fluorobenzaldehyde (3.60 g, 29.2 mmol), and 2-mercaptoacetic acid (3.00 mL, 3.89 g, 42.1 mmol). It was reflux 6 h for the first step and 18 h for the second step. After work-up, the crude product was purified by flash chromatography to give the desired product as a brown solid (6.70 g, 72%). ¹H NMR (CDCl₃, 400 MHz) δ 7.31 (dd, 2H), 6.97 (br s, 2H), 6.80-6.30 (br, 3H), 6.05-5.58 (br, 1H), 4.00 (d, 1H), 3.89 (d, 1H), 3.72 (s, 3H), 2.25 (br s, 3H); LC-MS (ESI) m/z 318.9 [M+H]⁺.

EXAMPLE 45

2-(4-Fluorophenyl)-3-(5-methoxy-2-methylphenyl)-1,3-thiazolidin-4-one

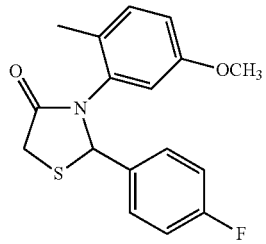

Compound 48

Following standard procedure A, 5-methoxy-2-methylaniline (0.381 g, 2.78 mmol), 4-fluorobenzaldehyde (0.448 g, 3.61 mmol), Na₂SO₄ (0.395 g, 2.78 mmol), 2-mercaptoacetic acid (0.350 mL, 5.02 mmol), and toluene (8.0 mL) were used to carry out the reaction. It was reflux 2 h for the first step and 18 h for the second step. After work-up, the residue was purified by Isco Combi-Flash Companion column chromatography (0-30% ethyl acetate in n-hexane) and then (0-5% ethyl acetate in CH₂Cl₂) to give 2-(4-fluorophenyl)-3-(5-methoxy-2-methylphenyl)-1,3-thiazolidin-4-one (149 mg, 17%) as a yellow solid. 1H NMR (CDCl₃, 400 MHz) δ 7.34-7.31 (m, 2H), 7.07 (br s, 1H), 6.96 (br t, 2H), 6.72 (dd, 1H), 6.10-5.60 (br, 1H), 4.00 (d, 1H), 3.90 (d, 1H), 3.62 (br s, 3H), 2.09 (br s, 3H); LC-MS (ESI) m/z 318.2 [M+H]⁺.

EXAMPLE 46

3-(5-Fluoro-4-methoxy-2-methylphenyl)-2-(4-fluorophenyl)thiazolidin-4-one

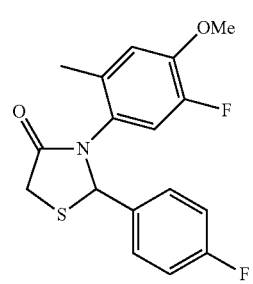

Compound 49

Step 1. Synthesis of 1-Fluoro-2-methoxy-4-methyl-5-nitrobenzene

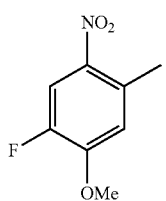

Compound 50

To a solution of 2-fluoro-5-methyl-4-nitrophenol (3.10 g, 18.1 mmol) in 30 mL of DMF was added $K_2CO_{3(s)}$ (3.75 g, 27.2 mmol) and iodomethane (5.60 mL, 12.7 g, 89.9 mmol). The reaction mixture was stirred at 60° C. for overnight then partitioned between ether (80 mL) and $H_2O$ (10 mL). The aqueous layer was washed with ether (50 mL×2). The combined organic layer was washed with brine (20 mL), dried over $MgSO_4$ and concentrated to give a crude solid (3.20 g) which was recrystallized to give a brown solid (2.18 g, 65%). $^1H$ NMR ($CDCl_3$, 300 MHz) δ 7.90 (d, 1H), 6.82 (d, 1H), 3.97 (s, 3H), 2.64 (s, 3H).

Step 2. Synthesis of
5-Fluoro-4-methoxy-2-methylaniline

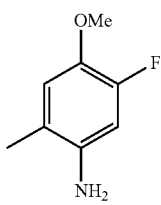

Compound 51

To a solution of dimethyl 1-fluoro-2-methoxy-4-methyl-5-nitrobenzene (2.04 g, 10.9 mmol) in 30 mL of acetic acid was added zinc dust$_{(s)}$ (5.27 g, 83.2 mmol) in one portion at r.t. The reaction mixture was stirred at r.t. for 3.5 h then passed through a pad of celite. The filtrate was partitioned between dichloromethane (80 mL) and saturated $NaHCO_{3(aq)}$ (30 mL). The organic layer was dried over $MgSO_4$ and concentrated to give a crude product which was purified by flash chromatography (ethyl acetate:hexane=1:2) to give the desired product as a yellow viscous liquid (1.30 g, 77%). $^1H$ NMR ($CDCl_3$, 400 MHz) δ 6.70 (d, 1H), 6.45 (d, 1H), 3.81 (s, 3H), 3.41 (br s, 2H), 2.12 (s, 3H).

Step 3. Synthesis of 3-(5-Fluoro-4-methoxy-2-methylphenyl)-2-(4-fluorophenyl)thiazolidin-4-one The compound was prepared by following the standard procedure A with 5-fluoro-4-methoxy-2-methylaniline (1.30 g, 8.30 mmol), 4-fluorobenzaldehyde (1.03 g, 8.30 mmol), and 2-mercaptoacetic acid (0.920 mL, 1.19 g, 12.9 mmol). It was reflux 6 h for the first step and 18 h for the second step. After work-up, the crude product was purified by flash chromatography (ethyl acetate:hexane=2:3) to give the desired product as a brown solid (1.03 g, 37%). $^1H$ NMR ($CDCl_3$, 300 MHz) δ 7.40-7.26 (m, 2H), 6.99 (br t, 2H), 6.73 (br s, 2H), 5.80 (br s, 1H), 3.98 (d, 1H), 3.88 (d, 1H), 3.82 (s, 3H), 2.08 (br s, 3H); LC-MS (ESI) m/z 336.9 [M+H]$^+$.

EXAMPLE 47

3-(4,5-Dimethoxy-2-methylphenyl)-2-(4-fluorophenyl)thiazolidin-4-one

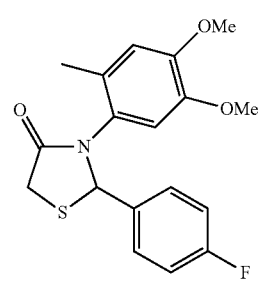

Compound 52

The compound was prepared by following the standard procedure A with 4,5-dimethoxy-2-methylaniline (66.9 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=5:4) to give the desired product as a yellow viscous liquid (108 mg, 78%). $^1H$ NMR ($C_6D_6$, 300 MHz) δ 6.81 (br s, 2H), 6.52 (t, 2H), 6.28 (br s, 1H), 6.03 (br s, 1H), 5.35 (br s, 1H), 3.54 (d, 1H), 3.44 (d, 1H), 3.25-3.15 (br, 6H), 1.94 (br s, 3H); LC-MS (ESI) m/z 348.9 [M+H]$^+$.

EXAMPLE 48

3-(4-(Dimethylamino)-2-methylphenyl)-2-(4-fluorophenyl)thiazolidin-4-one

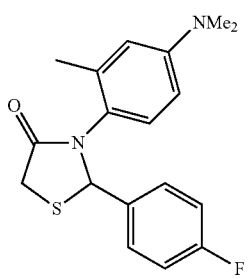

Compound 53

The compound was prepared by following the standard procedure A with N,N,3-trimethylbenzene-1,4-diamine (120 mg, 0.800 mmol), 4-fluorobenzaldehyde (99.2 mg, 0.800 mmol), and 2-mercaptoacetic acid (0.083 mL, 107 mg, 1.17 mmol). It was reflux 6 h for the first step and 18 h for the second step. After work-up, the crude product was purified by recrystallization (ethyl acetate:hexane=1:2) to give the desired product as a yellow solid (110 mg, 42%). $^1H$ NMR ($CDCl_3$, 400 MHz) δ 7.31 (dd, 2H), 6.97 (br s, 2H), 6.52 (br s, 1H), 6.30 (br s, 1H), 5.64 (br s, 1H), 4.00 (br d, 1H), 3.88 (d, 1H), 2.88 (s, 6H), 2.24 (br s, 3H); LC-MS (ESI) m/z 331.8 [M+H]$^+$.

EXAMPLE 49

3-(2-(4-Fluorophenyl)-4-oxothiazolidin-3-yl)-4-methylbenzoic acid

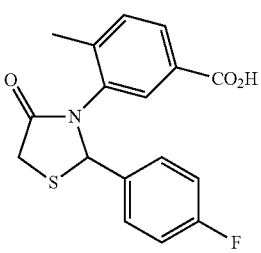

Compound 54

Step 1. Synthesis of Methyl 3-(2-(4-fluorophenyl)-4-oxothiazolidin-3-yl)-4-methylbenzoate

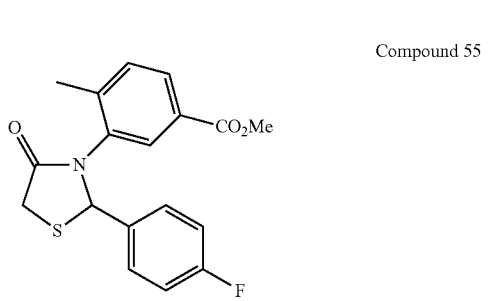 [SMILES: COC(=O)c1ccc(C)c(N2C(=O)CSC2c2ccc(F)cc2)c1]

Compound 55

The compound was prepared by following the standard procedure A with methyl 3-amino-4-methylbenzoate (165 mg, 1.00 mmol), 4-fluorobenzaldehyde (124 mg, 1.00 mmol), and 2-mercaptoacetic acid (0.210 mL, 272 mg, 2.95 mmol). It was reflux 6 h for the first step and 18 h for the second step. After work-up, the crude product was purified by flash chromatography (ethyl acetate:hexane=2:3) to give the desired product as a yellow viscous liquid (152 mg, 42%). $^1$H NMR (CDCl$_3$, 300 MHz) δ 7.90-7.88 (br, 2H), 7.32 (dd, 2H), 7.21 (br s, 1H), 6.95 (br s, 2H), 6.22-5.65 (br, 1H), 4.00 (d, 1H), 3.91 (d, 1H), 3.87 (br s, 3H), 2.45-1.90 (br, 3H).

Step 2. Synthesis of 3-(2-(4-Fluorophenyl)-4-oxothiazolidin-3-yl)-4-methylbenzoic acid The compound was prepared by following the standard procedure B with methyl 3-(2-(4-fluorophenyl)-4-oxothiazolidin-3-yl)-4-methylbenzoate (152 mg, 0.420 mmol) and 20% NaOH$_{(aq)}$ (1.00 mL, 5.00 mmol) to give the desired product as a yellow viscous liquid (130 mg, 89%). $^1$H NMR (CDCl$_3$, 400 MHz) δ 7.93-7.80 (br, 2H), 7.34 (dd, 2H), 7.26 (br s, 1H), 6.96 (br s, 2H), 6.20-5.65 (m, 1H), 4.02 (br d, 1H), 3.94 (br d, 1H), 2.45-1.95 (m, 3H); LC-MS (ESI) m/z 332.2 [M+H]$^+$.

EXAMPLE 50

4-[2-(4-Fluoro-phenyl)-4-oxo-thiazolidin-3-yl]-2-methyl-benzoic acid methyl ester

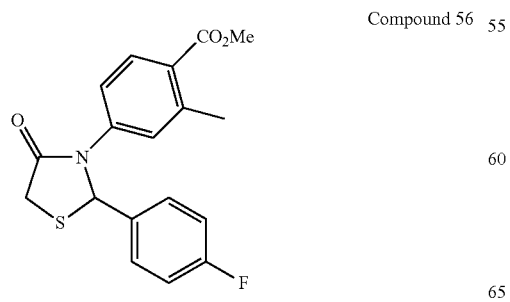

Compound 56

Step 1. Synthesis of methyl 4-amino-2-methylbenzoate

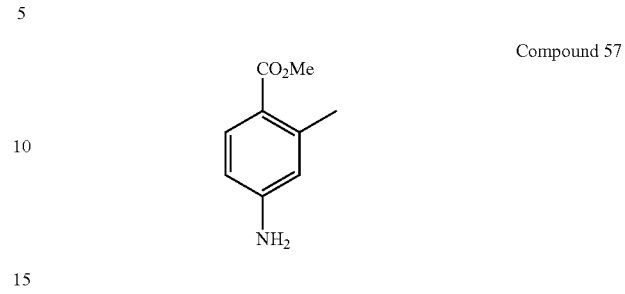

Compound 57

To a solution of 4-amino-2-methylbenzoic acid (1.00 g, 6.60 mmol) in 18 mL of methanol was treated concentrated HCl (2.30 mL, 27.6 mmol) in one portion at r.t. The reaction mixture was refluxed overnight then directly concentrated to give a crude product, which was partitioned between ethyl acetate (50 mL) and saturated NaHCO$_{3(aq)}$ (20 mL). The organic layer was washed with brine (10 mL), dried over MgSO$_4$ and concentrated to give the desired product (930 mg, 85%). $^1$H NMR (CDCl$_3$, 400 MHz) δ 7.83-7.80 (m, 1H), 6.51-6.48 (m, 2H), 4.15 (br s, 2H), 3.83 (s, 3H), 2.55 (s, 3H).

Step 2. Synthesis of 4-[2-(4-fluoro-phenyl)-4-oxo-thiazolidin-3-yl]-2-methyl-benzoic acid methyl ester The compound was prepared by following the standard procedure A with methyl 4-amino-2-methylbenzoate (165 mg, 1.00 mmol), 4-fluorobenzaldehyde (186 mg, 1.50 mmol), and 2-mercaptoacetic acid (0.128 mL, 165 mg, 1.80 mmol). It was stirred at room temperature 5 h for the first step and 16 h for the second step. After work-up, the crude product was purified by flash chromatography (ethyl acetate:hexane=1:2) to give the desired product as a yellow viscous liquid (150 mg, 43%). $^1$H NMR (CDCl$_3$, 300 MHz) δ 7.83 (d, 1H), 7.27 (dd, 2H), 7.13 (s, 1H), 7.03 (d, 1H), 6.98 (t, 2H), 6.15 (s, 1H), 3.96 (d, 1H), 3.86 (d, 1H), 3.84 (s, 3H), 2.52 (s, 3H); LC-MS (ESI) m/z 346.8 [M+H]$^+$.

EXAMPLE 51

4-(2-(4-Fluorophenyl)-4-oxothiazolidin-3-yl)-3-methylbenzoic acid

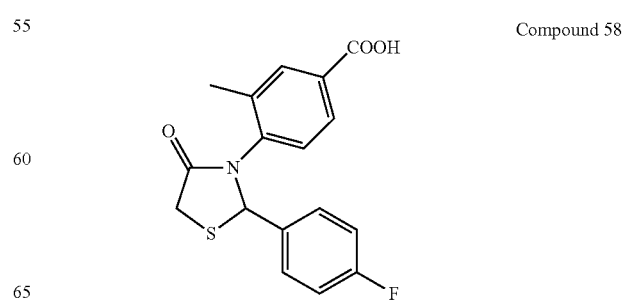

Compound 58

273

Step 1. Synthesis of Methyl 4-(2-(4-fluorophenyl)-4-oxothiazolidin-3-yl)-3-methylbenzoate

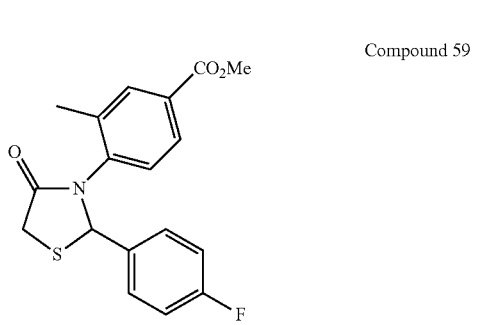

Compound 59

The compound was prepared by following the standard procedure A with methyl 4-amino-3-methylbenzenecarboxylate (1.50 g, 9.08 mmol), 4-fluorobenzaldehyde (1.20 g, 9.67 mmol), 2-mercaptoacetic acid (1.14 mL, 1.48 g, 16.0 mmol), and toluene (30 mL). It was reflux 6 h for the first step and 18 h for the second step. After work-up, the residue was purified by flash chromatography to give the desired product as yellow viscous liquid (500 mg, 16%). $^1$H NMR (CDCl$_3$, 300 MHz) δ 7.86 (br s, 1H), 7.74 (br d, 1H), 7.30 (dd, 2H), 6.95 (t, 2H), 5.94 (br s, 1H), 4.01 (d, 1H), 3.91 (d, 1H), 3.87 (s, 3H), 2.19 (br s, 3H); LC-MS (ESI) m/z 346.2 [M+H]$^+$.

Step 2. Synthesis of 4-(2-(4-Fluorophenyl)-4-oxothiazolidin-3-yl)-3-methylbenzoic acid The compound was prepared by following the standard procedure B with methyl 4-(2-(4-fluorophenyl)-4-oxothiazolidin-3-yl)-3-methylbenzoate (500 mg, 1.45 mmol), 20% NaOH$_{(aq)}$ (1.25 mL, 6.25 mmol), and ethanol (5.00 mL). The reaction mixture was stirred for 4 h and work-up to give the desired product (450 mg, 94%). $^1$H NMR (CDCl$_3$, 400 MHz) δ 7.89 (br s, 1H), 7.78 (br s, 1H), 7.31 (dd, 2H), 6.96 (t, 2H), 5.97 (br s, 1H), 4.03 (d, 1H), 3.94 (d, 1H), 2.21 (br s, 3H); LC-MS (ESI) m/z 332.2 [M+H]$^+$.

EXAMPLE 52

4-(2-(3-Fluorophenyl)-4-oxothiazolidin-3-yl)-3-methylbenzoic acid

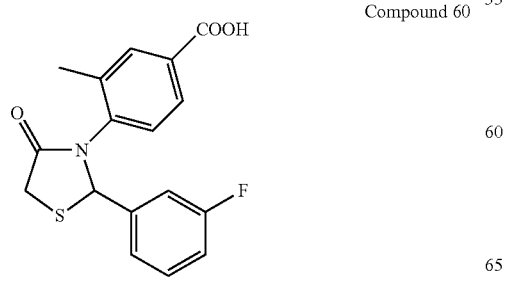

Compound 60

274

Step 1. Synthesis of Methyl 4-(2-(3-fluorophenyl)-4-oxothiazolidin-3-yl)-3-methylbenzoate

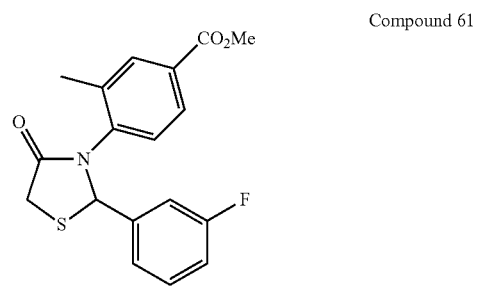 [SMILES: COC(=O)c1ccc(N2C(=O)CSC2c2cccc(F)c2)c(C)c1]

Compound 61

The compound was prepared by following the standard procedure A with methyl 4-amino-3-methylbenzenecarboxylate (1.65 g, 10.0 mmol), 3-fluorobenzaldehyde (2.48 g, 20.0 mmol), 2-mercaptoacetic acid (1.42 mL, 1.84 g, 20.0 mmol) and toluene (35 mL). It was stirred at room temperature 5 h for the first step and 16 h for the second step. After work-up, the residue was purified by flash chromatography to give the desired product as a yellow viscous liquid (1.30 g, 38%). $^1$H NMR (CDCl$_3$, 300 MHz) δ 7.88 (br s, 1H), 7.74 (br d, 1H), 7.28-7.16 (m, 1H), 7.10-7.04 (m, 2H), 6.97 (br t, 1H), 5.91 (br s, 1H), 4.03 (d, 1H), 3.91 (d, 1H), 3.86 (s, 3H), 2.21 (br s, 3H); LC-MS (ESI) m/z 346.2 [M+H]$^+$.

Step 2. Synthesis of 4-(2-(3-Fluorophenyl)-4-oxothiazolidin-3-yl)-3-methylbenzoic acid The compound was prepared by following the standard procedure B with methyl 4-(2-(3-fluorophenyl)-4-oxothiazolidin-3-yl)-3-methylbenzoate (1.23 g, 3.56 mmol), methanol (10 mL), and 20% NaOH$_{(aq)}$ (3.56 mL, 17.8 mmol). After the reaction mixture was stirred for 5 h and work-up, the residue was purified by flash chromatography to give the desired product (960 mg, 81%). $^1$H NMR (CDCl$_3$, 300 MHz) δ 7.90 (br s, 1H), 7.78 (br d, 1H), 7.27-7.20 (m, 1H), 7.11-7.04 (m, 2H), 6.98 (br t, 1H), 5.93 (br s, 1H), 4.04 (d, 1H), 3.93 (d, 1H), 2.22 (br s, 3H); LC-MS (ESI) m/z 332.2 [M+H]$^+$.

EXAMPLE 53

4-(2-(3,4-Difluorophenyl)-4-oxothiazolidin-3-yl)-3-methylbenzoic acid

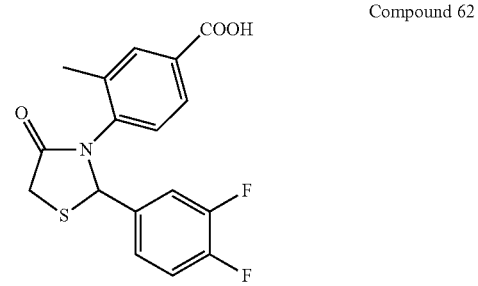 [SMILES: Cc1cc(C(=O)O)ccc1N1C(=O)CSC1c1ccc(F)c(F)c1]

Compound 62

Step 1. Synthesis of Methyl 4-(2-(3,4-difluorophenyl)-4-oxothiazolidin-3-yl)-3-methylbenzoate

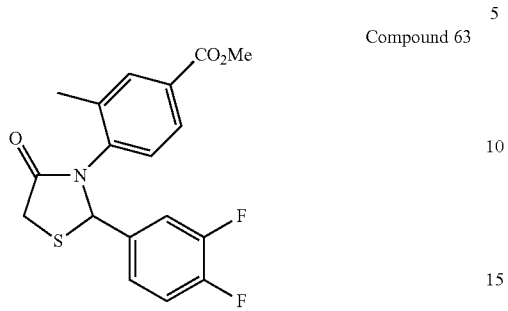

Compound 63

The compound was prepared by following the standard procedure A with methyl 4-amino-3-methylbenzenecarboxylate (825 mg, 5.00 mmol), 2,4-difluorobenzaldehyde (781 mg, 5.50 mmol), and 2-mercaptoacetic acid (0.63 mL, 921 mg, 10.0 mmol). It was stirred at room temperature 5 h for the first step and 16 h for the second step. After work-up, the crude product was purified by flash chromatography (ethyl acetate:hexane=1:2) to give the desired product as a yellow viscous liquid (480 mg, 26%). $^1$H NMR (CDCl$_3$, 300 MHz) δ 7.88 (br s, 1H), 7.76 (br d, 1H), 7.21 (t, 1H), 7.08-6.91 (m, 3H), 5.90 (br s, 1H), 4.00 (d, 1H), 3.91 (d, 1H), 3.87 (s, 3H), 2.20 (br s, 3H); LC-MS (ESI) m/z 364.2 [M+H]$^+$.

Step 2. Synthesis of 4-(2-(3,4-Difluorophenyl)-4-oxothiazolidin-3-yl)-3-methylbenzoic acid The compound was prepared by following the the standard procedure B with methyl 4-(2-(3,4-difluorophenyl)-4-oxothiazolidin-3-yl)-3-methylbenzoate (400 mg, 1.10 mmol), and 20% NaOH$_{(aq)}$ (1.00 mL, 5.00 mmol). The crude product was directly concentrated to give the desired product as a yellow viscous solid (380 mg, 99%). $^1$H NMR (CDCl$_3$, 400 MHz) δ 7.92 (br s, 1H), 7.80 (br s, 1H), 7.23 (t, 1H), 7.08-6.60 (m, 3H), 5.93 (br s, 1H), 4.02 (d, 1H), 3.93 (d, 1H), 2.22 (br s, 3H); LC-MS (ESI) m/z 350.2 [M+H]$^+$.

EXAMPLE 54

4-(2-(3,5-Difluorophenyl)-4-oxothiazolidin-3-yl)-3-methylbenzoic acid

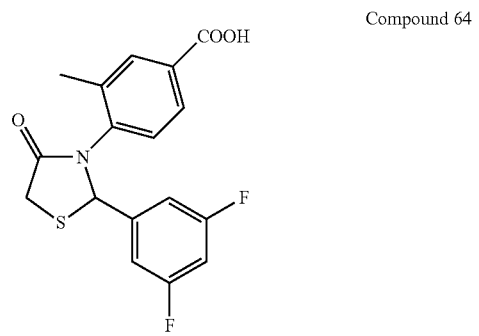 [SMILES: Cc1cc(C(=O)O)ccc1N1C(=O)CSC1c1cc(F)cc(F)c1]

Compound 64

Step 1. Synthesis of Methyl 4-(2-(3,5-difluorophenyl)-4-oxothiazolidin-3-yl)-3-methylbenzoate

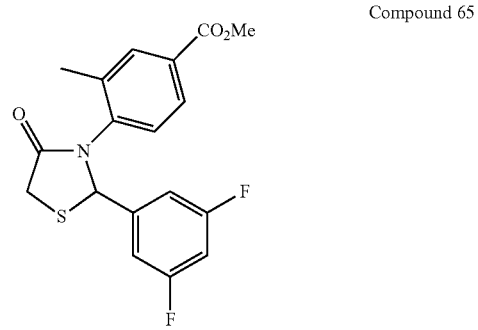 [SMILES: COC(=O)c1ccc(N2C(=O)CSC2c2cc(F)cc(F)c2)c(C)c1]

Compound 65

The compound was prepared by following the standard procedure A with methyl 4-amino-3-methylbenzoate (165 mg, 1.00 mmol), 3,5-difluorobenzaldehyde (284 mg, 2.00 mmol), and 2-mercaptoacetic acid (0.21 mL, 272 mg, 2.95 mmol). It was stirred at room temperature 5 h for the first step and 16 h for the second step. The crude product was purified by flash chromatography (ethyl acetate:hexane=2:3) to give the desired product as a yellow viscous liquid (100 mg, 29%). $^1$H NMR (CDCl$_3$, 400 MHz) δ 7.90 (br s, 1H), 7.78-7.72 (m, 1H), 7.10-6.82 (m, 3H), 6.73 (t, 1H), 5.87 (br s, 1H), 4.01 (d, 1H), 3.90 (d, 1H), 3.87 (s, 3H), 2.30 (br s, 3H).

Step 2. Synthesis of 4-(2-(3,5-Difluorophenyl)-4-oxothiazolidin-3-yl)-3-methylbenzoic acid The compound was prepared by following the standard procedure B with methyl 4-(2-(3,5-difluorophenyl)-4-oxothiazolidin-3-yl)-3-methylbenzoate (100 mg, 0.280 mmol) and 20% NaOH$_{(aq)}$ (0.500 mL, 2.50 mmol). The crude product was purified by flash chromatography (ethyl acetate:hexane:acetic acid=50:50:1) to give the desired product as a yellow viscous liquid (25.0 mg, 26%). $^1$H NMR (CD$_3$OD, 400 MHz) δ 7.87 (br s, 1H), 7.77 (br d, 1H), 7.12-7.06 (m, 2H), 6.89 (t, 1H), 6.26 (br s, 1H), 4.12 (d, 1H), 3.94 (d, 1H), 2.21 (br s, 3H); LC-MS (ESI) m/z 350.2 [M+H]$^+$.

EXAMPLE 55

4-(2-(4-Fluoro-2-methylphenyl)-4-oxothiazolidin-3-yl)-3-methylbenzoic acid

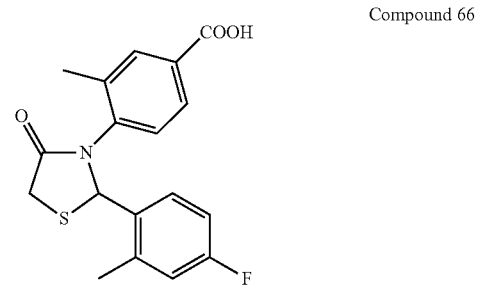 [SMILES: Cc1cc(F)ccc1C1SCC(=O)N1c1ccc(C(=O)O)cc1C]

Compound 66

277

Step 1. Synthesis of Methyl 4-(2-(4-fluoro-2-methylphenyl)-4-oxothiazolidin-3-yl)-3-methylbenzoate

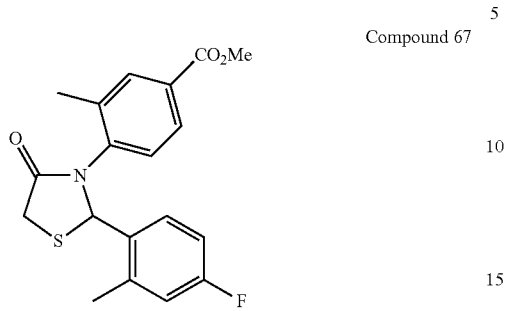

Compound 67

The compound was prepared by following the standard procedure A with methyl 4-amino-3-methylbenzoate (165 mg, 1.00 mmol), 4-fluoro-2-methylbenzaldehyde (138 mg, 1.00 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=2:3) to give the desired product as a yellow viscous liquid (29.0 mg, 8%). $^1$H NMR (CDCl$_3$, 400 MHz) δ 7.92 (br s, 1H), 7.72 (d, 1H), 7.61 (br s, 1H), 6.93 (br t, 1H), 6.85 (br s, 1H), 6.71 (d, 1H), 6.21 (br s, 1H), 4.00 (d, 1H), 3.90 (d, 1H), 3.87 (s, 3H), 2.29 (br s, 3H), 2.12 (br s, 3H).

Step 2. Synthesis of 4-(2-(4-Fluoro-2-methylphenyl)-4-oxothiazolidin-3-yl)-3-methylbenzoic acid The compound was prepared by following the standard procedure B with methyl 4-(2-(4-fluoro-2-methylphenyl)-4-oxothiazolidin-3-yl)-3-methylbenzoate (29.0 mg, 0.08 mmol) and 20% NaOH$_{(aq)}$ (0.500 mL, 2.50 mmol). The crude product was purified by flash chromatography (ethyl acetate:hexane:acetic acid=40:60:1) to give the desired product as a yellow viscous liquid (10.0 mg, 36%). $^1$H NMR (CDCl$_3$, 400 MHz) δ 7.93 (br s, 1H), 7.75 (br d, 1H), 7.61 (br s, 1H), 6.94 (br t, 1H), 6.88 (br s, 1H), 6.72 (br d, 1H), 6.23 (br s, 1H), 4.01 (d, 1H), 3.92 (d, 1H), 2.30 (br s, 3H), 2.13 (br s, 3H); LC-MS (ESI) m/z 346.2 [M+H]$^+$.

EXAMPLE 56

4-(2-(4-Fluoro-3-methylphenyl)-4-oxothiazolidin-3-yl)-3-methylbenzoic acid

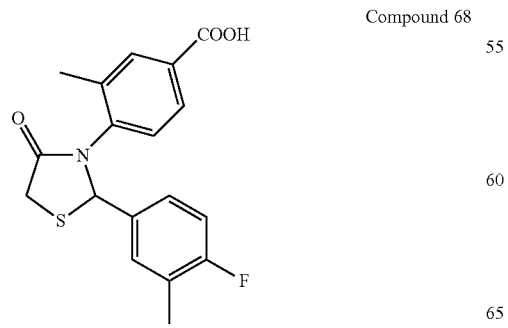

Compound 68

278

Step 1. Synthesis of Methyl 4-(2-(4-fluoro-3-methylphenyl)-4-oxothiazolidin-3-yl)-3-methylbenzoate

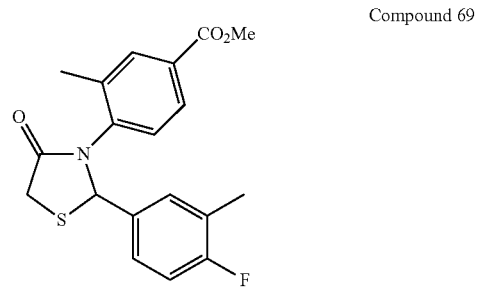 [SMILES: COC(=O)c1ccc(N2C(=O)CSC2c2ccc(F)c(C)c2)c(C)c1]

Compound 69

The compound was prepared by following the standard procedure A with methyl 4-amino-3-methylbenzoate (165 mg, 1.00 mmol), 4-fluoro-3-methylbenzaldehyde (276 mg, 2.00 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=1:2) to give the desired product as a yellow viscous liquid (62.0 mg, 17%). $^1$H NMR (CDCl$_3$, 300 MHz) δ 7.87 (br s, 1H), 7.74 (br d, 1H), 7.15 (dd, 1H), 7.11-7.06 (m, 1H), 6.87 (t, 1H), 5.89 (br s, 1H), 4.00 (d, 1H), 3.90 (d, 1H), 3.86 (s, 3H), 2.20 (br s, 6H); LC-MS (ESI) m/z 359.8 [M+H]$^+$.

Step 2. Synthesis of 4-(2-(4-Fluoro-3-methylphenyl)-4-oxothiazolidin-3-yl)-3-methylbenzoic acid The compound was prepared by following the standard procedure B with methyl 4-(2-(4-fluoro-3-methylphenyl)-4-oxothiazolidin-3-yl)-3-methylbenzoate (52.0 mg, 0.145 mmol) and 20% NaOH$_{(aq)}$ (0.500 mL, 2.50 mmol) to give the desired product as a yellow viscous liquid (50.0 mg, 100%). $^1$H NMR (CDCl$_3$, 300 MHz) δ 7.89 (br s, 1H), 7.76 (br d, 1H), 7.16 (d, 1H), 7.12-7.07 (m, 1H), 6.88 (t, 1H), 5.90 (br s, 1H), 4.03 (d, 1H), 3.92 (d, 1H), 2.20 (br s, 6H); LC-MS (ESI) m/z 346.2 [M+H]$^+$.

EXAMPLE 57

4-(2-(3-Fluoro-4-methylphenyl)-4-oxothiazolidin-3-yl)-3-methylbenzoic acid

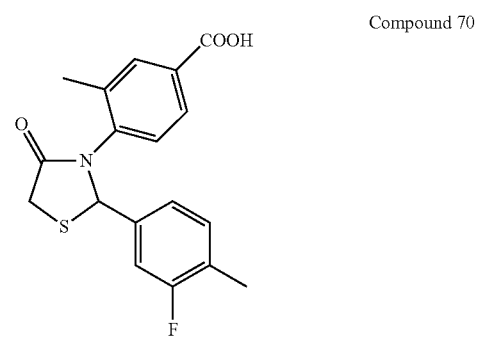 [SMILES: Cc1ccc(C2SCC(=O)N2c2ccc(C(=O)O)cc2C)cc1F]

Compound 70

Step 1. Synthesis of Methyl 4-(2-(3-fluoro-4-methylphenyl)-4-oxothiazolidin-3-yl)-3-methylbenzoate

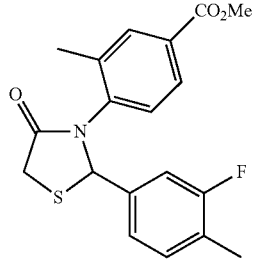

Compound 71

The compound was prepared by following the standard procedure A with methyl 4-amino-3-methylbenzoate (165 mg, 1.00 mmol), 4-fluoro-3-methylbenzaldehyde (276 mg, 2.00 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=1:2) to give the desired product as a yellow viscous liquid (70.0 mg, 19%). $^1$H NMR (CDCl$_3$, 400 MHz) δ 7.87 (br s, 1H), 7.74 (br d, 1H), 7.07-7.00 (m, 2H), 6.94 (dd, 1H), 5.88 (br s, 1H), 4.01 (d, 1H), 3.90 (d, 1H), 3.87 (s, 3H), 2.21 (br s, 6H).

Step 2. Synthesis of 4-(2-(3-Fluoro-4-methylphenyl)-4-oxothiazolidin-3-yl)-3-methylbenzoic acid The compound was prepared by following the standard procedure B with methyl 4-(2-(3-fluoro-4-methylphenyl)-4-oxothiazolidin-3-yl)-3-methylbenzoate (70.0 mg, 0.190 mmol) and 20% NaOH$_{(aq)}$ (0.500 mL, 2.50 mmol) to give the desired product as a yellow viscous liquid (52.0 mg, 77%). $^1$H NMR (CDCl$_3$, 300 MHz) δ 7.90 (br s, 1H), 7.78 (br d, 1H), 7.09-7.00 (m, 2H), 6.94 (dd, 1H), 5.90 (br s, 1H), 4.03 (d, 1H), 3.92 (d, 1H), 2.21 (br s, 6H); LC-MS (ESI) m/z 346.2 [M+H]$^+$.

EXAMPLE 58

4-(2-(5-Fluoro-2-methylphenyl)-4-oxothiazolidin-3-yl)-3-methylbenzoic acid

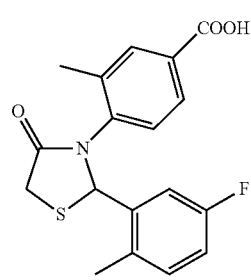

Compound 72

Step 1. Synthesis of Methyl 4-(2-(5-fluoro-2-methylphenyl)-4-oxothiazolidin-3-yl)-3-methylbenzoate

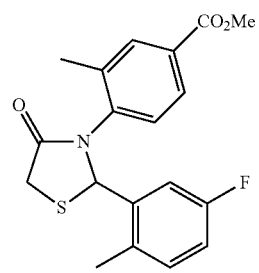

Compound 73

The compound was prepared by following the standard procedure A with methyl 4-amino-3-methylbenzoate (165 mg, 1.00 mmol), 5-fluoro-2-methylbenzaldehyde (138 mg, 1.00 mmol), and 2-mercaptoacetic acid (0.210 mL, 272 mg, 2.95 mmol). It was reflux 6 h for the first step and 18 h for the second step. After work-up, the crude product was purified by flash chromatography (ethyl acetate:hexane=1:2) to give the desired product as a yellow viscous liquid (60.0 mg, 17%). $^1$H NMR (CDCl$_3$, 300 MHz) δ 7.91 (br s, 1H), 7.75 (br s, 1H), 7.37-7.28 (m, 1H), 7.00-6.95 (m, 1H), 6.90-6.83 (m, 2H), 6.18 (br s, 1H), 3.98 (d, 1H), 3.88 (d, 1H), 3.87 (s, 3H), 2.30 (br s, 3H), 2.09 (br s, 3H).

Step 2. Synthesis of 4-(2-(5-Fluoro-2-methylphenyl)-4-oxothiazolidin-3-yl)-3-methylbenzoic acid The compound was prepared by following the standard procedure B with methyl 4-(2-(5-fluoro-2-methylphenyl)-4-oxothiazolidin-3-yl)-3-methylbenzoate (60.0 mg, 0.170 mmol) and 20% NaOH$_{(aq)}$ (0.500 mL, 2.50 mmol). The crude product was purified by flash chromatography (ethyl acetate:hexane=3:2) to give the desired product as a yellow viscous liquid (5.00 mg, 8.7%). $^1$H NMR (CDCl$_3$, 400 MHz) δ 7.94 (br s, 1H), 7.77 (br d, 1H), 7.32 (br s, 1H), 6.99 (dd, 1H), 6.93 (br s, 1H), 6.88 (td, 1H), 6.20 (br s, 1H), 4.03 (d, 1H), 3.91 (d, 1H), 2.32 (br s, 3H), 2.10 (br s, 3H); LC-MS (ESI) m/z 346.2 [M+H]$^+$.

EXAMPLE 59

3-Methyl-4-(4-oxo-2-(3-(trifluoromethyl)phenyl)thiazolidin-3-yl)benzoic acid

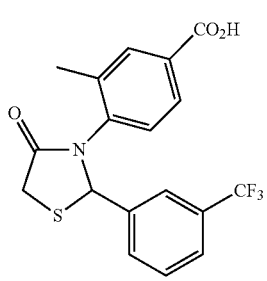

Compound 74

Step 1. Synthesis of Methyl 3-methyl-4-(4-oxo-2-(3-(trifluoromethyl)phenyl)thiazolidin-3-yl)benzoate

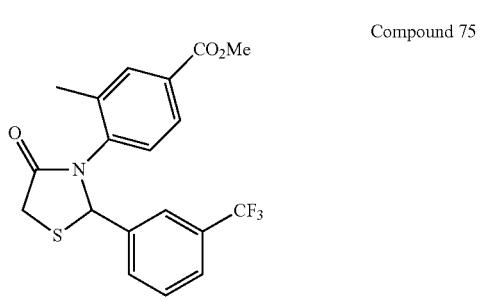 [SMILES: COC(=O)c1ccc(N2C(=O)CSC2c2cccc(C(F)(F)F)c2)c(C)c1]

Compound 75

The compound was prepared by following the standard procedure A with methyl 4-amino-3-methylbenzoate (165 mg, 1.00 mmol), 3-(trifluoromethyl)benzaldehyde (174 mg, 1.00 mmol), and 2-mercaptoacetic acid (0.210 mL, 272 mg, 2.95 mmol). It was reflux 6 h for the first step and 18 h for the second step. After work-up, the crude product was purified by flash chromatography (ethyl acetate:hexane=1:2) to give the desired product as a yellow viscous liquid (133 mg, 34%). $^1$H NMR (CDCl$_3$, 300 MHz) δ 7.87 (br s, 1H), 7.74 (br d, 1H), 7.62 (br s, 1H), 7.54 (br d, 1H), 7.47 (br d, 1H), 7.39 (dd, 1H), 6.94 (br s, 1H), 6.00 (br s, 1H), 4.05 (d, 1H), 3.94 (d, 1H), 3.86 (s, 3H), 2.21 (br s, 3H).

Step 2. Synthesis of 3-Methyl-4-(4-oxo-2-(3-(trifluoromethyl)phenyl)thiazolidin-3-yl)benzoic acid The compound was prepared by following the standard procedure B with methyl 3-methyl-4-(4-oxo-2-(3-(trifluoromethyl)phenyl)thiazolidin-3-yl)benzoate (133 mg, 0.33 mmol) and 20% NaOH$_{(aq)}$ (0.200 mL, 1.00 mmol) to give the desired product as a yellow viscous liquid (86.0 mg, 67%). $^1$H NMR (CDCl$_3$, 400 MHz)$^1$H NMR (CDCl$_3$, 400 MHz) δ 7.90 (br s, 1H), 7.78 (br s, 1H), 7.63 (br s, 1H), 7.55 (br d, 1H), 7.48 (br d, 1H), 7.41 (br t, 1H), 6.01 (br s, 1H), 4.06 (d, 1H), 3.96 (d, 1H), 2.20 (br s, 3H); LC-MS (ESI) m/z 382.1 [M+H]$^+$.

EXAMPLE 60

3-Methyl-4-(4-oxo-2-(4-(trifluoromethyl)phenyl)thiazolidin-3-yl)benzoic acid

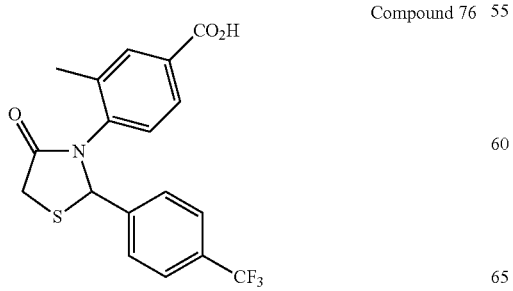

Compound 76

Step 1. Synthesis of Methyl 3-methyl-4-(4-oxo-2-(4-(trifluoromethyl)phenyl)thiazolidin-3-yl)benzoate

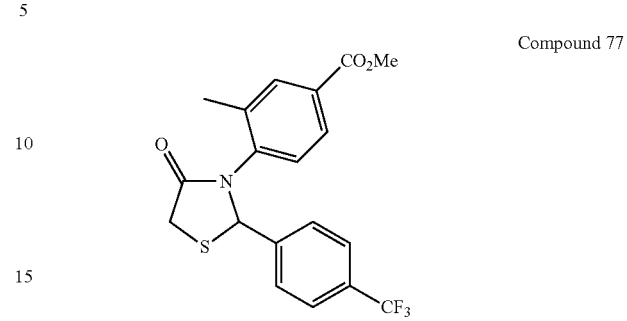

Compound 77

The compound was prepared by following the standard procedure A with methyl 4-amino-3-methylbenzoate (165 mg, 1.00 mmol), 4-(trifluoromethyl)benzaldehyde (174 mg, 1.00 mmol), and 2-mercaptoacetic acid (0.210 mL, 272 mg, 2.95 mmol). It was reflux 6 h for the first step and 18 h for the second step. After work-up, the crude product was purified by flash chromatography (ethyl acetate:hexane=2:3) to give the desired product as a yellow viscous liquid (110 mg, 28%). $^1$H NMR (CDCl$_3$, 400 MHz) δ 7.90 (br s, 1H), 7.75 (br d, 1H), 7.55 (d, 2H), 7.45 (d, 2H), 6.95 (br s, 1H), 5.98 (br s, 1H), 4.04 (d, 1H), 3.93 (d, 1H), 3.87 (s, 3H), 2.22 (br s, 3H).

Step 2. Synthesis of 3-Methyl-4-(4-oxo-2-(4-(trifluoromethyl)phenyl)thiazolidin-3-yl)benzoic acid The compound was prepared by following the standard procedure B with methyl 3-methyl-4-(4-oxo-2-(4-(trifluoromethyl)phenyl)thiazolidin-3-yl)benzoate (110 mg, 0.280 mmol) and 20% NaOH$_{(aq)}$ (0.200 mL, 1.00 mmol) to give the desired product as a yellow viscous liquid (86.0 mg, 81%). $^1$H NMR (CDCl$_3$, 300 MHz) δ 7.91 (br s, 1H), 7.77 (br d, 1H), 7.55 (d, 2H), 7.45 (d, 2H), 6.95 (br s, 1H), 6.00 (br s, 1H), 4.06 (d, 1H), 3.95 (d, 1H), 2.23 (br s, 3H); LC-MS (ESI) m/z 382.1 [M+H]$^+$.

EXAMPLE 61

4-[2-(4-Methoxy-phenyl)-4-oxo-thiazolidin-3-yl]-3-methyl-benzoic acid

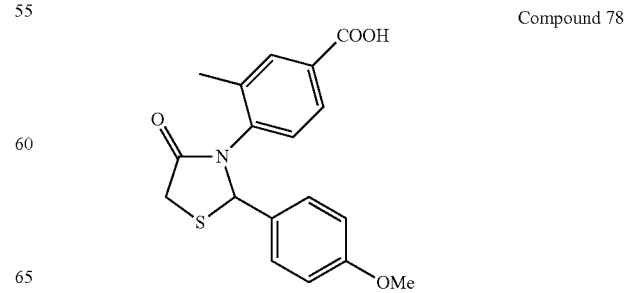

Compound 78

283

Step 1. Synthesis of 4-[2-(4-methoxy-phenyl)-4-oxo-thiazolidin-3-yl]-3-methyl-benzoic acid methyl ester

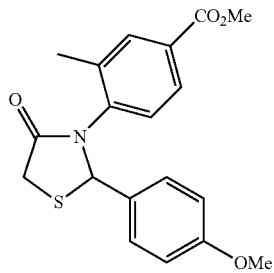

Compound 79

The compound was prepared by following the standard procedure A with methyl 4-amino-3-methylbenzoate (165 mg, 1.00 mmol), p-anisaldehyde (272 mg, 2.00 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=2:3) to give the desired product as a yellow viscous liquid (34.0 mg, 10%). $^1$H NMR (CDCl$_3$, 300 MHz) δ 7.85 (br s, 1H), 7.72 (br d, 1H), 7.23 (d, 2H), 6.76 (d, 2H), 5.93 (br s, 1H), 4.00 (d, 1H), 3.90 (d, 1H), 3.86 (s, 3H), 3.75 (s, 3H), 2.20 (br s, 3H).

Step 2. Synthesis of 4-[2-(4-methoxy-phenyl)-4-oxo-thiazolidin-3-yl]-3-methyl-benzoic acid The compound was prepared by following the standard procedure B with 4-[2-(4-methoxy-phenyl)-4-oxo-thiazolidin-3-yl]-3-methyl-benzoic acid methyl ester (34 mg, 0.095 mmol) and 20% NaOH$_{(aq)}$ (0.300 mL, 1.50 mmol). The crude product was purified by recrystallization to give the desired product as a white solid (20.0 mg, 61%). $^1$H NMR (CD$_3$Cl, 400 MHz) δ 7.87 (br s, 1H), 7.75 (br s, 1H), 7.24 (d, 2H), 6.77 (d, 2H), 5.96 (br s, 1H), 4.01 (d, 1H), 3.92 (d, 1H), 3.75 (s, 3H), 2.21 (br s, 3H); LC-MS (ESI) m/z 344.2 [M+H]$^+$.

EXAMPLE 62

4-[2-(4-Carboxy-phenyl)-4-oxo-thiazolidin-3-yl]-3-methyl-benzoic acid

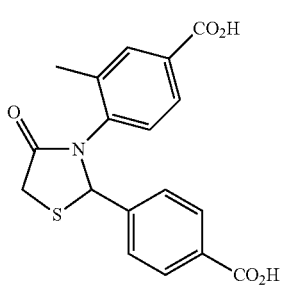

Compound 80

284

Step 1. Synthesis of 4-[2-(4-methoxycarbonyl-phenyl)-4-oxo-thiazolidin-3-yl]-3-methyl-benzoic acid methyl ester

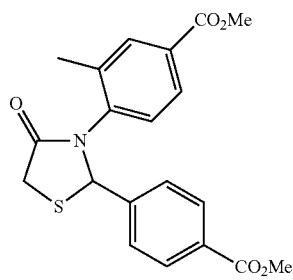

Compound 81

The compound was prepared by following the standard procedure A with methyl 4-amino-3-methylbenzoate (165 mg, 1.00 mmol), methyl 4-formylbenzenecarboxylate (328 mg, 2.00 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=2:3) to give the desired product as a yellow viscous liquid (84.0 mg, 11%). $^1$H NMR (CDCl$_3$, 400 MHz) δ 7.94 (d, 2H), 7.85 (br s, 1H), 7.70 (br s, 1H), 7.39 (d, 2H), 6.91 (br s, 1H), 5.96 (br s, 1H), 4.04 (d, 1H), 3.92 (d, 1H), 3.89 (s, 3H), 3.85 (s, 3H), 2.24 (br s, 3H); LC-MS (ESI) m/z 385.9 [M+H]$^+$.

Step 2. Synthesis of 4-[2-(4-carboxy-phenyl)-4-oxo-thiazolidin-3-yl]-3-methyl-benzoic acid The compound was prepared by following the standard procedure B with 4-[2-(4-methoxycarbonyl-phenyl)-4-oxo-thiazolidin-3-yl]-3-methyl-benzoic acid methyl ester (40.0 mg, 0.100 mmol) and 20% NaOH$_{(aq)}$ (0.500 mL, 2.50 mmol). The crude product was purified by recrystallization to give the desired product as a yellow solid (21.0 mg, 59%). $^1$H NMR (CD$_3$OD, 300 MHz) δ 7.93 (d, 2H), 7.84 (br s, 1H), 7.74 (br s, 1H), 7.54 (d, 2H), 7.20 (br s, 1H), 6.29 (br s, 1H), 4.12 (d, 1H), 3.96 (d, 1H), 2.21 (br s, 3H); LC-MS (ESI) m/z 357.9 [M+H]$^+$.

EXAMPLE 63

4-[2-(4-Methanesulfonyl-phenyl)-4-oxo-thiazolidin-3-yl]-3-methyl-benzoic acid

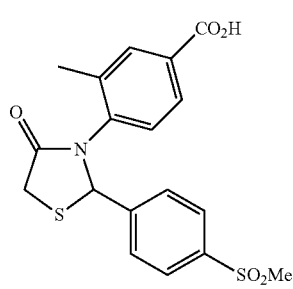

Compound 82

Step 1. Synthesis of 4-[2-(4-methanesulfonyl-phenyl)-4-oxo-thiazolidin-3-yl]-3-methyl-benzoic acid methyl ester

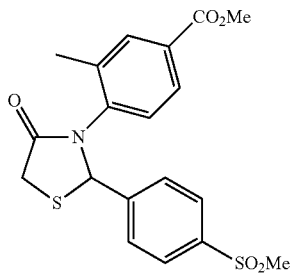

Compound 83

The compound was prepared by following the standard procedure A with methyl 4-amino-3-methylbenzoate (165 mg, 1.00 mmol), 4-methylsulphenylbenzaldehyde (202 mg, 1.10 mmol), and 2-mercaptoacetic acid (0.140 mL, 184 mg, 2.00 mmol). It was stirred at room temperature 5 h for the first step and 16 h for the second step. After work-up, the crude product was purified by flash chromatography (ethyl acetate:hexane=3:2) to give the desired product as a yellow viscous liquid (104 mg, 26%). $^1$H NMR (CDCl$_3$, 400 MHz) δ 7.88-7.86 (m, 3H), 7.74 (br d, 1H), 7.53 (d, 2H), 6.94 (br s, 1H), 6.00 (br s, 1H), 4.05 (d, 1H), 3.94 (d, 1H), 3.87 (s, 3H), 3.03 (s, 3H), 2.23 (br s, 3H); LC-MS (ESI) m/z 406.7 [M+H]$^+$.

Step 2. Synthesis of 4-[2-(4-methanesulfonyl-phenyl)-4-oxo-thiazolidin-3-yl]-3-methyl-benzoic acid The compound was prepared by following the standard procedure B with 4-[2-(4-Methanesulfonyl-phenyl)-4-oxo-thiazolidin-3-yl]-3-methyl-benzoic acid methyl ester (100 mg, 0.250 mmol) and 20% NaOH$_{(aq)}$ (0.500 mL, 2.50 mmol). The crude product was purified by flash chromatography (EA:Hexane:AcOH=50:20:7) to give the desired product as a yellow solid (80.0 mg, 80%). $^1$H NMR (CDCl$_3$, 300 MHz) δ 7.91 (br s, 1H), 7.87 (d, 2H), 7.78 (br d, 1H), 7.54 (d, 2H), 6.96 (br s, 1H), 6.02 (br s, 1H), 4.06 (d, 1H), 3.94 (d, 1H), 3.02 (s, 3H), 2.23 (br s, 3H); LC-MS (ESI) m/z 391.8 [M+H]$^+$.

EXAMPLE 64

4-[2-(4-Chloro-phenyl)-4-oxo-thiazolidin-3-yl]-3-methyl-benzoic acid

Compound 84

Step 1. Synthesis of 4-[2-(4-chloro-phenyl)-4-oxo-thiazolidin-3-yl]-3-methyl-benzoic acid methyl ester

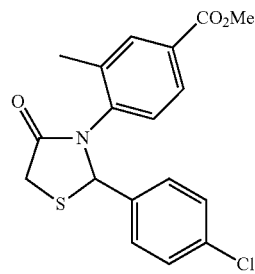

Compound 85

The compound was prepared by following the standard procedure A with methyl 4-amino-3-methylbenzoate (165 mg, 1.00 mmol), 4-chlorobenzaldehyde (168 mg, 1.20 mmol), and 2-mercaptoacetic acid (0.130 mL, 168 mg, 1.80 mmol). It was stirred at room temperature 5 h for the first step and 16 h for the second step. After work-up, the crude product was purified by flash chromatography (ethyl acetate:hexane=1:2) to give the desired product as a yellow viscous liquid (70.0 mg, 19%). $^1$H NMR (CDCl$_3$, 300 MHz) δ 7.87 (br s, 1H), 7.75 (br d, 1H), 7.30-7.18 (m, 4H), 6.91 (br s, 1H), 5.91 (br s, 1H), 4.01 (d, 1H), 3.92 (d, 1H), 3.87 (s, 3H), 2.20 (br s, 3H).

Step 2. Synthesis of 4-[2-(4-chloro-phenyl)-4-oxo-thiazolidin-3-yl]-3-methyl-benzoic acid The compound was prepared by following the standard procedure B with 4-[2-(4-chloro-phenyl)-4-oxo-thiazolidin-3-yl]-3-methyl-benzoic acid methyl ester (65 mg, 0.18 mmol) and 20% NaOH$_{(aq)}$ (0.500 mL, 2.50 mmol) to give the desired product as a yellow solid (39.0 mg, 62%). $^1$H NMR (CD$_3$OD, 400 MHz) δ 7.85 (br s, 1H), 7.75 (br s, 1H), 7.41 (d, 2H), 7.28 (d, 2H), 6.25 (br s, 1H), 4.07 (d, 1H), 3.95 (d, 1H), 2.17 (br s, 3H); LC-MS (ESI) m/z 347.8 [M+H]$^+$.

EXAMPLE 65

4-(2-(4-Fluorophenyl)-4-oxothiazolidin-3-yl)-5-methylphthalic acid

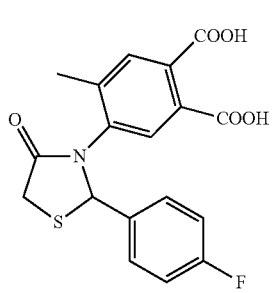

Compound 86

Step 1. Synthesis of Dimethyl 4-methyl-5-nitrophthalate

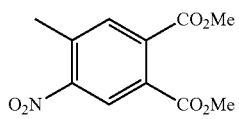

Compound 87

To a solution of 4-methylphthalic anhydride (1.95 g, 12.0 mmol) in 8 mL of concentrated $H_2SO_4$ was treated with concentrated $HNO_3$ slowly then added ice water after 5 min. After allowing to warm up to r.t. then extracted with ethyl acetate (120 mL). The organic layer was washed with brine (20 mL), dried over $MgSO_4$ and concentrated to give a white solid (2.31 g). To the white solid dissolved in 20 mL of methanol was added concentrated HCl in one portion at r.t. The reaction mixture was refluxed overnight then directly concentrated to give a crude product which was partitioned between ethyl acetate (70 mL) and saturated $NaHCO_{3(aq)}$ (20 mL). The organic layer was washed with brine (20 mL), dried over $MgSO_4$ and concentrated to give a colorless viscous liquid (700 mg, 23%). $^1H$ NMR ($CDCl_3$, 300 MHz) δ 8.41 (s, 1H), 7.61 (s, 1H), 3.95 (s, 3H), 3.94 (s, 3H), 2.67 (s, 3H).

Step 2. Synthesis of Dimethyl 4-amino-5-methylphthalate

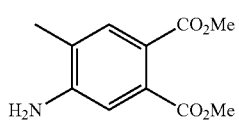

Compound 88

To a solution of dimethyl 4-methyl-5-nitrophthalate (700 mg, 2.76 mmol) in 7.6 mL of acetic acid was added zinc dust$_{(s)}$ (1.40 g, 22.0 mmol) in one portion at r.t. The reaction mixture was stirred at r.t. for 4 h then passed through a pad of celite. The filtrate was partitioned between ethyl acetate (70 mL) and saturated $NaHCO_{3(aq)}$ (20 mL). The organic layer was washed with brine (20 mL), dried over $MgSO_4$ and concentrated to give a crude product which was purified by flash chromatography (ethyl acetate:hexane=1:1) to give the desired product as a yellow viscous liquid (310 mg, 50%). $^1H$ NMR ($CDCl_3$, 300 MHz) δ 7.58 (s, 1H), 6.75 (s, 1H), 4.05 (br s, 2H), 3.87 (s, 3H), 3.83 (s, 3H), 2.16 (s, 3H).

Step 3. Synthesis of Dimethyl 4-(2-(4-fluorophenyl)-4-oxothiazolidin-3-yl)-5-methylphthalate

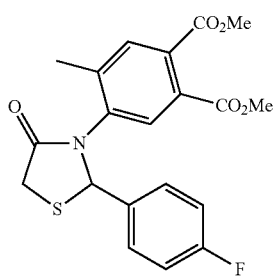

Compound 89

The compound was prepared by following the standard procedure B with dimethyl 4-amino-5-methylphthalate (90.0 mg, 0.400 mmol), 4-fluorobenzaldehyde (60.0 mg, 0.480 mmol), and 2-mercaptoacetic acid (0.084 mL, 109 mg, 1.18 mmol). It was stirred at room temperature 5 h for the first step and 16 h for the second step. After work-up, the crude product was purified by flash chromatography (ethyl acetate:hexane=1:1) to give the desired product as a yellow viscous liquid (43.0 mg, 27%). $^1H$ NMR ($CDCl_3$, 400 MHz) δ 7.44 (br s, 1H), 7.32 (dd, 2H), 6.97 (t, 2H), 6.00 (br s, 1H), 3.99 (d, 1H), 3.95-3.84 (m, 7H), 2.16 (br s, 3H).

Step 4. Synthesis of 4-(2-(4-Fluorophenyl)-4-oxothiazolidin-3-yl)-5-methylphthalic acid The compound was prepared by following the standard procedure B with dimethyl 4-(2-(4-fluorophenyl)-4-oxothiazolidin-3-yl)-5-methylphthalate (43.0 mg, 0.100 mmol) and 20% $NaOH_{(aq)}$ (0.100 mL, 0.500 mmol). The crude product was purified by flash chromatography (methanol:dichloromethane: acetic acid=20:80:1) to give the desired product as a yellow viscous liquid (14.0 mg, 37%). $^1H$ NMR ($CD_3OD$, 400 MHz) δ 7.97 (br s, 1H), 7.49-7.46 (m, 2H), 6.99 (br t, 2H), 6.37 (br s, 1H), 4.05 (br d, 1H), 3.97 (d, 1H), 2.14 (br s, 3H); LC-MS (ESI) m/z 376.2 [M+H]$^+$.

EXAMPLE 66

3-(5-Acetyl-2-methylphenyl)-2-(4-fluorophenyl)-1,3-thiazolidin-4-one

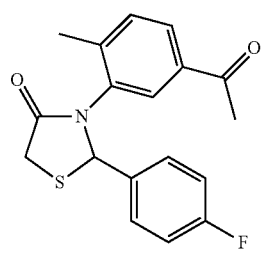

Compound 90

Step 1. 1-(3-Amino-4-methylphenyl)ethanone

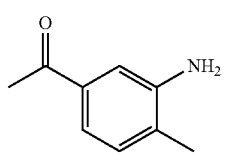

Compound 91

To a solution of 4-methyl-3-nitroacetophenone (1.00 g, 5.58 mmol) in methanol (40 mL) was added tin(II) chloride dehydrate (3.78 g, 16.7 mmol). After the reaction mixture was stirred at 60° C. for 20 h, then cooled to room temperature and concentrated. The crude was treated with $CH_2Cl_2$, and the undissolved solids were filtered off. The filtrate was washed with saturated $NaHCO_{3(aq)}$ and brine. The organic layer was dried over $MgSO_{4(s)}$, filtered, and concentrated. The residue was purified by Isco Combi-Flash Companion column chromatography (0-10% ethyl acetate in $CH_2Cl_2$) to give 1-(3-amino-4-methylphenyl)ethanone (0.610 g, 73%) as a dark green solid. 1H NMR ($CDCl_3$, 400 MHz) δ 7.34-7.32 (m, 2H), 7.14 (d, 1H), 2.55 (s, 3H), 2.25 (s, 3H).

Step 2. 3-(5-Acetyl-2-methylphenyl)-2-(4-fluorophenyl)-1,3-thiazolidin-4-one

Following standard procedure A, 1-(3-amino-4-methylphenyl)ethanone (0.284 g, 1.91 mmol), 4-fluorobenzaldehyde (0.354 g, 2.86 mmol), Na$_2$SO$_4$ (0.271 g, 1.91 mmol), 2-mercaptoacetic acid (0.270 mL, 3.87 mmol), and toluene (6.0 mL) were used to carry out the reaction. It was reflux 5 h for the first step and 22 h for the second step. After work-up, the residue was purified by Isco Combi-Flash Companion column chromatography (0-15% ethyl acetate in CH$_2$Cl$_2$) to give 3-(5-acetyl-2-methylphenyl)-2-(4-fluorophenyl)-1,3-thiazolidin-4-one (0.125 g, 20%) as a yellow gum. 1H NMR (CDCl$_3$, 400 MHz) δ 7.74 (br d, 1H), 7.36-7.32 (m, 2H), 6.97 (br s, 3H), 6.15-5.60 (br, 1H), 4.02 (d, 1H), 3.93 (d, 1H), 2.70-1.95 (br, 6H); LC-MS (ESI) m/z 330.2 [M+H]$^+$.

EXAMPLE 67

2-(4-Fluorophenyl)-3-[2-methyl-5-(trifluoromethyl)phenyl]-1,3-thiazolidin-4-one

Compound 92

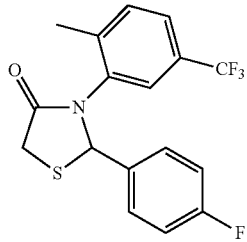

Following standard procedure A, 2-methyl-5-(trifluoromethyl)aniline (0.372 g, 2.22 mmol), 4-fluorobenzaldehyde (0.343 g, 2.76 mmol), Na$_2$SO$_4$ (0.315 g, 2.22 mmol), 2-mercaptoacetic acid (0.280 mL, 4.01 mmol), and toluene (7.0 mL) were used to carry out the reaction. It was reflux 5 h for the first step and 18 h for the second step. After work-up, the residue was purified by Isco Combi-Flash Companion column chromatography (0-50% ethyl acetate in n-hexane) to give 2-(4-fluorophenyl)-3-[2-methyl-5-(trifluoromethyl)phenyl]-1,3-thiazolidin-4-one (109 mg, 14%) as a white solid. 1H NMR (CDCl$_3$, 300 MHz) δ 7.41 (d, 1H), 7.34-7.29 (m, 3H), 6.97 (br t, 2H), 6.15-5.70 (br, 1H), 4.01 (d, 1H), 3.92 (d, 1H), 2.17 (br s, 3H); LC-MS (ESI) m/z 356.2 [M+H]$^+$.

EXAMPLE 68

Methyl {4-[2-(4-fluorophenyl)-4-oxo-1,3-thiazolidin-3-yl]-3-methylphenoxy}acetate Compound 93

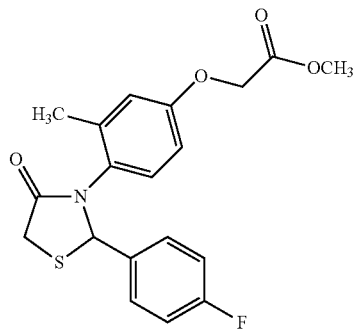

Step 1. Methyl (4-amino-3-methylphenoxy)acetate

Compound 94

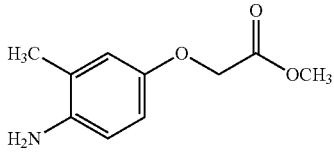

To a solution of 4-amino-m-cresol (1.02 g, 8.28 mmol) in acetone (16 mL) was added potassium carbonate (1.39 g, 10.0 mmol) and methyl chloroacetate (0.880 mL, 10.0 mmol) at room temperature. After the reaction was reflux for 18 h and cooled to room temperature, the reaction mixture was concentrated and quenched with water. The solution was extracted with CH$_2$Cl$_2$. The combined organic layers were dried over MgSO$_{4(s)}$, filtered, and concentrated under reduced pressure to afford a residue. The residue was purified by combi-flash column chromatography (0-20% ethyl acetate in CH$_2$Cl$_2$) to give methyl (4-amino-3-methylphenoxy)acetate (0.450 g, 28%) as a yellow solid. 1H NMR (CDCl$_3$, 300 MHz) δ 6.71 (s, 1H), 6.65-6.62 (m, 2H), 4.56 (s, 2H), 3.79 (s, 3H), 2.17 (s, 3H).

Step 2. Methyl {4-[2-(4-fluorophenyl)-4-oxo-1,3-thiazolidin-3-yl]-3-methylphenoxy}acetate Following standard procedure A, methyl (4-amino-3-methylphenoxy)acetate (0.311 g, 1.60 mmol), 4-fluorobenzaldehyde (0.257 g, 2.07 mmol), Na$_2$SO$_4$ (0.227 g, 1.60 mmol), 2-mercaptoacetic acid (0.200 mL, 2.87 mmol), and toluene (4.0 mL) were used to carry out the reaction. It was reflux 4 h for the first step and 20 h for the second step. After work-up, the residue was purified by Isco Combi-Flash Companion column chromatography (0-60% ethyl acetate in n-hexane) to give methyl {4-[2-(4-fluorophenyl)-4-oxo-1,3-thiazolidin-3-yl]-3-methylphenoxy}acetate (293 mg, 49%) as a yellow gum. $^1$H NMR (CDCl$_3$, 300 MHz) δ 7.32-7.26 (m, 2H), 6.99 (br t, 2H), 6.90-6.30 (br, 3H), 6.10-5.60 (br, 1H), 4.54 (s, 2H), 4.00 (d, 1H), 3.88 (d, 1H), 3.78 (s, 3H), 2.38-2.00 (br, 3H); LC-MS (ESI) m/z 376.2 [M+H]$^+$.

EXAMPLE 69

{4-[2-(4-Fluorophenyl)-4-oxo-1,3-thiazolidin-3-yl]-3-methylphenoxy}acetic acid

Compound 95

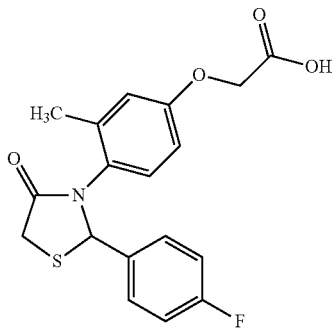

Following standard procedure B, methyl {4-[2-(4-fluorophenyl)-4-oxo-1,3-thiazolidin-3-yl]-3-methylphenoxy}acetate (0.198 g, 0.527 mmol), 20% NaOH$_{(aq)}$ (0.45 mL), and methanol (4.0 mL) were used to carry out the reaction. After the reaction was stirred for 4 h and work-up, the residue was purified by flash column chromatography (20% MeOH in CH$_2$Cl$_2$) to give {4-[2-(4-fluorophenyl)-4-oxo-1,3-thiazolidin-3-yl]-3-methylphenoxy}acetate acid (149 mg, 79%) as an orange solid. 1H NMR (CDCl$_3$, 300 MHz) δ 7.30 (dd, 2H), 6.97 (br t, 2H), 6.85-6.30 (br, 3H), 6.10-5.60 (br, 1H), 4.52 (s, 2H), 4.01 (d, 1H), 3.90 (d, 1H), 2.40-2.10 (br, 3H); LC-MS (ESI) m/z 362.2 [M+H]$^+$.

EXAMPLE 70

Methyl {4-[2-(4-fluorophenyl)-4-oxo-1,3-thiazolidin-3-yl]-3-methylphenyl}acetate

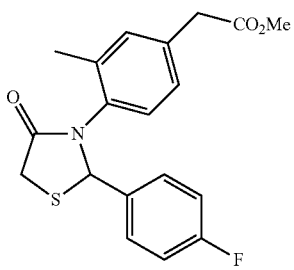

Compound 96

Step 1. Dimethyl (3-methyl-4-nitrophenyl)propanedioate

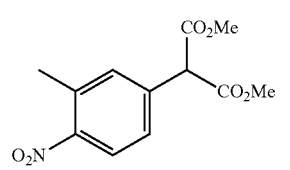

Compound 97

To a solution of dimethylmalonate (0.960 g, 7.27 mmol) in DMF anhydrous (15 mL) was added 60% sodium hydride in mineral oil (89.5 mg, 7.90 mmol) at 0° C., and the reaction mixture was stirred for 30 min. 4-Fluoro-2-methyl-1-nitrobenzene (1.02 g, 6.58 mmol) was added to the solution, and then stirred at 110° C. for 18 h. The reaction was quenched with water (60 mL) and extracted with ethyl acetate (50 mL×3). The combined organic layers were dried over MgSO$_{4(s)}$, filtered, and concentrated under reduced pressure to afford a residue. The residue was purified by column chromatography (30% ethyl acetate in n-hexane) to give dimethyl (3-methyl-4-nitrophenyl)propanedioate (0.550 g, 31%) as a yellow solid. 1H NMR (CDCl$_3$, 300 MHz) δ 7.98 (d, 1H), 7.41-7.39 (m, 2H), 4.69 (s, 1H,), 3.78 (s, 6H), 2.61 (s, 3H).

Step 2. (3-Methyl-4-nitrophenyl)acetic acid

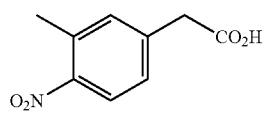

Compound 98

To a solution of dimethyl (3-methyl-4-nitrophenyl)propanedioate (0.540 g, 2.02 mmol) in water (10 mL) and methanol (10 mL) was added potassium hydroxide (0.340 g, 6.06 mmol) at room temperature, and it was reflux for 4 h. After the reaction was cooled and acidified by 2 N HCl$_{(aq)}$ (40 mL), the solution was extracted with ethyl acetate (20 mL×3). The combined organic layers were dried over MgSO$_{4(s)}$, filtered, and concentrated under reduced pressure to afford (3-methyl-4-nitrophenyl)acetic acid (0.480 g, quantitative yield) as an orange solid, which was directly used to next step without further purification. 1H NMR (CDCl$_3$, 400 MHz) δ 7.97 (d, 1H), 7.28-7.26 (m, 2H), 3.71 (s, 2H), 2.61 (s, 3H).

Step 3. Methyl (3-methyl-4-nitrophenyl)acetate

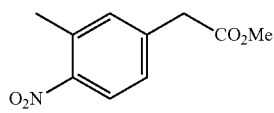

Compound 99

To a solution of (3-methyl-4-nitrophenyl)acetic acid (0.480 g, 2.46 mmol) in methanol (15 mL) was added concentrated HCl$_{(aq)}$ (1.50 mL). After the reaction mixture was reflux for 20 h and cooled to room temperature, the solvent was removed under reduced pressure. The residue was partitioned between ethyl acetate (30 mL) and water (30 mL). The organic layer was dried over MgSO$_{4(s)}$, filtered, and concentrated to give methyl (3-methyl-4-nitrophenyl)acetate (0.410 g, 80%) as a brown oil, which was directly used to next step without further purification. 1H NMR (CDCl$_3$, 400 MHz) δ 7.96 (d, 1H), 7.26 (br s, 2H), 3.72 (s, 3H), 3.67 (s, 2H), 2.60 (s, 3H).

Step 4. Methyl (4-amino-3-methylphenyl)acetate

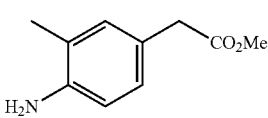

Compound 100

Tin(II) chloride dehydrate (1.33 g, 5.88 mmol) was added to a solution of methyl (3-methyl-4-nitrophenyl)acetate (0.410 g, 1.96 mmol) in methanol (20 mL). After the reaction mixture was stirred at 60° C. for 20 h, then cooled to room temperature and concentrated. The crude was treated with saturated NaHCO$_{3(aq)}$ (30 mL) and extracted with CH$_2$Cl$_2$ (30 mL×2). The combined organic layers were dried over MgSO$_{4(s)}$, filtered, and concentrated. The residue was purified by flash column chromatography (30% ethyl acetate in n-hexane) to give methyl (4-amino-3-methylphenyl)acetate (0.250 g, 35%) as a brown oil. 1H NMR (CDCl$_3$, 400 MHz) δ 6.97-6.94 (m, 2H), 6.66 (d, 1H), 3.67 (s, 3H), 3.50 (s, 2H), 2.17 (s, 3H).

Step 5. Methyl {4-[2-(4-fluorophenyl)-4-oxo-1,3-thiazolidin-3-yl]-3-methylphenyl}acetate Following standard procedure A, methyl (4-amino-3-methylphenyl)acetate (0.200 g, 1.12 mmol), 4-fluorobenzaldehyde (0.180 mL, 1.68 mmol), Na$_2$SO$_4$ (0.159 g, 1.12 mmol), 2-mercaptoacetic acid (0.160 mL, 2.29 mmol), and toluene (5.0 mL) were used to carry out the reaction. It was reflux 5 h for the first step and 20 h for the second step. After work-up, the residue was purified by Isco Combi-Flash Companion column chromatography (0-70% ethyl acetate in n-hexane) to give methyl {4-[2-(4-fluorophenyl)-4-oxo-1,3-thiazolidin-3-yl]-3-methylphenyl}acetate (183 mg, 45%) as a lightly yellow gum. 1H NMR (CDCl$_3$, 300 MHz) δ 7.33-7.28 (m, 2H), 7.12 (br s, 1H), 6.97 (br t, 2H), 6.80-6.40 (br, 1H), 6.10-5.60 (br, 1H), 4.01 (d, 1H), 3.89 (d, 1H), 3.66 (s, 3H), 3.51 (s, 2H), 2.16 (br s, 3H); LC-MS (ESI) m/z 382.2 [M+Na]$^+$.

EXAMPLE 71

{4-[2-(4-Fluorophenyl)-4-oxo-1,3-thiazolidin-3-yl]-3-methylphenyl}acetic acid

Compound 101

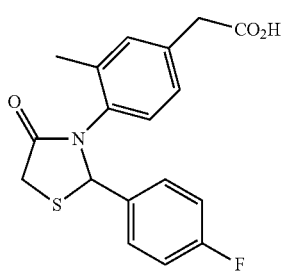

Following standard procedure B, methyl {4-[2-(4-fluorophenyl)-4-oxo-1,3-thiazolidin-3-yl]-3-methylphenyl}acetate (0.137 g, 0.382 mmol), 20% NaOH$_{(aq)}$ (0.50 mL), and methanol (2.0 mL) were used to carry out the reaction. After the reaction was stirred for 4 h and work-up, the residue was purified by Isco Combi-Flash Companion column chromatography (0-5% MeOH in CH$_2$Cl$_2$) to give {4-[2-(4-fluorophenyl)-4-oxo-1,3-thiazolidin-3-yl]-3-methylphenyl}acetic acid (79.9 mg, 61%) as a white solid. 1H NMR (DMSO-d$_6$, 300 MHz) δ 12.45-12.10 (br, 1H), 7.49-7.45 (m, 2H), 7.12-6.96 (m, 4H), 6.60-6.10 (br, 1H), 4.07 (d, 1H), 3.85 (d, 1H), 3.48 (s, 2H), 2.02 (br s, 3H); LC-MS (ESI) m/z 346.2 [M+H]$^+$.

EXAMPLE 72

3-(2,4-Dimethylphenyl)-2-(4-fluorophenyl)thiazolidin-4 one.

Compound 102

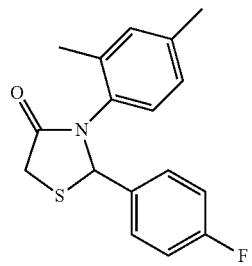

The compound was prepared by following the standard procedure A with 2,4-dimethylaniline (48.5 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (74.2 mg, 62%). $^1$H NMR (C$_6$D$_6$, 400 MHz) δ 6.80 (br s, 2H), 6.62 (br s, 1H), 6.60-6.40 (m, 4H), 5.38 (br s, 1H), 3.50 (d, 1H), 3.39 (d, 1H), 1.97 (br s, 3H), 1.87 (s, 3H); LC-MS (ESI) m/z 302.9 [M+H]$^+$.

EXAMPLE 73

3-(2,4-Dimethylphenyl)-2-(3-fluorophenyl)thiazolidin-4 one.

Compound 103

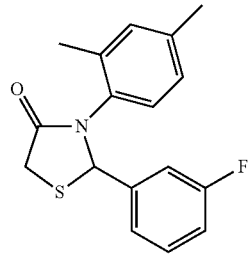

The compound was prepared by following the standard procedure A with 2,4-dimethylaniline (48.5 mg, 0.400 mmol), 3-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate hexane=1:3) to give the desired product as a yellow viscous liquid (100 mg, 83%). $^1$H NMR (CDCl$_3$, 400 MHz) δ 7.30-7.20 (br, 1H), 7.08 (d, 2H), 6.98-6.80 (m, 2H), 6.50 (br s, 1H), 5.73 (br s, 1H), 4.02 (d, 1H), 3.88 (d, 1H), 2.50-1.80 (br, 6H); LC-MS (ESI) m/z 302.8 [M+H]$^+$.

EXAMPLE 74

2-(3,4-Difluorophenyl)-3-(2,4-dimethylphenyl)thiazolidin-4-one

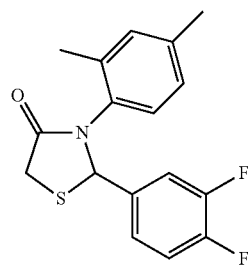

Compound 104

The compound was prepared by following the standard procedure A with 2,4-dimethylaniline (48.5 mg, 0.4 mmol), 3,4-difluorobenzaldehyde (56.8 mg, 0.4 mmol), and 2-mercaptoacetic acid (0.67 mL, 86.5 mg, 0.94 mmol). It was reflux 6 h for the first step and 18 h for the second step. After work-up, the crude product was purified by flash chromatography (ethyl acetate:hexane=1:2) to give the desired product as a yellow viscous liquid (60 mg, 0.19 mmol, 47%). $^1$H NMR (C$_6$D$_6$, 400 MHz) δ 6.79 (br s, 1H), 6.61 (br s, 1H), 6.55 (br s, 1H), 6.45-6.30 (m, 3H), 5.25 (br s, 1H), 3.40 (d, 1H), 3.32 (d, 1H), 1.94 (br s, 3H), 1.87 (s, 3H); LC-MS (ESI) m/z 320.9 [M+H]$^+$.

EXAMPLE 75

3-(2,5-Dimethylphenyl)-2-(4-fluorophenyl)thiazolidin-4-one

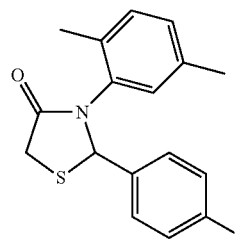

Compound 105

The compound was prepared by following the standard procedure A with 2,5-dimethylaniline (48.5 mg, 0.400 mmol), 4-fluorobenzaldehyde (49.6 mg, 0.400 mmol), and 2-mercpatoacetic acid (0.670 mL, 86.5 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (47.0 mg, 40%). $^1$H NMR (C$_6$D$_6$, 300 MHz) δ 6.85-6.67 (m, 3H), 6.63 (d, 1H), 6.50 (t, 2H), 6.39 (br s, 1H), 5.39 (br s, 1H), 3.51 (d, 1H), 3.40 (d, 1H), 1.95 (br s, 3H), 1.86 (s, 3H).

EXAMPLE 76

3-(2,5-Dimethylphenyl)-2-(3-fluorophenyl)thiazolidin-4-one

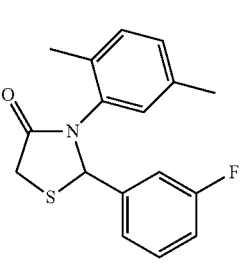

Compound 106

The compound was prepared by following the standard procedure A with 2,5-dimethylaniline (48.5 mg, 0.400 mmol), 3-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (85.0 mg, 71%). $^1$H NMR (C$_6$D$_6$, 400 MHz) δ 6.85 (br d, 1H), 6.74 (br d, 1H), 6.67-6.56 (m, 3H), 6.50 (br t, 1H), 6.43 (br s, 1H), 5.36 (br s, 1H), 3.46 (d, 1H), 3.35 (d, 1H), 1.97 (s, 3H), 1.84 (br s, 3H); LC-MS (ESI) m/z 302.9 [M+H]$^+$.

EXAMPLE 77

2-(3,4-Difluorophenyl)-3-(2,5-dimethylphenyl)thiazolidin-4-one

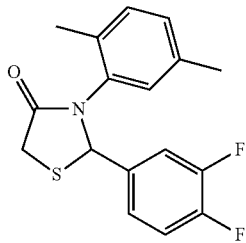

Compound 107

The compound was prepared by following the standard procedure A with 2,5-dimethylaniline (48.5 mg, 0.400 mmol), 3,4-difluorobenzaldehyde (56.8 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=3:7) to give the desired product as a yellow viscous liquid (56.0 mg, 44%). 1H NMR (C$_6$D$_6$, 400 MHz) δ 6.80-6.70 (m, 2H), 6.62 (d, 1H), 6.43-6.30 (m, 3H), 5.26 (br s, 1H), 3.42 (d, 1H), 3.34 (d, 1H), 1.92 (br s, 3H), 1.85 (br s, 3H); LC-MS (ESI) m/z 320.8 [M+H]$^+$.

EXAMPLE 78

3-(2-Fluoro-6-methylphenyl)-2-(4-fluorophenyl)thiazolidin-4-one

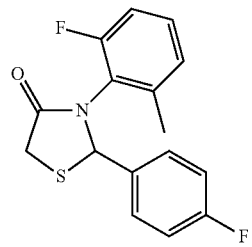

Compound 108

The compound was prepared by following the standard procedure A with 2-fluoro-6-methylaniline (50.1 mg, 0.400 mmol), 4-fluorobenzaldehyde (49.6 mg, 0.400 mmol), and 2-mercaptoacetic acid (0.670 mL, 86.7 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (20.0 mg, 16%). $^1$H NMR (CDCl$_3$, 400 MHz) δ 7.34 (dd, 2H), 7.12 (dd, 1H), 6.99 (d, 1H), 6.94 (t, 2H), 6.77 (t, 1H), 5.84 (s, 1H), 4.03 (d, 1H), 3.90 (d, 1H), 2.35 (s, 3H).

EXAMPLE 79

3-(3-Fluoro-2-methylphenyl)-2-(4-fluorophenyl)thiazolidin-4-one

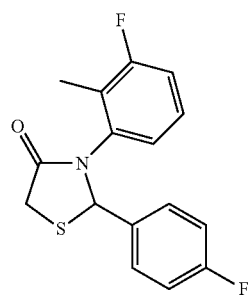

Compound 109

The compound was prepared by following the standard procedure A with 3-fluoro-2-methylaniline (50.0 mg, 0.400 mmol), 4-fluorobenzaldehyde (49.6 mg, 0.400 mmol), and 2-mercaptoacetic acid (0.500 mL, 64.7 mg, 0.700 mmol). It was reflux 6 h for the first step and 18 h for the second step. After work-up, the crude product was purified by flash chromatography (ethyl acetate:hexane=2:3) to give the desired product as a yellow viscous liquid (26.0 mg, 21%). $^1$H NMR (C$_6$D$_6$, 400 MHz) δ 6.73 (br s, 2H), 6.54-6.40 (m, 4H), 6.25 (br s, 1H), 5.30 (br s, 1H), 3.42 (br d, 1H), 3.31 (d, 1H) 1.95 (s, 3H); LC-MS (ESI) m/z 306.8 [M+H]$^+$.

EXAMPLE 80

3-(4-Fluoro-2-methylphenyl)-2-(4-fluorophenyl)thiazolidin-4-one

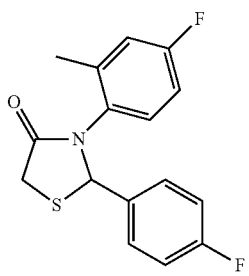

Compound 110

The compound was prepared by following the standard procedure A with 4-fluoro-2-methylaniline (50.0 mg, 0.400 mmol), 4-fluorobenzaldehyde (49.6 mg, 0.400 mmol), and 2-mercaptoacetic acid (0.670 mL, 86.7 mg, 0.940 mmol). It was reflux 6 h for the first step and 18 h for the second step. After work-up, the crude product was purified by flash chromatography (ethyl acetate:hexane=2:3) to give the desired product as a yellow viscous liquid (38.0 mg, 31%). $^1$H NMR (CDCl$_3$, 300 MHz) δ 7.30 (dd, 2H), 7.10-6.30 (br, 5H), 6.20-5.40 (br, 1H), 4.01 (d, 1H), 3.90 (d, 1H), 2.40-1.80 (br, 3H); LC-MS (ESI) m/z 306.8 [M+H]$^+$.

EXAMPLE 81

3-(4-Bromo-2-methylphenyl)-2-(4-fluorophenyl)-1,3-thiazolidin-4-one

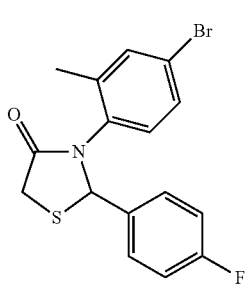

Compound 111

Following standard procedure A, 4-bromo-2-methylaniline (2.51 g, 13.5 mmol), 4-fluorobenzaldehyde (2.01 g, 16.2 mmol), Na$_2$SO$_4$ (1.92 g, 13.5 mmol), 2-mercaptoacetic acid (1.70 mL, 24.5 mmol), and toluene (40 mL) were used to carry out the reaction. It was reflux 7 h for the first step and 20 h for the second step. After work-up, the residue was purified by Isco Combi-Flash Companion column chromatography (0-30% ethyl acetate in n-hexane) to give 3-(4-bromo-2-methylphenyl)-2-(4-fluorophenyl)-1,3-thiazolidin-4-one (1.73 g, 35%) as a white solid. 1H NMR (DMSO-d$_6$, 300 MHz) δ 7.48 (dd, 2H), 7.43 (br s, 1H), 7.29 (br d, 1H), 7.11 (t, 2H), 6.50-6.05 (br, 1H), 4.07 (d, 1H), 3.88 (d, 1H), 2.07 (br s, 3H); LC-MS (ESI) m/z 366.1 [M+H]$^+$.

EXAMPLE 82

3-(5-Fluoro-2-methylphenyl)-2-(4-fluorophenyl)thiazolidin-4-one

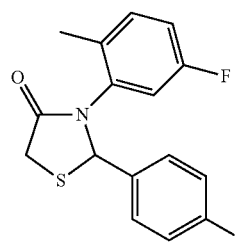

Compound 112

The compound was prepared by following the standard procedure A with 5-fluoro-2-methylaniline (2.00 g, 16.0 mmol), 4-fluorobenzaldehyde (2.00 g, 16.0 mmol), and 2-mercaptoacetic acid (1.33 mL, 1.72 g, 18.7 mmol). It was reflux 6 h for the first step and 18 h for the second step. After work-up, the crude product was purified by flash chromatography to give the desired product as a yellow viscous liquid (1.07 g, 22%). $^1$H NMR (CDCl$_3$, 400 MHz) δ 7.32 (dd, 2H), 7.13 (br s, 1H), 6.98 (t, 2H), 6.88 (td, 1H), 5.87 (br s, 1H), 4.00 (d, 1H), 3.90 (d, 1H), 2.10 (br s, 3H); LC-MS (ESI) m/z 306.8 [M+H]$^+$.

EXAMPLE 83

3-(5-Fluoro-2-methylphenyl)-2-(3-fluorophenyl)thiazolidin-4-one

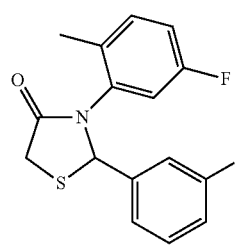

Compound 113

The compound was prepared by following the standard procedure A with 5-fluoro-2-methylaniline (50.0 mg, 0.400 mmol), 3-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (50.0 mg, 41%). $^1$H NMR (CDCl$_3$, 400 MHz) δ 7.30-7.20 (m, 1H), 7.15 (br t, 1H), 7.05 (d, 2H), 7.00 (t, 1H), 6.89 (td, 1H), 6.56 (br s, 1H), 5.83 (br s, 1H), 4.02 (d, 1H), 3.89 (d, 1H), 2.13 (br s, 3H); LC-MS (ESI) m/z 306.9 [M+H]$^+$.

EXAMPLE 84

3-(5-Fluoro-2-methylphenyl)-2-(4-(methylsulfonyl)phenyl)thiazolidin-4-one

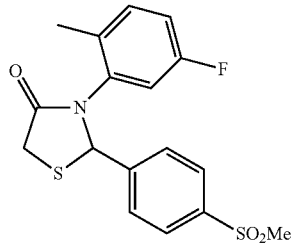

Compound 114

The compound was prepared by following the standard procedure A with 5-fluoro-2-methylaniline (50.0 mg, 0.400 mmol), 4-methylsulfonylbenzaldehyde (73.7 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=3:2) to give the desired product as a yellow viscous liquid (61.0 mg, 42%). $^1$H NMR (CDCl$_3$, 400 MHz) δ 7.89 (d, 2H), 7.54 (d, 2H), 7.15 (br t, 1H), 6.89 (td, 1H), 6.60 (br s, 1H), 5.94 (br s, 1H), 4.03 (d, 1H), 3.91 (d, 1H), 3.03 (s, 3H), 2.13 (br s, 3H); LC-MS (ESI) m/z 366.6 [M+H]$^+$.

EXAMPLE 85

4-(3-(5-Fluoro-2-methylphenyl)-4-oxothiazolidin-2-yl)benzonitrile

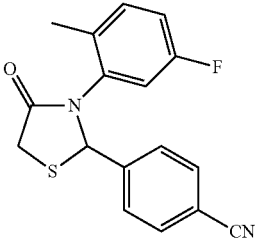

Compound 115

The compound was prepared by following the standard procedure A with 5-fluoro-2-methylaniline (50.0 mg, 0.400 mmol), 4-cyanobenzaldehyde (52.4 mg, 0.400 mmol), and 2-mercaptoacetic acid (0.670 mL, 86.5 mg, 0.940 mmol). It was reflux 6 h for the first step and 18 h for the second step. After work-up, the crude product was purified by recrystallization to give the desired product as a yellow solid (28.0 mg, 22%). $^1$H NMR (CDCl$_3$, 400 MHz) δ 7.61 (d, 2H), 7.46 (d, 2H), 7.16 (br t, 1H), 6.91 (td, 1H), 6.60 (br s, 1H), 5.88 (br s, 1H), 4.02 (d, 1H), 3.91 (d, 1H), 2.12 (br s, 3H); LC-MS (ESI) m/z 312.8 [M+H]$^+$.

EXAMPLE 86

3-[3-(5-Fluoro-2-methyl-phenyl)-4-oxo-thiazolidin-2-yl]-benzonitrile

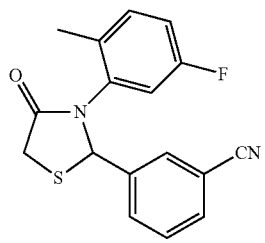

Compound 116

The compound was prepared by following the standard procedure A with 5-fluoro-2-methylaniline (63.0 mg, 0.500 mmol), 3-cyanobenzaldehyde (97.0 mg, 0.750 mmol), and thioglycolic acid (0.064 mL, 83.0 mg, 0.900 mmol). It was reflux 6 h for the first step and 18 h for the second step. After work-up, the crude product was purified by flash chromatography (ethyl acetate:hexane=1:2) to give the desired product as a yellow viscous liquid (95.0 mg, 60%). $^1$H NMR (CDCl$_3$, 400 MHz) δ 7.62-7.59 (m, 3H), 7.45 (br t, 1H), 7.17 (br t, 1H), 6.91 (t, 1H), 6.58 (br s, 1H), 5.88 (br s, 1H), 4.04 (d, 1H), 3.94 (d, 1H), 2.11 (br s, 3H); LC-MS (ESI) m/z 312.8 [M+H]$^+$.

EXAMPLE 87

2-(4-Ethyl-phenyl)-3-(5-fluoro-2-methyl-phenyl)-thiazolidin-4-one

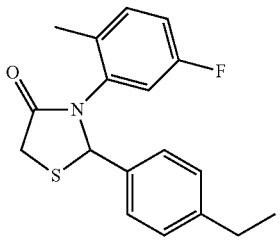

Compound 117

The compound was prepared by following the standard procedure A with 5-fluoro-2-methylaniline (63.0 mg, 0.500 mmol), 4-ethylbenzaldehyde (100 mg, 0.750 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:4) to give the desired product as a yellow viscous liquid (49.0 mg, 31%). $^1$H NMR (CDCl$_3$, 400 MHz) δ 7.25 (d, 2H), 7.20-7.10 (m, 3H), 6.87 (t, 1H), 6.55 (br s, 1H), 5.83 (br s, 1H), 4.02 (d, 1H), 3.89 (d, 1H), 2.62 (q, 2H), 2.14 (br s, 3H), 1.21 (t, 3H); LC-MS (ESI) m/z 316.9 [M+H]$^+$.

EXAMPLE 88

3-(5-Fluoro-2-methyl-phenyl)-2-(4-methylsulfanyl-phenyl)-thiazolidin-4-one

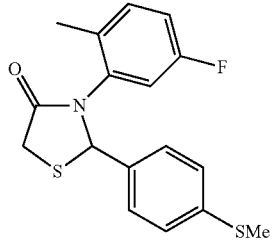

Compound 118

The compound was prepared by following the standard procedure A with 4-(methylthiol)benzaldehyde (228 mg, 1.50 mmol), 5-fluoro-2-methylaniline (125 mg, 1.00 mmol), and 2-mercaptoacetic acid (0.128 mL, 166 mg, 1.80 mmol). It was reflux 6 h for the first step and 18 h for the second step. After work-up, the crude product was purified by flash chromatography (ethyl acetate:hexane=2:5) to give the desired product as a yellow viscous liquid (75.0 mg, 22%). $^1$H NMR (CDCl$_3$, 400 MHz) δ 7.23 (d, 2H), 7.20-7.08 (m, 3H), 6.87 (td, 1H), 6.60 (br s, 1H), 5.83 (br s, 1H), 4.00 (d, 1H), 3.88 (d, 1H), 2.45 (s, 3H), 2.12 (br s, 3H); LC-MS (ESI) m/z 334.6 [M+H]$^+$.

EXAMPLE 89

3-(5-Fluoro-2-methylphenyl)-2-(3-fluoro-4-methyl-phenyl)thiazolidin-4-one

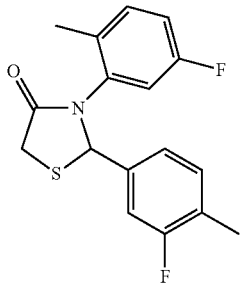

Compound 119

The compound was prepared by following the standard procedure A with 5-fluoro-2-methylaniline (50.0 mg, 0.400 mmol), 3-fluoro-4-methylbenzaldehyde (55.2 mg, 0.400 mmol), and 2-mercaptoacetic acid (0.500 mL, 64.7 mg, 0.700 mmol). It was reflux 6 h for the first step and 18 h for the second step. After work-up, the crude product was purified by flash chromatography (ethyl acetate:hexane=1:3) to give the desired product as a yellow viscous liquid (80.0 mg, 63%). $^1$H NMR (CDCl$_3$, 300 MHz) δ 7.19-6.95 (m, 4H), 6.89 (td, 1H), 6.57 (br s, 1H), 5.79 (br s, 1H), 4.00 (d, 1H), 3.87 (d, 1H), 2.23 (s, 3H), 2.13 (br s, 3H); LC-MS (ESI) m/z 320.9 [M+H]$^+$.

EXAMPLE 90

3-(5-Fluoro-2-methylphenyl)-2-(4-fluoro-3-methyl-phenyl)thiazolidin-4-one

Compound 120

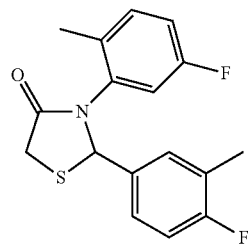

The compound was prepared by following the standard procedure A with 5-fluoro-2-methylaniline (50.0 mg, 0.400 mmol), 4-fluoro-3-methylbenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (32.0 mg, 25%). $^1$H NMR (CDCl$_3$, 400 MHz) δ 7.17-7.08 (m, 3H), 6.95-6.83 (m, 2H), 6.55 (br s, 1H), 5.81 (br s, 1H), 4.00 (d, 1H), 3.89 (d, 1H), 2.22 (s, 3H), 2.12 (br s, 3H); LC-MS (ESI) m/z 320.8 [M+H]$^+$.

EXAMPLE 91

2-(3,4-Difluorophenyl)-3-(5-fluoro-2-methylphenyl)thiazolidin-4-one

Compound 121

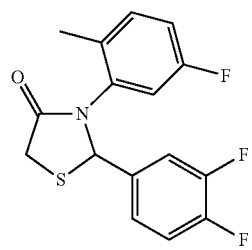

The compound was prepared by following the standard procedure A with 5-fluoro-2-methylaniline (50.0 mg, 0.400 mmol), 3,4-difluorobenzaldehyde (56.8 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:5) to give the desired product as a yellow viscous liquid (58.0 mg, 44%). $^1$H NMR (CDCl$_3$, 300 MHz) δ 7.22-7.00 (m, 4H), 6.91 (td, 1H), 6.56 (br s, 1H), 5.83 (br s, 1H), 4.00 (d, 1H), 3.89 (d, 1H), 2.11 (br s, 3H); LC-MS (ESI) m/z 324.9 [M+H]$^+$.

EXAMPLE 92

2-(3,5-Difluorophenyl)-3-(5-fluoro-2-methylphenyl)thiazolidin-4-one

Compound 122

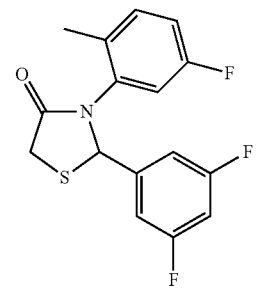

The compound was prepared by following the standard procedure A with 5-fluoro-2-methylaniline (50.0 mg, 0.400 mmol), 3,5-difluorobenzaldehyde (56.8 mg, 0.400 mmol), and 2-mercaptoacetic acid (0.067 mL, 81.2 mg, 0.880 mmol). It was reflux 6 h for the first step and 18 h for the second step. After work-up, the crude product was purified by flash chromatography (ethyl acetate:hexane=1:3) to give the desired product as a yellow viscous liquid (78.0 mg, 60%). $^1$H NMR (CDCl$_3$, 400 MHz) δ 7.17 (br t, 1H), 6.92 (td, 1H), 6.87 (d, 2H), 6.75 (br t, 1H), 6.60 (br s, 1H), 5.78 (br s, 1H), 4.01 (d, 1H), 3.88 (d, 1H), 2.13 (br s, 3H); LC-MS (ESI) m/z 324.7 [M+H]$^+$.

EXAMPLE 93

2-(4-Chloro-3-fluorophenyl)-3-(5-fluoro-2-methyl-phenyl)thiazolidin-4-one

Compound 123

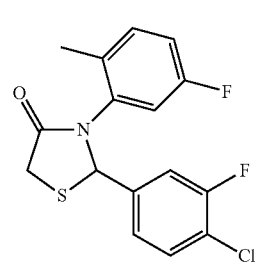

The compound was prepared by following the standard procedure A with 5-fluoro-2-methylaniline (50.0 mg, 0.400 mmol), 4-chloro-3-fluorobenzaldehyde (63.4 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:7) to give the desired product as a yellow viscous liquid (60.0 mg, 44%). $^1$H NMR (CDCl$_3$, 400 MHz) δ 7.32 (t, 1H), 7.20-7.10 (m, 2H), 7.04 (d, 1H), 6.91 (td, 1H), 6.60 (br s, 1H), 5.82 (br s, 1H), 4.00 (d, 1H), 3.89 (d, 1H), 2.12 (br s, 3H); LC-MS (ESI) m/z 339.9 [M+H]$^+$.

EXAMPLE 94

2-(3-Chloro-4-fluorophenyl)-3-(5-fluoro-2-methyl-phenyl)thiazolidin-4-one

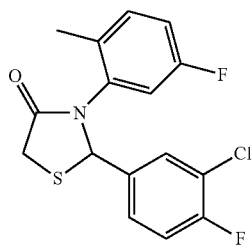

Compound 124

The compound was prepared by following the standard procedure A with 5-fluoro-2-methylaniline (50.0 mg, 0.400 mmol), 3-chloro-4-fluorobenzaldehyde (63.4 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=2:5) to give the desired product as a yellow viscous liquid (51.0 mg, 38%). $^1$H NMR (CDCl$_3$, 300 MHz) δ 7.42 (br d, 1H), 7.21-7.13 (m, 2H), 7.05 (t, 1H), 6.90 (td, 1H), 6.59 (br s, 1H), 5.82 (br s, 1H), 4.00 (d, 1H), 3.89 (d, 1H), 2.11 (br s, 3H); LC-MS (ESI) m/z 340.8 [M+H]$^+$.

EXAMPLE 95

2-(4-Fluoro-3-methoxy-phenyl)-3-(5-fluoro-2-methyl-phenyl)-thiazolidin-4-one

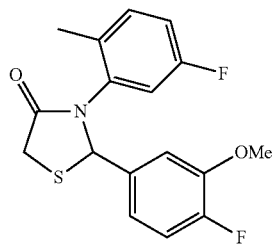

Compound 125

The compound was prepared by following the standard procedure A with 5-fluoro-2-methylaniline (125 mg, 1.00 mmol), 4-fluoro-3-methoxybenzaldehyde (231 mg, 1.50 mmol), and 2-mercaptoacetic acid (0.128 mL, 165 mg, 1.80 mmol). It was stirred at room temperature 5 h for the first step and 16 h for the second step. After work-up, the crude product was purified by flash chromatography (ethyl acetate: hexane=1:2) to give the desired product as a yellow viscous liquid (100 mg, 30%). $^1$H NMR (CDCl$_3$, 400 MHz) δ 7.15 (br t, 1H), 7.00-6.94 (m, 2H), 6.90 (t, 1H), 6.85-6.80 (m, 1H), 5.87 (br s, 1H), 3.99 (d, 1H), 3.90 (d, 1H), 3.85 (s, 3H), 2.13 (br s, 3H); LC-MS (ESI) m/z 336.7 [M+H]$^+$.

EXAMPLE 96

2-(3-Fluoro-4-methoxy-phenyl)-3-(5-fluoro-2-methyl-phenyl)-thiazolidin-4-one

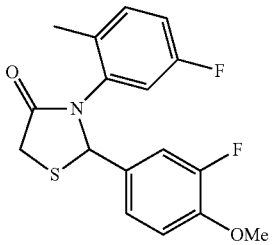

Compound 126

The compound was prepared by following the standard procedure A with 5-fluoro-2-methylaniline (125 mg, 1.00 mmol), 3-fluoro-4-methoxybenzaldehyde (231 mg, 1.50 mmol), and 2-mercaptoacetic acid (0.128 mL, 165 mg, 1.80 mmol). It was stirred at room temperature 5 h for the first step and 16 h for the second step. After work-up, the crude product was purified by flash chromatography (ethyl acetate: hexane=1:2) to give the desired product as a yellow viscous liquid (100 mg, 30%). $^1$H NMR (CDCl$_3$, 400 MHz) δ 7.20-7.15 (m, 2H), 6.98 (d, 1H), 6.89 (t, 1H), 6.83 (t, 1H), 6.60 (br s, 1H), 5.81 (br s, 1H), 3.99 (d, 1H), 3.89 (d, 1H), 3.86 (s, 3H), 2.12 (br s, 3H); LC-MS (ESI) m/z 335.8. [M+H]$^+$.

EXAMPLE 97

3-(5-Fluoro-2-methyl-phenyl)-2-(3-fluoro-4-trifluo-romethyl-phenyl)-thiazolidin-4-one

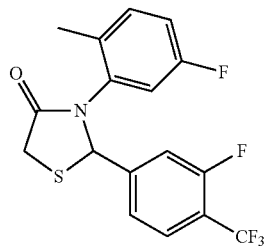

Compound 127

The compound was prepared by following the standard procedure A with 5-fluoro-2-methylaniline (125 mg, 1.00 mmol), 3-fluoro-4-(trifluoromethyl)benzaldehyde (288 mg, 1.50 mmol), and 2-mercaptoacetic acid (0.128 mL, 165 mg, 1.80 mmol). It was stirred at room temperature 5 h for the first step and 16 h for the second step. After work-up, the crude product was purified by flash chromatography (ethyl acetate:hexane=1:3) to give the desired product as a yellow viscous liquid (261 mg, 70%). $^1$H NMR (CDCl$_3$, 400 MHz) δ 7.56 (t, 1H), 7.26-7.17 (m, 3H), 6.93 (t, 1H), 6.62 (br s, 1H), 5.88 (br s, 1H), 4.03 (d, 1H), 3.91 (d, 1H), 2.14 (br s, 3H); LC-MS (ESI) m/z 373.7 [M+H]$^+$.

EXAMPLE 98

3-(5-Fluoro-2-methyl-phenyl)-2-(4-fluoro-3-trifluoromethyl-phenyl)-thiazolidin-4-one

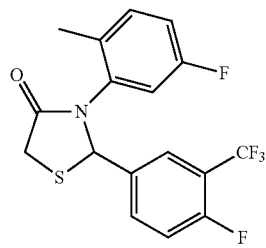

Compound 128

The compound was prepared by following the standard procedure A with 5-fluoro-2-methylaniline (63.0 mg, 0.500 mmol), 4-fluoro-3-(trifluoromethyl)benzaldehyde (144 mg, 0.750 mmol), and 2-mercpatoacetic acid (0.064 mL, 83.0 mg, 0.900 mmol). It was stirred at room temperature 5 h for the first step and 16 h for the second step. After work-up, the crude product was purified by flash chromatography (ethyl acetate:hexane=1:3) to give the desired product as a yellow viscous liquid (130 mg, 70%). $^1$H NMR (CDCl$_3$, 400 MHz) δ 7.59 (br s, 1H), 7.55-7.51 (m, 1H), 7.20-7.10 (m, 2H), 6.91 (t, 1H), 6.60 (br s, 1H), 5.92 (br s, 1H), 4.01 (d, 1H), 3.93 (d, 1H), 2.11 (br s, 3H); LC-MS (ESI) m/z 374.7 [M+H]$^+$.

EXAMPLE 99

3-(5-Fluoro-2-methyl-phenyl)-2-(3-fluoro-5-trifluoromethyl-phenyl)-thiazolidin-4-one

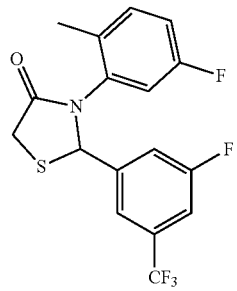

Compound 129

The compound was prepared by following the standard procedure A with 3-fluoro-5-(trifluoromethyl)benzaldehyde (144 mg, 0.750 mmol), 5-fluoro-2-methylaniline (63.0 mg, 0.500 mmol), and 2-mercaptoacetic acid (0.063 mL, 83.0 mg, 0.900 mmol). It was reflux 6 h for the first step and 18 h for the second step. After work-up, the crude product was purified by flash chromatography (ethyl acetate:hexane=3:11) to give the desired product as a yellow viscous liquid (110 mg, 59%). $^1$H NMR (CDCl$_3$, 400 MHz) δ 7.37 (s, 1H), 7.26 (d, 2H), 7.18 (br s, 1H), 6.92 (td, 1H), 6.60 (br s, 1H), 5.89 (br s, 1H), 4.03 (d, 1H), 3.92 (d, 1H), 2.13 (br s, 3H); LC-MS (ESI) m/z 373.7 [M+H]$^+$.

EXAMPLE 100

3-(5-Fluoro-2-methyl-phenyl)-2-(3-fluoro-5-methyl-phenyl)-thiazolidin-4-one

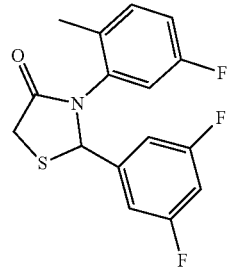

Compound 130

The compound was prepared by following the standard procedure A with 3-fluoro-5-methylbenzaldehyde (103 mg, 0.750 mmol), 5-fluoro-2-methylaniline (63.0 mg, 0.500 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:3) to give the desired product as a yellow viscous liquid (73.0 mg, 46%). $^1$H NMR (CDCl$_3$, 300 MHz) δ 7.16 (br t, 1H), 6.93-6.79 (m, 4H), 6.57 (br s, 1H), 5.77 (br s, 1H), 4.02 (d, 1H), 3.87 (d, 1H), 2.30 (s, 3H), 2.14 (br s, 3H); LC-MS (ESI) m/z 320.9 [M+H]$^+$.

EXAMPLE 101

2-(3-Fluoro-4-hydroxy-phenyl)-3-(5-fluoro-2-methyl-phenyl)-thiazolidin-4-one

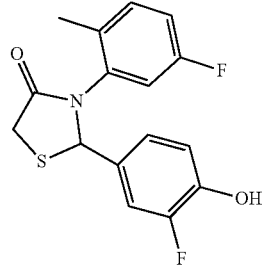

Compound 131

Step 1. Synthesis of 4-(tert-butyl-dimethyl-silanyloxy)-3-fluoro-benzaldehyde

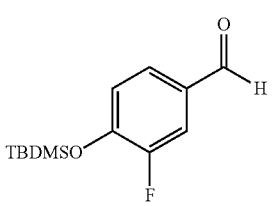

Compound 132

309

To a solution of 3-fluoro-4-hydroxybenzaldehyde (560 mg, 4.00 mmol) and TBDMSCl (900 mg, 6.00 mmol) in 10 mL of $CH_2Cl_2$ was added imidazole (544 mg, 8.00 mmol) in one portion at 0° C. The reaction mixture was stirred at room temperature for 4.5 h then partitioned between $CH_2Cl_2$ (50 mL) and $H_2O$ (20 mL). The organic layer was dried over $MgSO_4$ then concentrated to give a crude product. The crude product was purified by flash chromatography (ethyl acetate: hexane=1:8) to give the desired product as a colorless viscous liquid (750 mg, 75%). $^1H$ NMR (CDCl$_3$, 400 MHz) δ 9.85 (s, 1H), 7.59 (d, 1H), 7.56 (dd, 1H), 7.03 (t, 1H), 1.01 (s, 9H), 0.23 (s, 6H).

Step 2. Synthesis of 2-[4-(tert-butyl-dimethyl-silanyloxy)-3-fluoro-phenyl]-3-(5-fluoro-2-methyl-phenyl)-thiazolidin-4-one

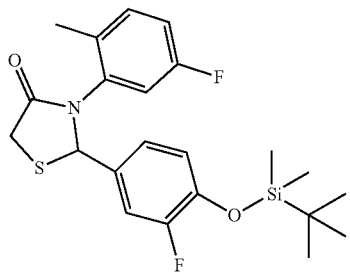

Compound 133

The compound was prepared by following the standard procedure A with 5-fluoro-2-methylaniline (125 mg, 1.00 mmol), 4-(tert-butyl-dimethyl-silanyloxy)-3-fluoro-benzalde hyde (305 mg, 1.20 mmol), and 2-mercaptoacetic acid (0.130 mL, 165 mg, 1.80 mmol). It was reflux 6 h for the first step and 18 h for the second step. After work-up, the crude product was purified by flash chromatography (ethyl acetate: hexane=1:4) to give the desired product as a yellow viscous liquid (93.0 mg, 21%). $^1H$ NMR (CDCl$_3$, 400 MHz) δ 7.18-7.06 (m, 2H), 6.95-6.85 (m, 2H), 6.79 (br t, 1H), 5.78 (br s, 1H), 3.98 (d, 1H), 3.88 (d, 1H), 2.09 (br s, 3H), 0.96 (s, 9H), 0.16 (s, 6H).

Step 3. Synthesis of 2-(3-fluoro-4-hydroxy-phenyl)-3-(5-fluoro-2-methyl-phenyl)-thiazolidin-4-one To a solution of 2-[4-(tert-butyl-dimethyl-silanyloxy)-3-fluoro-phenyl]-3-(5-fluoro-2-methyl-phenyl)-thiazolidin-4-one (93.0 mg, 0.210 mmol) in 2 mL of THF was added 75% TBAF$_{(aq)}$ (0.150 mL, 0.420 mmol) in one portion and stirred at room temperature for 1.5 h. The reaction mixture was directly concentrated to give a crude product which was partitioned between ethyl acetate (30 mL) and $H_2O$ (10 mL). The organic layer was washed with brine (10 mL) dried over $MgSO_4$ then concentrated to give a crude product. The crude product was purified by flash chromatography (ethyl acetate: hexane=2:3) to give the desired product as a yellow viscous liquid (68.0 mg, 100%). $^1H$ NMR (CDCl$_3$, 400 MHz) δ 7.13 (d, 2H), 6.96 (d, 1H), 6.89 (t, 2H), 6.54 (br s, 1H), 5.79 (br s, 1H), 5.26 (s, 1H), 3.98 (d, 1H), 3.88 (d, 1H), 2.11 (br s, 3H); LC-MS (ESI) m/z 322.9 [M+H]$^+$.

310

EXAMPLE 102

2-(2,3-Dihydro-benzo[1,4]dioxin-6-yl)-3-(5-fluoro-2-methyl-phenyl)-thiazolidin-4-one

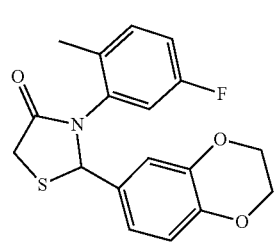

Compound 134

The compound was prepared by following the standard procedure A with 1,4-benzodioxane-6-carboxaldehyde (123 mg, 0.750 mmol), 5-fluoro-2-methylaniline (63.0 mg, 0.500 mmol), and 2-mercaptoacetic acid (0.063 mL, 83.0 mg, 0.900 mmol). It was reflux 6 h for the first step and 18 h for the second step. After work-up, the crude product was purified by flash chromatography (ethyl acetate:hexane=1:2) to give the desired product as a yellow viscous liquid (36.0 mg, 21%). $^1H$ NMR (CDCl$_3$, 400 MHz) δ 7.15 (br t, 1H), 6.89 (td, 1H), 6.87 (s, 1H), 6.83-6.77 (m, 2H), 6.59 (br s, 1H), 5.75 (br s, 1H), 4.23 (s, 4H), 3.99 (d, 1H), 3.86 (d, 1H), 2.14 (br s, 3H); LC-MS (ESI) m/z 346.8 [M+H]$^+$.

EXAMPLE 103

2-(3-Bromo-5-chloro-phenyl)-3-(5-fluoro-2-methyl-phenyl)-thiazolidin-4-one

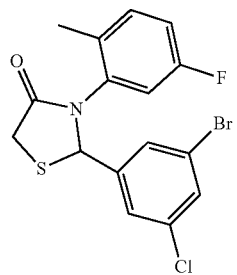

Compound 135

The compound was prepared by following the standard procedure A with 3-bromo-5-chlorobenzaldehyde (131 mg, 0.600 mmol), 5-fluoro-2-methylaniline (63.0 mg, 0.500 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:4) to give the desired product as a yellow viscous liquid (136 mg, 68%). $^1H$ NMR (CDCl$_3$, 300 MHz) δ 7.45 (s, 1H), 7.36 (s, 1H), 7.25 (s, 1H), 7.18 (br t, 1H), 6.93 (td, 1H), 6.59 (br s, 1H), 5.74 (br s, 1H), 4.02 (d, 1H), 3.88 (d, 1H), 2.14 (br s, 3H); LC-MS (ESI) m/z 401.7 [M+H]$^+$.

EXAMPLE 104

3-(5-Fluoro-2-methyl-phenyl)-2-(3,4,5-trifluoro-phenyl)-thiazolidin-4-one

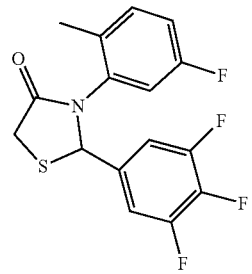

Compound 136

The compound was prepared by following the standard procedure A with 3,4,5-trifluorobenzaldehyde (120 mg, 0.750 mmol), 5-fluoro-2-methylaniline (63.0 mg, 0.500 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:4) to give the desired product as a yellow viscous liquid (120 mg, 71%). $^1$H NMR (CDCl$_3$, 400 MHz) δ 7.19 (br t, 1H), 6.99 (t, 2H), 6.93 (td, 1H), 6.60 (br s, 1H), 5.78 (br s, 1H), 3.99 (d, 1H), 3.89 (d, 1H), 2.12 (br s, 3H); LC-MS (ESI) m/z 341.8 [M+H]$^+$.

EXAMPLE 105

2-(3,4-Difluoro-5-methyl-phenyl)-3-(5-fluoro-2-methyl-phenyl)-thiazolidin-4-one

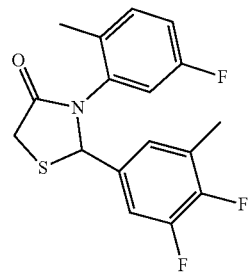

Compound 137

The compound was prepared by following the standard procedure A with 3,4-difluoro-5-methylbenzaldehyde (117 mg, 0.750 mmol), 5-fluoro-2-methylaniline (63.0 mg, 0.500 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:3) to give the desired product as a yellow viscous liquid (71.0 mg, 42%). $^1$H NMR (CDCl$_3$, 300 MHz) δ 7.16 (br t, 1H), 7.10-6.98 (m, 1H), 6.95-6.84 (m, 2H), 6.58 (br s, 1H), 5.77 (br s, 1H), 3.99 (d, 1H), 3.87 (d, 1H), 2.24 (s, 3H), 2.13 (br s, 3H); LC-MS (ESI) m/z 338.9 [M+H]$^+$.

EXAMPLE 106

2-(4-Fluoro-3,5-dimethyl-phenyl)-3-(5-fluoro-2-methyl-phenyl)-thiazolidin-4-one

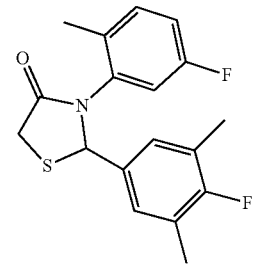

Compound 138

The compound was prepared by following the standard procedure A with 4-fluoro-3,5-dimethylbenzaldehyde (114 mg, 0.750 mmol), 5-fluoro-2-methylaniline (63.0 mg, 0.500 mmol), and 2-mercaptoacetic acid (0.100 mL, 129 mg, 1.40 mmol). It was reflux 6 h for the first step and 18 h for the second step. After work-up, the crude product was purified by flash chromatography (ethyl acetate:hexane=1:3) to give the desired product as a yellow viscous liquid (40.0 mg, 24%). $^1$H NMR (CDCl$_3$, 300 MHz) δ 7.15 (br t, 1H), 6.97 (s, 1H), 6.95 (s, 1H), 6.87 (td, 1H), 6.55 (br s, 1H), 5.75 (br s, 1H), 4.00 (d, 1H), 3.87 (d, 1H), 2.20 (s, 6H), 2.14 (br s, 3H); LC-MS (ESI) m/z 334.9 [M+H]$^+$.

EXAMPLE 107

2-(3-Chloro-4-ethoxy-5-fluoro-phenyl)-3-(5-fluoro-2-methyl-phenyl)-thiazolidin-4-one

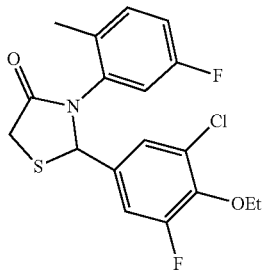

Compound 139

The compound was prepared by following the standard procedure A with 3-chloro-4-ethoxy-5-fluorobenzaldehyde (303 mg, 1.50 mmol), 5-fluoro-2-methylaniline (125 mg, 1.00 mmol), and 2-mercaptoacetic acid (0.128 mL, 166 mg, 1.80 mmol). It was reflux 6 h for the first step and 18 h for the second step. After work-up, the crude product was purified by flash chromatography (ethyl acetate:hexane=1:3) to give the desired product as a yellow viscous liquid (140 mg, 37%). $^1$H NMR (CDCl$_3$, 300 MHz) δ 7.17 (br t, 1H), 7.12 (s, 1H), 7.01 (d, 1H), 6.93 (br t, 1H), 6.59 (br s, 1H), 5.74 (br s, 1H), 4.17 (q, 2H), 4.00 (d, 1H), 3.87 (d, 1H), 2.12 (br s, 3H), 1.39 (t, 3H); LC-MS (ESI) m/z 384.9 [M+H]$^+$.

EXAMPLE 108

2-(3,5-Difluoro-4-methoxy-phenyl)-3-(5-fluoro-2-methyl-phenyl)-thiazolidin-4-one

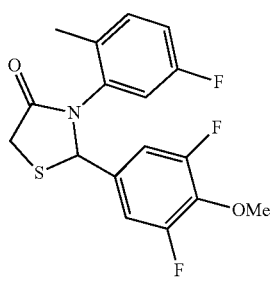

Compound 140

The compound was prepared by following the standard procedure A with 3,5-difluoro-4-methoxybenzaldehyde (206 mg, 1.20 mmol), 5-fluoro-2-methylaniline (125 mg, 1.00 mmol), and 2-mercaptoacetic acid (0.128 mL, 166 mg, 1.80 mmol). It was reflux 6 h for the first step and 18 h for the second step. After work-up, the crude product was purified by flash chromatography (ethyl acetate:hexane=1:3) to give the desired product as a yellow viscous liquid (123 mg, 35%). $^1$H NMR (CDCl$_3$, 300 MHz) δ 7.18 (br t, 1H), 6.95-6.85 (m, 3H), 6.60 (br s, 1H), 5.75 (br s, 1H), 4.02-3.95 (m, 4H), 3.87 (d, 1H), 2.13 (br s, 3H); LC-MS (ESI) m/z 354.9 [M+H]$^+$.

EXAMPLE 109

3-(5-Fluoro-2-methyl-phenyl)-2-(4-hydroxy-3,5-dimethyl-phenyl)-thiazolidin-4-one

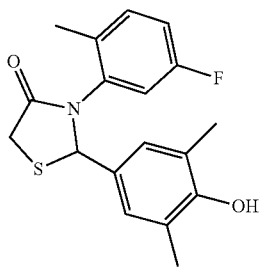

Compound 141

Step 1. Synthesis of 4-(tert-butyl-dimethyl-silanyloxy)-3,5-dimethyl-benzaldehyde

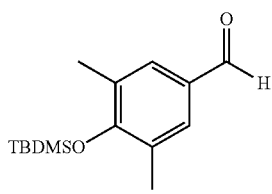

Compound 142

To a solution of 3,5-dimethyl-4-hydroxybenzaldehyde (600 mg, 4.00 mmol) and TBDMSCl (900 mg, 6.00 mmol) in 10 mL of CH$_2$Cl$_2$ was added imidazole (544 mg, 8.00 mmol) in one portion at 0° C. The reaction mixture was stirred at room temperature for 4.5 h then partitioned between CH$_2$Cl$_2$ (50 mL) and H$_2$O (20 mL). The organic layer was dried over MgSO$_4$ then concentrated to give a crude product. The crude product was purified by flash chromatography (ethyl acetate:hexane=1:8) to give the desired product as a colorless viscous liquid (600 mg, 60%). $^1$H NMR (CDCl$_3$, 300 MHz) δ 9.83 (s, 1H), 7.53 (s, 2H), 2.27 (s, 6H), 1.03 (s, 9H), 0.23 (s, 6H).

Step 2. Synthesis of 2-[4-(tert-butyl-dimethyl-silanyloxy)-3,5-dimethyl-phenyl]-3-(5-fluoro-2-methyl-phenyl)-thiazolidin-4-one

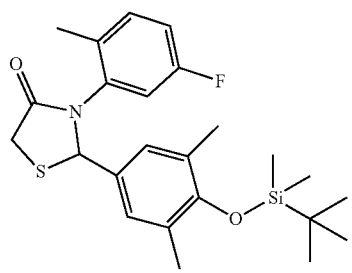

Compound 143

The compound was prepared by following the standard procedure A with 5-fluoro-2-methylaniline (125 mg, 1.00 mmol), 4-(tert-butyl-dimethyl-silanyloxy)-3,5-dimethyl-benzaldehyde (317 mg, 1.20 mmol), and 2-mercaptoacetic acid (0.128 mL, 165 mg, 1.80 mmol). It was reflux 6 h for the first step and 18 h for the second step. After work-up, the crude product was purified by flash chromatography (ethyl acetate:hexane=1:5) to give the desired product as a yellow viscous liquid (36.0 mg, 8%). $^1$H NMR (CDCl$_3$, 300 MHz) δ 7.12 (br t, 1H), 6.95-6.80 (m, 3H), 6.50 (br s, 1H), 5.71 (br s, 1H), 4.00 (d, 1H), 3.87 (d, 1H), 2.14 (br s, 9H), 0.98 (s, 9H), 0.16 (s, 6H).

Step 3. Synthesis of 3-(5-Fluoro-2-methyl-phenyl)-2-(4-hydroxy-3,5-dimethyl-phenyl)-thiazolidin-4-one To a solution of 2-[4-(tert-butyl-dimethyl-silanyloxy)-3,5-dimethyl-phenyl]-3-(5-fluoro-2-methyl-phenyl)-thiazolidin-4-one (36.0 mg, 0.08 mmol) in 1 mL of THF was added 75% TBAF$_{(aq)}$ (0.06 mL, 0.160 mmol) in one portion and stirred at room temperature for 4 h. The reaction mixture was directly concentrated to give a crude product which was partitioned between ethyl acetate (20 mL) and H$_2$O (10 mL). The organic layer was washed with brine (10 mL) dried over MgSO$_4$ then concentrated to give a crude product. The crude product was purified by flash chromatography (ethyl acetate:hexane=2:3) to give the desired product as a yellow viscous liquid (10.0 mg, 38%). $^1$H NMR (CDCl$_3$, 300 MHz) δ 7.16 (br t, 1H), 6.96 (s, 2H), 6.88 (br t, 1H), 6.55 (br s, 1H), 5.75 (br s, 1H), 5.14 (br s, 1H), 4.01 (d, 1H), 3.86 (d, 1H), 2.20-2.00 (m, 9H); LC-MS (ESI) m/z 332.7 [M+H]$^+$.

EXAMPLE 110

2-(3-Bromo-4-hydroxy-5-methoxy-phenyl)-3-(5-fluoro-2-methyl-phenyl)-thiazolidin-4-one

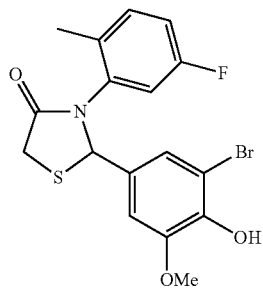

Compound 144

Step 1. Synthesis of 3-bromo-4-(tert-butyl-dimethyl-silanyloxy)-5-methoxy-benzaldehyde

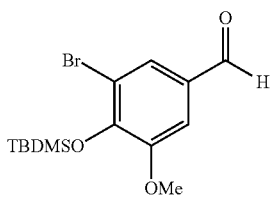

Compound 145

To a solution of 5-bromovanillin (924 mg, 4.00 mmol) and TBDMSCl (900 mg, 6.00 mmol) in 10 mL of $CH_2Cl_2$ was added imidazole (817 mg, 12.0 mmol) in one portion at 0° C. The reaction mixture was stirred at room temperature for 5.5 h then partitioned between $CH_2Cl_2$ (60 mL) and $H_2O$ (30 mL). The organic layer was dried over $MgSO_4$ then concentrated to give a crude product. The crude product was purified by flash chromatography (ethyl acetate:hexane=1:4) to give the desired product as a colorless viscous liquid (760 mg, 55%). $^1$H NMR (CDCl$_3$, 300 MHz) δ 9.79 (s, 1H), 7.64 (s, 1H), 7.33 (s, 1H), 3.87 (s, 3H), 1.04 (s, 9H), 0.25 (s, 6H).

Step 2. Synthesis of 2-[3-bromo-4-(tert-butyl-dimethyl-silanyloxy)-5-methoxy-phenyl]-3-(5-fluoro-2-methyl-phenyl)-thiazolidin-4-one

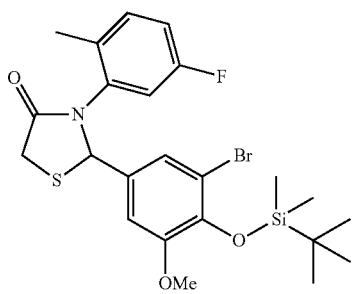

Compound 146

The compound was prepared by following the standard procedure A with 5-fluoro-2-methylaniline (125 mg, 1.00 mmol), 3-bromo-4-(tert-butyl-dimethyl-silanyloxy)-5-methoxybenzaldehyde (518 mg, 1.50 mmol), and 2-mercaptoacetic acid (0.130 mL, 165 mg, 1.80 mmol). It was reflux 6 h for the first step and 18 h for the second step. After work-up, the crude product was purified by flash chromatography (ethyl acetate:hexane=1:3) to give the desired product as a yellow viscous liquid (110 mg, 21%). $^1$H NMR (CDCl$_3$, 300 MHz) δ 7.14 (br d, 1H), 7.08 (s, 1H), 6.89 (t, 1H), 6.72 (s, 1H), 5.77 (br s, 1H), 3.98 (d, 1H), 3.88 (d, 1H), 3.72 (s, 3H), 2.11 (br s, 3H), 1.00 (s, 9H), 0.18 (s, 6H).

Step 3. Synthesis of 2-(3-bromo-4-hydroxy-5-methoxy-phenyl)-3-(5-fluoro-2-methyl-phenyl)-thiazolidin-4-one To a solution of 2-[3-bromo-4-(tert-butyl-dimethyl-silanyloxy)-5-methoxy-phenyl]-3-(5-fluoro-2-methyl-phenyl)-thiazolidin-4-one (110 mg, 0.210 mmol) in 2 mL of THF was added 75% TBAF$_{(aq)}$ (0.150 mL, 0.420 mmol) in one portion and stirred at room temperature for 2.5 h. The reaction mixture was directly concentrated to give a crude product which was partitioned between ethyl acetate (30 mL) and $H_2O$ (10 mL). The organic layer was washed with brine (10 mL), dried over $MgSO_4$, then concentrated to give a crude product. The crude product was purified by flash chromatography (ethyl acetate:hexane=3:4) to give the desired product as a yellow viscous liquid (69.0 mg, 80%). $^1$H NMR (CDCl$_3$, 400 MHz) δ 7.16 (br s, 1H), 7.06 (br s, 1H), 6.90 (td, 1H), 6.79 (s, 1H), 6.60 (br s, 1H), 5.97 (br s, 1H), 5.78 (br s, 1H), 4.00-3.80 (m, 5H), 2.13 (br s, 3H); LC-MS (ESI) m/z 411.6 [M+H]$^+$.

EXAMPLE 111

3-(5-Chloro-2-methylphenyl)-2-(4-fluorophenyl)thiazolidin-4-one

Compound 147

The compound was prepared by following the standard procedure A with 5-chloro-2-methylaniline (56.4 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (48.0 mg, 37%). $^1$H NMR (CDCl$_3$, 400 MHz) δ 7.32 (dd, 2H), 7.14-7.05 (m, 2H), 6.99 (br t, 2H), 5.89 (br s, 1H), 3.99 (d, 1H), 3.90 (d, 1H), 2.08 (br s, 3H); LC-MS (ESI) m/z 322.7 [M+H]$^+$.

EXAMPLE 112

3-(5-Chloro-2-methylphenyl)-2-(3-fluorophenyl)thiazolidin-4-one

Compound 148

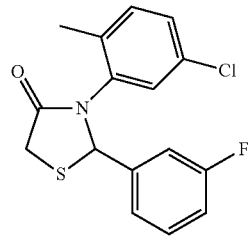

The compound was prepared by following the standard procedure A with 5-chloro-2-methylaniline (56.4 mg, 0.400 mmol), 3-fluorobenzaldehyde (49.6 mg, 0.400 mmol), and mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (77.0 mg, 60%). $^1$H NMR (CD$_3$OD, 400 MHz) δ 7.38-7.25 (br, 1H), 7.24-7.21 (m, 2H), 7.17 (br s, 2H), 7.03 (br t, 1H), 6.21 (br s, 1H), 4.07 (br d, 1H), 3.93 (d, 1H), 2.10 (br s, 3H); LC-MS (ESI) m/z 322.9 [M+H]$^+$.

EXAMPLE 113

3-5-Bromo-2-methylphenyl)-2-(4-fluorophenyl)thiazolidin-4-one

Compound 149

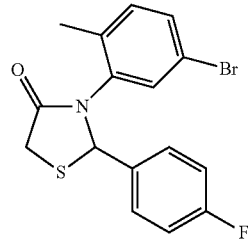

The compound was prepared by following the standard procedure A with 5-bromo-2-methylaniline (74.4 mg, 0.400 mmol), 4-fluorobenzaldehyde (49.6 mg, 0.400 mmol), and 2-mercaptoacetic acid (0.670 mL, 86.5 mg, 0.940 mmol). It was reflux 6 h for the first step and 18 h for the second step. After work-up, the crude product was purified by flash chromatography (dichloromethane:ethyl acetate:hexane=3:1:5) to give the desired product as a yellow viscous liquid (47.0 mg, 32%). $^1$H NMR (CD$_3$CN, 300 MHz) δ 7.49 (dd, 2H), 7.33 (d, 1H), 7.14 (br s, 1H), 7.06 (t, 2H), 6.12 (br s, 1H), 3.97 (d, 1H), 3.87 (d, 1H), 2.10 (br s, 3H); LC-MS (ESI) m/z 365.7 [M+H]$^+$.

EXAMPLE 114

3-(5-Bromo-2-methylphenyl)-2-(3-fluorophenyl)thiazolidin-4-one

Compound 150

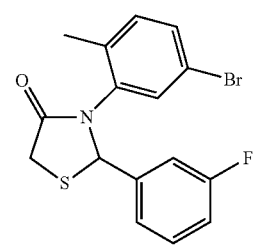

The compound was prepared by following the standard procedure A with 5-bromo-2-methylaniline (74.4 mg, 0.400 mmol), 3-fluorobenzaldehyde (49.6 mg, 0.4 mmol), and 2-mercaptoacetic acid (0.670 mL, 86.5 mg, 0.940 mmol). It was reflux 6 h for the first step and 18 h for the second step. After work-up, the crude product was purified by flash chromatography (ethyl acetate:hexane=1:3) to give the desired product as a yellow viscous liquid (72.0 mg, 49%). $^1$H NMR (CDCl$_3$, 300 MHz) δ 7.35-7.20 (m, 2H), 7.15-6.80 (m, 5H), 5.83 (br s, 1H), 4.01 (d, 1H), 3.88 (d, 1H), 2.09 (br s, 3H); LC-MS (ESI) m/z 365.7 [M+H]$^+$.

EXAMPLE 115

4-[2-(4-Fluorophenyl)-4-oxo-1,3-thiazolidin-3-yl]-N-hydroxy-3-methylbenzene carboximidamide Compound 151

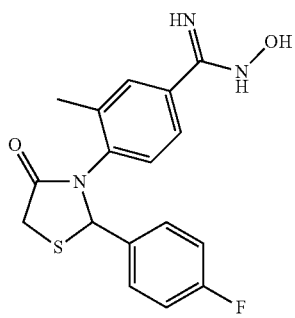

To a solution of 4-[2-(4-fluorophenyl)-4-oxo-1,3-thiazolidin-3-yl]-3-methylbenzonitrile (61.8 mg, 0.198 mmol) in ethanol (2.0 mL) and water (0.40 mL) was added sodium carbonate (44.1 mg, 0.356 mmol) and hydroxylamine hydrochloride (24.7 mg, 0.356 mmol) at room temperature, and the reaction mixture was stirred at 70° C. for 18 h. After the reaction was cooled and quenched with water, the solution was extracted with ethyl acetate. The combined organic layers were dried over MgSO$_{4(s)}$, filtered, and concentrated under reduced pressure to afford a residue. The residue was purified by Isco Combi-Flash Companion column chromatography (0-100% ethyl acetate in n-hexane) to give 4-[2-(4-fluorophenyl)-4-oxo-1,3-thiazolidin-3-yl]-N-hydroxy-3-methylbenzene carboximidamide (30.2 mg, 44%) as a yellow solid. 1H NMR (DMSO-d$_6$, 400 MHz) δ 9.64 (br s, 1H), 7.50-7.25 (m, 4H), 7.10 (br t, 2H), 6.60-6.20 (br, 1H), 5.77 (br s, 1H), 4.08 (d, 1H), 3.88 (d, 1H), 2.09 (br s, 3H); LC-MS (ESI) m/z 346.2 [M+H]+.

EXAMPLE 116

4-[2-(4-Fluoro-phenyl)-4-oxo-thiazolidin-3-yl]-3-methyl-benzoic acid ethyl ester

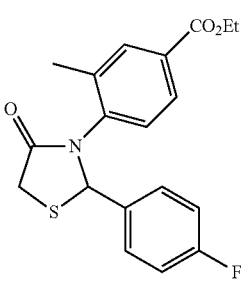

Compound 152

Step 1. Synthesis of 4-amino-3-methyl-benzoic acid ethyl ester

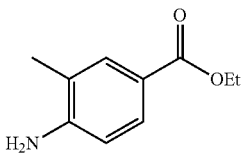

Compound 153

To a solution of ethyl 3-methyl-4-nitrobenzoate (1.26 g, 6.00 mmol) in 12.0 mL of acetic acid was added zinc dust$_{(s)}$ (1.90 g, 30.0 mmol) in one portion at r.t. The reaction mixture was stirred at r.t. for 4 h then passed through a pad of celite. The filtrate was partitioned between ethyl acetate (100 mL) and saturated NaHCO$_{3(aq)}$ (50 mL). The organic layer was washed with brine (20 mL), dried over MgSO$_4$ and concentrated to give a crude product which was purified by flash chromatography (ethyl acetate:hexane=1:3) to give the desired product as a white solid (540 mg, 50%). $^1$H NMR (CDCl$_3$, 400 MHz) δ 7.77-7.74 (m, 2H), 6.69 (d, 1H), 4.49 (br s, 2H), 4.32 (q, 2H), 2.21 (s, 3H), 1.36 (t, 3H).

Step 2. Synthesis of 4-[2-(4-fluoro-phenyl)-4-oxo-thiazolidin-3-yl]-3-methyl-benzoic acid ethyl ester The compound was prepared by following the standard procedure A with ethyl 4-amino-3-methylbenzoate (358 mg, 2.00 mmol), 4-fluorobenzaldehyde (273 mg, 2.20 mmol), and 2-mercaptoacetic acid (0.260 mL, 331 mg, 3.60 mmol). It was stirred at room temperature 5 h for the first step and 16 h for the second step. After work-up, the crude product was purified by flash chromatography (ethyl acetate:hexane=1:2) to give the desired product as a yellow viscous liquid (140 mg, 20%). $^1$H NMR (CDCl$_3$, 300 MHz) δ 7.86 (br s, 1H), 7.74 (br d, 1H), 7.30 (dd, 2H), 6.94 (br t, 2H), 5.94 (br s, 1H), 4.31 (q, 2H), 3.99 (d, 1H), 3.90 (d, 1H), 2.18 (br s, 3H), 1.34 (t, 3H); LC-MS (ESI) m/z 360.9 [M+H]+.

EXAMPLE 117

3-Ethyl-4-[2-(4-fluoro-phenyl)-4-oxo-thiazolidin-3-yl]-benzoic acid

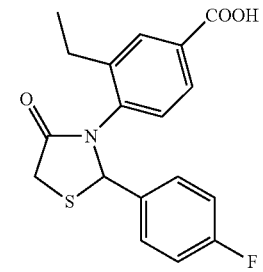

Compound 154

Step 1. Synthesis of 3-Ethyl-4-[2-(4-fluoro-phenyl)-4-oxo-thiazolidin-3-yl]-benzoic acid ethyl ester

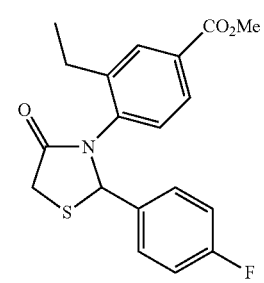

Compound 155

The compound was prepared by following the standard procedure A with methyl 3-amino-4-ethylbenzoate (268 mg, 1.50 mmol), 4-fluorobenzaldehyde (242 mg, 1.95 mmol), and 2-mercaptoacetic acid (0.192 mL, 248 mg, 2.70 mmol). It was reflux 6 h for the first step and 18 h for the second step. After work-up, the crude product was purified by flash chromatography (ethyl acetate:hexane=1:2) to give the desired product as a yellow viscous liquid (58.0 mg, 11%). $^1$H NMR (CDCl$_3$, 400 MHz) δ 8.00-7.60 (m, 2H), 7.32-7.26 (m, 2H), 6.95 (br s, 2H), 6.55 (br s, 1H), 6.20-5.60 (m, 1H), 4.02 (br d, 1H), 3.92 (d, 1H), 3.88 (s, 3H), 2.64 (br s, 2H), 1.40-0.85 (m, 3H); LC-MS (ESI) m/z 360.9 [M+H]+.

Step 2. Synthesis of 4-(2-(4-Fluorophenyl)-4-oxothiazolidin-3-yl)-3-ethylbenzoic acid The compound was prepared by following the standard procedure B with methyl 3-(2-(4-fluorophenyl)-4-oxothiazolidin-3-yl)-4-ethylbenzoate (58.0 mg, 0.160 mmol) and 20% NaOH$_{(aq)}$ (1.00 mL, 5.00 mmol) to give the desired product as a yellow solid (54.0 mg, 100%). $^1$H NMR (CDCl$_3$, 400 MHz) δ 7.98 (br s, 1H), 7.72 (br d, 1H), 7.40-7.26 (m, 2H), 6.97 (br s, 2H), 6.61 (br s, 1H), 6.20-5.60 (m, 1H), 4.03 (br d, 1H), 3.93 (d, 1H), 2.64 (br s, 2H), 1.40-1.00 (m, 3H); LC-MS (ESI) m/z 346.0 [M+H]+.

EXAMPLE 118

3-Ethyl-4-[2-(4-fluoro-phenyl)-4-oxo-thiazolidin-3-yl]-benzoic acid ethyl ester

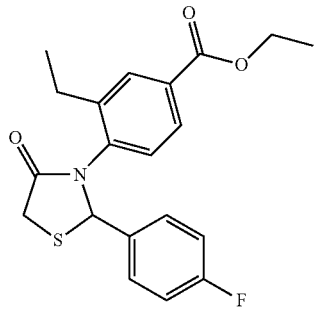

Compound 156

The compound was prepared by following the standard procedure C with 4-(2-(4-fluorophenyl)-4-oxothiazolidin-3-yl)-3-ethylbenzoic acid (50.0 mg, 0.145 mmol), EDCI • HCl (40.0 mg, 0.210 mmol), ethanol (0.5 mL) and DMAP (25.0 mg, 0.210 mmol). The desired product is a orange viscous liquid (24.0 mg, 44%). $^1$H NMR (CDCl$_3$, 400 MHz) δ 8.00-7.85 (m, 1H), 7.66 (br s, 1H), 7.31-7.28 (m, 2H), 6.96 (br s, 2H), 6.56 (br s, 1H), 6.20-5.60 (br, 1H), 4.34 (q, 2H), 4.02 (br d, 1H), 3.92 (d, 1H), 2.63 (br s, 2H), 1.45-1.00 (m, 6H); LC-MS (ESI) m/z 374.8 [M+H]$^+$.

EXAMPLE 119

3-Ethenyl-4-[2-(4 fluorophenyl)-4-oxo-1,3-thiazolidin-3-yl]benzoic acid

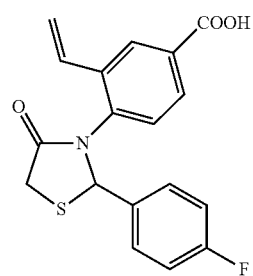

Compound 157

Step 1. Methyl 3-ethenyl-4-[2-(4-fluorophenyl)-4-oxo-1,3-thiazolidin-3-yl]benzoate

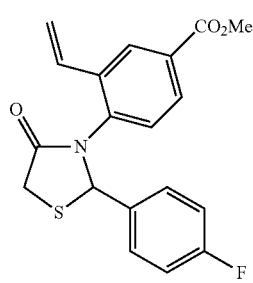

Compound 158

Following standard procedure A, methyl 4-amino-3-ethenylbenzoate (0.231 g, 1.30 mmol), 4-fluorobenzaldehyde (0.210 mL, 1.95 mmol), Na$_2$SO$_4$ (0.185 g, 1.30 mmol), 2-mercaptoacetic acid (0.160 mL, 2.29 mmol), and toluene (5.0 mL) were used to carry out the reaction. It was reflux 22 h for the first step and 8 h for the second step. After work-up, the residue was purified by Isco Combi-Flash Companion column chromatography (0-40% ethyl acetate in n-hexane) to give methyl 3-ethenyl-4-[2-(4-fluorophenyl)-4-oxo-1,3-thiazolidin-3-yl]benzoate (28.9 mg, 6%) as a yellow solid. 1H NMR (CDCl$_3$, 300 MHz) δ 8.19 (s, 1H), 7.79 (d, 1H), 7.28-7.22 (m, 2H), 6.95 (t, 2H), 6.70 (dd, 1H), 5.94 (s, 1H), 5.83 (d, 1H), 5.48 (d, 1H), 3.99-3.88 (m, 5H).

Step 2. 3-Ethenyl-4-[2-(4-fluorophenyl)-4-oxo-1,3-thiazolidin-3-yl]benzoic acid

Following standard procedure B, methyl 3-ethenyl-4-[2-(4-fluorophenyl)-4-oxo-1,3-thiazolidin-3-yl]benzoate (28.7 mg, 8.03×10$^{-5}$ mmol), 20% NaOH$_{(aq)}$ (0.10 mL), and methanol (0.50 mL) were used to carry out the reaction. After the reaction was stirred for 4 h and work-up, the residue was purified by Isco Combi-Flash Companion column chromatography (0-10% MeOH in CH$_2$Cl$_2$) to give 3-ethenyl-4-[2-(4-fluorophenyl)-4-oxo-1,3-thiazolidin-3-yl] benzoic acid (15.7 mg, 57%) as a brown gum. 1H NMR (CDCl$_3$, 400 MHz) δ 8.23 (s, 1H), 7.83 (d, 1H), 7.28-7.22 (m, 2H), 6.96-6.91 (m, 3H), 6.71 (dd, 1H), 5.96 (s, 1H), 5.84 (d, 1H), 5.50 (d, 1H), 4.03 (d, 1H), 3.95 (d, 1H); LC-MS (ESI) m/z 344.2 [M+H]$^+$.

EXAMPLE 120

4-[2-(4-Fluorophenyl)-4-oxo-1,3-thiazolidin-3-yl]-3-methyl-N-(methylsulfonyl)-benzamide

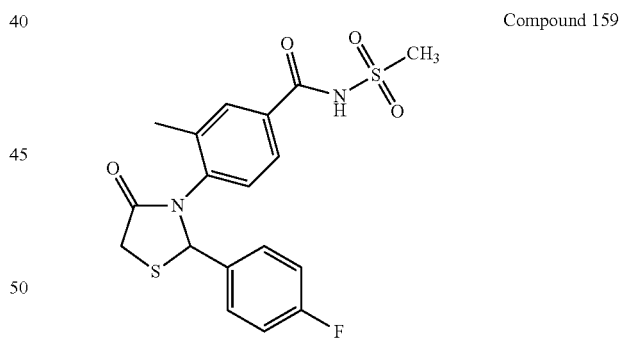

Compound 159

Following standard procedure C, 4-[2-(4-fluorophenyl)-4-oxo-1,3-thiazolidin-3-yl]-3-methylbenzoic acid (86.9 mg, 0.262 mmol), DMAP (80.0 mg, 0.655 mmol), EDCI • HCl (101 mg, 0.524 mmol), methanesulfonamide (29.9 mg, 0.314 mmol), and CH$_2$Cl$_2$ (5.0 mL) were used to carry out the reaction. After the reaction was stirred for 16 h and work-up, the residue was purified by Isco Combi-Flash Companion column chromatography (0-10% MeOH in CH$_2$Cl$_2$) to give 4-[2-(4-fluorophenyl)-4-oxo-1,3-thiazolidin-3-yl]-3-methyl-N-(methylsulfonyl)benzamide (85.1 mg, 80%) as a beige solid. 1H NMR (CDCl$_3$, 400 MHz) δ 9.06 (br s, 1H), 7.60-7.40 (br, 2H), 7.33-7.26 (m, 2H), 6.95 (t, 2H), 6.10-5.80 (br, 1H), 4.10-3.95 (m, 2H), 3.34 (s, 3H), 2.18 (br s, 3H); LC-MS (ESI) m/z 409.2 [M+H]$^+$.

EXAMPLE 121

4-[2-(4-Fluorophenyl)-4-oxo-1,3-thiazolidin-3-yl]-3-methyl-N-(propylsulfonyl)-benzamide Compound 160

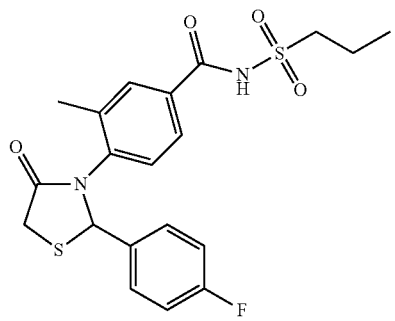

Step 1. 1-Propanesulfonamide

Compound 161

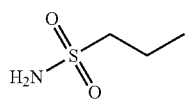

Following standard procedure D, 1-propanesulfonyl chloride (1.00 mL, 8.92 mmol), methanol (4.0 mL), and ammonium hydroxide solution (20 mL) were used to carry out the reaction. After the reaction was stirred at 0° C. for 1 h and room temperature for 2 h, 1-propanesulfonamide (0.610 g, 55%) was obtained as a white solid. 1H NMR (CDCl$_3$, 300 MHz) δ 4.70 (br s, 2H), 3.13-3.08 (m, 2H), 1.90 (sextet, 2H), 1.08 (t, 3H).

Step 2. 4-[2-(4-Fluorophenyl)-4-oxo-1, 3-thiazolidin-3-yl]-3-methyl-N-(propylsulfonyl)benzamide Following standard procedure C, 4-[2-(4-fluorophenyl)-4-oxo-1,3-thiazolidin-3-yl]-3-methylbenzoic acid (71.2 mg, 0.215 mmol), DMAP (65.7 mg, 0.538 mmol), EDCI • HCl (82.4 mg, 0.430 mmol), 1-propanesulfonamide (35.4 mg, 0.258 mmol), and CH$_2$Cl$_2$ (4.0 mL) were used to carry out the reaction. After the reaction was stirred for 18 h and work-up, the residue was purified by column chromatography (5% MeOH in CH$_2$Cl$_2$) to give 4-[2-(4-fluorophenyl)-4-oxo-1,3-thiazolidin-3-yl]-3-methyl-N-(propylsulfonyl)-benzamide (54.8 mg, 58%) as a beige solid. 1H NMR (CDCl$_3$, 300 MHz) δ 9.01 (br s, 1H), 7.61-7.45 (br, 2H), 7.33-7.28 (m, 2H), 6.95 (br t, 2H), 5.97 (br s, 1H), 4.00 (s, 2H), 3.49-3.44 (m, 2H), 2.17 (br s, 3H), 1.86 (sextet, 2H), 1.09 (t, 3H); LC-MS (ESI) m/z 437.2 [M+H]$^+$.

EXAMPLE 122

N-(Ethylsulfonyl)-4-[2-(4-fluorophenyl)-4-oxo-1,3-thiazolidin-3-yl]-3-methylbenzamide Compound 162

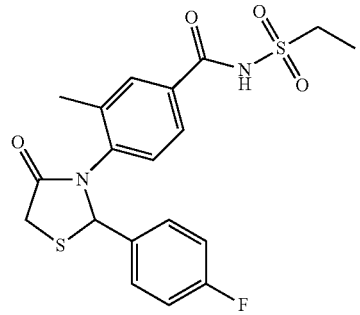

Following standard procedure C, 4-[2-(4-fluorophenyl)-4-oxo-1,3-thiazolidin-3-yl]-3-methylbenzoic acid (88.3 mg, 0.266 mmol), DMAP (81.3 mg, 0.665 mmol), EDCI • HCl (102 mg, 0.532 mmol), 1-ethanesulfonamide (34.9 mg, 0.320 mmol), and CH$_2$Cl$_2$ (5.0 mL) were used to carry out the reaction. After the reaction was stirred for 18 h and work-up, the residue was purified by Isco Combi-Flash Companion column chromatography (0-4% MeOH in CH$_2$Cl$_2$) to give N-(ethylsulfonyl)-4-[2-(4-fluorophenyl)-4-oxo-1,3-thiazolidin-3-yl]-3-methylbenzamide (99.8 mg, 89%) as a white solid. 1H NMR (CDCl$_3$, 300 MHz) δ 9.10-8.60 (br, 1H), 7.56 (br s, 1H), 7.48 (br d, 1H), 7.33-7.29 (m, 2H), 6.95 (t, 2H), 6.10-5.90 (br, 1H), 4.07-3.96 (m, 2H), 3.52 (q, 2H), 2.18 (br s, 3H), 1.39 (t, 3H); LC-MS (ESI) m/z 423.2 [M+H]$^+$.

EXAMPLE 123

N-(Butylsulfonyl)-4-[2-(4-fluorophenyl)-4-oxo-1,3-thiazolidin-3-yl]-3-methylbenzamide Compound 163

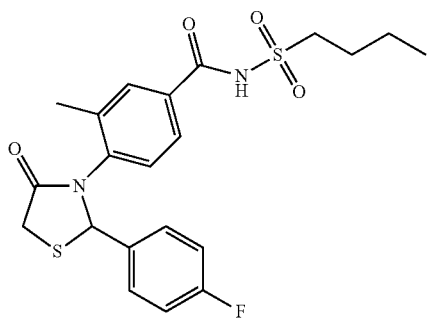

Step 1. 1-Butanesulfonamide

Compound 164

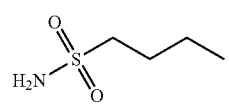

Following standard procedure D, 1-butanesulfonyl chloride (2.11 g, 13.5 mmol), methanol (10 mL), and ammonium hydroxide solution (30 mL) were used to carry out the reaction. After the reaction was stirred at 0° C. for 1 h and room temperature for 3 h, 1-butanesulfonamide (0.730 g, 39%) was obtained as a white solid. 1H NMR (CDCl$_3$, 400 MHz) δ 4.70 (br s, 2H), 3.14-3.10 (m, 2H), 1.84 (quint, 2H), 1.48 (sextet, 2H), 0.96 (t, 3H).

Step 2. N-(Butylsulfonyl)-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (83.4 mg, 0.252 mmol), DMAP (76.9 mg, 0.630 mmol), EDCI • HCl (96.6 mg, 0.504 mmol), 1-butanesulfonamide (41.4 mg, 0.302 mmol), and CH$_2$Cl$_2$ (6.0 mL) were used to carry out the reaction. After the reaction was stirred for 18 h and work-up, the residue was purified by Isco Combi-Flash Companion column chromatography (0-5% MeOH in CH$_2$Cl$_2$) to give N-(butylsulfonyl)-4-[2-(4-fluorophenyl)-4-oxo-1,3-thiazolidin-3-yl]-3-methylbenzamide (70.9 mg, 62%) as a beige solid. 1H NMR (DMSO-d$_6$, 400 MHz) δ 7.72 (br s, 1H), 7.61 (br s, 1H), 7.50-7.46 (m, 2H), 7.09 (t, 2H), 6.60-6.10 (br, 1H), 4.06 (d, 1H), 3.90 (d, 1H), 2.13 (br s, 3H), 1.62 (quint, 2H), 1.36 (sextet, 2H), 0.85 (t, 3H); LC-MS (ESI) m/z 451.2 [M+H]$^+$.

EXAMPLE 124

4-[2-(4-Fluorophenyl)-4-oxo-1,3-thiazolidin-3-yl]-3-methyl-N-(2-propanylsulfonyl)-benzamide

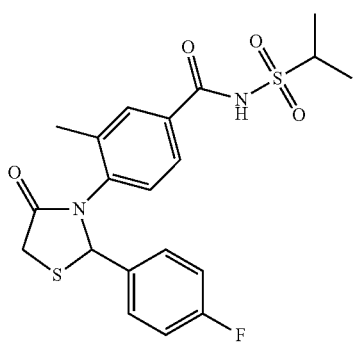

Compound 165

Step 1. 2-Propanesulfonamide

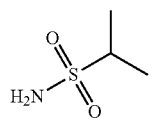

Compound 166

Following standard procedure D, 2-propanesulfonyl chloride (1.00 mL, 8.91 mmol), methanol (5.0 mL), and ammonium hydroxide solution (20 mL) were used to carry out the reaction. After the reaction was stirred at 0° C. for 1 h and room temperature for 2 h, 2-propanesulfonamide (0.260 g, 24%) was obtained as a brown solid. 1H NMR (CDCl$_3$, 400 MHz) δ 4.60-4.40 (br, 2H), 3.22 (heptet, 1H), 1.41 (d, 6H).

Step 2. 4-[2-(4-Fluorophenyl)-4-oxo-1, 3-thiazolidin-3-yl]-3-methyl-N-(2-propanylsulfonyl)-benzamide Following standard procedure C, 4-[2-(4-fluorophenyl)-4-oxo-1,3-thiazolidin-3-yl]-3-methylbenzoic acid (82.5 mg, 0.249 mmol), DMAP (76.1 mg, 0.623 mmol), EDCI • HCl (95.5 mg, 0.498 mmol), 2-propanesulfonamide (36.8 mg, 0.299 mmol), and CH$_2$Cl$_2$ (6.0 mL) were used to carry out the reaction. After the reaction was stirred for 18 h and work-up, the residue was purified by Isco Combi-Flash Companion column chromatography (0-10% MeOH in CH$_2$Cl$_2$) to give 4-[2-(4-Fluorophenyl)-4-oxo-1,3-thiazolidin-3-yl]-3-methyl-N-(2-propanylsulfonyl)benzamide (97.1 mg, 89%) as a white solid. 1H NMR (CDCl$_3$, 400 MHz) δ 9.00-8.70 (br, 1H), 7.56 (br s, 1H), 7.52 (br s, 1H), 7.33-7.29 (m, 2H), 6.95 (t, 2H), 6.20-5.80 (br, 1H), 4.05-3.88 (m, 3H), 2.17 (br s, 3H), 1.44-1.39 (m, 6H); LC-MS (ESI) m/z 437.2 [M+H]$^+$.

EXAMPLE 125

4-[2-(4-Fluorophenyl)-4-oxo-1,3-thiazolidin-3-yl]-3-methyl-N-[(2-methylpropyl)sulfonyl]benzamide

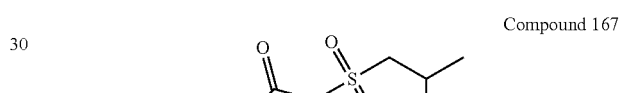

Compound 167

Step 1. 2-Methyl-propanesulfonamide

Compound 168

Following standard procedure D, isobutanesulfonyl chloride (1.00 g, 6.38 mmol), methanol (5.0 mL), and ammonium hydroxide solution (15 mL) were used to carry out the reaction. After the reaction was stirred at 0° C. for 1 h and room temperature for 2 h, 2-methyl-propanesulfonamide (0.330 g, 38%) was obtained as a colorless oil. 1H NMR (CDCl$_3$, 400 MHz) δ 4.87 (br s, 2H), 3.04 (d, 2H), 2.29 (heptet, 1H), 1.12 (d, 6H).

Step 2. 4-[2-(4-Fluorophenyl)-4-oxo-1,3-thiazolidin-3-yl]-3-methyl-N-[(2-methylpropyl)sulfonyl]benzamide Following standard procedure C, 4-[2-(4-fluorophenyl)-4-oxo-1,3-thiazolidin-3-yl]-3-methylbenzoic acid (82.7 mg,

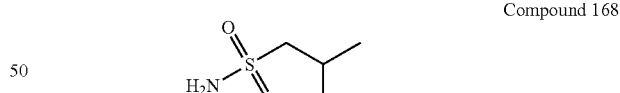

0.250 mmol), DMAP (76.4 mg, 0.625 mmol), EDCI • HCl (95.9 mg, 0.500 mmol), 2-methyl-propanesulfonamide (41.1 mg, 0.299 mmol), and CH$_2$Cl$_2$ (6.0 mL) were used to carry out the reaction. After the reaction was stirred for 18 h and work-up, the residue was purified by column chromatography (10% MeOH in CH$_2$Cl$_2$) to give 4-[2-(4-fluorophenyl)-4-oxo-1,3-thiazolidin-3-yl]-3-methyl-N-[(2-methylpropyl)sulfonyl]benzamide (29.6 mg, 26%) as a white solid. 1H NMR (DMSO-d$_6$, 400 MHz) δ 12.00 (br s, 1H), 7.74 (br s, 1H), 7.61 (br, 1H), 7.51-7.48 (m, 2H), 7.10 (t, 2H), 6.60-6.20 (br, 1H), 4.09 (d, 1H), 3.92 (d, 1H), 3.38 (d, 2H), 2.20-2.05 (m, 4H), 1.00 (d, 6H); LC-MS (ESI) m/z 451.2 [M+H]$^+$.

EXAMPLE 126

N-(Cyclopropylsulfonyl)-4-[2-(4-fluorophenyl)-4-oxo-1,3-thiazolidin-3-yl]-3-methylbenzamide

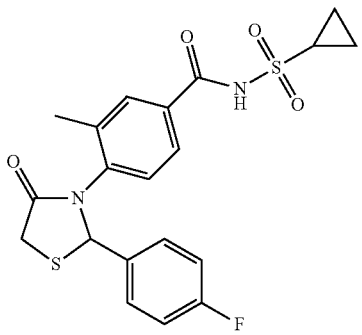

Compound 169

Step 1. Cyclopropanesulfonamide

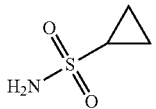

Compound 170

Following standard procedure D, cyclopropanesulfonyl chloride (0.400 mL, 3.95 mmol), methanol (3.0 mL), and ammonium hydroxide solution (15 mL) were used to carry out the reaction. After the reaction was stirred at room temperature for 16 h and work up, cyclopropanesulfonamide (0.249 g, 52%) was obtained as a white solid. 1H NMR (DMSO-d$_6$, 300 MHz) δ 6.78 (br s, 2H), 2.50-2.46 (m, 1H), 0.89-0.86 (m, 4H).

Step 2. N-(cyclopropylsulfonyl)-4-[2-(4-fluorophenyl)-4-oxo-1, 3-thiazolidin-3-yl]-3-methyl-benzamide Following standard procedure C, 4-[2-(4-fluorophenyl)-4-oxo-1,3-thiazolidin-3-yl]-3-methylbenzoic acid (72.7 mg, 0.219 mmol), DMAP (66.9 mg, 0.548 mmol), EDCI • HCl (83.9 mg, 0.438 mmol), cyclproanesulfonamide (26.6 mg, 0.219 mmol), and CH$_2$Cl$_2$ (6.0 mL) were used to carry out the reaction. After the reaction was stirred for 18 h and work-up, the residue was purified by column chromatography (0-5% MeOH in CH$_2$Cl$_2$) to give N-(cyclopropylsulfonyl)-4-[2-(4-fluorophenyl)-4-oxo-1,3-thiazolidin-3-yl]-3-methylbenzamide (50.9 mg, 53%) as a white solid. 1H NMR (CDCl$_3$, 300 MHz) δ 9.08 (br s, 1H), 7.60-7.40 (br, 2H), 7.33-7.27 (m, 2H), 6.94 (br t, 2H), 6.00 (br s, 1H), 4.05-3.94 (m, 2H), 3.06-2.98 (m, 1H), 2.16 (br s, 3H), 1.43-1.35 (br, 2H), 1.10 (d, 2H); LC-MS (ESI) m/z 435.2 [M+H]$^+$.

EXAMPLE 127

N-(Cyclohexylsulfonyl)-4-[2-(4-fluorophenyl)-4-oxo-1, 3-thiazolidin-3-yl]-3-methylbenzamide

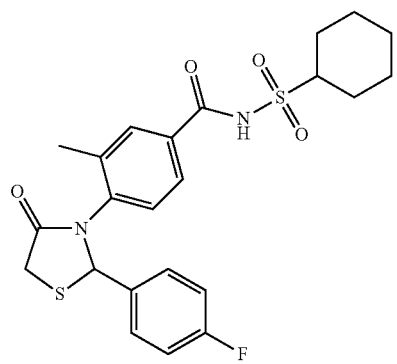

Compound 171

Step 1. Cyclohexanesulfonamide

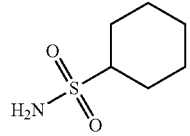

Compound 172

Following standard procedure D, 1-cyclohexanesulfonyl chloride (0.570 g, 3.12 mmol), methanol (3.0 mL), and ammonium hydroxide solution (20 mL) were used to carry out the reaction. After the reaction was stirred at room temperature for 7 h and work up, cyclohexanesulfonamide (0.143 g, 28%) was obtained as a white solid. 1H NMR (CDCl$_3$, 400 MHz) δ 4.45 (br s, 2H), 2.95-2.88 (m, 1H), 2.27-2.23 (m, 2H), 1.94-1.90 (m, 2H), 1.74-1.71 (m, 1H), 1.56-1.46 (m, 2H), 1.36-1.17 (m, 3H).

Step 2. N-(Cyclohexylsulfonyl)-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (76.9 mg, 0.232 mmol), DMAP (70.9 mg, 0.580 mmol), EDCI • HCl (88.9 mg, 0.464 mmol), cyclohexanesulfonamide (37.9 mg, 0.232 mmol), and CH$_2$Cl$_2$ (6.0 mL) were used to carry out the reaction. After the reaction was stirred for 18 h and work-up, the residue was purified by Isco Combi-Flash Companion column chromatography (0-5% MeOH in CH$_2$Cl$_2$) to give N-(cyclohexylsulfonyl)-4-[2-(4-fluorophenyl)-4-oxo-1,3-thiazolidin-3-yl]-3-methylbenzamide (62.4 mg, 56%) as a white solid. 1H NMR (CDCl$_3$, 400 MHz) δ 8.58 (br s, 1H), 7.57 (br s, 1H), 7.52 (br s, 1H), 7.31 (dd, 2H), 6.96 (br t, 2H), 6.20-5.80 (br, 1H), 4.03-3.94 (m, 2H), 3.67-3.61 (m, 1H), 2.19-2.04 (br, 5H), 1.92-1.88 (m, 2H), 1.72-1.50 (m, 3H), 1.35-1.18 (m, 3H); LC-MS (ESI) m/z 477.2 [M+H]$^+$.

EXAMPLE 128

4-[2-(4-Fluorophenyl)-4-oxo-1,3-thiazolidin-3-yl]-3-methyl-N-sulfamoylbenzamide

Compound 173

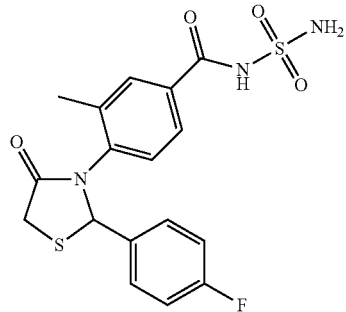

Following standard procedure C, 4-[2-(4-fluorophenyl)-4-oxo-1,3-thiazolidin-3-yl]-3-methylbenzoic acid (86.9 mg, 0.262 mmol), DMAP (48.0 mg, 0.393 mmol), EDCI • HCl (55.2 mg, 0.288 mmol), sulfamide (27.7 mg, 0.288 mmol), and CH$_2$Cl$_2$ (6.0 mL) were used to carry out the reaction. After the reaction was stirred for 20 h and work-up, the residue was purified by Isco Combi-Flash Companion column chromatography (0-3% MeOH in CH$_2$Cl$_2$) to give 4-[2-(4-fluorophenyl)-4-oxo-1,3-thiazolidin-3-yl]-3-methyl-N-sulfamoylbenzamide (18.1 mg, 17%) as a white solid. 1H NMR (CDCl$_3$, 300 MHz) δ 7.48 (br s, 1H), 7.40 (br s, 1H), 7.30 (dd, 2H), 6.94 (br t, 2H), 6.10-5.80 (br, 1H), 5.63 (br s, 2H), 4.04-3.93 (m, 2H), 2.09 (br s, 3H); LC-MS (ESI) m/z 410.2 [M+H]$^+$.

EXAMPLE 129

N-(Dimethylsulfamoyl)-4-[2-(4-fluorophenyl)-4-oxo-1,3-thiazolidin-3-yl]-3-methylbenzamide Compound 174

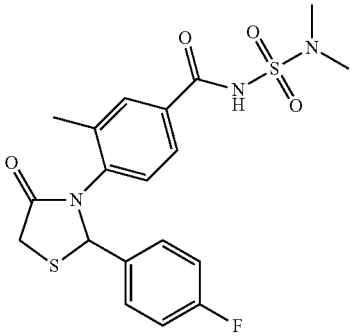

Following standard procedure C, 4-[2-(4-fluorophenyl)-4-oxo-1,3-thiazolidin-3-yl]-3-methylbenzoic acid (84.5 mg, 0.255 mmol), DMAP (62.3 mg, 0.510 mmol), EDCI • HCl (73.3 mg, 0.382 mmol), N,N-dmethylsulfamide (37.9 mg, 0.306 mmol), and CH$_2$Cl$_2$ (6.0 mL) were used to carry out the reaction. After the reaction was stirred for 18 h and work-up, the residue was purified by Isco Combi-Flash Companion column chromatography (0-20% MeOH in CH$_2$Cl$_2$) and recrystallized with CH$_2$Cl$_2$/diethyl ether to give N-(dimethylsulfamoyl)-4-[2-(4-fluorophenyl)-4-oxo-1,3-thiazolidin-3-yl]-3-methylbenzamide (58.5 mg, 52%) as a white solid. 1H NMR (DMSO-d$_6$, 400 MHz) δ 11.71 (br s, 1H), 7.73 (br s, 1H), 7.60 (br s, 1H), 7.49 (dd, 2H), 7.10 (t, 2H), 6.60-6.10 (br, 1H), 4.08 (d, 1H), 3.90 (d, 1H), 2.83 (s, 6H), 2.14 (br s, 3H); LC-MS (ESI) m/z 438.2 [M+H]$^+$.

EXAMPLE 130

4-[2-(4-Fluorophenyl)-4-oxo-1,3-thiazolidin-3-yl]-3-methyl-N-[(trifluoromethyl)sulfonyl]benzamide Compound 175

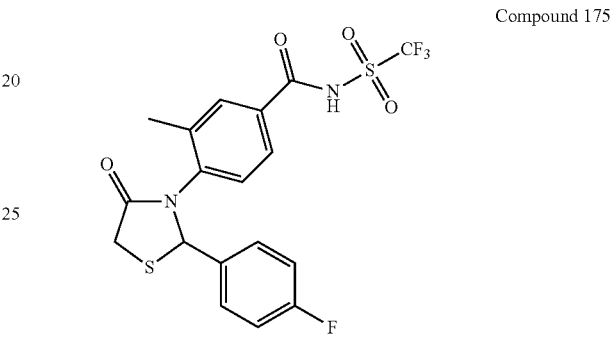

Following standard procedure C, 4-[2-(4-fluorophenyl)-4-oxo-1,3-thiazolidin-3-yl]-3-methylbenzoic acid (82.8 mg, 0.250 mmol), DMAP (76.3 mg, 0.625 mmol), EDCI • HCl (95.8 mg, 0.500 mmol), trifluoromethanesulfonamide (37.3 mg, 0.250 mmol), and CH$_2$Cl$_2$ (6.0 mL) were used to carry out the reaction. After the reaction was stirred for 16 h and work-up, the residue was purified by Isco Combi-Flash Companion column chromatography (0-5% MeOH in CH$_2$Cl$_2$) to give 4-[2-(4-fluorophenyl)-4-oxo-1,3-thiazolidin-3-yl]-3-methyl-N-[(trifluoromethyl)sulfonyl]benzamide (20.2 mg, 17%) as a white solid. 1H NMR (DMSO-d$_6$, 400 MHz) δ 7.67 (br s, 1H), 7.57 (br s, 1H), 7.48-7.45 (m, 2H), 7.09 (t, 2H), 6.60-6.10 (br, 1H), 4.08 (d, 1H), 3.90 (d, 1H), 2.06 (br s, 3H); LC-MS (ESI) m/z 463.2 [M+H]$^+$.

Example 131

N-(Benzylsulfonyl)-4-[2-(4-fluorophenyl)-4-oxo-1,3-thiazolidin-3-yl]-3-methylbenzamide Compound 176

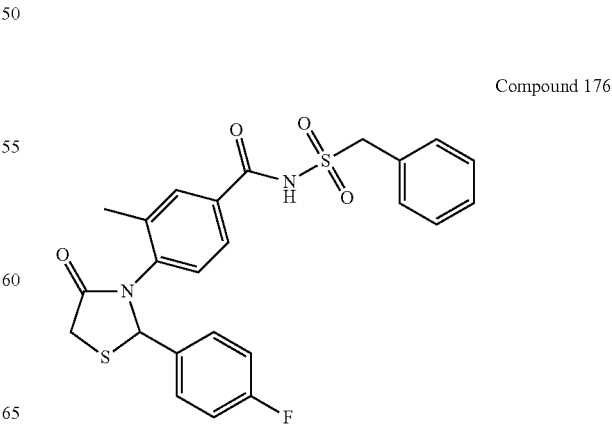

Following standard procedure C, 4-[2-(4-fluorophenyl)-4-oxo-1,3-thiazolidin-3-yl]-3-methylbenzoic acid (72.8 mg, 0.220 mmol), DMAP (67.2 mg, 0.550 mmol), EDCI • HCl (84.2 mg, 0.439 mmol), α-toluenesulfonamide (41.4 mg, 0.242 mmol), and CH$_2$Cl$_2$ (6.0 mL) were used to carry out the reaction. After the reaction was stirred for 18 h and work-up, the residue was purified by Isco Combi-Flash Companion column chromatography (0-4% MeOH in CH$_2$Cl$_2$) to give N-(benzylsulfonyl)-4-[2-(4-fluorophenyl)-4-oxo-1,3-thiazolidin-3-yl]-3-methylbenzamide (77.8 mg, 73%) as a white solid. 1H NMR (DMSO-d$_6$, 400 MHz) δ 11.93 (br s, 1H), 7.70 (br s, 1H), 7.57 (br s, 1H), 7.48 (dd, 2H), 7.34-7.27 (m, 6H), 7.10 (t, 2H), 6.60-6.10 (br, 1H), 4.79 (s, 2H), 4.08 (d, 1H), 3.91 (d, 1H), 2.12 (br s, 3H); LC-MS (ESI) m/z 485.2 [M+H]$^+$.

EXAMPLE 132

N-[(3-Fluorobenzyl)sulfonyl]-4-[2-(4-fluorophenyl)-4-oxo-1,3-thiazolidin-3-yl]-3-methylbenzamide

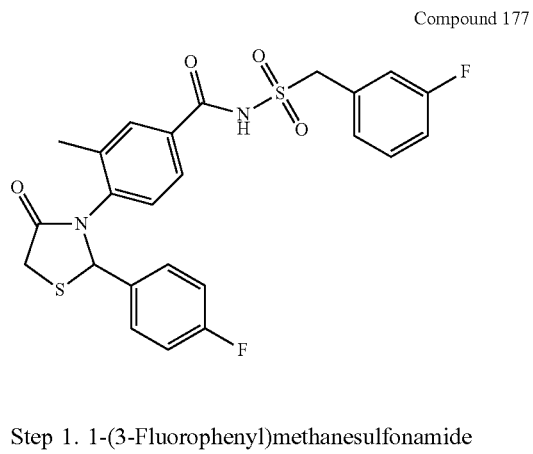

Compound 177

Step 1. 1-(3-Fluorophenyl)methanesulfonamide

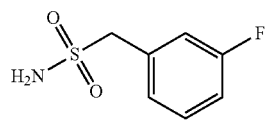

Compound 178

Following standard procedure D, 3-fluorobenzylsulfonyl chloride (0.251 mg, 1.20 mmol), methanol (1.0 mL), and ammonium hydroxide solution (5.0 mL) were used to carry out the reaction. After the reaction was stirred at room temperature for 3 h and work-up, 1-(3-fluorophenyl)methanesulfonamide (0.169 g, 74%) was obtained as a white solid. 1H NMR (CDCl$_3$, 400 MHz) δ 7.38 (dd, 1H), 7.22-7.08 (m, 3H), 4.54 (br s, 2H), 4.32 (s, 2H).

Step 2. N-[(3-Fluorobenzyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (70.8 mg, 0.214 mmol), DMAP (65.4 mg, 0.535 mmol), EDCI • HCl (82.0 mg, 0.428 mmol), 1-(3-fluorophenyl)methanesulfonamide (40.4 mg, 0.214 mmol), and CH$_2$Cl$_2$ (6.0 mL) were used to carry out the reaction. After the reaction was stirred for 18 h and work-up, the residue was purified by Isco Combi-Flash Companion column chromatography (0-10% MeOH in CH$_2$Cl$_2$) to give N-[(3-fluorobenzyl)sulfonyl]-4-[2-(4-fluorophenyl)-4-oxo-1,3-thiazolidin-3-yl]-3-methylbenzamide (84.6 mg, 79%) as a white solid. 1H NMR (DMSO-d$_6$, 300 MHz) δ 11.98 (br s, 1H), 7.69 (s, 1H), 7.57 (br d, 1H), 7.48 (dd, 2H), 7.42-7.31 (m, 1H), 7.28-7.07 (m, 6H), 6.38 (br s, 1H), 4.84 (s, 2H), 4.08 (d, 1H), 3.91 (d, 1H), 2.12 (br s, 3H); LC-MS (ESI) m/z 503.2 [M+H]$^+$.

EXAMPLE 133

N-[(3,5-Dimethylbenzyl)sulfonyl]-4-[2-(4-fluorophenyl)-4-oxo-1,3-thiazolidin-3-yl]-3-methylbenzamide

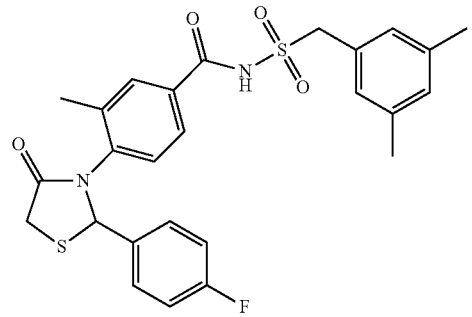

Compound 179

Step 1. Sodium (3,5-dimethylphenyl)methanesulfonate

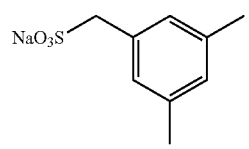

Compound 180

A solution of 3,5-dimethyl benzyl bromide (1.03 g, 5.17 mmol) and sodium sulfite (0.850 g, 0.674 mmol) in water (8.0 mL) was reflux for 18 h and cooled in ice bath. The white solid was collected by vacuum filtration and washed with cold water to give sodium (3,5-dimethylphenyl)methanesulfonate (0.890 g, 77%). 1H NMR (DMSO-d$_6$, 400 MHz) δ 6.87 (s, 2H), 6.81 (s, 1H), 3.59 (s, 2H), 2.21 (s, 6H).

Step 2. (3,5-Dimethylphenyl)methanesulfonyl chloride

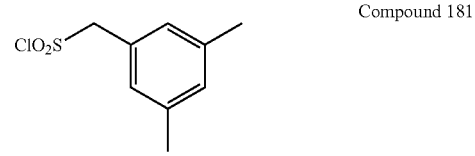

Compound 181

A solution of sodium (3,5-dimethylphenyl)methanesulfonate (0.590 g, 0.265 mmol) and phosphorus pentachloride (0.55 g, 0.265 mmol) in phosphoryl chloride (3.0 mL) was stirred at 60° C. for 6 h and cooled to room temperature. The solution was quenched with water and extracted with CH$_2$Cl$_2$. The combined organic layers were dried over MgSO$_{4(s)}$, filtered, and concentrated to give (3,5-dimethylphenyl)methanesulfonyl chloride (0.304 g, 52%) as a brown solid. 1H NMR (CDCl$_3$, 400 MHz) δ 7.10 (s, 1H), 7.08 (s, 2H), 4.80 (s, 2H), 2.35 (s, 6H).

Compound 182

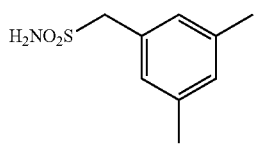

Step 3. 1-(3,5-Dimethylphenyl)methanesulfonamide

Following standard procedure D, (3,5-dimethylphenyl)methanesulfonyl chloride (0.251 g, 1.20 mmol), methanol (10 mL), and ammonium hydroxide solution (15 mL) were used to carry out the reaction. After the reaction was stirred at room temperature for 16 h and work up, 1-(3,5-dimethylphenyl)methanesulfonamide (0.121 g, 46%) was obtained as a yellow solid. 1H NMR (CDCl$_3$, 400 MHz) δ 7.03-7.01 (m, 3H), 4.50 (br s, 2H), 4.26 (s, 2H), 2.33 (s, 6H).

Step 4. N-[(3,5-Dimethylbenzyl)sulfonyl]-4-[2-(4-fluorophenyl)-4-oxo-1,3-thiazolidin-3-yl]-3-methyl-benzamide Following standard procedure C, 4-[2-(4-fluorophenyl)-4-oxo-1,3-thiazolidin-3-yl]-3-methylbenzoic acid (77.1 mg, 0.233 mmol), DMAP (56.9 mg, 0.465 mmol), EDCI • HCl (89.2 mg, 0.465 mmol), 1-(3,5-dimethylphenyl)methanesulfonamide (40.4 mg, 0.214 mmol), and CH$_2$Cl$_2$ (6.0 mL) were used to carry out the reaction. After the reaction was stirred for 18 h and work-up, the residue was purified by Isco Combi-Flash Companion column chromatography (0-10% MeOH in CH$_2$Cl$_2$) to give N-[(3,5-Dimethylbenzyl)sulfonyl]-4-[2-(4-fluorophenyl)-4-oxo-1,3-thiazolidin-3-yl]-3-methylbenzamide (59.8 mg, 50%) as a yellow solid. 1H NMR (CDCl$_3$, 400 MHz) δ 8.60 (br s, 1H), 7.55-7.39 (br, 2H), 7.31-7.25 (m, 2H), 6.98-6.90 (m, 5H), 5.94 (br s, 1H), 4.67 (d, 1H), 4.62 (d, 1H), 3.88 (s, 2H), 2.21 (s, 6H), 2.04 (br s, 3H); LC-MS (ESI) m/z 513.3 [M+H]$^+$.

EXAMPLE 134

4-[2-(4-Fluorophenyl)-4-oxo-1, 3-thiazolidin-3-yl]-3-methyl-N-(phenylsulfonyl)-benzamide Compound 183

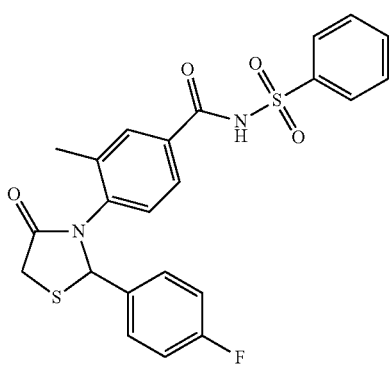

Step 1. Benzenesulfonamide

Compound 184

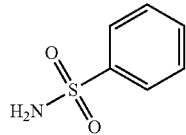

Following standard procedure D, benzenesulfonyl chloride (0.920 g, 5.21 mmol), methanol (8.0 mL), and ammonium hydroxide solution (20 mL) were used to carry out the reaction. After the reaction was stirred at room temperature for 3 h and work-up, benzenesulfonamide (0.550 g, 67%) was obtained as a white solid. 1H NMR (CDCl$_3$, 400 MHz) δ 7.93 (d, 2H), 7.62-7.51 (m, 3H), 4.81 (br s, 2H).

Step 2. 4-[2-(4-Fluorophenyl)-4-oxo-1,3-thiazolidin-3-yl]-3-methyl-N-(phenylsulfonyl)benzamide Following standard procedure C, 4-[2-(4-fluorophenyl)-4-oxo-1,3-thiazolidin-3-yl]-3-methylbenzoic acid (82.5 mg, 0.249 mmol), DMAP (76.1 mg, 0.623 mmol), EDCI • HCl (95.5 mg, 0.498 mmol), benzenesulfonamide (39.1 mg, 0.249 mmol), and CH$_2$Cl$_2$ (6.0 mL) were used to carry out the reaction. After the reaction was stirred for 18 h and work-up, the residue was purified by Isco Combi-Flash Companion column chromatography (0-5% MeOH in CH$_2$Cl$_2$) to give 4-[2-(4-fluorophenyl)-4-oxo-1,3-thiazolidin-3-yl]-3-methyl-N-(phenylsulfonyl)benzamide (91.7 mg, 83%) as a white solid. 1H NMR (DMSO-d$_6$, 400 MHz) δ 12.60-12.30 (br, 1H), 7.95 (d, 2H), 7.71-7.68 (m, 2H), 7.61 (dd, 2H), 7.58-7.52 (br, 1H), 7.47 (dd, 2H), 7.08 (t, 2H), 6.50-6.10 (br, 1H), 4.07 (d, 1H), 3.90 (d, 1H), 2.11 (br s, 3H); LC-MS (ESI) m/z 471.2 [M+H]$^+$.

EXAMPLE 135

4-[2-(4-Fluorophenyl)-4-oxo-1,3-thiazolidin-3-yl]-3-methyl-N-[(4-methylphenyl)sulfonyl]benzamide Compound 185

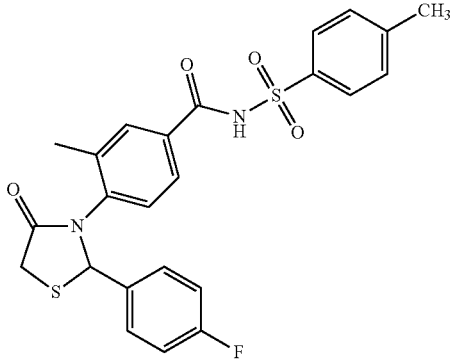

Following standard procedure C, 4-[2-(4-fluorophenyl)-4-oxo-1,3-thiazolidin-3-yl]-3-methylbenzoic acid (80.9 mg, 0.244 mmol), DMAP (74.5 mg, 0.610 mmol), EDCI • HCl (93.5 mg, 0.488 mmol), p-toluenesulfonamide (41.8 mg, 0.244 mmol), and CH$_2$Cl$_2$ (6.0 mL) were used to carry out the reaction. After the reaction was stirred for 16 h and work-up, the residue was purified by Isco Combi-Flash Companion column chromatography (0-5% MeOH in CH$_2$Cl$_2$) to give 4-[2-(4-fluorophenyl)-4-oxo-1,3-thiazolidin-3-yl]-3-methyl-N-[(4-methylphenyl)sulfonyl]benzamide (96.2 mg, 81%) as a white solid. 1H NMR (DMSO-d$_6$, 400 MHz) δ 12.38 (br s, 1H), 7.83 (d, 2H), 7.67 (br s, 1H), 7.53 (br s, 1H), 7.49-7.45 (m, 2H), 7.41 (d, 2H), 7.08 (t, 2H), 6.50-6.20 (br, 1H), 4.07 (d, 1H), 3.90 (d, 1H), 2.37 (s, 3H), 2.11 (br s, 3H); LC-MS (ESI) m/z 485.2 [M+H]$^+$.

EXAMPLE 136

N-[(4-Ethylphenyl)sulfonyl]-4-[2-(4-fluorophenyl)-4-oxo-1,3-thiazolidin-3-yl]-3-methylbenzamide Compound 186

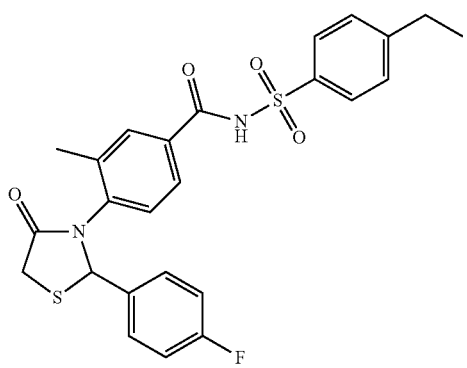

Following standard procedure C, 4-[2-(4-fluorophenyl)-4-oxo-1,3-thiazolidin-3-yl]-3-methylbenzoic acid (80.3 mg, 0.242 mmol), DMAP (73.9 mg, 0.605 mmol), EDCI • HCl (92.9 mg, 0.485 mmol), 4-ethylbenzenesulfonamide (44.9 mg, 0.242 mmol), and CH$_2$Cl$_2$ (6.0 mL) were used to carry out the reaction. After the reaction was stirred for 16 h and work-up, the residue was purified by Isco Combi-Flash Companion column chromatography (0-4% MeOH in CH$_2$Cl$_2$) to give N-[(4-ethylphenyl)sulfonyl]-4-[2-(4-fluorophenyl)-4-oxo-1,3-thiazolidin-3-yl]-3-methylbenzamide (103 mg, 85%) as a lightly yellow solid. 1H NMR (CDCl$_3$, 400 MHz) δ 9.32 (br s, 1H), 7.99 (d, 2H), 7.35-7.26 (m, 6H), 6.91 (br t, 2H), 6.20-5.80 (br, 1H), 4.05 (br s, 2H), 2.70 (q, 2H), 2.04 (br s, 3H), 1.24 (t, 3H); LC-MS (ESI) m/z 499.2 [M+H]$^+$.

EXAMPLE 137

N-[(4-Cyanophenyl)sulfonyl]-4-[2-(4-fluorophenyl)-4-oxo-1,3-thiazolidin-3-yl]-3-methylbenzamide Compound 187

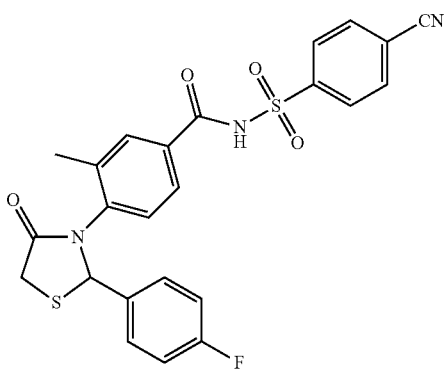

Following standard procedure C, 4-[2-(4-fluorophenyl)-4-oxo-1,3-thiazolidin-3-yl]-3-methylbenzoic acid (80.5 mg, 0.243 mmol), DMAP (74.2 mg, 0.608 mmol), EDCI • HCl (93.1 mg, 0.486 mmol), 4-cyanobenzenesulfonamide (44.3 mg, 0.243 mmol), and CH$_2$Cl$_2$ (6.0 mL) were used to carry out the reaction. After the reaction was stirred for 18 h and work-up, the residue was purified by Isco Combi-Flash Companion column chromatography (0-10% MeOH in CH$_2$Cl$_2$) to give N-[(4-cyanophenyl)sulfonyl]-4-[2-(4-fluorophenyl)-4-oxo-1,3-thiazolidin-3-yl]-3-methylbenzamide (105 mg, 87%) as a white solid. 1H NMR (DMSO-d$_6$, 400 MHz) δ 8.09 (s, 4H), 7.68 (br s, 1H), 7.55 (br d, 1H), 7.49-7.46 (m, 2H), 7.08 (t, 2H), 6.50-6.10 (br, 1H), 4.07 (d, 1H), 3.90 (d, 1H), 2.11 (br s, 3H); LC-MS (ESI) m/z 496.2 [M+H]$^+$.

EXAMPLE 138

4-[2-(4-Fluorophenyl)-4-oxo-1, 3-thiazolidin-3-yl]-N-[(4-methoxyphenyl)sulfonyl]-3-methylbenzamide Compound 188

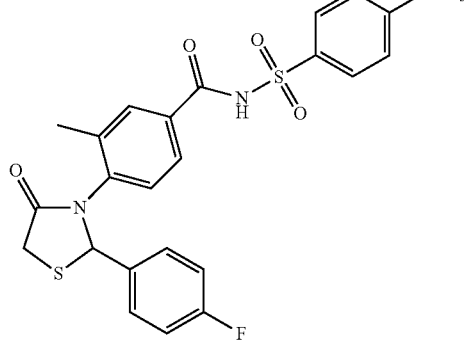

Following standard procedure C, 4-[2-(4-fluorophenyl)-4-oxo-1,3-thiazolidin-3-yl]-3-methylbenzoic acid (80.9 mg, 0.244 mmol), DMAP (74.5 mg, 0.610 mmol), EDCI • HCl (93.6 mg, 0.488 mmol), 4-methoxybenzenesulfonamide (45.7 mg, 0.244 mmol), and CH$_2$Cl$_2$ (6.0 mL) were used to carry out the reaction. After the reaction was stirred for 16 h and work-up, the residue was purified by Isco Combi-Flash Companion column chromatography (0-10% MeOH in CH$_2$Cl$_2$) to give 4-[2-(4-fluorophenyl)-4-oxo-1,3-thiazolidin-3-yl]-N-[(4-methoxyphenyl)sulfonyl]-3-methylbenzamide (116 mg, 85%) as a yellow solid. 1H NMR (DMSO-d$_6$, 300 MHz) δ 12.30 (br s, 1H), 7.87 (d, 2H), 7.66 (br s, 1H), 7.53 (br d, 1H), 7.46 (dd, 2H), 7.11-7.04 (m, 4H), 6.50-6.10 (br, 1H), 4.07 (d, 1H), 3.89 (d, 1H), 3.82 (s, 3H), 2.10 (br s, 3H); LC-MS (ESI) m/z 501.2 [M+H]$^+$.

EXAMPLE 139

4-[2-(4-Fluorophenyl)-4-oxo-1,3-thiazolidin-3-yl]-3-methyl-N-{[4-(trifluoromethoxy)phenyl]sulfonyl}benzamide

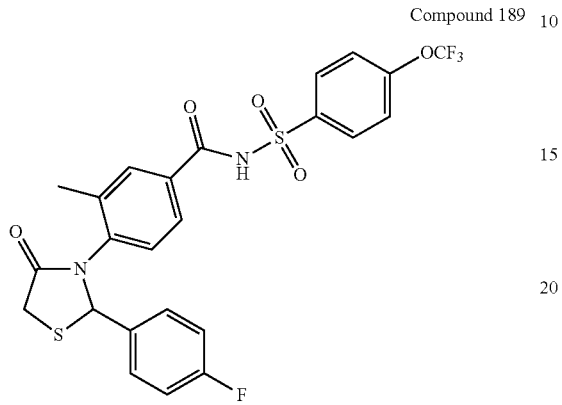

Compound 189

Following standard procedure C, 4-[2-(4-fluorophenyl)-4-oxo-1,3-thiazolidin-3-yl]-3-methylbenzoic acid (81.2 mg, 0.245 mmol), DMAP (74.8 mg, 0.613 mmol), EDCI • HCl (94.0 mg, 0.490 mmol), 4-(trifluoromethoxy)-benzenesulfonamide (59.1 mg, 0.245 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give 4-[2-(4-fluorophenyl)-4-oxo-1,3-thiazolidin-3-yl]-3-methyl-N-{[4-(trifluoromethoxy)phenyl]sulfonyl}benzamide (107 mg, 79%) as a white foam. 1H NMR (DMSO-$d_6$, 400 MHz) δ 8.08 (d, 2H), 7.69 (br s, 1H), 7.61 (d, 2H), 7.57 (br s, 1H), 7.47 (dd, 2H), 7.08 (t, 2H), 6.60-6.20 (br, 1H), 4.07 (d, 1H), 3.90 (d, 1H), 2.11 (br s, 3H); LC-MS (ESI) m/z 555.2 [M+H]$^+$.

EXAMPLE 140

Ethyl 4-({4-[2-(4-fluorophenyl)-4-oxo-1,3-thiazolidin-3-yl]-3-methylbenzoyl}sulfamoyl) benzoate

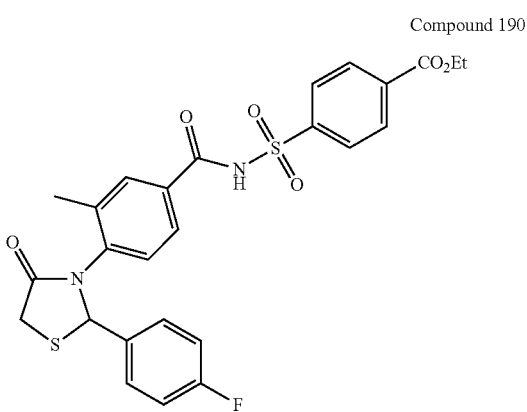 [SMILES: CCOC(=O)c1ccc(S(=O)(=O)NC(=O)c2ccc(N3C(=O)CSC3c3ccc(F)cc3)c(C)c2)cc1]

Compound 190

Step 1. Ethyl 4 sulfamoylbenzoate.

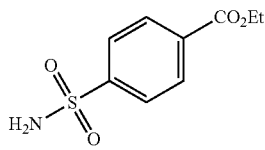

Compound 191

A solution of 4-aminosulfonylbenzoic acid (0.590 g, 0.265 mmol) in ethanol (3.0 mL) and concentrated $HCl_{(aq)}$ was reflux for 20 h and cooled to room temperature. After ethanol was removed under reduced pressure, the residue was partitioned between saturated $NaHCO_{3(aq)}$ and ethyl acetate. The organic layer was washed with brine, dried over $MgSO_{4(s)}$, filtered, and concentrated to give ethyl 4-sulfamoylbenzoate (0.304 g, 52%) as a white solid. 1H NMR ($CDCl_3$, 300 MHz) δ 8.18 (d, 2H), 7.99 (d, 2H), 4.93 (br s, 2H), 4.42 (q, 2H), 1.42 (t, 3H).

Step 2. Ethyl 4-({4-[2-(4-fluorophenyl)-4-oxo-1,3-thiazolidin-3-yl]-3-methylbenzoyl}sulfamoyl)benzoate Following standard procedure C, 4-[2-(4-fluorophenyl)-4-oxo-1,3-thiazolidin-3-yl]-3-methylbenzoic acid (71.2 mg, 0.215 mmol), DMAP (65.7 mg, 0.538 mmol), EDCI • HCl (82.4 mg, 0.430 mmol), ethyl 4-sulfamoylbenzoate (49.3 mg, 0.215 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give ethyl 4-({4-[2-(4-fluorophenyl)-4-oxo-1,3-thiazolidin-3-yl]-3-methylbenzoyl}sulfamoyl)benzoate (10.7 mg, 9%) as a white solid. 1H NMR ($CDCl_3$, 400 MHz) δ 9.80-9.30 (br, 1H), 8.15-7.80 (br, 4H), 7.60-7.20 (br, 4H), 6.90 (br s, 2H), 6.20-5.60 (br, 1H), 4.39 (q, 2H), 4.01 (br s, 2H), 2.11 (br s, 3H), 1.38 (t, 3H); LC-MS (ESI) m/z 543.2 [M+H]$^+$.

EXAMPLE 141

4-[2-(4-Fluorophenyl)-4-oxo-1, 3-thiazolidin-3-yl]-3-methyl-N-[(2,4,6-trimethylphenyl)-sulfonyl]benzamide

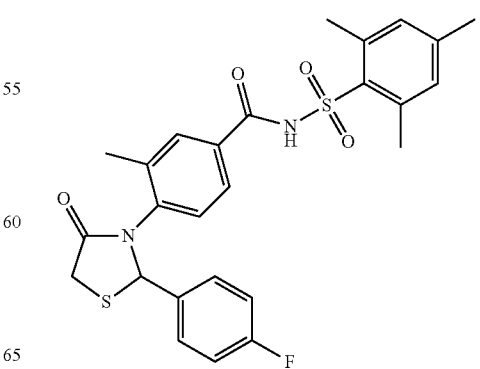

Compound 192

339

Step 1. 2,4,6-Trimethylbenzenesulfonamide

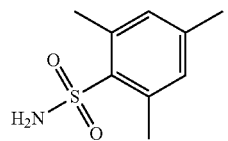

Compound 193

Following standard procedure D, 2-mesitylenesulfonyl chloride (0.890 g, 4.07 mmol), methanol (8.0 mL), and ammonium hydroxide solution (20 mL) were used to carry out the reaction. After the reaction was stirred at room temperature for 5 h and work-up, 2,4,6-trimethylbenzenesulfonamide (0.241 g, 30%) was obtained as a beige solid. 1H NMR (CDCl$_3$, 400 MHz) δ 6.96 (s, 2H), 4.81 (br s, 2H), 2.65 (s, 6H), 2.30 (s, 3H).

Step 2. 4-[2-(4-Fluorophenyl)-4-oxo-1,3-thiazolidin-3-yl]-3-methyl-N-[(2,4,6-trimethylphenyl)-sulfonyl]benzamide Following standard procedure C, 4-[2-(4-fluorophenyl)-4-oxo-1,3-thiazolidin-3-yl]-3-methylbenzoic acid (80.6 mg, 0.243 mmol), DMAP (74.2 mg, 0.608 mmol), EDCI • HCl (93.3 mg, 0.486 mmol), 2,4,6-trimethylbenzenesulfonamide (48.5 mg, 0.243 mmol), and CH$_2$Cl$_2$ (6.0 mL) were used to carry out the reaction. After the reaction was stirred for 18 h and work-up, the residue was purified by Isco Combi-Flash Companion column chromatography (0-6.5% MeOH in CH$_2$Cl$_2$) to give 4-[2-(4-fluorophenyl)-4-oxo-1,3-thiazolidin-3-yl]-3-methyl-N-[(2,4,6-trimethylphenyl)-sulfonyl]benzamide (78.2 mg, 63%) as a yellow solid. 1H NMR (CDCl$_3$, 400 MHz) δ 9.40 (br s, 1H), 7.50-7.35 (br, 2H), 7.31-7.27 (m, 2H), 7.00-6.85 (m, 4H), 6.20-5.80 (br, 1H), 4.04 (br s, 2H), 2.71 (s, 6H), 2.28 (s, 3H), 2.14 (br s, 3H); LC-MS (ESI) m/z 513.3 [M+H]$^+$.

EXAMPLE 142

4-[2-(4-Fluorophenyl)-4-oxo-1,3-thiazolidin-3-yl]-N-[(3-fluorophenyl)sulfonyl]-3-methylbenzamide

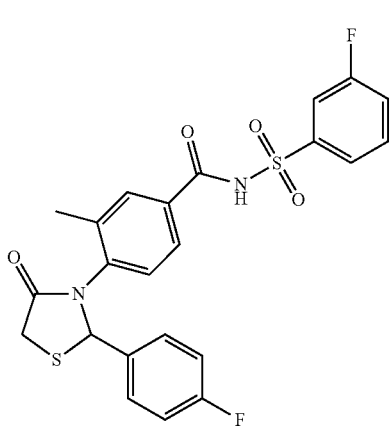

Compound 194

340

Step 1. 3-Fluorobenzenesulfonamide

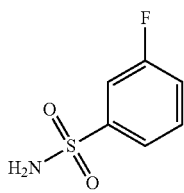

Compound 195

Following standard procedure D, 3-fluorobenzenesulfonyl chloride (0.590 g, 3.03 mmol), methanol (3.0 mL), and ammonium hydroxide solution (20 mL) were used to carry out the reaction. After the reaction was stirred at room temperature for 5 h, the solid was collected by vacuum filtration and washed with water to give 3-fluorobenzenesulfonamide (0.310 g, 58%) as a white solid. 1H NMR (CDCl$_3$, 400 MHz) δ 7.73 (d, 1H), 7.65-7.62 (m, 1H), 7.55-7.50 (m, 1H), 7.32-7.27 (m, 1H), 4.87 (br s, 2H).

Step 2. 4-[2-(4-Fluorophenyl)-4-oxo-1,3-thiazolidin-3-yl]-N-[(3-fluorophenyl)sulfonyl]-3-methylbenzamide Following standard procedure C, 4-[2-(4-fluorophenyl)-4-oxo-1,3-thiazolidin-3-yl]-3-methylbenzoic acid (78.6 mg, 0.237 mmol), DMAP (58.0 mg, 0.474 mmol), EDCI • HCl (90.9 mg, 0.474 mmol), 3-fluorobenzenesulfonamide (41.6 mg, 0.237 mmol), and CH$_2$Cl$_2$ (6.0 mL) were used to carry out the reaction. After the reaction was stirred for 18 h and work-up, the residue was purified by Isco Combi-Flash Companion column chromatography (0-10% MeOH in CH$_2$Cl$_2$) to give 4-[2-(4-fluorophenyl)-4-oxo-1,3-thiazolidin-3-yl]-N-[(3-fluorophenyl)sulfonyl]-3-methylbenzamide (82.2 mg, 71%) as a yellow solid. 1H NMR (CDCl$_3$, 400 MHz) δ 9.60-9.20 (br, 1H), 7.90 (d, 1H), 7.79 (br d, 1H), 7.54-7.50 (m, 1H), 7.50-7.26 (m, 5H), 6.92 (br t, 2H), 6.20-5.80 (br, 1H), 4.04 (br s, 2H), 2.14 (br s, 3H); LC-MS (ESI) m/z 489.2 [M+H]$^+$.

EXAMPLE 143

4-[2-(4-Fluorophenyl)-4-oxo-1,3-thiazolidin-3-yl]-N-[(4-fluorophenyl)sulfonyl]-3-methylbenzamide

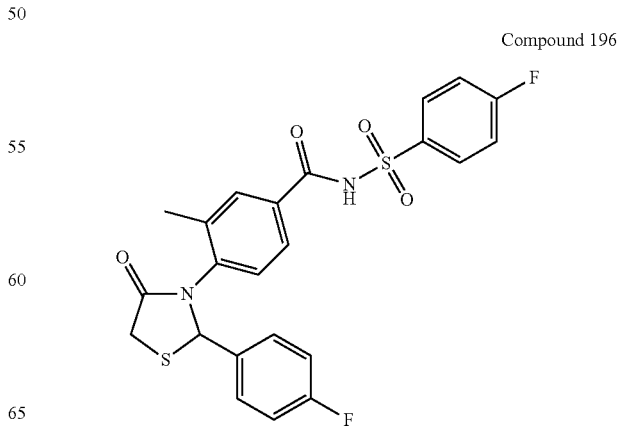

Compound 196

341

Step 1. 4-Fluorobenzenesulfonamide

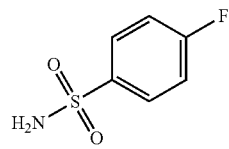

Compound 197

Following standard procedure D, 4-fluorobenzenesulfonyl chloride (0.580 g, 2.98 mmol), methanol (3.0 mL), and ammonium hydroxide solution (15 mL) were used to carry out the reaction. After the reaction was stirred at room temperature for 5 h, the solid was collected by vacuum filtration and washed with water to give 4-fluorobenzenesulfonamide (0.390 g, 75%) as a white solid. 1H NMR (DMSO-$d_6$, 400 MHz) δ 7.88-7.84 (m, 2H), 7.43-7.38 (m, 4H).

Step 2. 4-[2-(4-Fluorophenyl)-4-oxo-1,3-thiazolidin-3-yl]-N-[(4-fluorophenyl)sulfonyl]-3-methylbenzamide Following standard procedure C, 4-[2-(4-fluorophenyl)-4-oxo-1,3-thiazolidin-3-yl]-3-methylbenzoic acid (75.8 mg, 0.229 mmol), DMAP (69.9 mg, 0.573 mmol), EDCI • HCl (87.7 mg, 0.458 mmol), 4-fluorobenzenesulfonamide (40.1 mg, 0.229 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give 4-[2-(4-fluorophenyl)-4-oxo-1,3-thiazolidin-3-yl]-N-[(4-fluorophenyl)sulfonyl]-3-methylbenzamide (71.5 mg, 64%) as a white solid. 1H NMR (CDCl$_3$, 400 MHz) δ 9.30 (br s, 1H), 8.12 (dd, 2H), 7.43 (br s, 2H), 7.30-7.26 (m, 2H), 7.19 (t, 2H), 6.92 (br t, 2H), 6.20-5.70 (br, 1H), 4.03 (s, 2H), 2.13 (br s, 3H); LC-MS (ESI) m/z 489.2 [M+H]$^+$.

EXAMPLE 144

N-[(4-Chlorophenyl)sulfonyl]-4-[2-(4-fluorophenyl)-4-oxo-1,3-thiazolidin-3-yl]-3-methylbenzamide

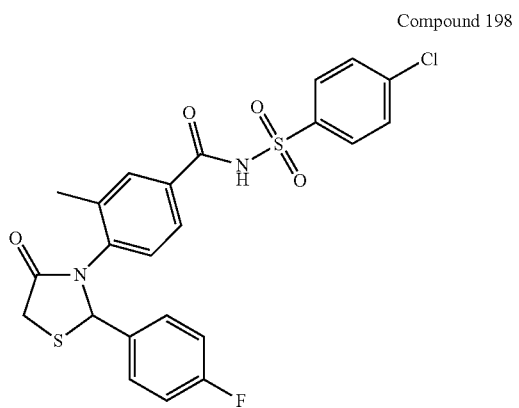 [SMILES: Cc1cc(C(=O)NS(=O)(=O)c2ccc(Br)cc2)ccc1N1C(=O)CSC1c1ccc(F)cc1]

Compound 198

342

Step 1. 4-Chlorobenzenesulfonamide

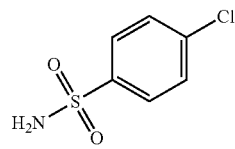

Compound 199

Following standard procedure D, 4-chlorobenzenesulfonyl chloride (0.650 g, 3.08 mmol), methanol (3.0 mL), and ammonium hydroxide solution (15 mL) were used to carry out the reaction. After the reaction was stirred at room temperature for 16 h, the solid was collected by vacuum filtration and washed with water to give 4-chlorobenzenesulfonamide (0.430 g, 73%) as a white solid. 1H NMR (DMSO-$d_6$, 400 MHz) δ 7.81 (d, 2H), 7.65 (d, 2H), 7.48 (br s, 2H).

Step 2. N-[(4-Chlorophenyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (75.9 mg, 0.229 mmol), DMAP (69.9 mg, 0.573 mmol), EDCI • HCl (87.8 mg, 0.458 mmol), 4-chlorobenzenesulfonamide (43.9 mg, 0.229 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give N-[(4-chlorophenyl)sulfonyl]-4-[2-(4-fluorophenyl)-4-oxo-1,3-thiazolidin-3-yl]-3-methylbenzamide (88.5 mg, 77%) as a white solid. 1H NMR (CDCl$_3$, 400 MHz) δ 9.39 (br s, 1H), 8.03 (d, 2H), 7.49 (d, 2H), 7.42 (br s, 2H), 7.30-7.26 (m, 2H), 6.92 (br t, 2H), 6.20-5.70 (br, 1H), 4.03 (br s, 2H), 2.13 (br s, 3H); LC-MS (ESI) m/z 505.2 [M+H]$^+$.

EXAMPLE 145

N-[(4-Bromophenyl)sulfonyl]-4-[2-(4-fluorophenyl)-4-oxo-1,3-thiazolidin-3-yl]-3-methylbenzamide

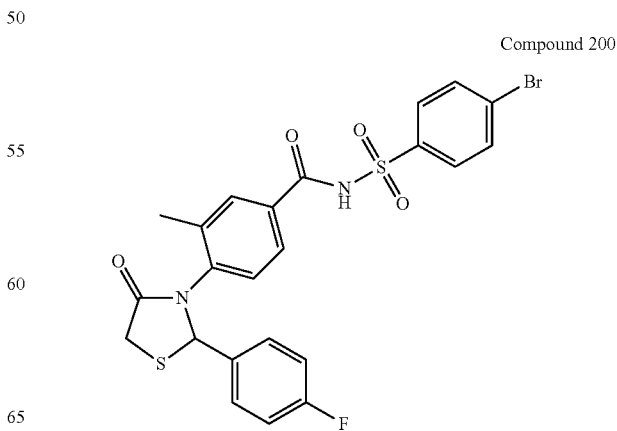

Compound 200

343

Step 1. 4-Bromobenzenesulfonamide

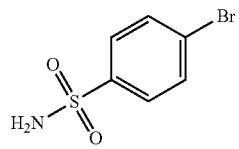

Compound 201

Following standard procedure D, 4-bromobenzenesulfonyl chloride (0.650 g, 2.54 mmol), methanol (5.0 mL), and ammonium hydroxide solution (20 mL) were used to carry out the reaction. After the reaction was stirred at room temperature for 16 h and work-up, 4-bromobenzenesulfonamide (0.370 g, 62%) was obtained as a white solid. 1H NMR (DMSO-$d_6$, 300 MHz) δ 7.79 (d, 2H), 7.73 (d, 2H), 7.46 (br s, 2H).

Step 2. N-[(4-Bromophenyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (76.8 mg, 0.232 mmol), DMAP (70.9 mg, 0.580 mmol), EDCI • HCl (88.9 mg, 0.464 mmol), 4-bromobenzenesulfonamide (54.7 mg, 0.232 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give N-[(4-bromophenyl)sulfonyl]-4-[2-(4-fluorophenyl)-4-oxo-1,3-thiazolidin-3-yl]-3-methylbenzamide (87.1 mg, 68%) as a white solid. 1H NMR (CDCl$_3$, 300 MHz) δ 9.44 (br s, 1H), 7.95 (d, 2H), 7.66 (d, 2H), 7.40 (br s, 2H), 7.31-7.26 (m, 2H), 6.92 (br t, 2H), 6.20-5.80 (br, 1H), 4.04 (br s, 2H), 2.12 (br s, 3H); LC-MS (ESI) m/z 549.1 [M+H]$^+$.

EXAMPLE 146

N-{[4-(Acetylamino)phenyl]sulfonyl}-4-[2-(4-fluorophenyl)-4-oxo-1,3-thiazolidin-3-yl]-3-methylbenzamide

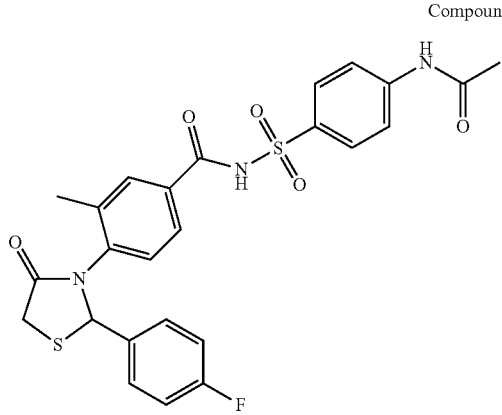

Compound 202

344

Step 1. N-(4-Sulfamoylphenyl)acetamide

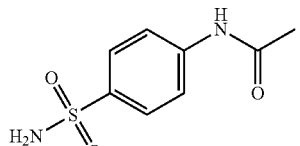

Compound 203

Following standard procedure D, N-acetylsulfanilyl chloride (0.651 g, 2.79 mmol), methanol (5.0 mL), and ammonium hydroxide solution (20 mL) were used to carry out the reaction. After the reaction was stirred at room temperature for 5 h and work-up, N-(4-sulfamoylphenyl)acetamide (0.340 g, 57%) was obtained as a white solid. 1H NMR (CDCl$_3$+CD$_3$OD, 400 MHz) δ 7.78 (d, 2H), 7.65 (d, 2H), 2.12 (s, 3H).

Step 2. N-{[4-(Acetylamino)phenyl]sulfonyl}-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (80.1 mg, 0.242 mmol), DMAP (73.9 mg, 0.605 mmol), EDCI • HCl (92.8 mg, 0.484 mmol), N-(4-sulfamoylphenyl)acetamide (51.8 mg, 0.242 mmol), and $CH_2Cl_2$ (6.0 mL) were used to carry out the reaction. After the reaction was stirred for 18 h and work-up, the residue was purified by Isco Combi-Flash Companion column chromatography (0-5% MeOH in $CH_2Cl_2$) to give N-{[4-(acetylamino)phenyl]sulfonyl}-4-[2-(4-fluorophenyl)-4-oxo-1,3-thiazolidin-3-yl]-3-methylbenzamide (51.1 mg, 40%) as a white solid. 1H NMR (DMSO-$d_6$, 300 MHz) δ 12.36 (br s, 1H), 10.39 (br s, 1H), 7.87 (d, 2H), 7.75 (d, 2H), 7.66 (br s, 1H), 7.52 (br d, 1H), 7.46 (dd, 2H), 7.08 (t, 2H), 6.40 (br s, 1H), 4.07 (d, 1H), 3.89 (d, 1H), 2.20-2.00 (m, 6H); LC-MS (ESI) m/z 528.2 [M+H]$^+$.

EXAMPLE 147

N-[(4-Chloro-2-fluorophenyl)sulfonyl]-4-[2-(4-fluorophenyl)-4-oxo-1,3-thiazolidin-3-yl]-3-methylbenzamide

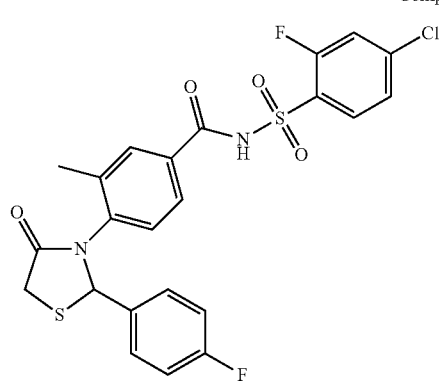

Compound 204

345

Step 1. 4-Chloro-2-fluorobenzenesulfonamide

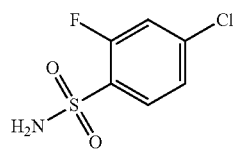

Compound 205

Following standard procedure D, 4-chloro-2-fluorobenzenesulfonyl chloride (0.450 g, 1.96 mmol), methanol (2.0 mL), and ammonium hydroxide solution (10 mL) were used to carry out the reaction. After the reaction was stirred at room temperature for 16 h and work-up, 4-chloro-2-fluorobenzenesulfonamide (0.360 g, 88%) was obtained as a white solid. 1H NMR (CDCl$_3$+CD$_3$OD, 400 MHz) δ 7.78 (t, 1H), 7.22 (d, 2H).

Step 2. N-[(4-Chloro-2-fluorophenyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (72.3 mg, 0.218 mmol), DMAP (66.6 mg, 0.545 mmol), EDCI • HCl (83.7 mg, 0.436 mmol), 4-chloro-2-fluorobenzenesulfonamide (45.7 mg, 0.218 mmol), and CH$_2$Cl$_2$ (6.0 mL) were used to carry out the reaction. After the reaction was stirred for 18 h and work-up, the residue was purified by Isco Combi-Flash Companion column chromatography (0-5% MeOH in CH$_2$Cl$_2$) to give N-[(4-chloro-2-fluorophenyl) sulfonyl]-4-[2-(4-fluorophenyl)-4-oxo-1,3-thiazolidin-3-yl]-3-methylbenzamide (77.4 mg, 68%) as a beige solid. 1H NMR (CDCl$_3$, 300 MHz) δ 8.07 (t, 1H), 7.51 (br s, 1H), 7.43 (br d, 1H), 7.34-7.26 (m, 3H), 7.20 (d, 1H), 6.94 (br t, 2H), 6.10-5.80 (br, 1H), 4.10-3.90 (m, 2H), 2.14 (br s, 3H); LC-MS (ESI) m/z 523.2 [M+H]$^+$.

EXAMPLE 148

N-[(2,4-Difluorophenyl)sulfonyl]-4-[2-(4-fluorophenyl)-4-oxo-1,3-thiazolidin-3-yl]-3-methylbenzamide

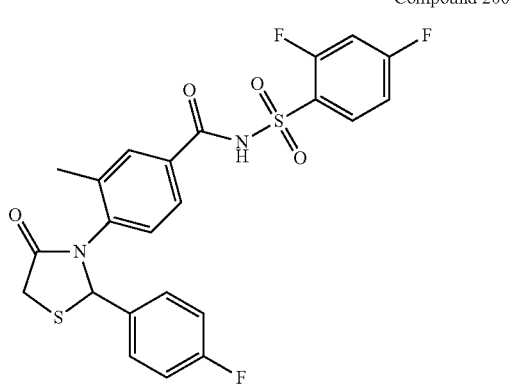

Compound 206

346

Step 1. 2,4-Difluorobenzenesulfonamide

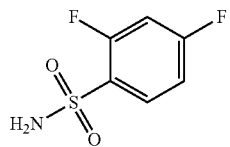

Compound 207

Following standard procedure D, 2,4-difluorobenzenesulfonyl chloride (0.470 g, 2.21 mmol), methanol (3.0 mL), and ammonium hydroxide solution (20 mL) were used to carry out the reaction. After the reaction was stirred at room temperature for 16 h, methanol was removed under reduce pressure. The solid was collected by vacuum filtration and washed with water to give 2,4-difluorobenzenesulfonamide (0.390 g, 91%) as a white solid. 1H NMR (DMSO-d$_6$, 300 MHz) δ 7.88-7.82 (m, 1H), 7.70 (br s, 2H), 7.54-7.47 (m, 1H), 7.28-7.21 (m, 1H).

Step 2. N-[(2,4-Difluorophenyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (81.6 mg, 0.247 mmol), DMAP (75.4 mg, 0.618 mmol), EDCI • HCl (94.6 mg, 0.494 mmol), 2,4-difluorobenzenesulfonamide (47.7 mg, 0.247 mmol), and CH$_2$Cl$_2$ (6.0 mL) were used to carry out the reaction. After the reaction was stirred for 16 h and work-up, the residue was purified by Isco Combi-Flash Companion column chromatography (0-6% MeOH in CH$_2$Cl$_2$) to give N-[(2,4-difluorophenyl) sulfonyl]-4-[2-(4-fluorophenyl)-4-oxo-1,3-thiazolidin-3-yl]-3-methylbenzamide (73.7 mg, 59%) as a white solid. 1H NMR (DMSO-d$_6$, 400 MHz) δ 8.04-7.99 (m, 1H), 7.69 (br s, 1H), 7.56 (br d, 1H), 7.49-7.45 (m, 3H), 7.38-7.31 (m, 1H), 7.08 (t, 2H), 6.60-6.20 (br, 1H), 4.07 (d, 1H), 3.90 (d, 1H), 2.11 (br s, 3H); LC-MS (ESI) m/z 507.2 [M+H]$^+$.

EXAMPLE 149

N-[(4-Chloro-2,5-dimethylphenyl)sulfonyl]-4-[2-(4-fluorophenyl)-4-oxo-1,3-thiazolidin-3-yl]-3-methylbenzamide

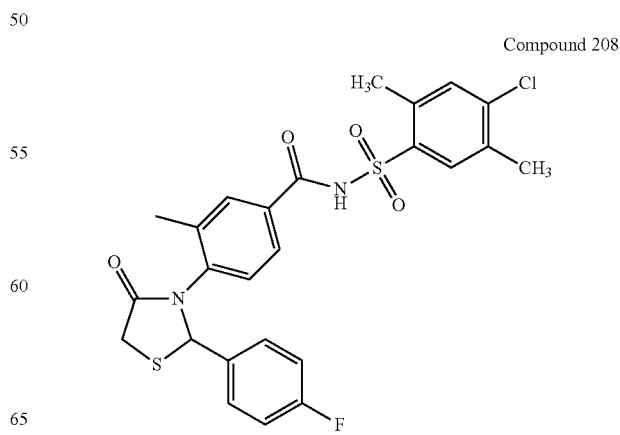

Compound 208

347

Step 1. 4-Chloro-2,5-dimethylbenzenesulfonamide

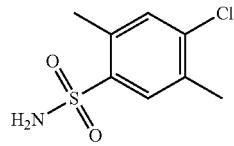

Compound 209

Following standard procedure D, 4-chloro-2,5-dimethyl-benzenesulfonyl chloride (0.620 g, 2.59 mmol), methanol (3.0 mL), and ammonium hydroxide solution (15 mL) were used to carry out the reaction. After the reaction was stirred at room temperature for 16 h, methanol was removed under reduce pressure. The solid was collected by vacuum filtration and washed with water to give 4-chloro-2,5-dimethyl-benzenesulfonamide (0.366 g, 64%) as a white solid. 1H NMR (DMSO-$d_6$, 300 MHz) δ 7.76 (s, 1H), 7.45 (s, 1H), 7.42 (br s, 2H), 2.50 (s, 3H), 2.32 (s, 3H).

Step 2. N-[(4-Chloro-2,5-dimethylphenyl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid (75.8 mg, 0.229 mmol), DMAP (69.9 mg, 0.573 mmol), EDCI • HCl (87.8 mg, 0.458 mmol), 4-chloro-2,5-dimethylbenzenesulfonamide (50.3 mg, 0.229 mmol), and CH$_2$Cl$_2$ (6.0 mL) were used to carry out the reaction. After the reaction was stirred for 18 h and work-up, the residue was purified by Isco Combi-Flash Companion column chromatography (0-5% MeOH in CH$_2$Cl$_2$) to give N-[(4-chloro-2,5-dimethylphenyl)sulfonyl]-4-[2-(4-fluorophenyl)-4-oxo-1,3-thiazolidin-3-yl]-3-methylbenzamide (86.7 mg, 71%) as a white solid. 1H NMR (CDCl$_3$, 300 MHz) δ 9.48 (br s, 1H), 8.05 (s, 1H), 7.50-7.38 (br, 2H), 7.32-7.24 (m, 3H), 6.90 (br t, 2H), 6.20-5.80 (br, 1H), 4.03 (br s, 2H), 2.57 (s, 3H), 2.40 (s, 3H), 2.15 (br s, 3H); LC-MS (ESI) m/z 533.2 [M+H]$^+$.

EXAMPLE 150

N-{[5-(Dimethylamino)-1-naphthalenyl]sulfonyl}-4-[2-(4-fluorophenyl)-4-oxo-1,3-thiazolidin-3-yl]-3-methylbenzamide Compound 210

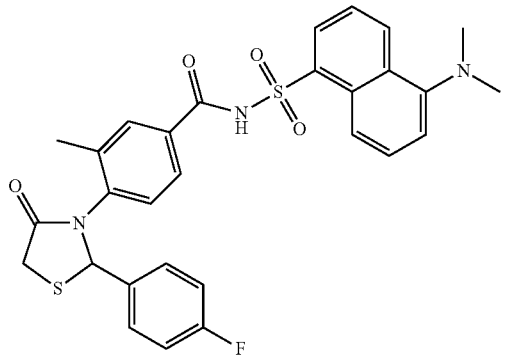

348

Following standard procedure C, 4-[2-(4-fluorophenyl)-4-oxo-1,3-thiazolidin-3-yl]-3-methylbenzoic acid (78.6 mg, 0.237 mmol), DMAP (72.4 mg, 0.593 mmol), EDCI • HCl (90.9 mg, 0.474 mmol), 1-(dimethylamino)-5-naphthalene sulfonamide (54.9 mg, 0.237 mmol), and CH$_2$Cl$_2$ (6.0 mL) were used to carry out the reaction. After the reaction was stirred for 20 h and work-up, the residue was purified by Isco Combi-Flash Companion column chromatography (0-10% MeOH in CH$_2$Cl$_2$) to give N-{[5-(dimethylamino)-1-naphthalenyl]sulfonyl}-4-[2-(4-fluorophenyl)-4-oxo-1,3-thiazolidin-3-yl]-3-methylbenzamide (63.6 mg, 48%) as a yellow solid. 1H NMR (CDCl$_3$, 300 MHz) δ 10.00-9.40 (br, 1H), 8.53 (br s, 2H), 8.40-8.23 (br, 1H), 7.70-7.30 (br, 3H), 7.30-7.20 (br, 2H), 7.12 (br d, 1H), 7.00-6.60 (br, 4H), 6.20-5.70 (br, 1H), 4.05 (br s, 2H), 2.84 (s, 6H), 2.09 (br s, 3H); LC-MS (ESI) m/z 564.3 [M+H]$^+$.

EXAMPLE 151

4-[2-(4-Fluorophenyl)-4-oxo-1,3-thiazolidin-3-yl]-3-methyl-N-(3-pyridinylsulfonyl)-benzamide Compound 211

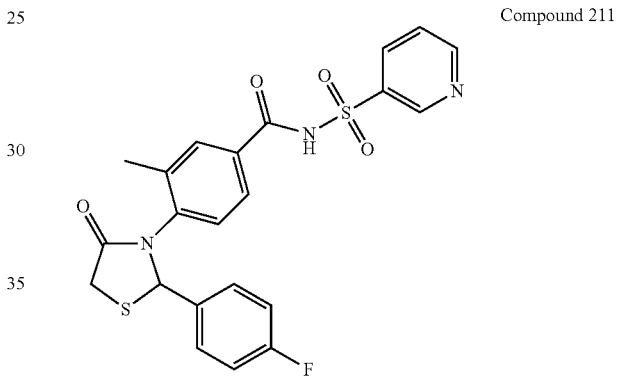

Step 1. 3-Pyridinesulfonamide

Compound 212

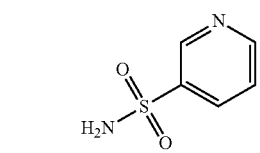

Following standard procedure D, pyridine-3-sulfonyl chloride (0.450 g, 2.53 mmol), methanol (3.0 mL), and ammonium hydroxide solution (15 mL) were used to carry out the reaction. After the reaction was stirred at room temperature for 20 h and work-up, 3-pyridinesulfonamide (35.7 mg, 9%) was obtained as a green solid. 1H NMR (DMSO-$d_6$, 400 MHz) δ 8.96 (s, 1H), 8.78 (d, 1H), 8.19-8.16 (m, 1H), 7.64-7.60 (m, 3H).

Step 2. 4-[2-(4-Fluorophenyl)-4-oxo-1,3-thiazolidin-3-yl]-3-methyl-N-(3-pyridinylsulfonyl)-benzamide Following standard procedure C, 4-[2-(4-fluorophenyl)-4-oxo-1,3-thiazolidin-3-yl]-3-methylbenzoic acid (70.2 mg, 0.212 mmol), DMAP (64.8 mg, 0.530 mmol), EDCI • HCl (81.3 mg, 0.424 mmol), 3-pyridinesulfonamide (33.5 mg, 0.212 mmol), and CH₂Cl₂ (6.0 mL) were used to carry out the reaction. After the reaction was stirred for 20 h and work-up, the residue was purified by Isco Combi-Flash Companion column chromatography (0-5% MeOH in CH₂Cl₂) to give 4-[2-(4-fluorophenyl)-4-oxo-1,3-thiazolidin-3-yl]-3-methyl-N-(3-pyridinylsulfonyl)-benzamide (64.3 mg, 64%) as a white solid. 1H NMR (DMSO-$d_6$, 400 MHz) δ 9.07 (d, 1H), 8.85 (d, 1H), 8.32 (dd, 1H), 7.68 (br s, 1H), 7.66 (dd, 1H), 7.55 (br d, 1H), 7.47 (dd, 2H), 7.08 (t, 2H), 6.50-6.10 (br, 1H), 4.07 (d, 1H), 3.90 (d, 1H), 2.11 (br s, 3H); LC-MS (ESI) m/z 472.2 [M+H]⁺.

EXAMPLE 152

N-[(3, 5-Dimethyl-1, 2-oxazol-4-yl)sulfonyl]-4-[2-(4-fluorophenyl)-4-oxo-1,3-thiazolidin-3-yl]-3-methylbenzamide Compound 213

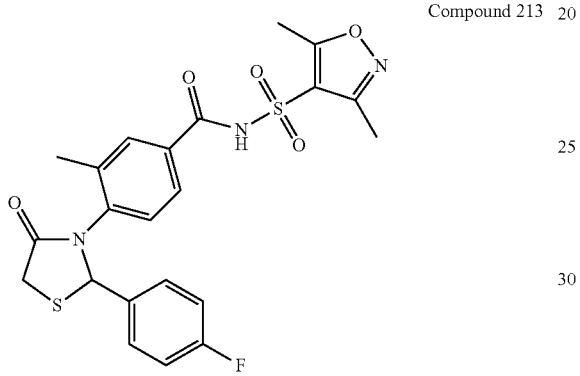

Step 1. 3,5-Dimethyl-1,2-oxazole-4-sulfonamide

Compound 214

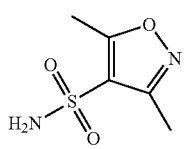

Following standard procedure D, 3,5-dimethylisoxazole-4-sulfonyl chloride (0.399 g, 2.04 mmol), methanol (3.0 mL), and ammonium hydroxide solution (12 mL) were used to carry out the reaction. After the reaction was stirred at room temperature for 16 h, methanol was removed under reduce pressure. The solid was collected by vacuum filtration and washed with water to give 3,5-dimethyl-1,2-oxazole-4-sulfonamide (0.271 g, 75%) as a white solid. 1H NMR (DMSO-$d_6$, 400 MHz) δ 7.60 (br s, 2H), 2.54 (s, 3H), 2.32 (s, 3H).

Step 2. N-[(3,5-dimethyl-1,2-oxazol-4-yl)sulfonyl]-4-[2-(4-fluorophenyl)-4-oxo-1,3-thiazolidin-3-yl]-3-methylbenzamide Following standard procedure C, 4-[2-(4-fluorophenyl)-4-oxo-1,3-thiazolidin-3-yl]-3-methylbenzoic acid 0 (80.9 mg, 0.244 mmol), DMAP (74.5 mg, 0.610 mmol), EDCI • HCl (93.6 mg, 0.488 mmol), 3,5-dimethyl-1,2-oxazole-4-sulfonamide (43.0 mg, 0.244 mmol), and CH₂Cl₂ (6.0 mL) were used to carry out the reaction. After the reaction was stirred for 20 h and work-up, the residue was purified by Isco Combi-Flash Companion column chromatography (0-5% MeOH in CH₂Cl₂) to give N-[(3,5-dimethyl-1,2-oxazol-4-yl)sulfonyl]-4-[2-(4-fluorophenyl)-4-oxo-1,3-thiazolidin-3-yl]-3-methylbenzamide (92.2 mg, 77%) as a white solid. 1H NMR (CDCl₃, 400 MHz) δ 9.70-9.50 (br, 1H), 7.50-7.30 (br, 2H), 7.30 (dd, 2H), 6.94 (br t, 2H), 6.20-5.80 (br, 1H), 4.10-3.95 (m, 2H), 2.76 (s, 3H), 2.44 (s, 3H), 2.17 (br s, 3H); LC-MS (ESI) m/z 490.2 [M+H]⁺.

EXAMPLE 153

N-Ethoxy-4-[2-(4-fluorophenyl)-4-oxo-1,3-thiazolidin-3-yl]-3-methylbenzamide

Compound 215

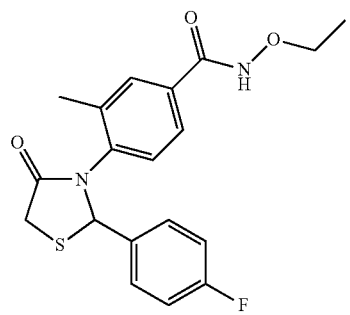

Following standard procedure E, 4-[2-(4-fluorophenyl)-4-oxo-1,3-thiazolidin-3-yl]-3-methylbenzoic acid (89.7 mg, 0.271 mmol), triethylamine (46.0 μL, 0.332 mmol), ethyl chloroformate (35.3 mg, 0.325 mmol), CH₂Cl₂ (4.0 mL), potassium hydroxide (23.0 mg, 0.332 mmol), O-ethylhydroxylamine hydrochloride (40.0 mg, 0.410 mmol), and methanol (4.0 mL) were used to carry out the reaction. It was stirred for 1 h for the first step and 5 h for the second step. The residue was purified by Isco Combi-Flash Companion column chromatography (0-80% ethyl acetate in n-hexane) to give N-ethoxy-4-[2-(4-fluorophenyl)-4-oxo-1,3-thiazolidin-3-yl]-3-methylbenzamide (46.3 mg, 46%) as a white solid. 1H NMR (CDCl₃, 400 MHz) δ 8.80-8.40 (br, 1H), 7.52 (br s, 1H), 7.40 (br s, 1H), 7.30 (dd, 2H), 6.96 (br t, 2H), 6.20-5.70 (br, 1H), 4.04 (q, 2H), 4.00 (d, 1H), 3.92 (d, 1H), 2.17 (br s, 3H), 1.30 (t, 3H); LC-MS (ESI) m/z 375.2 [M+H]⁺.

EXAMPLE 154

4-[2-(4-Fluorophenyl)-4-oxo-1,3-thiazolidin-3-yl]-N-methoxy-3-methylbenzamide

Compound 216

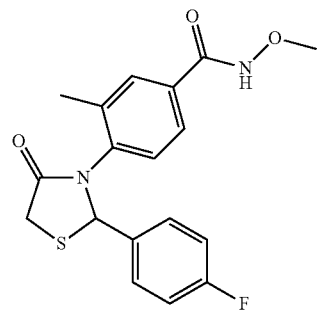

Following standard procedure E, 4-[2-(4-fluorophenyl)-4-oxo-1,3-thiazolidin-3-yl]-3-methylbenzoic acid (90.5 mg, 0.273 mmol), triethylamine (46.0 µL, 0.332 mmol), ethyl chloroformate (35.6 mg, 0.328 mmol), CH$_2$Cl$_2$ (4.0 mL), potassium hydroxide (23.0 mg, 0.332 mmol), O-methylhydroxylamine hydrochloride (34.2 mg, 0.410 mmol), and methanol (7.0 mL) were used to carry out the reaction. It was stirred for 1 h for the first step and 6 h for the second step. The residue was purified by Isco Combi-Flash Companion column chromatography (0-4% MeOH in CH$_2$Cl$_2$) to give 4-[2-(4-fluorophenyl)-4-oxo-1,3-thiazolidin-3-yl]-N-methoxy-3-methylbenzamide (66.3 mg, 67%) as a lightly yellow solid. 1H NMR (CDCl$_3$, 300 MHz) δ 8.85 (br s, 1H), 7.51 (br s, 1H), 7.37 (br s, 1H), 7.33-7.27 (m, 2H), 6.95 (t, 2H), 5.91 (br s, 1H), 4.01 (d, 1H), 3.92 (d, 1H), 3.83 (s, 3H), 2.14 (br s, 3H); LC-MS (ESI) m/z 361.2 [M+H]$^+$.

EXAMPLE 155

N-(Benzyloxy)-4-[2-(4-fluorophenyl)-4-oxo-1,3-thiazolidin-3-yl]-3-methylbenzamide Compound 217

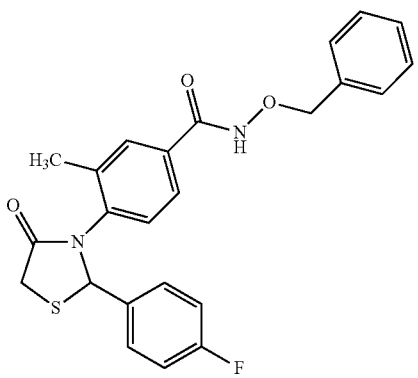

Following standard procedure E, 4-[2-(4-fluorophenyl)-4-oxo-1,3-thiazolidin-3-yl]-3-methylbenzoic acid (82.6 mg, 0.249 mmol), triethylamine (42.0 µL, 0.302 mmol), ethyl chloroformate (32.5 mg, 0.299 mmol), CH$_2$Cl$_2$ (5.0 mL), potassium hydroxide (15.4 mg, 0.274 mmol), O-benzylhydroxylamine hydrochloride (43.7 mg, 0.274 mmol), and methanol (8.0 mL) were used to carry out the reaction. It was stirred for 45 min for the first step and 6 h for the second step. The residue was purified by Isco Combi-Flash Companion column chromatography (0-60% ethyl acetate in n-hexane) to give N-(benzyloxy)-4-[2-(4-fluorophenyl)-4-oxo-1,3-thiazolidin-3-yl]-3-methylbenzamide (71.2 mg, 66%) as a white solid. 1H NMR (CDCl$_3$, 400 MHz) δ 8.40 (br s, 1H), 7.50-7.35 (m, 6H), 7.33-7.20 (m, 3H), 6.95 (br t, 2H), 6.10-5.70 (br, 1H), 5.12 (s, 2H), 3.99 (d, 1H), 3.90 (d, 1H), 2.17 (br s, 3H); LC-MS (ESI) m/z 437.3 [M+H]$^+$.

EXAMPLE 156

4-[2-(4-Fluorophenyl)-4-oxo-1,3-thiazolidin-3-yl]-3-methyl-N-phenoxybenzamide

Compound 218

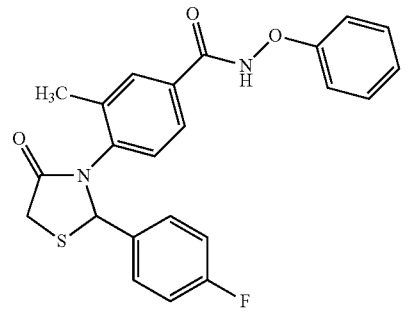

A solution of 4-[2-(4-fluorophenyl)-4-oxo-1,3-thiazolidin-3-yl]-3-methylbenzoic acid (82.1 mg, 0.248 mmol) in thionyl chloride (0.80 mL) was reflux for 1 h and cooled to room temperature. Thionyl chloride was removed under reduced pressure completely. The benzoyl chloride intermediate was dissolved in THF (4.0 mL), and a solution of triethylamine (0.100 mL, 0.714 mmol) and N-phenylhydroxylamine (60.3 mg, 0.414 mmol) was added to the reaction mixture. The reaction mixture was stirred at room temperature for 18 h and then concentrated. The residue was purified by Isco Combi-Flash Companion column chromatography (0-55% ethyl acetate in n-hexane) to give 4-[2-(4-fluorophenyl)-4-oxo-1,3-thiazolidin-3-yl]-3-methyl-N-phenoxybenzamide (15.7 mg, 13%) as a yellow solid. 1H NMR (CDCl$_3$, 300 MHz) δ 9.02 (br s, 1H), 7.63 (br s, 1H), 7.52 (br s, 1H), 7.36-7.24 (m, 5H), 7.11-7.04 (m, 2H), 6.97 (t, 2H), 6.05-5.85 (br, 1H), 4.01 (d, 1H), 3.91 (d, 1H), 2.20 (br s, 3H); LC-MS (ESI) m/z 423.2 [M+H]$^+$.

EXAMPLE 157

4-[2-(4-Fluorophenyl)-4-oxo-1,3-thiazolidin-3-yl]-N-hydroxy-3-methylbenzamide

Compound 219

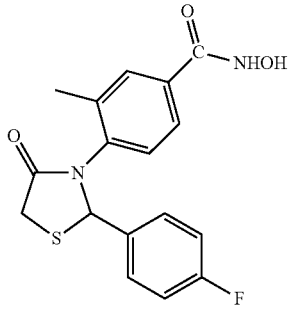

Following standard procedure E, 4-[2-(4-fluorophenyl)-4-oxo-1,3-thiazolidin-3-yl]-3-methylbenzoic acid (126 mg, 0.380 mmol), triethylamine (68.3 µL, 0.493 mmol), ethyl chloroformate (49.4 mg, 0.455 mmol), CH$_2$Cl$_2$ (3.0 mL), potassium hydroxide (15.4 mg, 0.274 mmol), hydroxylamine hydrochloride (34.1 mg, 0.607 mmol), and methanol (6.0 mL) were used to carry out the reaction. It was stirred for 1 h for the first step and 3 h for the second step. The residue was purified by Isco Combi-Flash Companion column chromatography (0-100% ethyl acetate in n-hexane) to give 4-[2-(4-fluorophenyl)-4-oxo-1,3-thiazolidin-3-yl]-N-hydroxy-3-methylbenzamide (71.9 mg, 55%) as a yellow solid. 1H NMR (DMSO-$d_6$, 400 MHz) δ 11.13 (br s, 1H), 9.02 (br s, 1H), 7.54-7.43 (m, 4H), 7.10 (t, 2H), 6.60-6.10 (br, 1H), 4.08 (d, 1H), 3.90 (d, 1H), 2.13 (br s, 3H); LC-MS (ESI) m/z 347.2 [M+H]$^+$.

EXAMPLE 158

4-[2-(4-Fluorophenyl)-4-oxo-1,3-thiazolidin-3-yl]-3-methylbenzohydrazide

Compound 220

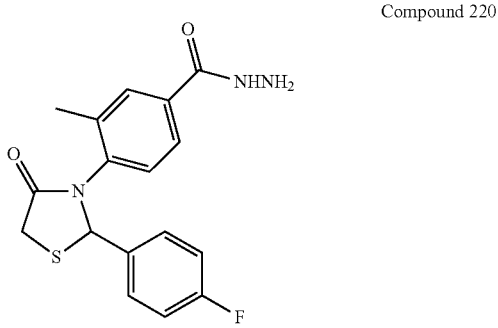 [SMILES: Cc1cc(C(=O)NN)ccc1N1C(=O)CSC1c1ccc(F)cc1]

A solution of methyl 4-[2-(4-fluorophenyl)-4-oxo-1,3-thiazolidin-3-yl]-3-methylbenzoate (158 mg, 0.458 mmol) in hydrazine monohydrate (0.30 mL) and methanol (3.0 mL) was reflux for 2.5 h and cooled to room temperature. Methanol was removed under reduced pressure. The mixture was diluted with ethyl acetate and washed with water. The organic layer was dried over $MgSO_{4(s)}$, filtered, and concentrated under reduced pressure to afford a residue. The residue was purified by Isco Combi-Flash Companion column chromatography (0-5% MeOH in $CH_2Cl_2$) to give 4-[2-(4-fluorophenyl)-4-oxo-1,3-thiazolidin-3-yl]-3-methylbenzohydrazide (107 mg, 67%) as a white solid. 1H NMR (CDCl$_3$, 400 MHz) δ 7.55 (br s, 1H), 7.41 (br s, 1H), 7.32-7.28 (m, 2H), 7.24 (br s, 1H), 6.96 (br t, 2H), 6.10-5.80 (br, 1H), 4.20-3.88 (m, 4H), 2.18 (br s, 3H); LC-MS (ESI) m/z 346.2 [M+H]$^+$.

EXAMPLE 159

2-(4-Fluorophenyl)-3-[2-methyl-4-(1H-tetrazol-5-yl)phenyl]-1,3-thiazolidin-4-one Compound 221

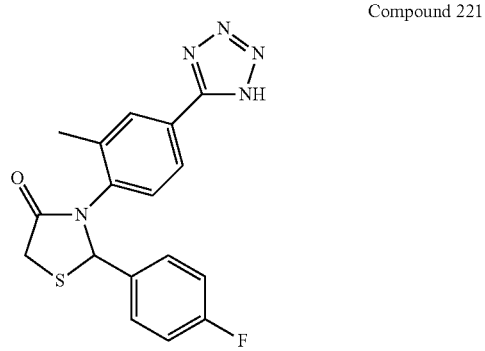 [SMILES: Cc1cc(-c2nnn[nH]2)ccc1N1C(=O)CSC1c1ccc(F)cc1]

To a solution of 4-[2-(4-fluorophenyl)-4-oxo-1,3-thiazolidin-3-yl]-3-methylbenzonitrile (59.4 mg, 0.190 mmol) in DMF (0.60 mL) was added silver nitrate (4.9 mg, 0.286 mmol) and sodium azide (30.9 mg, 0.475 mmol), and it was stirred at 120° C. for 18 h. Another 0.15 equivalent of silver nitrate and 2.5 equivalent of sodium azide were added to the reaction, and the solution was continued stirred at 140° C. for 8 h and cooled to room temperature. The reaction mixture was quenched with water and extracted with ethyl acetate. The organic layers were dried over $MgSO_{4(s)}$, filtered, and concentrated under reduced pressure to afford a residue. The residue was purified by Isco Combi-Flash Companion column chromatography (0-20% MeOH in $CH_2Cl_2$) to give 2-(4-fluorophenyl)-3-[2-methyl-4-(1H-tetrazol-5-yl)phenyl]-1,3-thiazolidin-4-one (31.1 mg, 46%) as a yellow solid. 1H NMR (DMSO-$d_6$, 400 MHz) δ 7.84 (br, 1H), 7.73 (br, 1H), 7.51 (dd, 2H), 7.11 (t, 2H), 6.60-6.20 (br, 1H), 4.10 (d, 1H), 3.93 (d, 1H), 2.17 (br s, 3H); LC-MS (ESI) m/z 356.1 [M+H]$^+$.

EXAMPLE 160

2-(4-Fluorophenyl)-3-[2-methyl-4-(3-thiophenyl)phenyl]-1,3-thiazolidin-4-one

Compound 222

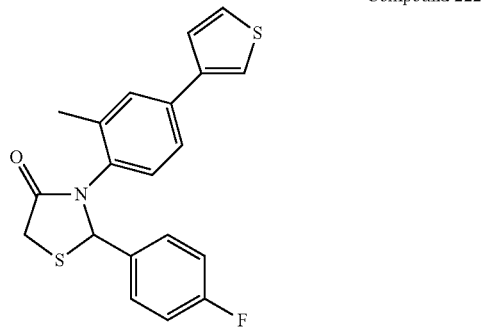

Following standard procedure F, 3-(4-bromo-2-methylphenyl)-2-(4-fluorophenyl)-1,3-thiazolidin-4-one (136 mg, 0.372 mmol), sodium bicarbonate (77.8 mg, 0.926 mmol), 3-thiophene boronic acid (94.7 mg, 0.740 mmol), Pd(PPh$_3$)$_4$ (21.4 mg, 0.0185 mmol), DME (4.0 mL), and water (2.0 mL) were used to carry out the reaction. After the reaction mixture was reflux for 4 h and work-up, the residue was purified by Isco Combi-Flash Companion column chromatography (0-20% ethyl acetate in n-hexane) to give 2-(4-fluorophenyl)-3-[2-methyl-4-(3-thiophenyl)phenyl]-1,3-thiazolidin-4-one (101 mg, 74%) as an orange solid. 1H NMR (CDCl$_3$, 400 MHz) δ 7.38-7.24 (m, 7H), 6.97 (br t, 2H), 6.10-5.60 (br, 1H), 4.03 (d, 1H), 3.92 (d, 1H), 2.20 (br s, 3H); LC-MS (ESI) m/z 370.2 [M+H]$^+$.

EXAMPLE 161

2-(4-Fluorophenyl)-3-[2-methyl-4-(2-thiophenyl)phenyl]-1,3-thiazolidin-4-one

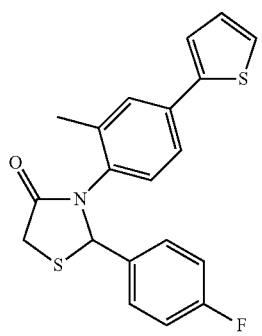

Compound 223

Following standard procedure F, 3-(4-bromo-2-methylphenyl)-2-(4-fluorophenyl)-1,3-thiazolidin-4-one (141 mg, 0.386 mmol), sodium bicarbonate (80.6 mg, 0.959 mmol), 2-thiophene boronic acid (98.2 mg, 0.767 mmol), Pd(PPh$_3$)$_4$ (22.2 mg, 0.0192 mmol), toluene (4.0 mL), and water (2.0 mL) were used to carry out the reaction. After the reaction mixture was reflux for 3.5 h and work-up, the residue was purified by Isco Combi-Flash Companion column chromatography (0-20% ethyl acetate in n-hexane) to give 2-(4-fluorophenyl)-3-[2-methyl-4-(2-thiophenyl)phenyl]-1,3-thiazolidin-4-one (65.4 mg, 46%) as a white solid. 1H NMR (CDCl$_3$, 300 MHz) δ 7.42 (br s, 1H), 7.36-7.31 (m, 3H), 7.26-7.23 (m, 2H), 7.04 (dd, 1H), 6.98 (br t, 2H), 6.10-5.60 (br, 1H), 4.03 (d, 1H), 3.91 (d, 1H), 2.17 (br s, 3H); LC-MS (ESI) m/z 370.2 [M+H]$^+$.

EXAMPLE 162

2-(4-Fluorophenyl)-3-[4-(2-furanyl)-2-methylphenyl]-1,3-thiazolidin-4-one

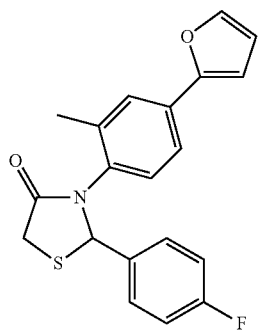

Compound 224

Following standard procedure F, 3-(4-bromo-2-methylphenyl)-2-(4-fluorophenyl)-1,3-thiazolidin-4-one (131 mg, 0.359 mmol), sodium bicarbonate (75.3 mg, 0.896 mmol), 2-furan boronic acid (80.3 mg, 0.718 mmol), Pd(PPh$_3$)$_4$ (20.7 mg, 0.0179 mmol), DME (4.0 mL), and water (2.0 mL) were used to carry out the reaction. After the reaction mixture was reflux for 3 h and work-up, the residue was purified by Isco Combi-Flash Companion column chromatography (0-20% ethyl acetate in n-hexane) to give 2-(4-fluorophenyl)-3-[4-(2-furanyl)-2-methylphenyl]-1,3-thiazolidin-4-one (102 mg, 80%) as a yellow solid. 1H NMR (CDCl$_3$, 300 MHz) δ 7.48 (br s, 1H), 7.42 (d, 1H), 7.35-7.31 (m, 3H), 6.96 (br t, 2H), 6.59 (d, 1H), 6.43 (dd, 1H), 6.10-5.70 (br, 1H), 4.02 (d, 1H), 3.91 (d, 1H), 2.17 (br s, 3H); LC-MS (ESI) m/z 354.2 [M+H]$^+$.

EXAMPLE 163

3-[4-(3,5-Dimethyl-1,2-oxazol-4-yl)-2-methylphenyl]-2-(4-fluorophenyl)-1,3-thiazolidin-4-one

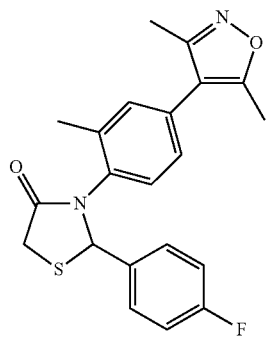

Compound 225

Following standard procedure F, 3-(4-bromo-2-methylphenyl)-2-(4-fluorophenyl)-1,3-thiazolidin-4-one (101 mg, 0.276 mmol), sodium bicarbonate (58.1 mg, 0.691 mmol), 3,5-dimethylisoxazole-4-boronic acid pinacol ester (123 mg, 0.553 mmol), Pd(PPh$_3$)$_4$ (16.0 mg, 0.0138 mmol), DME (4.0 mL), and water (2.0 mL) were used to carry out the reaction. After the reaction mixture was reflux for 4 h and work-up, the residue was purified by Isco Combi-Flash Companion column chromatography (0-30% ethyl acetate in n-hexane) to give 3-[4-(3,5-dimethyl-1,2-oxazol-4-yl)-2-methylphenyl]-2-(4-fluorophenyl)-1,3-thiazolidin-4-one (69.1 mg, 65%) as a yellow solid. 1H NMR (CDCl$_3$, 400 MHz) δ 7.36-7.33 (m, 2H), 7.07 (br s, 2H), 6.99 (br t, 2H), 6.10-5.60 (br, 1H), 4.04 (d, 1H), 3.92 (d, 1H), 2.35 (s, 3H), 2.30-2.00 (br, 6H); LC-MS (ESI) m/z 383.3 [M+H]$^+$.

EXAMPLE 164

2-(4-Fluorophenyl)-3-[2-methyl-4-(1-methyl-1H-pyrazol-4-yl)phenyl]-1,3-thiazolidin-4-one

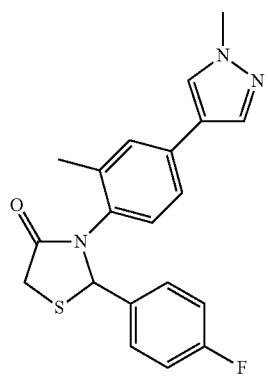

Compound 226

Following standard procedure F, 3-(4-bromo-2-methylphenyl)-2-(4-fluorophenyl)-1,3-thiazolidin-4-one (101 mg, 0.276 mmol), sodium bicarbonate (57.8 mg, 0.688 mmol), 1-methylpyrazole-4-boronic acid pinacol ester (115 mg, 0.551 mmol), Pd(PPh₃)₄ (15.9 mg, 0.0138 mmol), DME (4.0 mL), and water (2.0 mL) were used to carry out the reaction. After the reaction mixture was reflux for 3 h and work-up, the residue was purified by Isco Combi-Flash Companion column chromatography (0-80% ethyl acetate in n-hexane) to give 2-(4-fluorophenyl)-3-[2-methyl-4-(1-methyl-1H-pyrazol-4-yl)phenyl]-1,3-thiazolidin-4-one (53.5 mg, 53%) as a yellow gum. 1H NMR (CDCl₃, 400 MHz) δ 7.69-7.64 (m, 2H), 7.57-7.45 (m, 3H), 7.33 (dd, 2H), 6.97 (br t, 2H), 6.20-5.60 (br, 1H), 4.02 (d, 1H), 3.93-3.89 (m, 4H), 2.20-2.00 (br, 3H); LC-MS (ESI) m/z 368.3 [M+H]⁺.

EXAMPLE 165

2-(4-Fluorophenyl)-3-[2-methyl-4-(5-methyl-1,3,4-oxadiazol-2-yl)phenyl]-1,3-thiazolidin-4-one Compound 227

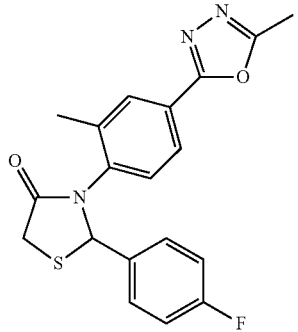

A solution of 4-[2-(4-fluorophenyl)-4-oxo-1,3-thiazolidin-3-yl]-3-methylbenzohydrazide (199 mg, 0.575 mmol) in triethyl orthoacetate (1.5 mL) was stirred at 90° C. for 20 h and cooled to room temperature. The reaction mixture was poured into water and extracted with ethyl acetate. The combined organic layers were dried over MgSO₄(s), filtered, and concentrated. The residue was purified by Isco Combi-Flash Companion column chromatography (0-70% ethyl acetate in n-hexane) to give 2-(4-fluorophenyl)-3-[2-methyl-4-(5-methyl-1,3,4-oxadiazol-2-yl)phenyl]-1,3-thiazolidin-4-one (38.2 mg, 18%) as a yellow solid. 1H NMR (CDCl₃, 300 MHz) δ 7.87 (br s, 1H), 7.73 (br s, 1H), 7.32 (dd, 2H), 6.96 (t, 2H), 5.95 (br s, 1H), 4.02 (d, 1H), 3.93 (d, 1H), 2.58 (s, 3H), 2.23 (br s, 3H); LC-MS (ESI) m/z 370.2 [M+H]⁺.

EXAMPLE 166

2-(4-Fluorophenyl)-3-{2-methyl-4-[5-(trifluoromethyl)-1,3,4-oxadiazol-2-yl]phenyl}-1,3-thiazolidin-4-one Compound 228

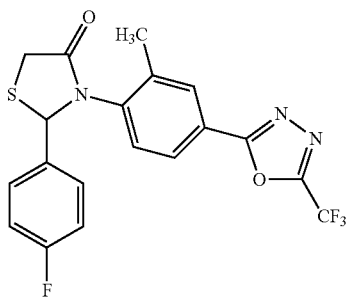

A solution of 4-[2-(4-fluorophenyl)-4-oxo-1,3-thiazolidin-3-yl]-3-methylbenzoic acid (159 mg, 0.478 mmol), trifluoroacetic acid hydrazide (61.3 mg, 0.478 mmol), 1-[bis(dimethylamino)methylene]-1H-1,2,3-triazolo[4,5-b]pyridinium 3-oxid hexafluorophosphate (HATU, 218 mg, 0.574 mmol), and N,N-diisopropylethylamine (0.170 mL, 0.980 mmol) in THF (4.0 mL) was stirred at room temperature for 45 min. Burgess reagent (285 mg, 1.20 mmol) was added to the reaction mixture, and it was stirred for 2 h. The crude was directly purified by Isco Combi-Flash Companion column chromatography (0-80% ethyl acetate in n-hexane) to give 2-(4-fluorophenyl)-3-{2-methyl-4-[5-(trifluoromethyl)-1,3,4-oxadiazol-2-yl]phenyl}-1,3-thiazolidin-4-one (68.9 mg, 34%) as a solid. 1H NMR (CDCl₃, 400 MHz) δ 7.93 (br s, 1H), 7.90-7.70 (br, 1H), 7.35-7.31 (m, 2H), 6.96 (br t, 2H), 6.15-5.70 (br, 1H), 4.02 (d, 1H), 3.94 (d, 1H), 2.24 (br s, 3H).

EXAMPLE 167

4-[2-(4-Fluoro-phenyl)-4-oxo-thiazolidin-3-yl]-3-methyl-benzoic acid propyl ester Compound 229

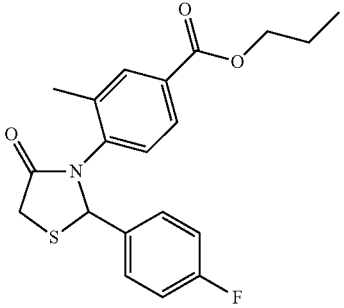

The compound was prepared by following the standard procedure C with 4-(2-(4-fluorophenyl)-4-oxothiazolidin-3-yl)-3-methylbenzoic acid (50.0 mg, 0.150 mmol), EDCI • HCl (43.0 mg, 0.230 mmol), n-propanol (0.5 mL) and DMAP (28.0 mg, 0.230 mmol). After the reaction was stirred for 16 h and work-up, the residue was purified by flash chromatography (ethyl acetate:hexane=1:3) to give the desired product as a white solid (44.0 mg, 79%). ¹H NMR (CDCl₃, 400 MHz) δ 7.87 (br s, 1H), 7.75 (br s, 1H), 7.31 (dd, 2H), 6.96 (br t, 2H), 5.94 (br s, 1H), 4.24 (t, 2H), 4.01 (d, 1H), 3.92 (d, 1H), 2.20 (br s, 3H), 1.76 (sextet, 2H), 1.00 (t, 3H); LC-MS (ESI) m/z 374.0 [M+H]⁺.

EXAMPLE 168

4-[2-(3,4-difluoro-phenyl)-4-oxo-thiazolidin-3-yl]-3-methyl-benzoic acid propyl ester Compound 230

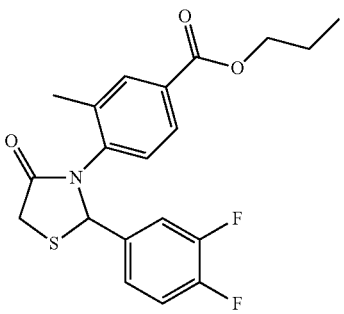

The compound was prepared by following the standard procedure C with 4-(2-(3,4-difluorophenyl)-4-oxothiazolidin-3-yl)-3-methylbenzoic acid (52.0 mg, 0.150 mmol), EDCI • HCl (43.0 mg, 0.230 mmol), n-propanol (0.5 mL) and DMAP (28.0 mg, 0.230 mmol). After the reaction was stirred for 18 h and work-up, the residue was purified by flash chromatography (ethyl acetate:hexane=1:3) to give the desired product as a white solid (50.0 mg, 85%). $^1$H NMR (CDCl$_3$, 400 MHz) δ 7.88 (br s, 1H), 7.77 (br d, 1H), 7.22 (t, 1H), 7.10-6.90 (m, 3H), 5.89 (br s, 1H), 4.24 (t, 2H), 4.00 (d, 1H), 3.91 (d, 1H), 2.21 (br s, 3H), 1.75 (sextet, 2H), 1.00 (t, 3H); LC-MS (ESI) m/z 392.9 [M+H]$^+$.

EXAMPLE 169

4-[2-(4-Fluoro-phenyl)-4-oxo-thiazolidin-3-yl]-3-methyl-benzoic acid isopropyl ester Compound 231

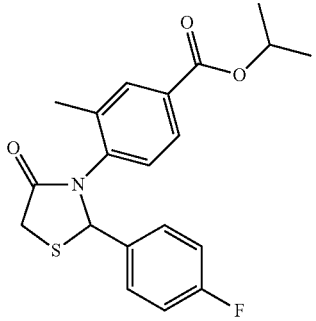

Step 1. Synthesis of 3-methyl-4-nitro-benzoic acid isopropyl ester

Compound 232

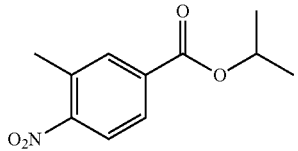

Fine powered Na$_2$CO$_{3(s)}$ (1.17 g, 11.0 mmol) was mixed with the SOCl$_2$ (0.800 mL, 11.0 mmol) and 4-nitro-3-methylbenzenecarboxylic acid (1.81 g, 10.0 mmol) in 20 mL of isopropanol. The reaction mixture was refluxed for 3.5 h. On completion of the reaction, the reaction mixture was poured into dilute solution of 10% NaHCO$_{3(aq)}$ untile the pH value of the reaction solution reached 9 and extracted with CH$_2$Cl$_2$ (80 mL). The organic layer was dried over MgSO$_4$ and concentrated to give the product (1.86 g, 83%). $^1$H NMR (CDCl$_3$, 300 MHz) δ 8.01-7.96 (m, 3H), 5.27 (septet, 1H), 2.63 (s, 3H), 1.39 (d, 6H).

Step 2. Synthesis of 4-amino-3-methyl-benzoic acid isopropyl ester

Compound 233

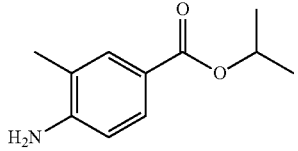

To a solution of 3-methyl-4-nitro-benzoic acid isopropyl ester (1.86 g, 8.30 mmol) and SnCl$_2$ (7.90 g, 41.7 mmol) in 40.0 mL of EtOH at 80° C. was added a solution of NaBH$_{4(s)}$ (157 mg, 4.15 mmol) in 10 mL of EtOH over 15 minutes with stirring. After being stirred for further 2 h, the mixture was partitioned between ethyl acetate (80 mL) and saturated NaHCO$_{3(aq)}$ (20 mL). The organic layer was washed with brine (20 mL), dried over MgSO$_4$ and concentrated to give the product (1.54 g, 96%). $^1$H NMR (CDCl$_3$, 400 MHz) δ 7.75-7.72 (m, 2H), 6.64 (d, 1H), 5.20 (septet, 1H), 4.00 (br s, 2H), 2.18 (s, 3H), 1.33 (d, 6H).

Step 3. Synthesis of 4-[2-(4-fluoro-phenyl)-4-oxo-thiazolidin-3-yl]-3-methyl-benzoic acid isopropyl ester The compound was prepared by following the standard procedure A with 4-amino-3-methyl-benzoic acid isopropyl ester (386 mg, 2.00 mmol), 4-fluorobenzaldehyde (496 mg, 4.00 mmol), and 2-mercaptoacetic acid (0.260 mL, 331 mg, 3.60 mmol). It was stirred at room temperature 5 h for the first step and 16 h for the second step. After work-up, the crude product was purified by flash chromatography (ethyl acetate:hexane=1:2) to give the desired product as a yellow viscous liquid (26.0 mg, 4%). $^1$H NMR (CDCl$_3$, 300 MHz) δ 7.85 (br s, 1H), 7.74 (br s, 1H), 7.31 (dd, 2H), 6.95 (br t, 2H), 5.94 (br s, 1H), 5.19 (septet, 1H), 4.01 (d, 1H), 3.91 (d, 1H), 2.19 (br s, 3H), 1.33 (d, 6H); LC-MS (ESI) m/z 373.9 [M+H]$^+$.

EXAMPLE 170

4-[2-(4-Fluoro-phenyl)-4-oxo-thiazolidin-3-yl]-3-methyl-benzoic acid butyl ester Compound 234

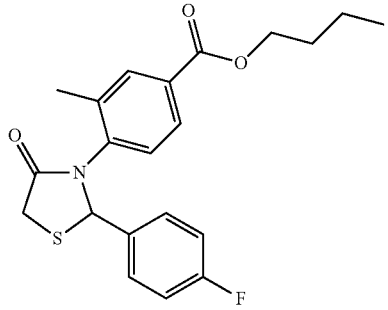

The compound was prepared by following the standard procedure C with 4-(2-(4-fluorophenyl)-4-oxothiazolidin-3-yl)-3-methylbenzoic acid (45.0 mg, 0.135 mmol), EDCI • HCl (40.0 mg, 0.210 mmol), n-butanol (0.500 mL) and DMAP (25.0 mg, 0.210 mmol). After the reaction was stirred for 16 h and work-up, the residue was purified by flash chromatography (ethyl acetate:hexane=1:3) to give the desired product as a yellow viscous liquid (45.0 mg, 86%). $^1$H NMR (CDCl$_3$, 300 MHz) δ 7.86 (br s, 1H), 7.74 (br d, 1H), 7.31 (dd, 2H), 6.96 (br t, 2H), 5.94 (br s, 1H), 4.27 (t, 2H), 4.01 (d, 1H), 3.91 (d, 1H), 2.20 (br s, 3H), 1.71 (quint, 2H), 1.43 (sextet, 2H), 0.95 (t, 3H); LC-MS (ESI) m/z 388.9 [M+H]$^+$.

EXAMPLE 171

2-Methyl-2-propanyl 4-[2-(4-fluorophenyl)-4-oxo-1,3-thiazolidin-3-yl]-3-methylbenzoate

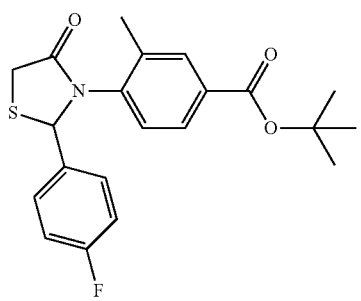

Compound 235

Following standard procedure G, 4-[2-(4-fluorophenyl)-4-oxo-1,3-thiazolidin-3-yl]-3-methylbenzoic acid (185 mg, 0.560 mmol), DMAP (171 mg, 1.40 mmol), EDCI • HCl (215 mg, 1.12 mmol), tert-butanol (0.50 mL), and CH$_2$Cl$_2$ (5.0 mL) were used to carry out the reaction. After the reaction was stirred for 16 h and work-up, the residue was purified by Isco Combi-Flash Companion column chromatography (0-25% ethyl acetate in n-hexane) to give 2-methyl-2-propanyl 4-[2-(4-fluorophenyl)-4-oxo-1,3-thiazolidin-3-yl]-3-methylbenzoate (124 mg, 57%) as a white solid. 1H NMR (CDCl$_3$, 400 MHz) δ 7.80 (br s, 1H), 7.69 (br s, 1H), 7.32-7.29 (m, 2H), 6.96 (br t, 2H), 6.10-5.70 (br, 1H), 4.00 (d, 1H), 3.91 (d, 1H), 2.18 (br s, 3H), 1.54 (s, 9H); LC-MS (ESI) m/z 388.3 [M+H]$^+$.

EXAMPLE 172

1-Methylcyclopropyl 4-[2-(4-fluorophenyl)-4-oxo-1,3-thiazolidin-3-yl]-3-methylbenzoate

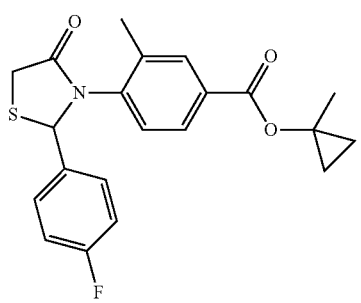

Compound 236

Following standard procedure G, 4-[2-(4-fluorophenyl)-4-oxo-1,3-thiazolidin-3-yl]-3-methylbenzoic acid (162 mg, 0.490 mmol), DMAP (120 mg, 0.980 mmol), EDCI • HCl (141 mg, 0.735 mmol), 1-methylcyclopropanol (42.4 mg, 0.588 mmol), and CH$_2$Cl$_2$ (5.0 mL) were used to carry out the reaction. After the reaction was stirred for 20 h and work-up, the residue was purified by Isco Combi-Flash Companion column chromatography (0-25% ethyl acetate in n-hexane) to give 1-methylcyclopropyl 4-[2-(4-fluorophenyl)-4-oxo-1,3-thiazolidin-3-yl]-3-methylbenzoate (148 mg, 78%) as a white solid. 1H NMR (CDCl$_3$, 300 MHz) δ 7.81 (br s, 1H), 7.71 (br d, 1H), 7.30 (dd, 2H), 6.95 (br t, 2H), 6.10-5.80 (br, 1H), 4.00 (d, 1H), 3.91 (d, 1H), 2.18 (br s, 3H), 1.59 (s, 3H), 1.00-0.90 (m, 2H), 0.80-0.68 (m, 2H); LC-MS (ESI) m/z 386.2 [M+H]$^+$.

EXAMPLE 173

3,3-Dimethylbutyl 4-[2-(4-fluorophenyl)-4-oxo-1,3-thiazolidin-3-yl]-3-methylbenzoate

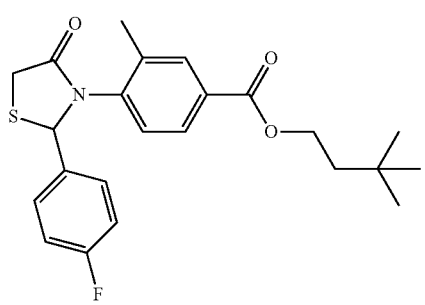

Compound 237

Following standard procedure G, 4-[2-(4-fluorophenyl)-4-oxo-1,3-thiazolidin-3-yl]-3-methylbenzoic acid (158 mg, 0.477 mmol), DMAP (146 mg, 1.19 mmol), EDCI • HCl (183 mg, 0.954 mmol), 3,3-dimethyl-1-butanol (88.0 µL, 0.727 mmol), and CH$_2$Cl$_2$ (5.0 mL) were used to carry out the reaction. After the reaction was stirred for 20 h and work-up, the residue was purified by Isco Combi-Flash Companion column chromatography (0-20% ethyl acetate in n-hexane) to give 3,3-dimethylbutyl 4-[2-(4-fluorophenyl)-4-oxo-1,3-thiazolidin-3-yl]-3-methylbenzoate (146 mg, 74%) as a lightly yellow foam. $^1$H NMR (CDCl$_3$, 400 MHz) δ 7.85 (br s, 1H), 7.75 (br s, 1H), 7.32-7.28 (m, 2H), 6.95 (br t, 2H), 6.10-5.80 (br, 1H), 4.32 (t, 2H), 4.00 (d, 1H), 3.91 (d, 1H), 2.19 (br s, 3H), 1.66 (t, 2H), 0.97 (s, 9H); LC-MS (ESI) m/z 416.3 [M+H]$^+$.

EXAMPLE 174

2-Cyclopropylethyl 4-[2-(4-fluorophenyl)-4-oxo-1,3-thiazolidin-3-yl]-3-methylbenzoate

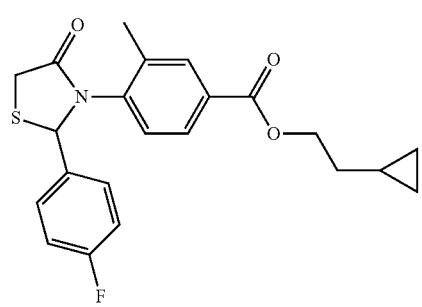

Compound 238

Following standard procedure G, 4-[2-(4-fluorophenyl)-4-oxo-1,3-thiazolidin-3-yl]-3-methylbenzoic acid (166 mg, 0.501 mmol), DMAP (153 mg, 1.25 mmol), EDCI • HCl (192 mg, 1.00 mmol), 2-cyclopropylethanol (51.8 mg, 0.601 mmol), and CH$_2$Cl$_2$ (5.0 mL) were used to carry out the reaction. After the reaction was stirred for 20 h and work-up, the residue was purified by Isco Combi-Flash Companion column chromatography (0-30% ethyl acetate in n-hexane) to give 2-cyclopropylethyl 4-[2-(4-fluorophenyl)-4-oxo-1,3-thiazolidin-3-yl]-3-methylbenzoate (88.3 mg, 44%) as a colorless gum. 1H NMR (CDCl$_3$, 400 MHz) δ 7.86 (br s, 1H), 7.75 (br s, 1H), 7.32-7.29 (m, 2H), 6.95 (br t, 2H), 6.10-5.80 (br, 1H), 4.33 (t, 2H), 4.00 (d, 1H), 3.92 (d, 1H), 2.19 (br s, 3H), 1.62 (q, 2H), 0.79-0.75 (m, 1H), 0.48-0.45 (m, 2H), 0.12-0.08 (m, 2H); LC-MS (ESI) m/z 400.3 [M+H]$^+$.

EXAMPLE 175

Cyclopentylmethyl 4-[2-(4-fluorophenyl)-4-oxo-1,3-thiazolidin-3-yl]-3-methylbenzoate Compound 239

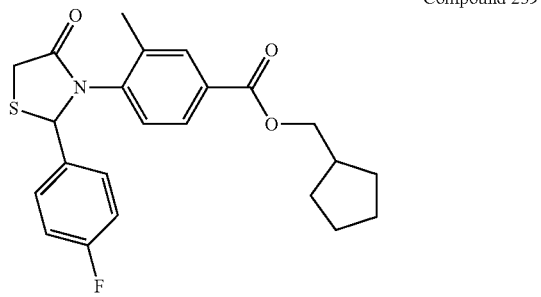

Following standard procedure G, 4-[2-(4-fluorophenyl)-4-oxo-1,3-thiazolidin-3-yl]-3-methylbenzoic acid (0.120 g, 0.362 mmol), cyclopentylmethanol (0.110 g, 0.725 mmol), EDCI • HCl (0.139 g, 0.725 mmol), DMAP (0.110 g, 0.906 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-5% MeOH in CH$_2$Cl$_2$) to give cyclopentylmethyl 4-[2-(4-fluorophenyl)-4-oxo-1,3-thiazolidin-3-yl]-3-methylbenzoate (97.4 mg, 65%). 1H NMR (CDCl$_3$, 300 MHz) δ 7.86 (br s, 1H), 7.74 (br d, 1H), 7.33-7.26 (m, 2H), 6.96 (t, 2H), 5.98 (br s, 1H), 4.16 (d, 2H), 4.01 (d, 1H), 3.91 (d, 1H), 2.35-2.20 (m, 4H), 1.82-1.78 (m, 2H), 1.64-1.57 (m, 2H), 1.34-1.25 (m, 4H); LC-MS (ACPI) m/z 414.5 [M+H]$^+$.

EXAMPLE 176

Cyclohexylmethyl 4-[2-(4-fluorophenyl)-4-oxo-1,3-thiazolidin-3-yl]-3-methylbenzoate Compound 240

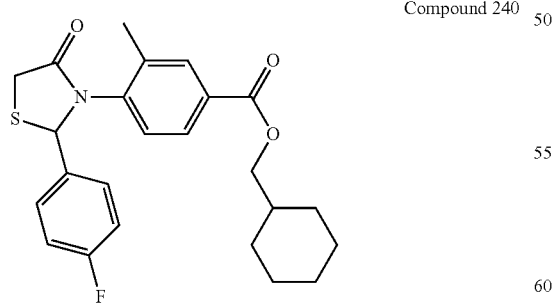

Following standard procedure G, 4-[2-(4-fluorophenyl)-4-oxo-1,3-thiazolidin-3-yl]-3-methylbenzoic acid (0.180 g, 0.540 mmol), cyclohexylmethanol (0.130 mL, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-20% ethyl acetate in n-hexane) to give cyclohexylmethyl 4-[2-(4-fluorophenyl)-4-oxo-1,3-thiazolidin-3-yl]-3-methylbenzoate (0.200 g, 86%). 1H NMR (CDCl$_3$, 400 MHz) δ 7.86 (br s, 1H), 7.74 (br, 1H), 7.31 (dd, 2H), 6.96 (t, 2H), 5.95 (br s, 1H), 4.12-4.04 (m, 2H), 4.01 (d, 1H), 3.92 (d, 1H), 2.20 (br s, 3H), 1.79-1.67 (m, 5H), 1.31-1.13 (m, 4H), 1.06-0.98 (m, 2H); LC-MS (ACPI) m/z 428.8 [M+H]$^+$.

EXAMPLE 177

4-[2-(4-Fluoro-phenyl)-4-oxo-thiazolidin-3-yl]-3-methyl-benzoic acid adamantan-1-ylmethyl ester Compound 241

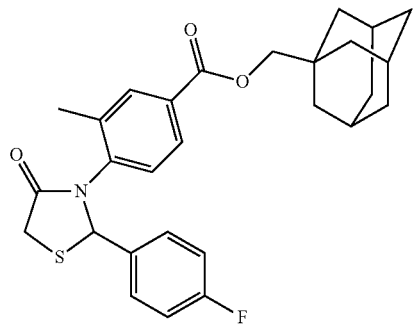

The compound was prepared by following the standard procedure C with 4-(2-(4-fluorophenyl)-4-oxothiazolidin-3-yl)-3-methylbenzoic acid (70.0 mg, 0.210 mmol), EDCI • HCl (48.3 mg, 0.250 mmol), 1-adamantanemethanol (70.0 mg, 0.42 mmol), DMAP (38.0 mg, 0.310 mmol), and CH$_2$Cl$_2$ (3.0 mL). After the reaction was stirred for 16 h and work-up, the residue was purified by flash chromatography (ethyl acetate:hexane=1:3) to give the desired product as a white solid (54.0 mg, 54%). $^1$H NMR (CDCl$_3$, 300 MHz) δ 7.86 (br s, 1H), 7.75 (br d, 1H), 7.31 (dd, 2H), 6.96 (br t, 2H), 5.94 (br s, 1H), 4.01 (d, 1H), 3.92 (d, 1H), 3.89 (d, 1H), 3.84 (d, 1H), 2.21 (br s, 3H), 2.07-1.95 (m, 3H), 1.80-1.50 (m, 12H); LC-MS (ESI) m/z 480.1 [M+H]$^+$.

EXAMPLE 178

4-[2-(4-Fluoro-phenyl)-4-oxo-thiazolidin-3-yl]-3-methyl-benzoic acid adamantan-1-yl ester Compound 242

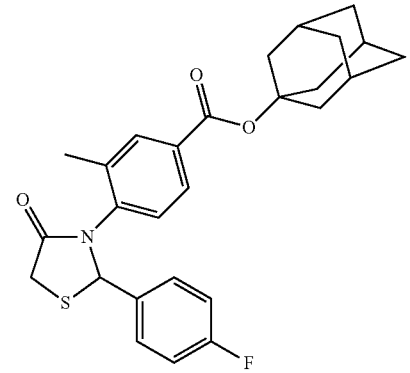

Step 1. Synthesis of 3-methyl-4-nitro-benzoic acid adamantan-1-yl ester

Compound 243

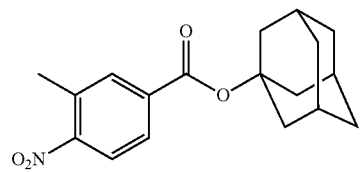

The compound was prepared by following the standard procedure C with 3-methyl-4-nitrobenzoic acid (2.00 g, 11.0 mmol), EDCI • HCl (2.32 g, 12.1 mmol), 1-adamantanol (3.35 g, 22.0 mmol), and DMAP (1.08 g, 8.80 mmol). After the reaction was stirred for 16 h and work-up, the residue was purified by flash chromatography (ethyl acetate: hexane=1:4) to give the desired product as a white solid (770 mg, 22%). $^1$H NMR (CDCl$_3$, 300 MHz) δ 7.96-7.92 (m, 3H), 2.61 (s, 3H), 2.25 (br s, 9H), 1.72 (br s, 6H).

Step 2. Synthesis of 4-amino-3-methyl-benzoic acid adamantan-1-yl ester

Compound 244

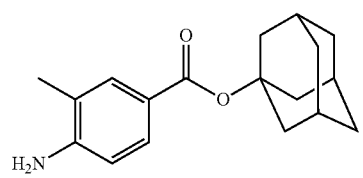

To a solution of 3-methyl-4-nitro-benzoic acid adamantan-1-yl ester (770 mg, 2.44 mmol) in 8.0 mL of acetic acid was added zinc dust$_{(s)}$ (1.55 g, 24.4 mmol) in one portion at r.t. The reaction mixture was stirred at r.t. for 4 h then passed through a pad of celite. The filtrate was partitioned between ethyl acetate (120 mL) and saturated NaHCO$_{3(aq)}$ (30 mL). The organic layer was washed with brine (20 mL), dried over MgSO$_4$ and concentrated to give a crude product which was purified by flash chromatography (ethyl acetate: hexane=1:4) to give the desired product as a white solid (440 mg, 63%). $^1$H NMR (CDCl$_3$, 400 MHz) δ 7.70-7.68 (m, 2H), 6.64 (d, 1H), 4.19 (br s, 2H), 2.24 (br s, 3H), 2.24-2.18 (m, 9H), 1.80-1.60 (m, 6H).

Step 3. Synthesis of 4-[2-(4-fluoro-phenyl)-4-oxo-thiazolidin-3-yl]-3-methyl-benzoic acid adamantan-1-yl ester The compound was prepared by following the standard procedure A with 4-amino-3-methyl-benzoic acid adamantan-1-yl ester (285.4 mg, 1.00 mmol), 4-fluorobenzaldehyde (248 mg, 2.0 mmol), and 2-mercaptoacetic acid (0.210 mL, 272 mg, 2.95 mmol). It was stirred at room temperature 5 h for the first step and 16 h for the second step. After work-up, the crude product was purified by flash chromatography (ethyl acetate:hexane=1:3) to give the desired product as a white solid (120 mg, 26%). $^1$H NMR (CDCl$_3$, 300 MHz) δ 7.79 (br s, 1H), 7.69 (br s, 1H), 7.30 (dd, 2H), 6.95 (br t, 2H), 5.92 (br s, 1H), 4.00 (d, 1H), 3.91 (d, 1H), 2.40-2.00 (m, 12H), 1.80-1.60 (m, 6H).

EXAMPLE 179

Phenyl 4-[2-(4-fluorophenyl)-4-oxo-1,3-thiazolidin-3-yl]-3-methylbenzoate

Compound 245

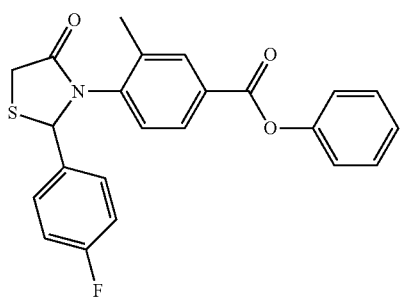

Following standard procedure G, 4-[2-(4-fluorophenyl)-4-oxo-1,3-thiazolidin-3-yl]-3-methylbenzoic acid (168 mg, 0.507 mmol), DMAP (124 mg, 1.01 mmol), EDCI • HCl (146 mg, 0.761 mmol), phenol (47.7 mg, 0.507 mmol), and CH$_2$Cl$_2$ (5.0 mL) were used to carry out the reaction. After the reaction was stirred for 18 h and work-up, the residue was purified by Isco Combi-Flash Companion column chromatography (0-30% ethyl acetate in n-hexane) to give phenyl 4-[2-(4-fluorophenyl)-4-oxo-1,3-thiazolidin-3-yl]-3-methylbenzoate (177 mg, 86%) as a white solid. 1H NMR (CDCl$_3$, 400 MHz) δ 8.03 (br s, 1H), 7.92 (br s, 1H), 7.41 (t, 2H), 7.34 (dd, 2H), 7.28-7.24 (m, 1H), 7.15 (d, 2H), 6.98 (br t, 2H), 6.10-5.80 (br, 1H), 4.02 (d, 1H), 3.93 (d, 1H), 2.25 (br s, 3H); LC-MS (ESI) m/z 408.2 [M+H]$^+$.

EXAMPLE 180

3-Nitrophenyl 4-[2-(4-fluorophenyl)-4-oxo-1,3-thiazolidin-3-yl]-3-methylbenzoate Compound 246

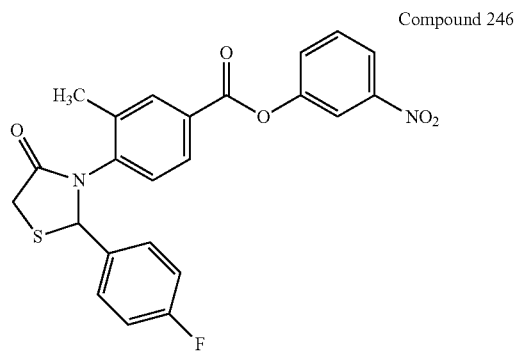 [SMILES: Cc1cc(C(=O)Oc2cccc([N+](=O)[O-])c2)ccc1N1C(=O)CSC1c1ccc(F)cc1]

Following standard procedure G, 4-[2-(4-fluorophenyl)-4-oxo-1,3-thiazolidin-3-yl]-3-methylbenzoic acid (142 mg, 0.427 mmol), DMAP (131 mg, 1.07 mmol), EDCI • HCl (164 mg, 0.855 mmol), 3-nitrophenol (63.1 mg, 0.453 mmol), and CH$_2$Cl$_2$ (3.0 mL) were used to carry out the reaction. After the reaction was stirred for 18 h and work-up, the residue was purified by Isco Combi-Flash Companion column chromatography (0-35% ethyl acetate in n-hexane) to give 3-nitrophenyl 4-[2-(4-fluorophenyl)-4-oxo-1,3-thiazolidin-3-yl]-3-methylbenzoate (144 mg, 74%) as a white solid. 1H NMR (CDCl₃, 400 MHz) δ 8.16 (ddd, 1H), 8.07 (t, 1H), 8.03 (br s, 1H), 7.91 (br d, 1H), 7.60 (t, 1H), 7.53 (ddd, 1H), 7.34 (dd, 2H), 6.99 (t, 2H), 6.10-5.90 (br, 1H), 4.03 (d, 1H), 3.95 (d, 1H), 2.26 (br s, 3H); LC-MS (ESI) m/z 453.2 [M+H]⁺.

EXAMPLE 181

2-Methoxyphenyl 4-[2-(4-fluorophenyl)-4-oxo-1,3-thiazolidin-3-yl]-3-methylbenzoate Compound 247

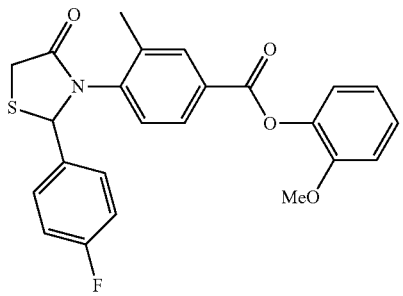

Following standard procedure G, 4-[2-(4-fluorophenyl)-4-oxo-1,3-thiazolidin-3-yl]-3-methylbenzoic acid (173 mg, 0.522 mmol), DMAP (128 mg, 1.04 mmol), EDCI • HCl (150 mg, 0.782 mmol), guaiacol (71.3 mg, 0.574 mmol), and CH₂Cl₂ (5.0 mL) were used to carry out the reaction. After the reaction was stirred for 20 h and work-up, the residue was purified by Isco Combi-Flash Companion column chromatography (0-25% ethyl acetate in n-hexane) to give 2-methoxyphenyl 4-[2-(4-fluorophenyl)-4-oxo-1,3-thiazolidin-3-yl]-3-methylbenzoate (142 mg, 63%) as a white solid. 1H NMR (CDCl₃, 400 MHz) δ 8.05 (br s, 1H), 7.93 (br s, 1H), 7.36-7.27 (m, 2H), 7.25-7.21 (m, 1H), 7.09 (dd, 1H), 7.01-6.95 (m, 4H), 6.10-5.80 (br, 1H), 4.03 (d, 1H), 3.93 (d, 1H), 3.79 (s, 3H), 2.24 (br s, 3H); LC-MS (ESI) m/z 438.2 [M+H]⁺.

EXAMPLE 182

2,3-Dihydro-1H-inden-5-yl 4-[2-(4-fluorophenyl)-4-oxo-1,3-thiazolidin-3-yl]-3-methylbenzoate Compound 248

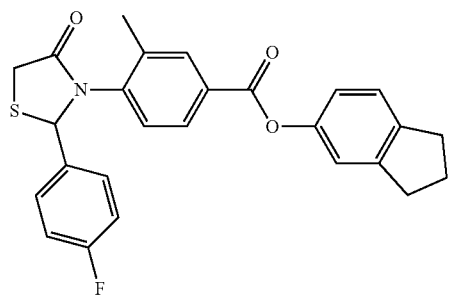

Following standard procedure G, 4-[2-(4-fluorophenyl)-4-oxo-1,3-thiazolidin-3-yl]-3-methylbenzoic acid (186 mg, 0.561 mmol), DMAP (171 mg, 1.40 mmol), EDCI•HCl (215 mg, 1.12 mmol), 5-indanol (82.6 mg, 0.616 mmol), and CH₂Cl₂ (6.0 mL) were used to carry out the reaction. After the reaction was stirred for 17 h and work-up, the residue was purified by Isco Combi-Flash Companion column chromatography (10-20% ethyl acetate in n-hexane) to give 2,3-dihydro-1H-inden-5-yl 4-[2-(4-fluorophenyl)-4-oxo-1,3-thiazolidin-3-yl]-3-methyl benzoate (211 mg, 84%) as a white solid. 1H NMR (CDCl₃, 300 MHz) δ 8.02 (br s, 1H), 7.90 (br d, 1H), 7.36-7.30 (m, 2H), 7.23-7.21 (m, 1H), 7.11-6.95 (m, 3H), 6.91-6.86 (m, 1H), 6.00 (br s, 1H), 4.03 (d, 1H), 3.94 (d, 1H), 2.91 (dd, 4H), 2.24 (br s, 3H), 2.11 (quint, 2H); LC-MS (ESI) m/z 448.3 [M+H]⁺.

EXAMPLE 183

2,3-Dihydro-1H-inden-4-yl 4-[2-(4-fluorophenyl)-4-oxo-1,3-thiazolidin-3-yl]-3-methylbenzoate Compound 249

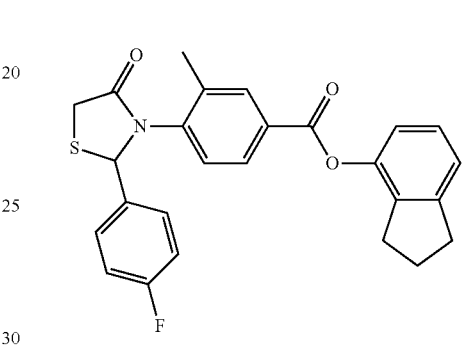

Following standard procedure G, 4-[2-(4-fluorophenyl)-4-oxo-1,3-thiazolidin-3-yl]-3-methylbenzoic acid (150 mg, 0.453 mmol), DMAP (111 mg, 0.906 mmol), EDCI • HCl (130 mg, 0.680 mmol), 4-indanol (60.7 mg, 0.453 mmol), and CH₂Cl₂ (5.0 mL) were used to carry out the reaction. After the reaction was stirred for 18 h and work-up, the residue was purified by Isco Combi-Flash Companion column chromatography (0-30% ethyl acetate in n-hexane) to give 2,3-dihydro-1H-inden-4-yl 4-[2-(4-fluorophenyl)-4-oxo-1,3-thiazolidin-3-yl]-3-methyl benzoate (157 mg, 77%) as a yellow solid. 1H NMR (CDCl₃, 400 MHz) δ 8.03 (br s, 1H), 7.91 (br s, 1H), 7.34 (dd, 2H), 7.20-7.12 (m, 2H), 6.99 (br t, 2H), 6.90 (d, 1H), 6.10-5.80 (br, 1H), 4.03 (d, 1H), 3.94 (d, 1H), 2.97 (t, 2H), 2.78 (t, 2H), 2.25 (br s, 3H), 2.05 (quint, 2H); LC-MS (ESI) m/z 448.3 [M+H]⁺.

EXAMPLE 184

4-(Trifluoromethyl)benzyl 4-[2-(4-fluorophenyl)-4-oxo-1,3-thiazolidin-3-yl]-3-methylbenzoate Compound 250

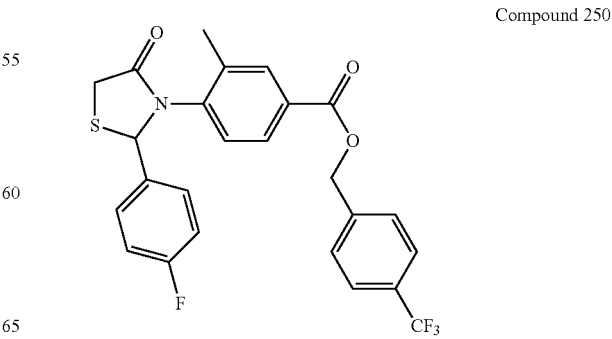

Following standard procedure G, 4-[2-(4-fluorophenyl)-4-oxo-1,3-thiazolidin-3-yl]-3-methylbenzoic acid (0.180 g, 0.540 mmol), 4-(trifluoromethyl)benzyl alcohol (0.150 mL, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-20% ethyl acetate in n-hexane) to give 4-(trifluoromethyl)benzyl 4-[2-(4-fluorophenyl)-4-oxo-1,3-thiazolidin-3-yl]-3-methylbenzoate (0.250 g, 94%). 1H NMR (CDCl$_3$, 300 MHz) δ 7.89 (br s, 1H), 7.78 (br d, 1H), 7.63 (d, 2H), 7.51 (d, 2H), 7.33-7.26 (m, 2H), 6.95 (t, 2H), 5.97 (br s, 1H), 5.36 (s, 2H), 4.00 (d, 1H), 3.91 (d, 1H), 2.20 (br s, 3H); LC-MS (ACPI) m/z 490.6 [M+H]$^+$.

EXAMPLE 185

1-Phenylethyl 4-[2-(4-fluorophenyl)-4-oxo-1, 3-thiazolidin-3-yl]-3-methylbenzoate Compound 251

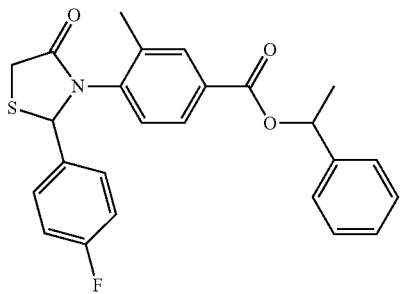

Following standard procedure G, 4-[2-(4-fluorophenyl)-4-oxo-1,3-thiazolidin-3-yl]-3-methylbenzoic acid (148 mg, 0.447 mmol), DMAP (126 mg, 1.03 mmol), EDCI • HCl (154 mg, 0.805 mmol), 1-phenylethanol (54.6 mg, 0.447 mmol), and CH$_2$Cl$_2$ (5.0 mL) were used to carry out the reaction. After the reaction was stirred for 16 h and work-up, the residue was purified by Isco Combi-Flash Companion column chromatography (0-25% ethyl acetate in n-hexane) to give 1-phenylethyl 4-[2-(4-fluorophenyl)-4-oxo-1,3-thiazolidin-3-yl]-3-methylbenzoate (157 mg, 81%) as a white foam. 1H NMR (CDCl$_3$, 400 MHz) δ 7.89 (br s, 1H), 7.78 (br s, 1H), 7.41-7.27 (m, 7H), 6.95 (br t, 2H), 6.10-5.80 (br, 1H), 6.07 (q, 1H), 4.00 (d, 1H), 3.91 (d, 1H), 2.20 (br s, 3H), 1.63 (d, 3H); LC-MS (ESI) m/z 436.1 [M+H]$^+$.

EXAMPLE 186

1-[4-(Trifluoromethyl)phenyl]ethyl 4-[2-(4-fluorophenyl)-4-oxo-1,3-thiazolidin-3-yl]-3-methylbenzoate Compound 252

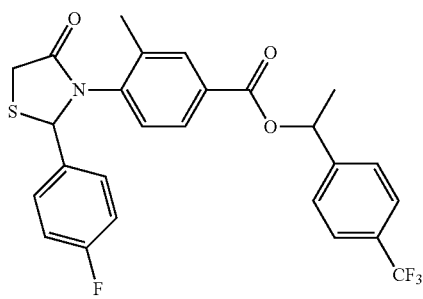

Following standard procedure G, 4-[2-(4-fluorophenyl)-4-oxo-1,3-thiazolidin-3-yl]-3-methylbenzoic acid (148 mg, 0.447 mmol), DMAP (126 mg, 1.03 mmol), EDCI • HCl (154 mg, 0.805 mmol), 1-[4-(trifluoromethyl)phenyl]ethanol (85.0 mg, 0.447 mmol), and CH$_2$Cl$_2$ (5.0 mL) were used to carry out the reaction. After the reaction was stirred for 18 h and work-up, the residue was purified by Isco Combi-Flash Companion column chromatography (0-25% ethyl acetate in n-hexane) to give 1-[4-(trifluoromethyl)phenyl]ethyl 4-[2-(4-fluorophenyl)-4-oxo-1,3-thiazolidin-3-yl]-3-methylbenzoate (192 mg, 85%) as a lightly yellow foam. 1H NMR (CDCl$_3$, 300 MHz) δ 7.88 (br s, 1H), 7.77 (br d, 1H), 7.61 (d, 2H), 7.49 (d, 2H), 7.33-7.29 (m, 2H), 6.96 (br t, 2H), 6.10-5.80 (br, 1H), 6.08 (q, 1H), 4.01 (d, 1H), 3.91 (d, 1H), 2.20 (br s, 3H), 1.64 (d, 3H); LC-MS (ESI) m/z 504.1 [M+H]$^+$.

EXAMPLE 187

3-Phenylpropyl 4-[2-(4-fluorophenyl)-4-oxo-1,3-thiazolidin-3-yl]-3-methylbenzoate Compound 253

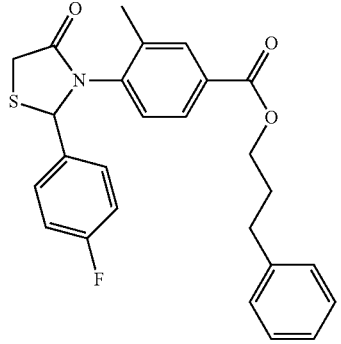

Following standard procedure G, 4-[2-(4-fluorophenyl)-4-oxo-1,3-thiazolidin-3-yl]-3-methylbenzoic acid (0.180 g, 0.540 mmol), 3-phenyl-1-propanol (0.150 mL, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-20% ethyl acetate in n-hexane) to give 3-phenylpropyl 4-[2-(4-fluorophenyl)-4-oxo-1,3-thiazolidin-3-yl]-3-methylbenzoate (0.160 g, 66%). 1H NMR (CDCl$_3$, 400 MHz) δ 7.84 (br s, 1H), 7.73 (br s, 1H), 7.33-7.28 (m, 4H), 7.20-7.17 (m, 3H), 6.96 (t, 2H), 5.97 (br s, 1H), 4.29 (t, 2H), 4.01 (d, 1H), 3.92 (d, 1H), 2.75 (t, 2H), 2.20 (br s, 3H), 2.07 (quint, 2H); LC-MS (ACPI) m/z 450.7 [M+H]$^+$.

EXAMPLE 188

[1-(4-Chlorophenyl)cyclopropyl]methyl 4-[2-(4-fluorophenyl)-4-oxo-1,3-thiazolidin-3-yl]-3-methylbenzoate

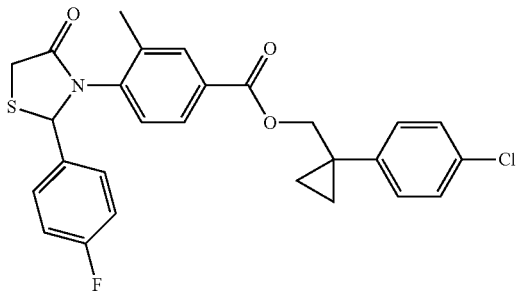

Compound 254

Following standard procedure G, 4-[2-(4-fluorophenyl)-4-oxo-1,3-thiazolidin-3-yl]-3-methylbenzoic acid (164 mg, 0.495 mmol), DMAP (151 mg, 1.24 mmol), EDCI • HCl (189 mg, 0.990 mmol), 1-(4-chlorophenyl)-1-cyclopropanemethanol (94.9 mg, 0.520 mmol), and $CH_2Cl_2$ (5.0 mL) were used to carry out the reaction. After the reaction was stirred for 18 h and work-up, the residue was purified by Isco Combi-Flash Companion column chromatography (0-30% ethyl acetate in n-hexane) to give [1-(4-chlorophenyl)cyclopropyl]methyl 4-[2-(4-fluorophenyl)-4-oxo-1,3-thiazolidin-3-yl]-3-methylbenzoate (206 mg, 86%) as a white solid. 1H NMR ($CDCl_3$, 400 MHz) δ 7.79 (br s, 1H), 7.66 (br s, 1H), 7.32-7.24 (m, 6H), 6.96 (br t, 2H), 6.10-5.80 (br, 1H), 4.36-4.28 (m, 2H), 4.00 (d, 1H), 3.91 (d, 1H), 2.19 (br s, 3H), 1.01-0.92 (m, 4H); LC-MS (ESI) m/z 518.1 [M+Na]+.

EXAMPLE 189

[1-(4-Chlorophenyl)cyclopentyl]methyl 4-[2-(4-fluorophenyl)-4-oxo-1,3-thiazolidin-3-yl]-3-methylbenzoate

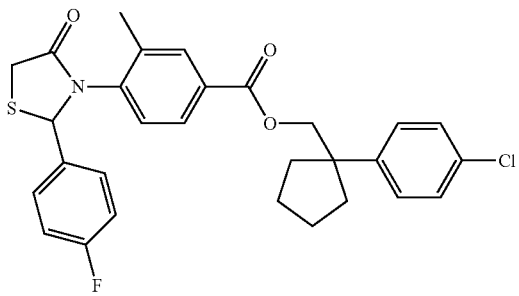

Compound 255

Step 1. Methyl 1-(4-chlorophenyl)cyclopentanecarboxylate

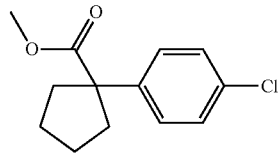

Compound 256

To a solution of 1-(4-chlorophenyl)-1-cyclopentane carboxylic acid (1.01 g, 4.50 mmol) in methanol (20 mL) was added thionyl chloride (0.660 mL, 9.10 mmol) slowly in ice-bath. The solution was stirred at room temperature for 5 h and concentrated to afford a residue. The residue was treated with $CH_2Cl_2$ (60 mL) and washed with saturated $NaHCO_{3(aq)}$ (40 mL). The organic layer was dried over $MgSO_{4(s)}$, filtered, concentrated, and dried under vacuum to obtain methyl 1-(4-chlorophenyl)cyclopentanecarboxylate (0.864 g, 81%) as a brown oil. 1H NMR ($CDCl_3$, 400 MHz) δ 7.31-7.25 (m, 4H), 3.62 (s, 3H), 2.65-2.59 (m, 2H), 1.91-1.83 (m, 2H), 1.75-1.71 (m, 4H).

Step 2. [1-(4-Chlorophenyl)cyclopentyl]methanol

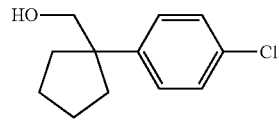

Compound 257

To a solution of methyl 1-(4-chlorophenyl)cyclopentanecarboxylate (0.748 g, 3.13 mmol) in THF (20 mL) was added lithium aluminium hydride (0.297 g, 7.83 mmol) in small portion in ice-bath. The reaction was warm up to room temperature and then reflux for 6 h. After the solution was cooled to room temperature, it was quenched with saturated $Na_2SO_{4(aq)}$ and 10% $NaOH_{(aq)}$, and diluted with diethyl ether. The undissolved solids were filtered off and washed with diethyl ether. The filtrate was dried over $MgSO_{4(s)}$, filtered, concentrated, and dried under vacuum to obtain [1-(4-chlorophenyl)cyclopentyl]methanol (0.614 g, 93%) as a lightly yellow solid. 1H NMR ($CDCl_3$, 400 MHz) δ 7.34-7.23 (m, 4H), 3.53 (s, 2H), 2.04-1.98 (m, 2H), 1.90-1.80 (m, 2H), 1.77-1.71 (m, 4H).

Step 3. [1-(4-Chlorophenyl)cyclopentyl]methyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (158 mg, 0.477 mmol), DMAP (146 mg, 1.19 mmol), EDCI • HCl (183 mg, 0.954 mmol), [1-(4-chlorophenyl)cyclopentyl]methanol (106 mg, 0.501 mmol), and $CH_2Cl_2$ (5.0 mL) were used to carry out the reaction. After the reaction was stirred for 18 h and work-up, the residue was purified by Isco Combi-Flash Companion column chromatography (0-30% ethyl acetate in n-hexane) to give [1-(4-chlorophenyl)cyclopentyl]methyl 4-[2-(4-fluorophenyl)-4-oxo-1,3-thiazolidin- 3-yl]-3-methylbenzoate (202 mg, 83%) as a white solid. 1H NMR (CDCl₃, 400 MHz) δ 7.71 (br s, 1H), 7.60 (br s, 1H), 7.36-7.27 (m, 6H), 6.95 (br t, 2H), 6.10-5.80 (br, 1H), 4.27-4.20 (m, 2H), 4.00 (d, 1H), 3.91 (d, 1H), 2.17 (br s, 3H), 2.05-1.92 (m, 4H), 1.79-1.76 (m, 4H); LC-MS (ESI) m/z 546.3 [M+Na]⁺.

EXAMPLE 190

2-(Benzyloxy)ethyl 4-[2-(4-fluorophenyl)-4-oxo-1,3-thiazolidin-3-yl]-3-methylbenzoate Compound 258

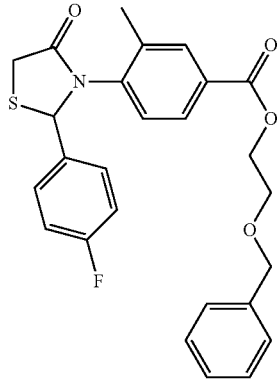

Following standard procedure G, 4-[2-(4-fluorophenyl)-4-oxo-1,3-thiazolidin-3-yl]-3-methylbenzoic acid (0.180 g, 0.540 mmol), 2-phenylmethoxyethanol (0.150 mL, 1.09 mmol), EDCI • HCl (0.210 g, 1.09 mmol), DMAP (0.160 g, 1.36 mmol) and CH₂Cl₂ (10.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 2-(benzyloxy)ethyl 4-[2-(4-fluorophenyl)-4-oxo-1,3-thiazolidin-3-yl]-3-methylbenzoate (0.140 g, 52%). 1H NMR (CDCl₃, 400 MHz) δ 7.88 (br s, 1H), 7.75 (br s, 1H), 7.32-7.29 (m, 8H), 6.96 (t, 2H), 5.98 (br s, 1H), 4.58 (s, 2H), 4.45 (dd, 2H), 4.01 (d, 1H), 3.92 (d, 1H), 3.77-3.75 (m, 2H), 2.20 (br s, 3H); LC-MS (ACPI) m/z 466.8 [M+H]⁺.

EXAMPLE 191

1,3-Benzodioxol-5-ylmethyl 4-[2-(4-fluorophenyl)-4-oxo-1,3-thiazolidin-3-yl]-3-methylbenzoate Compound 259

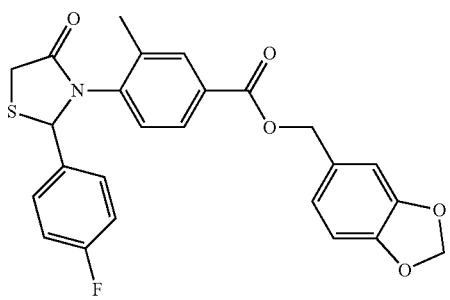

Following standard procedure G, 4-[2-(4-fluorophenyl)-4-oxo-1,3-thiazolidin-3-yl]-3-methylbenzoic acid (165 mg, 0.498 mmol), DMAP (152 mg, 1.25 mmol), EDCI • HCl (191 mg, 0.996 mmol), helioalcohol (79.6 mg, 0.523 mmol), and CH₂Cl₂ (5.0 mL) were used to carry out the reaction. After the reaction was stirred for 16 h and work-up, the residue was purified by Isco Combi-Flash Companion column chromatography (0-30% ethyl acetate in n-hexane) to give 1,3-benzodioxol-5-ylmethyl 4-[2-(4-fluorophenyl)-4-oxo-1,3-thiazolidin-3-yl]-3-methylbenzoate (175 mg, 75%) as a white solid. 1H NMR (CDCl₃, 400 MHz) δ 7.87 (br s, 1H), 7.75 (br s, 1H), 7.31-7.28 (m, 2H), 6.95 (br t, 2H), 6.89-6.87 (m, 2H), 6.79 (d, 1H), 6.05-5.85 (br, 3H), 5.20 (s, 2H), 4.00 (d, 1H), 3.91 (d, 1H), 2.18 (br s, 3H); LC-MS (ESI) m/z 466.2 [M+H]⁺.

EXAMPLE 192

2-(2-Chlorophenoxy)ethyl 4-[2-(4-fluorophenyl)-4-oxo-1,3-thiazolidin-3-yl]-3-methylbenzoate Compound 260

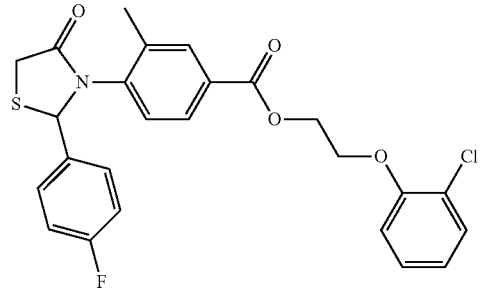

Following standard procedure G, 4-[2-(4-fluorophenyl)-4-oxo-1,3-thiazolidin-3-yl]-3-methylbenzoic acid (136 mg, 0.410 mmol), DMAP (100 mg, 0.820 mmol), EDCI • HCl (118 mg, 0.615 mmol), 2-(2-chlorophenoxy)ethanol (70.8 mg, 0.410 mmol), and CH₂Cl₂ (5.0 mL) were used to carry out the reaction. After the reaction was stirred for 18 h and work-up, the residue was purified by Isco Combi-Flash Companion column chromatography (0-35% ethyl acetate in n-hexane) to give 2-(2-chlorophenoxy)ethyl 4-[2-(4-fluorophenyl)-4-oxo-1,3-thiazolidin-3-yl]-3-methylbenzoate (152 mg, 76%) as a white solid. 1H NMR (CDCl₃, 400 MHz) δ 7.86 (br s, 1H), 7.75 (br s, 1H), 7.36 (dd, 1H), 7.32-7.28 (m, 2H), 7.22-7.18 (m, 1H), 6.97-6.90 (m, 4H), 6.10-5.80 (br, 1H), 4.65 (t, 2H), 4.34 (t, 2H), 4.00 (d, 1H), 3.91 (d, 1H), 2.18 (br s, 3H); LC-MS (ESI) m/z 486.2 [M+H]⁺.

EXAMPLE 193

3-Pyridinylmethyl 4-[2-(4-fluorophenyl)-4-oxo-1,3-thiazolidin-3-yl]-3-methylbenzoate Compound 261

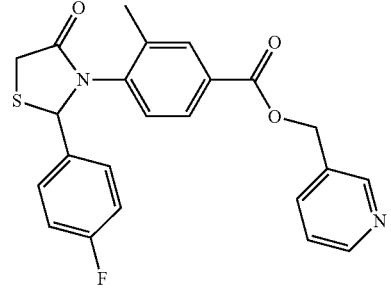

Following standard procedure G, 4-[2-(4-fluorophenyl)-4-oxo-1,3-thiazolidin-3-yl]-3-methylbenzoic acid (0.150 g, 0.453 mmol), nicotinyl alcohol (88.0 µL, 0.906 mmol), EDCI • HCl (0.170 g, 0.906 mmol), DMAP (0.140 g, 1.13 mmol) and CH₂Cl₂ (10.0 mL) were used to carry out the reaction. After the reaction mixture was stirred at room temperature for 16 h and work-up, the residue was purified by Isco Combi-Flash Companion column chromatography (0-5% MeOH in CH₂Cl₂) to give 3-pyridinylmethyl 4-[2-(4-fluorophenyl)-4-oxo-1,3-thiazolidin-3-yl]-3-methylbenzoate (0.106 g, 69%). 1H NMR (CDCl₃, 400 MHz) δ 8.68 (s, 1H), 8.59 (d, 1H), 7.87 (br s, 1H), 7.81-7.73 (m, 2H), 7.33-7.28 (m, 3H), 6.95 (t, 2H), 5.93 (br s, 1H), 5.33 (s, 2H), 4.00 (d, 1H), 3.92 (d, 1H), 2.20 (br s, 3H); LC-MS (APCI) m/z 423.7 [M+H]⁺.

EXAMPLE 194

2-(4-Pyridinyl)ethyl 4-[2-(4-fluorophenyl)-4-oxo-1,3-thiazolidin-3-yl]-3-methylbenzoate Compound 262

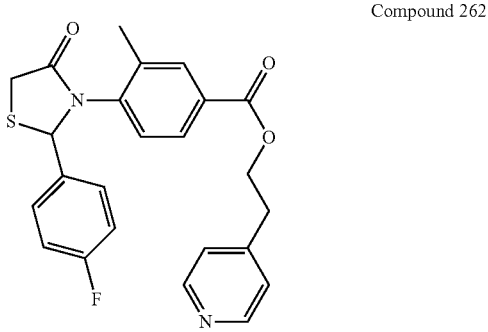 [SMILES: Cc1cc(C(=O)OCCc2ccncc2)ccc1N1C(=O)CSC1c1ccc(F)cc1]

Following standard procedure G, 4-[2-(4-fluorophenyl)-4-oxo-1,3-thiazolidin-3-yl]-3-methylbenzoic acid (0.180 g, 0.540 mmol), 4-pyridineethanol (0.120 mL, 1.09 mmol), EDCI • HCl (0.210 g, 1.09 mmol), DMAP (0.160 g, 1.36 mmol) and CH₂Cl₂ (10.0 mL) were used to carry out the reaction. After the reaction mixture was stirred at room temperature for 16 h and work-up, the residue was purified by Isco Combi-Flash Companion column chromatography (3% MeOH in CH₂Cl₂) to give 2-(4-pyridinyl)ethyl 4-[2-(4-fluorophenyl)-4-oxo-1,3-thiazolidin-3-yl]-3-methylbenzoate (0.210 g, 89%). 1H NMR (CDCl₃, 300 MHz) δ 8.53 (d, 2H), 7.80 (br s, 1H), 7.67 (br d, 1H), 7.33-7.28 (m, 2H), 7.19 (d, 2H), 6.95 (t, 2H), 5.96 (br s, 1H), 4.52 (t, 2H), 4.00 (d, 1H), 3.91 (d, 1H), 3.04 (t, 2H), 2.19 (br s, 3H); LC-MS (ACPI) m/z 437.6 [M+H]⁺.

EXAMPLE 195

3-(2-Pyridinyl)propyl 4-[2-(4-fluorophenyl)-4-oxo-1,3-thiazolidin-3-yl]-3-methylbenzoate Compound 263

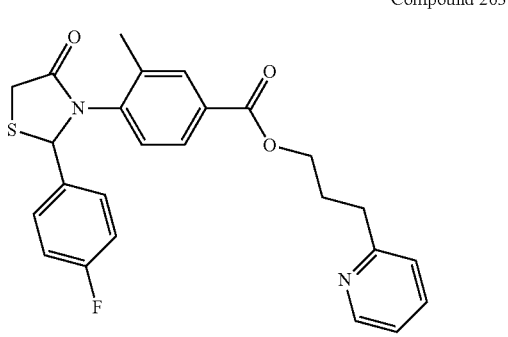

Following standard procedure G, 4-[2-(4-fluorophenyl)-4-oxo-1,3-thiazolidin-3-yl]-3-methylbenzoic acid (0.120 g, 0.362 mmol), 2-pyridinepropanol (94.0 µL, 0.725 mmol), EDCI • HCl (0.139 g, 0.725 mmol), DMAP (0.110 g, 0.906 mmol) and CH₂Cl₂ (10.0 mL) were used to carry out the reaction. After the reaction mixture was stirred at room temperature for 16 h and work-up, the residue was purified by Isco Combi-Flash Companion column chromatography (0-5% MeOH in CH₂Cl₂) to give 3-(2-pyridinyl)propyl 4-[2-(4-fluorophenyl)-4-oxo-1,3-thiazolidin-3-yl]-3-methylbenzoate (70.5 mg, 43%). 1H NMR (CDCl₃, 300 MHz) δ 8.52 (d, 1H), 7.83 (br s, 1H), 7.72 (br d, 1H), 7.58 (td, 1H), 7.33-7.27 (m, 2H), 7.14-7.08 (m, 2H), 6.96 (t, 2H), 5.97 (br s, 1H), 4.33 (t, 2H), 4.01 (d, 1H), 3.91 (d, 1H), 2.92 (dd, 2H), 2.25-2.16 (m, 5H); LC-MS (ACPI) m/z 451.6 [M+H]⁺.

EXAMPLE 196

2,3-Dihydro-1,4-benzodioxin-2-ylmethyl 4-[2-(4-fluorophenyl)-4-oxo-1,3-thiazolidin-3-yl]-3-methylbenzoate Compound 264

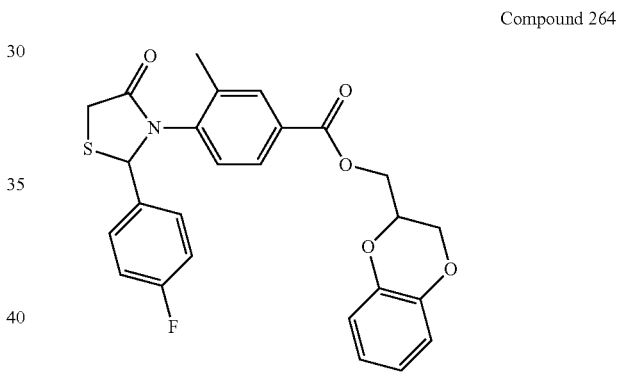

Following standard procedure G, 4-[2-(4-fluorophenyl)-4-oxo-1,3-thiazolidin-3-yl]-3-methylbenzoic acid (0.120 g, 0.362 mmol), 2-hydroxymethyl-1,4-benzodioxan (0.120 g, 0.725 mmol), EDCI • HCl (0.139 g, 0.725 mmol), DMAP (0.110 g, 0.906 mmol) and CH₂Cl₂ (10.0 mL) were used to carry out the reaction. After the reaction mixture was stirred at room temperature for 16 h and work-up, the residue was purified by Isco Combi-Flash Companion column chromatography (0-5% MeOH in CH₂Cl₂) to give 2,3-dihydro-1,4-benzodioxin-2-ylmethyl 4-[2-(4-fluorophenyl)-4-oxo-1,3-thiazolidin-3-yl]-3-methylbenzoate (80.5 mg, 46%). 1H NMR (CDCl₃, 400 MHz) δ 7.85 (br s, 1H), 7.75 (br s, 1H), 7.33-7.29 (m, 2H), 6.96 (t, 2H), 6.92-6.83 (m, 4H), 5.98 (br s, 1H), 4.58-4.47 (m, 3H), 4.33 (dd, 1H), 4.12 (dd, 1H), 4.00 (d, 1H), 3.94 (d, 1H), 2.20 (br s, 3H); LC-MS (APCI) m/z 480.5 [M+H]⁺.

EXAMPLE 197

2-(3-Thiophenyl)ethyl 4-[2-(4-fluorophenyl)-4-oxo-1,3-thiazolidin-3-yl]-3-methylbenzoate Compound 265

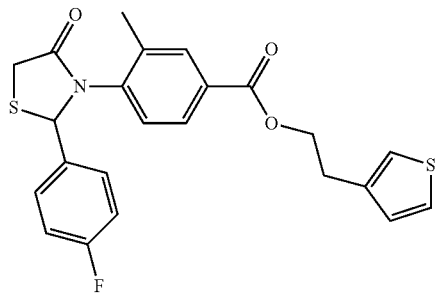

Following standard procedure G, 4-[2-(4-fluorophenyl)-4-oxo-1,3-thiazolidin-3-yl]-3-methylbenzoic acid (0.120 g, 0.362 mmol), 2-Thiopheneethanol (79.0 µL, 0.725 mmol), EDCI • HCl (0.139 g, 0.725 mmol), DMAP (0.110 g, 0.906 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-5% MeOH in CH$_2$Cl$_2$) to give 2-(3-thiophenyl)ethyl 4-[2-(4-fluorophenyl)-4-oxo-1,3-thiazolidin-3-yl]-3-methylbenzoate (79.2 mg, 50%). 1H NMR (CDCl$_3$, 300 MHz) δ 7.87 (br s, 1H), 7.75 (br d, 1H), 7.33-7.28 (m, 2H), 7.16 (dd, 1H), 6.99-6.88 (m, 4H), 5.96 (br s, 1H), 4.49 (t, 2H), 4.01 (d, 1H), 3.91 (d, 1H), 3.25 (t, 2H), 2.20 (br s, 3H); LC-MS (ACPI) m/z 442.4 [M+H]$^+$.

EXAMPLE 198

2-(4-Methyl-1,3-thiazol-5-yl)ethyl 4-[2-(4-fluorophenyl)-4-oxo-1,3-thiazolidin-3-yl]-3-methylbenzoate Compound 266

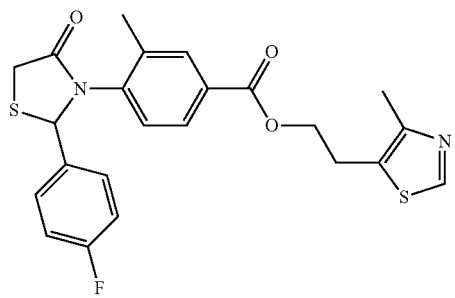

Following standard procedure G, 4-[2-(4-fluorophenyl)-4-oxo-1,3-thiazolidin-3-yl]-3-methylbenzoic acid (133 mg, 0.401 mmol), DMAP (73.5 mg, 0.602 mmol), EDCI • HCl (115 mg, 0.602 mmol), 4-methyl-5-thiazole ethanol (63.2 mg, 0.441 mmol), and CH$_2$Cl$_2$ (5.0 mL) were used to carry out the reaction. After the reaction was stirred for 18 h and work-up, the residue was purified by Isco Combi-Flash Companion column chromatography (0-65% ethyl acetate in n-hexane) to give 2-(4-methyl-1,3-thiazol-5-yl)ethyl 4-[2-(4-fluorophenyl)-4-oxo-1,3-thiazolidin-3-yl]-3-methylbenzoate (71.5 mg, 39%) as a yellow gum. 1H NMR (CDCl$_3$, 400 MHz) δ 8.61 (s, 1H), 7.85 (br s, 1H), 7.72 (br s, 1H), 7.32-7.29 (m, 2H), 6.96 (br t, 2H), 6.10-5.85 (br, 1H), 4.44 (t, 2H), 4.00 (d, 1H), 3.92 (d, 1H), 3.20 (t, 2H), 2.42 (s, 3H), 2.20 (br s, 3H); LC-MS (ESI) m/z 457.2 [M+H]$^+$.

EXAMPLE 199

3-Methoxypropyl 4-[2-(4-fluorophenyl)-4-oxo-1,3-thiazolidin-3-yl]-3-methylbenzoate Compound 267

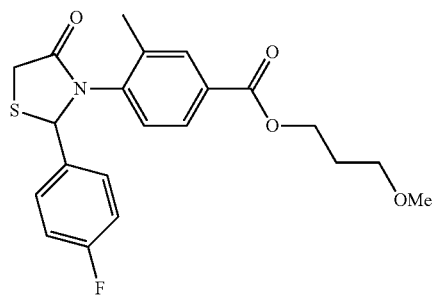

Following standard procedure G, 4-[2-(4-fluorophenyl)-4-oxo-1,3-thiazolidin-3-yl]-3-methylbenzoic acid (158 mg, 0.477 mmol), DMAP (109 mg, 0.892 mmol), EDCI • HCl (129 mg, 0.671 mmol), 3-methoxy-1-propanol (48.3 mg, 0.536 mmol), and CH$_2$Cl$_2$ (5.0 mL) were used to carry out the reaction. After the reaction was stirred for 20 h and work-up, the residue was purified by Isco Combi-Flash Companion column chromatography (0-30% ethyl acetate in n-hexane) to give 3-methoxypropyl 4-[2-(4-fluorophenyl)-4-oxo-1,3-thiazolidin-3-yl]-3-methylbenzoate (100 mg, 56%) as a colorless gum. 1H NMR (CDCl$_3$, 400 MHz) δ 7.86 (br s, 1H), 7.74 (br s, 1H), 7.31 (dd, 2H), 6.96 (br t, 2H), 6.10-5.80 (br, 1H), 4.36 (t, 2H), 4.00 (d, 1H), 3.92 (d, 1H), 3.49 (t, 2H), 3.34 (s, 3H), 2.20 (br s, 3H), 1.99 (quint, 2H); LC-MS (ESI) m/z 404.2 [M+H]$^+$.

EXAMPLE 200

2-Oxopropyl 4-[2-(4-fluorophenyl)-4-oxo-1,3-thiazolidin-3-yl]-3-methylbenzoate

Compound 268

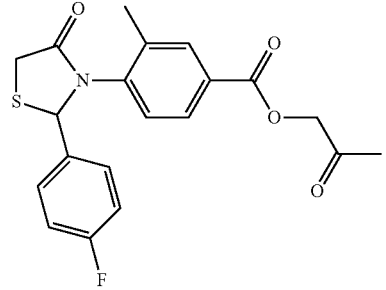

Following standard procedure G, 4-[2-(4-fluorophenyl)-4-oxo-1,3-thiazolidin-3-yl]-3-methylbenzoic acid (149 mg, 0.450 mmol), DMAP (110 mg, 0.900 mmol), EDCI • HCl (129 mg, 0.671 mmol), hydroxyacetone (40.0 mg, 0.540 mmol), and CH$_2$Cl$_2$ (5.0 mL) were used to carry out the reaction. After the reaction was stirred for 20 h and work-up, the residue was purified by Isco Combi-Flash Companion column chromatography (0-30% ethyl acetate in n-hexane) to give 2-oxopropyl 4-[2-(4-fluorophenyl)-4-oxo-1,3-thiazolidin-3-yl]-3-methylbenzoate (122 mg, 70%) as a white solid. 1H NMR (CDCl$_3$, 400 MHz) δ 7.92 (br s, 1H), 7.80 (br s, 1H), 7.33-7.30 (m, 2H), 6.97 (br t, 2H), 6.10-5.80 (br, 1H), 4.84 (s, 2H), 4.01 (d, 1H), 3.92 (d, 1H), 2.30-2.10 (br, 6H); LC-MS (ESI) m/z 388.2 [M+H]$^+$.

EXAMPLE 201

2-Cyanoethyl 4-[2-(4-fluorophenyl)-4-oxo-1,3-thiazolidin-3-yl]-3-methylbenzoate

Compound 269

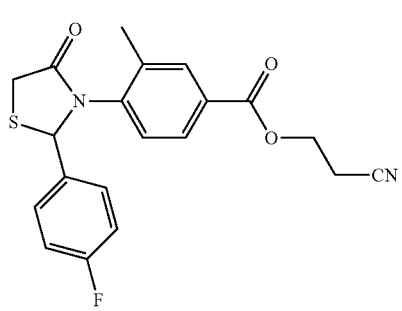

Following standard procedure G, 4-[2-(4-fluorophenyl)-4-oxo-1,3-thiazolidin-3-yl]-3-methylbenzoic acid 0 (158 mg, 0.477 mmol), DMAP (117 mg, 0.954 mmol), EDCI • HCl (140 mg, 0.730 mmol), 3-hydroxypropionitrile (50.0 µL, 0.732 mmol), and CH$_2$Cl$_2$ (5.0 mL) were used to carry out the reaction. After the reaction was stirred for 16 h and work-up, the residue was purified by Isco Combi-Flash Companion column chromatography (0-50% ethyl acetate in n-hexane) to give 2-cyanoethyl 4-[2-(4-fluorophenyl)-4-oxo-1,3-thiazolidin-3-yl]-3-methylbenzoate (143 mg, 77%) as a white solid. 1H NMR (CDCl$_3$, 400 MHz) δ 7.88 (br s, 1H), 7.77 (br s, 1H), 7.33-7.29 (m, 2H), 6.96 (br t, 2H), 6.10-5.80 (br, 1H), 4.48 (t, 2H), 4.00 (d, 1H), 3.92 (d, 1H), 2.80 (t, 2H), 2.21 (br s, 3H); LC-MS (ESI) m/z 385.2 [M+H]$^+$.

EXAMPLE 202

2-(Methylsulfanyl)ethyl 4-[2-(4-fluorophenyl)-4-oxo-1,3-thiazolidin-3-yl]-3-methylbenzoate Compound 270

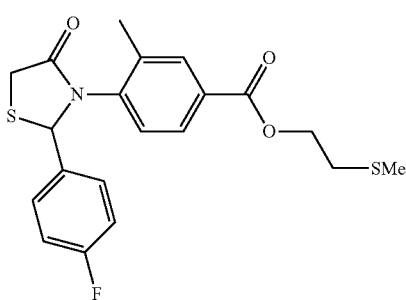

Following standard procedure G, 4-[2-(4-fluorophenyl)-4-oxo-1,3-thiazolidin-3-yl]-3-methylbenzoic acid (158 mg, 0.477 mmol), DMAP (117 mg, 0.954 mmol), EDCI • HCl (140 mg, 0.730 mmol), 2-(methylthio)ethanol (51.0 µL, 0.569 mmol), and CH$_2$Cl$_2$ (5.0 mL) were used to carry out the reaction. After the reaction was stirred for 18 h and work-up, the residue was purified by Isco Combi-Flash Companion column chromatography (0-30% ethyl acetate in n-hexane) to give 2-(methylsulfanyl)ethyl 4-[2-(4-fluorophenyl)-4-oxo-1,3-thiazolidin-3-yl]-3-methylbenzoate (140 mg, 73%) as a colorless gum. 1H NMR (CDCl$_3$, 400 MHz) δ 7.87 (br s, 1H), 7.75 (br s, 1H), 7.32-7.28 (m, 2H), 6.95 (br t, 2H), 6.10-5.80 (br, 1H), 4.44 (t, 2H), 4.00 (d, 1H), 3.92 (d, 1H), 2.81 (t, 2H), 2.30-2.10 (br, 6H); LC-MS (ESI) m/z 428.2 [M+Na]$^+$.

EXAMPLE 203

2-(Ethylsulfanyl)ethyl 4-[2-(4-fluorophenyl)-4-oxo-1,3-thiazolidin-3-yl]-3-methylbenzoate Compound 271

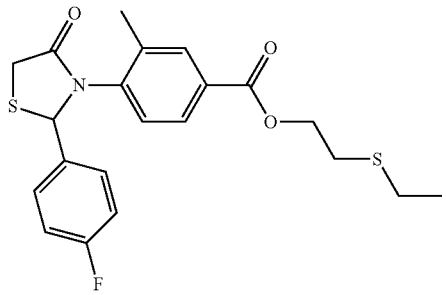

Following standard procedure G, 4-[2-(4-fluorophenyl)-4-oxo-1,3-thiazolidin-3-yl]-3-methylbenzoic acid (0.180 g, 0.540 mmol), 2-(ethylthio)ethanol (0.120 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 2-(ethylsulfanyl) ethyl 4-[2-(4-fluorophenyl)-4-oxo-1,3-thiazolidin-3-yl]-3-methylbenzoate (0.200 g, 88%). 1H NMR (CDCl$_3$, 400 MHz) δ 7.86 (br s, 1H), 7.75 (br s, 1H), 7.33-7.28 (m, 2H), 6.98 (t, 2H), 5.93 (br s, 1H), 4.42 (t, 2H), 4.00 (d, 1H), 3.92 (d, 1H), 2.84 (t, 2H), 2.61 (q, 2H), 2.20 (br s, 3H), 1.26 (t, 3H); LC-MS (ESI) m/z 442.4 [M+Na]$^+$.

EXAMPLE 204

2-(Acetyloxy)ethyl 4-[2-(4-fluorophenyl)-4-oxo-1,3-thiazolidin-3-yl]-3-methylbenzoate Compound 272

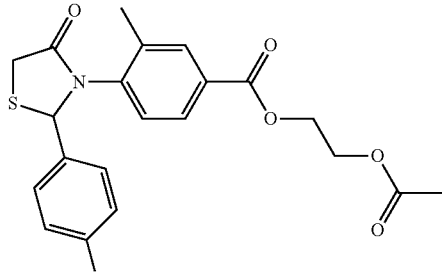

Following standard procedure G, 4-[2-(4-fluorophenyl)-4-oxo-1,3-thiazolidin-3-yl]-3-methylbenzoic acid (135 mg, 0.408 mmol), DMAP (74.8 mg, 0.612 mmol), EDCI • HCl (117 mg, 0.612 mmol), 2-hydroxyethyl acetate (42.5 mg, 0.408 mmol), and $CH_2Cl_2$ (5.0 mL) were used to carry out the reaction. After the reaction was stirred for 18 h and work-up, the residue was purified by Isco Combi-Flash Companion column chromatography (0-45% ethyl acetate in n-hexane) to give 2-(acetyloxy)ethyl 4-[2-(4-fluorophenyl)-4-oxo-1,3-thiazolidin-3-yl]-3-methylbenzoate (115 mg, 77%) as a colorless gum. 1H NMR ($CDCl_3$, 400 MHz) δ 7.87 (br s, 1H), 7.76 (br s, 1H), 7.33-7.29 (m, 2H), 6.96 (br t, 2H), 6.10-5.80 (br, 1H), 4.50-4.45 (m, 2H), 4.38-4.35 (m, 2H), 4.00 (d, 1H), 3.92 (d, 1H), 2.23 (br s, 3H), 2.06 (s, 3H); LC-MS (ESI) m/z 440.2 $[M+Na]^+$.

EXAMPLE 205

[(2,2-Dimethylpropanoyl)oxy]methyl 4-[2-(4-fluorophenyl)-4-oxo-1,3-thiazolidin-3-yl]-3-methylbenzoate

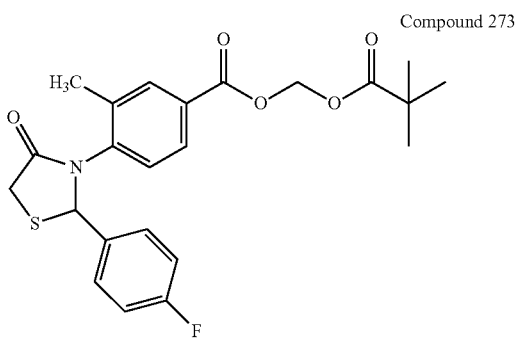 [SMILES: Cc1cc(C(=O)OCOC(=O)C(C)(C)C)ccc1N1C(=O)CSC1c1ccc(F)cc1]

Compound 273

4-[2-(4-fluorophenyl)-4-oxo-1,3-thiazolidin-3-yl]-3-methylbenzoic acid (190 mg, 0.573 mmol) was dissolved in DMF (2.0 mL) and chloromethyl pivalate (0.100 mL, 0.690 mmol) was added followed by triethylamine (0.120 mL, 0.861 mmol) and sodium iodide (94.4 mg, 0.630 mmol). The reaction was heated to 50° C. for 10 h, and then DMF was removed under reduced pressure. The crude was dissolved in ethyl acetate and washed with saturated $NaHCO_{3(aq)}$ and brine, dried over $MgSO_{4(s)}$, filtered, and concentrated. The residue was purified by Isco Combi-Flash Companion column chromatography (0-35% ethyl acetate in n-hexane) to give [(2,2-dimethylpropanoyl)oxy]methyl 4-[2-(4-fluorophenyl)-4-oxo-1,3-thiazolidin-3-yl]-3-methylbenzoate (201 mg, 79%) as a white solid. 1H NMR ($CDCl_3$, 300 MHz) δ 7.89 (br s, 1H), 7.77 (br d, 1H), 7.33-7.28 (m, 2H), 6.96 (br t, 2H), 6.10-5.80 (br, 3H), 4.01 (d, 1H), 3.91 (d, 1H), 2.20 (br s, 3H), 1.20 (s, 9H); LC-MS (ESI) m/z 468.2 $[M+Na]^+$.

EXAMPLE 206

Tetrahydro-3-furanyl 4-[2-(4-fluorophenyl)-4-oxo-1,3-thiazolidin-3-yl]-3-methylbenzoate

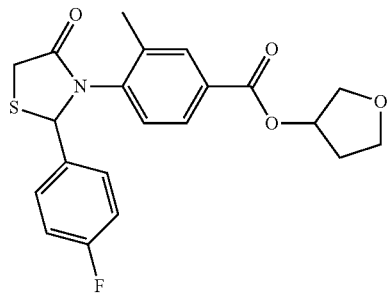

Compound 274

Following standard procedure G, 4-[2-(4-fluorophenyl)-4-oxo-1,3-thiazolidin-3-yl]-3-methylbenzoic acid (0.180 g, 0.540 mmol), 3-hydroxytetrahydrofuran (88.0 µL, 1.09 mmol), EDCI • HCl (0.210 g, 1.09 mmol), DMAP (0.150 g, 1.20 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give tetrahydro-3-furanyl 4-[2-(4-fluorophenyl)-4-oxo-1,3-thiazolidin-3-yl]-3-methylbenzoate (0.200 g, 92%). 1H NMR ($CDCl_3$, 400 MHz) δ 7.85 (br s, 1H), 7.74 (br s, 1H), 7.33-7.29 (m, 2H), 6.96 (t, 2H), 5.95 (br s, 1H), 5.51-5.47 (m, 1H), 4.02-3.86 (m, 6H), 2.30-2.07 (m, 5H); LC-MS (ACPI) m/z 402.9 $[M+H]^+$.

EXAMPLE 207

Tetrahydro-2-furanylmethyl 4-[2-(4-fluorophenyl)-4-oxo-1,3-thiazolidin-3-yl]-3-methylbenzoate

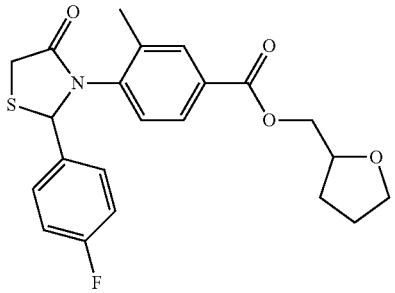

Compound 275

Following standard procedure G, 4-[2-(4-fluorophenyl)-4-oxo-1,3-thiazolidin-3-yl]-3-methylbenzoic acid (0.180 g, 0.540 mmol), tetrahydrofuryl alcohol (0.110 mL, 1.09 mmol), EDCI • HCl (0.210 g, 1.09 mmol), DMAP (0.150 g, 1.20 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give tetrahydro-2- furanylmethyl 4-[2-(4-fluorophenyl)-4-oxo-1,3-thiazolidin-3-yl]-3-methylbenzoate (0.180 g, 80%). 1H NMR (CDCl₃, 300 MHz) δ 7.88 (br s, 1H), 7.76 (br d, 1H), 7.32-7.28 (m, 3H), 6.95 (t, 2H), 5.93 (br s, 1H), 4.36-4.29 (m, 1H), 4.23-4.18 (m, 2H), 4.03-3.77 (m, 4H), 2.18 (br s, 3H), 2.10-1.97 (m, 1H), 1.95-1.90 (m, 2H), 1.71-1.65 (m, 1H); LC-MS (ACPI) m/z 416.7 [M+H]⁺.

EXAMPLE 208

(2,2-Dimethyl-1,3-dioxolan-4-yl)methyl 4-[2-(4-fluorophenyl)-4-oxo-1,3-thiazolidin-3-yl]-3-methylbenzoate Compound 276

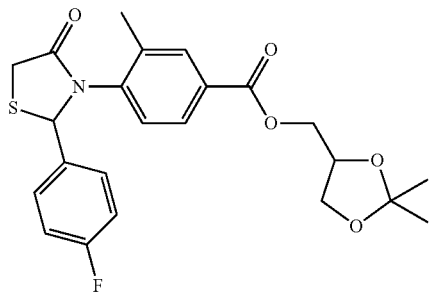

Following standard procedure G, 4-[2-(4-fluorophenyl)-4-oxo-1,3-thiazolidin-3-yl]-3-methylbenzoic acid (186 mg, 0.563 mmol), DMAP (137 mg, 1.13 mmol), EDCI • HCl (162 mg, 0.844 mmol), (±)-2,2-dimethyl-1,3-dioxolane-4-methanol (81.8 mg, 0.619 mmol), and CH₂Cl₂ (5.0 mL) were used to carry out the reaction. After the reaction was stirred for 18 h and work-up, the residue was purified by Isco Combi-Flash Companion column chromatography (0-30% ethyl acetate in n-hexane) to give (2,2-dimethyl-1,3-dioxolan-4-yl)methyl 4-[2-(4-fluorophenyl)-4-oxo-1,3-thiazolidin-3-yl]-3-methylbenzoate (171 mg, 68%) as a yellow gum. 1H NMR (CDCl₃, 300 MHz) δ 7.87 (br s, 1H), 7.75 (br d, 1H), 7.32-7.28 (m, 2H), 6.95 (br t, 2H), 6.10-5.80 (br, 1H), 4.43-4.30 (m, 3H), 4.11 (dd, 1H), 4.00 (d, 1H), 3.91 (d, 1H), 3.81 (dd, 1H), 2.20 (br s, 3H), 1.43 (s, 3H), 1.37 (s, 3H); LC-MS (ESI) m/z 406.2 [M+H]⁺ (deprotection of dimethylacetal to terminal diol compound by using 0.1% formic acid in H₂O and CH₃CN as the eluent of LC).

EXAMPLE 209

2,2-Dimethyl-1,3-dioxan-5-yl 4-[2-(4-fluorophenyl)-4-oxo-1,3-thiazolidin-3-yl]-3-methylbenzoate Compound 277

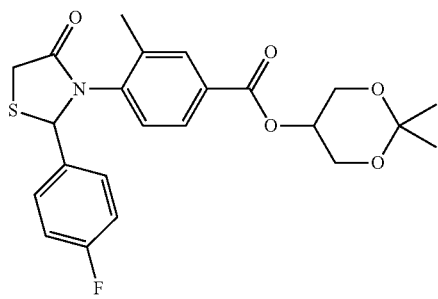

Following standard procedure G, 4-[2-(4-fluorophenyl)-4-oxo-1,3-thiazolidin-3-yl]-3-methylbenzoic acid (169 mg, 0.510 mmol), DMAP (156 mg, 1.28 mmol), EDCI • HCl (196 mg, 1.02 mmol), 2,2-dimethyl-1,3-dioxan-5-ol (80.9 mg, 0.612 mmol), and CH₂Cl₂ (5.0 mL) were used to carry out the reaction. After the reaction was stirred for 18 h and work-up, the residue was purified by Isco Combi-Flash Companion column chromatography (0-40% ethyl acetate in n-hexane) to give 2,2-dimethyl-1,3-dioxan-5-yl 4-[2-(4-fluorophenyl)-4-oxo-1,3-thiazolidin-3-yl]-3-methylbenzoate (169 mg, 74%) as a white solid. 1H NMR (CDCl₃, 400 MHz) δ 7.91 (br s, 1H), 7.80 (br s, 1H), 7.33-7.29 (m, 2H), 6.96 (br t, 2H), 5.95 (br s, 1H), 4.89 (quint, 1H), 4.16 (dd, 2H), 4.05-3.88 (m, 4H), 2.20 (br s, 3H), 1.46 (s, 3H), 1.45 (s, 3H); LC-MS (ESI) m/z 406.2 [M+H]⁺ (deprotection of dimethylacetal to terminal diol compound by using 0.1% formic acid in H₂O and CH₃CN as the eluent of LC).

EXAMPLE 210

1,3-Dimethoxy-2-propanyl 4-[2-(4-fluorophenyl)-4-oxo-1,3-thiazolidin-3-yl]-3-methylbenzoate Compound 278

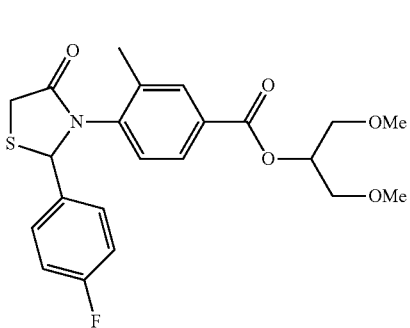

Following standard procedure G, 4-[2-(4-fluorophenyl)-4-oxo-1,3-thiazolidin-3-yl]-3-methylbenzoic acid (195 mg, 0.588 mmol), DMAP (144 mg, 1.18 mmol), EDCI • HCl (169 mg, 0.882 mmol), 1,3-dimethoxypropan-2-ol (84.8 mg, 0.706 mmol), and CH₂Cl₂ (5.0 mL) were used to carry out the reaction. After the reaction was stirred for 18 h and work-up, the residue was purified by Isco Combi-Flash Companion column chromatography (0-30% ethyl acetate in n-hexane) to give 1,3-dimethoxy-2-propanyl 4-[2-(4-fluorophenyl)-4-oxo-1,3-thiazolidin-3-yl]-3-methylbenzoate (129 mg, 51%) as a white solid. 1H NMR (CDCl₃, 400 MHz) δ 7.88 (br s, 1H), 7.77 (br s, 1H), 7.31 (dd, 2H), 6.96 (br t, 2H), 6.10-5.80 (br, 1H), 5.33 (quint, 1H), 4.00 (d, 1H), 3.91 (d, 1H), 3.66-3.53 (m, 4H), 3.36 (s, 6H), 2.19 (br s, 3H); LC-MS (ESI) m/z 434.3 [M+H]⁺.

EXAMPLE 211

1-Methoxy-2-propanyl 4-[2-(4-fluorophenyl)-4-oxo-1,3-thiazolidin-3-yl]-3-methylbenzoate Compound 279

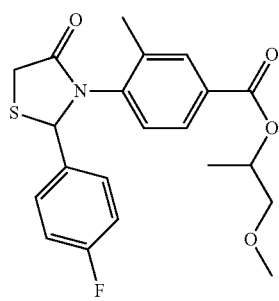

Following standard procedure G, 4-[2-(4-fluorophenyl)-4-oxo-1,3-thiazolidin-3-yl]-3-methylbenzoic acid (0.180 g, 0.540 mmol), 1-methoxy-2-propanol (0.110 mL, 1.09 mmol), EDCI • HCl (0.210 g, 1.09 mmol), DMAP (0.160 g, 1.36 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 1-methoxy-2-propanyl 4-[2-(4-fluorophenyl)-4-oxo-1,3-thiazolidin-3-yl]-3-methylbenzoate (0.190 g, 87%). 1H NMR (CDCl$_3$, 300 MHz) δ 7.87 (br s, 1H), 7.74 (br, 1H), 7.33-7.28 (m, 2H), 6.96 (t, 2H), 5.95 (br s, 1H), 5.33-5.23 (m, 1H), 4.01 (d, 1H), 3.91 (d, 1H), 3.55 (dd, 1H), 3.47 (dd, 1H), 3.37 (s, 3H). 2.19 (br s, 3H), 1.31 (d, 3H).

EXAMPLE 212

2-(2-Methoxyethoxy)ethyl 4-[2-(4-fluorophenyl)-4-oxo-1,3-thiazolidin-3-yl]-3-methylbenzoate Compound 280

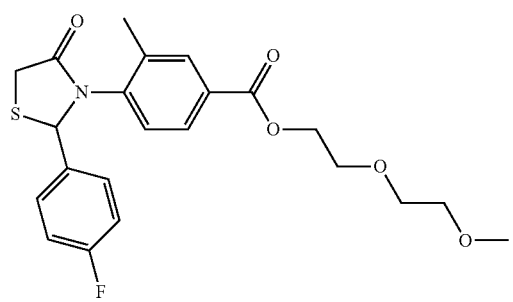

Following standard procedure G, 4-[2-(4-fluorophenyl)-4-oxo-1,3-thiazolidin-3-yl]-3-methylbenzoic acid (190 mg, 0.573 mmol), DMAP (178 mg, 1.43 mmol), EDCI • HCl (220 mg, 1.15 mmol), diethylene glycol monomethyl ether (0.50 mL), and $CH_2Cl_2$ (8.0 mL) were used to carry out the reaction. After the reaction was stirred for 18 h and work-up, the residue was purified by Isco Combi-Flash Companion column chromatography (0-70% ethyl acetate in n-hexane) to give 2-(2-methoxyethoxy)ethyl 4-[2-(4-fluorophenyl)-4-oxo-1,3-thiazolidin-3-yl]-3-methylbenzoate (119 mg, 48%) as a colorless gum. 1H NMR (CDCl$_3$, 400 MHz) δ 7.88 (br s, 1H), 7.75 (br s, 1H), 7.30 (dd, 2H), 6.95 (br t, 2H), 6.10-5.80 (br, 1H), 4.46-4.42 (m, 2H), 4.00 (d, 1H), 3.92 (d, 1H), 3.80-3.78 (m, 2H), 3.67-3.65 (m, 2H), 3.55-3.53 (m, 2H), 3.37 (s, 3H), 2.19 (br s, 3H); LC-MS (ESI) m/z 456.2 [M+Na]$^+$.

EXAMPLE 213

2-Ethoxyethyl 4-[2-(4-fluorophenyl)-4-oxo-1,3-thiazolidin-3-yl]-3-methylbenzoate Compound 281

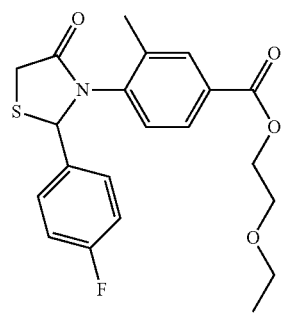

Following standard procedure G, 4-[2-(4-fluorophenyl)-4-oxo-1,3-thiazolidin-3-yl]-3-methylbenzoic acid (0.180 g, 0.540 mmol), 2-ethoxyethanol (0.110 mL, 1.09 mmol), EDCI • HCl (0.210 g, 1.09 mmol), DMAP (0.160 g, 1.36 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 2-ethoxyethyl 4-[2-(4-fluorophenyl)-4-oxo-1,3-thiazolidin-3-yl]-3-methylbenzoate (0.170 g, 78%). 1H NMR (CDCl$_3$, 300 MHz) δ 7.88 (br s, 1H), 7.76 (br d, 1H), 7.33-7.28 (m, 2H), 6.95 (t, 2H), 5.94 (br s, 1H), 4.42 (dd, 2H), 4.00 (d, 1H), 3.91 (d, 1H), 3.72 (dd, 2H), 3.55 (q, 2H), 2.19 (br s, 3H), 1.21 (t, 3H); LC-MS (ACPI) m/z 404.7 [M+H]$^+$.

EXAMPLE 214

2-(2-Ethoxyethoxy)ethyl 4-[2-(4-fluorophenyl)-4-oxo-1,3-thiazolidin-3-yl]-3-methylbenzoate Compound 282

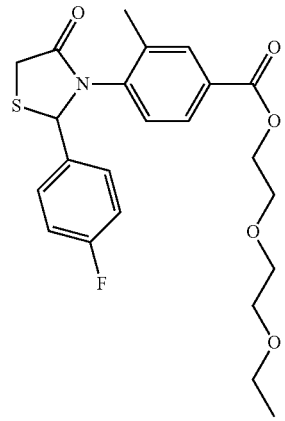

Following standard procedure G, 4-[2-(4-fluorophenyl)-4-oxo-1,3-thiazolidin-3-yl]-3-methylbenzoic acid (0.180 g, 0.540 mmol), 2-(2-ethoxyethoxy)ethanol (0.150 mL, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (30% ethyl acetate in n-hexane) to give 2-(2-ethoxyethoxy)ethyl 4-[2-(4-fluorophenyl)-4-oxo-1,3-thiazolidin-3-yl]-3-methylbenzoate (0.200 g, 82%). 1H NMR (CDCl$_3$, 400 MHz) δ 7.88 (br s, 1H), 7.76 (br s, 1H), 7.30 (dd, 2H), 6.95 (t, 2H), 5.96 (br s, 1H), 4.44-4.42 (m, 2H), 4.00 (d, 1H), 3.91 (d, 1H), 3.81-3.78 (m, 2H), 3.69-3.64 (m, 2H), 3.61-3.57 (m, 2H), 3.55-3.48 (m, 2H), 2.19 (br s, 3H), 1.20-1.16 (m, 3H); LC-MS (ACPI) m/z 448.7 [M+H]$^+$.

EXAMPLE 215

3-Methoxy-3-methylbutyl 4-[2-(4-fluorophenyl)-4-oxo-1,3-thiazolidin-3-yl]-3-methylbenzoate Compound 283

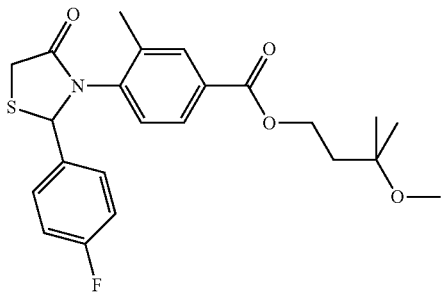

Following standard procedure G, 4-[2-(4-fluorophenyl)-4-oxo-1,3-thiazolidin-3-yl]-3-methylbenzoic acid (0.180 g, 0.540 mmol), 3-methoxy-3-methyl-1-butanol (0.140 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 3-methoxy-3-methylbutyl 4-[2-(4-fluorophenyl)-4-oxo-1,3-thiazolidin-3-yl]-3-methylbenzoate (0.170 g, 72%). 1H NMR (CDCl$_3$, 300 MHz) δ 7.85 (br s, 1H), 7.75 (br d, 1H), 7.33-7.28 (m, 2H), 6.95 (t, 2H), 5.95 (br, 1H), 4.37 (t, 2H), 4.01 (d, 1H), 3.91 (d, 1H), 3.21 (s, 3H), 2.19 (br s, 3H), 1.92 (t, 2H), 1.23 (s, 6H); LC-MS (ESI) m/z 454.3 [M+Na]$^+$.

EXAMPLE 216

3-(Trimethylsilyl)propyl 4-[2-(4-fluorophenyl)-4-oxo-1,3-thiazolidin-3-yl]-3-methylbenzoate Compound 284

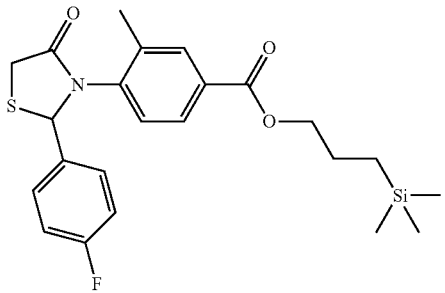

Following standard procedure G, 4-[2-(4-fluorophenyl)-4-oxo-1,3-thiazolidin-3-yl]-3-methylbenzoic acid (0.180 g, 0.540 mmol), 3-(trimethylsilyl)-1-propanol (0.170 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-20% ethyl acetate in n-hexane) to give 3-(trimethylsilyl)propyl 4-[2-(4-fluorophenyl)-4-oxo-1,3-thiazolidin-3-yl]-3-methylbenzoate (0.180 g, 74%). 1H NMR (CDCl$_3$, 400 MHz) δ 7.86 (br s, 1H), 7.75 (br s, 1H), 7.32-7.29 (m, 2H), 6.95 (t, 2H), 5.96 (br s, 1H), 4.22 (t, 2H), 4.00 (d, 1H), 3.91 (d, 1H), 2.19 (br s, 3H), 1.74-1.66 (m, 2H), 0.55-0.51 (m, 2H), 0.00 (s, 9H); LC-MS (ESI) m/z 446.2 [M+H].

EXAMPLE 217

1-Butoxy-1-oxo-2-propanyl 4-[2-(4-fluorophenyl)-4-oxo-1,3-thiazolidin-3-yl]-3-methylbenzoate Compound 285

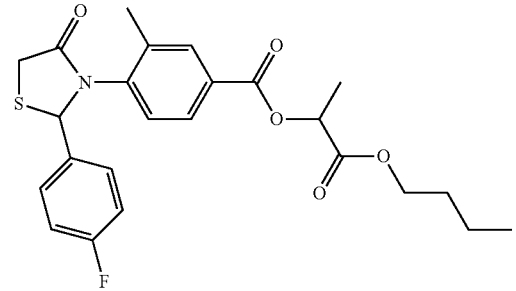

Following standard procedure G, 4-[2-(4-fluorophenyl)-4-oxo-1,3-thiazolidin-3-yl]-3-methylbenzoic acid (0.180 g, 0.540 mmol), butyl lactate (0.160 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 1-butoxy-1-oxo-2-propanyl 4-[2-(4-fluorophenyl)-4-oxo-1,3-thiazolidin-3-yl]-3-methylbenzoate (0.230 g, 92%). 1H NMR (CDCl$_3$, 400 MHz) δ 7.90 (br s, 1H), 7.79 (br s, 1H), 7.32-7.28 (m, 2H), 6.98 (t, 2H), 5.93 (br s, 1H), 5.26 (q, 1H), 4.18 (t, 2H), 4.00 (d, 1H), 3.92 (d, 1H), 2.20 (br s, 3H), 1.64-1.57 (m, 5H), 1.35 (sextet, 2H), 0.90 (t, 3H); LC-MS (ACPI) m/z 460.5 [M+H]$^+$.

EXAMPLE 218

2,2,2-Trifluoroethyl 4-[2-(4-fluorophenyl)-4-oxo-1,3-thiazolidin-3-yl]-3-methylbenzoate

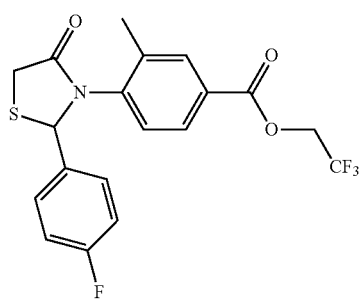

Compound 286

Following standard procedure G, 4-[2-(4-fluorophenyl)-4-oxo-1,3-thiazolidin-3-yl]-3-methylbenzoic acid (0.120 g, 0.362 mmol), 2,2,2-trifluoroethanol (52.0 µL, 0.725 mmol), EDCI • HCl (139 mg, 0.725 mmol), DMAP (110 mg, 0.906 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-5% MeOH in CH$_2$Cl$_2$) to give 2,2,2-trifluoroethyl 4-[2-(4-fluorophenyl)-4-oxo-1,3-thiazolidin-3-yl]-3-methylbenzoate (86.1 mg, 58%). 1H NMR (CDCl$_3$, 300 MHz) δ 7.90 (br s, 1H), 7.78 (br d, 1H), 7.31 (dd, 2H), 6.97 (t, 2H), 5.98 (br s, 1H), 4.65 (q, 2H), 4.01 (d, 1H), 3.92 (d, 1H), 2.22 (br s, 3H); LC-MS (APCI) m/z 414.9 [M+H]$^+$.

EXAMPLE 219

2-(Acetylamino)ethyl 4-[2-(4-fluorophenyl)-4-oxo-1,3-thiazolidin-3-yl]-3-methylbenzoate

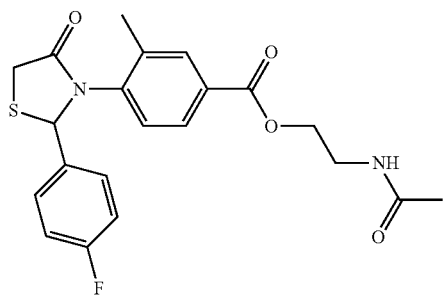

Compound 287

Following standard procedure G, 4-[2-(4-fluorophenyl)-4-oxo-1,3-thiazolidin-3-yl]-3-methylbenzoic acid (0.180 g, 0.540 mmol), N-acetylethanolamine (0.100 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (3% MeOH in CH$_2$Cl$_2$) to give 2-(acetylamino)ethyl 4-[2-(4-fluorophenyl)-4-oxo-1,3-thiazolidin-3-yl]-3-methylbenzoate (0.180 g, 80%). 1H NMR (CDCl$_3$, 400 MHz) δ 7.86 (br s, 1H), 7.74 (br s, 1H), 7.33-7.29 (m, 2H), 6.96 (t, 2H), 5.93 (br s, 1H), 5.79 (br s, 1H), 4.38-4.35 (m, 2H), 4.00 (d, 1H), 3.92 (d, 1H), 3.61 (q, 2H), 2.21 (br s, 3H), 1.98 (s, 3H); LC-MS (ACPI) m/z 417.7 [M+H]$^+$.

EXAMPLE 220

2-[2-(Acetylamino)ethoxy]ethyl 4-[2-(4-fluorophenyl)-4-oxo-1,3-thiazolidin-3-yl]-3-methylbenzoate

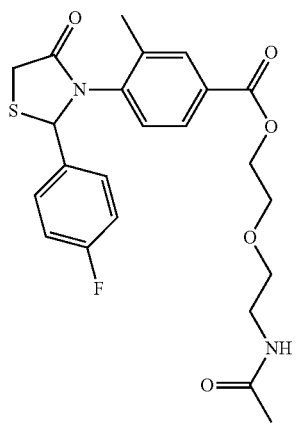

Compound 288

Step 1. Synthesis of N-[2-(2-hydroxyethoxy)ethyl]acetamide

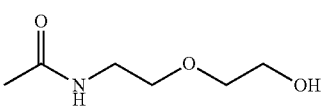

Compound 289

To a solution of 2-(2-aminoethoxy)ethanol (0.480 mL, 4.76 mmol) and acetic anhydride (0.450 mL, 4.76 mmol) in CH$_2$Cl$_2$ (10.0 mL) was stirred at room temperature for 5 h. The reaction mixture was extracted with CH$_2$Cl$_2$. The water layer was concentrated. The residue was used directly for next step without further purification. 1H NMR (CDCl$_3$, 400 MHz) δ 6.25 (br s, 1H), 3.74 (dd, 2H), 3.58-3.55 (m, 4H), 3.47-3.43 (m, 2H), 1.98 (s, 3H).

Step 2. Synthesis of 2-[2-(acetylamino)ethoxy]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.540 mmol), N-[2-(2-hydroxyethoxy)ethyl]acetamide (0.160 g, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (3% MeOH in CH$_2$Cl$_2$) to give 2-[2-(acetylamino)ethoxy]ethyl 4-[2-(4-fluorophenyl)-4-oxo-1,3-thiazolidin-3-yl]-3-methylbenzoate (0.230 g, 92%). 1H NMR (CDCl$_3$, 300 MHz) δ 7.87 (br s, 1H), 7.75 (br d, 1H), 7.32-7.28 (m, 2H), 6.96 (t, 2H), 5.88 (br s, 1H), 4.44 (dd, 2H), 4.00 (d, 1H), 3.91 (d, 1H), 3.77-3.74 (m, 2H), 3.57 (dd, 2H), 3.46-3.40 (m, 2H), 2.20 (br s, 3H), 1.92 (s, 3H); LC-MS (ACPI) m/z 461.7 [M+H]⁺.

EXAMPLE 221

2-(Dimethylamino)ethyl 4-[2-(4-fluorophenyl)-4-oxo-1,3-thiazolidin-3-yl]-3-methylbenzoate Compound 290

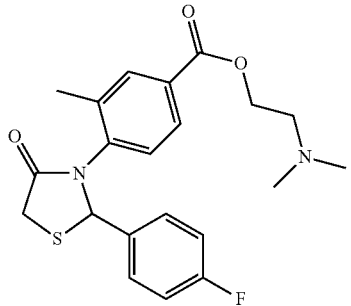

To a solution of 4-[2-(4-fluorophenyl)-4-oxo-1,3-thiazolidin-3-yl]-3-methylbenzoic acid (139 mg, 0.421 mmol) in CH$_2$Cl$_2$ (5.0 mL) was added 2-(dimethylamino)ethanol (84.0 µL, 0.840 mmol) and EDCI • HCl (121 mg, 0.631 mmol) at room temperature. After the reaction mixture was stirred for 20 h, it was diluted with CH$_2$Cl$_2$ and washed with water. The organic layer was dried over MgSO$_{4(s)}$, filtered, and concentrated. The residue was purified by Isco Combi-Flash Companion column chromatography (0-20% MeOH in CH$_2$Cl$_2$) to give 2-(dimethylamino)ethyl 4-[2-(4-fluorophenyl)-4-oxo-1,3-thiazolidin-3-yl]-3-methylbenzoate (63.6 mg, 38%) as a colorless gum. 1H NMR (CDCl$_3$, 400 MHz) δ 7.86 (br s, 1H), 7.74 (br s, 1H), 7.29 (dd, 2H), 6.95 (br t, 2H), 6.10-5.80 (br, 1H), 4.37 (t, 2H), 4.00 (d, 1H), 3.92 (d, 1H), 2.67 (t, 2H), 2.30 (s, 6H), 2.17 (br s, 3H); LC-MS (ESI) m/z 403.3 [M+H]⁺.

EXAMPLE 222

3-(Dimethylamino)propyl 4-[2-(4-fluorophenyl)-4-oxo-1,3-thiazolidin-3-yl]-3-methylbenzoate Compound 291

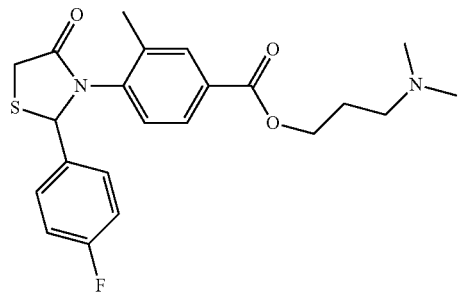

Following standard procedure K, 4-[2-(4-fluorophenyl)-4-oxo-1,3-thiazolidin-3-yl]-3-methylbenzoic acid (100 mg, 0.302 mmol), 3-(dimethylamino)propan-1-ol (39.0 µL, 0.332 mmol), HBTU (170 mg, 0.453 mmol), triethylamine (92.0 µL, 0.664 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (5% MeOH in CH$_2$Cl$_2$) to give 3-(dimethylamino)propyl 4-[2-(4-fluorophenyl)-4-oxo-1,3-thiazolidin-3-yl]-3-methylbenzoate (81.2 mg, 65%). 1H NMR (CDCl$_3$, 400 MHz) δ 7.85 (br s, 1H), 7.73 (br s, 1H), 7.32-7.29 (m, 2H), 6.95 (t, 2H), 5.97 (br s, 1H), 4.31 (t, 2H), 4.00 (d, 1H), 3.91 (d, 1H), 2.40 (dd, 2H), 2.24 (s, 6H), 2.20 (br s, 3H), 1.90 (quint, 2H); LC-MS (ESI) m/z 417.1 [M+H]⁺.

EXAMPLE 223

2-(Diethylamino)ethyl 4-[2-(4-fluorophenyl)-4-oxo-1,3-thiazolidin-3-yl]-3-methylbenzoate Compound 292

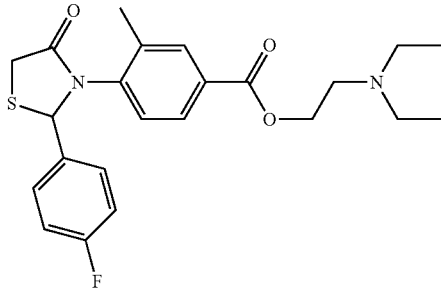

Following standard procedure K, 4-[2-(4-fluorophenyl)-4-oxo-1,3-thiazolidin-3-yl]-3-methylbenzoic acid (100 mg, 0.302 mmol), 2-(diethylamino)ethan-1-ol (65.0 µL, 0.604 mmol), HBTU (170 mg, 0.453 mmol), triethylamine (93.0 µL, 0.664 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (10% MeOH in CH$_2$Cl$_2$) to give 2-(diethylamino)ethyl 4-[2-(4-fluorophenyl)-4-oxo-1,3-thiazolidin-3-yl]-3-methylbenzoate (40.1 mg, 31%). 1H NMR (CDCl$_3$, 400 MHz) δ 7.86 (br s, 1H), 7.75 (br s, 1H), 7.32-7.28 (m, 2H), 6.95 (t, 2H), 5.96 (br s, 1H), 4.34 (t, 2H), 4.00 (d, 1H), 3.91 (d, 1H), 2.80 (t, 2H), 2.60 (q, 4H), 2.19 (br s, 3H), 1.04 (t, 6H); LC-MS (APCI) m/z 431.8 [M+H]⁺.

EXAMPLE 224

2-[Ethyl(phenyl)amino]ethyl 4-[2-(4-fluorophenyl)-4-oxo-1,3-thiazolidin-3-yl]-3-methylbenzoate Compound 293

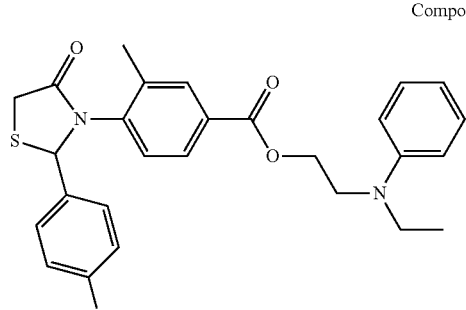

Following standard procedure G, 4-[2-(4-fluorophenyl)-4-oxo-1,3-thiazolidin-3-yl]-3-methylbenzoic acid (0.180 g, 0.540 mmol), 2-(N-ethylanilino)ethanol (0.180 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 2-[ethyl(phenyl)amino]ethyl 4-[2-(4-fluorophenyl)-4-oxo-1,3-thiazolidin-3-yl]-3-methylbenzoate (0.260 g, 99%). 1H NMR (CDCl$_3$, 300 MHz) δ 7.82 (br s, 1H), 7.71 (br d, 1H), 7.33-7.28 (m, 2H), 7.22 (t, 2H), 6.96 (t, 2H), 6.80-6.74 (m, 2H), 6.68 (t, 1H), 5.95 (br s, 1H), 4.42 (t, 2H), 4.01 (d, 1H), 3.92 (d, 1H), 3.65 (t, 2H), 3.42 (q, 2H), 2.18 (br s, 3H), 1.17 (t, 3H); LC-MS (ACPI) m/z 479.7 [M+H]$^+$.

EXAMPLE 225

2-(1-Pyrrolidinyl)ethyl 4-[2-(4-fluorophenyl)-4-oxo-1,3-thiazolidin-3-yl]-3-methylbenzoate Compound 294

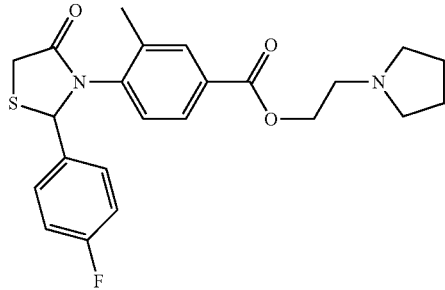

Following standard procedure K, 4-[2-(4-fluorophenyl)-4-oxo-1,3-thiazolidin-3-yl]-3-methylbenzoic acid (100 mg, 0.302 mmol), 2-(pyrrolidin-1-yl)ethan-1-ol (38.0 mg, 0.332 mmol), HBTU (170 mg, 0.453 mmol), triethylamine (92.6 µL, 0.664 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (5% MeOH in CH$_2$Cl$_2$) to give 2-(1-pyrrolidinyl)ethyl 4-[2-(4-fluorophenyl)-4-oxo-1,3-thiazolidin-3-yl]-3-methylbenzoate (33.0 mg, 26%). 1H NMR (CDCl$_3$, 300 MHz) δ 7.86 (br s, 1H), 7.80-7.70 (br, 1H), 7.32-7.28 (m, 2H), 7.15-6.92 (m, 3H), 5.94 (br s, 1H), 4.41 (t, 2H), 4.00 (d, 1H), 3.91 (d, 1H), 2.83 (t, 2H), 2.68-2.55 (m, 4H), 2.19 (br s, 3H), 1.84-1.76 (br, 4H); LC-MS (APCI) m/z 428.9 [M+H]$^+$.

EXAMPLE 226

2-(1-Piperidinyl)ethyl 4-[2-(4-fluorophenyl)-4-oxo-1, 3-thiazolidin-3-yl]-3-methylbenzoate Compound 295

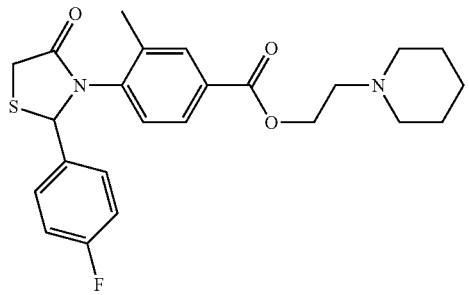

Following standard procedure K, 4-[2-(4-fluorophenyl)-4-oxo-1,3-thiazolidin-3-yl]-3-methylbenzoic acid (120 mg, 0.362 mmol), 2-(piperidin-1-yl)ethan-1-ol (96.0 µL, 0.725 mmol), HBTU (210 mg, 0.544 mmol), triethylamine (0.11 mL, 0.797 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (10% MeOH in CH$_2$Cl$_2$) to give 2-(1-piperidinyl)ethyl 4-[2-(4-fluorophenyl)-4-oxo-1,3-thiazolidin-3-yl]-3-methylbenzoate (9.9 mg, 6%). 1H NMR (CDCl$_3$, 400 MHz) δ 7.85 (br s, 1H), 7.74 (br s, 1H), 7.32-7.29 (m, 2H), 6.95 (t, 2H), 5.93 (br s, 1H), 4.40 (t, 2H), 4.01 (d, 1H), 3.92 (d, 1H), 2.71 (t, 2H), 2.55-2.42 (br, 4H), 2.20 (br s, 3H), 1.61-1.55 (m, 4H), 1.45-1.42 (m, 2H); LC-MS (APCI) m/z 443.7 [M+H]$^+$.

EXAMPLE 227

2-(4-Morpholinyl)ethyl 4-[2-(4-fluorophenyl)-4-oxo-1, 3-thiazolidin-3-yl]-3-methylbenzoate Compound 296

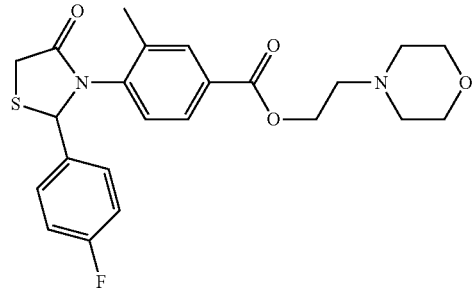

Following standard procedure G, 4-[2-(4-fluorophenyl)-4-oxo-1,3-thiazolidin-3-yl]-3-methylbenzoic acid (0.100 g, 0.302 mmol), 2-morpholinoethanol (89.0 µL, 0.398 mmol), EDCI • HCl (86.8 mg, 0.453 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (10% MeOH in CH$_2$Cl$_2$) to give 2-(4-morpholinyl)ethyl 4-[2-(4-fluorophenyl)-4-oxo-1,3-thiazolidin-3-yl]-3-methylbenzoate (12.0 mg, 9%). 1H NMR (CDCl$_3$, 300 MHz) δ 7.85 (br s, 1H), 7.80-7.70 (br, 1H), 7.33-7.26 (m, 2H), 6.98-6.93 (m, 3H), 5.94 (br s, 1H), 4.40 (t, 2H), 4.00 (d, 1H), 3.91 (d, 1H), 3.75-3.62 (m, 4H), 2.72 (t, 2H), 2.59-2.47 (m, 4H), 2.20 (br s, 3H); LC-MS (APCI) m/z 445.8 [M+H]$^+$.

EXAMPLE 228

3-(4-Morpholinyl)propyl 4-[2-(4-fluorophenyl)-4-oxo-1,3-thiazolidin-3-yl]-3-methylbenzoate Compound 297

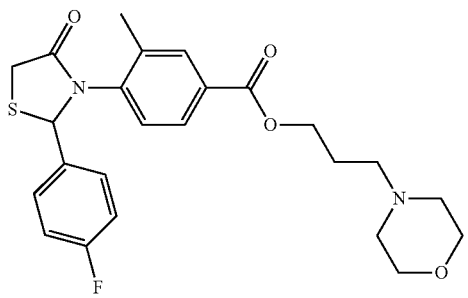

To a solution of 4-[2-(4-fluorophenyl)-4-oxo-1,3-thiazolidin-3-yl]-3-methylbenzoic acid (191 mg, 0.576 mmol) in CH$_2$Cl$_2$ (5.0 mL) was added 3-(4-morpholinyl)-1-propanol (200 µL, 1.44 mmol) and EDCI • HCl (166 mg, 0.866 mmol) at room temperature. After the reaction mixture was stirred for 18 h, it was diluted with CH$_2$Cl$_2$ and washed with water. The organic layer was dried over MgSO$_{4(s)}$, filtered, and concentrated. The residue was purified by Isco Combi-Flash Companion column chromatography (0-5% MeOH in CH$_2$Cl$_2$) to give 3-(4-morpholinyl)propyl 4-[2-(4-fluorophenyl)-4-oxo-1,3-thiazolidin-3-yl]-3-methylbenzoate (105 mg, 40%) as a lightly yellow solid. 1H NMR (CDCl$_3$, 400 MHz) δ 7.85 (br s, 1H), 7.73 (br s, 1H), 7.33-7.29 (m, 2H), 6.96 (br t, 2H), 6.10-5.80 (br, 1H), 4.36-4.32 (m, 2H), 4.00 (d, 1H), 3.91 (d, 1H), 3.81 (br s, 4H), 2.61 (br s, 6H), 2.19 (br s, 3H), 2.05 (br s, 2H); LC-MS (ESI) m/z 459.3 [M+H]$^+$.

EXAMPLE 229

3-(1-Piperidinyl)propyl 4-[2-(4-fluorophenyl)-4-oxo-1,3-thiazolidin-3-yl]-3-methylbenzoate Compound 298

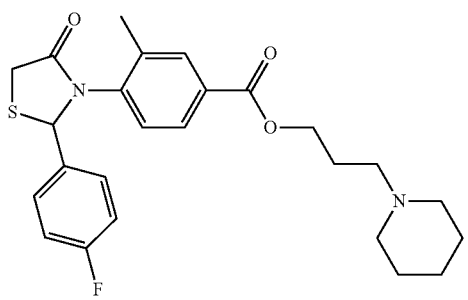

To a solution of 4-[2-(4-fluorophenyl)-4-oxo-1,3-thiazolidin-3-yl]-3-methylbenzoic acid (191 mg, 0.576 mmol) in CH$_2$Cl$_2$ (5.0 mL) was added 1-piperidinepropanol (210 µL, 1.39 mmol) and EDCI • HCl (160 mg, 0.832 mmol) at room temperature. After the reaction mixture was stirred for 20 h, it was diluted with CH$_2$Cl$_2$ and washed with water. The organic layer was dried over MgSO$_{4(s)}$, filtered, and concentrated. The residue was purified by Isco Combi-Flash Companion column chromatography (0-10% MeOH in CH$_2$Cl$_2$) to give 3-(1-piperidinyl)propyl 4-[2-(4-fluorophenyl)-4-oxo-1,3-thiazolidin-3-yl]-3-methylbenzoate (102 mg, 40%) as a yellow gum. 1H NMR (CDCl$_3$, 400 MHz) δ 7.85 (br s, 1H), 7.72 (br s, 1H), 7.32-7.28 (m, 2H), 6.95 (br t, 2H), 6.10-5.80 (br, 1H), 4.32-4.29 (m, 2H), 4.00 (d, 1H), 3.91 (d, 1H), 2.43-2.38 (m, 6H), 2.20 (br s, 3H), 1.92 (quint, 2H), 1.65-1.54 (m, 4H), 1.45-1.41 (m, 2H); LC-MS (ESI) m/z 457.3 [M+H]$^+$.

EXAMPLE 230

2-(1-Acetyl-4-piperidinyl)ethyl 4-[2-(4-fluorophenyl)-4-oxo-1,3-thiazolidin-3-yl]-3-methylbenzoate Compound 299

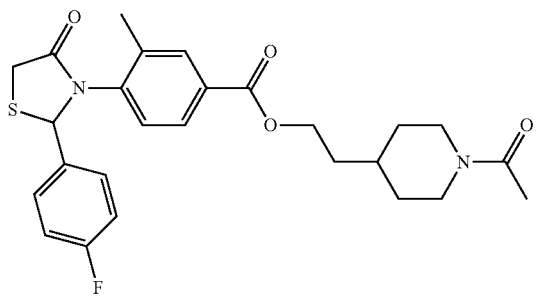

Following standard procedure G, 4-[2-(4-fluorophenyl)-4-oxo-1,3-thiazolidin-3-yl]-3-methylbenzoic acid (136 mg, 0.410 mmol), DMAP (75.1 mg, 0.615 mmol), EDCI • HCl (118 mg, 0.614 mmol), 1-[4-(2-hydroxyethyl)-1-piperidinyl]-ethanone (84.2 mg, 0.492 mmol), and CH$_2$Cl$_2$ (5.0 mL) were used to carry out the reaction. After the reaction was stirred for 20 h and work-up, the residue was purified by Isco Combi-Flash Companion column chromatography (0-5% MeOH in CH$_2$Cl$_2$) to give 2-(1-acetyl-4-piperidinyl)ethyl 4-[2-(4-fluorophenyl)-4-oxo-1,3-thiazolidin-3-yl]-3-methylbenzoate (71.5 mg, 36%) as a colorless gum. 1H NMR (CDCl$_3$, 400 MHz) δ 7.84 (br s, 1H), 7.73 (br s, 1H), 7.31 (dd, 2H), 6.96 (br t, 2H), 6.10-5.80 (br, 1H), 4.36-4.30 (m, 2H), 4.01 (d, 1H), 3.92 (d, 1H), 3.00-2.60 (br, 2H), 2.30-2.00 (m, 9H), 1.82-1.76 (m, 2H), 1.72-1.68 (m, 2H), 1.23-1.14 (m, 2H); LC-MS (ESI) m/z 507.1 [M+Na]$^+$.

EXAMPLE 231

1-Methyl-3-pyrrolidinyl 4-[2-(4-fluorophenyl)-4-oxo-1,3-thiazolidin-3-yl]-3-methylbenzoate Compound 300

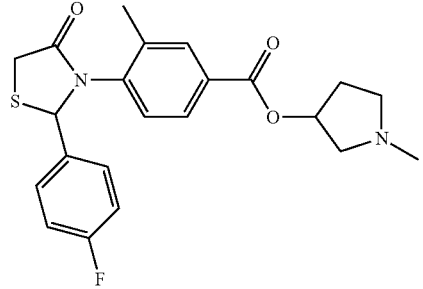

Following standard procedure K, 4-[2-(4-fluorophenyl)-4-oxo-1,3-thiazolidin-3-yl]-3-methylbenzoic acid (100 mg, 0.302 mmol), 1-methylpyrrolidin-3-ol (66.0 μL, 0.604 mmol), HBTU (170 mg, 0.453 mmol), triethylamine (93.0 μL, 0.664 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 1-methyl-3-pyrrolidinyl 4-[2-(4-fluorophenyl)-4-oxo-1,3-thiazolidin-3-yl]-3-methylbenzoate (10.8 mg, 8%). 1H NMR (CDCl$_3$, 400 MHz) δ 7.86 (br s, 1H), 7.74 (br s, 1H), 7.31-7.28 (m, 2H), 6.94 (t, 2H), 5.96 (br s, 1H), 5.36 (br, 1H), 3.99 (d, 1H), 3.91 (d, 1H), 2.87-2.72 (m, 3H), 2.40-2.30 (m, 4H), 2.17 (br s, 3H), 2.00-1.92 (m, 2H); LC-MS (APCI) m/z 415.9 [M+H]$^+$.

EXAMPLE 232

1-Methyl-4-piperidinyl 4-[2-(4-fluorophenyl)-4-oxo-1,3-thiazolidin-3-yl]-3-methylbenzoate

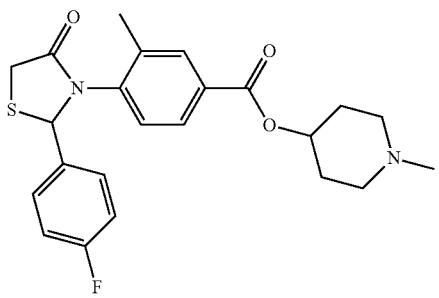

Compound 301

Following standard procedure K, 4-[2-(4-fluorophenyl)-4-oxo-1,3-thiazolidin-3-yl]-3-methylbenzoic acid (100 mg, 0.302 mmol), 1-methylpiperidin-4-ol (38.0 mg, 0.332 mmol), HBTU (170 mg, 0.453 mmol), triethylamine (92.0 μL, 0.664 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (5% MeOH in CH$_2$Cl$_2$) to give 1-methyl-4-piperidinyl 4-[2-(4-fluorophenyl)-4-oxo-1,3-thiazolidin-3-yl]-3-methylbenzoate (48.1 mg, 37%). 1H NMR (CDCl$_3$, 400 MHz) δ 7.85 (br s, 1H), 7.74 (br s, 1H), 7.33-7.29 (m, 2H), 6.96 (br t, 2H), 5.98 (br s, 1H), 5.01-4.99 (m, 1H), 4.00 (d, 1H), 3.91 (d, 1H), 2.69 (br s, 2H), 2.36 (br s, 2H), 2.32 (s, 3H), 2.20 (br s, 3H), 2.00-1.96 (m, 2H), 1.87-1.79 (m, 2H); LC-MS (ESI) m/z 429.1 [M+H]$^+$.

EXAMPLE 233

(1-Methyl-3-piperidinyl)methyl 4-[2-(4-fluorophenyl)-4-oxo-1,3-thiazolidin-3-yl]-3-methylbenzoate

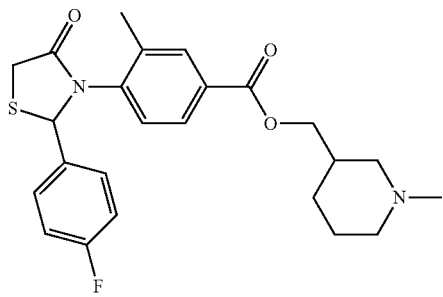

Compound 302

Following standard procedure G, 4-[2-(4-fluorophenyl)-4-oxo-1,3-thiazolidin-3-yl]-3-methylbenzoic acid (0.180 g, 0.540 mmol), 3-(hydroxymethyl)-1-methylpiperidine (0.150 mL, 1.09 mmol), EDCI • HCl (0.210 g, 1.09 mmol), DMAP (0.150 g, 1.20 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-20% ethyl acetate in n-hexane) to give (1-methyl-3-piperidinyl)methyl 4-[2-(4-fluorophenyl)-4-oxo-1,3-thiazolidin-3-yl]-3-methylbenzoate (0.240 g, 99%). 1H NMR (CDCl$_3$, 400 MHz) δ 7.84 (br s, 1H), 7.72 (br s, 1H), 7.34-7.31 (m, 2H), 6.97 (t, 2H), 5.98 (br s, 1H), 4.28-4.13 (m, 2H), 4.01 (d, 1H), 3.92 (d, 1H), 3.35 (br, 2H), 2.68 (br s, 3H), 2.58-2.30 (br, 3H), 2.21 (br s, 3H), 1.91 (t, 2H), 1.27-1.20 (m, 2H); LC-MS (ESI) m/z 443.4 [M+H]$^+$.

EXAMPLE 234

2-(2-Aminoethoxy)ethyl 4-[2-(4-fluorophenyl)-4-oxo-1,3-thiazolidin-3-yl]-3-methylbenzoate

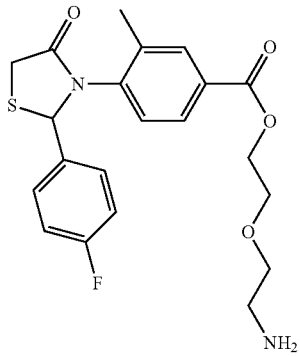

Compound 303

Step 1. Synthesis of 2-methyl-2-propanyl [2-(2-hydroxyethoxy)ethyl]carbamate

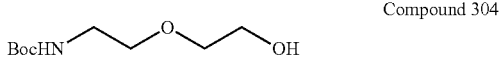 [SMILES: CC(C)(C)OC(=O)NCCOCCO]

Compound 304

To a solution of diethylene glycolamine (0.480 mL, 4.76 mmol) and di-tert-butyl dicarbonate (1.04 g, 4.76 mmol) in CH$_2$Cl$_2$ (5.0 mL) was stirred at room temperature for 2 h. The result mixture was extracted with CH$_2$Cl$_2$, dried over MgSO$_{4(s)}$, filtered, and concentrated. The residue was used directly for next step without further purification. 1H NMR (CDCl$_3$, 400 MHz) δ 5.03 (br s, 1H), 3.72 (br, 2H), 3.58-3.52 (m, 4H), 3.33-3.31 (br, 2H), 1.44 (s, 9H).

Step 2. Synthesis of 2-[2-({[(2-methyl-2-propanyl)oxy]carbonyl}amino)ethoxy]ethyl 4-[2-(4-fluorophenyl)-4-oxo-1,3-thiazolidin-3-yl]-3-methylbenzoate

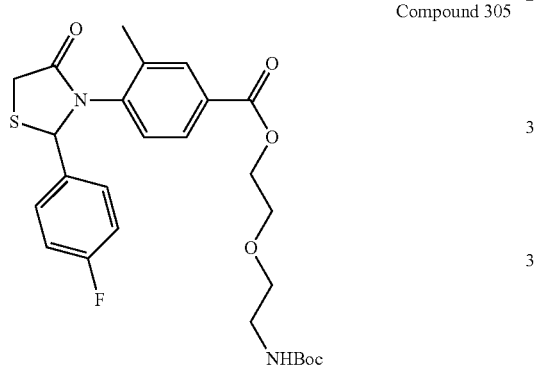

Compound 305

Following standard procedure G, 4-[2-(4-fluorophenyl)-4-oxo-1,3-thiazolidin-3-yl]-3-methylbenzoic acid (0.200 g, 0.604 mmol), 2-methyl-2-propanyl [2-(2-hydroxyethoxy)ethyl]carbamate (0.250 g, 1.21 mmol), EDCI • HCl (0.230 g, 1.21 mmol), DMAP (0.160 g, 1.33 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-[2-({[(2-methyl-2-propanyl)oxy]carbonyl}amino)ethoxy]ethyl 4-[2-(4-fluorophenyl)-4-oxo-1,3-thiazolidin-3-yl]-3-methylbenzoate (0.300 g, 96%). 1H NMR (CDCl$_3$, 400 MHz) δ 7.87 (br s, 1H), 7.76 (br s, 1H), 7.33-7.28 (m, 2H), 6.95 (t, 2H), 5.94 (br s, 1H), 4.89 (br s, 1H), 4.45-4.40 (m, 2H), 4.00 (d, 1H), 3.91 (d, 1H), 3.74 (t, 2H), 3.58-3.54 (m, 4H), 2.20 (br s, 3H), 1.43 (s, 9H).

Step 3. Synthesis of 2-(2-aminoethoxy)ethyl 4-[2-(4-fluorophenyl)-4-oxo-1,3-thiazolidin-3-yl]-3-methylbenzoate To a solution of 2-[2-({[(2-methyl-2-propanyl)oxy]carbonyl}amino)ethoxy]ethyl 4-[2-(4-fluorophenyl)-4-oxo-1,3-thiazolidin-3-yl]-3-methylbenzoate (0.350 g) and TFA (0.250 mL) in CH$_2$Cl$_2$ (10.0 mL) was stirred at room temperature for 3 h. To the reaction mixture was added saturated NaHCO$_{3(aq)}$ to adjust the pH value to above 8 and extracted with CH$_2$Cl$_2$. The organic layers were dried over MgSO$_{4(s)}$, filtered and concentrated. The residue was purified by Isco Combi-Flash Companion column chromatography (10% MeOH in CH$_2$Cl$_2$) to give 2-(2-aminoethoxy)ethyl 4-[2-(4-fluorophenyl)-4-oxo-1,3-thiazolidin-3-yl]-3-methylbenzoate (32.7 mg, 12%). 1H NMR (CDCl$_3$, 400 MHz) δ 7.86 (br s, 1H), 7.73 (br s, 1H), 7.33-7.29 (m, 2H), 6.95 (t, 2H), 6.81 (br s, 1H), 5.98 (br s, 1H), 4.44 (dd, 2H), 4.00 (d, 1H), 3.92 (d, 1H), 3.78-3.76 (m, 2H), 3.65-3.59 (m, 2H), 3.55 (quint, 2H), 2.21 (br s, 3H).

EXAMPLE 235

2-[2-(Dimethylamino)ethoxy]ethyl 4-[2-(4-fluorophenyl)-4-oxo-1,3-thiazolidin-3-yl]-3-methylbenzoate

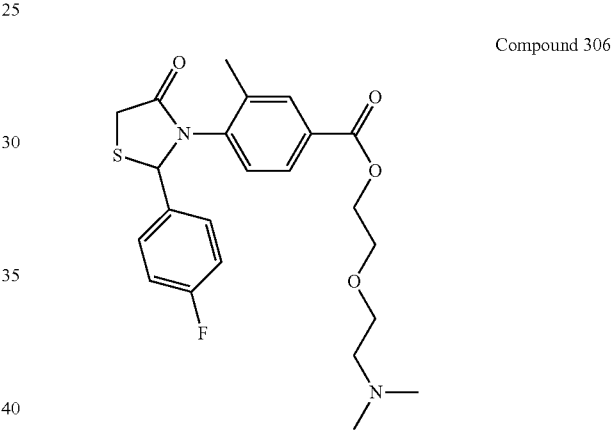

Compound 306

Following standard procedure G, 4-[2-(4-fluorophenyl)-4-oxo-1,3-thiazolidin-3-yl]-3-methylbenzoic acid (0.180 g, 0.540 mmol), 2-[2-(dimethylamino)ethoxy]ethanol (0.150 mL, 1.09 mmol), EDCI • HCl (0.210 g, 1.09 mmol), DMAP (0.160 g, 1.36 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-[2-(dimethylamino)ethoxy]ethyl 4-[2-(4-fluorophenyl)-4-oxo-1,3-thiazolidin-3-yl]-3-methylbenzoate (85.4 mg, 36%). 1H NMR (CDCl$_3$, 400 MHz) δ 7.87 (br s, 1H), 7.76 (br s, 1H), 7.31 (dd, 2H), 6.95 (t, 2H), 5.98 (br s, 1H), 4.43 (t, 2H), 4.00 (d, 1H), 3.92 (d, 1H), 3.76-3.74 (m, 2H), 3.62 (t, 2H), 2.55 (t, 2H), 2.28 (s, 6H), 2.20 (br s, 3H); LC-MS (ESI) m/z 447.4 [M+H]$^+$.

EXAMPLE 236

2-[2-(1-Pyrrolidinyl)ethoxy]ethyl 4-[2-(4-fluorophenyl)-4-oxo-1,3-thiazolidin-3-yl]-3-methylbenzoate

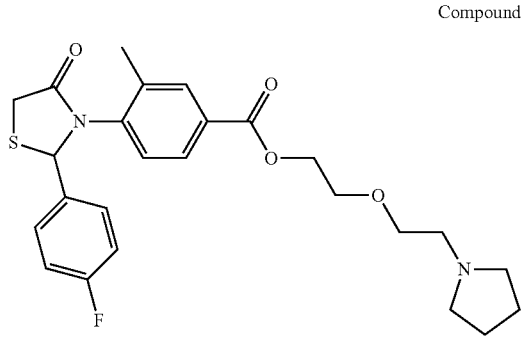
Compound 307

Step 1. Synthesis of 2-[2-(1-pyrrolidinyl)ethoxy]ethanol

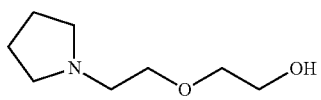
Compound 308

To a solution of pyrrolidine (0.350 mL, 4.01 mmol) and 2-(2-chloroethoxy)ethanol (0.450 mL, 4.01 mmol) in CH$_2$Cl$_2$ (7.0 mL) was stirred at room temperature for 5 h. The reaction mixture was extracted with CH$_2$Cl$_2$. The water layer was concentrated. The residue was used directly for next step without further purification. 1H NMR (CDCl$_3$, 400 MHz) δ 3.83-3.80 (m, 2H), 3.79-3.70 (m, 2H), 3.68-3.58 (m, 2H), 3.33-3.29 (m, 6H), 2.15-2.03 (m, 3H), 1.97 (br s, 1H).

Step 2. Synthesis of 2-[2-(1-pyrrolidinyl)ethoxy]ethyl 4-[2-(4-fluorophenyl)-4-oxo-1,3-thiazolidin-3-yl]-3-methylbenzoate Following standard procedure K, 4-[2-(4-fluorophenyl)-4-oxo-1,3-thiazolidin-3-yl]-3-methylbenzoic acid (275 mg, 1.06 mmol), 2-[2-(1-pyrrolidinyl)ethoxy]ethanol (260 mg, 1.66 mmol), HBTU (470 mg, 1.24 mmol), triethylamine (0.250 mL, 1.83 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-5% MeOH in CH$_2$Cl$_2$) to give 2-[2-(1-pyrrolidinyl)ethoxy]ethyl 4-[2-(4-fluorophenyl)-4-oxo-1,3-thiazolidin-3-yl]-3-methylbenzoate (0.130 g, 33%). 1H NMR (CDCl$_3$, 300 MHz) δ 7.86 (br s, 1H), 7.77 (br s, 1H), 7.33 (dd, 2H), 6.95 (t, 2H), 5.99 (br s, 1H), 4.51-4.42 (m, 2H), 4.00 (d, 1H), 3.94-3.81 (m, 3H), 3.35 (br s, 2H), 3.32-3.29 (m, 2H), 2.20 (br s, 3H), 2.07-1.98 (m, 4H), 1.80-1.49 (br, 4H); LC-MS (ESI) m/z 473.3 [M+H]$^+$.

EXAMPLE 237

1,3-Bis(acetylamino)-2-propanyl 4-[2-(4-fluorophenyl)-4-oxo-1,3-thiazolidin-3-yl]-3-methylbenzoate

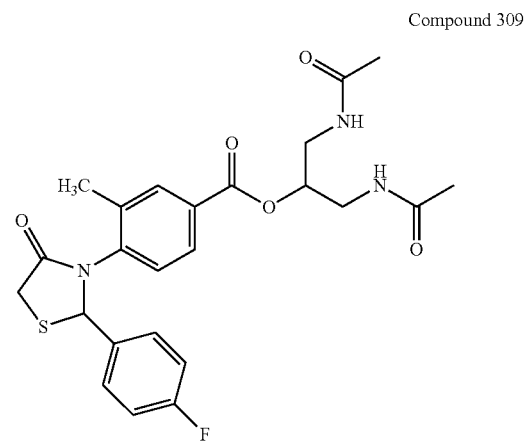 [SMILES: CC(=O)NCC(CNC(C)=O)OC(=O)c1ccc(N2C(=O)CSC2c2ccc(F)cc2)c(C)c1]
Compound 309

Following standard procedure G, 4-[2-(4-fluorophenyl)-4-oxo-1,3-thiazolidin-3-yl]-3-methylbenzoic acid (100 mg, 0.303 mmol), DMAP (92.5 mg, 0.757 mmol), EDCI • HCl (116 mg, 0.605 mmol), 1,3-diacetaminopropan-2-ol (52.8 mg, 0.303 mmol), and CH$_2$Cl$_2$ (3.0 mL) were used to carry out the reaction. After the reaction was stirred for 18 h and work-up, the residue was purified by Isco Combi-Flash Companion column chromatography (0-10% MeOH in ethyl acetate) to give 1,3-bis(acetylamino)-2-propanyl 4-[2-(4-fluorophenyl)-4-oxo-1,3-thiazolidin-3-yl]-3-methyl benzoate (96.8 mg, 66%) as a white solid. 1H NMR (CDCl$_3$, 400 MHz) δ 7.83 (br s, 1H), 7.72 (br, 1H), 7.31 (dd, 2H), 6.97 (br t, 2H), 6.30 (br s, 2H), 6.10-5.80 (br, 1H), 5.01 (quint, 1H), 4.00 (d, 1H), 3.91 (d, 1H), 3.64-3.58 (m, 2H), 3.45-3.38 (m, 2H), 2.17 (br s, 3H), 2.00 (s, 6H); LC-MS (ESI) m/z 488.3 [M+H]$^+$.

EXAMPLE 238

1,3-Bis(acetyloxy)-2-propanyl 4-[2-(4-fluorophenyl)-4-oxo-1,3-thiazolidin-3-yl]-3-methylbenzoate

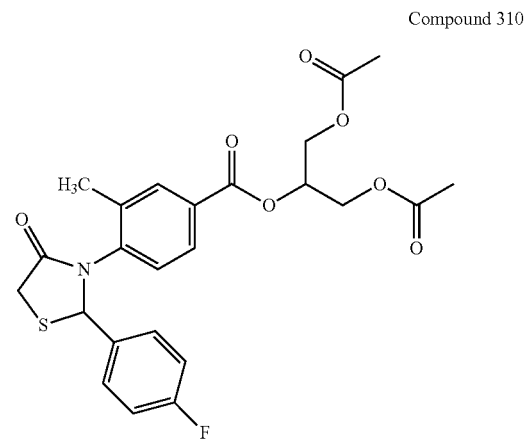 [SMILES: CC(=O)OCC(COC(C)=O)OC(=O)c1ccc(N2C(=O)CSC2c2ccc(F)cc2)c(C)c1]
Compound 310

Following standard procedure G, 4-[2-(4-fluorophenyl)-4-oxo-1,3-thiazolidin-3-yl]-3-methylbenzoic acid (101 mg, 0.304 mmol), DMAP (92.8 mg, 0.760 mmol), EDCI • HCl (117 mg, 0.608 mmol), 1,3-diacetylglycerol (58.9 mg, 0.334 mmol), and $CH_2Cl_2$ (5.0 mL) were used to carry out the reaction. After the reaction was stirred for 18 h and work-up, the residue was purified by Isco Combi-Flash Companion column chromatography (0-70% ethyl acetate in n-hexane) to give 1,3-bis(acetyloxy)-2-propanyl 4-[2-(4-fluorophenyl)-4-oxo-1,3-thiazolidin-3-yl]-3-methylbenzoate (115 mg, 77%) as a gum. 1H NMR ($CDCl_3$, 300 MHz) δ 7.86 (br s, 1H), 7.74 (br d, 1H), 7.32 (dd, 2H), 6.97 (br t, 2H), 5.95 (br s, 1H), 5.45 (quint, 1H), 4.38-4.24 (m, 4H), 4.01 (d, 1H), 3.91 (d, 1H), 2.21 (br s, 3H), 2.05 (s, 6H); LC-MS (ESI) m/z 512.2 $[M+Na]^+$.

EXAMPLE 239

(5-Methyl-2-oxo-1,3-dioxol-4-yl)methyl 4-[2-(4-fluorophenyl)-4-oxo-1,3-thiazolidin-3-yl]-3-methylbenzoate Compound 311

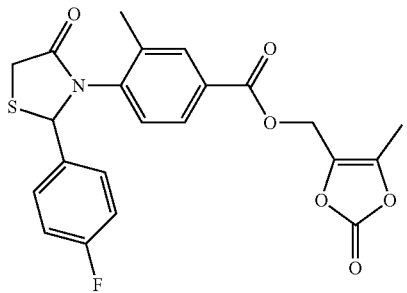

Following standard procedure H, 4-[2-(4-fluorophenyl)-4-oxo-1,3-thiazolidin-3-yl]-3-methylbenzoic acid (159 mg, 0.480 mmol), $K_2CO_3$ (133 mg, 0.960 mmol), 4-chloromethyl-5-methyl-1,3-dioxal-2-one (74.8 mg, 0.504 mmol), and DMF (1.0 mL) were used to carry out the reaction. The desird product was collected by filtered and washed with water and diethyl ether to give (5-methyl-2-oxo-1,3-dioxol-4-yl)methyl 4-[2-(4-fluorophenyl)-4-oxo-1,3-thiazolidin-3-yl]-3-methylbenzoate (145 mg, 68%) as a beige solid. 1H NMR ($CDCl_3$, 400 MHz) δ 7.86 (br s, 1H), 7.75 (br s, 1H), 7.32-7.28 (m, 2H), 6.96 (br t, 2H), 6.10-5.80 (br, 1H), 5.03 (s, 2H), 4.00 (d, 1H), 3.92 (d, 1H), 2.30-2.10 (br, 6H); LC-MS (ESI) m/z 466.2 $[M+Na]^+$.

EXAMPLE 240

1-{[(Cyclohexyloxy)carbonyl]oxy}ethyl 4-[2-(4-fluorophenyl)-4-oxo-1,3-thiazolidin-3-yl]-3-methylbenzoate Compound 312

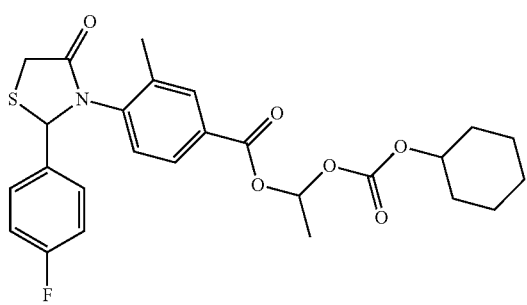

Following standard procedure H, 4-[2-(4-fluorophenyl)-4-oxo-1,3-thiazolidin-3-yl]-3-methylbenzoic acid (167 mg, 0.504 mmol), $K_2CO_3$ (139 mg, 1.01 mmol), 1-chloroethyl cyclohexyl carbonate (0.102 mL, 0.554 mmol), and DMF (1.0 mL) were used to carry out the reaction. The residue was purified by column chromatography (0-25% ethyl acetate in n-hexane) to give 1-{[(cyclohexyloxy)carbonyl]oxy}ethyl 4-[2-(4-fluorophenyl)-4-oxo-1,3-thiazolidin-3-yl]-3-methylbenzoate (214 mg, 85%) as a white solid. 1H NMR ($CDCl_3$, 400 MHz) δ 7.87 (br s, 1H), 7.75 (br s, 1H), 7.30 (dd, 2H), 6.98-6.94 (m, 3H), 6.10-5.80 (br, 1H), 4.62 (quint, 1H), 4.00 (d, 1H), 3.91 (d, 1H), 2.19 (br s, 3H), 1.93-1.90 (m, 2H), 1.75-1.72 (m, 2H), 1.60 (d, 3H), 1.53-1.42 (m, 2H), 1.38-1.22 (m, 4H); LC-MS (ESI) m/z 524.3 $[M+Na]^+$.

EXAMPLE 241

1-[(Ethoxycarbonyl)oxy]ethyl 4-[2-(4-fluorophenyl)-4-oxo-1,3-thiazolidin-3-yl]-3-methylbenzoate Compound 313

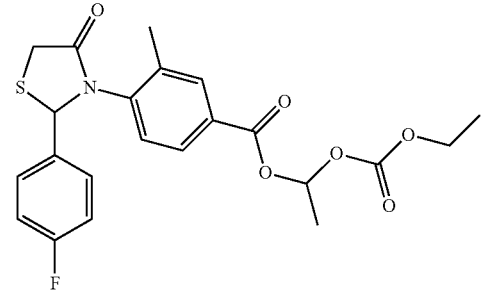

Following standard procedure H, 4-[2-(4-fluorophenyl)-4-oxo-1,3-thiazolidin-3-yl]-3-methylbenzoic acid (163 mg, 0.492 mmol), $K_2CO_3$ (136 mg, 0.984 mmol), 1-chlorodiethyl carbonate (80.0 μL, 0.597 mmol), and DMF (1.0 mL) were used to carry out the reaction. The residue was purified by column chromatography (0-25% ethyl acetate in n-hexane) to give 1-[(ethoxycarbonyl)oxy]ethyl 4-[2-(4-fluorophenyl)-4-oxo-1,3-thiazolidin-3-yl]-3-methylbenzoate (178 mg, 81%) as a lightly yellow solid. 1H NMR ($CDCl_3$, 400 MHz) δ 7.87 (br s, 1H), 7.76 (br s, 1H), 7.30 (dd, 2H), 6.99-6.94 (m, 3H), 6.10-5.80 (br, 1H), 4.21 (q, 2H), 4.00 (d, 1H), 3.91 (d, 1H), 2.20 (br s, 3H), 1.60 (d, 3H), 1.30 (t, 3H); LC-MS (ESI) m/z 470.2 $[M+Na]^+$.

EXAMPLE 242

{[(2-Propanyloxy)carbonyl]oxy}methyl 4-[2-(4-fluorophenyl)-4-oxo-1,3-thiazolidin-3-yl]-3-methylbenzoate Compound 314

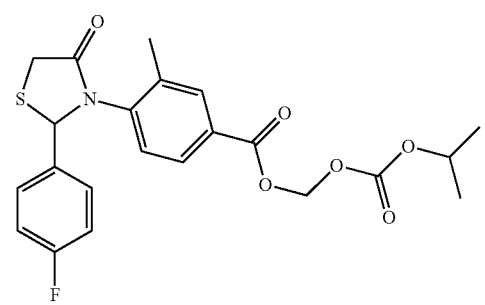

Following standard procedure H, 4-[2-(4-fluorophenyl)-4-oxo-1,3-thiazolidin-3-yl]-3-methylbenzoic acid (168 mg, 0.507 mmol), K$_2$CO$_3$ (140 mg, 1.01 mmol), carbonic acid chloromethyl isopropyl ether (80.0 µL, 0.599 mmol), and DMF (1.0 mL) were used to carry out the reaction. The residue was purified by column chromatography (0-30% ethyl acetate in n-hexane) to give {[(2-propanyloxy)carbonyl]oxy}methyl 4-[2-(4-fluorophenyl)-4-oxo-1,3-thiazolidin-3-yl]-3-methylbenzoate (169 mg, 74%) as a yellow solid. 1H NMR (CDCl$_3$, 400 MHz) δ 7.90 (br s, 1H), 7.77 (br s, 1H), 7.31 (dd, 2H), 6.96 (br t, 2H), 6.10-5.80 (br, 3H), 4.92 (septet, 1H), 4.00 (d, 1H), 3.92 (d, 1H), 2.20 (br s, 3H), 1.31 (d, 6H); LC-MS (ESI) m/z 470.2 [M+Na]$^+$.

EXAMPLE 243

6-O-{4-[2-(4-Fluorophenyl)-4-oxo-1,3-thiazolidin-3-yl]-3-methylbenzoyl}-D-glucopyranose Compound 315

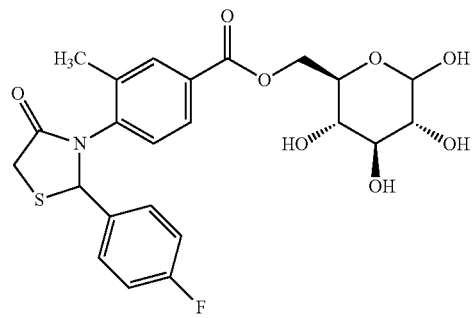

Step 1. 1,2,3,4,6-Penta-O-trimethylsilyl-β-D-glucopyranose

Compound 316

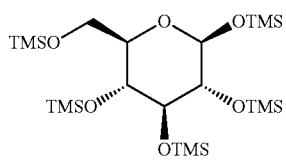

To a solution of D-glucose (1.01 g, 4.50 mmol) in DMF (10 mL) was added chlorotrimethylsilane (4.50 mL, 35.5 mmol) and triethylamine (4.90 mL, 35.3 mmol) in ice-bath. After the solution was stirred at room temperature for 5 h, crushed ice and n-hexane were added to the reaction. The aqueous layer was extracted with n-hexane. The combined organic layers were dried over MgSO$_{4(s)}$, filtered, concentrated, and dried under vacuum to obtain 1,2,3,4,6-penta-O-trimethylsilyl-3-D-glucopyranose (2.89 g, 91%) as a yellow oil. 1H NMR (CDCl$_3$, 400 MHz) δ 5.00 (d, 1H), 3.77 (t, 1H), 3.73-3.65 (m, 3H), 3.39 (t, 1H), 3.33 (dd, 1H), 0.19-0.09 (m, 45H).

Step 2. 1,2,3,4-Tetra-O-trmethylsilyl-β-D-glucopyranose

Compound 317

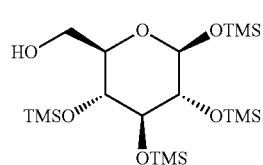

To a solution of 1,2,3,4,6-penta-O-trimethylsilyl-β-D-glucopyranose (1.43 g, 2.64 mmol) in methanol (10 mL) and CH$_2$Cl$_2$ (10 mL) was added ammonium acetate (0.410 g, 5.32 mmol). After the solution was stirred at room temperature for 30 h, the solvent was removed under reduced pressure. The residue was dissolved in n-hexane and washed with water. The organic layer was dried over MgSO$_{4(s)}$, filtered, and concentrated. The crude was purified by column chromatography (0-100% ethyl acetate in n-hexane) to give 1,2,3,4-tetra-O-trimethylsilyl-β-D-glucopyranose (0.730 g, 59%) as a yellow oil. 1H NMR (CDCl$_3$, 400 MHz) δ 5.00 (d, 1H), 3.81-3.67 (m, 4H), 3.44 (t, 1H), 3.33 (dd, 1H), 0.22-0.10 (m, 36H).

Step 3. 6-O-{4-[2-(4-Fluorophenyl)-4-oxo-1,3-thiazolidin-3-yl]-3-methylbenzoyl}-1,2,3,4-tetrakis-O-(trimethylsilyl)-D-glucopyranose Compound 318

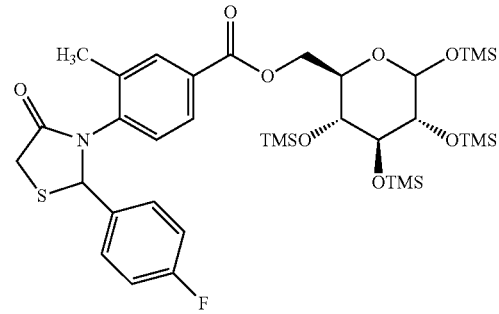

Following standard procedure G, 4-[2-(4-fluorophenyl)-4-oxo-1,3-thiazolidin-3-yl]-3-methylbenzoic acid (147 mg, 0.442 mmol), DMAP (135 mg, 1.11 mmol), EDCI • HCl (170 mg, 0.884 mmol), 1,2,3,4-tetra-O-trimethylsilyl-β-D-glucopyranose (228 mg, 0.486 mmol), and CH$_2$Cl$_2$ (3.0 mL) were used to carry out the reaction. After the reaction was stirred for 16 h and work-up, the residue was purified by Isco Combi-Flash Companion column chromatography (0-15% ethyl acetate in n-hexane) to give 6-O-{4-[2-(4-fluorophenyl)-4-oxo-1,3-thiazolidin-3-yl]-3-methylbenzoyl}-1,2,3,4-tetrakis-O-(trimethylsilyl)-D-glucopyranose (289 mg, 84%) as a white foam. 1H NMR (CDCl$_3$, 400 MHz) δ 7.87 (br s, 1H), 7.75 (br s, 1H), 7.31-7.27 (m, 2H), 6.94 (br t, 2H), 6.10-5.80 (br, 1H), 5.00 (d, 1H), 4.55 (ddd, 1H), 4.23 (dt, 1H), 4.03-3.95 (m, 2H), 3.83-3.67 (m, 2H), 3.51-3.42 (m, 1H), 3.40-3.32 (m, 1H), 2.17 (br s, 3H), 0.22-0.06 (m, 36H).

Step 4. 6-O-{4-[2-(4-Fluorophenyl)-4-oxo-1,3-thiazolidin-3-yl]-3-methylbenzoyl}-D-glucopyranose To a solution of 6-O-{4-[2-(4-fluorophenyl)-4-oxo-1,3-thiazolidin-3-yl]-3-methylbenzoyl}-1,2,3,4-tetrakis-O-

(trimethylsilyl)-D-glucopyranose (285 mg, 0.365 mmol) in CH$_2$Cl$_2$ (5.0 mL) was added trifluoroacetic acid (1.50 mL). After the solution was stirred at room temperature for 5 h, the solvent was removed under reduced pressure. The residue was purified by Isco Combi-Flash Companion column chromatography (0-10% methanol in CH$_2$Cl$_2$) to give 6-O-{4-[2-(4-fluorophenyl)-4-oxo-1,3-thiazolidin-3-yl]-3-methylbenzoyl}-D-glucopyranose (104 mg, 58%) as a beige solid. 1H NMR (Acetone-d$_6$, 400 MHz) δ 7.81 (br s, 1H), 7.72 (br d, 1H), 7.55 (dd, 2H), 7.05 (t, 2H), 6.50-6.20 (br, 1H), 5.80-5.70 (br, 1H), 5.55 (br s, 1H), 5.09 (br s, 1H), 4.59-4.49 (m, 1H), 4.42-4.34 (m, 1H), 4.30 (br s, 1H), 4.10-4.05 (m, 2H), 4.02 (d, 1H), 3.89 (d, 1H), 3.69 (t, 1H), 3.42-3.30 (m, 2H), 2.19 (br s, 3H); LC-MS (ESI) m/z 516.2 [M+Na]$^+$.

EXAMPLE 244

6-O-{4-[2-(4-Fluorophenyl)-4-oxo-1,3-thiazolidin-3-yl]-3-methylbenzoyl}-D-galactopyranose Compound 319

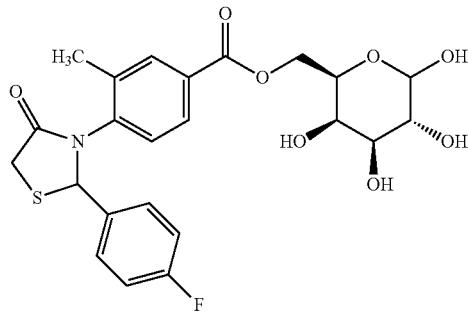

Step 1. 6-O-{4-[2-(4-fluorophenyl)-4-oxo-1,3-thiazolidin-3-yl]-3-methylbenzoyl}-1,2,3,4-di-O-isopropylidene-D-galactopyranose Compound 320

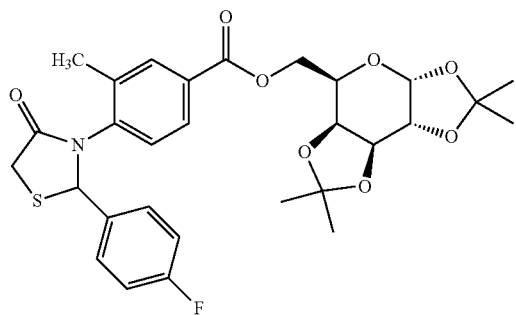

Following standard procedure G, 4-[2-(4-fluorophenyl)-4-oxo-1,3-thiazolidin-3-yl]-3-methylbenzoic acid (140 mg, 0.421 mmol), DMAP (129 mg, 1.05 mmol), EDCI • HCl (161 mg, 0.840 mmol), 1,2,3,4-di-O-isopropylidene-t-D-galactopyranose (121 mg, 0.463 mmol), and CH$_2$Cl$_2$ (2.0 mL) were used to carry out the reaction. After the reaction was stirred for 16 h and work-up, the residue was purified by Isco Combi-Flash Companion column chromatography (0-60% ethyl acetate in n-hexane) to give 6-O-{4-[2-(4-fluorophenyl)-4-oxo-1,3-thiazolidin-3-yl]-3-methylbenzoyl}-1,2,3,4-di-O-isopropylidene-D-galactopyranose (174 mg, 72%) as a white solid. 1H NMR (CDCl$_3$, 400 MHz) δ 7.87 (br s, 1H), 7.75 (br s, 1H), 7.30 (dd, 2H), 6.96 (br t, 2H), 6.10-5.70 (br, 1H), 5.54 (d, 1H), 4.63 (dd, 1H), 4.48 (dt, 1H), 4.39-4.32 (m, 2H), 4.28 (dd, 1H), 4.13 (t, 1H), 4.00 (d, 1H), 3.92 (d, 1H), 2.19 (br s, 3H), 1.46 (s, 3H), 1.43 (s, 3H), 1.37 (s, 3H), 1.34 (s, 3H).

Step 2. 6-O-{4-[2-(4-Fluorophenyl)-4-oxo-1,3-thiazolidin-3-yl]-3-methylbenzoyl}-D-galactopyranose A solution of 6-O-{4-[2-(4-fluorophenyl)-4-oxo-1,3-thiazolidin-3-yl]-3-methylbenzoyl}-1,2,3,4-di-O-isopropylidene-D-galactopyranose (172 mg, 0.299 mmol) in CH$_2$Cl$_2$ (2.0 mL) and trifluoroacetic acid (1.0 mL) was stirred at room temperature for 24 h. The solvent was removed under reduced pressure. The residue was purified by Isco Combi-Flash Companion column chromatography (0-15% methanol in CH$_2$Cl$_2$) to give 6-O-{4-[2-(4-fluorophenyl)-4-oxo-1,3-thiazolidin-3-yl]-3-methylbenzoyl}-D-galactopyranose (63.2 mg, 43%) as a beige solid. 1H NMR (CD$_3$OD-d$_4$, 300 MHz) δ 7.84 (br s, 1H), 7.76 (br s, 1H), 7.48-7.43 (m, 2H), 7.40-7.10 (br, 1H), 7.00 (br t, 2H), 6.50-6.10 (br, 1H), 5.14 (d, 1H), 4.46-4.31 (m, 3H), 4.08-3.75 (m, 4H), 3.49-3.47 (m, 1H), 2.17 (br s, 3H); LC-MS (ESI) m/z 516.2 [M+Na]$^+$.

EXAMPLE 245

3-O-{4-[2-(4-Fluorophenyl)-4-oxo-1,3-thiazolidin-3-yl]-3-methylbenzoyl}-D-glucopyranose Compound 321

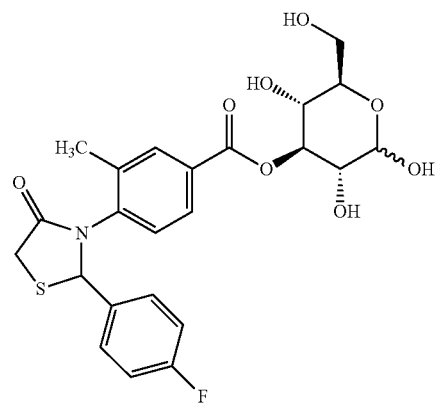

Step 1. 3-O-{4-[2-(4-Fluorophenyl)-4-oxo-1,3-thiazolidin-3-yl]-3-methylbenzoyl}-1,2,5,6-di-O-isopropylidene-D-glucopyranose Compound 322

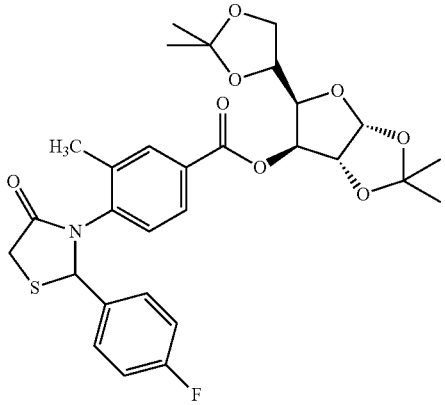

Following standard procedure G, 4-[2-(4-fluorophenyl)-4-oxo-1,3-thiazolidin-3-yl]-3-methylbenzoic acid (174 mg, 0.526 mmol), DMAP (161 mg, 1.32 mmol), EDCI • HCl (202 mg, 1.052 mmol), 1,2,5,6-di-O-isopropylidene-α-D-glucofuranose (151 mg, 0.579 mmol), and CH$_2$Cl$_2$ (3.0 mL) were used to carry out the reaction. After the reaction was stirred for 18 h and work-up, the residue was purified by Isco Combi-Flash Companion column chromatography (0-50% ethyl acetate in n-hexane) to give 3-O-{4-[2-(4-Fluorophenyl)-4-oxo-1,3-thiazolidin-3-yl]-3-methylbenzoyl}-1,2,5,6-di-O-isopropylidene-D-glucopyranose (214 mg, 71%) as a yellow solid. 1H NMR (CDCl$_3$, 400 MHz) δ 7.83 (br s, 1H), 7.72 (br s, 1H), 7.31 (dd, 2H), 6.96 (br t, 2H), 6.10-5.80 (m, 2H), 5.44 (s, 1H), 4.55 (d, 1H), 4.28-4.27 (m, 2H), 4.13-4.03 (m, 2H), 4.00 (d, 1H), 3.92 (d, 1H), 2.21 (br s, 3H), 1.55 (s, 3H), 1.40 (s, 3H), 1.32 (s, 3H), 1.27 (s, 3H).

Step 2. 3-O-{4-[2-(4-Fluorophenyl)-4-oxo-1,3-thiazolidin-3-yl]-3-methylbenzoyl}-D-glucopyranose A solution of 3-O-{4-[2-(4-Fluorophenyl)-4-oxo-1,3-thiazolidin-3-yl]-3-methylbenzoyl}-1,2,5,6-di-O-isopropylidene-D-glucopyranose (210 mg, 0.366 mmol) in CH$_2$Cl$_2$ (1.0 mL) and trifluoroacetic acid (1.0 mL) was stirred at room temperature for 48 h. The solvent was removed under reduced pressure. The residue was purified by Isco Combi-Flash Companion column chromatography (0-10% methanol in CH$_2$Cl$_2$) to give 3-O-{4-[2-(4-fluorophenyl)-4-oxo-1,3-thiazolidin-3-yl]-3-methylbenzoyl}-D-glucopyranose (90.6 mg, 51%) as a beige solid. 1H NMR (CD$_3$OD-d$_4$, 400 MHz) δ 7.89 (br s, 1H), 7.81 (br s, 1H), 7.45 (dd, 2H), 6.99 (br t, 2H), 6.50-6.10 (br, 1H), 5.41 (t, 1H), 5.20-5.10 (m, 1H), 4.05 (d, 1H), 3.97 (d, 1H), 3.91-3.54 (m, 4H), 3.42-3.38 (m, 1H), 2.17 (br s, 3H); LC-MS (ESI) m/z 516.2 [M+Na]$^+$.

EXAMPLE 246

O-[4-[2-(4-Fluorophenyl)-4-oxo-1,3-thiazolidin-3-yl]-3-methylbenzoyl]-L-tyrosine Compound 323

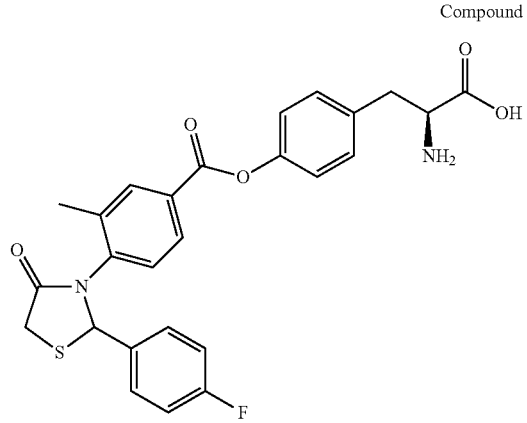

Step 1. 2-Methyl-2-propanyl N-{[(2-methyl-2-propanyl)oxy]carbonyl}-L-tyrosinate

Compound 324

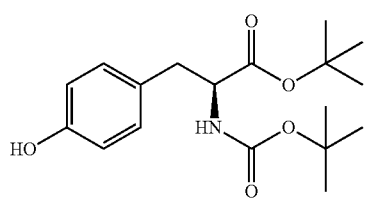

To a solution of L-tyrosine tert-butyl ester (1.43 g, 2.64 mmol) in CH$_2$Cl$_2$ (5.0 mL) was added triethylamine (0.320 mL, 2.31 mmol) and di-tert-butyldicarbonate (0.303 g, 1.39 mmol) at 0° C. After the solution was stirred at room temperature for 18 h, the solution was diluted with CH$_2$Cl$_2$ and washed with 2 N HCl$_{(aq)}$. The organic layer was dried over MgSO$_{4(s)}$, filtered, and concentrated. The residue was purified by Isco Combi-Flash Companion column chromatography (0-30% ethyl acetate in n-hexane) to give 2-methyl-2-propanyl N-{[(2-methyl-2-propanyl)oxy]carbonyl}-L-tyrosinate (299 mg, 77%) as a white solid. 1H NMR (CDCl$_3$, 400 MHz) δ 7.02 (d, 2H), 6.73 (d, 2H), 5.59 (br s, 1H), 5.00 (br d, 1H), 4.39 (q, 1H), 3.01-2.92 (m, 2H), 1.42 (s, 9H), 1.41 (s, 9H).

Step 2. 2-Methyl-2-propanyl O-[4-[2-(4-fluorophenyl)-4-oxo-1,3-thiazolidin-3-yl]-3-methylbenzoyl]-N-{[(2-methyl-2-propanyl)oxy]carbonyl}-L-tyrosinate Compound 325

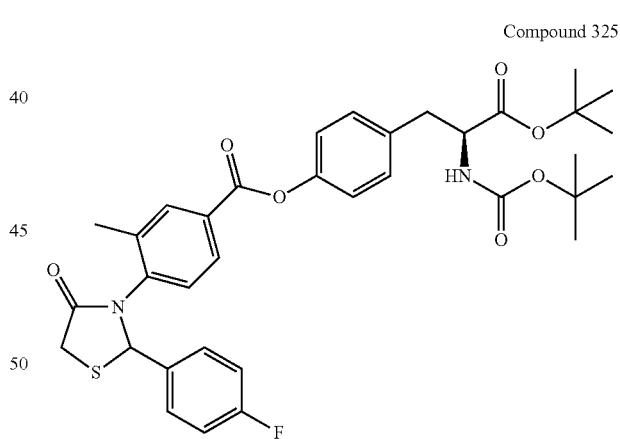

Following standard procedure G, 4-[2-(4-fluorophenyl)-4-oxo-1,3-thiazolidin-3-yl]-3-methylbenzoic acid (164 mg, 0.496 mmol), DMAP (151 mg, 1.24 mmol), EDCI • HCl (190 mg, 0.991 mmol), 2-methyl-2-propanyl N-{[(2-methyl-2-propanyl)oxy]carbonyl}-L-tyrosinate (167 mg, 0.496 mmol), and CH$_2$Cl$_2$ (5.0 mL) were used to carry out the reaction. After the reaction was stirred for 18 h and work-up, the residue was purified by Isco Combi-Flash Companion column chromatography (0-40% ethyl acetate in n-hexane) to give 2-methyl-2-propanyl O-{4-[2-(4-fluorophenyl)-4-oxo-1,3-thiazolidin-3-yl]-3-methylbenzoyl}-N-{[(2-methyl-2-propanyl)oxy]carbonyl}-L-tyrosinate (232 mg, 72%) as a beige solid. 1H NMR (CDCl$_3$, 400 MHz) δ 8.01

(br s, 1H), 7.89 (br s, 1H), 7.35-7.32 (m, 2H), 7.21 (d, 2H), 7.07 (d, 2H), 6.98 (t, 2H), 6.10-5.80 (br, 1H), 5.02 (d, 1H), 4.44 (q, 1H), 4.02 (d, 1H), 3.94 (d, 1H), 3.06 (d, 2H), 2.23 (br s, 3H), 1.43 (s, 9H), 1.40 (s, 9H).

Step 3. O-{4-[2-(4-Fluorophenyl)-4-oxo-1,3-thiazolidin-3-yl]-3-methylbenzoyl}-L-tyrosine A solution of 2-methyl-2-propanyl O-{4-[2-(4-fluorophenyl)-4-oxo-1,3-thiazolidin-3-yl]-3-methylbenzoyl}-N-{[(2-methyl-2-propanyl)oxy]carbonyl}-L-tyrosinate (119 mg, 0.182 mmol) in $CH_2Cl_2$ (3.0 mL) and trifluoroacetic acid (3.0 mL) was stirred at room temperature for 6 h. The solvent was removed under reduced pressure. The residue was purified by Isco Combi-Flash Companion column chromatography (0-20% methanol in $CH_2Cl_2$) to give O-{4-[2-(4-fluorophenyl)-4-oxo-1,3-thiazolidin-3-yl]-3-methylbenzoyl}-L-tyrosine (67.7 mg, 75%) as a white solid. 1H NMR ($CD_3OD$-$d_4$, 400 MHz) δ 7.98 (br s, 1H), 7.89 (br s, 1H), 7.51-7.47 (m, 2H), 7.38 (d, 2H), 7.17 (d, 2H), 7.02 (t, 2H), 6.50-6.10 (br, 1H), 4.07 (d, 1H), 3.99 (d, 1H), 3.79 (dd, 1H), 3.35 (dd, 1H), 3.03 (dd, 1H), 2.22 (br s, 3H); LC-MS (ESI) m/z 495.3 $[M+H]^+$.

EXAMPLE 247

1-[(3-Pyridinylcarbonyl)amino]-2-propanyl 4-[2-(4-fluorophenyl)-4-oxo-1,3-thiazolidin-3-yl]-3-methylbenzoate Compound 326

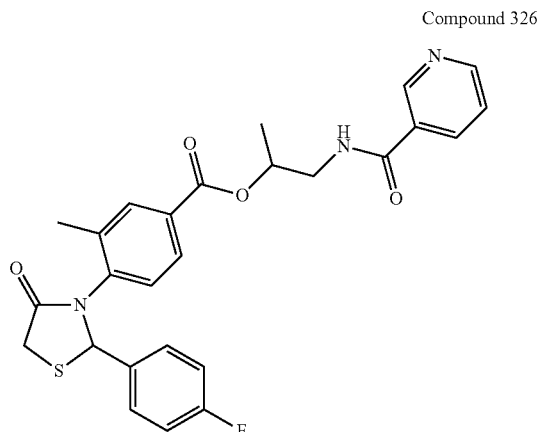 [SMILES: Cc1cc(C(=O)OC(C)CNC(=O)c2cccnc2)ccc1N1C(=O)CSC1c1ccc(F)cc1]

Step 1.
N-(2-Hydroxypropyl)-3-pyridinecarboxamide

Compound 327

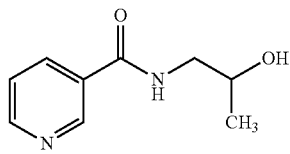

A solution of methyl nicotinate (1.03 g, 7.51 mmol) and DL-1-amino-2-propanol (0.590 mL, 7.54 mmol) in ethanol (8.0 mL) was heated to reflux for 24 h. The reaction mixture was cooled to room temperature and ethanol was removed under reduced pressure. The residue was purified by Isco Combi-Flash Companion column chromatography (0-10% MeOH in $CH_2Cl_2$) to give N-(2-hydroxypropyl)-3-pyridinecarboxamide (889 mg, 66%) as a lightly yellow oil. 1H NMR ($CDCl_3$, 400 MHz) δ 8.98 (d, 1H), 8.66 (dd, 1H), 8.13-8.09 (m, 1H), 7.35 (dd, 1H), 7.20 (br t, 1H), 4.04 (br quint, 1H), 3.70-3.62 (m, 1H), 3.59 (br s, 1H), 3.33-3.24 (m, 1H), 1.25 (d, 3H).

Step 2. 1-[(3-Pyridinylcarbonyl)amino]-2-propanyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (485 mg, 1.46 mmol), DMAP (179 mg, 1.46 mmol), EDCI·HCl (421 mg, 2.20 mmol), N-(2-hydroxypropyl)-3-pyridinecarboxamide (277 mg, 1.54 mmol), and $CH_2Cl_2$ (5.0 mL) were used to carry out the reaction. After the reaction was stirred for 20 h and work-up, the residue was purified by Isco Combi-Flash Companion column chromatography (0-5% methanol in $CH_2Cl_2$) to give 1-[(3-pyridinylcarbonyl)amino]-2-propanyl 4-[2-(4-fluorophenyl)-4-oxo-1,3-thiazolidin-3-yl]-3-methylbenzoate (650 mg, 90%) as a lightly yellow solid. 1H NMR ($CDCl_3$, 400 MHz) δ 8.93 (s, 1H), 8.70 (d, 1H), 8.05 (dt, 1H), 7.84 (br s, 1H), 7.73 (br s, 1H), 7.37-7.34 (m, 1H), 7.31 (dd, 2H), 6.95 (br t, 2H), 6.83 (br t, 1H), 5.95 (br, 1H), 5.33 (sextet, 1H), 3.99 (d, 1H), 3.90 (d, 1H), 3.81-3.74 (m, 1H), 3.69-3.61 (m, 1H), 2.18 (br s, 3H), 1.35 (d, 3H); LC-MS (ESI) m/z 494.3 $[M+H]^+$.

EXAMPLE 248

3-{[2-({4-[2-(4-Fluorophenyl)-4-oxo-1,3-thiazolidin-3-yl]-3-methylbenzoyl}oxy)propyl]carbamoyl}-1-methylpyridinium iodide Compound 328

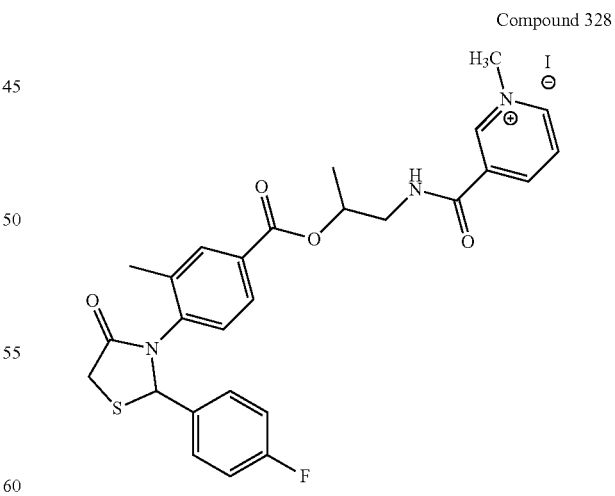

A solution of 1-[(3-pyridinylcarbonyl)amino]-2-propanyl 4-[2-(4-fluorophenyl)-4-oxo-1,3-thiazolidin-3-yl]-3-methylbenzoate (0.310 g, 0.628 mmol) and methyl iodide (0.140 mL, 2.25 mmol) in $CH_2Cl_2$ (6.0 mL) and acetonitrile (2.0 mL) was stirred in a closed system at room temperature for 24 h. Another portion of methyl iodide (0.140 mL, 2.25 mmol) was added to the reaction mixture and the reaction mixture was continually stirred for 48 h. The solvent was removed under reduced pressure and dried under high vacuum to give 3-{[2-({4-[2-(4-fluorophenyl)-4-oxo-1,3-thiazolidin-3-yl]-3-methylbenzoyl}oxy)propyl]carbamoyl}-1-methylpyridinium iodide (399 mg, quantitative yield) as a yellow solid. 1H NMR (DMSO-$d_6$, 300 MHz) δ 9.35-9.20 (m, 2H), 9.01 (d, 1H), 8.79 (d, 1H), 8.16 (dd, 1H), 7.75 (br s, 1H), 7.68 (br s, 1H), 7.47 (dd, 2H), 7.09 (br t, 2H), 6.60-6.10 (br s, 1H), 5.20-5.16 (m, 1H), 4.34 (s, 3H), 4.06 (d, 1H), 3.90 (d, 1H), 2.13 (br s, 3H), 1.28 (d, 3H); LC-MS (ESI) m/z 508.3 [M]$^+$.

EXAMPLE 249

4-(2-(4-Fluorophenyl)-4-oxothiazolidin-3-yl)-3-methylbenzamide

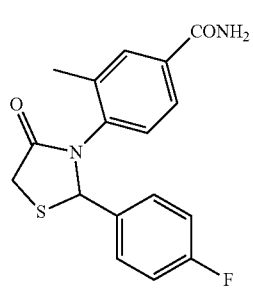

Compound 329

Step 1. Synthesis of 4-(2-(4-Fluorophenyl)-4-oxothiazolidin-3-yl)-3-methylbenzoyl azide

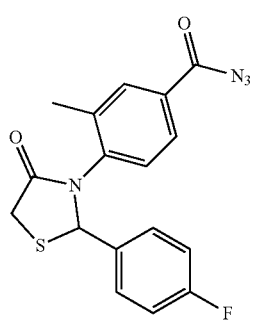

Compound 330

To a solution of 4-(2-(4-fluorophenyl)-4-oxothiazolidin-3-yl)-3-methylbenzoic acid (200 mg, 0.58 mmol) and diphenylphosphorous azide (220 mg, 0.800 mmol) in THF (3 mL) was treated DIPEA (0.140 mL, 103.4 mg, 0.800 mmol) in one portion. The reaction mixture was stirred at r.t. for overnight then directly concentrated to give a crude product which was purified by flash chromatography (ethyl acetate:hexane=1:2) to give the desired product as a yellow viscous liquid (150 mg, 73%). $^1$H NMR (CDCl$_3$, 400 MHz) δ 7.85 (br s, 1H), 7.73 (br d, 1H), 7.30 (dd, 2H), 6.96 (br t, 2H), 5.96 (br s, 1H), 4.00 (d, 1H), 3.92 (d, 1H) 2.00 (br s, 3H).

Step 2. Synthesis of 4-(2-(4-Fluorophenyl)-4-oxothiazolidin-3-yl)-3-methylbenzamide To a solution of 4-(2-(4-fluorophenyl)-4-oxothiazolidin-3-yl)-3-methylbenzoyl azide (120 mg, 0.34 mmol) in 2 mL of co-solvent (ethanol:H$_2$O=3:1) was added zinc dust$_{(s)}$ (39 mg, 0.6 mmol) in one portion at r.t. The reaction mixture was stirred at r.t. overnight then passed through a pad of celite. The filtrate was partitioned between ethyl acetate (50 mL) and H$_2$O (10 mL). The organic layer was washed with brine (10 mL), dried over MgSO$_4$ and concentrated to give a crude product which was purified by flash chromatography (ethyl acetate:hexane=6:1) to give the desired product as a yellow viscous liquid (45 mg, 0.14 mmol, 40%). $^1$H NMR (CDCl$_3$, 400 MHz) δ 7.62 (br s, 1H), 7.47 (br s, 1H), 7.30 (dd, 2H), 6.96 (br t, 2H), 6.03-5.80 (br, 2H), 5.67 (br s, 1H), 4.01 (d, 1H), 3.92 (d, 1H), 2.18 (br s, 3H); LC-MS (ESI) m/z 331.9 [M+H]$^+$.

EXAMPLE 250

N-Methyl-4-(2-(4-fluorophenyl)-4-oxothiazolidin-3-yl)-3-methylbenzamide

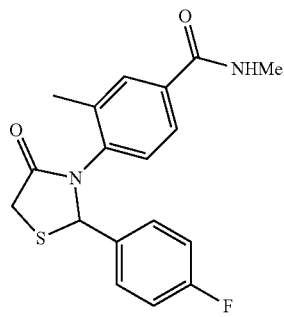

Compound 331

The compound was prepared by following the standard procedure K with 4-(2-(4-fluorophenyl)-4-oxothiazolidin-3-yl)-3-methylbenzoic acid (50.0 mg, 0.150 mmol), HBTU (85.3 mg, 0.225 mmol), methylamine (40% in methanol, 0.500 mL), and DIPEA (0.052 mL, 38.7 mg, 0.300 mmol). After the reaction mixture was stirred at room temperature for 16 h and work-up, the residue was purified by flash chromatography (dichloromethane:methanol=9:1) to give the desired product as a yellow viscous liquid (20.0 mg, 40%). $^1$H NMR (CDCl$_3$, 400 MHz) δ 7.88 (br s, 1H), 7.76 (br s, 1H), 7.31 (dd, 2H), 7.07-6.60 (br, 3H), 5.95 (br s, 1H), 5.88 (br s, 1H), 4.01 (d, 1H), 3.93 (d, 1H), 2.99 (s, 3H), 2.19 (br s, 3H); LC-MS (ESI) m/z 345.7 [M+H]$^+$.

EXAMPLE 251

4-(2-(4-Fluorophenyl)-4-oxothiazolidin-3-yl)-N,N,3-trimethylbenzamide

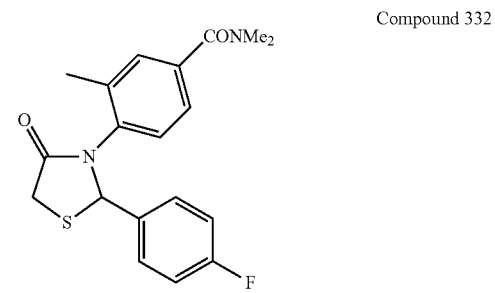

Compound 332

Step 1. Synthesis of 4-Amino-N,N,3-trimethylbenzamide

Compound 333

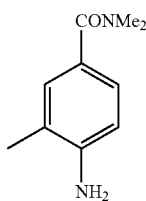

To a solution of 4-amino-3-methylbenzoic acid (1.00 g, 6.60 mmol), EDCI • HCl (1.89 g, 9.90 mmol), HOBt (1.34 g, 9.90 mmol), and dimethylamine hydrochloride (0.650 g, 7.90 mmol) in THF (12 mL) was treated DIPEA (4.00 mL, 2.89 g, 23.1 mmol) in one portion. The reaction mixture was stirred at r.t. overnight then partitioned between ethyl acetate (60 mL) and 5N NaOH (10 mL). The organic layer was washed with brine (10 mL) dried over MgSO$_4$ and concentrated to give a crude product which was purified by flash chromatography to give the desired product as a brown viscous liquid (1.08 g, 92%). $^1$H NMR (CDCl$_3$, 300 MHz) δ 7.19 (s, 1H), 7.14 (d, 1H), 6.63 (d, 1H), 3.77 (br s, 2H), 3.05 (s, 6H), 2.16 (s, 3H).

Step 2. Synthesis of 4-(2-(4-Fluorophenyl)-4-oxothiazolidin-3-yl)-N,N,3-trimethylbenzamide The compound was prepared by following the standard procedure A with 4-amino-N,N-trimethylbenzamide (200 mg, 1.12 mmol), 4-fluorobenzaldehyde (153 mg, 1.24 mmol), and 2-mercaptoacetic acid (0.140 mL, 181 mg, 1.97 mmol). It was reflux 6 h for the first step and 18 h for the second step. After work-up, the crude product was purified by flash chromatography (ethyl acetate) to give the desired product as a yellow viscous liquid (90.0 mg, 23%). $^1$H NMR (CDCl$_3$, 300 MHz) δ 7.36-7.26 (m, 3H), 7.11 (br s, 1H), 6.96 (br t, 2H), 5.90 (br s, 1H), 4.02 (d, 1H), 3.90 (d, 1H), 3.10-2.83 (br, 6H), 2.17 (br s, 3H); LC-MS (ESI) m/z 359.2 [M+H]$^+$.

EXAMPLE 252

4-[2-(4-Fluoro-phenyl)-4-oxo-thiazolidin-3-yl]-3-methyl-N-propyl-benzamide

Compound 334

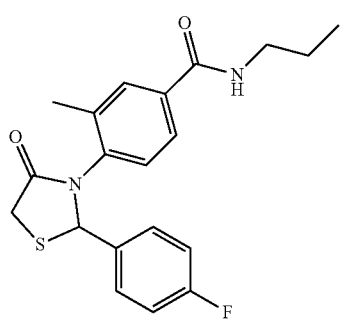

The compound was prepared by following the standard procedure K with 4-(2-(4-fluorophenyl)-4-oxothiazolidin-3-yl)-3-methylbenzoic acid (50.0 mg, 0.150 mmol), HBTU (85.3 mg, 0.225 mmol), propylamine (0.300 mmol, 17.7 mg), DIPEA (52.0 µL, 38.7 mg, 0.300 mmol), and CH$_2$Cl$_2$ (2.0 mL). After the reaction mixture was stirred at room temperature for 16 h and work-up, the residue was purified by flash chromatography (ethyl acetate:hexane=2:1) to give the desired product as a yellow viscous liquid (36.0 mg, 64%). $^1$H NMR (CDCl$_3$, 400 MHz) δ 7.55 (br s, 1H), 7.40 (br s, 1H), 7.30 (dd, 2H), 6.95 (br t, 2H), 6.12 (br s, 1H), 5.88 (br s, 1H), 4.00 (d, 1H), 3.91 (d, 1H), 3.35 (q, 2H), 2.16 (br s, 3H), 1.59 (sextet, 2H), 0.95 (t, 3H); LC-MS (ESI) m/z 373.9 [M+H]$^+$.

EXAMPLE 253

N-Ethyl-4-[2-(4-fluoro-phenyl)-4-oxo-thiazolidin-3-yl]-3-methyl-benzamide(

Compound 335

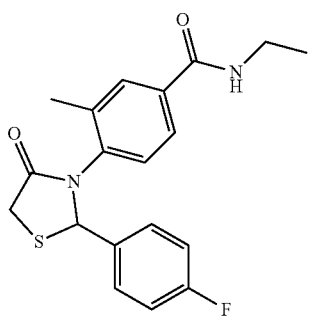

To a solution of 4-(2-(4-fluorophenyl)-4-oxothiazolidin-3-yl)-3-methylbenzoic acid (50.0 mg, 0.150 mmol) and ethylchloroformate (19.7 mg, 0.180 mmol) in tetrahydrofuran (0.5 mL) was treated DIPEA (34.0 µL, 25.0 mg, 0.195 mmol) in one portion. The reaction mixture was stirred at rt for 40 min then treated the solution of ethylamine (1.0 mL, 2 M) at room temperature. The reaction mixture was stirred at room temperature for 5 h then partitioned between CH$_2$Cl$_2$ (30 mL) and 2N HCl (10 mL). The organic layer was dried over MgSO$_4$ and concentrated to give a crude product which was purified by flash chromatography (ethyl acetate:hexane=5:2) to give the desired product as a yellow viscous liquid (39.0 mg, 72%). $^1$H NMR (CDCl$_3$, 400 MHz) δ 7.57 (br s, 1H), 7.40 (br s, 1H), 7.30 (dd, 2H), 6.95 (br t, 2H), 5.96 (br s, 2H), 4.01 (d, 1H), 3.92 (d, 1H), 3.44 (quint, 2H), 2.18 (br s, 3H), 1.23 (t, 3H); LC-MS (ESI) m/z 359.9 [M+H]$^+$.

EXAMPLE 254

N-Cyclopropyl-4-[2-(4-fluoro-phenyl)-4-oxo-thiazolidin-3-yl]-3-methyl-benzamide Compound 336

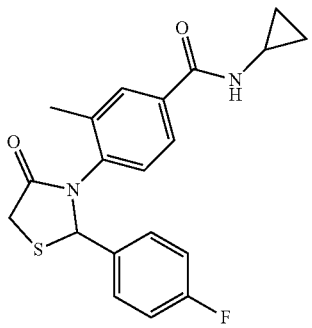

The compound was prepared by following the standard procedure K with 4-(2-(4-fluorophenyl)-4-oxothiazolidin-3-yl)-3-methylbenzoic acid (50.0 mg, 0.150 mmol), HBTU (85.3 mg, 0.225 mmol), cyclopropylamine (0.225 mmol, 12.8 mg), DIPEA (0.052 mL, 38.7 mg, 0.300 mmol), and CH$_2$Cl$_2$ (3.0 mL). After the reaction mixture was stirred at room temperature for 16 h and work-up, the residue was purified by flash chromatography (ethyl acetate:hexane=2:1) to give the desired product as a yellow viscous liquid (50.0 mg, 85%). $^1$H NMR (CDCl$_3$, 400 MHz) δ 7.52 (br s, 1H), 7.39 (br s, 1H), 7.29 (dd, 2H), 6.94 (br t, 2H), 6.19 (br s, 1H), 5.90 (br s, 1H), 3.99 (d, 1H), 3.90 (d, 1H), 2.85-2.75 (m, 1H), 2.16 (br s, 3H), 0.86-0.80 (m, 2H), 0.58-0.53 (m, 2H).

EXAMPLE 255

N-Cyclobutyl-4-[2-(4-fluorophenyl)-4-oxo-1,3-thiazolidin-3-yl]-3-methylbenzamide Compound 337

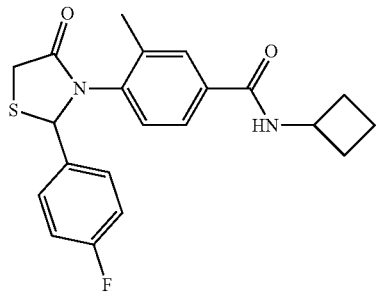

Following standard procedure K, 4-[2-(4-fluorophenyl)-4-oxo-1,3-thiazolidin-3-yl]-3-methylbenzoic acid (100 mg, 0.300 mmol), cyclobutanamine (28.0 μL, 0.330 mmol), HBTU (172 mg, 0.450 mmol), triethylamine (90.0 μL, 0.660 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (50% ethyl acetate in n-hexane) to give N-cyclobutyl-4-[2-(4-fluorophenyl)-4-oxo-1,3-thiazolidin-3-yl]-3-methylbenzamide (87.0 mg, 75%). 1H NMR (CDCl$_3$, 400 MHz) δ 7.55 (br s, 1H), 7.43 (br s, 1H), 7.31-7.28 (m, 2H), 6.95 (dd, 2H), 6.14 (d, 1H), 5.98 (br s, 1H), 4.52 (sextet, 1H), 4.00 (d, 1H), 3.91 (d, 1H), 2.43-2.36 (m, 2H), 2.20 (br s, 3H), 1.90 (quint, 2H), 1.78-1.67 (m, 2H); LC-MS (ACPI) m/z 385.6 [M+H]$^+$.

EXAMPLE 256

N-Cyclopentyl-4-[2-(4-fluorophenyl)-4-oxo-1,3-thiazolidin-3-yl]-3-methylbenzamide Compound 338

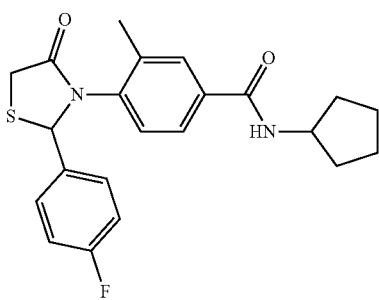

Following standard procedure K, 4-[2-(4-fluorophenyl)-4-oxo-1,3-thiazolidin-3-yl]-3-methylbenzoic acid (120 mg, 0.360 mmol), cyclopentanamine (38.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give N-cyclopentyl-4-[2-(4-fluorophenyl)-4-oxo-1,3-thiazolidin-3-yl]-3-methylbenzamide (84.0 mg, 58%). 1H NMR (CDCl$_3$, 400 MHz) δ 7.53 (br s, 1H), 7.41 (br s, 1H), 7.29 (dd, 2H), 6.94 (dd, 2H), 6.10-5.80 (m, 2H), 4.32 (sextet, 1H), 3.99 (d, 1H), 3.90 (d, 1H), 2.17 (br s, 3H), 2.10-2.01 (m, 2H), 1.75-1.55 (m, 4H), 1.50-1.38 (m, 2H); LC-MS (APCI) m/z 399.6 [M+H]$^+$.

EXAMPLE 257

N-Cyclohexyl-4-[2-(4-fluorophenyl)-4-oxo-1,3-thiazolidin-3-yl]-3-methylbenzamide Compound 339

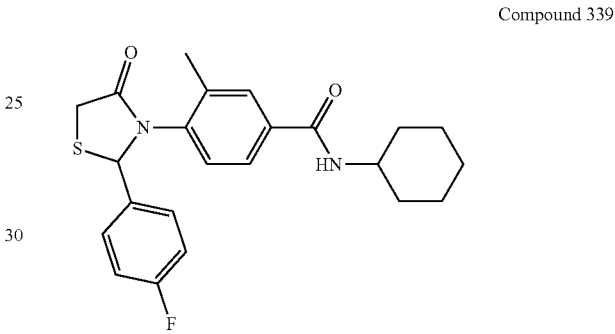

Following standard procedure K, 4-[2-(4-fluorophenyl)-4-oxo-1,3-thiazolidin-3-yl]-3-methylbenzoic acid (120 mg, 0.360 mmol), cyclohexanamine (45.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give N-cyclohexyl-4-[2-(4-fluorophenyl)-4-oxo-1,3-thiazolidin-3-yl]-3-methylbenzamide (70.0 mg, 47%). 1H NMR (CDCl$_3$, 400 MHz) δ 7.60-7.35 (m, 2H), 7.35-7.28 (m, 2H), 6.95 (dd, 2H), 6.10-5.80 (m, 2H), 4.00 (d, 1H), 3.91-3.87 (m, 2H), 2.23 (br s, 3H), 2.05-1.95 (m, 2H), 1.80-1.58 (m, 4H), 1.50-1.14 (m, 4H); LC-MS (ESI) m/z 413.8 [M+H]$^+$.

EXAMPLE 258

N-[2-(Dimethylamino)ethyl]-4-[2-(4-fluorophenyl)-4-oxo-1,3-thiazolidin-3-yl]-3-methylbenzamide Compound 340

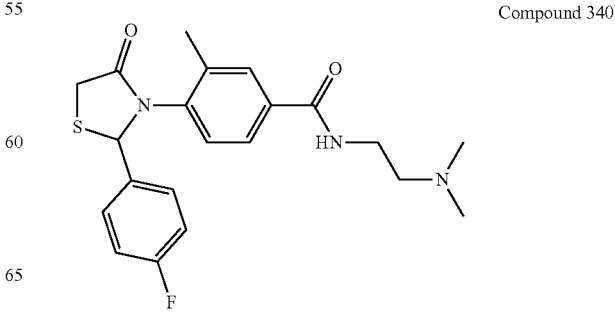

Following standard procedure K, 4-[2-(4-fluorophenyl)-4-oxo-1,3-thiazolidin-3-yl]-3-methylbenzoic acid (0.100 g, 0.302 mmol), N,N-dimethylethane-1,2-diamine (36.0 µL, 0.332 mmol), HBTU (0.170 g, 0.453 mmol), triethylamine (93.0 µL, 0.664 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give N-[2-(dimethylamino)ethyl]-4-[2-(4-fluorophenyl)-4-oxo-1,3-thiazolidin-3-yl]-3-methylbenzamide (43.7 mg, 36%). 1H NMR (CDCl$_3$, 300 MHz) δ 7.62 (br s, 1H), 7.48 (br s, 1H), 7.32-7.26 (m, 2H), 6.95 (br s, 3H), 5.93 (br s, 1H), 4.00 (d, 1H), 3.90 (d, 1H), 3.52-3.47 (m, 2H), 2.52 (t, 2H), 2.26 (br s, 6H), 2.19 (br s, 3H); LC-MS (ESI) m/z 402.1 [M+H]$^+$.

EXAMPLE 259

N-(2-(Diethylamino)ethyl)-4-(2-(4-fluorophenyl)-4-oxothiazolidin-3-yl)-3-methylbenzamide

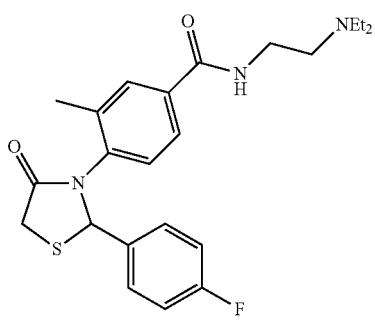

Compound 341

To a solution of 4-(2-(4-fluorophenyl)-4-oxothiazolidin-3-yl)-3-methylbenzoic acid (87.0 mg, 0.260 mmol), EDCI (99.0 mg, 0.520 mmol), HOBt (35.0 mg, 0.260 mmol), and N,N-diethylethylenediamine (0.048 mL, 40.0 mg, 0.340 mmol) in CH$_2$Cl$_2$ (2.0 mL) was treated DIPEA (90.0 µL, 67.2 mg, 0.520 mmol) in one portion. The reaction mixture was stirred at r.t. for 5.5 h then partitioned between ethyl acetate (80 mL) and saturated NH$_4$Cl$_{(aq)}$ (10 mL). The organic layer was washed with brine (10 mL) dried over MgSO$_4$ and concentrated to give a crude product which was purified by PLC (Alumium oxide) (eluent: ethyl acetate) to give the desired product as a yellow viscous liquid (29.0 mg, 26%). $^1$H NMR (CD$_3$OD, 400 MHz) δ 7.62 (br s, 1H), 7.56 (br s, 1H), 7.46 (dd, 2H), 6.99 (br t, 2H), 6.19 (br s, 1H), 4.05 (br d, 1H), 3.96 (d, 1H), 3.44 (dd, 2H), 2.67-2.58 (m, 6H), 2.16 (br s, 3H), 1.06 (t, 6H); LC-MS (ESI) m/z 429.9 [M+H]$^+$.

EXAMPLE 260

N-[3-(Dimethylamino)propyl]-4-[2-(4-fluorophenyl)-4-oxo-1, 3-thiazolidin-3-yl]-3-methylbenzamide

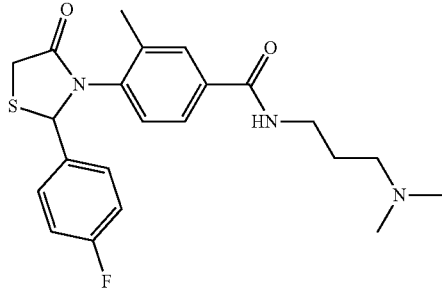

Compound 342

Following standard procedure K, 4-[2-(4-fluorophenyl)-4-oxo-1,3-thiazolidin-3-yl]-3-methylbenzoic acid (0.100 g, 0.302 mmol), N,N-dimethylpropane-1,3-diamine (42.0 µL, 0.332 mmol), HBTU (0.170 g, 0.453 mmol), triethylamine (93.0 µL, 0.664 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give N-[3-(dimethylamino)propyl]-4-[2-(4-fluorophenyl)-4-oxo-1,3-thiazolidin-3-yl]-3-methylbenzamide (21.7 mg, 17%). 1H NMR (CDCl$_3$, 400 MHz) δ 8.38 (br s, 1H), 7.63 (br s, 1H), 7.50 (br s, 1H), 7.31-7.27 (m, 2H), 6.94 (t, 2H), 5.90 (br s, 1H), 3.99 (d, 1H), 3.90 (d, 1H), 3.49 (q, 2H), 2.58 (t, 2H), 2.35 (s, 6H), 2.18 (br s, 3H), 1.79 (quint, 2H); LC-MS (APCI) m/z 416.5 [M+H]$^+$.

EXAMPLE 261

4-[2-(4-Fluorophenyl)-4-oxo-1,3-thiazolidin-3-yl]-N-(3-methoxypropyl)-3-methylbenzamide

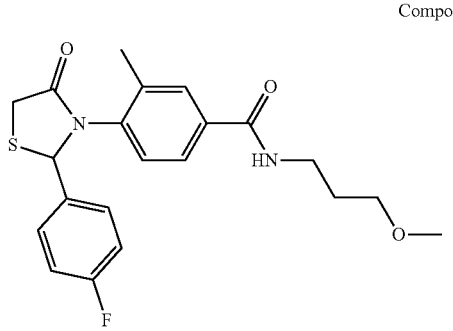

Compound 343

Following standard procedure K, 4-[2-(4-fluorophenyl)-4-oxo-1,3-thiazolidin-3-yl]-3-methylbenzoic acid (0.100 g, 0.302 mmol), 3-methoxypropan-1-amine (34.0 µL, 0.332 mmol), HBTU (0.170 g, 0.453 mmol), triethylamine (93.0 µL, 0.664 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 4-[2-(4-fluorophenyl)-4-oxo-1,3-thiazolidin-3-yl]-N-(3-methoxypropyl)-3-methylbenzamide (29.5 mg, 24%). 1H NMR (CDCl$_3$, 400 MHz) δ 7.56 (br s, 1H), 7.42 (br s, 1H), 7.31-7.27 (m, 2H), 6.94 (br t, 2H), 6.88 (br s, 1H), 5.95 (br s, 1H), 4.00 (d, 1H), 3.90 (d, 1H), 3.57-3.48 (m, 4H), 3.34 (s, 3H), 2.16 (br s, 3H), 1.84 (quint, 2H); LC-MS (APCI) m/z 403.7 [M+H]$^+$.

EXAMPLE 262

4-[2-(4-Fluorophenyl)-4-oxo-1,3-thiazolidin-3-yl]-3-methyl-N-[2-(4-morpholinyl)ethyl]benzamide Compound 344

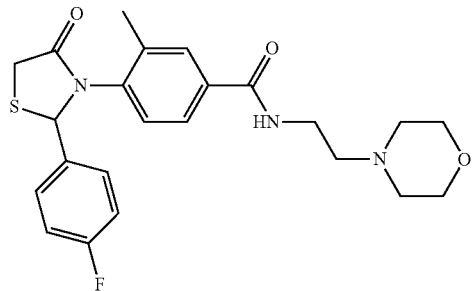

Following standard procedure K, 4-[2-(4-fluorophenyl)-4-oxo-1,3-thiazolidin-3-yl]-3-methylbenzoic acid (0.100 g, 0.302 mmol), 2-morpholinoethan-1-amine (44.0 µL, 0.332 mmol), HBTU (0.170 g, 0.453 mmol), triethylamine (93.0 µL, 0.664 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 4-[2-(4-fluorophenyl)-4-oxo-1,3-thiazolidin-3-yl]-3-methyl-N-[2-(4-morpholinyl)ethyl]benzamide (28.5 mg, 21%). 1H NMR (CDCl$_3$, 400 MHz) δ 7.58 (br s, 1H), 7.52 (br s, 1H), 7.32-7.29 (m, 2H), 6.95 (br t, 2H), 6.71 (br s, 1H), 5.95 (br s, 1H), 4.01 (d, 1H), 3.91 (d, 1H), 3.72-3.69 (m, 4H), 3.49 (br q, 2H), 2.56 (t, 2H), 2.48 (br s, 4H), 2.20 (br s, 3H); LC-MS (APCI) m/z 444.7 [M+H]$^+$.

EXAMPLE 263

N-(3-Aminopropyl)-4-[2-(4-fluorophenyl)-4-oxo-1,3-thiazolidin-3-yl]-3-methylbenzamide Compound 345

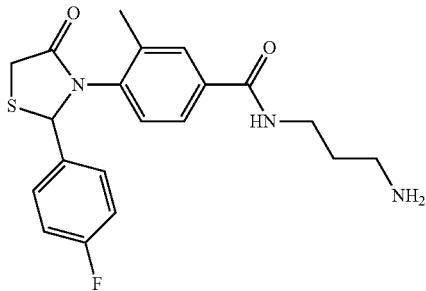

Step 1. Synthesis of 2-methyl-2-propanyl [3-({4-[2-(4-fluorophenyl)-4-oxo-1,3-thiazolidin-3-yl]-3-methylbenzoyl}amino)propyl]carbamate Compound 346

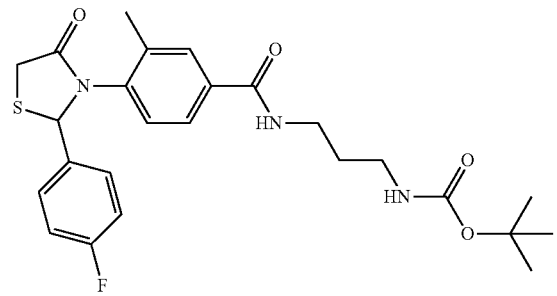

Following standard procedure E, 4-[2-(4-fluorophenyl)-4-oxo-1,3-thiazolidin-3-yl]-3-methylbenzoic acid (0.200 g, 0.604 mmol), ethyl carbonochloridate (64.0 µL, 0.665 mmol), triethylamine (0.170 mL, 1.21 mmol) and CH$_2$Cl$_2$ (10.0 mL) were used to carry out the reaction. After the reaction was stirred for 1 h, tert-butyl (3-aminopropyl) carbamate (0.120 mL, 0.665 mmol) was added and then stirred at room temperature for 22 h and work up. The residue was purified by Isco Combi-Flash Companion column chromatography (0-70% ethyl acetate in n-hexane) to give 2-methyl-2-propanyl [3-({4-[2-(4-fluorophenyl)-4-oxo-1,3-thiazolidin-3-yl]-3-methylbenzoyl}amino)propyl] carbamate (0.204 g, 69%). 1H NMR (CDCl$_3$, 400 MHz) δ 7.69 (br s, 1H), 7.52 (br s, 1H), 7.32-7.28 (m, 2H), 7.24 (br s, 1H), 6.95 (br t, 2H), 4.86 (br s, 1H), 4.01 (d, 1H), 3.91 (d, 1H), 3.44 (q, 2H), 3.20 (br q, 2H), 2.20 (br s, 3H), 1.70-1.67 (m, 2H), 1.43 (s, 9H).

Step 2. Synthesis of N-(3-aminopropyl)-4-[2-(4-fluorophenyl)-4-oxo-1,3-thiazolidin-3-yl]-3-methylbenzamide The solution of 2-methyl-2-propanyl [3-({4-[2-(4-fluorophenyl)-4-oxo-1,3-thiazolidin-3-yl]-3-methylbenzoyl}amino)propyl]carbamate (0.150 g) and TFA (3.00 µL) in CH$_2$Cl$_2$ (10.0 mL) was stirred at room temperature for 3 h. To the reaction mixture was added saturated NaHCO$_{3(aq)}$ to adjust the pH value to above 8 and extracted with CH$_2$Cl$_2$. The organic layers were dried over MgSO$_{4(s)}$, filtered and concentrated. The residue was purified by Isco Combi-Flash Companion column chromatography (10% MeOH in CH$_2$Cl$_2$) to give N-(3-Aminopropyl)-4-[2-(4-fluorophenyl)-4-oxo-1,3-thiazolidin-3-yl]-3-methylbenzamide (70.0 mg, 60%). 1H NMR (CDCl$_3$, 400 MHz) δ 7.57 (br s, 1H), 7.46 (br s, 1H), 7.30-7.28 (m, 3H), 6.91, (br s, 2H), 3.96 (d, 1H), 3.88 (d, 1H), 3.37-3.32 (m, 2H), 2.84 (t, 2H), 2.30-2.00 (br, 3H), 1.81 (quint, 2H); LC-MS (ESI) m/z 388.1 [M+H]$^+$.

EXAMPLE 264

4-[2-(4-Fluorophenyl)-4-oxo-1,3-thiazolidin-3-yl]-3-methyl-N-[3-(4-morpholinyl)propyl]benzamide Compound 347

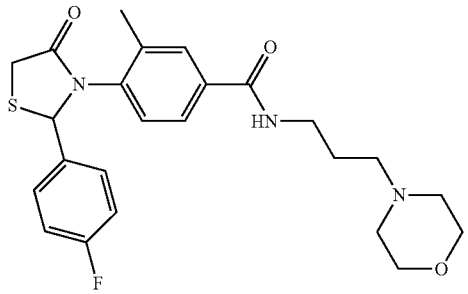

Following standard procedure K, 4-[2-(4-fluorophenyl)-4-oxo-1,3-thiazolidin-3-yl]-3-methylbenzoic acid (0.100 g, 0.302 mmol), 3-morpholinopropan-1-amine (32.0 µL, 0.332 mmol), HBTU (0.170 g, 0.453 mmol), triethylamine (93.0 µL, 0.664 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (5% MeOH in $CH_2Cl_2$) to give 4-[2-(4-fluorophenyl)-4-oxo-1,3-thiazolidin-3-yl]-3-methyl-N-[3-(4-morpholinyl)propyl]benzamide (21.4 mg, 16%). 1H NMR (CDCl₃, 400 MHz) δ 7.85 (br s, 1H), 7.63 (br s, 1H), 7.50 (br s, 1H), 7.30 (dd, 2H), 6.95 (br t, 2H), 4.00 (d, 1H), 3.92 (d, 1H), 3.67 (br s, 4H), 3.50 (q, 2H), 2.55-2.50 (m, 6H), 2.19 (br s, 3H), 1.76 (quint, 2H); LC-MS (APCI) m/z 458.8 [M+H]⁺.

EXAMPLE 265

4-[2-(4-Fluorophenyl)-4-oxo-1,3-thiazolidin-3-yl]-N-[3-(1H-imidazol-1-yl)propyl]-3-methylbenzamide Compound 348

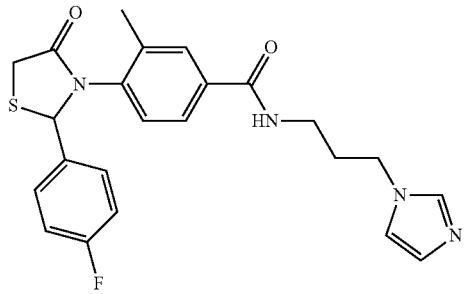

Following standard procedure K, 4-[2-(4-fluorophenyl)-4-oxo-1,3-thiazolidin-3-yl]-3-methylbenzoic acid (0.100 g, 0.302 mmol), 3-(1H-imidazol-1-yl)propan-1-amine (40.0 µL, 0.332 mmol), HBTU (0.170 g, 0.453 mmol), triethylamine (93.0 µL, 0.664 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (10% MeOH in $CH_2Cl_2$) to give 4-[2-(4-fluorophenyl)-4-oxo-1,3-thiazolidin-3-yl]-N-[3-(1H-imidazol-1-yl)propyl]-3-methylbenzamide (26.1 mg, 20%). 1H NMR (CDCl₃, 300 MHz) δ 7.54 (br s, 1H), 7.44-7.40 (m, 2H), 7.30 (dd, 2H), 7.01 (s, 1H), 7.00-6.90 (m, 3H), 6.73 (t, 1H), 5.90 (br s, 1H), 4.02-3.96 (m, 3H), 3.88 (d, 1H), 3.37 (q, 2H), 2.15 (br s, 3H), 2.09-2.03 (m, 2H); LC-MS (APCI) m/z 439.6 [M+H]⁺.

EXAMPLE 266

3-(4-{[(3R)-3-(Dimethylamino)-1-pyrrolidinyl]carbonyl}-2-methylphenyl)-2-(4-fluorophenyl)-1,3-thiazolidin-4-one Compound 349

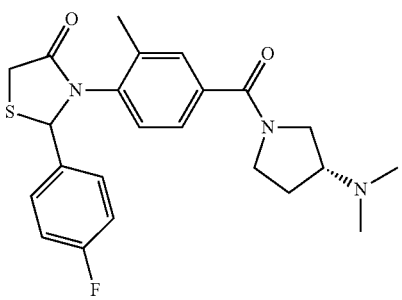

Following standard procedure K, 4-[2-(4-fluorophenyl)-4-oxo-1,3-thiazolidin-3-yl]-3-methylbenzoic acid (0.100 g, 0.302 mmol), (R)—N,N-dimethylpyrrolidin-3-amine (41.0 µL, 0.332 mmol), HBTU (0.170 g, 0.453 mmol), triethylamine (93.0 µL, 0.664 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (10% MeOH in $CH_2Cl_2$) to give 3-(4-{[(3R)-3-(dimethylamino)-1-pyrrolidinyl]carbonyl}-2-methylphenyl)-2-(4-fluorophenyl)-1,3-thiazolidin-4-one (97.3 mg, 75%). 1H NMR (CDCl₃, 400 MHz) δ 7.34 (br s, 0.4H), 7.31-7.28 (m, 2H), 7.20 (br s, 1.6H), 6.99 (br, 2H), 4.01 (d, 1H), 3.91 (d, 1H), 3.87-3.72 (m, 1H), 3.60-3.49 (m, 1.5H), 3.43-3.35 (m, 1H), 3.26-3.21 (m, 0.5H), 2.78-2.58 (m, 1H), 2.29 (s, 3H), 2.25-2.17 (m, 6H), 2.20-2.03 (m, 1H), 1.84-1.76 (m, 1H); LC-MS (APCI) m/z 428.8 [M+H]⁺.

EXAMPLE 267

Ethyl 4-({4-[2-(4-fluorophenyl)-4-oxo-1,3-thiazolidin-3-yl]-3-methylbenzoyl}amino)-1-piperidinecarboxylate Compound 350

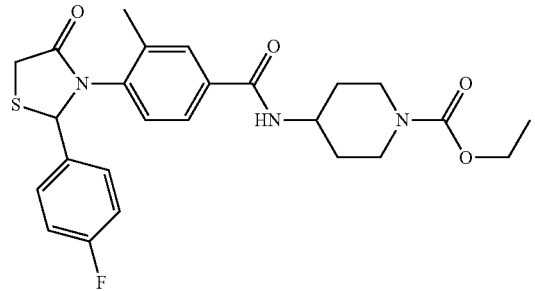

Following standard procedure K, 4-[2-(4-fluorophenyl)-4-oxo-1,3-thiazolidin-3-yl]-3-methylbenzoic acid (0.120 g, 0.362 mmol), ethyl 4-aminopiperidine-1-carboxylate (68.0 mg, 0.398 mmol), HBTU (0.210 g, 0.544 mmol), triethylamine (0.11 mL, 0.800 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-80% ethyl acetate in n-hexane) to give ethyl 4-({4-[2-(4-fluorophenyl)-4-oxo-1,3-thiazolidin-3-yl]-3-methylbenzoyl}amino)-1-piperidinecarboxylate (90.0 mg, 51%). 1H NMR ($CDCl_3$, 400 MHz) δ 7.55 (br s, 1H), 7.47 (br s, 1H), 7.30 (dd, 2H), 6.95 (br t, 2H), 6.12 (d, 1H), 5.95 (br s, 1H), 4.22-4.05 (m, 5H), 3.99 (d, 1H), 3.89 (d, 1H), 2.91 (br t, 2H), 2.17 (br s, 3H), 2.00-1.90 (m, 2H), 1.34 (qd, 2H), 1.25 (t, 3H); LC-MS (APCI) m/z 486.7 $[M+H]^+$.

EXAMPLE 268

3-[4-[(3-Amino-1-pyrrolidinyl)carbonyl]-2-methylphenyl]-2-(4-fluorophenyl)-1,3-thiazolidin-4-one

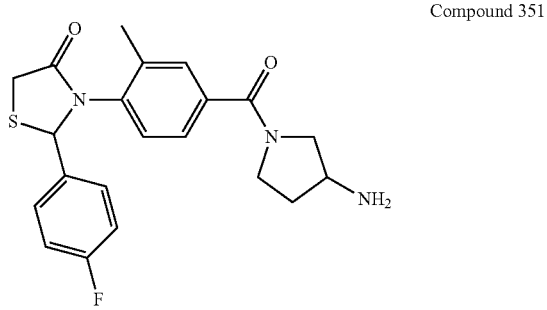 [SMILES: Cc1cc(C(=O)N2CCC(N)C2)ccc1N1C(=O)CSC1c1ccc(F)cc1]

Compound 351

Step 1. Synthesis of 2-methyl-2-propanyl (1-{4-[2-(4-fluorophenyl)-4-oxo-1,3-thiazolidin-3-yl]-3-methylbenzoyl}-3-pyrrolidinyl)carbamate

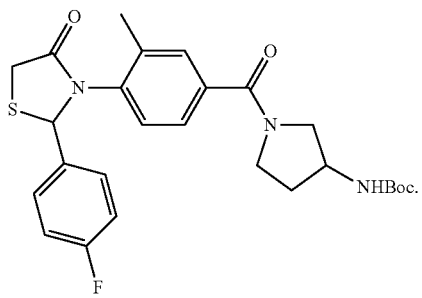

Compound 352

Following standard procedure E, 4-[2-(4-fluorophenyl)-4-oxo-1,3-thiazolidin-3-yl]-3-methylbenzoic acid (100 mg, 0.302 mmol), triethylamine (84.0 μL, 0.604 mmol), ethyl chloroformate (36.0 mg, 0.332 mmol), $CH_2Cl_2$ (10.0 mL) were used to carry out the reaction. After the reaction was stirred for 1 h, tert-butyl pyrrolidin-3-ylcarbamate (61.9 mg, 0.332 mmol) was added and then stirred at room temperature for 16 h and work up. The residue was purified by Isco Combi-Flash Companion column chromatography (0-80% ethyl acetate in n-hexane) to give 2-methyl-2-propanyl (1-{4-[2-(4-fluorophenyl)-4-oxo-1,3-thiazolidin-3-yl]-3-methylbenzoyl}-3-pyrrolidinyl)carbamate (33.6 mg, 22%). 1H NMR ($CDCl_3$, 400 MHz) δ 7.34 (br s, 1H), 7.31-7.27 (m, 2H), 7.26-7.40 (br, 2H), 6.96 (br t, 2H), 4.62-4.55 (br, 1H), 4.01 (d, 1H), 3.91 (d, 1H), 3.78-3.63 (m, 2H), 3.49-3.41 (m, 2H), 3.26-3.20 (m, 1H), 2.22 (br s, 3H), 1.86 (br s, 1H), 1.45-1.41 (m, 9H).

Step 2. Synthesis of 3-[4-[(3-Amino-1-pyrrolidinyl)carbonyl]-2-methylphenyl]-2-(4-fluorophenyl)-1,3-thiazolidin-4-one To a solution of 2-methyl-2-propanyl (1-{4-[2-(4-fluorophenyl)-4-oxo-1,3-thiazolidin-3-yl]-3-methylbenzoyl}-3-pyrrolidinyl)carbamate (33.6 mg) and TFA (5.00 μL) in $CH_2Cl_2$ (10.0 mL) was stirred at room temperature for 2 h. The reaction mixture was added saturated $NaHCO_{3(aq)}$ to adjust the pH value to above 8 and extracted with $CH_2Cl_2$. The organic layers were dried over $MgSO_{4(s)}$, filtered and concentrated. It was purified by Isco Combi-Flash Companion column chromatography (10% MeOH in $CH_2Cl_2$) to give 3-{4-[(3-amino-1-pyrrolidinyl)carbonyl]-2-methylphenyl}-2-(4-fluorophenyl)-1,3-thiazolidin-4-one (17.6 mg, 66%). 1H NMR ($CDCl_3$, 400 MHz) δ 7.35 (br s, 0.4H), 7.29 (dd, 2H), 7.25-7.03 (br, 1.6H), 6.99 (br, 2H), 4.01 (d, 1H), 3.90 (d, 1H), 3.79-3.74 (m, 2H), 3.64-3.54 (m, 2H), 3.40-3.32 (m, 1.5H), 3.20-3.10 (br, 0.5H), 2.20-2.00 (br, 4H); LC-MS (APCI) m/z 400.6 $[M+H]^+$.

EXAMPLE 269

2-(4-Fluorophenyl)-3-[4-[(3-hydroxy-1-piperidinyl)carbonyl]-2-methylphenyl]-1,3-thiazolidin-4-one

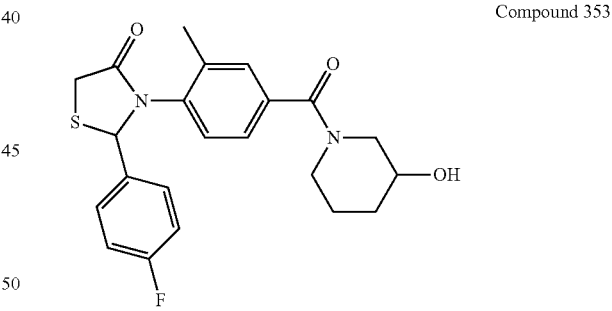

Compound 353

Following standard procedure K, 4-[2-(4-fluorophenyl)-4-oxo-1,3-thiazolidin-3-yl]-3-methylbenzoic acid (100 mg, 0.302 mmol), piperidin-3-ol (33.6 mg, 0.332 mmol), HBTU (170 mg, 0.453 mmol), triethylamine (92.0 μL, 0.664 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(4-fluorophenyl)-3-{4-[(3-hydroxy-1-piperidinyl)carbonyl]-2-methylphenyl}-1,3-thiazolidin-4-one (40.0 mg, 32%). 1H NMR ($CDCl_3$, 400 MHz) δ 7.31-7.28 (m, 3H), 7.10 (br s, 1H), 6.96 (br, 2H), 5.80 (br s, 1H), 4.02 (d, 1H), 3.92-3.88 (m, 2H), 3.70 (br s, 1H), 3.60-3.10 (br, 3H), 2.30-2.20 (br, 4H), 1.89 (br s, 2H), 1.74 (br s, 1H); LC-MS (APCI) m/z 415.7 $[M+H]^+$.

EXAMPLE 270

2-(4-Fluorophenyl)-3-{4-[(3-hydroxy-1-azetidinyl)carbonyl]-2-methylphenyl}-1,3-thiazolidin-4-one Compound 354

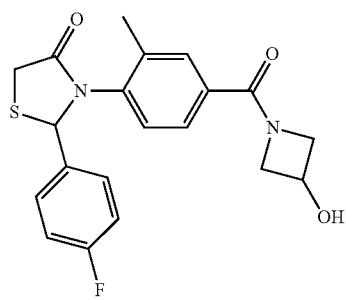

Following standard procedure K, 4-[2-(4-fluorophenyl)-4-oxo-1,3-thiazolidin-3-yl]-3-methylbenzoic acid (100 mg, 0.302 mmol), azetidin-3-ol (25.6 mg, 0.332 mmol), HBTU (170 mg, 0.453 mmol), triethylamine (92.0 μL, 0.664 mmol) and $CH_2Cl_2$ (10.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(4-fluorophenyl)-3-{4-[(3-hydroxy-1-azetidinyl)carbonyl]-2-methylphenyl}-1,3-thiazolidin-4-one (24.0 mg, 21%). 1H NMR ($CDCl_3$, 400 MHz) δ 7.52-7.41 (m, 2H), 7.31-7.27 (m, 3H), 6.95 (br t, 2H), 4.68 (br s, 1H), 4.42-4.38 (m, 2H), 4.14-4.09 (m, 1H), 4.03-3.99 (m, 2H), 3.91 (d, 1H), 2.20 (br s, 3H); LC-MS (APCI) m/z 387.8 $[M+H]^+$.

EXAMPLE 271

2-(4-Fluorophenyl)-3-(4-{[(2S)-2-(methoxymethyl)-1-pyrrolidinyl]carbonyl}-2-methylphenyl)-1,3-thiazolidin-4-one Compound 355

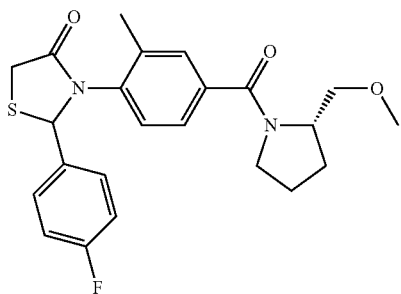

Following standard procedure K, 4-[2-(4-fluorophenyl)-4-oxo-1,3-thiazolidin-3-yl]-3-methylbenzoic acid (100 mg, 0.302 mmol), (S)-2-(methoxymethyl)pyrrolidine (41.0 μL, 0.332 mmol), HBTU (170 mg, 0.453 mmol), triethylamine (92.0 μL, 0.664 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(4-fluorophenyl)-3-(4-{[(2S)-2-(methoxymethyl)-1-pyrrolidinyl]carbonyl}-2-methylphenyl)-1,3-thiazolidin-4-one (17.6 mg, 14%). 1H NMR ($CDCl_3$, 400 MHz) δ 7.38-7.20 (m, 5H), 6.96 (br, 2H), 4.38 (br s, 1H), 4.01 (d, 1H), 3.90 (d, 1H), 3.59 (br s, 2H), 3.37 (br s, 3H), 2.16 (br s, 3H), 2.05-1.85 (br, 4H), 1.75-1.52 (m, 2H); LC-MS (APCI) m/z 429.7 $[M+H]^+$.

EXAMPLE 272

4-[2-(4-Fluorophenyl)-4-oxo-1,3-thiazolidin-3-yl]-N-(2-methoxyethyl)-N,3-dimethylbenzamide Compound 356

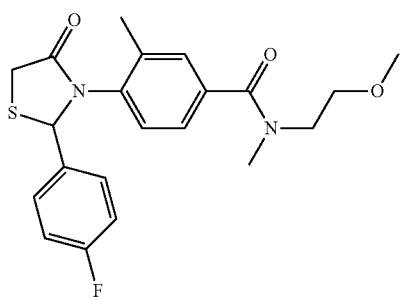

Following standard procedure K, 4-[2-(4-fluorophenyl)-4-oxo-1,3-thiazolidin-3-yl]-3-methylbenzoic acid (100 mg, 0.302 mmol), 2-methoxy-N-methylethan-1-amine (36.0 μL, 0.332 mmol), HBTU (170 mg, 0.453 mmol), triethylamine (92.0 μL, 0.664 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 4-[2-(4-fluorophenyl)-4-oxo-1,3-thiazolidin-3-yl]-N-(2-methoxyethyl)-N,3-dimethylbenzamide (15.0 mg, 12%). 1H NMR ($CDCl_3$, 400 MHz) δ 7.31-7.27 (m, 3H), 7.16 (br s, 1H), 6.97-6.90 (br, 2H), 5.81 (br s, 1H), 4.01 (d, 1H), 3.89 (d, 1H), 3.70-3.60 (br, 2H), 3.42-3.30 (br, 4H), 3.24 (br s, 1H), 3.10-2.97 (br, 3H), 2.15 (br s, 3H); LC-MS (APCI) m/z 403.8 $[M+H]^+$.

EXAMPLE 273

3-{4-[(4-Amino-1-piperidinyl)carbonyl]-2-methylphenyl}-2-(4-fluorophenyl)-1,3-thiazolidin-4-one Compound 357

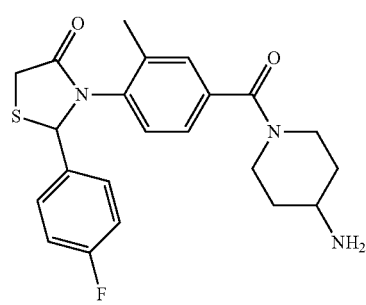

429

Step 1. Synthesis of 2-methyl-2-propanyl (1-{4-[2-(4-fluorophenyl)-4-oxo-1,3-thiazolidin-3-yl]-3-methylbenzoyl}-4-piperidinyl)carbamate Compound 358

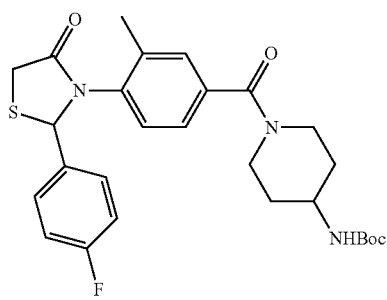

Following standard procedure E, 4-[2-(4-fluorophenyl)-4-oxo-1,3-thiazolidin-3-yl]-3-methylbenzoic acid (130 mg, 0.393 mmol), triethylamine (0.110 mL, 0.785 mmol), ethyl chloroformate (46.0 mg, 0.431 mmol), CH$_2$Cl$_2$ (10.0 mL) were used to carry out the reaction. After the reaction was stirred for 1 h, tert-butyl piperidin-4-ylcarbamate (87.0 mg, 0.431 mmol) was added and then stirred at room temperature for 16 h and work up. The residue was purified by Isco Combi-Flash Companion column chromatography (0-80% ethyl acetate in n-hexane) to give 2-methyl-2-propanyl (1-{4-[2-(4-fluorophenyl)-4-oxo-1,3-thiazolidin-3-yl]-3-methylbenzoyl}-4-piperidinyl)carbamate (96.0 mg, 48%). 1H NMR (CDCl$_3$, 400 MHz) δ 7.31-7.27 (m, 2H), 7.21-7.19 (br, 1H), 7.12-7.09 (br, 1H), 7.03-6.96 (m, 2H), 4.51-4.46 (m, 4H), 4.06 (d, 1H), 3.94 (d, 1H), 3.78-3.64 (m, 4H), 3.03-2.91 (br, 1H), 2.20 (br s, 3H), 1.44 (s, 9H).

Step 2. Synthesis of 3-{4-[(4-amino-1-piperidinyl)carbonyl]-2-methylphenyl}-2-(4-fluorophenyl)-1,3-thiazolidin-4-one The solution of (1-{4-[2-(4-fluorophenyl)-4-oxo-1,3-thiazolidin-3-yl]-3-methylbenzoyl}-4-piperidinyl)carbamate (90.0 mg) and TFA (5.00 µL) in CH$_2$Cl$_2$ (10.0 mL) was stirred at room temperature for 2 h. To the reaction mixture was added saturated NaHCO$_{3(aq)}$ to adjust the pH value to above 8 and extracted with CH$_2$Cl$_2$. The organic layers were dried over MgSO$_{4(s)}$, filtered and concentrated. The residue was purified by Isco Combi-Flash Companion column chromatography (15% MeOH in CH$_2$Cl$_2$) to give 3-{4-[(4-amino-1-piperidinyl)carbonyl]-2-methylphenyl}-2-(4-fluorophenyl)-1,3-thiazolidin-4-one (6.80 mg, 9%). 1H NMR (CDCl$_3$, 400 MHz) δ 7.31-7.28 (m, 2H), 7.22 (br s, 1H), 7.08 (br s, 1H), 6.95 (br s, 2H), 4.51 (br s, 1H), 3.95 (d, 1H), 3.89 (d, 1H), 3.64 (br s, 1H), 3.06-2.97 (br, 2H), 2.84 (br s, 1H), 2.24 (br s, 5H), 1.92 (br s, 2H), 1.76 (br s, 2H); LC-MS (ACPI) m/z 414.5 [M+H]$^+$.

430

EXAMPLE 274

N-(Adamantan-1-yl)-4-(2-(4-fluorophenyl)-4-oxothiazolidin-3-yl)-3-methylbenzamide Compound 359

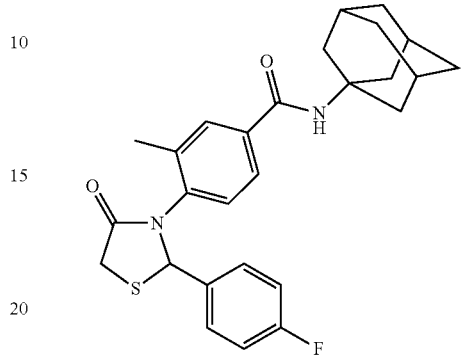

The compound was prepared by following the standard procedure K with 4-(2-(4-fluorophenyl)-4-oxothiazolidin-3-yl)-3-methylbenzoic acid (50.0 mg, 0.150 mmol), HBTU (85.3 mg, 0.225 mmol), 1-adamantamine (27.2 mg, 0.180 mmol), DIPEA (52.0 µL, 38.7 mg, 0.300 mmol), and CH$_2$Cl$_2$ (3.0 mL). After the reaction mixture was stirred for 16 h and work-up, the residue was purified by recrystallization to give the desired product as a white solid (50.0 mg, 72%). 1H NMR (CDCl$_3$, 300 MHz) δ 7.51 (br s, 1H), 7.38 (br s, 1H), 7.30 (dd, 2H), 6.95 (br t, 2H), 5.90 (br s, 1H), 5.66 (br s, 1H), 4.00 (d, 1H), 3.90 (d, 1H), 2.28-2.00 (br, 9H), 1.80 (br s, 3H), 1.70 (br s, 6H); LC-MS (ESI) m/z 465.9 [M+H]$^+$.

EXAMPLE 275

N-(Adamantan-1-ylmethyl)-4-(2-(4-fluorophenyl)-4-oxothiazolidin-3-yl)-3-methylbenzamide Compound 360

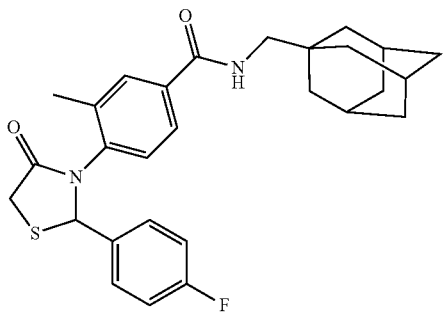

The compound was prepared by following the standard procedure K with 4-(2-(4-fluorophenyl)-4-oxothiazolidin-3-yl)-3-methylbenzoic acid (50.0 mg, 0.150 mmol), HBTU (85.3 mg, 0.225 mmol), 1-adamantanemethylamine (24.9 mg, 0.150 mmol), DIPEA (52.0 µL, 38.7 mg, 0.300 mmol), and CH$_2$Cl$_2$ (9.0 mL). After the reaction mixture was stirred for 16 h and work-up, the residue was purified by flash chromatography (ethyl acetate:hexane=1:1) to give the desired product as a yellow viscous liquid (48.0 mg, 67%). 1H NMR (CDCl3, 400 MHz) δ 7.56 (br s, 1H), 7.43 (br s, 1H), 7.31 (dd, 2H), 6.96 (br t, 2H), 6.20-5.70 (br, 2H), 4.01 (d, 1H), 3.92 (d, 1H), 3.20-3.00 (m, 2H), 2.19 (br s, 3H), 1.98 (br s, 3H), 1.73-1.58 (m, 6H), 1.51 (s, 6H); LC-MS (ESI) m/z 479.9 [M+H]+.

EXAMPLE 276

4-[2-(4-Fluorophenyl)-4-oxo-1,3-thiazolidin-3-yl]-3-methyl-N-phenylbenzamide

Compound 361

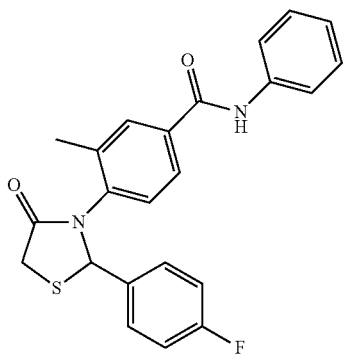

Following standard procedure K, 4-[2-(4-fluorophenyl)-4-oxo-1,3-thiazolidin-3-yl]-3-methylbenzoic acid (85.3 mg, 0.257 mmol), aniline (26.3 mg, 0.283 mmol), triethylamine (80.0 µL, 0.569 mmol), HBTU (146 mg, 0.386 mmol), and CH2Cl2 (6.0 mL) were used to carry out the reaction. After the reaction mixture was stirred at room temperature for 15 h and work-up, the residue was purified by Isco Combi-Flash Companion column chromatography (0-50% ethyl acetate in n-hexane) to give 4-[2-(4-fluorophenyl)-4-oxo-1,3-thiazolidin-3-yl]-3-methyl-N-phenylbenzamide (40.5 mg, 39%) as a beige solid. 1H NMR (CDCl3, 400 MHz) δ 7.77 (s, 1H), 7.70-7.45 (m, 4H), 7.39-7.32 (m, 4H), 7.16 (t, 1H), 7.01-6.96 (m, 3H), 6.10-5.70 (br, 1H), 4.04 (d, 1H), 3.95 (d, 1H), 2.22 (br s, 3H); LC-MS (ESI) m/z 407.3 [M+H]+.

EXAMPLE 277

4-[2-(4-Fluorophenyl)-4-oxo-1, 3-thiazolidin-3-yl]-N-(4-methoxyphenyl)-3-methylbenzamide Compound 362

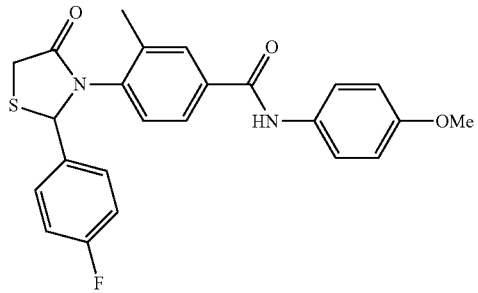

Following standard procedure K, 4-[2-(4-fluorophenyl)-4-oxo-1,3-thiazolidin-3-yl]-3-methylbenzoic acid (150 mg, 0.450 mmol), 4-methoxyaniline (60.0 mg, 0.490 mmol), HBTU (260 mg, 0.680 mmol), triethylamine (0.300 mL, 1.00 mmol) and CH2Cl2 (10.0 mL) were used to carry out the reaction. After the reaction mixture was stirred at room temperature for 16 h and work-up, the resulting residue was purified by Isco Combi-Flash Companion column chromatography (0-50% ethyl acetate in n-hexane) to give 4-[2-(4-fluorophenyl)-4-oxo-1,3-thiazolidin-3-yl]-N-(4-methoxyphenyl)-3-methylbenzamide (73.0 mg, 37%) as a yellow solid. 1H NMR (CDCl3, 400 MHz) δ 7.86 (s, 1H), 7.60 (br s, 1H), 7.56-7.51 (m, 3H), 7.32-7.27 (m, 2H), 6.98 (t, 2H), 6.88-6.85 (m, 2H), 5.99 (br s, 1H), 4.00 (d, 1H), 3.91 (d, 1H), 3.80 (s, 3H), 2.17 (br s, 3H); LC-MS (APCI) m/z 437.8 [M+H]+.

EXAMPLE 278

4-[2-(4-Fluorophenyl)-4-oxo-1,3-thiazolidin-3-yl]-3-methyl-N-(4-methylphenyl)benzamide Compound 363

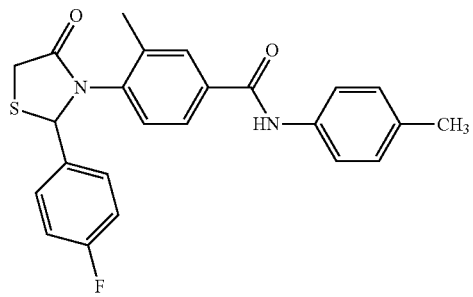

Following standard procedure K, 4-[2-(4-fluorophenyl)-4-oxo-1,3-thiazolidin-3-yl]-3-methylbenzoic acid (110 mg, 0.330 mmol), p-toluidine (39.0 mg, 0.370 mmol), HBTU (189 mg, 0.500 mmol), triethylamine (0.100 mL, 0.730 mmol) and CH2Cl2 (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 4-[2-(4-fluorophenyl)-4-oxo-1,3-thiazolidin-3-yl]-3-methyl-N-(4-methylphenyl)benzamide (46.0 mg, 33%) as a yellow solid. 1H NMR (CDCl3, 400 MHz) δ 8.15 (br s, 1H), 7.53 (br s, 1H), 7.47 (d, 2H), 7.43-7.39 (m, 2H), 7.27 (t, 2H), 7.12 (d, 2H), 6.93 (t, 2H), 5.95 (br s, 1H), 3.99 (d, 1H), 3.89 (d, 1H), 2.31 (s, 3H), 2.09 (br s, 3H); LC-MS (APCI) m/z 421.6 [M+H]+.

EXAMPLE 279

N-(4-Fluorophenyl)-4-[2-(4-fluorophenyl)-4-oxo-1,3-thiazolidin-3-yl]-3-methylbenzamide Compound 364

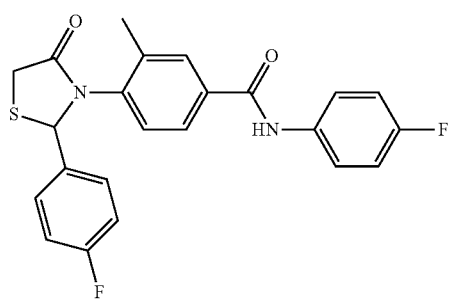

Following standard procedure K, 4-[2-(4-fluorophenyl)-4-oxo-1,3-thiazolidin-3-yl]-3-methylbenzoic acid (150 mg, 0.450 mmol), 4-fluoroaniline (48.0 µL, 0.500 mmol), HBTU (260 mg, 0.680 mmol), triethylamine (0.140 mL, 1.00 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(4-fluorophenyl)-4-[2-(4-fluorophenyl)-4-oxo-1,3-thiazolidin-3-yl]-3-methylbenzamide (190 mg, 98%) as a white solid. 1H NMR (CDCl$_3$, 400 MHz) δ 7.95 (br s, 1H), 7.60-7.50 (m, 2H), 7.46 (br s, 1H), 7.30 (dd, 2H), 7.07-7.01 (m, 2H), 6.96 (t, 2H), 5.95 (br s, 1H), 4.01 (d, 1H), 3.92 (d, 1H), 2.07 (br s, 3H); LC-MS (APCI) m/z 425.7 [M+H]$^+$.

EXAMPLE 280

N-(4-Chlorophenyl)-4-[2-(4-fluorophenyl)-4-oxo-1,3-thiazolidin-3-yl]-3-methylbenzamide Compound 365

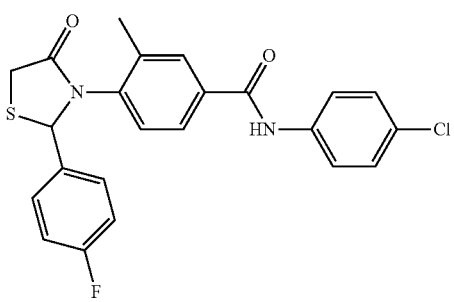

Following standard procedure K, 4-[2-(4-fluorophenyl)-4-oxo-1,3-thiazolidin-3-yl]-3-methylbenzoic acid (150 mg, 0.450 mmol), 4-chloroaniline (63.0 µL, 0.500 mmol), HBTU (260 mg, 0.680 mmol), triethylamine (0.140 mL, 0.100 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(4-chlorophenyl)-4-[2-(4-fluorophenyl)-4-oxo-1,3-thiazolidin-3-yl]-3-methylbenzamide (193 mg, 78%) as a white solid. 1H NMR (CDCl$_3$, 400 MHz) δ 7.98 (s, 1H), 7.57-7.51 (m, 2H), 7.45 (br s, 1H), 7.31-7.28 (m, 4H), 6.96 (t, 2H), 4.01 (d, 1H), 3.92 (d, 1H), 2.13 (br s, 3H); LC-MS (APCI) m/z 441.9 [M+H]$^+$.

EXAMPLE 281

N-(3-Fluorophenyl)-4-[2-(4-fluorophenyl)-4-oxo-1,3-thiazolidin-3-yl]-3-methylbenzamide Compound 366

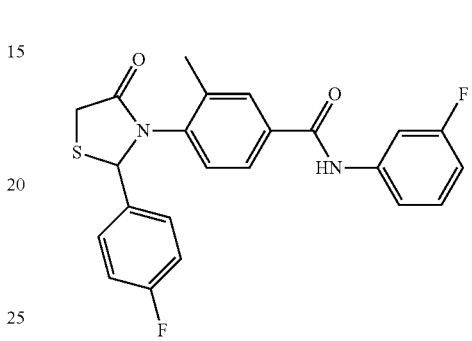

Following standard procedure K, 4-[2-(4-fluorophenyl)-4-oxo-1,3-thiazolidin-3-yl]-3-methylbenzoic acid (120 mg, 0.360 mmol), 3-fluoroaniline (48.0 µL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(3-fluorophenyl)-4-[2-(4-fluorophenyl)-4-oxo-1,3-thiazolidin-3-yl]-3-methylbenzamide (33.0 mg, 21%). 1H NMR (CDCl$_3$, 400 MHz) δ 7.99 (s, 1H), 7.58 (br s, 1H), 7.54 (dd, 1H), 7.46 (br s, 1H), 7.35-7.22 (m, 4H), 6.96 (t, 2H), 6.84 (t, 1H), 5.97 (br s, 1H), 4.02 (d, 1H), 3.92 (d, 1H), 2.16 (br s, 3H); LC-MS (APCI) m/z 425.6 [M+H]$^+$.

EXAMPLE 282

N-(3-Chlorophenyl)-4-[2-(4-fluorophenyl)-4-oxo-1,3-thiazolidin-3-yl]-3-methylbenzamide Compound 367

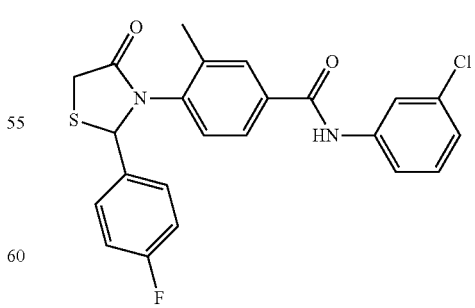

Following standard procedure K, 4-[2-(4-fluorophenyl)-4-oxo-1,3-thiazolidin-3-yl]-3-methylbenzoic acid (120 mg, 0.360 mmol), 3-chloroaniline (42.0 µL, 0.400 mmol), HBTU (210 mg, 0.540 mmol), triethylamine (0.110 mL, 0.790 mmol) and CH₂Cl₂ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give N-(3-chlorophenyl)-4-[2-(4-fluorophenyl)-4-oxo-1,3-thiazolidin-3-yl]-3-methylbenzamide (13.0 mg, 8%). 1H NMR (CDCl₃, 400 MHz) δ 7.98 (s, 1H), 7.68 (d, 1H), 7.57 (br s, 1H), 7.48 (d, 1H), 7.40-7.22 (m, 4H), 7.11 (d, 1H), 6.96 (t, 2H), 5.99 (br s, 1H), 4.02 (d, 1H), 3.92 (d, 1H), 2.15 (br s, 3H); LC-MS (APCI) m/z 441.5 [M+H]⁺.

EXAMPLE 283

4-[2-(4-Fluorophenyl)-4-oxo-1,3-thiazolidin-3-yl]-N-(3-methoxyphenyl)-3-methylbenzamide Compound 368

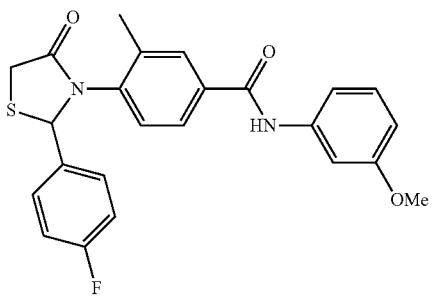

Following standard procedure K, 4-[2-(4-fluorophenyl)-4-oxo-1,3-thiazolidin-3-yl]-3-methylbenzoic acid (120 mg, 0.360 mmol), 3-methoxyaniline (44.0 μL, 0.400 mmol), HBTU (210 mg, 0.540 mmol), triethylamine (0.110 mL, 0.790 mmol) and CH₂Cl₂ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 4-[2-(4-fluorophenyl)-4-oxo-1,3-thiazolidin-3-yl]-N-(3-methoxyphenyl)-3-methylbenzamide (82.0 mg, 52%). 1H NMR (CDCl₃, 400 MHz) δ 7.90 (br s, 1H), 7.60 (br s, 1H), 7.48 (br s, 1H), 7.36 (t, 1H), 7.30 (dd, 2H), 7.26-7.20 (m, 1H), 7.06 (dd, 1H), 6.96 (dd, 2H), 6.67 (dd, 1H), 5.95 (br s, 1H), 4.01 (d, 1H), 3.92 (d, 1H), 3.80 (s, 3H), 2.17 (br s, 3H); LC-MS (ESI) m/z 437.6 [M+H]⁺.

EXAMPLE 284

4-[2-(4-Fluorophenyl)-4-oxo-1,3-thiazolidin-3-yl]-3-methyl-N-[4-(trifluoromethyl)phenyl]benzamide Compound 369

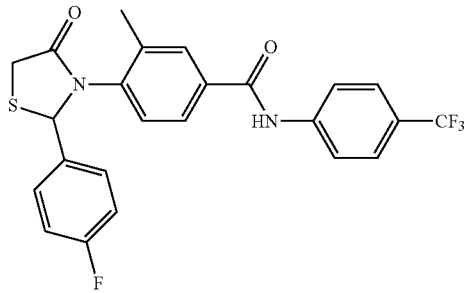

Following standard procedure K, 4-[2-(4-fluorophenyl)-4-oxo-1,3-thiazolidin-3-yl]-3-methylbenzoic acid (120 mg, 0.360 mmol), 4-(trifluoromethyl)aniline (50.0 μL, 0.400 mmol), HBTU (210 mg, 0.540 mmol), triethylamine (0.110 mL, 0.790 mmol) and CH₂Cl₂ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 4-[2-(4-fluorophenyl)-4-oxo-1,3-thiazolidin-3-yl]-3-methyl-N-[4-(trifluoromethyl)phenyl]benzamide (21.0 mg, 12%). 1H NMR (CDCl₃, 400 MHz) δ 8.43 (s, 1H), 7.74 (d, 2H), 7.58 (d, 2H), 7.52 (br s, 1H), 7.41 (br s, 1H), 7.28 (dd, 2H), 6.94 (dd, 2H), 5.95 (br s, 1H), 4.01 (d, 1H), 3.91 (d, 1H), 2.07 (br s, 3H); LC-MS (APCI) m/z 475.8 [M+H]⁺.

EXAMPLE 285

4-[2-(4-Fluorophenyl)-4-oxo-1,3-thiazolidin-3-yl]-3-methyl-N-(3-methylphenyl)benzamide Compound 370

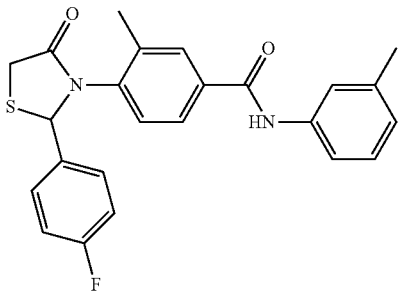

Following standard procedure K, 4-[2-(4-fluorophenyl)-4-oxo-1,3-thiazolidin-3-yl]-3-methylbenzoic acid (120 mg, 0.360 mmol), m-toluidine (43.0 μL, 0.400 mmol), HBTU (210 mg, 0.540 mmol), triethylamine (0.110 mL, 0.790 mmol) and CH₂Cl₂ (5.0 mL) were used to carry out the reaction. After the reaction mixture was stirred at room temperature for 16 h and work-up, the residue was purified by Isco Combi-Flash Companion column chromatography (50% ethyl acetate in n-hexane) to give 4-[2-(4-fluorophenyl)-4-oxo-1,3-thiazolidin-3-yl]-3-methyl-N-(3-methylphenyl)benzamide (88.0 mg, 58%). 1H NMR (CDCl₃, 400 MHz) δ 7.76 (br s, 1H), 7.63 (br s, 1H), 7.49 (br s, 1H), 7.43 (s, 1H), 7.37-7.30 (m, 3H), 7.25-7.20 (m, 2H), 7.03-6.95 (m, 3H), 5.95 (br s, 1H), 4.01 (d, 1H), 3.92 (d, 1H), 2.35 (s, 3H), 2.20 (br s, 3H); LC-MS (ACPI) m/z 421.7 [M+H]⁺.

EXAMPLE 286

N-(3,5-Dimethylphenyl)-4-[2-(4-fluorophenyl)-4-oxo-1,3-thiazolidin-3-yl]-3-methylbenzamide Compound 371

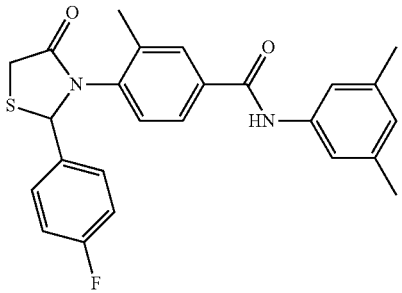

Following standard procedure K, 4-[2-(4-fluorophenyl)-4-oxo-1,3-thiazolidin-3-yl]-3-methylbenzoic acid (100 mg, 0.300 mmol), 3,5-dimethylaniline (40.0 µL, 0.330 mmol), HBTU (172 mg, 0.450 mmol), triethylamine (90.0 µL, 0.660 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give N-(3,5-dimethylphenyl)-4-[2-(4-fluorophenyl)-4-oxo-1,3-thiazolidin-3-yl]-3-methylbenzamide (62.0 mg, 47%). 1H NMR (CDCl$_3$, 400 MHz) δ 7.98 (br s, 1H), 7.56 (br s, 1H), 7.45 (br s, 1H), 7.30-7.26 (m, 2H), 6.95 (dd, 2H), 6.77 (br s, 1H), 5.97 (br s, 1H), 3.99 (d, 1H), 3.89 (d, 1H), 2.28 (s, 6H), 2.12 (br s, 3H); LC-MS (ACPI) m/z 435.7 [M+H]$^+$.

EXAMPLE 287

N-(2,3-Dihydro-1H-inden-5-yl)-4-[2-(4-fluorophenyl)-4-oxo-1,3-thiazolidin-3-yl]-3-methylbenzamide Compound 372

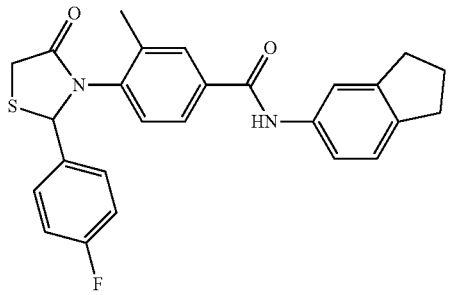

Following standard procedure K, 4-[2-(4-fluorophenyl)-4-oxo-1,3-thiazolidin-3-yl]-3-methylbenzoic acid (100 mg, 0.300 mmol), 2,3-dihydro-1H-inden-5-amine (44.0 mg, 0.330 mmol), HBTU (172 mg, 0.450 mmol), and triethylamine (90.0 µL, 0.660 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (50% ethyl acetate in n-hexane) to give N-(2,3-dihydro-1H-inden-5-yl)-4-[2-(4-fluorophenyl)-4-oxo-1,3-thiazolidin-3-yl]-3-methylbenzamide (39.0 mg, 40%). 1H NMR (CDCl$_3$, 400 MHz) δ 7.73 (s, 1H), 7.63 (br s, 1H), 7.52 (s, 1H), 7.33-7.29 (m, 2H), 7.23 (dd, 1H), 7.17 (d, 1H), 6.97 (t, 2H), 6.20-5.70 (br, 1H), 4.02 (d, 1H), 3.92 (d, 1H), 2.92-2.84 (m, 4H), 2.21 (br s, 3H), 2.10-2.04 (m, 2H); LC-MS (ACPI) m/z 447.6 [M+H]$^+$.

EXAMPLE 288

4-[2-(4-Fluorophenyl)-4-oxo-1,3-thiazolidin-3-yl]-N-(2-methoxyphenyl)-3-methylbenzamide Compound 373

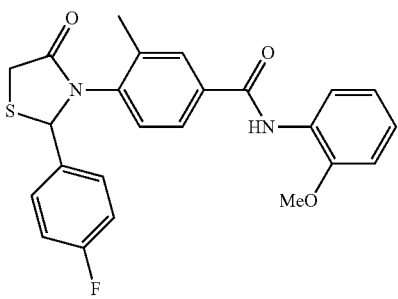

Following standard procedure K, 4-[2-(4-fluorophenyl)-4-oxo-1,3-thiazolidin-3-yl]-3-methylbenzoic acid (100 mg, 0.300 mmol) was added 2-methoxyaniline (44.0 mg, 0.330 mmol), HBTU (172 mg, 0.450 mmol), triethylamine (90.0 µL, 0.660 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (50% ethyl acetate in n-hexane) to give 4-[2-(4-fluorophenyl)-4-oxo-1,3-thiazolidin-3-yl]-N-(2-methoxyphenyl)-3-methylbenzamide (39.0 mg, 40%). 1H NMR (CDCl$_3$, 400 MHz) δ 8.43 (d, 1H), 8.39 (s, 1H), 7.69 (br s, 1H), 7.59 (br s, 1H), 7.35-7.30 (m, 2H), 7.07 (dd, 1H), 7.03-6.95 (m, 3H), 6.89 (d, 1H), 5.95 (br s, 1H), 4.02 (d, 1H), 3.92-3.84 (m, 4H), 2.20 (br s, 3H); LC-MS (ACPI) m/z 437.8 [M+H]$^+$.

EXAMPLE 289

N-Benzyl-4-[2-(4-fluorophenyl)-4-oxo-1,3-thiazolidin-3-yl]-3-methylbenzamide

Compound 374

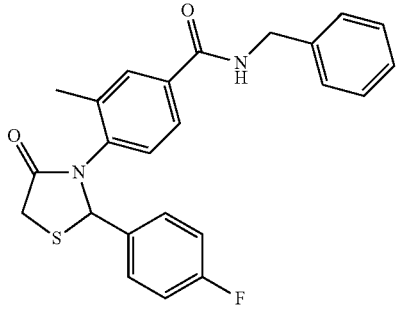

Following standard procedure K, 4-[2-(4-fluorophenyl)-4-oxo-1,3-thiazolidin-3-yl]-3-methylbenzoic acid (82.1 mg, 0.248 mmol), benzyl amine (30.0 µL, 0.274 mmol), diisopropylethylamine (64.1 mg, 0.496 mmol), O-(benzotriazol-1-yl)-N,N,N',N'-tetramethyluronium hexafluorophosphate (HBTU, 141 mg, 0.372 mmol), and CH$_2$Cl$_2$ (6.0 mL) were use to carry out the reaction. After the reaction mixture was stirred at room temperature for 16 h and work-up, the residue was purified by Isco Combi-Flash Companion column chromatography (0-90% ethyl acetate in n-hexane) to give N-benzyl-4-[2-(4-fluorophenyl)-4-oxo-1,3-thiazolidin-3-yl]-3-methylbenzamide (47.9 mg, 46%) as a white solid. 1H NMR (CDCl$_3$, 400 MHz) δ 7.65-7.40 (br, 2H), 7.37-7.28 (m, 8H), 6.95 (br t, 2H), 6.26 (br t, 1H), 6.20-5.80 (br, 1H), 4.60 (d, 2H), 4.00 (d, 1H), 3.91 (d, 1H), 2.17 (br s, 3H); LC-MS (ESI) m/z 421.3 [M+H]$^+$.

EXAMPLE 290

N-(4-Chloro-2-fluorobenzyl)-4-[2-(4-fluorophenyl)-4-oxo-1,3-thiazolidin-3-yl]-3-methylbenzamide

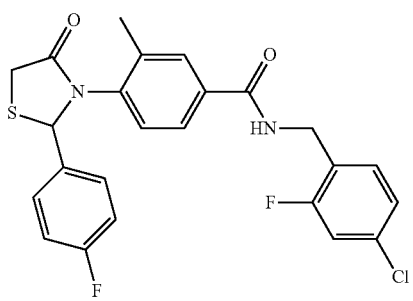

Compound 375

Following standard procedure K, 4-[2-(4-fluorophenyl)-4-oxo-1,3-thiazolidin-3-yl]-3-methylbenzoic acid (120 mg, 0.360 mmol), (4-chloro-2-fluorophenyl)methanamine (50.0 µL, 0.400 mmol), HBTU (210 mg, 0.540 mmol), triethylamine (0.110 mL, 0.790 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane, 5% MeOH in $CH_2Cl_2$) to give N-(4-chloro-2-fluorobenzyl)-4-[2-(4-fluorophenyl)-4-oxo-1,3-thiazolidin-3-yl]-3-methylbenzamide (977 mg, 57%). 1H NMR ($CDCl_3$, 400 MHz) δ 7.57 (br s, 1H), 7.45 (br s, 1H), 7.34-7.25 (m, 3H), 7.11-7.07 (m, 3H), 6.95 (t, 2H), 6.44 (br s, 1H), 5.93 (br s, 1H), 4.58 (d, 2H), 3.99 (d, 1H), 3.90 (d, 1H), 2.17 (br s, 3H); LC-MS (APCI) m/z 473.6 [M+H]$^+$.

EXAMPLE 291

N-(2,5-Difluorobenzyl)-4-[2-(4-fluorophenyl)-4-oxo-1, 3-thiazolidin-3-yl]-3-methylbenzamide

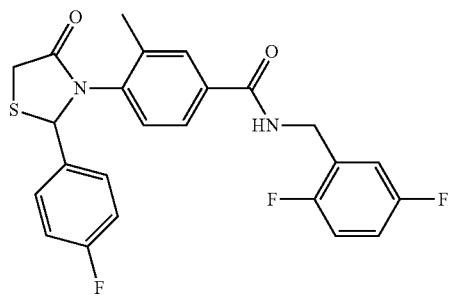

Compound 376

Following standard procedure K, 4-[2-(4-fluorophenyl)-4-oxo-1,3-thiazolidin-3-yl]-3-methylbenzoic acid (120 mg, 0.360 mmol), (2,5-difluorophenyl)methanamine (40.0 µL, 0.400 mmol), HBTU (210 mg, 0.540 mmol), triethylamine (0.110 mL, 0.790 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane, 5% MeOH in $CH_2Cl_2$) to give N-(2,5-difluorobenzyl)-4-[2-(4-fluorophenyl)-4-oxo-1,3-thiazolidin-3-yl]-3-methylbenzamide (0.120 g, 73%). 1H NMR ($CDCl_3$, 400 MHz) δ 7.58 (br s, 1H), 7.45 (br s, 1H), 7.30-7.28 (m, 2H), 7.10-6.85 (m, 6H), 6.56 (br s, 1H), 5.91 (br s, 1H), 4.58 (d, 2H), 3.99 (d, 1H), 3.90 (d, 1H), 2.17 (br s, 3H); LC-MS (APCI) m/z 457.7 [M+H]$^+$.

EXAMPLE 292

4-[2-(4-Fluorophenyl)-4-oxo-1,3-thiazolidin-3-yl]-3-methyl-N-[3-(trifluoromethyl)benzyl]benzamide

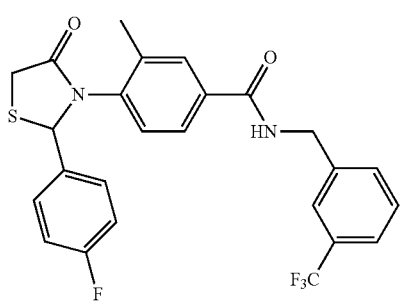

Compound 377

Following standard procedure K, 4-[2-(4-fluorophenyl)-4-oxo-1,3-thiazolidin-3-yl]-3-methylbenzoic acid (120 mg, 0.360 mmol), 3-(trifluoromethyl)benzylamine (69.0 µL, 0.400 mmol), HBTU (210 mg, 0.540 mmol), triethylamine (0.110 mL, 0.790 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 4-[2-(4-fluorophenyl)-4-oxo-1,3-thiazolidin-3-yl]-3-methyl-N-[3-(trifluoromethyl)benzyl]benzamide (120 mg, 79%). 1H NMR ($CDCl_3$, 400 MHz) δ 7.60-7.37 (m, 7H), 7.29-7.26 (m, 2H), 6.93 (t, 2H), 6.84 (t, 1H), 5.90 (br s, 1H), 4.56 (d, 2H), 3.97 (d, 1H), 3.87 (d, 1H), 2.10 (br s, 3H); LC-MS (ACPI) m/z 489.7 [M+H]$^+$.

EXAMPLE 293

N-(3,4-Difluorobenzyl)-4-[2-(4-fluorophenyl)-4-oxo-1, 3-thiazolidin-3-yl]-3-methylbenzamide

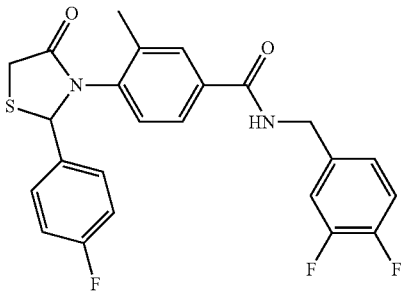

Compound 378

Following standard procedure K, 4-[2-(4-fluorophenyl)-4-oxo-1,3-thiazolidin-3-yl]-3-methylbenzoic acid (120 mg, 0.360 mmol), (3,4-difluorophenyl)methanamine (57.0 mg, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(3,4-difluorobenzyl)-4-[2-(4-fluorophenyl)-4-oxo-1,3-thiazolidin-3-yl]-3-methylbenzamide (100 mg, 60%). 1H NMR (CDCl$_3$, 400 MHz) δ 7.58 (br s, 1H), 7.46 (br s, 1H), 7.31-7.26 (m, 2H), 7.12 (dd, 3H), 7.03 (br s, 1H), 6.95 (t, 2H), 6.44 (br s, 1H), 5.92 (br s, 1H), 4.52 (d, 2H), 4.00 (d, 1H), 3.91 (d, 1H), 2.18 (br s, 3H); LC-MS (ACPI) m/z 457.8 [M+H]$^+$.

EXAMPLE 294

N-(3,4-Dichlorobenzyl)-4-[2-(4-fluorophenyl)-4-oxo-1,3-thiazolidin-3-yl]-3-methylbenzamide Compound 379

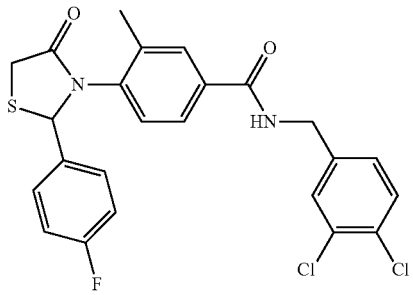

Following standard procedure K, 4-[2-(4-fluorophenyl)-4-oxo-1,3-thiazolidin-3-yl]-3-methylbenzoic acid (120 mg, 0.360 mmol), (3,4-dichlorophenyl)methanamine (53.0 mg, 0.400 mmol), HBTU (210 mg, 0.540 mmol), and triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(3,4-dichlorobenzyl)-4-[2-(4-fluorophenyl)-4-oxo-1,3-thiazolidin-3-yl]-3-methylbenzamide (130 mg, 73%). 1H NMR (CDCl$_3$, 400 MHz) δ 7.51 (br s, 1H), 7.43-7.32 (m, 3H), 7.28-7.25 (m, 2H), 7.14-7.07 (m, 2H), 6.98 (t, 1H), 6.92 (t, 2H), 5.90 (br s, 1H), 4.42 (d, 2H), 3.96 (d, 1H), 3.86 (d, 1H), 2.07 (br s, 3H); LC-MS (ACPI) m/z 490.6 [M+H]$^+$.

EXAMPLE 295

N-(3,5-Dimethoxybenzyl)-4-[2-(4-fluorophenyl)-4-oxo-1,3-thiazolidin-3-yl]-3-methylbenzamide Compound 380

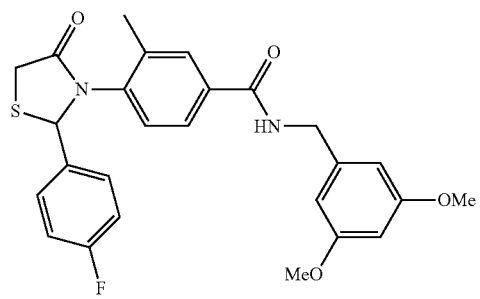

Following standard procedure K, 4-[2-(4-fluorophenyl)-4-oxo-1,3-thiazolidin-3-yl]-3-methylbenzoic acid (120 mg, 0.360 mmol), (3,5-dimethoxyphenyl)methanamine (60.0 µL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(3,5-dimethoxybenzyl)-4-[2-(4-fluorophenyl)-4-oxo-1,3-thiazolidin-3-yl]-3-methylbenzamide (110 mg, 63%). 1H NMR (CDCl$_3$, 400 MHz) δ 7.59 (br s, 1H), 7.46 (br s, 1H), 7.31-7.27 (m, 2H), 6.95 (t, 2H), 6.45 (d, 2H), 6.38 (t, 1H), 6.29 (t, 1H), 5.95 (br s, 1H), 4.52 (d, 2H), 4.00 (d, 1H), 3.91 (d, 1H), 3.78 (s, 6H), 2.18 (br s, 3H); LC-MS (ACPI) m/z 481.6 [M+H]$^+$.

EXAMPLE 296

N-(3,5-Difluorobenzyl)-4-[2-(4-fluorophenyl)-4-oxo-1,3-thiazolidin-3-yl]-3-methylbenzamide Compound 381

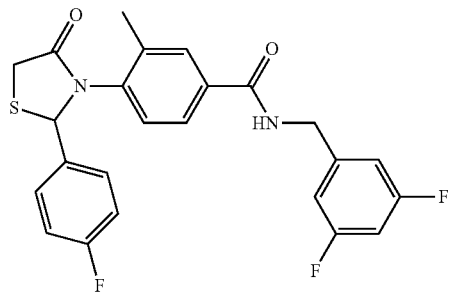

Following standard procedure K, 4-[2-(4-fluorophenyl)-4-oxo-1,3-thiazolidin-3-yl]-3-methylbenzoic acid (120 mg, 0.360 mmol), (3,5-difluorophenyl)methanamine (57.0 mg, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-(3,5-difluorobenzyl)-4-[2-(4-fluorophenyl)-4-oxo-1,3-thiazolidin-3-yl]-3-methylbenzamide (120 mg, 73%). 1H NMR (CDCl$_3$, 300 MHz) δ 7.60 (br s, 1H), 7.48 (br, 1H), 7.32-7.27 (m, 2H), 6.96 (t, 2H), 6.88-6.79 (m, 2H), 6.75-6.64 (m, 1H), 6.50 (t, 1H), 5.93 (br s, 1H), 4.57 (d, 2H), 4.00 (d, 1H), 3.89 (d, 1H), 2.18 (br s, 3H); LC-MS (ACPI) m/z 457.7 [M+H]$^+$.

EXAMPLE 297

4-[2-(4-Fluorophenyl)-4-oxo-1,3-thiazolidin-3-yl]-3-methyl-N-(1-naphthalenylmethyl)benzamide Compound 382

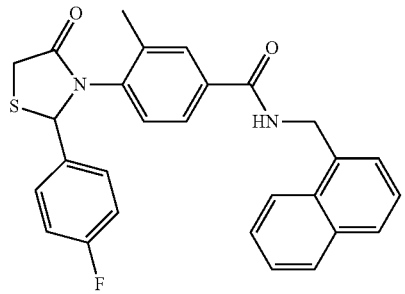

Following standard procedure K, 4-[2-(4-fluorophenyl)-4-oxo-1,3-thiazolidin-3-yl]-3-methylbenzoic acid (120 mg, 0.360 mmol), 1-naphthalenemethylamine (60.0 µL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (50% ethyl acetate in n-hexane, 5% MeOH in CH$_2$Cl$_2$) to give 4-[2-(4-fluorophenyl)-4-oxo-1,3-thiazolidin-3-yl]-3-methyl-N-(1-naphthalenylmethyl)benzamide (60.0 mg, 31%). 1H NMR (CDCl$_3$, 400 MHz) δ 8.03 (d, 1H), 7.89 (dd, 1H), 7.84 (d, 1H), 7.56-7.49 (m, 3H), 7.48-7.42 (m, 2H), 7.30-7.22 (m, 3H), 6.93 (t, 2H), 6.26 (br s, 1H), 5.92 (br s, 1H), 5.03 (d, 2H), 3.97 (d, 1H), 3.88 (d, 1H), 2.14 (br s, 3H); LC-MS (APCI) m/z 471.6 [M+H]$^+$.

EXAMPLE 298

N-[2-(2-Fluorophenyl)ethyl]-4-[2-(4-fluorophenyl)-4-oxo-1,3-thiazolidin-3-yl]-3-methylbenzamide Compound 383

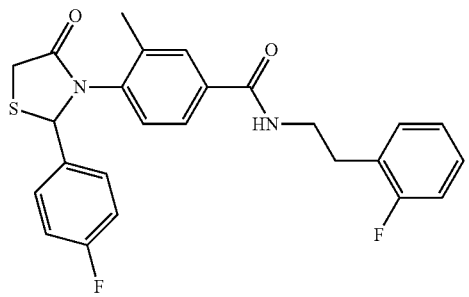

Following standard procedure K, 4-[2-(4-fluorophenyl)-4-oxo-1,3-thiazolidin-3-yl]-3-methylbenzoic acid (120 mg, 0.360 mmol), 2-(2-fluorophenyl)ethanamine (50.0 mg, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-[2-(2-fluorophenyl)ethyl]-4-[2-(4-fluorophenyl)-4-oxo-1,3-thiazolidin-3-yl]-3-methylbenzamide (120 mg, 73%). 1H NMR (CDCl$_3$, 400 MHz) δ 7.51 (br s, 1H), 7.38 (br s, 1H), 7.30-7.27 (m, 2H), 7.23-7.19 (m, 2H), 7.09-7.01 (m, 2H), 6.95 (t, 2H), 6.14 (br s, 1H), 5.90 (br s, 1H), 3.99 (d, 1H), 3.90 (d, 1H), 3.65 (q, 2H), 2.93 (t, 2H), 2.16 (br s, 3H); LC-MS (ACPI) m/z 453.8 [M+H]$^+$.

EXAMPLE 299

N-[2-(2-Chlorophenyl)ethyl]-4-[2-(4-fluorophenyl)-4-oxo-1,3-thiazolidin-3-yl]-3-methylbenzamide Compound 384

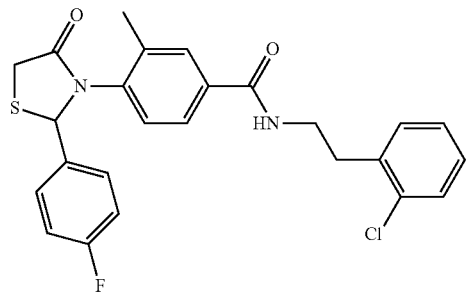

Following standard procedure K, 4-[2-(4-fluorophenyl)-4-oxo-1,3-thiazolidin-3-yl]-3-methylbenzoic acid (120 mg, 0.360 mmol), 2-(2-chlorophenyl)ethanamine (62.0 mg, 0.400 mmol), HBTU (210 mg, 0.540 mmol), triethylamine (0.110 mL, 0.790 mmol) and CH$_2$Cl$_2$ (5.0 mL) were carry out the reaction. After the reaction mixture was stirred at room temperature for 16 h and work-up, the residue was purified by Isco Combi-Flash Companion column chromatography (0-50% ethyl acetate in n-hexane) to give N-[2-(2-chlorophenyl)ethyl]-4-[2-(4-fluorophenyl)-4-oxo-1,3-thiazolidin-3-yl]-3-methylbenzamide (110 mg, 65%). 1H NMR (CDCl$_3$, 400 MHz) δ 7.52 (br s, 1H), 7.40-7.38 (m, 2H), 7.35-7.27 (m, 2H), 7.25-7.16 (m, 3H), 6.95 (t, 2H), 6.12 (br s, 1H), 5.90 (br s, 1H), 4.00 (d, 1H), 3.91 (d, 1H), 3.68 (q, 2H), 3.04 (t, 2H), 2.17 (br s, 3H); LC-MS (ACPI) m/z 469.6 [M+H]$^+$.

EXAMPLE 300

N-[2-(3-Fluorophenyl)ethyl]-4-[2-(4-fluorophenyl)-4-oxo-1,3-thiazolidin-3-yl]-3-methylbenzamide Compound 385

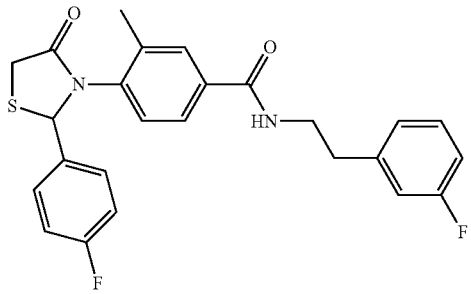

Following standard procedure K, 4-[2-(4-fluorophenyl)-4-oxo-1,3-thiazolidin-3-yl]-3-methylbenzoic acid (120 mg, 0.360 mmol), 2-(3-fluorophenyl)ethanamine (52.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give N-[2-(3-fluorophenyl)ethyl]-4-[2-(4-fluorophenyl)-4-oxo-1,3-thiazolidin-3-yl]-3-methylbenzamide (93.0 mg, 57%). 1H NMR (CDCl$_3$, 400 MHz) δ 7.50 (br s, 1H), 7.36 (br s, 1H), 7.31-7.24 (m, 4H), 6.98-6.90 (m, 4H), 6.03 (br s, 1H), 5.95 (br s, 1H), 4.00 (d, 1H), 3.90 (d, 1H), 3.65 (q, 2H), 2.89 (t, 2H), 2.17 (br s, 3H); LC-MS (ACPI) m/z 453.7 [M+H]$^+$.

EXAMPLE 301

N-[2-(3-Chlorophenyl)ethyl]-4-[2-(4-fluorophenyl)-4-oxo-1,3-thiazolidin-3-yl]-3-methylbenzamide Compound 386

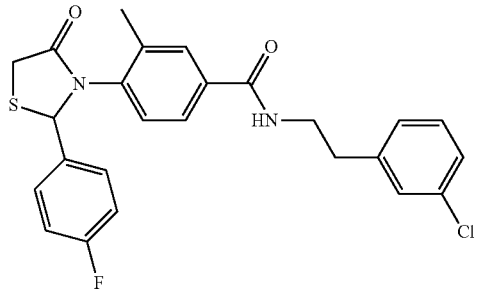

Following standard procedure K, 4-[2-(4-fluorophenyl)-4-oxo-1,3-thiazolidin-3-yl]-3-methylbenzoic acid (120 mg, 0.360 mmol), 2-(3-chlorophenyl)ethanamine (55.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-[2-(3-chlorophenyl)ethyl]-4-[2-(4-fluorophenyl)-4-oxo-1,3-thiazolidin-3-yl]-3-methylbenzamide (55.0 mg, 33%). 1H NMR (CDCl$_3$, 400 MHz) δ 7.50 (br s, 1H), 7.39 (br s, 1H), 7.32-7.27 (m, 2H), 7.24-7.20 (m, 3H), 7.08 (dt, 1H), 6.95 (t, 2H), 6.05 (br t, 1H), 5.95 (br s, 1H), 4.00 (d, 1H), 3.90 (d, 1H), 3.63 (q, 2H), 2.86 (t, 2H), 2.17 (br s, 3H); LC-MS (APCI) m/z 469.6 [M+H]$^+$.

EXAMPLE 302

N-[2-(4-Fluorophenyl)ethyl]-4-[2-(4-fluorophenyl)-4-oxo-1,3-thiazolidin-3-yl]-3-methylbenzamide Compound 387

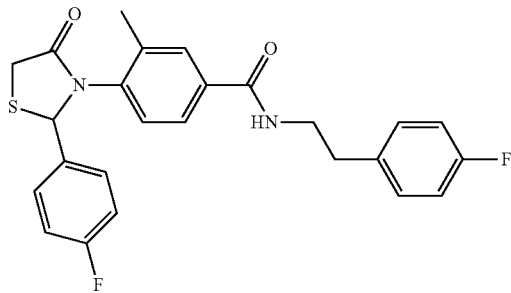

Following standard procedure K, 4-[2-(4-fluorophenyl)-4-oxo-1,3-thiazolidin-3-yl]-3-methylbenzoic acid (0.120 g, 0.360 mmol), 2-(4-fluorophenyl)ethan-1-amine (52.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give N-[2-(4-fluorophenyl)ethyl]-4-[2-(4-fluorophenyl)-4-oxo-1,3-thiazolidin-3-yl]-3-methylbenzamide (25.0 mg, 15%). 1H NMR (CDCl$_3$, 400 MHz) δ 7.48 (br s, 1H), 7.40-7.26 (m, 3H), 7.17-7.12 (m, 2H), 7.00-6.92 (m, 4H), 6.18 (br t, 1H), 5.90 (br s, 1H), 3.98 (d, 1H), 3.89 (d, 1H), 3.60 (q, 2H), 2.84 (t, 2H), 2.14 (br s, 3H); LC-MS (APCI) m/z 453.8 [M+H]$^+$.

EXAMPLE 303

N-[2-(4-Chlorophenyl)ethyl]-4-[2-(4-fluorophenyl)-4-oxo-1,3-thiazolidin-3-yl]-3-methylbenzamide Compound 388

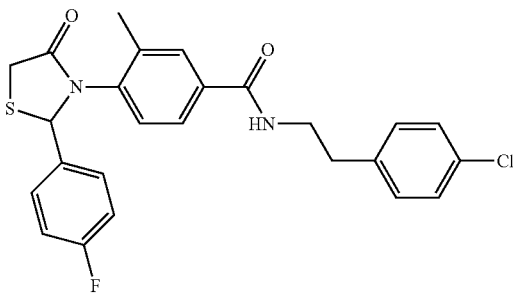

Following standard procedure K, 4-[2-(4-fluorophenyl)-4-oxo-1,3-thiazolidin-3-yl]-3-methylbenzoic acid (0.100 g, 0.300 mmol), 2-(4-chlorophenyl)ethan-1-amine (46.0 μL, 0.330 mmol), HBTU (0.170 g, 0.450 mmol), triethylamine (93.0 μL, 0.670 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give N-[2-(4-chlorophenyl)ethyl]-4-[2-(4-fluorophenyl)-4-oxo-1,3-thiazolidin-3-yl]-3-methylbenzamide (72.0 mg, 51%). 1H NMR (CDCl$_3$, 400 MHz) δ 7.48 (br s, 1H), 7.40-7.25 (m, 5H), 7.11 (d, 2H), 6.94 (t, 2H), 6.17 (br t, 1H), 5.95 (br s, 1H), 3.98 (d, 1H), 3.89 (d, 1H), 3.59 (q, 2H), 2.84 (t, 2H), 2.15 (br s, 3H); LC-MS (APCI) m/z 469.6 [M+H]$^+$.

EXAMPLE 304

N-[2-(2,4-Dichlorophenyl)ethyl]-4-[2-(4-fluorophenyl)-4-oxo-1,3-thiazolidin-3-yl]-3-methylbenzamide Compound 389

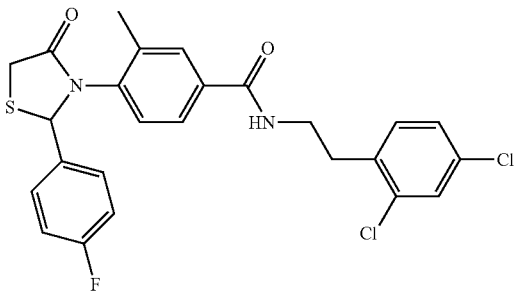

447

Following standard procedure K, 4-[2-(4-fluorophenyl)-4-oxo-1,3-thiazolidin-3-yl]-3-methylbenzoic acid (120 mg, 0.360 mmol), 1-(2,4-dichloro-phenyl)-ethylamine (60.0 μL, 0.400 mmol), HBTU (210 mg, 0.540 mmol), triethylamine (0.110 mL, 0.790 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (5% MeOH in CH$_2$Cl$_2$) to give N-[2-(2,4-dichlorophenyl)ethyl]-4-[2-(4-fluorophenyl)-4-oxo-1,3-thiazolidin-3-yl]-3-methylbenzamide (14.0 mg, 8%). 1H NMR (CDCl$_3$, 400 MHz) δ 7.52 (br s, 1H), 7.38 (s, 2H), 7.30 (dd, 2H), 7.20-7.14 (m, 2H), 6.97 (t, 2H), 6.08 (br s, 1H), 5.91 (br s, 1H), 4.00 (d, 1H), 3.91 (d, 1H), 3.65 (q, 2H), 3.01 (t, 2H), 2.17 (br s, 3H); LC-MS (APCI) m/z 504.7 [M+H]$^+$.

EXAMPLE 305

Oxydi-2,1-ethanediyl bis{4-[2-(4-fluorophenyl)-4-oxo-1,3-thiazolidin-3-yl]-3-methylbenzoate}

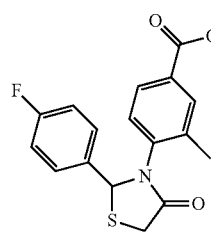

Compound 390

Following standard procedure G, 4-[2-(4-fluorophenyl)-4-oxo-1,3-thiazolidin-3-yl]-3-methylbenzoic acid (270 mg, 0.815 mmol), DMAP (398 mg, 3.26 mmol), EDCI • HCl (469 mg, 2.45 mmol), diethylene glycol (43.2 mg, 0.408 mmol), and CH$_2$Cl$_2$ (5.0 mL) were used to carry out the reaction. After the reaction was stirred for 18 h and work-up, the residue was purified by Isco Combi-Flash Companion column chromatography (0-65% ethyl acetate in n-hexane) to give oxydi-2,1-ethanediyl bis {4-[2-(4-fluorophenyl)-4-oxo-1,3-thiazolidin-3-yl]-3-methylbenzoate} (137 mg, 46%) as a white solid. 1H NMR (CDCl$_3$, 400 MHz) δ 7.86 (br s, 2H), 7.71 (br d, 2H), 7.30 (dd, 4H), 6.94 (br t, 4H), 6.10-5.80 (br, 2H), 4.43-4.41 (m, 4H), 4.01 (d, 2H), 3.93 (d, 2H), 3.82-3.79 (m, 4H), 2.17 (br s, 6H); LC-MS (ESI) m/z 755.3 [M+Na]$^+$.

448

EXAMPLE 306

{2-(4-Fluorophenyl)-3-[4-(methoxycarbonyl)-2-methylphenyl]-4-oxo-1,3-thiazolidin-5-yl}acetic acid

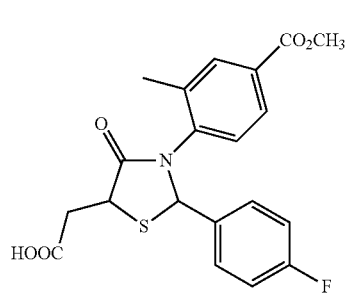

Compound 391

Step 1. Methyl 4-{[(E)-(4-fluorophenyl)methylidene]amino}-3 methylbenzoate.

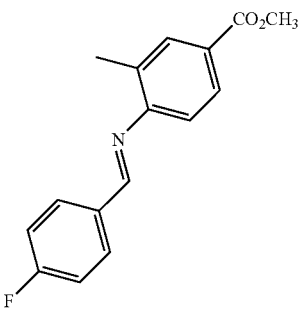

Compound 392

A solution of methyl 4-amino-3-methylbenzene carboxylate (1.68 g, 10.2 mmol) and 4-fluorobenzaldehyde (1.39 g, 11.2 mmol) in ethanol (12 mL) was reflux for 20 h. Ethanol was removed under reduced pressure and dried under high vacuum. The crude solids were washed with n-hexane to give methyl 4-{[(E)-(4-fluorophenyl)methylidene]amino}-3-methylbenzoate (2.77 g, 100%) as a white solid. 1H NMR (CDCl$_3$, 300 MHz) δ 8.31 (s, 1H), 7.95-7.91 (m, 3H), 7.18 (t, 2H), 6.91 (d, 1H), 3.91 (s, 3H), 2.36 (s, 3H).

Step 2. {2-(4-fluorophenyl)-3-[4-(methoxycarbonyl)-2-methylphenyl]-4-oxo-1, 3-thiazolidin-5-yl}acetic acid To a solution of methyl 4-{[(E)-(4-fluorophenyl)methylidene]amino}-3-methylbenzoate (1.43 g, 2.64 mmol) in toluene (5.0 mL) was added DL-mercaptosuccinic acid (0.320 mL, 2.31 mmol). The solution was reflux for 16 h and cooled to room temperature. The solution was diluted with ethyl acetate and washed with 10% NaOH$_{(aq)}$. The organic layer was dried over MgSO$_{4(s)}$, filtered, and concentrated. The residue was purified by Isco Combi-Flash Companion column chromatography (0-10% methanol in CH$_2$Cl$_2$) to give {2-(4-fluorophenyl)-3-[4-(methoxycarbonyl)-2-methylphenyl]-4-oxo-1,3-thiazolidin-5-yl}acetic acid (206 mg, 44%) as a white solid. 1H NMR (CDCl$_3$, 300 MHz) δ 7.84

(br s, 1H), 7.77 (br s, 1H), 7.33-7.27 (m, 2H), 6.94 (br t, 2H), 6.00 (br s, 1H), 4.60-4.42 (br, 1H), 3.90 (s, 3H), 3.30-3.00 (br, 2H), 2.15 (br s, 3H); LC-MS (ESI) m/z 404.2 [M+H]$^+$.

EXAMPLE 307

Ethyl 4-[5-(2-ethoxy-2-oxoethyl)-2-(4-fluorophenyl)-4-oxo-1,3-thiazolidin-3-yl]-3-methylbenzoate

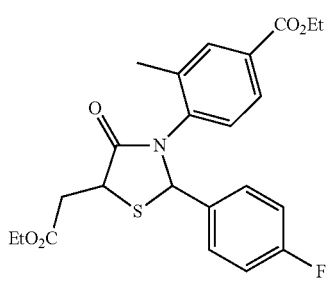

Compound 393

A solution of {2-(4-fluorophenyl)-3-[4-(methoxycarbonyl)-2-methylphenyl]-4-oxo-1,3-thiazolidin-5-yl}acetic acid (1.43 g, 2.64 mmol) in concentrated HCl$_{(aq)}$ (0.50 mL) and ethanol (4.0 mL) was reflux for 16 h and cooled to room temperature. Ethanol was removed under reduced pressure. The residue was treated with water and extracted with ethyl acetate. The organic layers were washed with water and brine, dried over MgSO$_{4(s)}$, filtered, and concentrated. The residue was purified by Isco Combi-Flash Companion column chromatography (0-25% ethyl acetate in n-hexane) to give ethyl 4-[5-(2-ethoxy-2-oxoethyl)-2-(4-fluorophenyl)-4-oxo-1,3-thiazolidin-3-yl]-3-methylbenzoate (47.9 mg, 47%) as a colorless gum. 1H NMR (CDCl$_3$, 300 MHz) δ 7.90-7.70 (br, 2H), 7.32 (dd, 2H), 6.93 (t, 2H), 6.20-5.90 (br, 1H), 4.55-4.42 (br, 1H), 4.32 (q, 2H), 4.23 (q, 2H), 3.15 (br s, 2H), 2.14 (br s, 3H), 1.37-1.25 (m, 6H); LC-MS (ESI) m/z 446.3 [M+H]$^+$.

EXAMPLE 308

3-(5-Fluoro-2-methyphenylphenyl)-2-(4-fluorophenyl)thiazolidin-4-one 1,1-dioxide

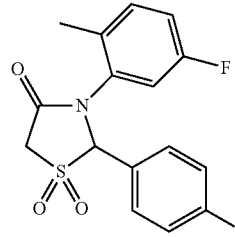

Compound 394

To a solution of 3-(5-fluoro-2-methylphenyl)-2-(4-fluorophenyl)thiazolidin-4-one (60.0 mg, 0.200 mmol) in 1 mL of acetic acid was added H$_2$O$_{2(aq)}$ (30%) (0.300 mL, 2.60 mmol) in one portion at r.t. The reaction mixture was stirred at 65° C. overweekend then partitioned between ethyl acetate (20 mL) and saturated NaHCO$_{3(aq)}$ (10 mL). The organic layer was washed with brine (5 mL), dried over MgSO$_4$ and concentrated to give a crude product which was purified by flash chromatography (ethyl acetate:hexane=1:2) to give the desired product as a yellow viscous liquid (47.0 mg, 69%). $^1$H NMR (CDCl$_3$, 400 MHz) δ 7.38 (dd, 2H), 7.24 (dd, 1H), 7.17 (br t, 2H), 6.96 (td, 1H), 6.67 (dd, 1H), 5.75 (br s, 1H), 4.13-4.00 (m, 2H), 2.31 (s, 3H).

EXAMPLE 309

3-(3,4-Dimethyl-1,2-oxazol-5-yl)-2-(4-fluorophenyl)-1,3-thiazolidin-4-one

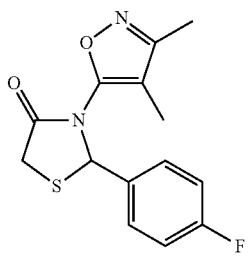

Compound 395

Following standard procedure A, 5-amino-3,4-dimethylisoxazole (0.254 g, 2.26 mmol), 4-fluorobenzaldehyde (0.562 g, 4.53 mmol), Na$_2$SO$_4$ (0.321 g, 2.26 mmol), 2-mercaptoacetic acid (0.320 mL, 4.58 mmol), and toluene (6.0 mL) were used to carry out the reaction. It was reflux 4 h for the first step and 18 h for the second step. After work-up, the residue was purified by column chromatography (40% ethyl acetate in n-hexane) to give 3-(3,4-dimethyl-1,2-oxazol-5-yl)-2-(4-fluorophenyl)-1,3-thiazolidin-4-one (44.3 mg, 7%) as a yellow solid. 1H NMR (CDCl$_3$, 400 MHz) δ 7.37 (dd, 2H), 7.00 (t, 2H), 6.16 (s, 1H), 3.90 (s, 2H), 2.11 (s, 3H), 1.75 (s, 3H); LC-MS (ESI) m/z 293.2 [M+H]$^+$.

EXAMPLE 310

2-(4-Fluorophenyl)-3-(5-methyl-1,2-oxazol-4-yl)-1,3-thiazolidin-4-one

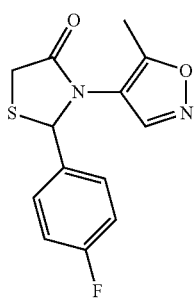

Compound 396

Following standard procedure A, 5-methylisoxazol-3-amine (0.500 g, 5.20 mmol), 4-fluorobenzaldehyde (0.840 mL, 7.80 mmol), Na$_2$SO$_4$ (0.730 g, 5.20 mmol), 2-mercaptoacetic acid (0.730 mL, 10.4 mmol) and toluene (10.0 mL) were used to carry out the reaction. It was reflux 4 h for the first step and 18 h for the second step. The reaction mixture was treated with saturated NaHCO$_{3(aq)}$ and extracted with ethyl acetate. The organic layer was dried over MgSO$_{4(s)}$, filtered, and concentrated. The residue was purified by Isco Combi-Flash Companion column chromatography (0-50% ethyl acetate in n-hexane) to give 2-(4-fluorophenyl)-3-(5-methyl-1,2-oxazol-4-yl)-1,3-thiazolidin-4-one (0.420 g, 29%). 1H NMR (DMSO-d$_6$, 400 MHz) δ 7.42-7.37 (m, 2H), 7.13 (dd, 2H), 6.79 (s, 1H), 6.40 (s, 1H), 4.10 (d, 1H), 3.83 (d, 1H), 2.33 (s, 3H); LC-MS (APCI) m/z 279.0 [M+H]$^+$.

EXAMPLE 311

2-(3,5-Difluorophenyl)-3-(1, 5-dimethyl-3-oxo-2-phenyl-2,3-dihydro-1H-pyrazol-4-yl)thiazolidin-4-one

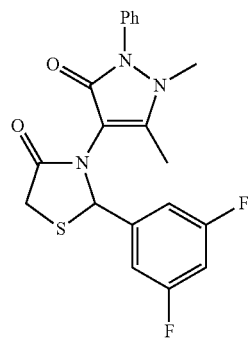

Compound 397

The compound was prepared by following the standard procedure A with 3,5-difluorobenzaldehyde (35.5 mg, 0.25 mmol), 4-aminoantipyrine (55.8 mg, 0.280 mmol), and 2-mercaptoacetic acid (21.0 μL, 27.0 mg, 0.300 mmol). It was reflux 6 h for the first step and 18 h for the second step. After work-up, the crude product was purified by flash chromatography (dichloromethane:ethanol=30:1) to give the desired product as a yellow viscous liquid (48.9 mg, 49%). $^1$H NMR (CDCl$_3$, 400 MHz) δ 7.43 (t, 2H), 7.30 (t, 1H), 7.24-7.21 (m, 2H), 6.97-6.92 (m, 2H), 6.73 (tt, 1H), 6.45 (s, 1H), 3.85 (s, 2H), 3.02 (s, 3H), 2.02 (s, 3H); LC-MS (ESI) m/z 402.8 [M+H]$^+$.

EXAMPLE 312

2-(2,4-Difluorophenyl)-3-(1, 5-dimethyl-3-oxo-2-phenyl-2,3-dihydro-1H-pyrazol-4-yl)thiazolidin-4-one

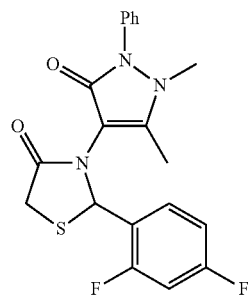

Compound 398

The compound was prepared by following the standard procedure A with 2,4-difluorobenzaldehyde (71.0 mg, 0.500 mmol), 4-aminoantipyrine (102 mg, 0.500 mmol), and 2-mercaptoacetic acid (42.0 μL, 55.0 mg, 0.600 mmol). It was reflux 6 h for the first step and 18 h for the second step. After work-up, the crude product was purified by flash chromatography (dichloromethane:ethanol=30:1) to give the desired product as a yellow viscous liquid (179 mg, 89%). $^1$H NMR (CDCl$_3$, 400 MHz) δ 7.41 (t, 2H), 7.36-7.26 (m, 2H), 7.23 (d, 2H), 6.81-6.75 (m, 2H), 6.56 (s, 1H), 3.93 (d, 1H), 3.79 (d, 1H), 3.02 (s, 3H), 2.03 (s, 3H); LC-MS (ESI) m/z 402.9 [M+H]$^+$.

EXAMPLE 313

3-(1,5-Dimethyl-3-oxo-2-phenyl-2,3-dihydro-1H-pyrazol-4-yl)-2-(4-(methylthi)phenyl)thiazolidin-4-one

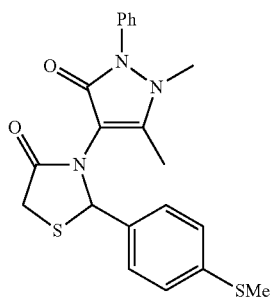

Compound 399

The compound was prepared by following the standard procedure A with 4-methylthiobenzaldehyde (76.0 mg, 0.500 mmol), 4-aminoantipyrine (102 mg, 0.500 mmol), and 2-mercaptoacetic acid (42.0 μL, 55.0 mg, 0.600 mmol). It was reflux 6 h for the first step and 18 h for the second step. After work-up, the crude product was purified by flash chromatography (dichloromethane:ethanol=30:1) to give the desired product as a yellow viscous liquid (153 mg, 75%). $^1$H NMR (CDCl$_3$, 400 MHz) δ 7.41 (t, 2H), 7.33-7.20 (m, 5H), 7.13 (d, 2H), 6.41 (s, 1H), 3.88 (d, 1H), 3.82 (d, 1H), 2.99 (s, 3H), 2.45 (s, 3H), 1.97 (s, 3H); LC-MS (ESI) m/z 412.8 [M+H]$^+$.

EXAMPLE 314

4-(3-(1,5-Dimethyl-3-oxo-2-phenyl-2,3-dihydro-1H-pyrazol-4-yl)-4-oxothiazolidin-2-yl)benzonitrile

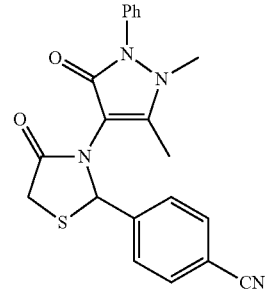

Compound 400

The compound was prepared by following the standard procedure A with 4-cyanobenzaldehyde (65.6 mg, 0.500 mmol), 4-aminoantipyrine (102 mg, 0.500 mmol), and 2-mercaptoacetic acid (42.0 μL, 55.0 mg, 0.600 mmol). It was reflux 6 h for the first step and 18 h for the second step. After work-up, the crude product was purified by flash chromatography (dichloromethane:ethanol=30:1) to give the desired product as a yellow viscous liquid (149 mg, 76%). ¹H NMR (CDCl₃, 300 MHz) δ 7.58 (d, 2H), 7.52 (d, 2H), 7.42 (t, 2H), 7.30 (t, 1H), 7.21 (d, 2H), 6.54 (s, 1H), 3.92-3.80 (m, 2H), 3.01 (s, 3H), 2.02 (s, 3H); LC-MS (ESI) m/z 391.9 [M+H]⁺.

EXAMPLE 315

3-(1,5-Dimethyl-3-oxo-2-phenyl-2,3-dihydro-1H-pyrazol-4-yl)-2-(4-methoxyphenyl)thiazolidin-4-one

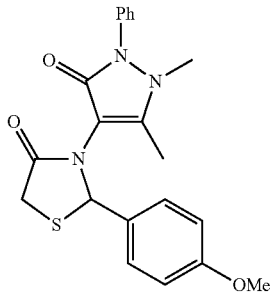

Compound 401

The compound was prepared by following the standard procedure A with 4-methoxybenzaldehyde (68.0 mg, 0.500 mmol), 4-aminoantipyrine (102 mg, 0.500 mmol), and 2-mercaptoacetic acid (42.0 μL, 55.0 mg, 0.600 mmol). It was reflux 6 h for the first step and 18 h for the second step. After work-up, the crude product was purified by flash chromatography (dichloromethane:ethanol=30:1) to give the desired product as a yellow viscous liquid (108 mg, 55%). ¹H NMR (CDCl₃, 400 MHz) δ 7.41 (t, 2H), 7.33 (d, 2H), 7.28 (t, 1H), 7.21 (d, 2H), 6.79 (dd, 2H), 6.37 (s, 1H), 3.88 (d, 1H), 3.81 (d, 1H), 3.77 (s, 3H), 2.97 (s, 3H), 1.94 (s, 3H); LC-MS (ESI) m/z 396.9 [M+H]⁺.

EXAMPLE 316

3-(1,5-Dimethyl-3-oxo-2-phenyl-2,3-dihydro-1H-pyrazol-4-yl)-2-(4-ethylphenyl)thiazolidin-4-one

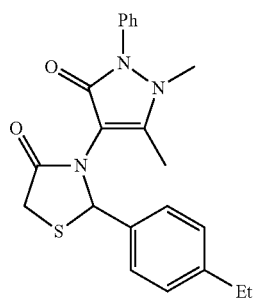

Compound 402

The compound was prepared by following the standard procedure A with 4-ethybenzaldehyde (67.0 mg, 0.500 mmol), 4-aminoantipyrine (102 mg, 0.500 mmol), and 2-mercaptoacetic acid (42.0 μL, 55.0 mg, 0.600 mmol). It was reflux 6 h for the first step and 18 h for the second step. After work-up, the crude product was purified by flash chromatography (dichloromethane:ethanol=30:1) to give the desired product as a yellow viscous liquid (153 mg, 78%). ¹H NMR (CDCl₃, 300 MHz) δ 7.41 (t, 2H), 7.32-7.27 (m, 3H), 7.24-7.20 (m, 2H), 7.10 (d, 2H), 6.39 (s, 1H), 3.92-3.80 (m, 2H), 2.96 (s, 3H), 2.60 (q, 2H), 1.95 (s, 3H), 1.19 (t, 3H); LC-MS (ESI) m/z 394.9 [M+H]⁺.

EXAMPLE 317

3-(1,5-Dimethyl-3-oxo-2-phenyl-2,3-dihydro-1H-pyrazol-4-yl)-2-(4-(trifluoromethyl)phenyl)thiazolidin-4-on

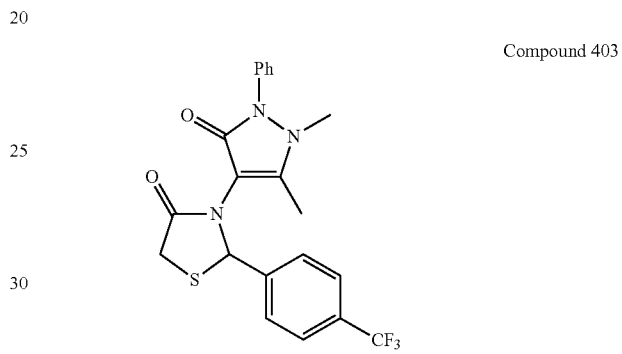

Compound 403

The compound was prepared by following the standard procedure A with 4-trifluoromethylbenzaldehyde (174 mg, 1.00 mmol), 4-aminoantipyrine (203 mg, 1.00 mmol), and 2-mercaptoacetic acid (83.0 μL, 110 mg, 1.20 mmol). It was reflux 6 h for the first step and 18 h for the second step. After work-up, the crude product was purified by flash chromatography (dichloromethane:ethanol=30:1) to give the desired product as a yellow viscous liquid (300 mg, 69%). ¹H NMR (CDCl₃, 300 MHz) δ 7.57-7.51 (m, 4H), 7.42 (t, 2H), 7.30 (t, 1H), 7.19 (d, 2H), 6.55 (s, 1H), 3.92-3.80 (m, 2H), 3.00 (s, 3H), 2.01 (s, 3H); LC-MS (ESI) m/z 434.9 [M+H]⁺.

EXAMPLE 318

3-(1,5-Dimethyl-3-oxo-2-phenyl-2,3-dihydro-1H-pyrazol-4-yl)-2-(3-fluorophenyl)thiazolidin-4-one

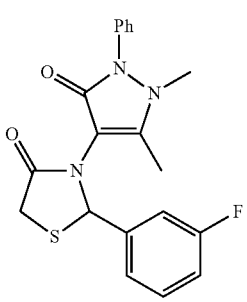

Compound 404

The compound was prepared by following the standard procedure A with 3-fluorobenzaldehyde (124 mg, 1.00 mmol), 4-aminoantipyrine (203 mg, 1.00 mmol), and 2-mercaptoacetic acid (83.0 µL, 110 mg, 1.20 mmol). It was reflux 6 h for the first step and 18 h for the second step. After work-up, the crude product was purified by flash chromatography (dichloromethane:ethanol=30:1) to give the desired product as a white solid (310 mg, 81%). ¹H NMR (CDCl₃, 400 MHz) δ 7.42 (t, 2H), 7.29 (t, 1H), 7.25-7.16 (m, 4H), 7.15 (dd, 1H), 6.98 (td, 1H), 6.43 (s, 1H), 3.88 (d, 1H), 3.84 (d, 1H), 2.99 (s, 3H), 1.99 (s, 3H); LC-MS (ESI) m/z 384.9 [M+H]⁺.

EXAMPLE 319

2-(4-(tert-butyl)phenyl)-3-(1,5-dimethyl-3-oxo-2-phenyl-2,3-dihydro-1H-pyrazol-4-yl)thiazolidin-4-one

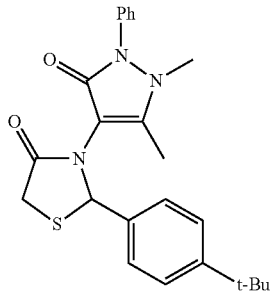

Compound 405

The compound was prepared by following the standard procedure A with 4-tert-butylbenzaldehyde (162 mg, 1.00 mmol), 4-aminoantipyrine (203 mg, 1.00 mmol), and 2-mercaptoacetic acid (83.0 µL, 110 mg, 1.20 mmol). It was reflux 6 h for the first step and 18 h for the second step. After work-up, the crude product was purified by flash chromatography (dichloromethane:ethanol=30:1) to give the desired product as a yellow viscous liquid (330 mg, 78%). ¹H NMR (CDCl₃, 400 MHz) δ 7.43 (t, 2H), 7.34-7.27 (m, 5H), 7.23 (dd, 2H), 6.40 (s, 1H), 3.88 (s, 2H), 2.98 (s, 3H), 1.96 (s, 3H), 1.29 (s, 9H); LC-MS (ESI) m/z 422.9 [M+H]⁺.

EXAMPLE 320

3-(1,5-Dimethyl-3-oxo-2-phenyl-2,3-dihydro-1H-pyrazol-4-yl)-2-(2-fluorophenyl)thiazolidin-4-one

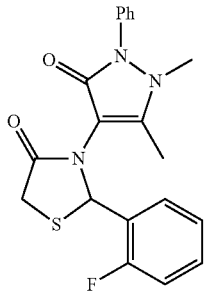

Compound 406

The compound was prepared by following the standard procedure A with 2-fluorobenzaldehyde (124 mg, 1.00 mmol), 4-aminoantipyrine (203 mg, 1.00 mmol), and 2-mercaptoacetic acid (83.0 µL, 110 mg, 1.20 mmol). It was reflux 6 h for the first step and 18 h for the second step. After work-up, the crude product was purified by flash chromatography (dichloromethane:ethanol=30:1) to give the desired product as a white viscous liquid (212 mg, 55%). ¹H NMR (CDCl₃, 400 MHz) δ 7.41 (t, 2H), 7.33 (td, 1H), 7.31-7.22 (m, 4H), 7.07-7.00 (m, 2H), 6.58 (s, 1H), 3.96 (d, 1H), 3.79 (d, 1H), 3.00 (s, 3H), 2.02 (s, 3H); LC-MS (ESI) m/z 384.9 [M+H]⁺.

EXAMPLE 321

2-(4-Bromophenyl)-3-(1,5-dimethyl-3-oxo-2-phenyl-2,3-dihydro-1H-pyrazol-4-yl)thiazolidin-4-one

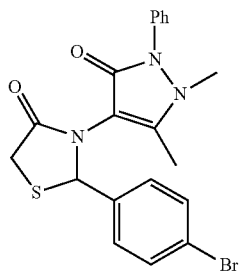

Compound 407

The compound was prepared by following the standard procedure A with 4-bromobenzaldehyde (185 mg, 1.00 mmol), 4-aminoantipyrine (203 mg, 1.00 mmol), and 2-mercaptoacetic acid (83.0 µL, 110 mg, 1.20 mmol). It was reflux 6 h for the first step and 18 h for the second step. After work-up, the crude product was purified by flash chromatography (ethyl acetate:hexane=3:2) to give the desired product as a white viscous liquid (404 mg, 91%). ¹H NMR (CDCl₃, 400 MHz) δ 7.44-7.39 (m, 4H), 7.32-7.27 (m, 3H), 7.21 (d, 2H), 6.43 (s, 1H), 3.88 (d, 1H), 3.82 (d, 1H), 3.00 (s, 3H), 1.99 (s, 3H); LC-MS (ESI) m/z 444.8 [M+H]⁺.

EXAMPLE 322

3-(1,5-Dimethyl-3-oxo-2-phenyl-2,3-dihydro-1H-pyrazol-4-yl)-2-phenylthiazolidin-4-one

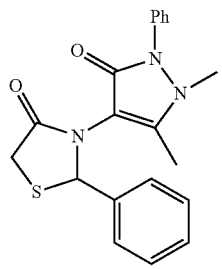

Compound 408

The compound was prepared by following the standard procedure A with benzaldehyde (106 mg, 1.00 mmol), 4-aminoantipyrine (203 mg, 1.00 mmol), and 2-mercaptoacetic acid (83.0 µL, 110 mg, 1.20 mmol). It was reflux 6 h for the first step and 18 h for the second step. After work-up, the crude product was purified by flash chromatography (ethyl acetate:hexane=3:2) to give the desired product as a white viscous liquid (292 mg, 80%). $^1$H NMR (CDCl$_3$, 400 MHz) δ 7.43-7.38 (m, 4H), 7.30-7.26 (m, 4H), 7.20 (d, 2H), 6.42 (s, 1H), 3.89 (d, 1H), 3.85 (d, 1H), 2.95 (s, 3H), 1.95 (s, 3H); LC-MS (ESI) m/z 366.9 [M+H]$^+$.

EXAMPLE 323

3-(1,5-Dimethyl-3-oxo-2-phenyl-2,3-dihydro-1H-pyrazol-4-yl)-2-(4-(dimethylamino)phenyl)thiazolidin-4-one

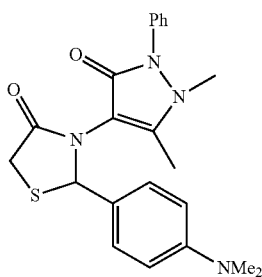

Compound 409

The compound was prepared by following the standard procedure A with 4-dimethylbenzaldehyde (149 mg, 1.00 mmol), 4-aminoantipyrine (203 mg, 1.00 mmol), and 2-mercaptoacetic acid (83.0 μL, 110 mg, 1.20 mmol). It was reflux 6 h for the first step and 18 h for the second step. After work-up, the crude product was purified by flash chromatography (ethyl acetate:hexane=3:2) to give the desired product as a yellow viscous liquid (230 mg, 56%). $^1$H NMR (CDCl$_3$, 400 MHz) δ 7.41 (t, 2H), 7.29-7.22 (m, 5H), 6.59 (d, 2H), 6.32 (s, 1H), 3.87 (d, 1H), 3.81 (d, 1H), 2.96 (s, 3H), 2.92 (s, 6H), 1.95 (s, 3H); LC-MS (ESI) m/z 409.9 [M+H]$^+$.

EXAMPLE 324

2-(4-Chlorophenyl)-3-(1,5-dimethyl-3-oxo-2-phenyl-2,3-dihydro-1H-pyrazol-4-yl)thiazolidin-4-one

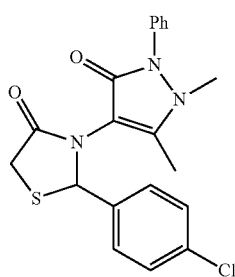

Compound 410

The compound was prepared by following the standard procedure A with 4-chlorobenzaldehyde (141 mg, 1.00 mmol), 4-aminoantipyrine (203 mg, 1.00 mmol), and 2-mercaptoacetic acid (83.0 μL, 110 mg, 1.20 mmol). It was reflux 6 h for the first step and 18 h for the second step. After work-up, the crude product was purified by flash chromatography (dichloromethane:ethanol=20:1) to give the desired product as a white solid (160 mg, 40%). $^1$H NMR (CDCl$_3$, 300 MHz) δ 7.42 (t, 2H), 7.39-7.19 (m, 7H), 6.44 (s, 1H), 3.94-3.78 (m, 2H), 2.99 (s, 3H), 1.98 (s, 3H); LC-MS (ESI) m/z 400.9 [M+H]$^+$.

EXAMPLE 325

3-(1,5-Dimethyl-3-oxo-2-phenyl-2,3-dihydro-1H-pyrazol-4-yl)-2-(4-fluorophenyl)thiazolidin-4-one

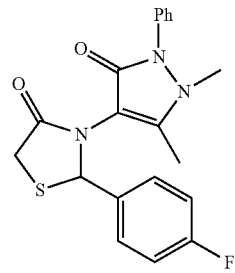

Compound 411

The compound was prepared by following the standard procedure A with 4-fluorobenzaldehyde (122 mg, 0.980 mmol), 4-aminoantipyrine (200 mg, 0.980 mmol), and 2-mercaptoacetic acid (70.0 μL, 92.8 mg, 1.00 mmol). It was reflux 6 h for the first step and 18 h for the second step. After work-up, the crude product was purified by flash chromatography (dichloromethane:ethanol=8:1) to give the desired product as a white solid (246 mg, 64%). $^1$H NMR (CDCl$_3$, 400 MHz) δ 7.44-7.38 (m, 4H), 7.29 (t, 1H), 7.20 (d, 2H), 6.96 (t, 2H), 6.44 (s, 1H), 3.89 (d, 1H), 3.82 (d, 1H), 2.98 (s, 3H), 1.96 (s, 3H); LC-MS (ESI) m/z 384.9 [M+H]$^+$.

EXAMPLE 326

Methyl 4-[2-(5-fluoro-2-pyridinyl)-4-oxo-1,3-thiazolidin-3-yl]-3-methylbenzoate

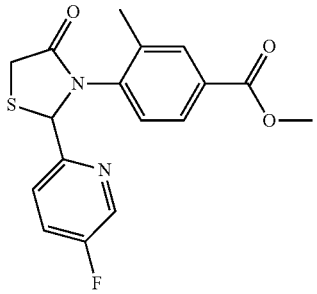

Compound 412

Following standard procedure A, 5-methylisoxazol-3-amine (0.330 g, 1.99 mmol), 5-fluoropicolinaldehyde (0.500 mL, 2.99 mmol), Na$_2$SO$_4$ (0.280 g, 1.99 mmol), 2-mercaptoacetic acid (0.280 mL, 3.99 mmol) and toluene (15.0 mL) were used to carry out the reaction. It was reflux 4 h for the first step and 18 h for the second step. The reaction mixture was treated with saturated NaHCO$_{3(aq)}$ and extracted with ethyl acetate. The organic layer was dried over MgSO$_{4(s)}$, filtered, and concentrated. The residue was purified by Isco Combi-Flash Companion column chromatography (0-40% ethyl acetate in n-hexane) to give methyl 4-[2-(5-fluoro-2-pyridinyl)-4-oxo-1,3-thiazolidin-3-yl]-3-methylbenzoate (0.226 g, 33%). 1H NMR (CDCl₃, 400 MHz) δ 8.41 (br s, 1H), 7.89 (br s, 1H), 7.72 (br d, 1H), 7.32 (td, 1H), 7.21 (dd, 1H), 6.91 (br s, 1H), 5.89 (br s, 1H), 4.16 (d, 1H), 3.86 (s, 3H), 3.80 (d, 1H), 2.29 (br s, 3H); LC-MS (APCI) m/z 347.9 [M+H]⁺.

EXAMPLE 327

Methyl 4-(2-cyclohexyl-4-oxo-1,3-thiazolidin-3-yl)-3-methylbenzoate

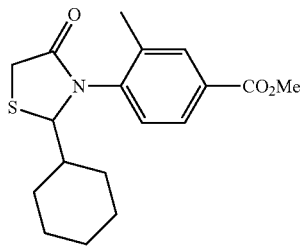

Compound 413

Following standard procedure A, methyl 4-amino-3-methylbenzoate (0.500 g, 3.03 mmol), cyclohexanecarbaldehyde (0.550 mL, 4.54 mmol), Na₂SO₄ (0.450 g, 3.03 mmol), 2-mercaptoacetic acid (0.420 mL, 6.05 mmol) and toluene (10.0 mL) were used to carry out the reaction. It was reflux 4 h for the first step and 18 h for the second step. The reaction mixture was treated with saturated NaHCO₃(aq) and extracted with ethyl acetate. The organic layer was dried over MgSO₄(s), filtered, and concentrated. The residue was purified by Isco Combi-Flash Companion column chromatography (0-40% ethyl acetate in n-hexane and 20% acetone in n-hexane) to give methyl 4-(2-cyclohexyl-4-oxo-1,3-thiazolidin-3-yl)-3-methylbenzoate (10.3 mg, 33%). 1H NMR (CDCl₃, 400 MHz) δ 7.99 (br s, 1H), 7.93-7.91 (m, 1H), 7.16 (br s, 1H), 4.64 (br s, 1H), 3.91 (s, 3H), 3.71 (d, 1H), 3.58 (d, 1H), 2.30 (s, 3H), 1.85-1.34 (m, 9H), 1.27-1.23 (m, 2H); LC-MS (APCI) m/z 334.9 [M+H]⁺.

EXAMPLE 328

Methyl 3-methyl-4-[4-oxo-2-(2-pentanyl)-1,3-thiazolidin-3-yl]benzoate

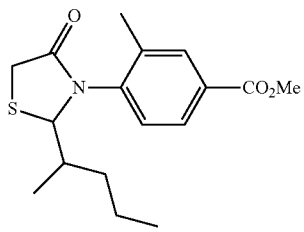

Compound 414

Following standard procedure A, methyl 4-amino-3-methylbenzoate (0.500 g, 3.03 mmol), 2-methylpentanal (0.550 mL, 4.54 mmol), Na₂SO₄ (0.450 g, 3.03 mmol), 2-mercaptoacetic acid (0.420 mL, 6.05 mmol) and toluene (10.0 mL) were used to carry out the reaction. It was reflux 4 h for the first step and 18 h for the second step. The reaction mixture was treated with saturated NaHCO₃(aq) and extracted with ethyl acetate. The organic layer was dried over MgSO₄(s), filtered, and concentrated. The residue was purified by Isco Combi-Flash Companion column chromatography (100% n-hexane) to give methyl 3-methyl-4-[4-oxo-2-(2-pentanyl)-1,3-thiazolidin-3-yl]benzoate (76.1 mg, 8%). 1H NMR (CDCl₃, 300 MHz) δ 7.99 (br s, 1H), 7.91 (d, 1H), 7.25-7.10 (m, 1H), 4.80-4.70 (br d, 1H), 3.90 (s, 3H), 3.72 (d, 1H), 3.61 (d, 1H), 2.30 (s, 3H), 1.78 (br s, 1H), 1.53-1.06 (m, 4H), 1.00-0.78 (m, 6H); LC-MS (APCI) m/z 322.8 [M+H]⁺.

EXAMPLE 329

Methyl 3-methyl-4-[2-(2-methylpropyl)-4-oxo-1,3-thiazolidin-3-yl]benzoate

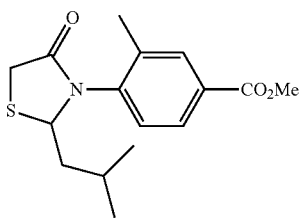

Compound 415

Following standard procedure A, methyl 4-amino-3-methylbenzoate (0.500 g, 3.03 mmol), 3-methylbutanal (0.490 mL, 4.54 mmol), Na₂SO₄ (0.450 g, 3.03 mmol), 2-mercaptoacetic acid (0.420 mL, 6.05 mmol) and toluene (10.0 mL) were used to carry out the reaction. It was reflux 4 h for the first step and 18 h for the second step. The reaction mixture was treated with saturated NaHCO₃(aq) and extracted with ethyl acetate. The organic layer was dried over MgSO₄(s), filtered, and concentrated. The residue was purified by Isco Combi-Flash Companion column chromatography (30% ethyl acetate in n-hexane) to give methyl 3-methyl-4-[2-(2-methylpropyl)-4-oxo-1,3-thiazolidin-3-yl]benzoate (0.100 g, 11%). 1H NMR (CDCl₃, 400 MHz) δ 7.99 (d, 1H), 7.91 (dd, 1H), 7.18 (d, 1H), 5.19 (br s, 0.6H), 4.82 (br s, 0.4H), 3.91 (s, 3H), 3.73-3.70 (m, 2H), 2.15 (s, 3H), 1.76-1.40 (m, 3H), 0.90-0.82 (m, 3H), 0.76 (d, 3H); LC-MS (ESI) m/z 308.1 [M+H]⁺.

EXAMPLE 330

Methyl 4-[2-(3-furanyl)-4-oxo-1,3-thiazolidin-3-yl]-3-methylbenzoate

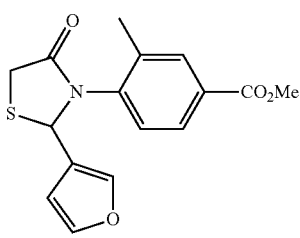

Compound 416

Following standard procedure A, methyl 4-amino-3-methylbenzoate (0.500 g, 3.03 mmol), furan-3-carbaldehyde (0.390 mL, 4.54 mmol), Na₂SO₄ (0.450 g, 3.03 mmol), 2-mercaptoacetic acid (0.420 mL, 6.05 mmol) and toluene (10.0 mL) were used to carry out the reaction. It was reflux 4 h for the first step and 18 h for the second step. The reaction mixture was treated with saturated $NaHCO_{3(aq)}$ and extracted with ethyl acetate. The organic layer was dried over $MgSO_{4(s)}$, filtered, and concentrated. The residue was purified by Isco Combi-Flash Companion column chromatography (50% ethyl acetate in n-hexane) to give methyl 4-[2-(3-furanyl)-4-oxo-1,3-thiazolidin-3-yl]-3-methylbenzoate (13.0 mg, 1%). 1H NMR (CDCl₃, 300 MHz) δ 7.91 (br s, 1H), 7.81 (d, 1H), 7.33 (br s, 1H), 7.27 (s, 1H), 7.02 (br s, 1H), 6.37 (br s, 1H), 5.97 (br s, 1H), 4.00-3.84 (m, 5H), 2.20 (br s, 3H); LC-MS (APCI) m/z 318.8 [M+H]⁺.

EXAMPLE 331

3-Benzyl-2-(4-fluorophenyl)-1,3-thiazolidin-4-one

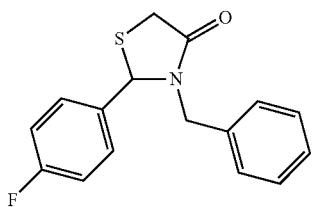

Compound 417

To a solution of 4-fluorobenzaldehyde (0.530 mL, 4.90 mmol) in CH₂Cl₂ (10.0 mL) was added phenylmethanamine (0.500 g, 4.67 mmol), 2-mercaptoacetic acid (0.650 mL, 9.33 mmol) and silica gel (2.30 g) at room temperature, and it was stirred for 16 h. After the reaction was quenched with water and extracted with ethyl acetate, the combined organic layers were dried over $MgSO_{4(s)}$, filtered, and concentrated under reduced pressure to afford a residue. The residue was purified by Isco Combi-Flash Companion column chromatography (0-20% ethyl acetate in n-hexane) to give 3-benzyl-2-(4-fluorophenyl)-1,3-thiazolidin-4-one (0.880 g, 66%). 1H NMR (CDCl₃, 400 MHz) δ 7.29-7.25 (m, 3H), 7.22-7.18 (m, 2H), 7.13-7.03 (m, 4H), 5.38 (d, 1H), 5.12 (d, 1H), 3.90 (d, 1H), 3.77 (d, 1H), 3.53 (d, 1H); LC-MS (ACPI) m/z 288.8 [M+H]⁺.

EXAMPLE 332

4-{[2-(4-Fluorophenyl)-4-oxo-1,3-thiazolidin-3-yl]methyl}benzoic acid

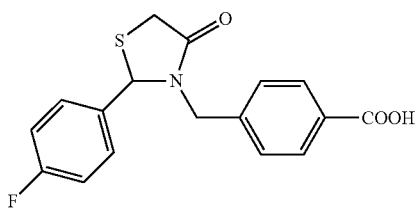

Compound 418

Step 1. Synthesis of methyl 4-(aminomethyl)benzoate

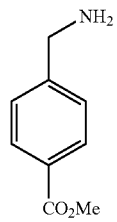

Compound 419

To a solution of 4-(aminomethyl)benzoic acid (0.500 g, 3.31 mmol) in methanol (15.0 mL) was added concentrated $HCl_{(aq)}$ (0.8 mL). After the reaction mixture was reflux for overnight and cooled to room temperature, the solvent was removed under reduced pressure. The residue was partitioned between ethyl acetate and water. The organic layer was dried over $MgSO_{4(s)}$, filtered, and concentrated to give a residue. The residue was purified by Isco Combi-Flash Companion column chromatography (100% ethyl acetate and 15% MeOH in CH₂Cl₂) to give methyl 4-(aminomethyl)benzoate (200 mg, 37%). 1H NMR (CDCl₃, 400 MHz) δ 7.98 (d, 2H), 7.36 (d, 2H), 3.91 (s, 2H), 3.88 (s, 3H).

Step 2. Synthesis of methyl 4-{[2-(4-fluorophenyl)-4-oxo-1,3-thiazolidin-3-yl]methyl}benzoate

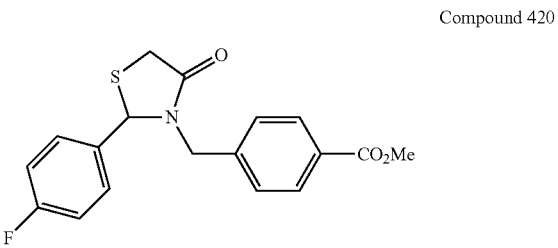 [SMILES: COC(=O)c1ccc(CN2C(=O)CSC2c2ccc(F)cc2)cc1]

Compound 420

To a solution of 4-fluorobenzaldehyde (0.140 mL, 1.27 mmol) in CH₂Cl₂ (5.0 mL) was added methyl 4-(aminomethyl)benzoate (200 mg, 1.20 mmol), thiogly acid (0.160 mL, 2.42 mmol) and silica gel (0.600 g) at room temperature, and it was stirred for 16 h. After the reaction was quenched with water and extracted with ethyl acetate, the combined organic layers were dried over $MgSO_{4(s)}$, filtered, and concentrated under reduced pressure to afford a residue. The residue was purified by Isco Combi-Flash Companion column chromatography (0-30% ethyl acetate in n-hexane) to give methyl 4-{[2-(4-fluorophenyl)-4-oxo-1,3-thiazolidin-3-yl]methyl}benzoate (170 mg, 31%). 1H NMR (CDCl₃, 400 MHz) δ 7.95 (dd, 2H), 7.21-7.16 (m, 2H), 7.12 (d, 2H), 7.08-7.03 (m, 2H), 5.36 (s, 1H), 5.09 (d, 1H), 3.95-3.88 (m, 4H), 3.81 (d, 1H), 3.64 (d, 1H).

Step 3. 4-{[2-(4-Fluorophenyl)-4-oxo-1,3-thiazolidin-3-yl]methyl}benzoic acid

Following standard procedure B, methyl 4-{[2-(4-fluorophenyl)-4-oxo-1,3-thiazolidin-3-yl]methyl}benzoate (180 mg) in methanol (5.0 mL) and 20% $NaOH_{(aq)}$ (2.0 mL) were used to carry out the reaction. After the reaction mixture was stirred at room temperature for 2 h and work-up. The residue purified by Isco Combi-Flash Companion column chromatography (4% MeOH in CH₂Cl₂) to give 4-{[2-(4-Fluorophenyl)-4-oxo-1,3-thiazolidin-3-yl]methyl}benzoic acid (90.0 mg, 53%). 1H NMR (CDCl₃, 400 MHz) δ 8.04 (d, 2H), 7.23-7.17 (m, 4H), 7.09-7.05 (m, 2H), 5.39 (s, 1H), 5.13 (d, 1H), 3.93 (d, 1H), 3.82 (d, 1H), 3.68 (d, 1H); LC-MS (ESI) m/z 332.9 [M+H]⁺.

EXAMPLE 333

3-[(5-Fluoro-2-methylphenyl)sulfonyl]-2-(4-fluorophenyl)-1,3-thiazolidin-4-one

Compound 421

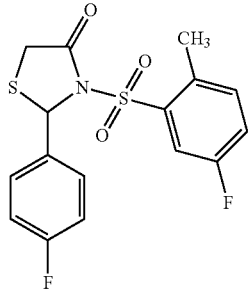

Step 1. 2-(4-Fluorophenyl)-1,3-thiazolidin-4-one

Compound 422

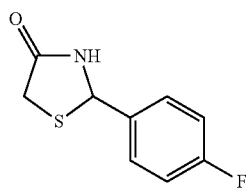

A solution of 4-fluorobenzaldehyde (0.680 g, 5.48 mmol), 2-mercaptoacetic acid (0.480 mL, 7.10 mmol), and ammonium carbonate (2.74 g, 28.5 mmol) in toluene (18 mL) was reflux for 18 h and cooled to room temperature. Toluene was removed under reduced pressure. The residue was purified by Isco Combi-Flash Companion column chromatography (0-80% ethyl acetate in n-hexane) to give 2-(4-fluorophenyl)-1,3-thiazolidin-4-one (0.520 g, 48%) as a lightly yellow solid. 1H NMR (CDCl₃, 400 MHz) δ 7.41-7.38 (m, 2H), 7.07 (t, 2H), 6.93 (br s, 1H), 5.77 (s, 1H), 3.67 (s, 2H).

Step 2. 3-[(5-Fluoro-2-methylphenyl)sulfonyl]-2-(4-fluorophenyl)-1,3-thiazolidin-4-one Following standard procedure I, 2-(4-fluorophenyl)-1,3-thiazolidin-4-one (110 mg, 0.559 mmol), triethylamine (0.120 mL, 0.866 mmol), DMAP (6.8 mg, 0.557 mmol), and 5-fluoro-2-methyl benzene sulfonyl chloride (175 mg, 0.839 mmol), and CH₂Cl₂ (5.0 mL) were used to carry out the reaction. After the reaction mixture was stirred for 18 h and work-up, the residue was purified by Isco Combi-Flash Companion column chromatography (0-20% ethyl acetate in n-hexane) to give 3-[(5-fluoro-2-methylphenyl)sulfonyl]-2-(4-fluorophenyl)-1,3-thiazolidin-4-one (58.7 mg, 28%) as a white solid. 1H NMR (CDCl₃, 400 MHz) δ 7.74 (dd, 1H), 7.41 (dd, 2H), 7.31-7.21 (m, 2H), 7.11 (t, 2H), 6.29 (s, 1H), 3.86 (d, 1H), 3.51 (d, 1H), 2.60 (s, 3H); LC-MS (ESI) m/z 370.1 [M+H]⁺.

EXAMPLE 334

Methyl 4-{[2-(4-fluorophenyl)-4-oxo-1,3-thiazolidin-3-yl]sulfonyl}benzoate

Compound 423

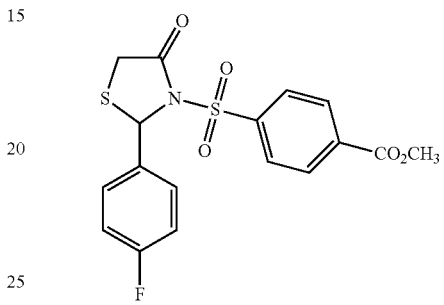

Following standard procedure I, 2-(4-fluorophenyl)-1,3-thiazolidin-4-one (111 mg, 0.564 mmol), triethylamine (0.120 mL, 0.866 mmol), DMAP (6.9 mg, 0.564 mmol), and methyl 4-(chlorosulfonyl)benzene (132 mg, 0.564 mmol), and CH₂Cl₂ (5.0 mL) were used to carry out the reaction. After the reaction mixture was stirred for 6 h and work-up, the residue was purified by Isco Combi-Flash Companion column chromatography (0-30% ethyl acetate in n-hexane) to give methyl 4-{[2-(4-fluorophenyl)-4-oxo-1,3-thiazolidin-3-yl]sulfonyl}benzoate (8.5 mg, 4%) as a beige solid. 1H NMR (CDCl₃, 300 MHz) δ 8.05 (d, 2H), 7.70 (d, 2H), 7.26-7.20 (m, 2H), 7.02 (t, 2H), 6.28 (s, 1H), 3.96 (s, 3H), 3.86 (d, 1H), 3.70 (d, 1H); LC-MS (ESI) m/z 396.1 [M+H]⁺.

EXAMPLE 335

2-(4-Fluorophenyl)-3-[(2-methylphenyl)sulfonyl]-1,3-thiazolidin-4-one

Compound 424

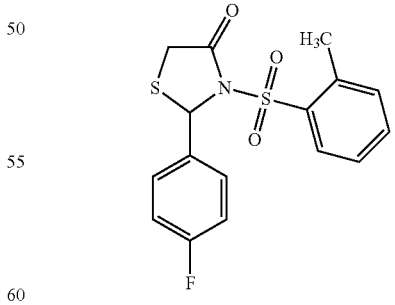

Following standard procedure I, 2-(4-fluorophenyl)-1,3-thiazolidin-4-one (119 mg, 0.603 mmol), triethylamine (0.125 mL, 0.902 mmol), DMAP (7.4 mg, 0.603 mmol), and O-toluenesulfonyl chloride (127 mg, 0.664 mmol), and CH₂Cl₂ (5.0 mL) were used to carry out the reaction. After the reaction mixture was stirred for 6 h and work-up, the residue was purified by Isco Combi-Flash Companion column chromatography (0-100% CH$_2$Cl$_2$ in n-hexane) to give 2-(4-fluorophenyl)-3-[(2-methylphenyl)sulfonyl]-1,3-thiazolidin-4-one (67.5 mg, 32%) as a white solid. 1H NMR (CDCl$_3$, 400 MHz) δ 8.07 (d, 1H), 7.54 (td, 1H), 7.44-7.31 (m, 4H), 7.10 (t, 2H), 6.32 (s, 1H), 3.84 (d, 1H), 3.48 (d, 1H), 2.65 (s, 3H); LC-MS (ESI) m/z 374.1 [M+Na]$^+$.

EXAMPLE 336

Methyl 4-{[2-(4-fluorophenyl)-4-oxo-1,3-thiazolidin-3-yl]amino}-3-methylbenzoate Compound 425

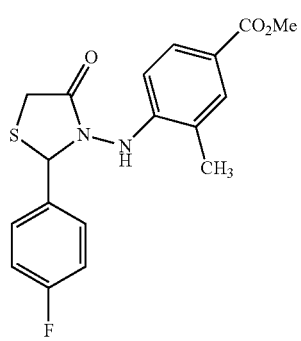

Step 1. Methyl 4-hydrazinyl-3-methylbenzoate hydrochloride

Compound 426

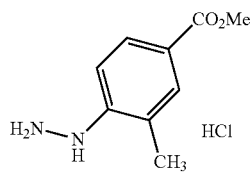

To a solution of methyl 4-amino-3-methylbenzene carboxylate (1.02 g, 6.17 mmol) in concentrated HCl$_{(aq)}$ (6.0 mL) and water (2.0 mL) was added a solution of sodium nitrite (0.640 g, 9.28 mmol) in water (2.0 mL) slowly at 0° C. After the reaction mixture was stirred at 0° C. for 1 h, a solution of tin(II) chloride (3.51 g, 18.5 mmol) in concentrated HCl$_{(aq)}$ (3.0 mL) was added. The solution was stirred for another 3 h at room temperature. The solids were collected by filtration and washed with cold water and n-hexane to give methyl 4-hydrazinyl-3-methylbenzoate hydrochloride (0.980 g, 73%) as a lightly yellow solid. 1H NMR (DMSO-d$_6$, 300 MHz) δ 8.50-8.10 (br, 1H), 7.77 (d, 1H), 7.69 (s, 1H), 6.90 (d, 1H), 3.76 (s, 3H), 2.18 (s, 3H).

Step 2. Methyl 4-{[2-(4-fluorophenyl)-4-oxo-1,3-thiazolidin-3-yl]amino}-3-methylbenzoate A solution of methyl 4-hydrazinyl-3-methylbenzoate hydrochloride (0.190 g, 1.06 mmol), 4-fluorobenzaldehyde (0.140 mL, 1.30 mmol), and Na$_2$SO$_4$ (0.150 g, 1.06 mmol) in toluene (3.0 mL) was reflux for 18 h. The solution was filtered off, and the filtrate was concentrated to obtain methyl 4-[2-(4-fluorobenzylidene)hydrazinyl]-3-methylbenzoate. A solution of previously prepared compound in 2-mercaptoacetic acid (1.0 mL) was stirred at 60° C. for 3 h and cooled to room temperature. The solution was quenched with saturated NaHCO$_{3(aq)}$ and extracted with ethyl acetate. The organic layers were dried over MgSO$_{4(s)}$, filtered, and concentrated. The residue was purified by Isco Combi-Flash Companion column chromatography (0-30% ethyl acetate in n-hexane) to give methyl 4-{[2-(4-fluorophenyl)-4-oxo-1,3-thiazolidin-3-yl]amino}-3-methylbenzoate (16.2 mg, 4%) as a yellow gum. 1H NMR (CDCl$_3$, 400 MHz) δ 7.84 (d, 1H), 7.74 (s, 1H), 7.32 (dd, 2H), 7.08 (t, 2H), 6.69 (d, 1H), 5.72 (s, 1H), 3.96-3.80 (m, 5H), 1.99 (s, 3H); LC-MS (ESI) m/z 361.2 [M+H]$^+$.

EXAMPLE 337

3-[(5-Fluoro-2-methylphenyl)amino]-2-(4-fluorophenyl)-1,3-thiazolidin-4-one

Compound 427

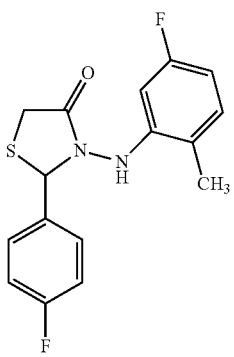

Step 1. (5-Fluoro-2-methylphenyl)hydrazine hydrochloride

Compound 428

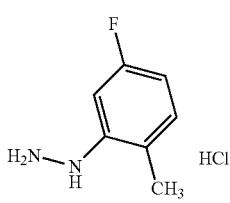

To a solution of 2-methyl-5-fluoroaniline (1.31 g, 10.5 mmol) in concentrated HCl$_{(aq)}$ (12 mL) was added a solution of sodium nitrite (1.08 g, 15.7 mmol) in water (4.0 mL) slowly at 0° C. After the reaction mixture was stirred at 0° C. for 1 h, a solution of tin(II) chloride (5.97 g, 31.5 mmol) in concentrated HCl$_{(aq)}$ (6.0 mL) was added. The solution was stirred for another 2 h at room temperature. The solids were collected by filtration and washed with cold water and n-hexane to give (5-fluoro-2-methylphenyl)hydrazine hydrochloride (1.34 g, 72%) as a yellow solid. $^1$H NMR (DMSO-d$_6$, 400 MHz) δ 10.26 (br s, 2H), 8.06 (br s, 1H), 7.11 (dd, 1H), 6.75 (dd, 1H), 6.66 (ddd, 1H), 2.11 (s, 3H).

Step 2. 3-[(5-Fluoro-2-methylphenyl)amino]-2-(4-fluorophenyl)-1,3-thiazolidin-4-one To a solution of (5-fluoro-2-methylphenyl)hydrazine hydrochloride (0.410 g, 2.93 mmol) in toluene (4.0 mL) was added 4-fluorobenzaldehyde (0.380 mL, 3.52 mmol) and Na₂SO₄ (0.420 g, 2.93 mmol). The reaction was stirred at 70° C. for 2 h. The solvent was removed to obtain N-(4-fluoro-benzylidene)-N'-(5-fluoro-2-methylphenyl)hydrazine. A solution of previously prepared compound in 2-mercaptoacetic acid (3.0 mL) was stirred at 60° C. for 5 h and cooled to room temperature. The solution was quenched with saturated NaHCO₃(aq) and extracted with ethyl acetate. The organic layers were dried over MgSO₄(s), filtered, and concentrated. The residue was purified by Isco Combi-Flash Companion column chromatography (0-30% ethyl acetate in n-hexane) to give 3-[(5-fluoro-2-methylphenyl)amino]-2-(4-fluorophenyl)-1,3-thiazolidin-4-one (195 mg, 21%) as a yellow solid. 1H NMR (CDCl₃, 400 MHz) δ 7.34-7.30 (m, 2H), 7.08 (t, 2H), 6.97 (dd, 1H), 6.58-6.53 (m, 1H), 6.42 (dd, 1H), 5.71 (s, 1H), 5.59 (br s, 1H), 3.87 (d, 1H), 3.81 (d, 1H), 1.91 (s, 3H); LC-MS (ESI) m/z 321.2 [M+H]⁺.

EXAMPLE 338

(2Z)-3-(5-Fluoro-2-methylphenyl)-2-[(4-fluorophenyl)imino]-1,3-thiazolidin-4-one

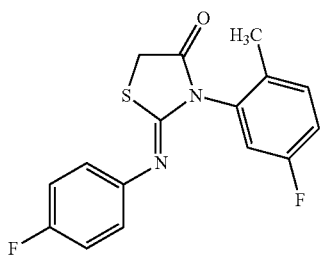

Compound 429

Step 1. 2-Chloro-N-(5-fluoro-2-methylphenyl)acetamide

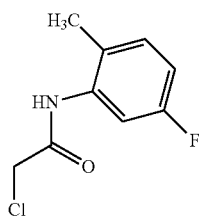

Compound 430

A solution of 2-methyl-5-fluoroaniline (0.880 g, 7.03 mmol) and chloroacetyl chloride (1.12 mL, 14.1 mmol) in THF (10 mL) was stirred at room temperature for 20 h. The solvent was concentrated and dried under high vacuum to give 2-chloro-N-(5-fluoro-2-methylphenyl)acetamide (1.46 g, 100%) as a gray solid. 1H NMR (CDCl₃, 400 MHz) δ 8.30 (br s, 1H), 7.86 (dd, 1H), 7.14 (dd, 1H), 6.81 (td, 1H), 4.24 (s, 2H), 2.27 (s, 3H); LC-MS (ESI) m/z 224.0 [M+Na]⁺.

Step 2. (2Z)-3-(5-Fluoro-2-methylphenyl)-2-[(4-fluorophenyl)imino]-1,3-thiazolidin-4-one Following standard procedure J, 2-chloro-N-(5-fluoro-2-methylphenyl)acetamide (271 mg, 1.35 mmol), 60% NaH in mineral oil (59.2 mg, 1.48 mmol), and 4-fluorophenyl isothiocyanate (217 mg, 1.41 mmol) were used to carry out the reaction. After work-up, the residue was purified by Isco Combi-Flash Companion column chromatography (0-20% ethyl acetate in n-hexane) to give (2Z)-3-(5-fluoro-2-methylphenyl)-2-[(4-fluorophenyl)imino]-1,3-thiazolidin-4-one (211 mg, 49%) as an orange solid. 1H NMR (CDCl₃, 400 MHz) δ 7.32 (dd, 1H), 7.09 (td, 1H), 7.03-6.98 (m, 3H), 6.86 (dd, 2H), 4.02 (s, 2H), 2.23 (s, 3H); LC-MS (ESI) m/z 319.0 [M+H]⁺.

EXAMPLE 339

Methyl 4-{(2Z)-2-[(4-fluorophenyl)imino]-4-oxo-1,3-thiazolidin-3-yl}-3-methylbenzoate

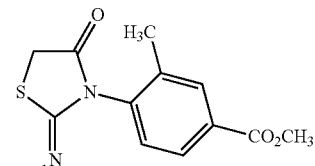

Compound 431

Step 1. Methyl 4-[(chloroacetyl)amino]-3-methylbenzoate.

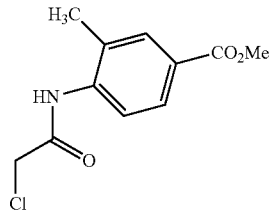

Compound 432

A solution of methyl 4-amino-3-methylbenzene carboxylate (1.01 g, 6.11 mmol) and chloroacetyl chloride (0.980 mL, 6.11 mmol) in THF (10 mL) was stirred at room temperature for 20 h. The solvent was concentrated and dried under high vacuum to give methyl 4-[(chloroacetyl)amino]-3-methylbenzoate (1.48 g, 100%) as a white solid. 1H NMR (CDCl₃, 400 MHz) δ 8.42 (br s, 1H), 8.19 (d, 1H), 7.94-7.91 (m, 2H), 4.26 (s, 2H), 3.91 (s, 3H), 2.37 (s, 3H); LC-MS (ESI) m/z 264.0 [M+Na]⁺.

Step 2. Methyl 4-{(2Z)-2-[(4-fluorophenyl)imino]-4-oxo-1,3-thiazolidin-3-yl}-3-methylbenzoate Following standard procedure J, methyl 4-[(chloroacetyl)amino]-3-methylbenzoate (282 mg, 1.17 mmol), 60% NaH in mineral oil (51.6 mg, 1.29 mmol), and 4-fluorophenyl isothiocyanate (188 mg, 1.23 mmol) were used to carry out the reaction. After work-up, the residue was purified by Isco Combi-Flash Companion column chromatography (0-30% ethyl acetate in n-hexane) to give methyl 4-{(2Z)-2-[(4- fluorophenyl)imino]-4-oxo-1,3-thiazolidin-3-yl}-3-methyl-benzoate (244 mg, 55%) as a yellow solid. 1H NMR (CDCl$_3$, 300 MHz) δ 8.06 (s, 1H), 8.01 (dd, 1H), 7.32 (d, 1H), 7.00 (t, 2H), 6.88-6.83 (m, 2H), 4.04 (s, 2H), 3.92 (s, 3H), 2.32 (s, 3H); LC-MS (ESI) m/z 359.2 [M+H]$^+$.

EXAMPLE 340

(2Z)-2-[(4-Fluorophenyl)imino]-3-(4-methoxyphenyl)-1,3-thiazolidin-4-one

Compound 433

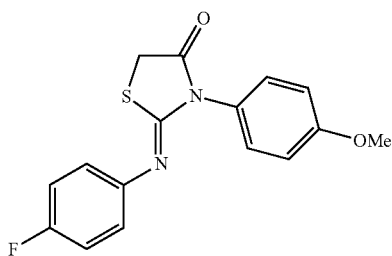

Step 1. 2-Chloro-N-(4-methoxyphenyl)acetamide

Compound 434

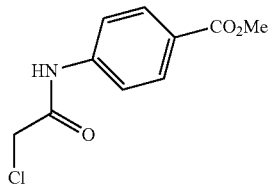

A solution of para-anisidine (1.01 g, 6.11 mmol) and chloroacetyl chloride (0.980 mL, 6.11 mmol) in THF (10 mL) was stirred at room temperature for 18 h. The solvent was concentrated and dried under high vacuum to give 2-chloro-N-(4-methoxyphenyl)acetamide (1.68 g, 100%) as a purple solid. 1H NMR (CDCl$_3$, 400 MHz) δ 8.14 (br s, 1H), 7.44 (d, 2H), 6.89 (d, 2H), 4.22 (s, 2H), 3.80 (s, 3H).

Step 2. (2Z)-2-[(4-Fluorophenyl)imino]-3-(4-methoxyphenyl)-1,3-thiazolidin-4-one Following standard procedure J, 2-chloro-N-(4-methoxyphenyl)acetamide (243 mg, 1.22 mmol), 60% NaH in mineral oil (58.6 mg, 1.47 mmol), and 4-fluorophenyl isothiocyanate (196 mg, 1.28 mmol) were used to carry out the reaction. After work-up, the residue was purified by Isco Combi-Flash Companion column chromatography (0-30% ethyl acetate in n-hexane) to give (2Z)-2-[(4-fluorophenyl)imino]-3-(4-methoxyphenyl)-1,3-thiazolidin-4-one (208 mg, 54%) as a yellow solid. 1H NMR (CDCl$_3$, 400 MHz) δ 7.28 (d, 2H), 7.04-6.98 (m, 4H), 6.89-6.85 (m, 2H), 3.98 (s, 2H), 3.83 (s, 3H); LC-MS (ESI) m/z 317.2 [M+H]$^+$.

EXAMPLE 341

(2Z)-3-(3-Chlorophenyl)-2-[(4-fluorophenyl)imino]-1,3-thiazolidin-4-one

Compound 435

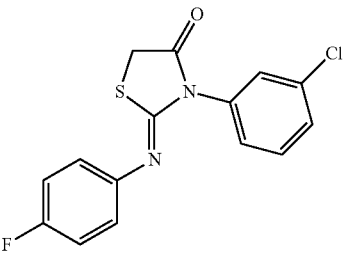

Step 1. 2-Chloro-N-(3-chlorophenyl)acetamide

Compound 436

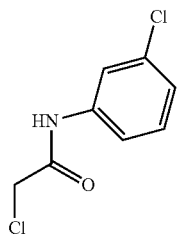

A solution of 2-chloroaniline (0.500 mL, 4.74 mmol) and chloroacetyl chloride (0.570 mL, 7.16 mmol) in THF (10 mL) was stirred at room temperature for 18 h. The solvent was concentrated and dried under high vacuum to give 2-chloro-N-(3-chlorophenyl)acetamide (0.976 g, 100%) as a white solid. 1H NMR (CDCl$_3$, 400 MHz) δ 8.23 (br s, 1H), 7.67 (s, 1H), 7.40 (ddd, 1H), 7.28 (t, 1H), 7.15 (ddd, 1H), 4.20 (s, 2H).

Step 2. (2Z)-3-(3-Chlorophenyl)-2-[(4-fluorophenyl)imino]-1,3-thiazolidin-4-one Following standard procedure J, 2-chloro-N-(3-chlorophenyl)acetamide (259 mg, 1.27 mmol), 60% NaH in mineral oil (61.0 mg, 1.53 mmol), and 4-fluorophenyl isothiocyanate (204 mg, 1.33 mmol) were used to carry out the reaction. After work-up, the residue was purified by column chromatography (25% ethyl acetate in n-hexane) to give (2Z)-3-(3-chlorophenyl)-2-[(4-fluorophenyl)imino]-1,3-thiazolidin-4-one (88.7 mg, 22%) as a yellow solid. 1H NMR (CDCl$_3$, 400 MHz) δ 7.48-7.40 (m, 3H), 7.29 (dt, 1H), 7.02 (dd, 2H), 6.88 (dd, 2H), 4.00 (s, 2H); LC-MS (ESI) m/z 321.1 [M+H]$^+$.

EXAMPLE 342

4-[5-(4-Fluorophenyl)-1H-pyrazol-1-yl]-3-methylbenzoic acid

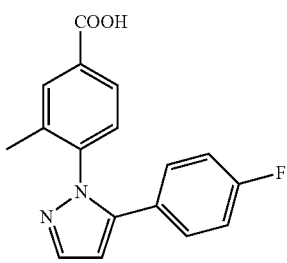

Compound 437

Step 1. Synthesis of methyl 4-hydrazinyl-3-methylbenzoate hydrochloride

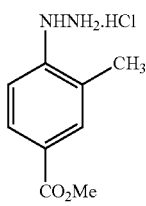

Compound 438

A solution of methyl 4-amino-3-methylbenzoate (1.00 g, 6.06 mmol) in concentrated $HCl_{(aq)}$ (2.7 mL) and sodium nitrite (0.460 g, 6.67 mmol) in water (2.2 mL) were used to carry out the reaction at 0° C. for 1 h. To the above mixture, a solution of $SnCl_2$ (3.45 g, 6.67 mmol) in concentrated $HCl_{(aq)}$ (4.4 mL) was added. After the reaction was stirred at room temperature for 3 h, the white solid was collected by vacuum filtration and washed with ethyl acetate to give methyl 4-hydrazinyl-3-methylbenzoate hydrochloride (0.250 g, 19%). 1H NMR (DMSO-$d_6$, 400 MHz) δ 10.38 (br s, 2H), 8.39 (br s, 1H), 7.77 (dd, 1H), 7.70 (d, 1H), 6.96 (d, 1H), 3.78 (s, 3H), 2.20 (s, 3H).

Step 2. Synthesis of (2E)-3-(Dimethylamino)-1-(4-fluorophenyl)-2-propen-1-one

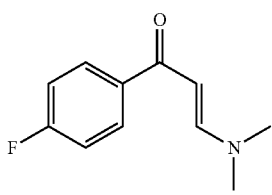

Compound 439

A solution of 1-(4-fluorophenyl)ethanone (0.875 mL, 7.24 mmol) in toluene (5.0 mL) and N,N-dimethylformamide dimethyl acetal (DIFDA, 1.35 mL, 10.1 mmol) were used to carry out the reaction. After the reaction was reflux for 4 h and work-up, the residue was purified by Isco Combi-Flash Companion column chromatography (0-60% ethyl acetate in n-hexane) to give (2E)-3-(dimethylamino)-1-(4-fluorophenyl)-2-propen-1-one (0.987 g, 71%). 1H NMR (CDCl$_3$, 400 MHz) δ 7.91 (dd, 2H), 7.80 (d, 1H), 7.07 (dd, 2H), 5.67 (d, 1H), 3.15 (br s, 3H), 2.93 (br s, 3H).

Step 3. Synthesis of methyl 4-[5-(4-fluorophenyl)-1H-pyrazol-1-yl]-3-methylbenzoate

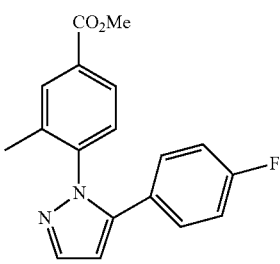

Compound 440

A solution of 2-(E)-3-(Dimethylamino)-1-(4-fluorophenyl)prop-2-en-1-one (24.0 mg, 0.130 mmol) in MeOH (5.0 mL) and water (1.0 mL), methyl 4-hydrazinyl-3-methylbenzoate hydrochloride (30.0 mg, 0.140 mmol) and sodium carbonate (9.00 mg, 0.0900 mmol) were added and then to the above mixture, acetic acid was added to adjust the pH value to above 4. After the reaction mixture was stirred at 135° C. for 2 h and work-up, the residue was purified by Isco Combi-Flash Companion column chromatography (0-5% MeOH in $CH_2Cl_2$) to give methyl 4-[5-(4-fluorophenyl)-1H-pyrazol-1-yl]-3-methylbenzoate (38.0 mg, 99%) as a white solid. 1H NMR (CDCl$_3$, 400 MHz) δ 7.94 (s, 1H), 7.89 (d, 1H), 7.74 (s, 1H), 7.28 (d, 1H), 7.13-7.08 (m, 2H), 6.96-6.90 (m, 2H), 6.53 (s, 1H), 3.92 (s, 3H), 2.02 (s, 3H). LC-MS (ESI) m/z 311.1 [M+H]$^+$.

Step 4. Synthesis of 4-[5-(4-fluorophenyl)-1H-pyrazol-1-yl]-3-methylbenzoic acid

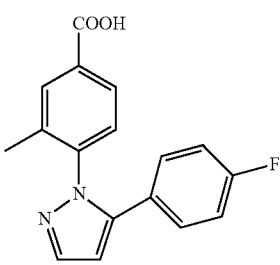

Compound 441

Following standard procedure B, 4-[5-(4-fluorophenyl)-1H-pyrazol-1-yl]-3-methylbenzoate (38.0 mg) in methanol (5.0 mL) and 20% NaOH$_{(aq)}$ (1.0 mL) were used to carry out the reaction. After the reaction was stirred at room temperature for 3 h and work-up, the residue was purified by Isco Combi-Flash Companion column chromatography (0-5% MeOH in $CH_2Cl_2$) to give 4-[5-(4-fluorophenyl)-1H-pyrazol-1-yl]-3-methylbenzoic acid (4.00 mg, 13%) as a white solid. 1H NMR (CDCl$_3$, 400 MHz) δ 8.00 (s, 1H), 7.96 (d, 1H), 7.79 (s, 1H), 7.32 (d, 1H), 7.14-7.11 (m, 2H), 6.95 (dd, 2H), 6.55 (s, 1H), 2.05 (s, 3H); LC-MS (APCI) m/z 297.9 [M+H]$^+$.

EXAMPLE 343

4-[3-(4-Fluorophenyl)-4H-1,2,4-triazol-4-yl]-3-methylbenzoic acid

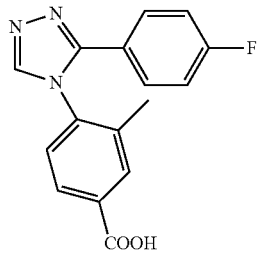

Compound 442

Step 1. Synthesis of methyl 4-[(4-fluorobenzoyl)amino]-3-methylbenzoate

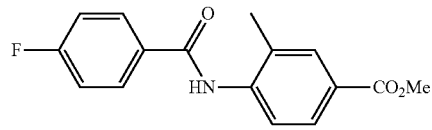

Compound 443

Following standard procedure, 4-fluorobenzoic acid (0.510 g, 3.63 mmol), methyl 4-amino-3-methylbenzoate (0.500 g, 3.03 mmol), EDCI • HCl (1.16 g, 6.06 mmol), DMAP (0.930 g, 7.57 mmol) and CH$_2$Cl$_2$ (7.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give methyl 4-[(4-fluorobenzoyl)amino]-3-methylbenzoate (0.380 g, 44%). $^1$H NMR (CDCl$_3$, 400 MHz) δ 8.23 (d, 1H), 7.96-7.88 (m, 4H), 7.75 (br s, 1H), 7.20 (td, 2H), 3.91 (s, 3H), 2.39 (s, 3H).

Step 2. Synthesis of methyl 4-{[(Z)-(4-fluorophenyl)(hydrazinyl)methylidene]amino}-3-methylbenzoate

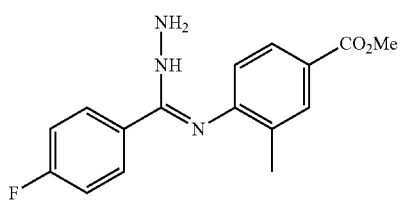

Compound 444

The solution of methyl 4-[(4-fluorobenzoyl)amino]-3-methylbenzoate (0.140 g, 0.490 mmol) and PCl$_5$ (0.110 g, 0.540 mmol) in benzene (10.0 mL) was reflux for 4 h. To the mixture was added a solution of N$_2$H$_4$.H$_2$O (0.240 g, 4.87 mmol) in THF (5.0 mL). After stirring at room temperature for 1 h, the reaction mixture was extracted with ethyl acetate, dried over MgSO$_{4(s)}$, filtered and concentrated. The residue was used directly for next step without further purification. 1H NMR (CDCl$_3$, 300 MHz) δ 7.85 (s, 1H), 7.65 (dd, 1H), 7.47 (dd, 2H), 6.99 (dd, 2H), 6.33 (d, 1H), 3.84 (s, 3H), 2.37 (s, 3H).

Step 3. Synthesis of methyl 4-[3-(4-fluorophenyl)-4H-1,2,4-triazol-4-yl]-3-methylbenzoate

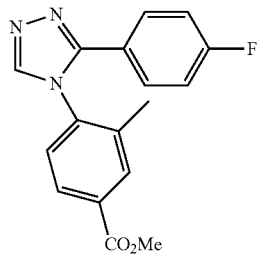

Compound 445

To a solution of methyl 4-{[(Z)-(4-fluorophenyl)(hydrazinyl)methylidene]amino}-3-methylbenzoate (0.190 g, 0.630 mmol) was added p-toluenesulfonic acid (PTSA, 54.0 mg, 0.320 mmol) and 1,1-dimethoxy-N,N-dimethylmethanamine (0.110 mL, 0.820 mmol) in toluene (5.0 mL). After the reaction was reflux for 3 h, the reaction mixture was extracted with ethyl acetate, dried over MgSO$_{4(s)}$, filtered and concentrated. The residue was purified by Isco Combi-Flash Companion column chromatography (0-10% MeOH in CH$_2$Cl$_2$) to give methyl 4-[3-(4-fluorophenyl)-4H-1,2,4-triazol-4-yl]-3-methylbenzoate (0.110 g, 56%). 1H NMR (CDCl$_3$, 400 MHz) δ 8.22 (s, 1H), 8.01-7.98 (m, 2H), 7.42-7.38 (m, 2H), 7.32 (d, 1H), 6.99-6.94 (m, 2H), 3.94 (s, 3H), 1.98 (s, 3H).

Step 4. Synthesis of 4-[3-(4-fluorophenyl)-4H-1,2,4-triazol-4-yl]-3-methylbenzoic acid Following standard procedure B, methyl 4-[3-(4-fluorophenyl)-4H-1,2,4-triazol-4-yl]-3-methylbenzoate (0.110 g) in methanol (10.0 mL) and 20% NaOH$_{(aq)}$ (3.0 mL) were used to carry out the reaction. After the reaction was stirred at room temperature for 3 h and work-up, the residue was purified by Isco Combi-Flash Companion column chromatography (0-10% MeOH in CH$_2$Cl$_2$) to give 4-[3-(4-fluorophenyl)-4H-1,2,4-triazol-4-yl]-3-methylbenzoic acid (88.0 mg, 84%). 1H NMR (CDCl$_3$, 400 MHz) δ 8.25 (s, 1H), 7.99-7.97 (m, 2H), 7.38-7.34 (m, 2H), 7.28 (d, 1H), 6.96 (dd, 2H), 1.95 (s, 3H); LC-MS (APCI) m/z 298.8 [M+H]$^+$.

EXAMPLE 344

2-(2-Hydroxyethoxy)ethoxy)ethyl 4-[2-(4-fluorophenyl)-4-oxo-1, 3-thiazolidin-3-yl]-3-methylbenzoate Compound 446

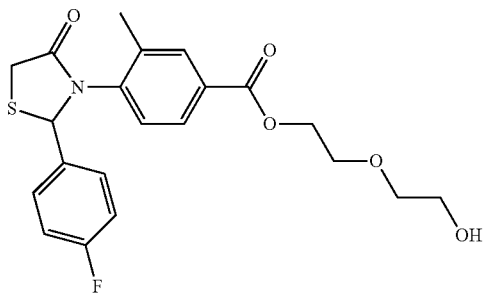

Step 1. Synthesis of tert-butyl[2-(2-chloroethoxy)ethoxy]dimethylsilane

Compound 447

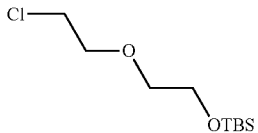

To a solution of 2-(2-chloroethoxy)ethanol (3.00 mL, 28.4 mmol) in THF (120 mL) was added tert-butyldimethylsilyl chloride (5.56 g, 36.9 mmol) and imidazole (2.90 g, 42.6 mmol) at 0° C. The reaction mixture was stirred at room temperature for 16 h. The solution was concentrated. The residue was treated with 1.0 N HCl$_{(aq)}$ and extracted with CH$_2$Cl$_2$. The combined organic layers were dried over MgSO$_{4(s)}$, filtered, and concentrated to give tert-butyl[2-(2-chloroethoxy)ethoxy]dimethylsilane (6.75 g, 99%) as colorless oil which was directly used to next step without further purification. $^1$H NMR (CDCl$_3$, 300 MHz) δ 3.79-3.74 (m, 4H), 3.64-3.57 (m, 4H), 0.89 (s, 9H), 0.07 (s, 6H).

Step 2. Synthesis of 2-(2-{[tert-butyl(dimethyl)silyl]oxy}ethoxy)ethyl 4-[2-(4-fluorophenyl)-4-oxo-1,3-thiazolidin-3-yl]-3 methylbenzoate.

Compound 448

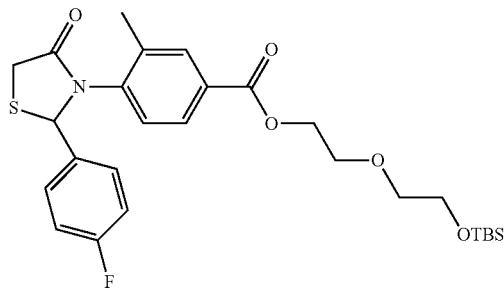

Following standard procedure L, 4-[2-(4-fluorophenyl)-4-oxo-1,3-thiazolidin-3-yl]-3-methylbenzoic acid (158 mg, 0.477 mmol), K$_2$CO$_3$ (79.1 mg, 0.572 mmol), tert-butyl[2-(2-chloroethoxy)ethoxy]dimethylsilane (137 mg, 0.572 mmol) and DMF (1.0 mL) were used to carry out the reaction. After work-up, we got 2-(2-{[tert-butyl(dimethyl)silyl]oxy}ethoxy)ethyl 4-[2-(4-fluorophenyl)-4-oxo-1,3-thiazolidin-3-yl]-3-methylbenzoate (255 mg, 0.477 mmol) which was directly used to next step without further purification. $^1$H NMR (CDCl$_3$, 300 MHz) δ 7.88 (s, 1H), 7.76 (br d, 1H), 7.30 (dd, 2H), 6.95 (br t, 2H), 6.05-5.80 (br, 1H), 4.41 (dd, 2H), 4.00 (d, 1H), 3.92 (d, 1H), 3.80-3.72 (m, 4H), 3.64-3.56 (m, 2H), 2.19 (br s, 3H), 0.87 (s, 9H), 0.04 (s, 6H).

Step 3. Synthesis of 2-(2-hydroxyethoxy)ethyl 4-[2-(4-fluorophenyl)-4-oxo-1,3-thiazolidin-3-yl]-3-methylbenzoate To a solution of 2-(2-{[tert-butyl(dimethyl)silyl]oxy}ethoxy)ethyl 4-[2-(4-fluorophenyl)-4-oxo-1,3-thiazolidin-3-yl]-3-methylbenzoate (255 mg, 0.477 mmol) in THF (4.0 mL) was added 1.0 M tetra-n-butylammonium fluoride in THF solution (0.80 mL, 0.80 mmol) at room temperature. The reaction mixture was stirred for 1 h and concentrated. The residue was purified by Isco Combi-Flash Companion column chromatography (0-80% ethyl acetate in n-hexane) to give 2-(2-hydroxyethoxy)ethyl 4-[2-(4-fluorophenyl)-4-oxo-1,3-thiazolidin-3-yl]-3-methylbenzoate (161 mg, 81%) as a colorless gum. $^1$H NMR (CDCl$_3$, 400 MHz) δ 7.88 (s, 1H), 7.76 (br s, 1H), 7.31 (dd, 2H), 6.96 (dd, 2H), 6.10-5.80 (br, 1H), 4.44 (dd, 2H), 4.00 (d, 1H), 3.92 (d, 1H), 3.79 (dd, 2H), 3.74 (dd, 2H), 3.62 (dd, 2H), 2.20 (br s, 3H); LC-MS (ESI) m/z 442.1 [M+Na]$^+$.

EXAMPLE 345

2-[2-(Methylamino)ethoxy]ethyl 4-[2-(4-fluorophenyl)-4-oxo-1,3-thiazolidin-3-yl]-3-methylbenzoate Compound 449

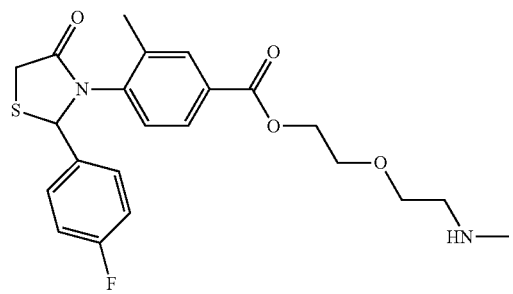

Step 1. Synthesis of ethyl {2-[(tert-butoxycarbonyl)(methyl)amino]ethoxy}acetate Compound 450

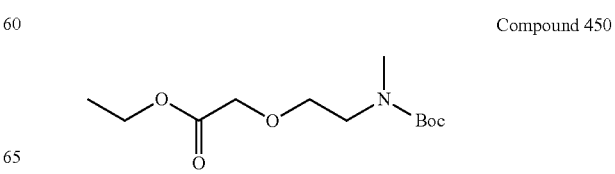

A solution of ethyl 2-diazoacetate (0.900 mL, 8.56 mmol), tert-butyl (2-hydroxyethyl)(methyl)carbamate (1.50 g, 8.56 mmol) and rhodium(II) acetate dimer (0.380 g, 0.856 mmol) in CH$_2$Cl$_2$ (10.0 mL) were used to carry out the reaction. After the reaction was stirred at room temperature for 16 h and work-up, the residue was purified by Isco Combi-Flash Companion column chromatography (0-10% ethyl acetate in n-hexane) to give ethyl {2-[(tert-butoxycarbonyl)(methyl)amino]ethoxy}acetate (0.690 g, 31%). $^1$H NMR (CDCl$_3$, 300 MHz) δ 4.28-4.18 (m, 2H), 4.07 (br s, 2H), 3.65 (br s, 2H), 3.42 (br s, 2H), 2.93-2.92 (m, 3H), 1.45-1.44 (m, 9H), 1.25 (br t, 3H).

Step 2. Synthesis of tert-butyl [2-(2-hydroxyethoxy)ethyl]methylcarbamate

Compound 451

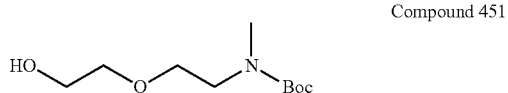

A solution of ethyl {2-[(tert-butoxycarbonyl)(methyl)amino]ethoxy}acetate (0.688 g, 2.63 mmol) in methanol (10.0 mL) and sodium borohydride (0.120 g, 3.16 mmol) were used to carry out the reaction. After the reaction was stirred at room temperature for 16 h and work-up, the residue was purified by Isco Combi-Flash Companion column chromatography (0-50% ethyl acetate in n-hexane) to give tert-butyl [2-(2-hydroxyethoxy)ethyl]methylcarbamate (0.167 g, 29%). $^1$H NMR (CDCl$_3$, 300 MHz) δ 3.70 (br s, 2H), 3.57 (br s, 4H), 3.40 (br s, 2H), 2.89 (br s, 3H), 1.44 (s, 9H).

Step 3. Synthesis of 2-{2-[(tert-butoxycarbonyl)(methyl)amino]ethoxy}ethyl 4-[2-(4-fluorophenyl)-4-oxo-1,3-thiazolidin-3-yl]-3-methylbenzoate Compound 452

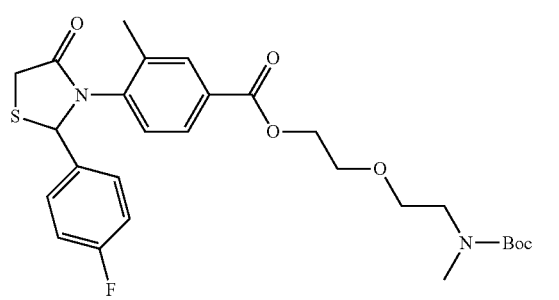

Following standard procedure G, 4-[2-(4-fluorophenyl)-4-oxo-1,3-thiazolidin-3-yl]-3-methylbenzoic acid (0.250 g, 0.760 mmol), tert-butyl [2-(2-hydroxyethoxy)ethyl]methylcarbamate (0.167 mg, 0.760 mmol), EDCI • HCl (0.290 g, 1.51 mmol), DMAP (0.200 g, 1.66 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-{2-[(tert-butoxycarbonyl)(methyl)amino]ethoxy}ethyl 4-[2-(4-fluorophenyl)-4-oxo-1,3-thiazolidin-3-yl]-3-methylbenzoate (0.370 g, 92%). $^1$H NMR (CDCl$_3$, 400 MHz) δ 7.87 (br s, 1H), 7.75 (br s, 1H), 7.32-7.28 (m, 2H), 6.96 (br t, 2H), 6.10-5.70 (br, 1H), 4.41-4.39 (m, 2H), 4.00 (d, 1H), 3.92 (d, 1H), 3.73 (br t, 2H), 3.60 (br s, 2H), 3.38 (br s, 2H), 2.88 (br s, 3H), 2.20 (br s, 3H), 1.46 (s, 9H).

Step 4. Synthesis of 2-[2-(methylamino)ethoxy]ethyl 4-[2-(4-fluorophenyl)-4-oxo-1,3-thiazolidin-3-yl]-3-methylbenzoate The solution of 2-{2-[(tert-butoxycarbonyl)(methyl)amino]ethoxy}ethyl 4-[2-(4-fluorophenyl)-4-oxo-1,3-thiazolidin-3-yl]-3-methylbenzoate (0.350 g) and TFA (5.0 mL) in CH$_2$Cl$_2$ (10.0 mL) was stirred at room temperature for 3 h. To the reaction mixture was added saturated NaHCO$_{3(aq)}$ to adjust the pH value>8 and extracted with CH$_2$Cl$_2$. The organic layers were dried over MgSO$_{4(s)}$, filtered and concentrated. The residue was purified by Isco Combi-Flash Companion column chromatography (0-10% MeOH in CH$_2$Cl$_2$) to give 2-[2-(methylamino)ethoxy]ethyl 4-[2-(4-fluorophenyl)-4-oxo-1,3-thiazolidin-3-yl]-3-methylbenzoate (0.180 g, 63%). 1H NMR (CDCl$_3$, 400 MHz) δ 7.85 (br s, 1H), 7.73 (br s, 1H), 7.33-7.28 (m, 2H), 6.96 (br t. 2H), 5.99 (br s, 1H), 4.41 (br t, 2H), 4.00 (d, 1H), 3.91 (d, 1H), 3.78-3.75 (m, 4H), 3.11 (t, 2H), 2.66 (s, 3H), 2.19 (br s, 3H); LC-MS (ESI) m/z 433.2 [M+H]$^+$.

EXAMPLE 346

2-[2-(Pyridin-2-ylmethoxy)ethoxy]ethyl 4-[2-(4-fluorophenyl)-4-oxo-1,3-thiazolidin-3-yl]-3-methylbenzoate Compound 453

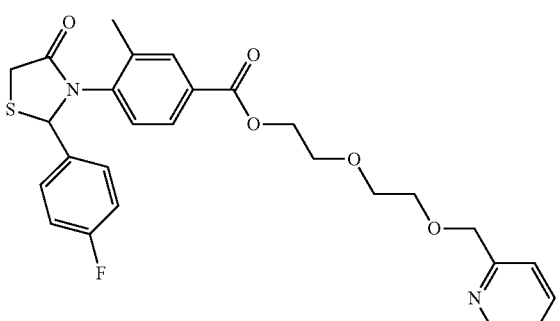

Step 1. Synthesis of 2-(2-chloroethoxy)ethyl 4 methylbenzenesulfonate.

Compound 454

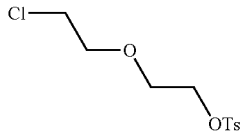

A solution of 2-(2-chloroethoxy)ethanol (2.50 mL, 23.7 mmol), DMAP (289 mg, 2.36 mmol), p-toluenesulfonyl chloride (4.51 g, 23.7 mmol), and pyridine (1.90 mL, 23.6 mmol) in CH₂Cl₂ (50 mL) was stirred at room temperature for 5 h. The solution was diluted with CH₂Cl₂ and washed with 2 N HCl$_{(aq)}$, 5% NaOH$_{(aq)}$, and water. The organic layer was dried over MgSO$_{4(s)}$, filtered, and concentrated. The residue was purified by Isco Combi-Flash Companion column chromatography (0-20% ethyl acetate in n-hexane) to give 2-(2-chloroethoxy)ethyl 4-methylbenzenesulfonate (245 mg, 37%) as a colorless oil. ¹H NMR (CDCl₃, 400 MHz) δ 7.80 (d, 2H), 7.35 (d, 2H), 4.17 (dd, 2H), 3.72-3.66 (m, 4H), 3.54 (t, 2H), 2.45 (s, 3H).

Step 2. Synthesis of 2-{[2-(2-chloroethoxy)ethoxy]methyl}pyridine

Compound 455

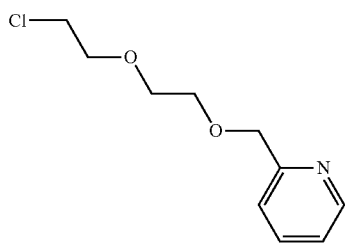

To a solution of pyridine-2-methanol (231 mg, 2.11 mmol) in THF (15 mL) was added 60% NaH in mineral oil (127 mg, 3.17 mmol) at 0° C., and it was stirred for 30 min. Then a solution of 2-(2-chloroethoxy)ethyl 4-methylbenzenesulfonate (765 mg, 2.75 mmol) in THF (3.0 mL) was added to the reaction mixture. The reaction was stirred at room temperature for 20 h. The mixture was quenched with water and extracted with ethyl acetate. The combined organic layers were dried over MgSO$_{4(s)}$, filtered, and concentrated. The residue was purified by Isco Combi-Flash Companion column chromatography (0-35% ethyl acetate in n-hexane) to give 2-{[2-(2-chloroethoxy)ethoxy]methyl}pyridine (285 mg, 63%) as a yellow oil. ¹H NMR (CDCl₃, 400 MHz) δ 8.54 (d, 1H), 7.69 (dd, 1H), 7.47 (d, 1H), 7.18 (dd, 1H), 4.69 (s, 2H), 3.79-3.74 (m, 4H), 3.66-3.63 (m, 2H).

Step 3. Synthesis of 2-[2-(pyridin-2-ylmethoxy)ethoxy]ethyl 4-[2-(4-fluorophenyl)-4-oxo-1,3-thiazolidin-3-yl]-3-methylbenzoate Following standard procedure L, 4-[2-(4-fluorophenyl)-4-oxo-1,3-thiazolidin-3-yl]-3-methylbenzoic acid (149 mg, 0.450 mmol), 2-{[2-(2-chloroethoxy)ethoxy]methyl}pyridine (116 mg, 0.540 mmol), K₂CO₃ (93.3 mg, 0.675 mmol), and DMF (1.0 mL) were used to carry out the reaction. After work-up, the residue was purified by Isco Combi-Flash Companion column chromatography (0-80% ethyl acetate in n-hexane) to give 2-[2-(pyridin-2-ylmethoxy)ethoxy]ethyl 4-[2-(4-fluorophenyl)-4-oxo-1,3-thiazolidin-3-yl]-3-methylbenzoate (183 mg, 80%) as a yellow gum. ¹H NMR (CDCl₃, 400 MHz) δ 8.53 (d, 1H), 7.87 (br s, 1H), 7.76 (br s, 1H), 7.64 (dd, 1H), 7.44 (d, 1H), 7.31-7.28 (m, 2H), 7.17 (dd, 1H), 6.95 (br t, 2H), 6.10-5.80 (br, 1H), 4.68 (s, 2H), 4.44 (dd, 2H), 4.00 (d, 1H), 3.91 (d, 1H), 3.81 (dd, 2H), 3.73 (s, 4H), 2.17 (br s, 3H); LC-MS (ESI) m/z 511.2 [M+H]⁺.

EXAMPLE 347

2-[2-(Pyridin-3-ylmethoxy)ethoxy]ethyl 4-[2-(4-fluorophenyl)-4-oxo-1,3-thiazolidin-3-yl]-3-methylbenzoate Compound 456

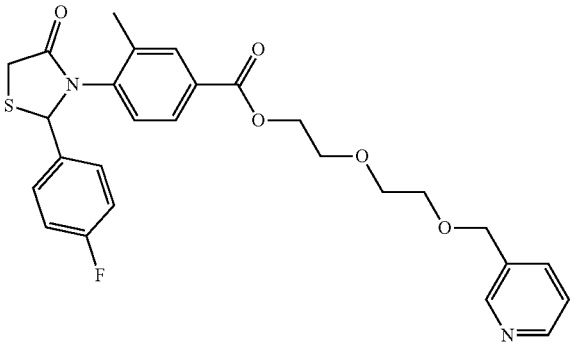

Step 1. Synthesis of 3-{[2-(2-chloroethoxy)ethoxy]methyl}pyridine

Compound 457

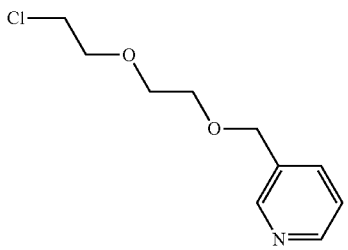

To a solution of 3-(hydroxymethyl)pyridine (231 mg, 2.11 mmol) in THF (15 mL) was added 60% NaH in mineral oil (127 mg, 3.17 mmol) at 0° C., and it was stirred for 30 min. Then a solution of 2-(2-chloroethoxy)ethyl 4-methylbenzenesulfonate (833 mg, 2.99 mmol) in THF (3.0 mL) was added to the reaction mixture. The reaction was stirred at room temperature for 16 h and 60° C. for 8 h. The mixture was quenched with water and extracted with ethyl acetate. The combined organic layers were dried over MgSO$_{4(s)}$, filtered, and concentrated. The residue was purified by Isco Combi-Flash Companion column chromatography (0-80% ethyl acetate in n-hexane) to give 3-{[2-(2-chloroethoxy)ethoxy]methyl}pyridine (129 mg, 26%) as a yellow oil. ¹H NMR (CDCl₃, 400 MHz) δ 8.58 (d, 1H), 8.53 (dd, 1H), 7.70 (dd, 1H), 7.28 (dd, 1H), 4.60 (s, 2H), 3.78-3.62 (m, 8H).

Step 2. Synthesis of 2-[2-(pyridin-3-ylmethoxy)ethoxy]ethyl 4-[2-(4-fluorophenyl)-4-oxo-1,3-thiazolidin-3-yl]-3-methylbenzoate Following standard procedure L, 4-[2-(4-fluorophenyl)-4-oxo-1,3-thiazolidin-3-yl]-3-methylbenzoic acid (165 mg, 0.498 mmol), 3-{[2-(2-chloroethoxy)ethoxy]methyl}pyridine (129 mg, 0.598 mmol), K₂CO₃ (103 mg, 0.747 mmol), and DMF (1.0 mL) were used to carry out the reaction. After work-up, the residue was purified by Isco Combi-Flash Companion column chromatography (0-80% ethyl acetate in n-hexane) to give 2-[2-(pyridin-3-yl-methoxy)ethoxy]ethyl 4-[2-(4-fluorophenyl)-4-oxo-1,3-thiazolidin-3-yl]-3-methylbenzoate (183 mg, 80%) as a yellow gum. $^1$H NMR (CDCl$_3$, 400 MHz) δ 8.56 (d, 1H), 8.53 (dd, 1H), 7.87 (br s, 1H), 7.75 (br s, 1H), 7.67 (d, 1H), 7.32-7.27 (m, 3H), 6.95 (br t, 2H), 6.10-5.80 (br, 1H), 4.57 (s, 2H), 4.43 (dd, 2H), 4.00 (d, 1H), 3.92 (d, 1H), 3.80 (dd, 2H), 3.71-3.64 (m, 4H), 2.18 (br s, 3H); LC-MS (ESI) m/z 511.2 [M+H]$^+$.

EXAMPLE 348

2-[2-(Pyridin-4-ylmethoxy)ethoxy]ethyl 4-[2-(4-fluorophenyl)-4-oxo-1,3-thiazolidin-3-yl]-3-methylbenzoate Compound 458

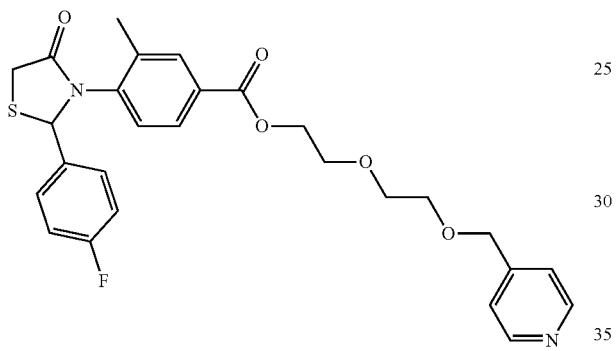

Step 1. Synthesis of 4-{[2-(2-chloroethoxy)ethoxy]methyl}pyridine

Compound 459

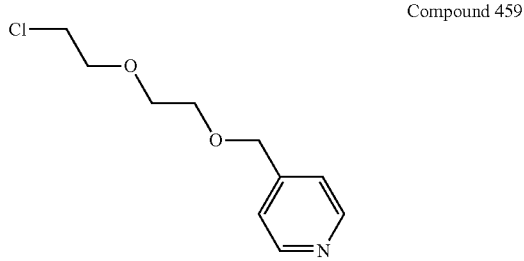 [SMILES: ClCCOCCOCc1ccncc1]

To a solution of 4-(hydroxymethyl)pyridine (251 mg, 2.30 mmol) in THF (15 mL) was added 60% NaH in mineral oil (138 mg, 3.45 mmol) at 0° C., and it was stirred for 30 min. Then a solution of 2-(2-chloroethoxy)ethyl 4-methylbenzenesulfonate (833 mg, 2.99 mmol) in THF (3.0 mL) was added to the reaction mixture. The reaction was stirred at room temperature for 16 h and 60° C. for 8 h. The mixture was quenched with water and extracted with ethyl acetate. The combined organic layers were dried over MgSO$_{4(s)}$, filtered, and concentrated. The residue was purified by Isco Combi-Flash Companion column chromatography (0-70% ethyl acetate in n-hexane) to give 4-{[2-(2-chloroethoxy)ethoxy]methyl}pyridine (202 mg, 41%) as a lightly brown oil. $^1$H NMR (CDCl$_3$, 400 MHz) δ 8.56 (d, 2H), 7.27 (d, 2H), 4.60 (s, 2H), 3.79-3.63 (m, 8H).

Step 2. Synthesis of 2-[2-(pyridin-4-ylmethoxy)ethoxy]ethyl 4-[2-(4-fluorophenyl)-4-oxo-1,3-thiazolidin-3-yl]-3-methylbenzoate Following standard procedure L, 4-[2-(4-fluorophenyl)-4-oxo-1,3-thiazolidin-3-yl]-3-methylbenzoic acid (195 mg, 0.587 mmol), 4-{[2-(2-chloroethoxy)ethoxy]methyl}pyridine (152 mg, 0.705 mmol), K$_2$CO$_3$ (122 mg, 0.881 mmol), and DMF (1.0 mL) were used to carry out the reaction. After work-up, the residue was purified by Isco Combi-Flash Companion column chromatography (0-80% ethyl acetate in n-hexane) to give 2-[2-(pyridin-4-ylmethoxy)ethoxy]ethyl 4-[2-(4-fluorophenyl)-4-oxo-1,3-thiazolidin-3-yl]-3-methylbenzoate (224 mg, 75%) as a lightly yellow gum. $^1$H NMR (CDCl$_3$, 400 MHz) δ 8.54 (d, 2H), 7.87 (br s, 1H), 7.75 (br s, 1H), 7.32-7.28 (m, 2H), 7.24 (d, 2H), 6.94 (br t, 2H), 6.10-5.80 (br, 1H), 4.57 (s, 2H), 4.45 (dd, 2H), 4.00 (d, 1H), 3.92 (d, 1H), 3.81 (dd, 2H), 3.73-3.66 (m, 4H), 2.17 (br s, 3H); LC-MS (ESI) m/z 511.2 [M+H]$^+$.

EXAMPLE 349

2-[2-(2-Methoxyethoxy)ethoxy]ethyl 4-[2-(4-fluorophenyl)-4-oxo-1,3-thiazolidin-3-yl]-3-methylbenzoate Compound 460

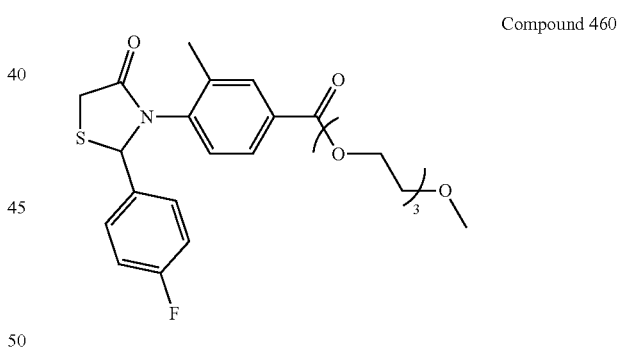

Following standard procedure G, 4-[2-(4-fluorophenyl)-4-oxo-1,3-thiazolidin-3-yl]-3-methylbenzoic acid (168 mg, 0.507 mmol), DMAP (155 mg, 1.27 mmol), EDCI • HCl (175 mg, 0.913 mmol), triethylene glycol monomethyl ether (87.4 mg, 0.532 mmol), and CH$_2$Cl$_2$ (5.0 mL) were used to carry out the reaction. After the reaction was stirred for 16 h and work-up, the residue was purified by Isco Combi-Flash Companion column chromatography (0-60% ethyl acetate in n-hexane) to give 2-[2-(2-methoxyethoxy)ethoxy]ethyl 4-[2-(4-fluorophenyl)-4-oxo-1,3-thiazolidin-3-yl]-3-methylbenzoate (198 mg, 82%) as a lightly yellow gum. $^1$H NMR (CDCl$_3$, 300 MHz) δ 7.87 (br s, 1H), 7.75 (br d, 1H), 7.32-7.27 (m, 2H), 6.95 (br t, 2H), 6.10-5.80 (br, 1H), 4.42 (dd, 2H), 4.01 (d, 1H), 3.91 (d, 1H), 3.79 (dd, 2H), 3.70-3.61 (m, 6H), 3.54-3.50 (m, 2H), 3.37 (s, 3H), 2.19 (br s, 3H); LC-MS (ESI) m/z 500.2 [M+Na]$^+$.

EXAMPLE 350

2-[2-(Morpholin-4-yl)ethoxy]ethyl 4-[2-(4-fluorophenyl)-4-oxo-1,3-thiazolidin-3-yl]-3-methylbenzoate

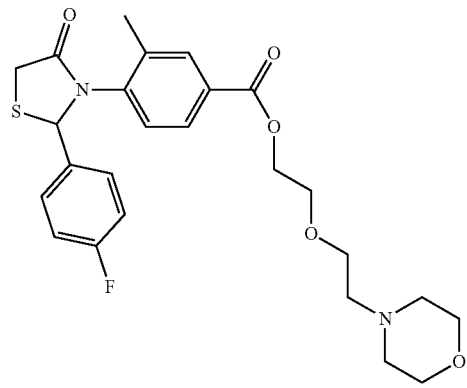

Compound 461

Step 1. Synthesis of 2-[2-(morpholin-4-yl)ethoxy]ethanol

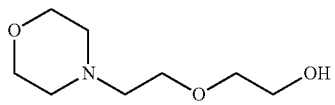

Compound 462

To the solution of morpholine (1.00 mL, 11.5 mmol) in DMF (5.0 mL), 2-(2-chloroethoxy)ethanol (1.10 mL, 10.4 mmol) and K$_2$CO$_3$ (1.59 g, 11.5 mmol) were used to carry out the reaction. After the reaction mixture was stirred at 80° C. for 16 h and work-up, the residue was purified by Isco Combi-Flash Companion column chromatography (50% ethyl acetate in n-hexane) to give 2-(2-morpholinoethoxy) ethanol (0.130 g, 8%); $^1$H NMR (CDCl$_3$, 400 MHz) δ 3.74-3.60 (m, 10H), 2.59-2.57 (m, 3H), 2.55-2.52 (br, 3H).

Step 2. Synthesis of 2-[2-(morpholin-4-yl)ethoxy]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.240 g, 0.740 mmol), 2-[2-(morpholin-4-yl)ethoxy]ethanol (0.130 g, 0.740 mmol), EDCI • HCl (0.280 g, 1.48 mmol), DMAP (0.190 g, 1.59 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 2-[2-(morpholin-4-yl)ethoxy]ethyl 4-[2-(4-fluorophenyl)-4-oxo-1,3-thiazolidin-3-yl]-3-methylbenzoate (0.210 g, 59%). $^1$H NMR (CDCl$_3$, 300 MHz) δ 7.86 (br s, 1H), 7.75 (br d, 1H), 7.33-7.29 (m, 2H), 6.96 (br t, 2H), 4.45-4.39 (m, 2H), 4.01 (d, 1H), 3.91 (d, 1H), 3.75-3.71 (m, 8H), 2.75-2.50 (br, 6H), 2.20 (br s, 3H); LC-MS (ESI) m/z 489.2 [M+H]$^+$.

EXAMPLE 351

5-(Morpholin-4-yl)pentyl 4-[2-(4-fluorophenyl)-4-oxo-1,3-thiazolidin-3-yl]-3-methylbenzoate

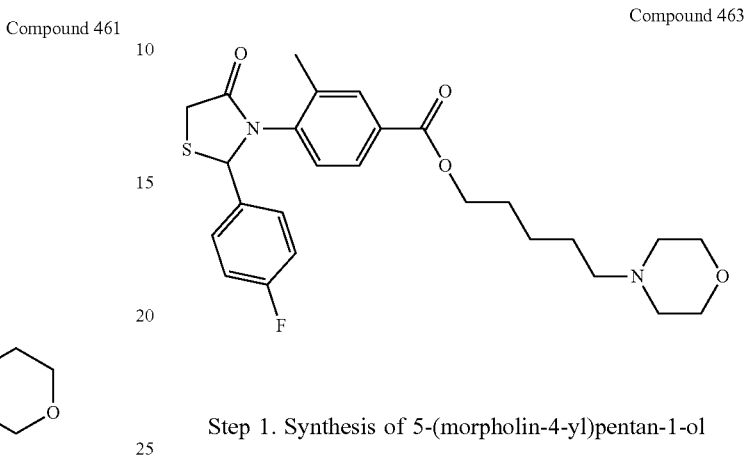

Compound 463

Step 1. Synthesis of 5-(morpholin-4-yl)pentan-1-ol

Compound 464

To the solution of 5-bromopentanol (0.720 mL, 5.99 mmol) in DMF (5.0 mL), morpholine (0.520 mL, 5.99 mmol) and K$_2$CO$_3$ (0.900 g, 6.59 mmol) were used to carry out the reaction. After the reaction mixture was stirred at 80° C. for 16 h and work-up, the residue was used directly for next step without further purification. (0.300 g, crude yield 29%). $^1$H NMR (CDCl$_3$, 300 MHz) δ 3.71-3.66 (m, 4H), 3.63 (br t, 2H), 2.50-2.40 (br, 4H), 2.34 (br t, 2H), 1.61-1.23 (m, 6H).

Step 2. Synthesis of 5-morpholinopentyl 4-(2-(4-fluorophenyl)-4-oxothiazolidin-3-yl)-3-methylbenzoate Following standard procedure G, 4-[2-(4-fluorophenyl)-4-oxo-1,3-thiazolidin-3-yl]-3-methylbenzoic acid (0.180 g, 0.544 mmol), 5-(morpholin-4-yl)pentan-1-ol (0.100 g, 0.598 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 5-(morpholin-4-yl)pentyl 4-[2-(4-fluorophenyl)-4-oxo-1,3-thiazolidin-3-yl]-3-methylbenzoate (0.200 g, 76%). $^1$H NMR (CDCl$_3$, 400 MHz) δ 7.85 (br s, 1H), 7.73 (br s, 1H), 7.33-7.28 (m, 2H), 6.96 (br t, 2H), 4.31-4.25 (m, 2H), 4.03-3.90 (m, 6H), 3.00-2.60 (br, 4H), 2.20 (br s, 3H), 1.81-1.74 (m, 4H), 1.49-1.41 (m, 2H); LC-MS (ESI) m/z 487.2 [M+H]$^+$.

EXAMPLE 352

2-[2-(Acetyloxy)ethoxy]ethyl 4-[2-(4-fluorophenyl)-4-oxo-1,3-thiazolidin-3-yl]-3-methylbenzoate

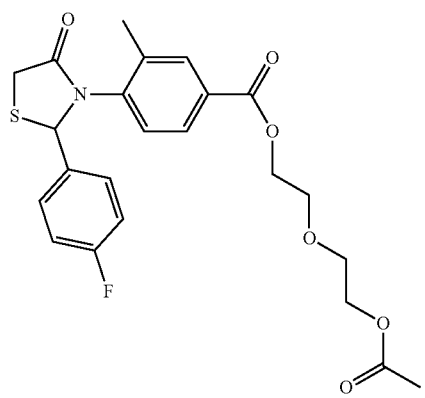

Compound 465

Step 1. Synthesis of 2-(2-chloroethoxy)ethyl acetate

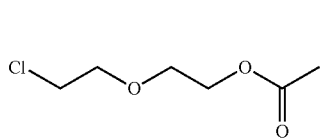

Compound 466

To the solution of 2-(2-chloroethoxy)ethyl acetate (0.510 mL, 4.82 mmol) and acetic anhydride (0.500 mL, 5.29 mmol) were used to carry out the reaction. After the reaction was stirred at room temperature for 16 h and work-up, the residue was used directly for next step without further purification. (0.79 g, crude yield 98%). $^1$H NMR (CDCl$_3$, 300 MHz) δ 4.23 (dd, 2H), 3.77-3.70 (m, 4H), 3.63 (t, 2H), 2.08 (s, 3H).

Step 2. Synthesis of 2-[2-(acetyloxy)ethoxy]ethyl 4-[2-(4-fluorophenyl)-4-oxo-1,3-thiazolidin-3-yl]-3-methylbenzoate Following standard procedure L, 4-[2-(4-fluorophenyl)-4-oxo-1,3-thiazolidin-3-yl]-3-methylbenzoic acid (0.180 g, 0.544 mmol), 2-(2-chloroethoxy)ethyl acetate (90.0 mg, 0.544 mmol) and K$_2$CO$_3$ (83.0 g, 0.598 mmol) and DMF (5.0 mL) were used to carry out the reaction. After the reaction mixture was stirred at 80° C. for 16 h and work-up, the residue was purified by Isco Combi-Flash Companion column chromatography (0-40% ethyl acetate in n-hexane) to give 2-[2-(acetyloxy)ethoxy]ethyl 4-[2-(4-fluorophenyl)-4-oxo-1,3-thiazolidin-3-yl]-3-methylbenzoate (0.220 g, 88%). $^1$H NMR (CDCl$_3$, 400 MHz) δ 7.88 (br s, 1H), 7.76 (br s, 1H), 7.31 (dd, 2H), 6.95 (br t, 2H), 6.10-5.80 (br, 1H), 4.43 (m, 2H), 4.22 (m, 2H), 4.00 (d, 1H), 3.92 (d, 1H), 3.79 (m, 2H), 3.71 (m, 2H), 2.19 (br s, 3H), 2.05 (s, 3H); LC-MS (ESI) m/z 484.6 [M+Na]$^+$.

EXAMPLE 353

2-[2-(Pyrrolidin-2-ylmethoxy)ethoxy]ethyl 4-[2-(4-fluorophenyl)-4-oxo-1,3-thiazolidin-3-yl]-3-methylbenzoate

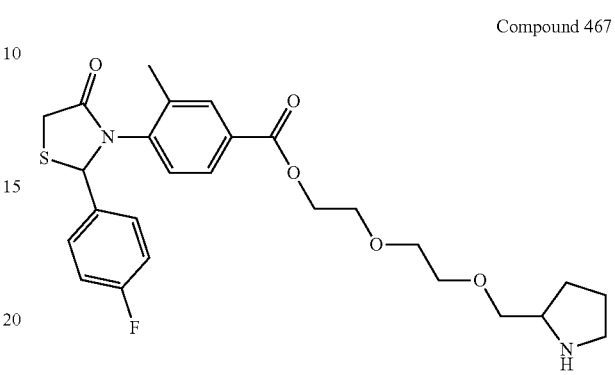

Compound 467

Step 1. Synthesis of tert-butyl 2-(hydroxymethyl)pyrrolidine-1-carboxylate

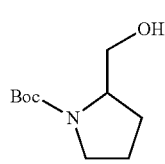

Compound 468

A solution of 2-pyrrolidinemethanol (0.300 g, 1.98 mmol) in CH$_2$Cl$_2$ (5.0 mL) and di-tert-butyl dicarbonate (0.650 g, 1.98 mmol) were used to carry out the reaction. After the reaction was stirred at room temperature for 16 h and work-up, the residue was purified by Isco Combi-Flash Companion column chromatography (0-10% MeOH in CH$_2$Cl$_2$) to give tert-butyl 2-(hydroxymethyl)pyrrolidine-1-carboxylate (0.590 g, 98%). $^1$H NMR (CDCl$_3$, 300 MHz) δ 4.78 (br d, 1H), 4.05-3.90 (br, 1H), 3.67-3.53 (m, 2H), 3.49-3.41 (m, 1H), 3.34-3.26 (m, 1H), 2.00 (dddd, 1H), 1.85-1.72 (m, 2H), 1.60-1.50 (m, 1H), 1.46 (s, 9H).

Step 2. Synthesis of tert-butyl 2-((2-(2-chloroethoxy)ethoxy)methyl)pyrrolidine-1-carboxylate

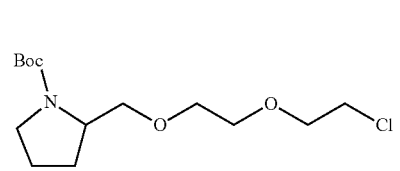

Compound 469

A solution of 2-(2-chloroethoxy)ethyl 4-methylbenzenesulfonate (0.990 g, 3.58 mmol) in DMF (10.0 mL), tert-butyl 2-(hydroxymethyl)pyrrolidine-1-carboxylate (0.600 g, 2.98 mmol) and sodium hydride (0.140 g, 3.58 mmol) were used to carry out the reaction. After the reaction was stirred at 80° C. for 16 h and work-up, the residue was used directly for next step without further purification. (0.240 g, crude yield 26%). ¹H NMR (CDCl₃, 300 MHz) δ 3.80-3.63 (br, 1H), 3.63-3.44 (br, 8H), 3.31 (br s, 4H), 1.98-1.65 (br, 4H), 1.44 (br s, 9H).

Step 3. Synthesis of tert-butyl 2-({2-[2-([4-[2-(4-fluorophenyl)-4-oxo-1,3-thiazolidin-3-yl]-3-methylbenzoyl}oxy)ethoxy]ethoxy]methyl)pyrrolidine-1-carboxylate

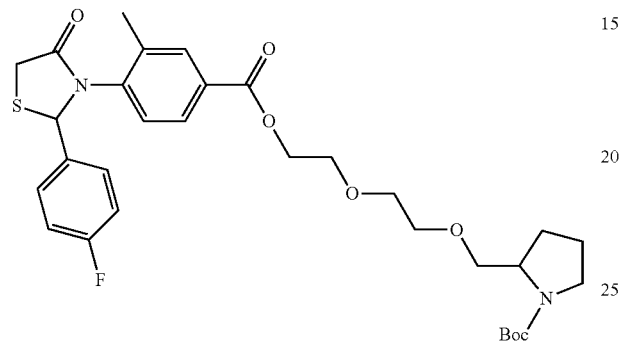

Compound 470

Following standard procedure L, 4-[2-(4-fluorophenyl)-4-oxo-1,3-thiazolidin-3-yl]-3-methylbenzoic acid (0.258 g, 0.780 mmol), tert-butyl 2-((2-(2-chloroethoxy)ethoxy) methyl)pyrrolidine-1-carboxylate (0.240 mg, 0.780 mmol) and K₂CO₃ (0.120 g, 0.857 mmol) were used to carry out the reaction. After the reaction mixture was stirred at 80° C. for 16 h and work-up, the residue was purified by Isco Combi-Flash Companion column chromatography (0-50% ethyl acetate in n-hexane) to give tert-butyl 2-({2-[2-({4-[2-(4-fluorophenyl)-4-oxo-1,3-thiazolidin-3-yl]-3-methylbenzoyl}oxy)ethoxy]ethoxy}methyl)pyrrolidine-1-carboxylate (0.192 g, 41%). ¹H NMR (CDCl₃, 400 MHz) δ 7.87 (br s, 1H), 7.76 (br s, 1H), 7.32-7.28 (m, 2H), 6.97 (br t, 2H), 6.10-5.80 (br, 1H), 4.42 (br t, 2H), 4.02-3.93 (m, 3H), 3.79 (dd, 2H), 3.64-3.55 (m, 5H), 3.37-3.28 (m, 3H), 2.20 (br s, 3H), 1.92-1.74 (m, 4H), 1.45 (s, 9H).

Step 4. Synthesis of 2-[2-(pyrrolidin-2-ylmethoxy) ethoxy]ethyl 4-[2-(4-fluorophenyl)-4-oxo-1,3-thiazolidin-3-yl]-3-methylbenzoate The solution of tert-butyl 2-({2-[2-({4-[2-(4-fluorophenyl)-4-oxo-1,3-thiazolidin-3-yl]-3-methylbenzoyl}oxy)ethoxy]ethoxy}methyl)pyrrolidine-1-carboxylate (0.192 g) and TFA (5.00 mL) in CH₂Cl₂ (10.0 mL) was stirred at room temperature for 3 h. To the reaction mixture was added saturated NaHCO₃₍aq₎ to adjust the pH>8 and extracted with CH₂Cl₂. The organic layers were dried over MgSO₄₍s₎, filtered and concentrated. The residue was purified by Isco Combi-Flash Companion column chromatography (0-10% MeOH in CH₂Cl₂) to give 2-[2-(pyrrolidin-2-ylmethoxy) ethoxy]ethyl 4-[2-(4-fluorophenyl)-4-oxo-1,3-thiazolidin-3-yl]-3-methylbenzoate (76.7 mg, 48%). ¹H NMR (CDCl₃, 300 MHz) δ 7.88 (br s, 1H), 7.76 (br d, 1H), 7.33-7.28 (m, 2H), 6.95 (br t, 2H), 4.44-4.41 (m, 2H), 4.00 (d, 1H), 3.91 (d, 1H), 3.82-3.75 (m, 2H), 3.68-3.60 (m, 4H), 3.52-3.41 (m, 1H), 3.40-3.30 (m, 2H), 3.02-2.87 (m, 2H), 2.19 (br s, 3H), 1.88-1.67 (m, 4H); LC-MS (ESI) m/z 503.2 [M+H]⁺.

EXAMPLE 354

2-[(2-Methoxyethyl)(methyl)amino]ethyl 4-[2-(4-fluorophenyl)-4-oxo-1,3-thiazolidin-3-yl]-3-methylbenzoate

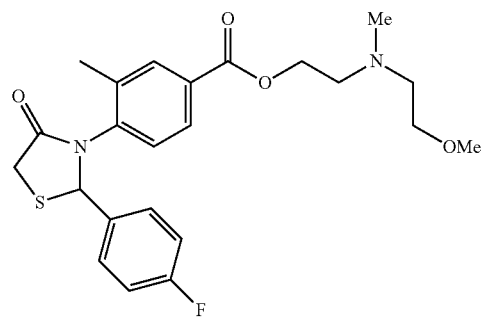

Compound 471

Step 1. Synthesis of ethyl N-(2-methoxyethyl)-N-methylglycinate

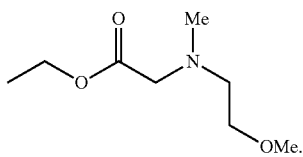

Compound 472

A solution of N-(2-methoxyethyl)methyl amine (0.698 g, 5.81 mmol), triethylamine (1.00 mL, 7.17 mmol), ethyl bromoacetate (0.800 mL, 7.21 mmol) in CH₂Cl₂ (10 mL) was stirred at room temperature for 8 h. The solution was diluted with CH₂Cl₂ and washed with saturated NaHCO₃₍aq₎. The organic layer was dried over MgSO₄₍s₎, filtered, and concentrated to give ethyl N-(2-methoxyethyl)-N-methylglycinate (0.952 g, 92%) as a yellow liquid. ¹H NMR (CDCl₃, 400 MHz) δ 4.17 (q, 2H), 3.49 (t, 2H), 3.35 (s, 2H), 3.34 (s, 3H), 2.77 (t, 2H), 2.44 (s, 3H), 1.26 (t, 3H).

Step 2. Synthesis of 2-[(2-methoxyethyl)(methyl)amino]ethanol

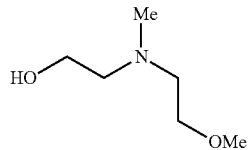

Compound 473

To a solution of ethyl N-(2-methoxyethyl)-N-methylglycinate (0.952 g, 5.91 mmol) in THF (30 mL) was added lithium aluminium hydride (0.355 g, 9.35 mmol) at 0° C. slowly. The solution was stirred at room temperature for 16 h and quenched with saturated Na₂SO₄₍aq₎ and 10% NaOH₍aq₎. The mixture was diluted with diethyl ether and filtered off. The filtrate was dried over over MgSO$_{4(s)}$, filtered, and concentrated to give 2-[(2-methoxyethyl)(methyl)amino]ethanol (657 mg, 93%) as a colorless oil. $^1$H NMR (CDCl$_3$, 400 MHz) δ 3.58 (dd, 2H), 3.47 (t, 2H), 3.35 (s, 3H), 2.63 (t, 2H), 2.57 (dd, 2H), 2.32 (s, 3H).

Step 3. Synthesis of 2-[(2-methoxyethyl)(methyl)amino]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (151 mg, 0.456 mmol), 2-[(2-methoxyethyl)(methyl)amino]ethanol (81.5 mg, 0.684 mmol), EDCI • HCl (131 mg, 0.684 mmol), and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 2-[(2-methoxyethyl)(methyl)amino]ethyl 4-[2-(4-fluorophenyl)-4-oxo-1,3-thiazolidin-3-yl]-3-methylbenzoate (54.8 mg, 27%) as a yellow gum. $^1$H NMR (CDCl$_3$, 400 MHz) δ 7.86 (br s, 1H), 7.74 (br s, 1H), 7.32-7.28 (m, 2H), 6.95 (br t, 2H), 6.10-5.80 (br, 1H), 4.38 (t, 2H), 4.00 (d, 1H), 3.91 (d, 1H), 3.47 (t, 2H), 3.33 (s, 3H), 2.81 (t, 2H), 2.67 (t, 2H), 2.37 (s, 3H), 2.20 (br s, 3H); LC-MS (ESI) m/z 447.3 [M+H]$^+$.

EXAMPLE 355

Octyl 4-[2-(4-fluorophenyl)-4-oxo-1,3-thiazolidin-3-yl]-3-methylbenzoate

Compound 474

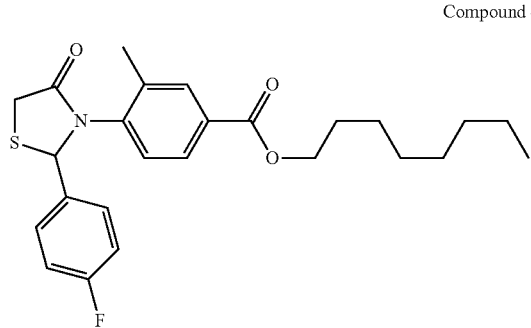

Following standard procedure G, 4-[2-(4-fluorophenyl)-4-oxo-1,3-thiazolidin-3-yl]-3-methylbenzoic acid (152 mg, 0.459 mmol), 1-octanol (65.7 mg, 0.725 mmol), EDCI • HCl (0.158 g, 0.826 mmol), DMAP (0.140 g, 1.15 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-22% ethyl acetate in n-hexane) to give octyl 4-[2-(4-fluorophenyl)-4-oxo-1,3-thiazolidin-3-yl]-3-methylbenzoate (135 mg, 66%) as a yellow gum. $^1$H NMR (CDCl$_3$, 400 MHz) δ 7.86 (br s, 1H), 7.74 (br s, 1H), 7.32-7.29 (m, 2H), 6.95 (br t, 2H), 6.10-5.70 (br s, 1H) 4.25 (t, 2H), 4.01 (d, 1H), 3.92 (d, 1H), 2.20 (br s, 3H), 1.71 (quint, 2H), 1.40-1.20 (m, 10H), 0.87 (t, 3H); LC-MS (ESI) m/z 444.2 [M+H]$^+$.

EXAMPLE 356

2-Ethoxy-2-oxoethyl 4-[2-(4-fluorophenyl)-4-oxo-1,3-thiazolidin-3-yl]-3-methylbenzoate Compound 475

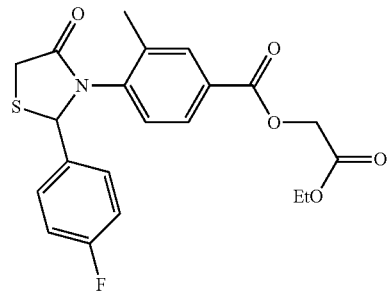

Following standard procedure H, 4-[2-(4-fluorophenyl)-4-oxo-1,3-thiazolidin-3-yl]-3-methylbenzoic acid (173 mg, 0.783 mmol), chloroacetic acid ethyl ester (70.4 mg, 0.574 mmol), K$_2$CO$_3$ (108 mg, 0.881 mmol), and DMF (1.0 mL) were used to carry out the reaction. The solution was quenched with water and extracted with ethyl acetate. The combined organic layers were dried over MgSO$_{4(s)}$, filtered, and concentrated. The residue was purified by Isco Combi-Flash Companion column chromatography (0-35% ethyl acetate in n-hexane) to give 2-ethoxy-2-oxoethyl 4-[2-(4-fluorophenyl)-4-oxo-1,3-thiazolidin-3-yl]-3-methylbenzoate (181 mg, 83%) as a lightly yellow foam. $^1$H NMR (CDCl$_3$, 300 MHz) δ 7.92 (br s, 1H), 7.80 (br d, 1H), 7.33-7.27 (m, 2H), 6.96 (br t, 2H), 5.95 (br s, 1H), 4.79 (s, 2H), 4.23 (q, 2H), 4.00 (d, 1H), 3.92 (d, 1H), 2.20 (br s, 3H), 1.28 (t, 3H); LC-MS (ESI) m/z 440.1 [M+Na]$^+$.

EXAMPLE 357

(2-Methylcyclopropyl)methyl 4-[2-(4-fluorophenyl)-4-oxo-1,3-thiazolidin-3-yl]-3-methylbenzoate Compound 476

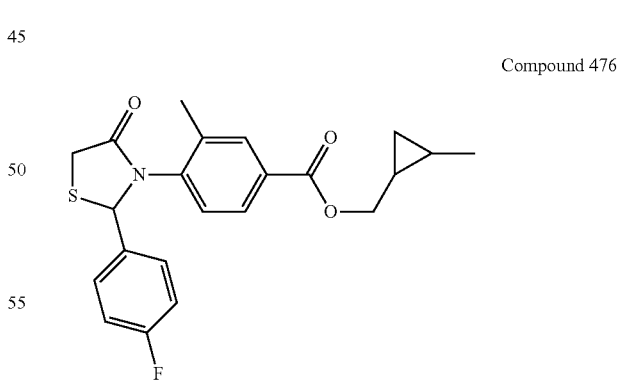

Following standard procedure G, 4-[2-(4-fluorophenyl)-4-oxo-1,3-thiazolidin-3-yl]-3-methylbenzoic acid (0.180 g, 0.544 mmol), 2-methylcyclopropanemethanol (80.0 µL, 0.816 mmol), EDCI • HCl (0.210 g, 1.09 mmol), DMAP (0.210 g, 1.08 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-5% MeOH in CH$_2$Cl$_2$) to give (2-methylcyclopropyl)methyl 4-[2-(4-fluorophenyl)-4-oxo-1,3-thiazolidin-3-yl]-3-methylbenzoate (0.210 g, 97%). $^1$H NMR (CDCl$_3$, 400 MHz) δ 7.88 (br s, 1H), 7.77 (br s, 1H), 7.32 (dd, 2H), 6.95 (br t, 2H), 5.99 (br s, 1H), 4.16-4.06 (m, 2H), 4.01 (d, 1H), 3.92 (d, 1H), 2.20 (br s, 3H), 1.07 (d, 3H), 0.98-0.83 (m, 1H), 0.81-0.71 (m, 1H), 0.50-0.46 (m, 1H), 0.36-0.31 (m, 1H); LC-MS (ESI) m/z 400.2 [M+H]$^+$.

EXAMPLE 358

3,3-Diethoxypropyl 4-[2-(4-fluorophenyl)-4-oxo-1,3-thiazolidin-3-yl]-3-methylbenzoate Compound 477

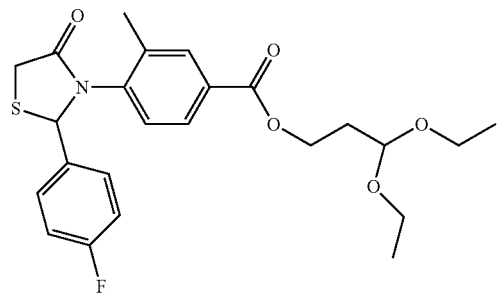

Following standard procedure G, 4-[2-(4-fluorophenyl)-4-oxo-1,3-thiazolidin-3-yl]-3-methylbenzoic acid (0.180 g, 0.544 mmol), 3,3-diethoxy-1-propanol (0.130 mL, 0.816 mmol), EDCI • HCl (0.210 g, 1.09 mm ol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 3,3-diethoxypropyl 4-[2-(4-fluorophenyl)-4-oxo-1,3-thiazolidin-3-yl]-3-methylbenzoate (0.240 g, 96%). $^1$H NMR (CDCl$_3$, 400 MHz) δ 7.84 (br s, 1H), 7.77 (br s, 1H), 7.30 (dd, 2H), 6.95 (br t, 2H), 5.98 (br s, 1H), 4.69-4.64 (m, 1H), 4.35 (t, 2H), 4.00 (d, 1H), 3.91 (d, 1H), 3.71-3.62 (m, 2H), 3.55-3.46 (m, 2H), 2.19 (br s, 3H), 2.04 (q, 2H), 1.24-1.17 (m, 6H).

EXAMPLE 359

(1-Methylpiperidin-4-yl)methyl 4-[2-(4-fluorophenyl)-4-oxo-1,3-thiazolidin-3-yl]-3-methylbenzoate Compound 478

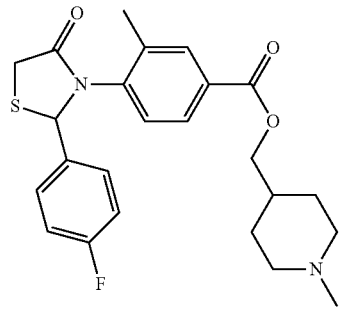

Following standard procedure G, 4-[2-(4-fluorophenyl)-4-oxo-1,3-thiazolidin-3-yl]-3-methylbenzoic acid (0.180 g, 0.544 mmol), (1-methylpiperidin-4-yl)methanol (0.110 mL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give (1-methylpiperidin-4-yl)methyl 4-[2-(4-fluorophenyl)-4-oxo-1,3-thiazolidin-3-yl]-3-methylbenzoate (0.160 g, 67%). $^1$H NMR (CDCl$_3$, 400 MHz) δ 7.87 (br s, 1H), 7.75 (br s, 1H), 7.33-7.29 (m, 2H), 6.96 (br t, 2H), 5.98 (br s, 1H), 4.22-4.17 (m, 2H), 4.00 (d, 1H), 3.91 (d, 1H), 3.37-3.34 (br, 2H), 2.64 (s, 3H), 2.54 (br t, 2H), 2.21 (br s, 3H), 2.04-1.89 (m, 5H); LC-MS (ESI) m/z 443.6 [M+H]$^+$.

EXAMPLE 360

Tetrahydro-2H-pyran-4-yl 4-[2-(4-fluorophenyl)-4-oxo-1,3-thiazolidin-3-yl]-3-methylbenzoate Compound 479

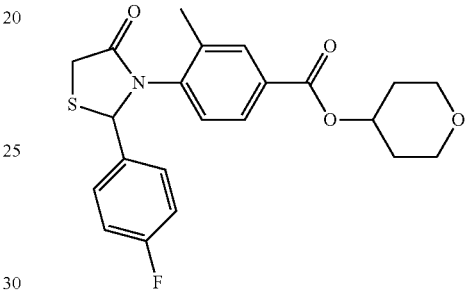

Following standard procedure G, 4-[2-(4-fluorophenyl)-4-oxo-1,3-thiazolidin-3-yl]-3-methylbenzoic acid (0.180 g, 0.544 mmol), tetrahydro-2H-pyran-4-ol (80.0 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give tetrahydro-2H-pyran-4-yl 4-[2-(4-fluorophenyl)-4-oxo-1,3-thiazolidin-3-yl]-3-methylbenzoate (0.200 g, 89%). $^1$H NMR (CDCl$_3$, 400 MHz) δ 7.87 (br s, 1H), 7.78 (br s, 1H), 7.31 (dd, 2H), 6.96 (br t, 2H), 5.96 (br s, 1H), 5.15 (quint, 1H), 4.03-3.90 (m, 4H), 3.59 (td, 2H), 2.20 (br s, 3H), 2.04-1.97 (m, 2H), 1.81-1.73 (m, 2H); LC-MS (ESI) m/z 416.7 [M+H]$^+$.

EXAMPLE 361

3-Methoxybutyl 4-[2-(4-fluorophenyl)-4-oxo-1,3-thiazolidin-3-yl]-3-methylbenzoate Compound 480

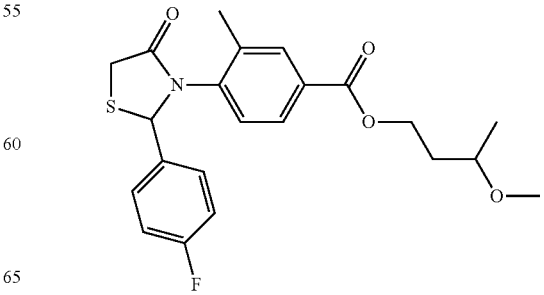

Following standard procedure G, 4-[2-(4-fluorophenyl)-4-oxo-1,3-thiazolidin-3-yl]-3-methylbenzoic acid (0.180 g, 0.544 mmol), 3-methoxy-1-butanol (90.0 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 3-methoxybutyl 4-[2-(4-fluorophenyl)-4-oxo-1,3-thiazolidin-3-yl]-3-methylbenzoate (0.190 g, 84%). $^1$H NMR (CDCl$_3$, 400 MHz) δ 7.85 (br s, 1H), 7.73 (br s, 1H), 7.33-7.28 (m, 2H), 6.96 (br t, 2H), 5.99 (br s, 1H), 4.40-4.33 (m, 2H), 4.00 (d, 1H), 3.92 (d, 1H), 3.46 (quint, 1H), 3.31 (s, 3H), 2.20 (br s, 3H), 1.93-1.81 (m, 2H), 1.18 (d, 3H); LC-MS (ESI) m/z 418.7 [M+H]$^+$.

EXAMPLE 362

(2-Oxo-1,3-dioxolan-4-yl)methyl 4-[2-(4-fluorophenyl)-4-oxo-1,3-thiazolidin-3-yl]-3-methylbenzoate Compound 481

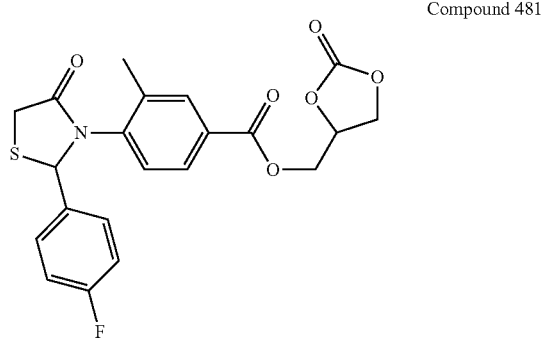 [SMILES: Cc1cc(C(=O)OCC2COC(=O)O2)ccc1N1C(=O)CSC1c1ccc(F)cc1]

Following standard procedure G, 4-[2-(4-fluorophenyl)-4-oxo-1,3-thiazolidin-3-yl]-3-methylbenzoic acid (0.180 g, 0.544 mmol), 4-(hydroxymethyl)-1,3-dioxolan-2-one (70.0 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give (2-oxo-1,3-dioxolan-4-yl)methyl 4-[2-(4-fluorophenyl)-4-oxo-1,3-thiazolidin-3-yl]-3-methylbenzoate (0.220 g, 94%). $^1$H NMR (CDCl$_3$, 400 MHz) δ 7.85 (br s, 1H), 7.73 (br s, 1H), 7.33-7.30 (m, 2H), 6.97 (br t, 2H), 5.03-5.01 (br, 1H), 4.63-4.33 (m, 4H), 4.00 (d, 1H), 3.92 (d, 1H), 2.21 (br s, 3H); LC-MS (ESI) m/z 432.6 [M+H]$^+$.

EXAMPLE 363

1-Ethoxypropan-2-yl 4-[2-(4-fluorophenyl)-4-oxo-1,3-thiazolidin-3-yl]-3-methylbenzoate Compound 482

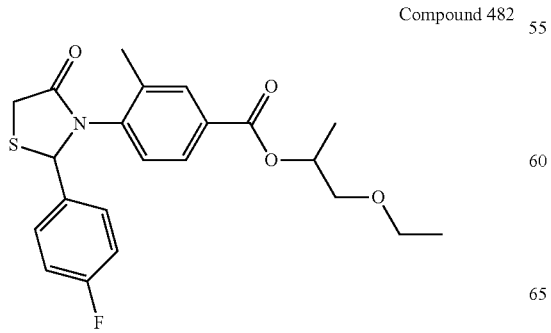

Following standard procedure G, 4-[2-(4-fluorophenyl)-4-oxo-1,3-thiazolidin-3-yl]-3-methylbenzoic acid (0.180 g, 0.544 mmol), 1-ethoxy-2-propanol (95.0 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 1-ethoxypropan-2-yl 4-[2-(4-fluorophenyl)-4-oxo-1,3-thiazolidin-3-yl]-3-methylbenzoate (0.150 g, 66%). $^1$H NMR (CDCl$_3$, 300 MHz) δ 7.86 (br s, 1H), 7.75 (br d, 1H), 7.33-7.28 (m, 2H), 6.96 (br t, 2H), 5.99 (br s, 1H), 5.29-5.23 (m, 1H), 4.00 (d, 1H), 3.91 (d, 1H), 3.61-3.46 (m, 4H), 2.19 (br s, 3H), 1.31 (d, 3H), 1.17 (t, 3H); LC-MS (ESI) m/z 418.1 [M+H]$^+$.

EXAMPLE 364

1-(Morpholin-4-yl)propan-2-yl 4-[2-(4-fluorophenyl)-4-oxo-1,3-thiazolidin-3-yl]-3-methylbenzoate Compound 483

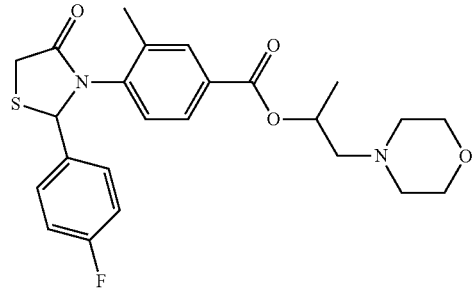

Following standard procedure G, 4-[2-(4-fluorophenyl)-4-oxo-1,3-thiazolidin-3-yl]-3-methylbenzoic acid (0.180 g, 0.544 mmol), 2-(morpholin-4-yl)ethanol (90.0 μL, 0.652 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give 1-(morpholin-4-yl)propan-2-yl 4-[2-(4-fluorophenyl)-4-oxo-1,3-thiazolidin-3-yl]-3-methylbenzoate (0.110 g, 44%). $^1$H NMR (CDCl$_3$, 400 MHz) δ 7.84 (br s, 1H), 7.72 (br s, 1H), 7.31 (dd, 2H), 6.96 (br t, 2H), 6.10-5.80 (br, 1H), 5.31-5.26 (m, 1H), 4.01 (d, 1H), 3.92 (d, 1H), 3.65-3.62 (m, 4H), 2.61 (dd, 1H), 2.56-2.51 (m, 2H), 2.47-2.41 (m, 3H), 2.20 (br s, 3H), 1.31 (d, 3H); LC-MS (ESI) m/z 459.2 [M+H]$^+$.

EXAMPLE 365

2-Phenylpropan-2-yl 4-[2-(4-fluorophenyl)-4-oxo-1,3-thiazolidin-3-yl]-3-methylbenzoate Compound 484

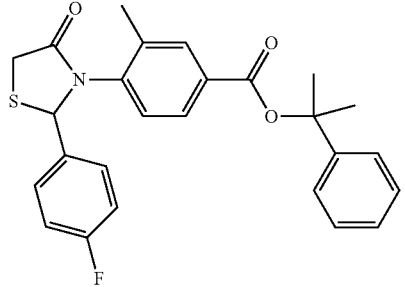

Following standard procedure G, 4-[2-(4-fluorophenyl)-4-oxo-1,3-thiazolidin-3-yl]-3-methylbenzoic acid (0.180 g, 0.544 mmol), α,α-dimethylbenzenemethanol (74.0 mg, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 2-phenylpropan-2-yl 4-[2-(4-fluorophenyl)-4-oxo-1,3-thiazolidin-3-yl]-3-methylbenzoate (56.8 mg, 23%). $^1$H NMR (CDCl$_3$, 400 MHz) δ 7.85 (br s, 1H), 7.74 (br s, 1H), 7.39-7.30 (m, 6H), 7.25-7.22 (m, 2H), 6.97 (br t, 2H), 4.01 (d, 1H), 3.92 (d, 1H), 2.20 (br s, 3H), 1.86 (s, 6H); LC-MS (ESI) m/z 472.1 [M+Na]$^+$.

EXAMPLE 366

4,4-Dimethyl-2-oxotetrahydrofuran-3-yl 4-[2-(4-fluorophenyl)-4-oxo-1,3-thiazolidin-3-yl]-3-methylbenzoate

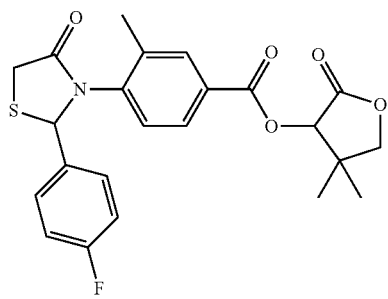

Compound 485

Following standard procedure G, 4-[2-(4-fluorophenyl)-4-oxo-1,3-thiazolidin-3-yl]-3-methylbenzoic acid (0.180 g, 0.544 mmol), 3-hydroxy-4,4-dimethyldihydrofuran-2 (3H)-one (0.140 mL, 1.09 mmol), EDCI • HCl (0.210 g, 1.09 mmol), DMAP (0.160 g, 1.36 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 4,4-dimethyl-2-oxotetrahydrofuran-3-yl 4-[2-(4-fluorophenyl)-4-oxo-1,3-thiazolidin-3-yl]-3-methylbenzoate (0.200 g, 83%). $^1$H NMR (CDCl$_3$, 400 MHz) δ 7.91 (br s, 1H), 7.81 (br s, 1H), 7.33-7.27 (m, 2H), 6.97 (br t, 2H), 5.96 (br s, 1H), 5.56 (s, 1H), 4.15-4.06 (m, 2H), 4.01 (d, 1H), 3.92 (d, 1H), 2.22 (br s, 3H), 1.25 (s, 3H), 1.18 (s, 3H); LC-MS (ESI) m/z 444.2 [M+H]$^+$.

EXAMPLE 367

Benzyl 4-[2-(4-fluorophenyl)-4-oxo-1,3-thiazolidin-3-yl]-3-methylbenzoate

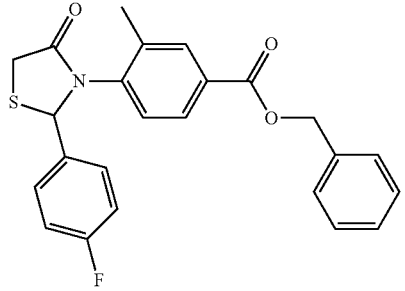

Compound 486

Following standard procedure G, 4-[2-(4-fluorophenyl)-4-oxo-1,3-thiazolidin-3-yl]-3-methylbenzoic acid (0.180 g, 0.544 mmol), benzyl alcohol (56.0 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give benzyl 4-[2-(4-fluorophenyl)-4-oxo-1,3-thiazolidin-3-yl]-3-methylbenzoate (0.200 g, 91%). $^1$H NMR (CDCl$_3$, 400 MHz) δ 7.89 (br s, 1H), 7.77 (br s, 1H), 7.42-7.27 (m, 8H), 6.95 (br t, 2H), 5.31 (s, 2H), 4.00 (d, 1H), 3.91 (d, 1H), 2.19 (br s, 3H); LC-MS (ESI) m/z 422.2 [M+H]$^+$.

EXAMPLE 368

2-Methoxyethyl 4-[2-(4-fluorophenyl)-4-oxo-1,3-thiazolidin-3-yl]-3-methylbenzoate

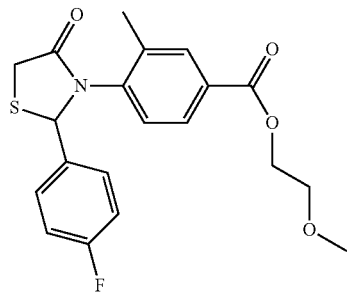

Compound 487

Following standard procedure G, 4-[2-(4-fluorophenyl)-4-oxo-1,3-thiazolidin-3-yl]-3-methylbenzoic acid (0.180 g, 0.544 mmol), 2-methoxyethanol (42.8 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-methoxyethyl 4-[2-(4-fluorophenyl)-4-oxo-1,3-thiazolidin-3-yl]-3-methylbenzoate (0.190 g, 90%). $^1$H NMR (CDCl$_3$, 300 MHz) δ

7.88 (br s, 1H), 7.77 (br d, 1H), 7.30 (dd, 2H), 6.95 (br t, 2H), 6.10-5.80 (br, 1H), 4.42 (dd, 2H), 4.00 (d, 1H), 3.91 (d, 1H), 3.69-3.65 (m, 2H), 3.40 (s, 3H), 2.19 (br s, 3H); LC-MS (ESI) m/z 412.1 [M+Na]$^+$.

EXAMPLE 369

2,3-Dihydroxypropyl 4-[2-(4-fluorophenyl)-4-oxo-1,3-thiazolidin-3-yl]-3-methylbenzoate Compound 488

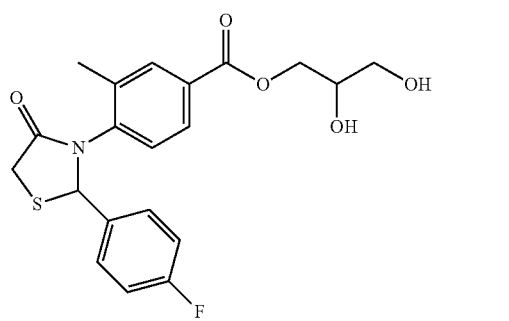

Following standard procedure G, 4-[2-(4-fluorophenyl)-4-oxo-1,3-thiazolidin-3-yl]-3-methylbenzoic acid (188 mg, 0.567 mmol), 2,2-dimethyl-1,3-dioxolane-4-methanol (82.5 mg, 0.624 mmol), EDCI • HCl (163 mg, 0.851 mmol), DMAP (139 mg, 1.13 mmol) and CH$_2$Cl$_2$ (5.0 mL) were used to carry out the reaction. After the reaction mixture was stirred at room temperature for 16 h and work-up, the residue was purified by column chromatography (80% ethyl acetate in n-hexane) to give 2,3-dihydroxypropyl 4-[2-(4-fluorophenyl)-4-oxo-1,3-thiazolidin-3-yl]-3-methylbenzoate (124 mg, 54%) as a yellow gum. $^1$H NMR (CDCl$_3$, 300 MHz) δ 7.86 (br s, 1H), 7.74 (br d, 1H), 7.33-7.27 (m, 2H), 6.96 (t, 2H), 6.10-5.85 (br, 1H), 4.51-4.38 (m, 4H), 4.36-4.26 (m, 1H), 4.01 (d, 1H), 3.92 (d, 1H), 2.20 (br s, 3H); LC-MS (ESI) m/z 406.1 [M+H]$^+$.

EXAMPLE 370

Oxetan-3-yl 4-[2-(4-fluorophenyl)-4-oxo-1,3-thiazolidin-3-yl]-3-methylbenzoate

Compound 489

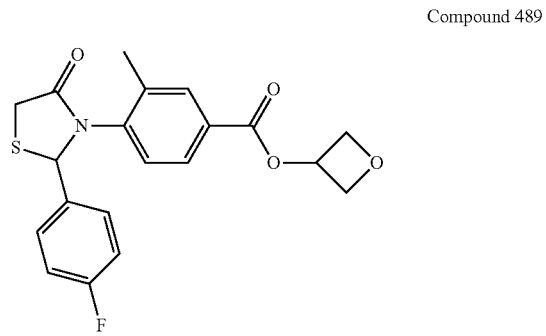 [SMILES: Cc1cc(C(=O)OC2COC2)ccc1N1C(=O)CSC1c1ccc(F)cc1]

Following standard procedure G, 4-[2-(4-fluorophenyl)-4-oxo-1,3-thiazolidin-3-yl]-3-methylbenzoic acid (0.180 g, 0.544 mmol), 3-oxetanol (34.0 µL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give oxetan-3-yl 4-[2-(4-fluorophenyl)-4-oxo-1,3-thiazolidin-3-yl]-3-methylbenzoate (0.190 g, 90%). $^1$H NMR (CDCl$_3$, 400 MHz) δ 7.89 (br s, 1H), 7.77 (br s, 1H), 7.34-7.29 (m, 2H), 6.96 (br t, 2H), 5.97 (br s, 1H), 5.61 (quint, 1H), 4.97 (dd, 2H), 4.73 (dd, 2H), 4.01 (d, 1H), 3.93 (d, 1H), 2.20 (br s, 3H); LC-MS (ESI) m/z 388.6 [M+H]$^+$.

EXAMPLE 371

(3-Methyloxetan-3-yl)methyl 4-[2-(4-fluorophenyl)-4-oxo-1,3-thiazolidin-3-yl]-3-methylbenzoate Compound 490

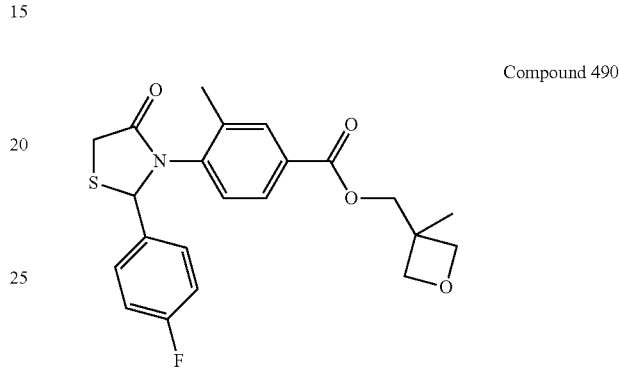

Following standard procedure G, 4-[2-(4-fluorophenyl)-4-oxo-1,3-thiazolidin-3-yl]-3-methylbenzoic acid (0.180 g, 0.544 mmol), 3-methyl-3-oxetanemethanol (54.0 µL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give (3-methyloxetan-3-yl)methyl 4-[2-(4-fluorophenyl)-4-oxo-1,3-thiazolidin-3-yl]-3-methylbenzoate (0.210 g, 98%). $^1$H NMR (CDCl$_3$, 300 MHz) δ 7.87 (br s, 1H), 7.75 (br s, 1H), 7.33-7.29 (m, 2H), 6.96 (br t, 2H), 5.94 (br s, 1H), 4.59 (d, 2H), 4.43 (d, 2H), 4.34 (s, 2H), 4.01 (d, 1H), 3.92 (d, 1H), 2.21 (br s, 3H), 1.39 (s, 3H); LC-MS (APCI) m/z 416.7 [M+H]$^+$.

EXAMPLE 372

3-Hydroxy-2-(hydroxymethyl)-2-methylpropyl 4-[2-(4-fluorophenyl)-4-oxo-1,3-thiazolidin-3-yl]-3-methylbenzoate Compound 491

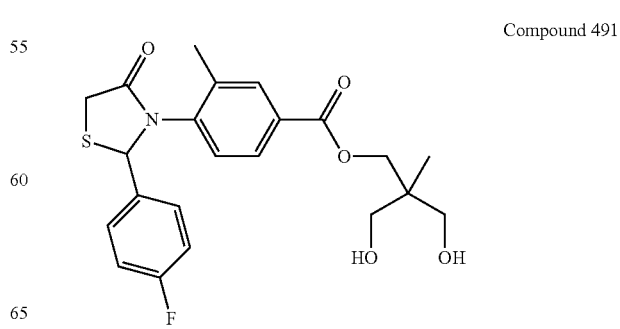

To the solution of (3-methyloxetan-3-yl)methyl 4-[2-(4-fluorophenyl)-4-oxo-1,3-thiazolidin-3-yl]-3-methylbenzoate (50.0 mg, 0.120 mmol) in CH$_2$Cl$_2$ (5.0 mL) and boron trifluoride diethyl etherate were used to carry out the reaction. After the reaction mixture was stirred at 0° C.--10° C. for 3 h and work-up, trimethylamine (4.50 μL) was added and then work-up. The residue was extracted with ethyl acetate, dried over MgSO$_{4(s)}$, filtered and concentrated to yield 3-hydroxy-2-(hydroxymethyl)-2-methylpropyl 4-[2-(4-fluorophenyl)-4-oxo-1,3-thiazolidin-3-yl]-3-methylbenzoate as a white solid. (16.0 mg, 31%). $^1$H NMR (CDCl$_3$, 400 MHz) δ 7.86 (br s, 1H), 7.75 (br s, 1H), 7.32 (dd, 2H), 6.96 (br t, 2H), 6.10-5.80 (br, 1H), 4.41 (d, 1H), 4.36 (d, 1H), 4.00 (d, 1H), 3.92 (d, 1H), 3.61 (d, 2H), 3.55 (d, 2H), 2.21 (br s, 3H), 0.86 (s, 3H); LC-MS (ESI) m/z 434.2 [M+H]$^+$.

EXAMPLE 373

Cyclobutyl 4-[2-(4-fluorophenyl)-4-oxo-1,3-thiazolidin-3-yl]-3-methylbenzoate

Compound 492

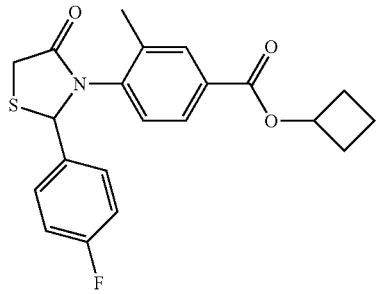

Following standard procedure G, 4-[2-(4-fluorophenyl)-4-oxo-1,3-thiazolidin-3-yl]-3-methylbenzoic acid (0.180 g, 0.544 mmol), cyclobutanol (43.0 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give cyclobutyl 4-[2-(4-fluorophenyl)-4-oxo-1,3-thiazolidin-3-yl]-3-methylbenzoate (0.180 g, 86%). $^1$H NMR (CDCl$_3$, 400 MHz) δ 7.85 (br s, 1H), 7.74 (br s, 1H), 7.30 (dd, 2H), 6.96 (br t, 2H), 5.94 (br s, 1H), 5.16 (quint, 1H), 4.01 (d, 1H), 3.93 (d, 1H), 2.45-2.38 (m, 3H), 2.38-2.10 (m, 4H), 1.87-1.80 (m, 1H), 1.73-1.61 (m, 1H); LC-MS (ESI) m/z 386.2 [M+H]$^+$.

EXAMPLE 374 tert-Butyl 4-({4-[2-(4-fluorophenyl)-4-oxo-1,3-thiazolidin-3-yl]-3-methylbenzoyl}oxy)piperidine-1-carboxylate Compound 493

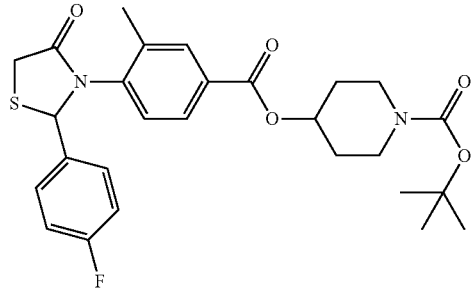

Following standard procedure G, 4-[2-(4-fluorophenyl)-4-oxo-1,3-thiazolidin-3-yl]-3-methylbenzoic acid (0.200 g, 0.604 mmol), 1-Boc-4-hydroxypiperidine (0.120 g, 0.604 mmol), EDCI • HCl (0.230 g, 1.33 mmol), DMAP (0.160 g, 1.33 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give tert-butyl 4-({4-[2-(4-fluorophenyl)-4-oxo-1,3-thiazolidin-3-yl]-3-methylbenzoyl}oxy)piperidine-1-carboxylate (0.290 g, 93%). $^1$H NMR (CDCl$_3$, 400 MHz) δ 7.85 (br s, 1H), 7.75 (br s, 1H), 7.31 (dd, 2H), 6.96 (br t, 2H), 5.16-5.10 (m, 1H), 4.01 (d, 1H), 3.92 (d, 1H), 3.78-3.72 (br, 2H), 3.34-3.28 (m, 2H), 2.22 (br s, 3H), 1.94-1.89 (m, 2H), 1.73-1.62 (m, 2H), 1.46 (s, 9H); LC-MS (ESI) m/z 537.3 [M+Na]$^+$.

EXAMPLE 375

Piperidin-4-yl 4-[2-(4-fluorophenyl)-4-oxo-1,3-thiazolidin-3-yl]-3-methylbenzoate Compound 494

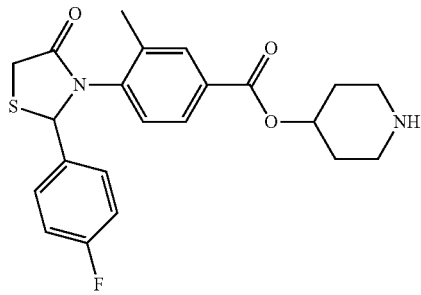

The solution of tert-butyl 4-({4-[2-(4-fluorophenyl)-4-oxo-1,3-thiazolidin-3-yl]-3-methylbenzoyl}oxy)piperidine-1-carboxylate (0.230 g) and TFA (5.00 mL) in CH$_2$Cl$_2$ (10.0 mL) was stirred at room temperature for 3 h. To the reaction mixture was added saturated NaHCO$_{3(aq)}$ to adjust the pH>8 and extracted with CH$_2$Cl$_2$. The organic layers were dried over MgSO$_{4(s)}$, filtered and concentrated to give pure piperidin-4-yl 4-[2-(4-fluorophenyl)-4-oxo-1,3-thiazolidin-3-yl]-3-methylbenzoate (0.170 g, 92%). $^1$H NMR (CDCl$_3$, 400 MHz) δ 7.86 (br s, 1H), 7.75 (br s, 1H), 7.32 (dd, 2H), 6.97 (br t, 2H), 5.96 (br s, 1H), 5.18-5.14 (m, 1H), 4.01 (d, 1H), 3.92 (d, 1H), 3.22-3.19 (m, 2H), 3.01-2.97 (m, 2H), 2.22 (br s, 3H), 2.17-2.07 (m, 2H), 1.89-1.85 (m, 2H); LC-MS (ESI) m/z 415.2 [M+H]$^+$.

EXAMPLE 376

2-(4,4-Difluoropiperidin-1-yl)ethyl 4-[2-(4-fluorophenyl)-4-oxo-1,3-thiazolidin-3-yl]-3-methylbenzoate

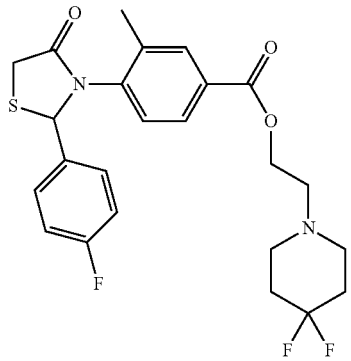

Compound 495

Step 1. Synthesis of 2-(4,4-difluoropiperidin-1-yl)ethanol

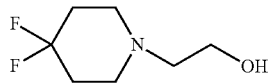

Compound 496

To the solution of 2-chloroethanol (0.190 mL, 2.86 mmol) in acetonitrile (5.0 mL), 4,4-difluoropiperidine (0.300 g, 1.90 mmol) and $K_2CO_3$ (0.290 g, 2.09 mmol) were used to carry out the reaction. After the reaction mixture was stirred at 80° C. for 16 h and work-up, the residue was used directly for next step without further purification. (59.0 mg, crude yield 19%). $^1$H NMR (CDCl$_3$, 400 MHz) δ 3.70 (dd, 2H), 2.77-2.75 (m, 4H), 2.73-2.68 (m, 2H), 2.15-2.06 (m, 4H).

Step 2. Synthesis of 2-(4,4-difluoropiperidin-1-yl)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.110 g, 0.357 mmol), 2-(4,4-difluoropiperidin-1-yl)ethanol (59.0 mg, 0.357 mmol), EDCI•HCl (0.130 g, 0.660 mmol), DMAP (89.3 mg, 0.730 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-90% ethyl acetate in n-hexane) to give trace 2-(4,4-difluoropiperidin-1-yl)ethyl 4-[2-(4-fluorophenyl)-4-oxo-1,3-thiazolidin-3-yl]-3-methylbenzoate.
$^1$H NMR (CDCl$_3$, 400 MHz) δ 7.85 (br s, 1H), 7.73 (br s, 1H), 7.31 (dd, 2H), 6.96 (br t, 2H), 6.05-5.83 (br, 1H), 4.43-4.37 (m, 2H), 4.00 (d, 1H), 3.91 (d, 1H), 2.77 (t, 2H), 2.65-2.62 (m, 4H), 2.21 (br s, 3H), 2.02-1.92 (m, 4H); LC-MS (ESI) m/z 479.6 [M+H]$^+$.

EXAMPLE 377

2-(3,3-Difluoropyrrolidin-1-yl)ethyl 4-[2-(4-fluorophenyl)-4-oxo-1,3-thiazolidin-3-yl]-3-methylbenzoate

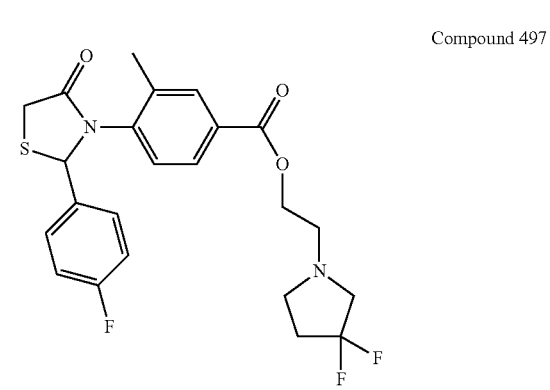 [SMILES: Cc1cc(C(=O)OCCN2CCC(F)(F)C2)ccc1N1C(=O)CSC1c1ccc(F)cc1]

Compound 497

Step 1. Synthesis of 2-(3,3-difluoropyrrolidin-1-yl)ethanol

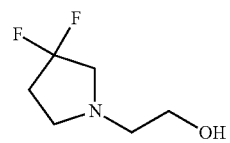

Compound 498

To the solution of 2-chloroethanol (0.420 mL, 6.27 mmol) in DMF (5 mL), 3,3-difluoropyrrolidine (0.300 g, 2.09 mmol) and $K_2CO_3$ (0.320 g, 2.30 mmol) were used to carry out the reaction. After the reaction mixture was stirred at 80° C. for 16 h and work-up, the residue was used directly for next step without further purification. (0.220 g, crude yield 70%). $^1$H NMR (CDCl$_3$, 400 MHz) δ 3.83-3.60 (m, 4H), 3.24-3.14 (m, 1H), 3.10-3.00 (m, 1H), 2.90-2.80 (m, 1H), 2.50-2.30 (m, 3H).

Step 2. Synthesis of 2-(3,3-difluoropyrrolidin-1-yl)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 2-(3,3-difluoropyrrolidin-1-yl)ethanol (98.6 mg, 0.652 mmol), EDCI•HCl (0.210 g, 1.09 mmol), DMAP (0.150 g, 1.20 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(3,3-difluoropyrrolidin-1-yl)ethyl 4-[2-(4-fluorophenyl)-4-oxo-1,3-thiazolidin-3-yl]-3-methylbenzoate (73.6 mg, 29%). $^1$H NMR (CDCl$_3$, 400 MHz) δ 7.84 (br s, 1H), 7.73 (br s, 1H), 7.33-7.29 (m, 2H), 6.95 (br t, 2H), 6.10-5.80 (br, 1H), 4.41-4.37 (m, 2H), 4.00 (d, 1H), 3.96 (d, 1H), 3.02 (t, 2H), 2.87-2.83 (m, 4H), 2.32-2.19 (m, 5H); LC-MS (ESI) m/z 465.1 [M+H]$^+$.

EXAMPLE 378 tert-Butyl 3-({4-[2-(4-fluorophenyl)-4-oxo-1, 3-thiazolidin-3-yl]-3-methylbenzoyl}oxy)azetidine-1-carboxylate Compound 499

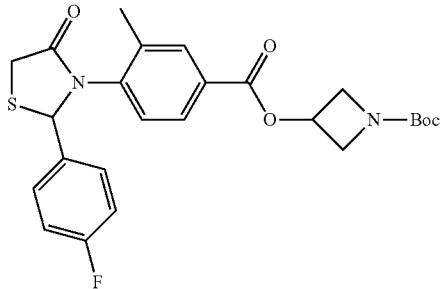

Following standard procedure G, 4-[2-(4-fluorophenyl)-4-oxo-1,3-thiazolidin-3-yl]-3-methylbenzoic acid (0.180 g, 0.544 mmol), tert-butyl 3-hydroxyazetidine-1-carboxylate (94.1 mg, 0.544 mmol), EDCI • HCl (0.210 g, 1.09 mmol), DMAP (0.150 g, 1.20 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give tert-butyl 3-({4-[2-(4-fluorophenyl)-4-oxo-1,3-thiazolidin-3-yl]-3-methylbenzoyl}oxy)azetidine-1-carboxylate (0.240 g, 91%). $^1$H NMR (CDCl$_3$, 300 MHz) δ 7.87 (br s, 1H), 7.75 (br d, 1H), 7.30 (dd, 2H), 6.96 (br t, 2H), 6.05-5.93 (br, 1H), 5.34-5.27 (m, 1H), 4.34-4.28 (m, 2H), 4.04-3.89 (m, 4H), 2.21 (br s, 3H), 1.44 (s, 9H); LC-MS (ESI) m/z 509.2 [M+Na]$^+$.

EXAMPLE 379

Azetidin-3-yl 4-[2-(4-fluorophenyl)-4-oxo-1,3-thiazolidin-3-yl]-3-methylbenzoate Compound 500

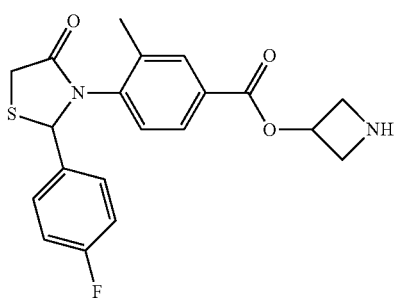

The solution of tert-butyl 3-({4-[2-(4-fluorophenyl)-4-oxo-1,3-thiazolidin-3-yl]-3-methylbenzoyl}oxy)azetidine-1-carboxylate (0.310 g) and TFA (5.0 mL) in CH$_2$Cl$_2$ (10.0 mL) was stirred at room temperature for 3 h. To the reaction mixture was added saturated NaHCO$_{3(aq)}$ to adjust the pH>8 and extracted with CH$_2$Cl$_2$. The organic layers were dried over MgSO$_{4(s)}$, filtered and concentrated to give pure azetidin-3-yl 4-[2-(4-fluorophenyl)-4-oxo-1,3-thiazolidin-3-yl]-3-methylbenzoate (0.220 g, 89%). $^1$H NMR (CDCl$_3$, 400 MHz) δ 7.88 (br s, 1H), 7.77 (br s, 1H), 7.33-7.29 (m, 2H), 6.96 (br t, 2H), 5.47-5.42 (m, 1H), 4.03-3.90 (m, 4H), 3.79-3.75 (m, 2H), 2.18 (br s, 3H); LC-MS (ESI) m/z 387.2 [M+H]$^+$.

EXAMPLE 380

1-Methylazetidin-3-yl 4-[2-(4-fluorophenyl)-4-oxo-1,3-thiazolidin-3-yl]-3-methylbenzoate Compound 501

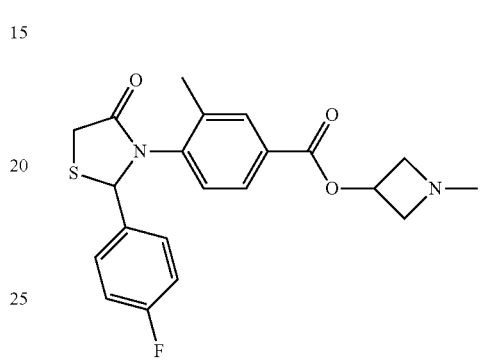

Step 1. Synthesis of 1-methylazetidin-3-ol

Compound 502

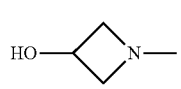

To a solution of methylamine (0.700 mL, 0.0160 mmol) in MeOH (5.0 mL), 2-(chloromethyl)oxirane (1.26 mL, 0.0160 mmol) was added. The reaction mixture was stirred at room temperature for 16 h. After removed the solvent, the residue was used directly for next step without further purification. $^1$H NMR (CDCl$_3$, 400 MHz) δ 3.96-3.91 (m, 1H), 3.63-3.53 (m, 2H), 2.61-2.54 (m, 2H), 2.39 (s, 3H).

Step 2. Synthesis of 1-methylazetidin-3-yl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.120 g, 0.362 mmol), 1-methylazetidin-3-ol (34.7 mg, 0.398 mmol), EDCI • HCl (0.140 g, 0.604 mmol), DMAP (97.3 mg, 0.797 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, CH$_2$Cl$_2$:ethyl acetate:n-hexane=1:1:2) to give 1-methylazetidin-3-yl 4-[2-(4-fluorophenyl)-4-oxo-1,3-thiazolidin-3-yl]-3-methylbenzoate (57.7 g, 40%). $^1$H NMR (CDCl$_3$, 400 MHz) δ 7.87 (br s. 1H), 7.75 (br s, 1H), 7.33-7.29 (m, 2H), 6.96 (br t, 2H), 5.95 (br s, 1H), 5.31 (s, 1H), 4.01 (d, 1H), 3.92 (d, 1H), 3.80-3.70 (m, 2H), 2.87-2.71 (m, 2H), 2.36 (s, 3H), 2.21 (br s, 3H); LC-MS (ESI) m/z 423.1 [M+Na]$^+$.

EXAMPLE 381

3-({4-[2-(4-Fluorophenyl)-4-oxo-1,3-thiazolidin-3-yl]-3-methylbenzoyl}oxy)-1,1-dimethylazetidinium Compound 503

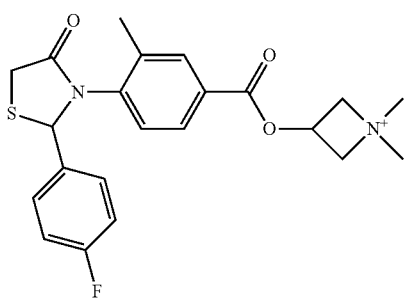

To the solution of azetidin-3-yl 4-[2-(4-fluorophenyl)-4-oxo-1,3-thiazolidin-3-yl]-3-methylbenzoate (80.0 mg, 0.207 mmol) in CH$_2$Cl$_2$ (5.0 mL), iodomethane (14.0 μL, 0.228 mmol) and N,N-diisopropylethylamine (38.0 μL, 0.228 mmol) were used to carry out the reaction. After the reaction mixture was stirred at room temperature for 4 h and work-up, the residue was had no further purification to give 3-({4-[2-(4-fluorophenyl)-4-oxo-1,3-thiazolidin-3-yl]-3-methylbenzoyl}oxy)-1,1-dimethylazetidinium (8.20 mg, 10%). $^1$H NMR (CDCl$_3$, 400 MHz) δ 7.88 (br s, 1H), 7.76 (br s, 1H), 7.35-7.29 (m, 2H), 6.97-6.93 (m, 2H), 5.68-5.63 (m, 1H), 5.18-5.14 (m, 2H), 4.63-4.58 (m, 2H), 4.02-3.89 (m, 2H), 3.58-3.56 (m, 6H), 2.20 (br s, 3H). LC-MS (ESI) m/z 416.1 [M+H]$^+$.

EXAMPLE 382

1-tert-Butylazetidin-3-yl 4-[2-(4-fluorophenyl)-4-oxo-1,3-thiazolidin-3-yl]-3-methylbenzoate Compound 504

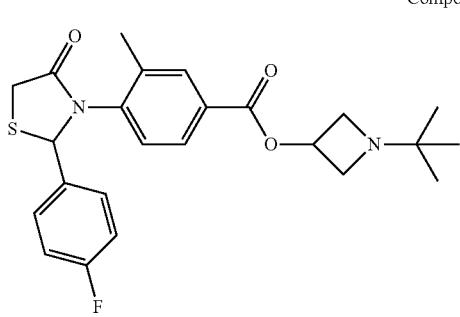

Following standard procedure G, 4-[2-(4-fluorophenyl)-4-oxo-1,3-thiazolidin-3-yl]-3-methylbenzoic acid (0.180 g, 0.544 mmol), 1-tert-butylazetidin-3-ol (77.2 mg, 0.598 mmol), EDCI • HCl (0.210 g, 1.09 mmol), DMAP (0.150 g, 1.20 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 1-tert-butylazetidin-3-yl 4-[2-(4-fluorophenyl)-4-oxo-1,3-thiazolidin-3-yl]-3-methylbenzoate (0.220 g, 92%). $^1$H NMR (CDCl$_3$, 400 MHz) δ 7.85 (br s, 1H), 7.74 (br d, 1H), 7.31-7.27 (m, 2H), 6.96 (br t, 2H), 5.30-5.28 (m, 1H), 4.02-3.86 (m, 4H), 3.54 (br s, 2H), 2.20 (br s, 3H), 1.15 (s, 9H); LC-MS (ESI) m/z 443.7 [M+H]$^+$.

EXAMPLE 383

1-(Oxetan-3-yl)azetidin-3-yl 4-[2-(4-fluorophenyl)-4-oxo-1,3-thiazolidin-3-yl]-3-methylbenzoate Compound 505

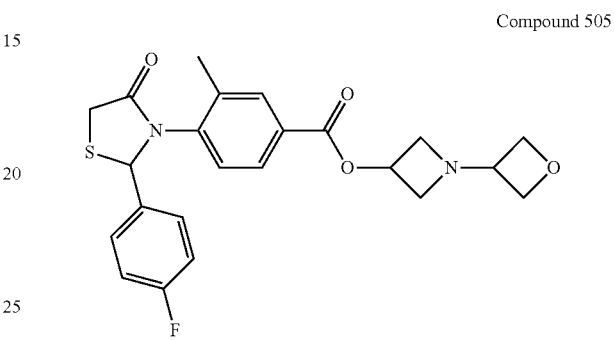

Step 1. Synthesis of 1-(oxetan-3-yl)azetidin-3-ol

Compound 506

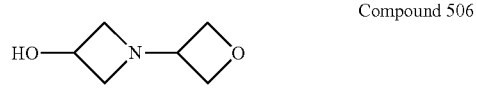

A mixture of azetidin-3-ol hydrochloride salt (0.200 g, 1.83 mmol), 3-oxetanone (71.0 μL, 1.22 mmol) and 4A molecular sieves (0.600 g) in CH$_2$Cl$_2$ (10.0 mL) was stirred at room temperature for 4 h. To the above reaction, NaBH(OAc)$_3$ (0.520 g, 2.43 mmol) was added. After the reaction mixture was stirred at room temperature for 16 h, the precipitate was filtered through a pad of celite and the filtrate was diluted with ethyl acetate and filtered again. The residue was used directly for next step without further purification (0.115 g, crude yield 49%). $^1$H NMR (CDCl$_3$, 400 MHz) δ 4.76-4.69 (m, 2H), 4.52-4.46 (m, 3H), 3.81 (quint, 1H), 3.66 (dd, 2H), 3.17 (dd, 2H).

Step 2. Synthesis of 1-(oxetan-3-yl)azetidin-3-yl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.260 g, 0.809 mmol), 1-(oxetan-3-yl)azetidin-3-ol (0.115 g, 0.891 mmol), EDCI • HCl (0.300 g, 1.57 mmol), DMAP (0.210 g, 1.73 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 10% MeOH in CH$_2$Cl$_2$) to give 1-(oxetan-3-yl)azetidin-3-yl 4-[2-(4-fluorophenyl)-4-oxo-1,3-thiazolidin-3-yl]-3-methylbenzoate (0.160 g, 46%). $^1$H NMR (CDCl$_3$, 400 MHz) δ 7.87 (br s, 1H), 7.75 (br s, 1H), 7.33-7.29 (m, 2H), 6.96 (br t, 2H), 5.30-5.27 (m, 1H), 4.71

(t, 2H), 4.53 (t, 2H), 4.01 (d, 1H), 3.92 (d, 1H), 3.86-3.79 (m, 3H), 3.29 (dd, 2H), 2.11 (br s, 3H); LC-MS (ESI) m/z 443.1 [M+H]+.

EXAMPLE 384

2-[(3-Methyloxetan-3-yl)methoxy]-2-oxoethyl 4-[2-(4-fluorophenyl)-4-oxo-1,3-thiazolidin-3-yl]-3-methylbenzoate

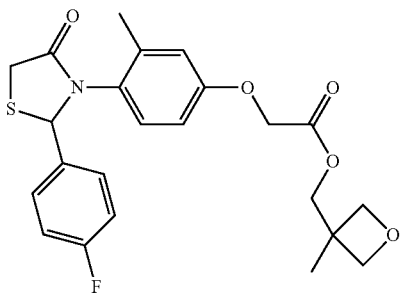

Compound 507

Following standard procedure G, 4-[2-(4-fluorophenyl)-4-oxo-1,3-thiazolidin-3-yl]-3-methylbenzoic acid (0.180 g, 0.499 mmol), (3-methyloxetan-3-yl)methanol (50.0 µL, 0.499 mmol), EDCI • HCl (0.190 g, 0.990 mmol), DMAP (0.130 g, 1.09 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-[(3-methyloxetan-3-yl)methoxy]-2-oxoethyl 4-[2-(4-fluorophenyl)-4-oxo-1,3-thiazolidin-3-yl]-3-methylbenzoate (0.160 g, 72%). $^1$H NMR (CDCl$_3$, 400 MHz) δ 7.29 (dd, 2H), 6.97 (br s, 2H), 6.80-6.18 (br, 3H), 6.08-5.45 (br, 1H), 4.60 (s, 2H), 4.51 (d, 2H), 4.39 (d, 2H), 4.27 (s, 2H), 3.99 (d, 1H), 3.88 (d, 1H), 2.33-1.81 (br, 3H), 1.26 (s, 3H).

EXAMPLE 385

2-[(3R)-3-Methoxypyrrolidin-1-yl]ethyl 4-[2-(4-fluorophenyl)-4-oxo-1,3-thiazolidin-3-yl]-3-methylbenzoate Step 1. Synthesis of 2-[(3R)-3-methoxypyrrolidin-1-yl]ethanol

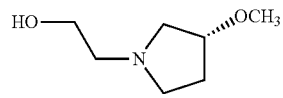

Compound 509

A solution of (3R)-3-methoxypyrrolidine hydrochloride (282 mg, 2.05 mmol), 2-bromoethanol (0.145 mL, 2.05 mmol), and potassium carbonate (566 mg, 4.10 mmol) in CH$_3$CN (8.0 mL) was stirred at room temperature for 18 h. The solution was filtered off and washed with CH$_2$Cl$_2$. The filtrate was concentrated and dried under high vacuum to give 2-[(3R)-3-methoxypyrrolidin-1-yl]ethanol (308 mg, quantitative yield) as a colorless oil which was directly used to next step without further purification. $^1$H NMR (CDCl$_3$, 400 MHz) δ 3.95-3.90 (m, 1H), 3.63 (dd, 2H), 3.27 (s, 3H), 2.80-2.72 (m, 2H), 2.67-2.63 (m, 3H), 2.56-2.50 (m, 1H), 2.11-2.02 (m, 1H), 1.85-1.79 (m, 1H).

Step 2. Synthesis of 2-[(3R)-3-methoxypyrrolidin-1-yl]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (189 mg, 0.572 mmol), 2-[(3R)-3-methoxypyrrolidin-1-yl]ethanol (83.1 mg, 0.572 mmol), DMAP (105 mg, 0.858 mmol), EDCI • HCl (164 mg, 0.858 mmol) and CH$_2$Cl$_2$ (5.0 mL) were used to carry out the reaction. After the reaction mixture was stirred at room temperature for 16 h and concentrated, the residue was purified by preparative thin layer chromatography plates (2.0 mm of silica gel on glass support, 5% methanol in ethyl acetate) to give 2-[(3R)-3-methoxypyrrolidin-1-yl]ethyl 4-[2-(4-fluorophenyl)-4-oxo-1,3-thiazolidin-3-yl]-3-methylbenzoate (134 mg, 51%) as a lightly yellow gum. $^1$H NMR (CDCl$_3$, 400 MHz) δ 7.86 (br s, 1H), 7.80-7.70 (br, 1H), 7.32-7.29 (m, 2H), 6.95 (br t, 2H), 6.10-5.80 (br, 1H), 4.41 (t, 2H), 4.00 (d, 1H), 3.93-3.89 (m, 2H), 3.28 (s, 3H), 2.83-2.77 (m, 4H), 2.68 (dd, 1H), 2.54 (dd, 1H), 2.19 (br s, 3H), 2.08-2.03 (m, 1H), 1.84-1.78 (m, 1H); LC-MS (ESI) m/z 459.3 [M+H]+.

EXAMPLE 386

2-[(3S)-3-Methoxypyrrolidin-1-yl]ethyl 4-[2-(4-fluorophenyl)-4-oxo-1,3-thiazolidin-3-yl]-3-methylbenzoate

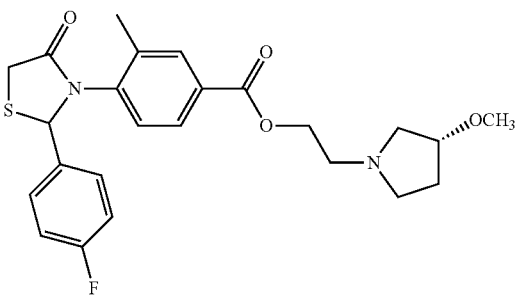

Compound 508                                    Compound 510

Step 1. Synthesis of 2-[(3S)-3-methoxypyrrolidin-1-yl]ethanol

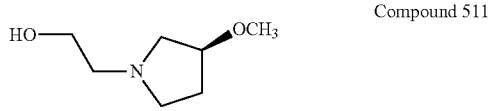

Compound 511

A solution of (3S)-3-methoxypyrrolidine hydrochloride (282 mg, 2.05 mmol), 2-bromoethanol (0.145 mL, 2.05 mmol), and potassium carbonate (566 mg, 4.10 mmol) in CH$_3$CN (8.0 mL) was stirred at room temperature for 18 h. The solution was filtered off and washed with CH$_2$Cl$_2$. The filtrate was concentrated and dried under high vacuum to give 2-[(3S)-3-methoxypyrrolidin-1-yl]ethanol (313 mg, quantitative yield) as a colorless oil which was directly used to next step without further purification. $^1$H NMR (CDCl$_3$, 400 MHz) δ 3.95-3.90 (m, 1H), 3.63 (dd, 2H), 3.27 (s, 3H), 2.80-2.72 (m, 2H), 2.67-2.63 (m, 3H), 2.56-2.50 (m, 1H), 2.11-2.02 (m, 1H), 1.85-1.79 (m, 1H); LC-MS (ESI) m/z 146.2 [M+H]$^+$.

Step 2. Synthesis of 2-[(3S)-3-methoxypyrrolidin-1-yl]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (189 mg, 0.572 mmol), 2-[(3S)-3-methoxypyrrolidin-1-yl]ethanol (83.1 mg, 0.572 mmol), DMAP (105 mg, 0.858 mmol), EDCI • HCl (164 mg, 0.858 mmol) and CH$_2$Cl$_2$ (5.0 mL) were used to carry out the reaction. After the reaction mixture was stirred at room temperature for 16 h and concentrated, the residue was purified by preparative thin layer chromatography plates (2.0 mm of silica gel on glass support, 5% methanol in ethyl acetate) to give 2-[(3S)-3-methoxypyrrolidin-1-yl]ethyl 4-[2-(4-fluorophenyl)-4-oxo-1,3-thiazolidin-3-yl]-3-methylbenzoate (117 mg, 45%) as a lightly yellow gum. $^1$H NMR (CDCl$_3$, 400 MHz) δ 7.86 (br s, 1H), 7.74 (br s, 1H), 7.30 (dd, 2H), 6.96 (br t, 2H), 6.10-5.80 (br, 1H), 4.41 (t, 2H), 4.00 (d, 1H), 3.94-3.90 (m, 2H), 3.28 (s, 3H), 2.85-2.76 (m, 4H), 2.67 (dd, 1H), 2.55 (dd, 1H), 2.20 (br s, 3H), 2.10-2.01 (m, 1H), 1.86-1.78 (m, 1H); LC-MS (ESI) m/z 459.3 [M+H]$^+$.

EXAMPLE 387

Octane-1,8-diyl bis{4-[2-(4-fluorophenyl)-4-oxo-1,3-thiazolidin-3-yl]-3-methylbenzoate}

To a solution of 4-[2-(4-fluorophenyl)-4-oxo-1,3-thiazolidin-3-yl]-3-methylbenzoic acid (289 mg, 0.872 mmol) in DMF (1.0 mL) was added K$_2$CO$_3$ (145 mg, 1.05 mmol) and 1,6-dibromohexane (106 mg, 0.436 mmol). The solution was stirred at 60° C. for 20 h and cooled to room temperature. The solution was quenched with water and extracted with ethyl acetate. The combined organic layers were dried over MgSO$_{4(s)}$, filtered, and concentrated. The residue was purified by Isco Combi-Flash Companion column chromatography (0-40% 0-80% ethyl acetate in n-hexane) to give octane-1,8-diyl bis {4-[2-(4-fluorophenyl)-4-oxo-1,3-thiazolidin-3-yl]-3-methylbenzoate} (269 mg, 40%) as a white foam. $^1$H NMR (CDCl$_3$, 400 MHz) δ 7.85 (br s, 2H), 7.74 (br s, 2H), 7.31 (dd, 4H), 6.95 (br t, 4H), 6.10-5.70 (br, 2H), 4.25 (t, 4H), 4.01 (d, 2H), 3.92 (d, 2H), 2.19 (br s, 6H), 1.73-1.68 (m, 4H), 1.36-1.26 (m, 8H); LC-MS (ESI) m/z 773.3 [M+H]$^+$.

EXAMPLE 388

1-(Pyridin-3-yl)ethyl 4-[2-(4-fluorophenyl)-4-oxo-1,3-thiazolidin-3-yl]-3-methylbenzoate

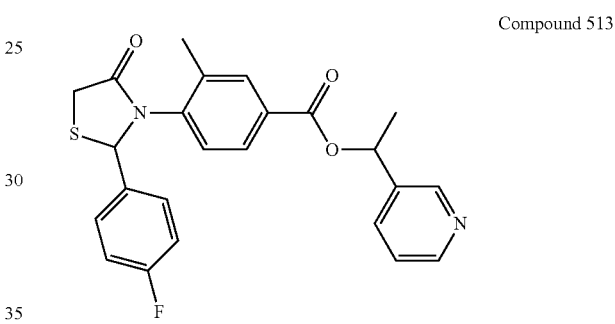

Compound 513

Following standard procedure G, 4-[2-(4-fluorophenyl)-4-oxo-1,3-thiazolidin-3-yl]-3-methylbenzoic acid (0.180 g, 0.544 mmol), 3-pyridylmethylcarbinol (93.0 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-40% ethyl acetate in n-hexane) to give 1-(pyridin-3-yl)ethyl 4-[2-(4-fluorophenyl)-4-oxo-1,3-thiazolidin-3-yl]-3-methylbenzoate (0.220 g, 95%). $^1$H NMR (CDCl$_3$, 300 MHz) δ 8.68 (s, 1H), 8.56 (br s, 1H), 7.87 (s, 1H), 7.76 (br d, 1H), 7.71 (d, 1H), 7.33-7.28 (m, 4H), 6.95 (br t, 2H), 6.09

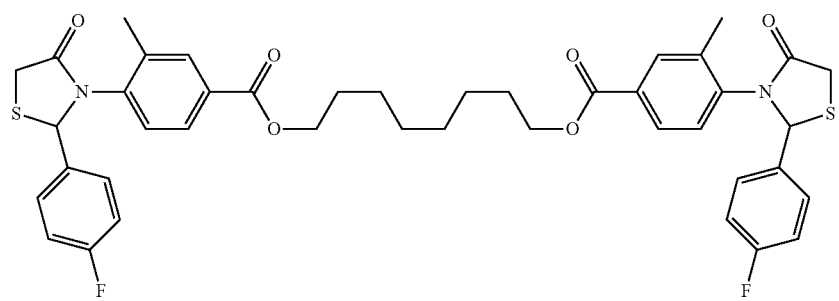

Compound 512

(q, 1H), 5.94 (br s, 1H), 4.00 (d, 1H), 3.91 (d, 1H), 2.20 (br s, 3H), 1.66 (d, 3H); LC-MS (ESI) m/z 437.1 [M+H]$^+$.

EXAMPLE 389

1-(Pyridin-4-yl)ethyl 4-[2-(4-fluorophenyl)-4-oxo-1,3-thiazolidin-3-yl]-3-methylbenzoate

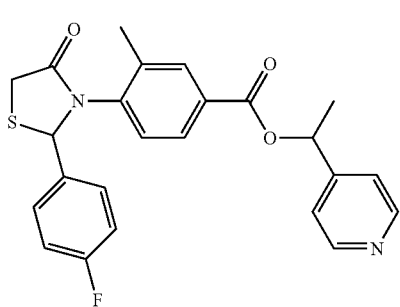

Compound 514

Following standard procedure G, 4-[2-(4-fluorophenyl)-4-oxo-1,3-thiazolidin-3-yl]-3-methylbenzoic acid (0.180 g, 0.544 mmol), 4-pyridylmethylcarbinol (80.4 μL, 0.816 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give 1-(pyridin-4-yl) ethyl 4-[2-(4-fluorophenyl)-4-oxo-1,3-thiazolidin-3-yl]-3-methylbenzoate (0.190 g, 80%). $^1$H NMR (CDCl$_3$, 300 MHz) δ 8.59 (br d, 2H), 7.90 (br s, 1H), 7.79 (br d, 1H), 7.34-7.28 (m, 5H), 6.96 (br t, 2H), 6.02 (q, 1H), 5.96 (br s, 1H), 4.01 (d, 1H), 3.92 (d, 1H), 2.22 (br s, 3H), 1.61 (d, 3H); LC-MS (ESI) m/z 437.1 [M+H]$^+$.

EXAMPLE 390

2-(Pyridin-4-yl)propan-2-yl 4-[2-(4-fluorophenyl)-4-oxo-1,3-thiazolidin-3-yl]-3-methylbenzoate

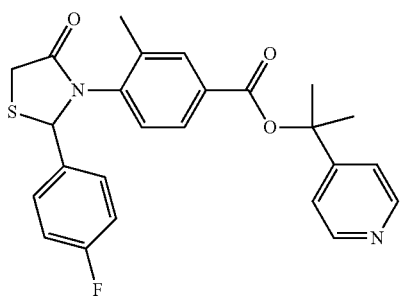

Compound 515

Following standard procedure G, 4-[2-(4-fluorophenyl)-4-oxo-1,3-thiazolidin-3-yl]-3-methylbenzoic acid (0.180 g, 0.544 mmol), 2-(4-pyridyl)-2-propanol (74.6 mg, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give 2-(pyridin-4-yl) propan-2-yl 4-[2-(4-fluorophenyl)-4-oxo-1,3-thiazolidin-3-yl]-3-methylbenzoate (83.5 mg, 34%). $^1$H NMR (CDCl$_3$, 400 MHz) δ 8.56 (d, 2H), 7.85 (br s, 1H), 7.73 (br s, 1H), 7.33 (dd, 2H), 7.29-7.24 (m, 2H), 6.98 (br t, 2H), 6.10-5.80 (br, 1H), 4.02 (d, 1H), 3.92 (d, 1H), 2.21 (br s, 3H), 1.83 (s, 6H); LC-MS (ESI) m/z 451.1 [M+H]$^+$.

EXAMPLE 391

Pyridin-3-yl 4-[2-(4-fluorophenyl)-4-oxo-1,3-thiazolidin-3-yl]-3-methylbenzoate

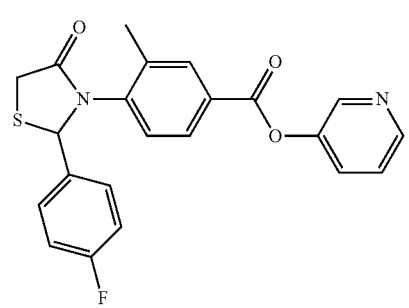

Compound 516

Following standard procedure G, 4-[2-(4-fluorophenyl)-4-oxo-1,3-thiazolidin-3-yl]-3-methylbenzoic acid (0.180 g, 0.544 mmol), 3-pyridinol (51.7 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give pyridin-3-yl 4-[2-(4-fluorophenyl)-4-oxo-1,3-thiazolidin-3-yl]-3-methylbenzoate (0.206 g, 93%). $^1$H NMR (CDCl$_3$, 400 MHz) δ 8.53-8.50 (m, 2H), 8.04 (br s, 1H), 7.91 (br s, 1H), 7.55 (d, 1H), 7.39-7.32 (m, 3H), 6.98 (br t, 2H), 4.02 (d, 1H), 3.94 (d, 1H), 2.26 (br s, 3H); LC-MS (ESI) m/z 408.9 [M+H]$^+$.

EXAMPLE 392

Pyridin-2-yl 4-[2-(4-fluorophenyl)-4-oxo-1,3-thiazolidin-3-yl]-3-methylbenzoate

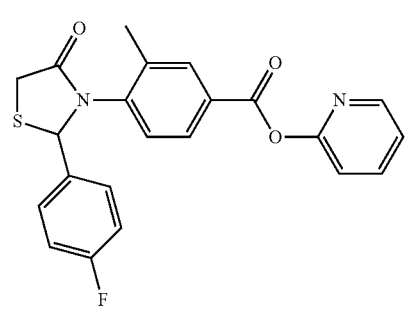

Compound 517

Following standard procedure G, 4-[2-(4-fluorophenyl)-4-oxo-1,3-thiazolidin-3-yl]-3-methylbenzoic acid (0.180 g, 0.544 mmol), 2-pyridinol (51.7 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give pyridin-2-yl 4-[2-(4-fluorophenyl)-4-oxo-1,3-thiazolidin-3-yl]-3-methylbenzoate (93.8 mg, 42%). $^1$H NMR (CDCl$_3$, 400 MHz) δ 8.44 (d, 1H), 8.05 (br s, 1H), 7.94 (br s, 1H), 7.83 (t, 1H), 7.32 (dd, 2H), 7.28-7.25 (m, 1H), 7.17 (d, 1H), 6.97 (br t, 2H), 4.02 (d, 1H), 3.94 (d, 1H), 2.23 (br s, 3H); LC-MS (ESI) m/z 409.2 [M+H]$^+$.

EXAMPLE 393

Pyridin-4-yl 4-[2-(4-fluorophenyl)-4-oxo-1,3-thiazolidin-3-yl]-3-methylbenzoate

Compound 518

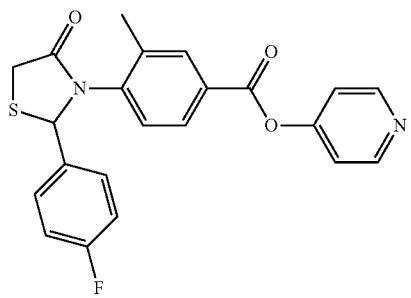

Following standard procedure G, 4-[2-(4-fluorophenyl)-4-oxo-1,3-thiazolidin-3-yl]-3-methylbenzoic acid (0.174 g, 0.530 mmol), 2-pyridinol (50.0 mg, 0.530 mmol), EDCI • HCl (0.200 g, 1.05 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give pyridin-4-yl 4-[2-(4-fluorophenyl)-4-oxo-1,3-thiazolidin-3-yl]-3-methylbenzoate (0.129 g, 60%). $^1$H NMR (CDCl$_3$, 400 MHz) δ 8.66 (d, 2H), 8.01 (br s, 1H), 7.91 (br s, 1H), 7.34 (dd, 2H), 7.19 (d, 2H), 6.98 (br t, 2H), 4.02 (d, 1H), 3.94 (d, 1H), 2.26 (br s, 3H); LC-MS (ESI) m/z 409.3 [M+H]$^+$.

EXAMPLE 394

4-Methylpyridin-3-yl 4-[2-(4-fluorophenyl)-4-oxo-1,3-thiazolidin-3-yl]-3-methylbenzoate Compound 519

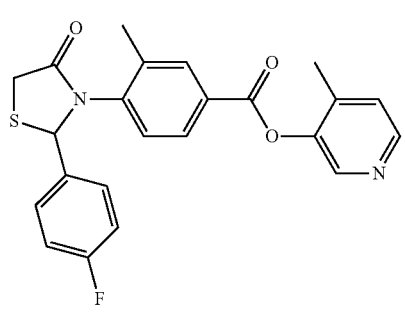

Following standard procedure G, 4-[2-(4-fluorophenyl)-4-oxo-1,3-thiazolidin-3-yl]-3-methylbenzoic acid (126 mg, 0.380 mmol), 3-hydroxy-4-methylpyridine (41.5 mg, 0.380 mmol), EDCI • HCl (109 mg, 0.570 mmol) and CH$_2$Cl$_2$ (3.0 mL) were used to carry out the reaction. After the reaction mixture was stirred at room temperature for 18 h and work-up, the residue was purified by preparative thin layer chromatography plates (1.0 mm of silica gel on glass support, 60% ethyl acetate in n-hexane) to give 4-methylpyridin-3-yl 4-[2-(4-fluorophenyl)-4-oxo-1,3-thiazolidin-3-yl]-3-methylbenzoate (102 mg, 63%) as a white solid. $^1$H NMR (CDCl$_3$, 400 MHz) δ 8.39 (d, 1H), 8.35 (s, 1H), 8.05 (br s, 1H), 7.93 (br d, 1H), 7.35 (dd, 2H), 7.22 (d, 1H), 6.99 (t, 2H), 6.10-5.90 (br, 1H), 4.03 (d, 1H), 3.94 (d, 1H), 2.26 (br s, 3H), 2.23 (s, 3H); LC-MS (ESI) m/z 423.1 [M+H]$^+$.

EXAMPLE 395

6-Methylpyridin-3-yl 4-[2-(4-fluorophenyl)-4-oxo-1,3-thiazolidin-3-yl]-3-methylbenzoate Compound 520

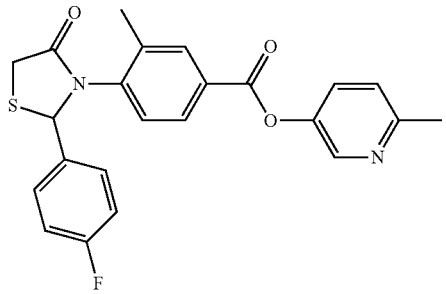

Following standard procedure G, 4-[2-(4-fluorophenyl)-4-oxo-1,3-thiazolidin-3-yl]-3-methylbenzoic acid (122 mg, 0.368 mmol), 5-hydroxy-2-methylpyridine (40.2 mg, 0.368 mmol), EDCI • HCl (106 mg, 0.552 mmol) and CH$_2$Cl$_2$ (3.0 mL) were used to carry out the reaction. After the reaction mixture was stirred at room temperature for 18 h and work-up, the residue was purified by preparative thin layer chromatography plates (1.0 mm of silica gel on glass support, 60% ethyl acetate in n-hexane) to give 6-methylpyridin-3-yl 4-[2-(4-fluorophenyl)-4-oxo-1,3-thiazolidin-3-yl]-3-methylbenzoate (114 mg, 74%) as a white solid. $^1$H NMR (CDCl$_3$, 400 MHz) δ 8.36 (d, 1H), 8.02 (br s, 1H), 7.91 (br d, 1H), 7.43 (dd, 1H), 7.34 (dd, 2H), 7.21 (d, 1H), 6.98 (t, 2H), 6.10-5.90 (br, 1H), 4.02 (d, 1H), 3.94 (d, 1H), 2.58 (s, 3H), 2.25 (br s, 3H); LC-MS (ESI) m/z 423.2 [M+H]$^+$.

EXAMPLE 396

5-Methylpyridin-3-yl 4-[2-(4-fluorophenyl)-4-oxo-1,3-thiazolidin-3-yl]-3-methylbenzoate Compound 521

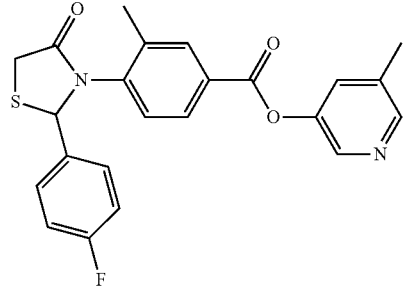

Following standard procedure G, 4-[2-(4-fluorophenyl)-4-oxo-1,3-thiazolidin-3-yl]-3-methylbenzoic acid (126 mg, 0.380 mmol), 3-hydroxy-5-methylpyridine (41.5 mg, 0.380 mmol), DMAP (69.6 mg, 0.570 mmol), EDCI • HCl (109 mg, 0.570 mmol) and CH$_2$Cl$_2$ (3.0 mL) were used to carry out the reaction. After the reaction mixture was stirred at room temperature for 16 h and work-up, the residue was purified by preparative thin layer chromatography plates (1.0 mm of silica gel on glass support, 60% ethyl acetate in n-hexane) to give 5-methylpyridin-3-yl 4-[2-(4-fluorophenyl)-4-oxo-1,3-thiazolidin-3-yl]-3-methylbenzoate (104 mg, 65%) as a white foam. $^1$H NMR (CDCl$_3$, 400 MHz) δ 8.35 (s, 1H), 8.30 (d, 1H), 8.02 (br s, 1H), 7.90 (br d, 1H), 7.36-7.32 (m, 3H), 6.98 (t, 2H), 6.10-5.90 (br, 1H), 4.02 (d, 1H), 3.94 (d, 1H), 2.38 (s, 3H), 2.25 (br s, 3H); LC-MS (ESI) m/z 423.2 [M+H]$^+$.

EXAMPLE 397

2-Fluoropyridin-3-yl 4-[2-(4-fluorophenyl)-4-oxo-1,3-thiazolidin-3-yl]-3-methylbenzoate

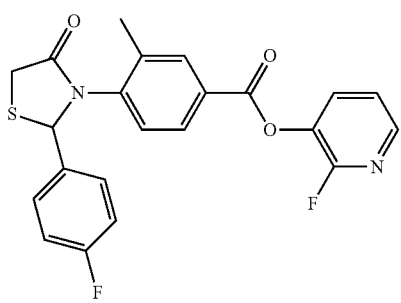

Compound 522

Following standard procedure G, 4-[2-(4-fluorophenyl)-4-oxo-1,3-thiazolidin-3-yl]-3-methylbenzoic acid (124 mg, 0.374 mmol), 2-fluoro-3-hydroxypyridine (42.3 mg, 0.374 mmol), DMAP (68.5 mg, 0.561 mmol), EDCI • HCl (108 mg, 0.561 mmol) and CH$_2$Cl$_2$ (5.0 mL) were used to carry out the reaction. After the reaction mixture was stirred at room temperature for 18 h and work-up, the residue was purified by preparative thin layer chromatography plates (1.0 mm of silica gel on glass support, 60% ethyl acetate in n-hexane) to give 2-fluoropyridin-3-yl 4-[2-(4-fluorophenyl)-4-oxo-1,3-thiazolidin-3-yl]-3-methylbenzoate (108 mg, 68%) as a white solid. $^1$H NMR (CDCl$_3$, 400 MHz) δ 8.11 (d, 1H), 8.03 (br s, 1H), 7.90 (br d, 1H), 7.67 (dd, 1H), 7.34 (dd, 2H), 7.27-7.24 (m, 1H), 6.99 (br t, 2H), 6.10-5.90 (br, 1H), 4.02 (d, 1H), 3.94 (d, 1H), 2.26 (br s, 3H); LC-MS (ESI) m/z 449.2 [M+Na]$^+$.

EXAMPLE 398

6-Fluoropyridin-3-yl 4-[2-(4-fluorophenyl)-4-oxo-1,3-thiazolidin-3-yl]-3-methylbenzoate

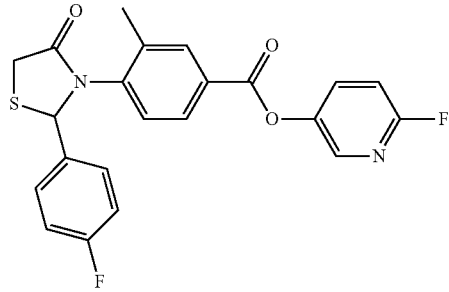

Compound 523

Following standard procedure G, 4-[2-(4-fluorophenyl)-4-oxo-1,3-thiazolidin-3-yl]-3-methylbenzoic acid (124 mg, 0.374 mmol), 6-fluoro-3-hydroxypyridine (42.3 mg, 0.374 mmol), DMAP (68.5 mg, 0.561 mmol), EDCI • HCl (108 mg, 0.561 mmol) and CH$_2$Cl$_2$ (5.0 mL) were used to carry out the reaction. After the reaction mixture was stirred at room temperature for 18 h and work-up, the residue was purified by preparative thin layer chromatography plates (1.0 mm of silica gel on glass support, 60% ethyl acetate in n-hexane) to give 6-fluoropyridin-3-yl 4-[2-(4-fluorophenyl)-4-oxo-1,3-thiazolidin-3-yl]-3-methylbenzoate (87.5 mg, 55%) as a white foam. $^1$H NMR (CDCl$_3$, 400 MHz) δ 8.09 (s, 1H), 8.02 (br s, 1H), 7.90 (br d, 1H), 7.67-7.62 (m, 1H), 7.34 (dd, 2H), 7.01-6.96 (m, 3H), 6.10-5.90 (br, 1H), 4.02 (d, 1H), 3.94 (d, 1H), 2.26 (br s, 3H); LC-MS (ESI) m/z 449.1 [M+Na]$^+$.

EXAMPLE 399

5-Fluoropyridin-3-yl 4-[2-(4-fluorophenyl)-4-oxo-1,3-thiazolidin-3-yl]-3-methylbenzoate

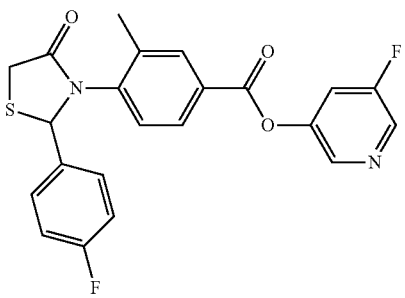

Compound 524

Following standard procedure G, 4-[2-(4-fluorophenyl)-4-oxo-1,3-thiazolidin-3-yl]-3-methylbenzoic acid (115 mg, 0.347 mmol), 3-fluoro-5-hydroxypyridine (39.2 mg, 0.347 mmol), DMAP (63.6 mg, 0.521 mmol), EDCI • HCl (99.8 mg, 0.521 mmol) and CH$_2$Cl$_2$ (3.0 mL) were used to carry out the reaction. After the reaction mixture was stirred at room temperature for 16 h and work-up, the residue was purified by preparative thin layer chromatography plates (1.0 mm of silica gel on glass support, 60% ethyl acetate in n-hexane) to give 5-fluoropyridin-3-yl 4-[2-(4-fluorophenyl)-4-oxo-1,3-thiazolidin-3-yl]-3-methylbenzoate (89.5 mg, 60%) as a white solid. $^1$H NMR (CDCl$_3$, 400 MHz) δ 8.42 (d, 1H), 8.37 (s, 1H), 8.02 (br s, 1H), 7.90 (br d, 1H), 7.40-7.32 (m, 3H), 6.98 (t, 2H), 6.10-5.90 (br, 1H), 4.02 (d, 1H), 3.94 (d, 1H), 2.26 (br s, 3H); LC-MS (ESI) m/z 427.2 [M+H]$^+$.

EXAMPLE 400

5-Chloropyridin-3-yl 4-[2-(4-fluorophenyl)-4-oxo-1,3-thiazolidin-3-yl]-3-methylbenzoate Compound 525

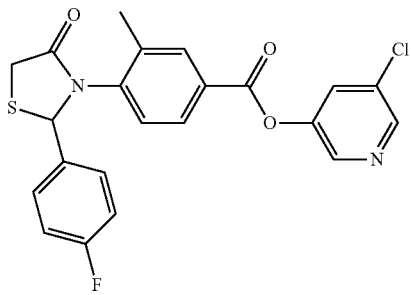

Following standard procedure G, 4-[2-(4-fluorophenyl)-4-oxo-1,3-thiazolidin-3-yl]-3-methylbenzoic acid (97.4 mg, 0.294 mmol), 5-chloro-3-hydroxypyridine (38.1 mg, 0.294 mmol), EDCI • HCl (84.5 mg, 0.441 mmol) and CH$_2$Cl$_2$ (3.0 mL) were used to carry out the reaction. After the reaction mixture was stirred at room temperature for 18 h and work-up, the residue was purified by preparative thin layer chromatography plates (1.0 mm of silica gel on glass support, 50% ethyl acetate in n-hexane) to give 5-chloropyridin-3-yl 4-[2-(4-fluorophenyl)-4-oxo-1,3-thiazolidin-3-yl]-3-methylbenzoate (46.1 mg, 35%) as a colorless gum. $^1$H NMR (CDCl$_3$, 300 MHz) δ 8.50 (d, 1H), 8.41 (d, 1H), 8.01 (br s, 1H), 7.90 (br d, 1H), 7.62 (s, 1H), 7.36-7.32 (m, 2H), 6.98 (t, 2H), 6.10-5.90 (br, 1H), 4.03 (d, 1H), 3.94 (d, 1H), 2.26 (br s, 3H); LC-MS (ESI) m/z 443.2 [M+H]$^+$.

EXAMPLE 401

6-Chloropyridin-3-yl 4-[2-(4-fluorophenyl)-4-oxo-1,3-thiazolidin-3-yl]-3-methylbenzoate Compound 526

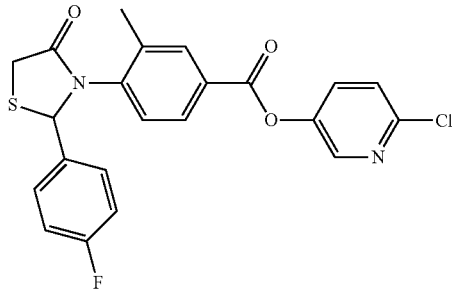

Following standard procedure G, 4-[2-(4-fluorophenyl)-4-oxo-1,3-thiazolidin-3-yl]-3-methylbenzoic acid (112 mg, 0.338 mmol), 2-chloro-5-hydroxypyridine (43.8 mg, 0.338 mmol), DMAP (41.3 mg, 0.338 mmol), EDCI • HCl (97.2 mg, 0.507 mmol) and CH$_2$Cl$_2$ (3.0 mL) were used to carry out the reaction. After the reaction mixture was stirred at room temperature for 16 h and work-up, the residue was purified by preparative thin layer chromatography plates (1.0 mm of silica gel on glass support, 40% ethyl acetate in n-hexane) to give 6-chloropyridin-3-yl 4-[2-(4-fluorophenyl)-4-oxo-1,3-thiazolidin-3-yl]-3-methylbenzoate (93.1 mg, 62%) as a white foam. $^1$H NMR (CDCl$_3$, 400 MHz) δ 8.29 (d, 1H), 8.02 (br s, 1H), 7.89 (br d, 1H), 7.54 (dd, 1H), 7.39 (d, 1H), 7.34 (dd, 2H), 6.98 (t, 2H), 6.10-5.90 (br, 1H), 4.02 (d, 1H), 3.94 (d, 1H), 2.26 (br s, 3H); LC-MS (ESI) m/z 465.1 [M+Na]$^+$.

EXAMPLE 402

2-Chloropyridin-3-yl 4-[2-(4-fluorophenyl)-4-oxo-1,3-thiazolidin-3-yl]-3-methylbenzoate Compound 527

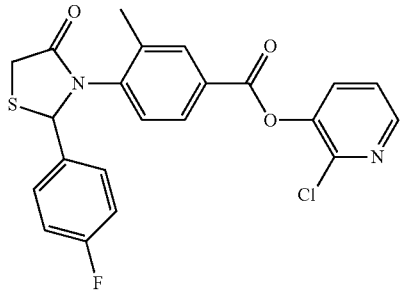

Following standard procedure G, 4-[2-(4-fluorophenyl)-4-oxo-1,3-thiazolidin-3-yl]-3-methylbenzoic acid (135 mg, 0.407 mmol), 2-chloro-3-hydroxypyridine (52.8 mg, 0.407 mmol), DMAP (74.6 mg, 0.611 mmol), EDCI • HCl (116 mg, 0.611 mmol) and CH$_2$Cl$_2$ (5.0 mL) were used to carry out the reaction. After the reaction mixture was stirred at room temperature for 18 h and work-up, the residue was purified by preparative thin layer chromatography plates (1.0 mm of silica gel on glass support, 50% ethyl acetate in n-hexane) to give 2-chloropyridin-3-yl 4-[2-(4-fluorophenyl)-4-oxo-1,3-thiazolidin-3-yl]-3-methylbenzoate (89.4 mg, 50%) as a lightly beige solid. $^1$H NMR (CDCl$_3$, 400 MHz) δ 8.33 (dd, 1H), 8.06 (br s, 1H), 7.94 (br d, 1H), 7.61 (dd, 1H), 7.37-7.31 (m, 3H), 6.99 (t, 2H), 6.10-5.90 (br, 1H), 4.03 (d, 1H), 3.94 (d, 1H), 2.27 (br s, 3H); LC-MS (ESI) m/z 443.1 [M+H]$^+$.

EXAMPLE 403

2-(Morpholin-4-ylmethyl)pyridin-3-yl 4-[2-(4-fluorophenyl)-4-oxo-1,3-thiazolidin-3-yl]-3-methylbenzoate

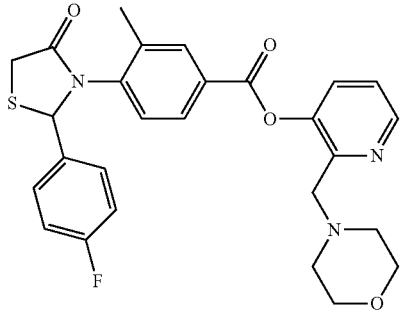

Compound 528

Step 1. Synthesis of 2-(morpholin-4-ylmethyl)pyridin-3-ol

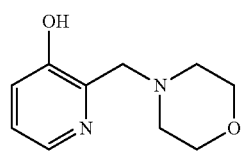

Compound 529

To the solution of 3-pyridinol (0.500 g, 5.26 mmol) in benzene (40.0 mL), morpholine (0.550 mL, 6.31 mmol) and paraformaldehyde (0.440 mL, 6.31 mmol) were used to carry out the reaction. After the reaction mixture was stirred at 80° C. for 16 h and work-up, the residue was purified by Isco Combi-Flash Companion column chromatography (0-10% MeOH in $CH_2Cl_2$) to give 2-(morpholin-4-ylmethyl)pyridin-3-ol (0.950 g, 93%). $^1$H NMR ($CDCl_3$, 400 MHz) δ 8.02 (d, 1H), 7.13-7.07 (m, 2H), 3.92 (s, 2H), 3.77 (br s, 4H), 2.63 (br s, 4H).

Step 2. Synthesis of 2-(morpholin-4-ylmethyl)pyridin-3-yl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 2-(morpholin-4-ylmethyl)pyridin-3-ol (0.110 g, 0.544 mmol), EDCI • HCl (0.210 g, 1.09 mmol), DMAP (0.150 g, 1.19 mmol) and $CH_2Cl_2$ (5.0 mL) were used to carry out the reaction. After the reaction mixture was stirred at room temperature for 16 h and work-up, the residue was purified by Isco Combi-Flash Companion column chromatography (0-75% ethyl acetate in n-hexane) to give 2-(morpholin-4-ylmethyl)pyridin-3-yl 4-[2-(4-fluorophenyl)-4-oxo-1,3-thiazolidin-3-yl]-3-methylbenzoate (68.7 mg, 25%). $^1$H NMR ($CDCl_3$, 400 MHz) δ 8.49 (dd, 1H), 8.03 (br s, 1H), 7.92 (br d, 1H), 7.47 (dd, 1H), 7.37-7.30 (m, 3H), 6.98 (br t, 2H), 4.02 (d, 1H), 3.95 (d, 1H), 3.65 (s, 2H), 3.34 (br s, 4H), 2.34-2.20 (m, 7H); LC-MS (ESI) m/z 508.2 $[M+H]^+$.

EXAMPLE 404

5-(Morpholin-4-yl)pyridin-3-yl 4-[2-(4-fluorophenyl)-4-oxo-1,3-thiazolidin-3-yl]-3-methylbenzoate

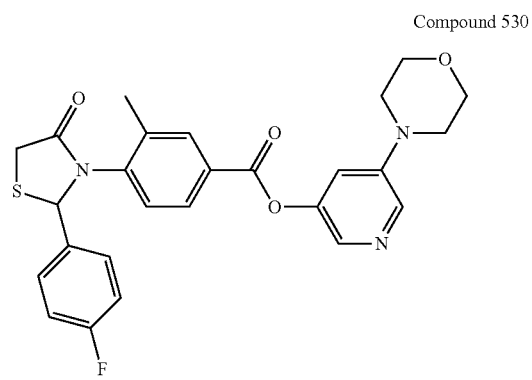 [SMILES: Cc1cc(C(=O)Oc2cncc(N3CCOCC3)c2)ccc1N1C(=O)CSC1c1ccc(F)cc1]

Compound 530

Following standard procedure G, 4-[2-(4-fluorophenyl)-4-oxo-1,3-thiazolidin-3-yl]-3-methylbenzoic acid (110 mg, 0.332 mmol), 5-(morpholin-4-yl)pyridin-3-ol (59.8 mg, 0.332 mmol), EDCI • HCl (95.5 mg, 0.498 mmol) and $CH_2Cl_2$ (3.0 mL) were used to carry out the reaction. After the reaction mixture was stirred at room temperature for 18 h and work-up, the residue was purified by preparative thin layer chromatography plates (1.0 mm of silica gel on glass support, 20% ethyl acetate in $CH_2Cl_2$) to give 5-(morpholin-4-yl)pyridin-3-yl 4-[2-(4-fluorophenyl)-4-oxo-1,3-thiazolidin-3-yl]-3-methylbenzoate (57.4 mg, 35%) as a lightly yellow solid. $^1$H NMR ($CDCl_3$, 400 MHz) δ 8.06 (s, 1H), 8.02 (br s, 1H), 7.89 (br s, 1H), 7.37-7.32 (m, 3H), 6.98 (t, 2H), 6.66 (d, 1H), 6.10-5.90 (br, 1H), 4.02 (d, 1H), 3.94 (d, 1H), 3.83 (dd, 4H), 3.49 (dd, 4H), 2.24 (br s, 3H); LC-MS (ESI) m/z 494.1 $[M+H]^+$.

EXAMPLE 405

6-(Morpholin-4-yl)pyridin-3-yl 4-[2-(4-fluorophenyl)-4-oxo-1,3-thiazolidin-3-yl]-3-methylbenzoate

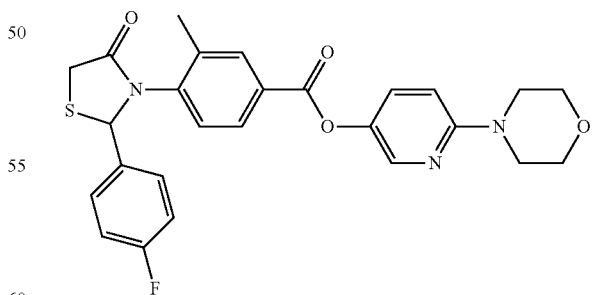

Compound 531

Following standard procedure G, 4-[2-(4-fluorophenyl)-4-oxo-1,3-thiazolidin-3-yl]-3-methylbenzoic acid (121 mg, 0.365 mmol), 6-(morpholin-4-yl)pyridin-3-ol (65.8 mg, 0.365 mmol), DMAP (66.9 mg, 0.548 mmol), EDCI • HCl (105 mg, 0.548 mmol) and $CH_2Cl_2$ (5.0 mL) were used to carry out the reaction. After the reaction mixture was stirred at room temperature for 18 h and work-up, the residue was purified by preparative thin layer chromatography plates (1.0 mm of silica gel on glass support, 70% ethyl acetate in n-hexane) to give 6-(morpholin-4-yl)pyridin-3-yl 4-[2-(4-fluorophenyl)-4-oxo-1,3-thiazolidin-3-yl]-3-methylbenzoate (48.2 mg, 27%) as a white solid. $^1$H NMR (CDCl$_3$, 400 MHz) δ 8.20 (d, 1H), 8.02-8.00 (m, 2H), 7.90 (br s, 1H), 7.34 (dd, 2H), 7.00-6.96 (m, 3H), 6.10-5.90 (br, 1H), 4.02 (d, 1H), 3.94 (d, 1H), 3.86 (dd, 4H), 3.21 (dd, 4H), 2.25 (br s, 3H); LC-MS (ESI) m/z 494.2 [M+H]$^+$.

EXAMPLE 406

2-(Pyridin-2-yl)ethyl 4-[2-(4-fluorophenyl)-4-oxo-1,3-thiazolidin-3-yl]-3-methylbenzoate Compound 532

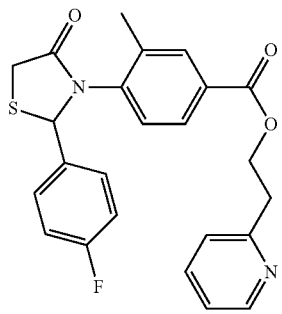

Following standard procedure G, 4-[2-(4-fluorophenyl)-4-oxo-1,3-thiazolidin-3-yl]-3-methylbenzoic acid (0.180 g, 0.544 mmol), 2-pyridineethanol (61.0 μL, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(pyridin-2-yl)ethyl 4-[2-(4-fluorophenyl)-4-oxo-1,3-thiazolidin-3-yl]-3-methylbenzoate (0.190 g, 80%). $^1$H NMR (CDCl$_3$, 300 MHz) δ 8.55 (d, 1H), 7.80 (br s, 1H), 7.68 (br s, 1H), 7.61 (t, 1H), 7.32-7.27 (m, 2H), 7.21-7.13 (m, 2H), 6.95 (t, 2H), 4.66 (t, 2H), 4.00 (d, 1H), 3.91 (d, 1H), 3.21 (t, 2H), 2.17 (br s, 3H); LC-MS (ESI) m/z 437.1 [M+H]$^+$.

EXAMPLE 407

2-({4-[2-(4-Fluorophenyl)-4-oxo-1,3-thiazolidin-3-yl]-3-methylbenzoyl}oxy)ethyl pyridine-3-carboxylate Compound 533

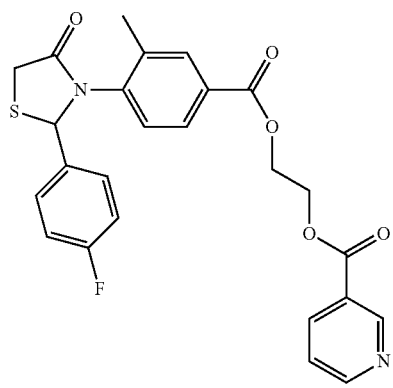

Step 1. Synthesis of pyridine-3-carbonyl chloride

Compound 534

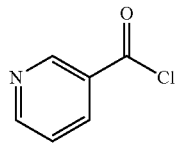

A solution of nicotinic acid (0.220 g) in SOCl$_2$ (5.0 mL) was carried out the reaction. After the reaction was stirred at 55° C. for 3 h and work-up, the residue was used directly for next step without further purification. (0.300 g, crude yield 99%). $^1$H NMR (DMSO-d$_6$, 400 MHz) δ 9.17 (s, 1H), 8.96 (d, 1H), 8.64 (d, 1H), 7.91-7.87 (m, 1H).

Step 2. Synthesis of 2-chloroethyl pyridine-3-carboxylate

Compound 535

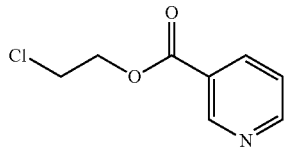

A solution of pyridine-3-carbonyl chloride (0.280 g, 1.57 mmol) in pyridine (10.0 mL) and 2-chloroehtanol (0.210 mL, 3.15 mmol) were used to carry out the reaction. After the reaction was stirred at 100° C. for 3 h and work-up, the residue was used directly for next step without further purification. (82.8 mg, crude yield 29%). $^1$H NMR (CDCl$_3$, 400 MHz) δ 9.29 (s, 1H), 8.87-8.86 (m, 1H), 8.50 (br d, 1H), 7.59 (dd, 1H), 4.65-4.62 (m, 2H), 3.85-3.82 (m, 2H).

Step 3. Synthesis of 2-({4-[2-(4-fluorophenyl)-4-oxo-1,3-thiazolidin-3-yl]-3-methylbenzoyl}oxy) ethyl pyridine-3-carboxylate Following standard procedure L, 4-[2-(4-fluorophenyl)-4-oxo-1,3-thiazolidin-3-yl]-3-methylbenzoic acid (0.148 g, 0.450 mmol), 2-chloroethyl pyridine-3-carboxylate (82.8 mg, 0.450 mmol), K$_2$CO$_3$ (68.0 g, 0.490 mmol) and DMF (5.0 mL) were used to carry out the reaction. After the reaction mixture was stirred at 80° C. for 16 h and work-up, the residue was purified by Isco Combi-Flash Companion column chromatography (0-40% ethyl acetate in n-hexane) to give 2-({4-[2-(4-fluorophenyl)-4-oxo-1,3-thiazolidin-3-yl]-3-methylbenzoyl}oxy)ethyl pyridine-3-carboxylate (0.110 g, 51%). $^1$H NMR (CDCl$_3$, 400 MHz) δ 9.22 (s, 1H), 8.79-8.78 (m, 1H), 8.29 (d, 1H), 7.87 (br s, 1H), 7.75 (br s, 1H), 7.42-7.38 (m, 1H), 7.32-7.29 (m, 2H), 6.95 (br t, 2H), 6.10-5.80 (br, 1H), 4.66-4.62 (m, 4H), 4.00 (d, 1H), 3.91 (d, 1H), 2.19 (br s, 3H); LC-MS (ESI) m/z 481.1[M+H]$^+$.

EXAMPLE 408

2-({4-[2-(4-Fluorophenyl)-4-oxo-1,3-thiazolidin-3-yl]-3-methylbenzoyl}oxy)ethyl pyridine-4-carboxylate

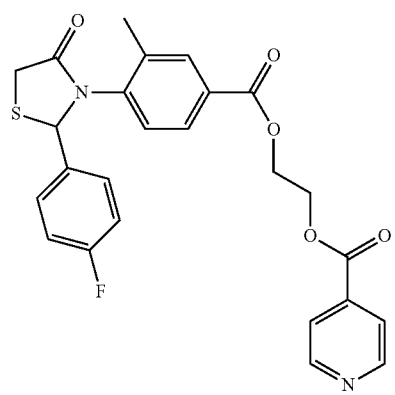

Compound 536

Step 1. Synthesis of 2-hydroxyethyl pyridine-4-carboxylate

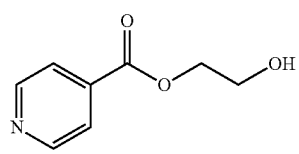

Compound 537

To the solution of 2-bromoethanol (0.380 mL, 5.36 mmol) in DMF (10.0 mL), isonicotinic acid (0.600 g, 4.87 mmol) and $K_2CO_3$ (0.740 g, 5.36 mmol) were used to carry out the reaction. After the reaction mixture was stirred at 60° C. for 16 h and work-up, the residue was used directly for next step without further purification. (0.350 g, crude yield 43%). $^1$H NMR (CDCl$_3$, 300 MHz) δ 8.80-8.77 (m, 2H), 7.87-7.84 (m, 2H), 4.52-4.49 (m, 4H), 3.99 (dd, 1H).

Step 2. Synthesis of 2-({4-[2-(4-fluorophenyl)-4-oxo-1,3-thiazolidin-3-yl]-3-methylbenzoyl}oxy)ethyl pyridine-4-carboxylate Following standard procedure G, 4-[2-(4-fluorophenyl)-4-oxo-1,3-thiazolidin-3-yl]-3-methylbenzoic acid (0.180 g, 0.544 mmol), 2-hydroxyethyl pyridine-4-carboxylate (90.8 mg, 0.544 mmol), EDCI•HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-70% ethyl acetate in n-hexane) to give 2-({4-[2-(4-fluorophenyl)-4-oxo-1,3-thiazolidin-3-yl]-3-methylbenzoyl}oxy)ethyl pyridine-4-carboxylate (0.168 g, 64%). $^1$H NMR (CDCl$_3$, 400 MHz) δ 8.78 (dd, 2H), 7.86 (br s, 1H), 7.83 (dd, 2H), 7.75 (br s, 1H), 7.32-7.27 (m, 2H), 6.95 (br t, 2H), 6.10-5.80 (br, 1H), 4.67-4.61 (m, 4H), 4.00 (d, 1H), 3.92 (d, 1H), 2.19 (br s, 3H); LC-MS (ESI) m/z 481.1 [M+H]$^+$.

EXAMPLE 409

2-({4-[2-(4-Fluorophenyl)-4-oxo-1,3-thiazolidin-3-yl]-3-methylbenzoyl}oxy)ethyl pyridine-2-carboxylate

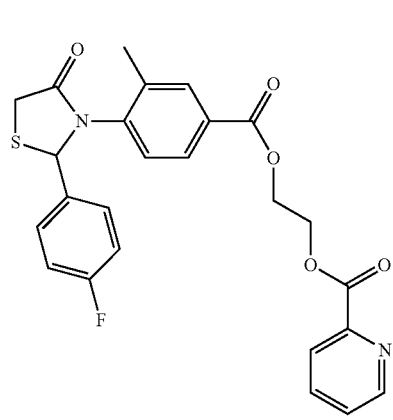

Compound 538

Step 1. Synthesis of 2-hydroxyethyl pyridine-2-carboxylate

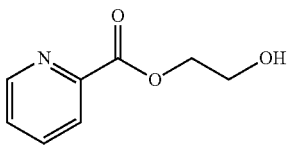

Compound 539

To the solution of 2-bromoethanol (0.380 mL, 5.36 mmol) in DMF (10.0 mL), picolinic acid (0.600 g, 4.87 mmol) and $K_2CO_3$ (0.740 g, 5.36 mmol) were used to carry out the reaction. After the reaction mixture was stirred at 60° C. for 16 h and work-up, the residue was used directly for next step without further purification. (0.160 g, curde yield 20%). $^1$H NMR (CDCl$_3$, 400 MHz) δ 8.73 (d, 1H), 8.17 (d, 1H), 7.87 (t, 1H), 7.53-7.47 (m, 1H), 4.53-4.52 (m, 2H), 4.01-3.99 (m, 2H).

Step 2. Synthesis of 2-({4-[2-(4-fluorophenyl)-4-oxo-1,3-thiazolidin-3-yl]-3-methylbenzoyl}oxy)ethyl pyridine-2-carboxylate Following standard procedure G, 4-[2-(4-fluorophenyl)-4-oxo-1,3-thiazolidin-3-yl]-3-methylbenzoic acid (0.180 g, 0.544 mmol), 2-hydroxyethyl pyridine-2-carboxylate (90.8 mg, 0.544 mmol), EDCI•HCl (0.210 g, 1.09 mmol), DMAP (0.150 g, 1.19 mmol) and CH$_2$Cl$_2$ (10.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give 2-({4-[2-(4-fluorophenyl)-4-oxo-1,3-thiazolidin-3-yl]-3-methylbenzoyl}oxy)ethyl pyridine-2-carboxylate (0.106 g, 46%). $^1$H NMR (CDCl$_3$, 300 MHz) δ 8.77 (br d, 1H), 8.12 (d, 1H), 7.87-7.82 (m, 2H), 7.75 (br s, 1H), 7.50 (dd, 1H), 7.31-7.25 (m, 3H), 6.94 (br t, 2H), 4.75-4.72 (m, 2H), 4.65-4.62 (m, 2H), 3.99 (d, 1H), 3.91 (d, 1H), 2.17 (br s, 3H); LC-MS (ESI) m/z 503.1 [M+Na]$^+$.

EXAMPLE 410

2-(Pyridin-4-ylmethoxy)ethyl 4-[2-(4-fluorophenyl)-4-oxo-1,3-thiazolidin-3-yl]-3-methylbenzoate

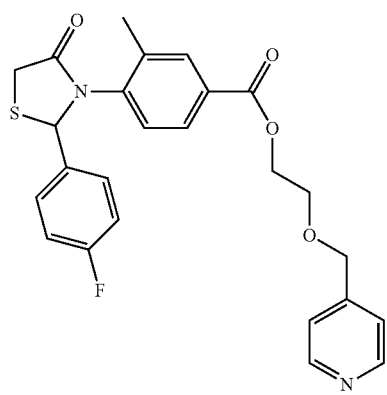

Compound 540

Step 1. Synthesis of 2-(pyridin-4-ylmethoxy)ethanol

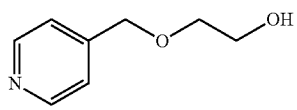

Compound 541

To the solution of ethylene glycol (0.490 g, 7.91 mmol) in THF (10.0 mL), 4-(bromomethyl)pyridine (0.200 g, 0.790 mmol) and sodium hydride (47.4 mg, 1.19 mmol) were used to carry out the reaction. After the reaction mixture was stirred at 80° C. for 16 h and work-up, the residue was purified by Isco Combi-Flash Companion column chromatography (0-100% ethyl acetate in n-hexane) to give 2-(pyridin-4-ylmethoxy)ethanol (42.6 mg, 35%). $^1$H NMR (CDCl$_3$, 300 MHz) δ 8.58 (br s, 2H), 7.28 (br s, 2H), 4.59 (br s, 2H), 3.83-3.81 (m, 2H), 3.66-3.64 (m, 2H).

Step 2. Synthesis of 2-(pyridin-4-ylmethoxy)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (92.1 mg, 0.278 mmol), 2-(pyridin-4-ylmethoxy)ethanol (42.6 mg, 0.278 mmol), EDCI • HCl (0.110 g, 0.556 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-90% ethyl acetate in n-hexane) to give 2-(pyridin-4-ylmethoxy)ethyl 4-[2-(4-fluorophenyl)-4-oxo-1,3-thiazolidin-3-yl]-3-methylbenzoate (10.5 mg, 8%). $^1$H NMR (CDCl$_3$, 400 MHz) δ 8.55 (br s, 2H), 7.88 (br s, 1H), 7.76 (br s, 1H), 7.33-7.30 (m, 2H), 7.29-7.30 (m, 2H), 6.97 (br t, 2H), 4.59 (s, 2H), 4.48 (br s, 2H), 4.01 (d, 1H), 3.92 (d, 1H), 3.80 (br s, 2H), 2.20 (br s, 3H); LC-MS (ESI) m/z 467.1 [M+H]$^+$.

EXAMPLE 411

2-(Pyridin-2-ylmethoxy)ethyl 4-[2-(4-fluorophenyl)-4-oxo-1,3-thiazolidin-3-yl]-3-methylbenzoate

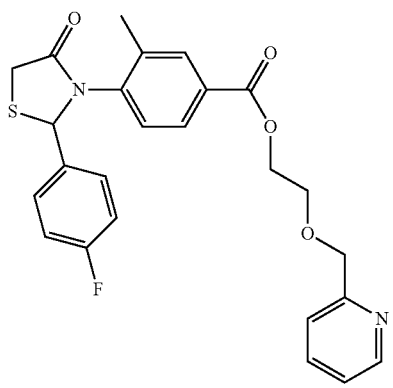

Compound 542

Step 1. Synthesis of 2-(pyridin-2-ylmethoxy)ethanol

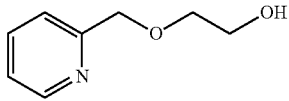

Compound 543

To the solution of ethylene glycol (0.130 mL, 2.37 mmol) in THF (5.0 mL), 2-(bromomethyl)pyridine (0.300 g, 1.19 mmol) and sodium hydride (71.1 mg, 1.78 mmol) were used to carry out the reaction. After the reaction mixture was stirred at 80° C. for 16 h and work-up, the residue was purified by Isco Combi-Flash Companion column chromatography (0-70% ethyl acetate in n-hexane) to give 2-(pyridin-2-ylmethoxy)ethanol (0.110 g, 61/%). $^1$H NMR (CDCl$_3$, 400 MHz) δ 8.57 (d, 1H), 7.70 (t, 1H), 7.36 (d, 1H), 7.24-7.20 (m, 1H), 4.71 (s, 2H), 3.82-3.79 (m, 2H), 3.76-3.73 (m, 2H).

Step 2. Synthesis of 2-(pyridin-2-ylmethoxy)ethyl 4-(2-(4-fluorophenyl)-4-oxothiazolidin-3-yl)-3-methylbenzoate Following standard procedure G, 4-[2-(4-fluorophenyl)-4-oxo-1,3-thiazolidin-3-yl]-3-methylbenzoic acid (0.21 g, 0.653 mmol), 2-(pyridin-2-ylmethoxy)ethanol (0.110 g, 0.719 mmol), EDCI • HCl (0.240 g, 1.27 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 60% ethyl acetate in n-hexane) to give 2-(pyridin-2-ylmethoxy)ethyl 4-[2-(4-fluorophenyl)-4-oxo-1,3-thiazolidin-3-yl]-3-methylbenzoate (38.2 mg, 13%). $^1$H NMR (CDCl$_3$, 400 MHz) δ 8.54 (d, 1H), 7.87 (br s, 1H), 7.77 (br s, 1H), 7.63 (t, 1H), 7.42 (d, 1H), 7.32-7.29 (m, 2H), 7.18

(dd, 1H), 6.95 (br t, 2H), 5.96 (br s, 1H), 4.71 (s, 2H), 4.49-4.47 (m, 2H), 4.00 (d, 1H), 3.92 (d, 1H), 3.89-3.85 (m, 2H), 2.19 (br s, 3H); LC-MS (APCI) m/z 467.7 [M+H]⁺.

EXAMPLE 412

2-(Pyridin-3-ylmethoxy)ethyl 4-[2-(4-fluorophenyl)-4-oxo-1,3-thiazolidin-3-yl]-3-methylbenzoate

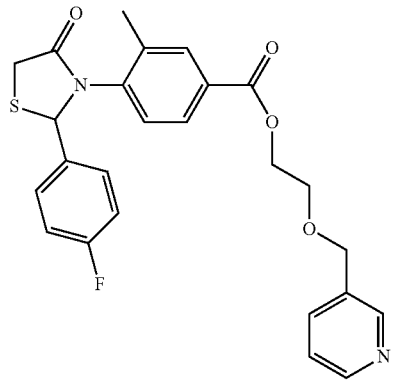

Compound 544

Step 1. Synthesis of 2-(pyridin-3-ylmethoxy)ethanol

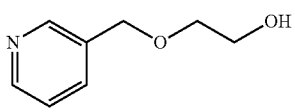

Compound 545

To the solution of ethylene glycol (0.130 mL, 2.37 mmol) in THF (10.0 mL), 3-(bromomethyl)pyridine (0.300 g, 1.18 mmol) and sodium hydride (71.1 mg, 1.78 mmol) were used to carry out the reaction. After the reaction mixture was stirred at 80° C. for 16 h and work-up, the residue was purified by Isco Combi-Flash Companion column chromatography (0-100% ethyl acetate in n-hexane) to give 2-(pyridin-3-ylmethoxy)ethanol (61.3 mg, 19%). ¹H NMR (CDCl₃, 300 MHz) δ 8.58 (s, 1H), 8.55 (d, 1H), 7.70 (d, 1H), 7.30 (dd, 1H), 4.58 (s, 2H), 3.80-3.77 (m, 2H), 3.64-3.61 (m, 2H).

Step 2. Synthesis of 2-(pyridin-3-ylmethoxy)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.130 g, 0.393 mmol), 2-(pyridin-3-ylmethoxy)ethanol (61.3 mg, 0.393 mmol), EDCI • HCl (0.150 g, 0.785 mmol) and CH₂Cl₂ (5.0 mL) were used to carry out the reaction. After the reaction mixture was stirred at room temperature for 16 h and work-up, the residue was purified by Isco Combi-Flash Companion column chromatography (0-90% ethyl acetate in n-hexane) to give less 2-(pyridin-3-ylmethoxy)ethyl 4-[2-(4-fluorophenyl)-4-oxo-1,3-thiazolidin-3-yl]-3-methylbenzoate. ¹H NMR (CDCl₃, 400 MHz) δ 8.58 (s, 1H), 8.54 (br d, 1H), 7.87 (br s, 1H), 7.75 (br s, 1H), 7.67 (d, 1H), 7.31 (dd, 2H), 7.26-7.23 (m, 1H), 6.95 (br t, 2H), 6.10-5.80 (br, 1H), 4.59 (s, 2H), 4.46 (dd, 2H), 4.00 (d, 1H), 3.92 (d, 1H), 3.79 (dd, 2H), 2.20 (br s, 3H); LC-MS (ESI) m/z 467.2 [M+H]⁺.

EXAMPLE 413

2-(Pyridin-3-yloxy)ethyl 4-[2-(4-fluorophenyl)-4-oxo-1,3-thiazolidin-3-yl]-3-methylbenzoate

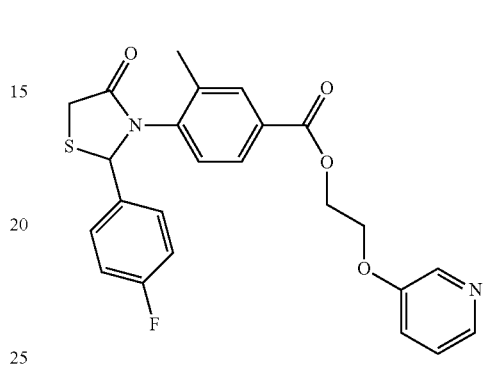

Compound 546

Step 1. Synthesis of 2-(pyridin-3-yloxy)ethanol

Compound 547

To the solution of ethylene glycol (1.90 mL, 3.41 mmol), 3-bromopyridine (0.180 mL, 1.90 mmol), CuCl₂ (12.8 mg, 0.0900 mmol) and K₂CO₃ (0.790 g, 5.70 mmol) were used to carry out the reaction. After the reaction mixture was stirred at 130° C. for 16 h and work-up, the residue was purified by preparative thin layer chromatography plates (1.0 mm of silica gel on glass support, 10% MeOH in CH₂Cl₂) to give 2-(pyridin-3-yloxy)ethanol (67.7 mg, 26%). ¹H NMR (CDCl₃, 300 MHz) δ 8.33 (br s, 1H), 8.24 (br t, 1H), 7.24-7.22 (m, 2H), 4.14 (dd, 2H), 3.99 (dd, 2H).

Step 2. Synthesis of 2-(pyridin-3-yloxy)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.160 g, 0.487 mmol), 2-(pyridin-3-yloxy)ethanol (67.7 mg, 0.487 mmol), EDCI • HCl (0.190 g, 0.967 mmol), DMAP (0.130 g, 1.06 mmol) and CH₂Cl₂ (5.0 mL) were used to carry out the reaction. After the reaction mixture was stirred at room temperature for 16 h and work-up, the residue was purified by preparative thin layer chromatography plates (1.0 mm of silica gel on glass support, 50% ethyl acetate in n-hexane) to give 2-(pyridin-3-yloxy)ethyl 4-[2-(4-fluorophenyl)-4-oxo-1,3-thiazolidin-3-yl]-3-methylbenzoate (0.168 g, 77%). ¹H NMR (CDCl₃, 400 MHz) δ 8.35 (br s, 1H), 8.25 (br s, 1H), 7.86 (br s, 1H), 7.76 (br s, 1H), 7.30 (dd, 2H), 7.24-7.20 (m, 2H), 6.95 (br t, 2H), 5.94 (br s, 1H), 4.67-4.62 (m, 2H), 4.33-4.31 (m, 2H), 4.00 (d, 1H), 3.91 (d, 1H), 2.20 (br s, 3H); LC-MS (ESI) m/z 453.2 [M+H]+.

EXAMPLE 414

2-(Pyridin-2-yloxy)ethyl 4-[2-(4-fluorophenyl)-4-oxo-1,3-thiazolidin-3-yl]-3-methylbenzoate

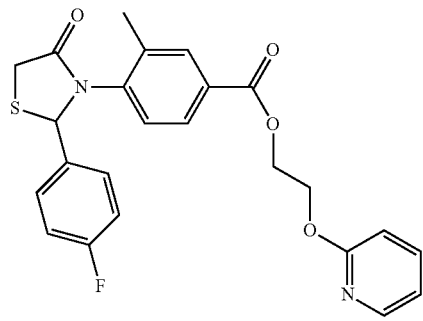

Compound 548

Step 1. Synthesis of 2-(pyridin-2-yloxy)ethanol

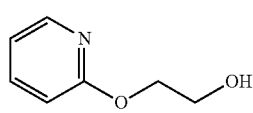

Compound 549

To the solution of ethylene glycol (3.80 mL, 6.84 mmol), 2-bromopyridine (0.360 mL, 3.80 mmol), CuCl$_2$ (25.5 mg, 0.190 mmol) and K$_2$CO$_3$ (1.57 g, 11.4 mmol) were used to carry out the reaction. After the reaction mixture was stirred at 130° C. for 16 h and work-up, the residue was purified by preparative thin layer chromatography plates (1.0 mm of silica gel on glass support, 10% MeOH in CH$_2$Cl$_2$) to give 2-(pyridin-2-yloxy)ethanol (60.6 mg, 12%). $^1$H NMR (CDCl$_3$, 300 MHz) δ 8.11 (d, 1H), 7.60 (dd, 1H), 6.90 (dd, 1H), 6.80 (d, 1H), 4.48-4.45 (m, 2H), 3.96-3.93 (m, 2H), 3.84 (br s, 1H).

Step 2. Synthesis of 2-(pyridin-2-yloxy)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.140 g, 0.436 mmol), 2-(pyridin-2-yloxy)ethanol (60.6 mg, 0.436 mmol), EDCI • HCl (0.170 g, 0.871 mmol), DMAP (0.120 g, 0.950 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(pyridin-2-yloxy)ethyl 4-[2-(4-fluorophenyl)-4-oxo-1,3-thiazolidin-3-yl]-3-methylbenzoate (0.168 g, 88%). $^1$H NMR (CDCl$_3$, 400 MHz) δ 8.12 (br d, 1H), 7.85 (br s, 1H), 7.74 (br s, 1H), 7.58 (dd, 1H), 7.32-7.29 (m, 2H), 6.95 (br t, 2H), 6.87 (dd, 1H), 6.76 (d, 1H), 6.10-5.80 (br s, 1H), 4.64-4.62 (br, 4H), 4.00 (d, 1H), 3.91 (d, 1H), 2.18 (br s, 3H); LC-MS (ESI) m/z 453.2 [M+H]+.

EXAMPLE 415

2-(Pyridin-4-yloxy)ethyl 4-[2-(4-fluorophenyl)-4-oxo-1,3-thiazolidin-3-yl]-3-methylbenzoate

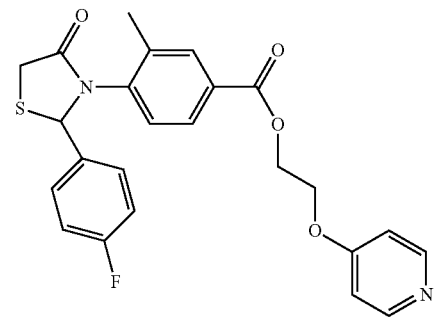

Compound 550

Step 1. Synthesis of 2-(pyridin-4-yloxy)ethanol

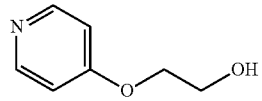

Compound 551

To the solution of ethylene glycol (3.80 mL, 6.84 mmol), 4-bromopyridine (0.360 mL, 3.80 mmol), CuCl$_2$ (20.7 mg, 0.150 mmol) and K$_2$CO$_3$ (1.28 g, 9.26 mmol) were used to carry out the reaction. After the reaction mixture was stirred at 130° C. for 16 h and work-up, the residue was purified by preparative thin layer chromatography plates (1.0 mm of silica gel on glass support, 10% MeOH in CH$_2$Cl$_2$) to give 2-(pyridin-4-yloxy)ethanol (26.9 mg, 6%). 1H NMR (CDCl$_3$, 300 MHz) δ 8.43 (d, 2H), 6.83 (d, 2H), 4.14 (t, 2H), 4.00 (t, 2H).

Step 2. Synthesis of 2-(pyridin-4-yloxy)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (64.0 mg, 0.193 mmol), 2-(pyridin-4-yloxy)ethanol (26.9 mg, 0.193 mmol), EDCI • HCl (74.2 mg, 0.387 mmol), DMAP (52.0 mg, 0.426 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 50% ethyl acetate in n-hexane) to give 2-(pyridin-4-yloxy)ethyl 4-[2-(4-fluorophenyl)-4-oxo-1,3-thiazolidin-3-yl]-3-methylbenzoate (46.7 mg, 53%). $^1$H NMR (CDCl$_3$, 400 MHz) δ 8.44 (d, 2H), 7.86 (br s, 1H), 7.75 (br s, 1H), 7.30 (dd, 2H), 6.95 (br t, 2H), 6.83 (d, 2H), 6.10-5.82 (br, 1H), 4.67-4.62 (m, 2H), 4.32 (t, 2H), 4.00 (d, 1H), 3.92 (d, 1H), 2.20 (br s, 3H); LC-MS (ESI) m/z 453.1 [M+H]+.

EXAMPLE 416

5-(Pyridin-2-ylmethoxy)pentyl 4-[2-(4-fluorophenyl)-4-oxo-1,3-thiazolidin-3-yl]-3-methylbenzoate Compound 552

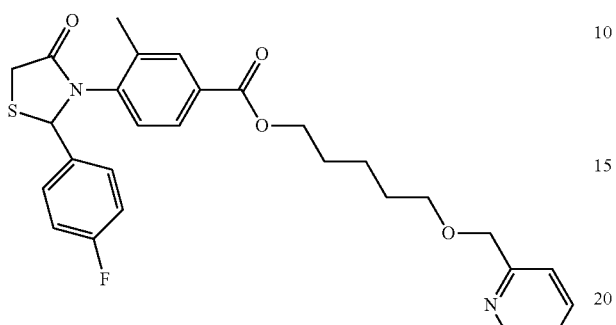

Step 1. Synthesis of [(5-bromopentyl)oxy](tert-butyl)dimethylsilane

Compound 553

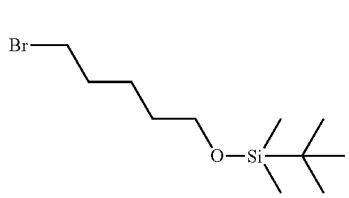

A solution of 5-bromo-1-pentanol (0.80 mL, 6.64 mmol), tert-butyldimethylsilyl chloride (1.20 g, 7.97 mmol) and imidazole (0.542 g, 7.97 mmol) in CH$_2$Cl$_2$ (30 mL) was stirred at room temperature for 18 h. The solution was washed with 1 N HCl$_{(aq)}$, dried over MgSO$_{4(s)}$, filtered, and concentrated to give [(5-bromopentyl)oxy](tert-butyl)dimethylsilane (1.62 g, 87%) as a colorless oil. $^1$H NMR (CDCl$_3$, 400 MHz) δ 3.61 (t, 2H), 3.41 (t, 2H), 1.87 (quint, 2H), 1.57-1.48 (m, 4H), 0.88 (s, 9H), 0.05 (s, 6H).

Step 2. Synthesis of 2-{[(5-{[tert-butyl(dimethyl)silyl]oxy}pentyl)oxy]methyl}pyridine Compound 554

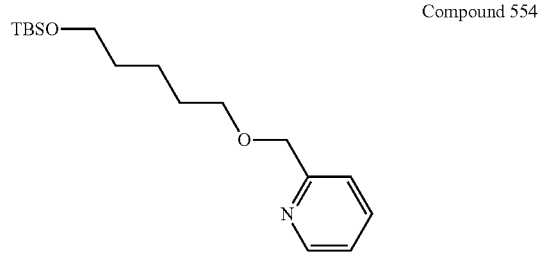 [SMILES: CC(C)(C)[Si](C)(C)OCCCCCOCc1ccccn1]

To a solution of pyridine-2-methanol (194 mg, 1.78 mmol) in THF (10 mL) was added 60% NaH in mineral oil (85.4 mg, 2.14 mmol) at 0° C., and it was stirred for 30 min. Then a solution of [(5-bromopentyl)oxy](tert-butyl)dimethylsilane (550 mg, 1.96 mmol) in THF (3.0 mL) was added to the reaction mixture. The reaction was stirred at room temperature for 16 h. The mixture was quenched with water and extracted with CH$_2$Cl$_2$. The combined organic layers were dried over MgSO$_{4(s)}$, filtered, and concentrated to give 2-{[(5-{[tert-butyl(dimethyl)silyl]oxy}pentyl)oxy]methyl}pyridine (428 mg, 78%) as a yellow oil. $^1$H NMR (CDCl$_3$, 300 MHz) δ 8.54 (dd, 1H), 7.69 (td, 1H), 7.44 (d, 1H), 7.19-7.15 (m, 1H), 4.62 (s, 2H), 3.63-3.54 (m, 2H), 3.41 (t, 2H), 1.70-1.44 (m, 6H), 0.88 (s, 9H), 0.04 (s, 6H).

Step 3. Synthesis of 5-(pyridin-2-ylmethoxy)pentan-1-ol

Compound 555

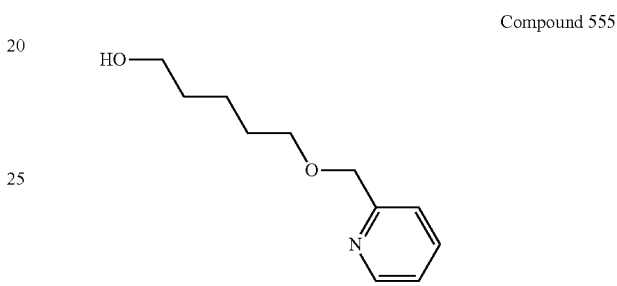

A solution of 2-{[(5-{[tert-butyl(dimethyl)silyl]oxy}pentyl)oxy]methyl}pyridine (0.428 g, 1.38 mmol) in ethanol (5.0 mL) and 12 M HCl$_{(aq)}$ (0.50 mL) was stirred at room temperature for 3 h and then concentrated. The residue was treated with saturated NaHCO$_{3(aq)}$ and extracted with CH$_2$Cl$_2$. The combined organic layers were dried over MgSO$_{4(s)}$, filtered, and concentrated. The crude product was purified by Isco Combi-Flash Companion column chromatography (0-5% methanol in CH$_2$Cl$_2$) to give 5-(pyridin-2-ylmethoxy)pentan-1-ol (116 mg, 51%) as a colorless oil. $^1$H NMR (CDCl$_3$, 300 MHz) δ 8.53 (d, 1H), 7.69 (td, 1H), 7.43 (d, 1H), 7.19-7.15 (m, 1H), 4.62 (s, 2H), 3.65 (t, 2H), 3.57 (t, 2H), 1.73-1.44 (m, 6H).

Step 4. Synthesis of 5-(pyridin-2-ylmethoxy)pentyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (175 mg, 0.528 mmol), 5-(pyridin-2-ylmethoxy)pentan-1-ol (103 mg, 0.528 mmol), EDCI • HCl (152 mg, 0.791 mmol) and CH$_2$Cl$_2$ (3.0 mL) were used to carry out the reaction. After the reaction mixture was stirred at room temperature for 18 h and work-up, the residue was purified by preparative thin layer chromatography plates (2.0 mm of silica gel on glass support, 60% ethyl acetate in n-hexane) to give 5-(pyridin-2-ylmethoxy)pentyl 4-[2-(4-fluorophenyl)-4-oxo-1,3-thiazolidin-3-yl]-3-methylbenzoate (72.7 mg, 27%) as a lightly yellow gum. $^1$H NMR (CDCl$_3$, 400 MHz) δ 8.54 (d, 1H), 7.85 (br s, 1H), 7.74 (br s, 1H), 7.67 (td, 1H), 7.42 (d, 1H), 7.32-7.29 (m, 2H), 7.18 (dd, 1H), 6.95 (br t, 2H), 6.05-5.80 (br, 1H), 4.62 (s, 2H), 4.28 (t, 2H), 4.00 (d, 1H), 3.92 (d, 1H), 3.57 (t, 2H), 2.19 (br s, 3H), 1.80-1.67 (m, 4H), 1.56-1.48 (m, 2H); LC-MS (ESI) m/z 509.3 [M+H]$^+$.

EXAMPLE 417

2-[(Pyridin-3-ylmethyl)sulfanyl]ethyl 4-[2-(4-fluorophenyl)-4-oxo-1,3-thiazolidin-3-yl]-3-methylbenzoate

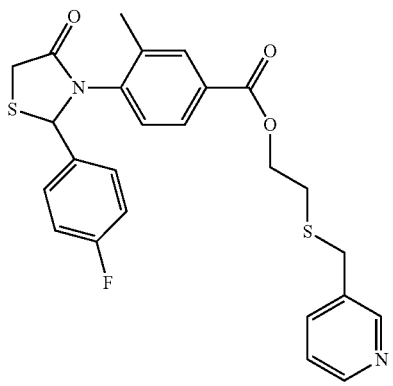

Compound 556

Step 1. Synthesis of 2-[(pyridin-3-ylmethyl)sulfanyl]ethanol

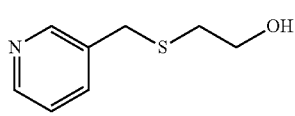

Compound 557

To the solution of 2-mercaptoethanol (0.143 mL, 2.08 mmol) in DMF (5.0 mL), 3-(bromomethyl)pyridine (0.500 g, 1.98 mmol) and Cs$_2$CO$_3$ (0.680 g, 2.08 mmol) were used to carry out the reaction. After the reaction mixture was stirred at 60° C. for 4 h, 6 h at room temperature and work-up, the residue was purified by preparative thin layer chromatography plates (1.0 mm of silica gel on glass support, 75% ethyl acetate in n-hexane) to give 2-[(pyridin-3-ylmethyl)sulfanyl]ethanol (50.0 mg, 17%). $^1$H NMR (CDCl$_3$, 400 MHz) δ 8.51 (s, 1H), 8.49-8.47 (m, 1H), 7.70-7.68 (m, 1H), 7.28-7.25 (m, 1H), 3.73-3.70 (m, 4H), 2.67-2.61 (m, 2H).

Step 2. Synthesis of 2-[(pyridin-3-ylmethyl)sulfanyl]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.100 g, 0.297 mmol), 2-[(pyridin-3-ylmethyl)sulfanyl]ethanol (50.0 mg, 0.327 mmol), EDCI • HCl (0.120 g, 0.604 mmol), DMAP (81.2 mg, 0.664 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-[(pyridin-3-ylmethyl) sulfanyl]ethyl 4-[2-(4-fluorophenyl)-4-oxo-1,3-thiazolidin-3-yl]-3-methylbenzoate (93.3 mg, 64%). $^1$H NMR (CDCl$_3$, 400 MHz) δ 8.55 (s, 1H), 8.50 (dd, 1H), 7.85 (br s, 1H), 7.74 (br d, 1H), 7.69 (dd, 2H), 7.33-7.28 (m, 2H), 7.27-7.21 (m, 1H), 6.97 (br t, 2H), 6.10-5.80 (br, 1H), 4.39 (t, 2H), 4.00 (d, 1H), 3.92 (d, 1H), 3.78 (s, 2H), 2.74 (t, 2H), 2.20 (br s, 3H); LC-MS (ESI) m/z 483.6 [M+H]$^+$.

EXAMPLE 418

2-[(Pyridin-2-ylmethyl)sulfanyl]ethyl 4-[2-(4-fluorophenyl)-4-oxo-1,3-thiazolidin-3-yl]-3-methylbenzoate

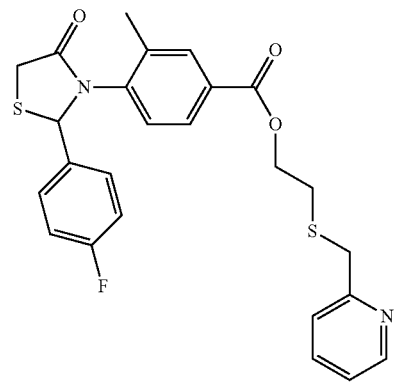

Compound 558

Step 1. Synthesis of 2-[(pyridin-2-ylmethyl)sulfanyl]ethanol

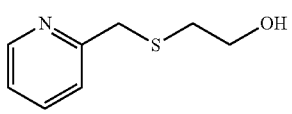

Compound 559

To the solution of 2-mercaptoethanol (0.150 mL, 2.08 mmol) in DMF (5.0 mL), 2-(bromomethyl)pyridine (0.500 g, 1.98 mmol) and Cs$_2$CO$_3$ (0.680 g, 2.08 mmol) were used to carry out the reaction. After the reaction mixture was stirred at 60° C. for 4 h, 6 h at room temperature and work-up, the residue was purified by preparative thin layer chromatography plates (1.0 mm of silica gel on glass support, 75% ethyl acetate in n-hexane) to give 2-[(pyridin-2-ylmethyl)sulfanyl]ethanol (91.5 mg, 30%). $^1$H NMR (CDCl$_3$, 400 MHz) δ 8.53 (dd, 1H), 7.67 (t, 1H), 7.29-7.25 (m, 1H), 7.19 (dd, 1H), 3.91 (s, 2H), 3.86-3.82 (m, 2H), 2.80-2.77 (m, 2H).

Step 2. Synthesis of 2-[(pyridin-2-ylmethyl)sulfanyl]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 2-[(pyridin-2-ylmethyl)sulfanyl]ethanol (91.5 mg, 0.598 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 60% ethyl acetate in n-hexane) to give 2-[(pyridin-2-ylmethyl) sulfanyl]ethyl 4-[2-(4-fluorophenyl)-4-oxo-1,3-thiazolidin-3-yl]-3-methylbenzoate (0.148 g, 57%). $^1$H NMR (CDCl$_3$, 400 MHz) δ 8.52 (dd, 1H), 7.86 (br s, 1H), 7.74 (br s, 1H), 7.64 (t, 1H), 7.36 (d, 1H), 7.32-7.28 (m, 2H), 7.16 (dd, 1H), 6.95 (br t, 2H), 4.38 (t, 2H), 4.00 (d, 1H), 3.94-3.85 (m, 3H), 2.84 (t, 2H), 2.20 (br s, 3H); LC-MS (ESI) m/z 483.6 [M+H]$^+$.

EXAMPLE 419

2-[(Pyridin-4-ylmethyl)sulfanyl]ethyl 4-[2-(4-fluorophenyl)-4-oxo-1,3-thiazolidin-3-yl]-3-methylbenzoate Compound 560

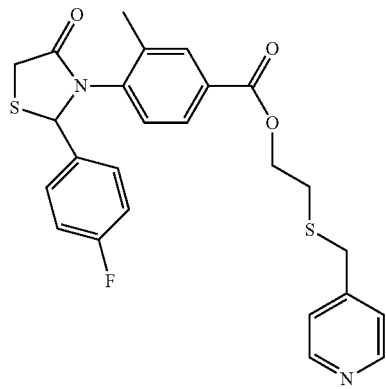

Step 1. Synthesis of 2-[(pyridin-4-ylmethyl)sulfanyl]ethanol

Compound 561

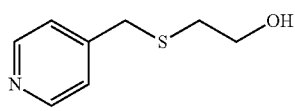

To the solution of 2-mercaptoethanol (0.150 mL, 2.08 mmol) in DMF (5.0 mL), 4-(bromomethyl)pyridine (0.500 g, 1.98 mmol) and Cs$_2$CO$_3$ (0.680 g, 2.08 mmol) were used to carry out the reaction. After the reaction mixture was stirred at 60° C. for 4 h, 6 h at room temperature and work-up, the residue was purified by preparative thin layer chromatography plates (1.0 mm of silica gel on glass support, 80% ethyl acetate in n-hexane) to give 2-[(pyridin-4-ylmethyl)sulfanyl]ethanol (61.0 mg, 20%). $^1$H NMR (CDCl$_3$, 400 MHz) δ 8.55 (dd, 2H), 7.27-7.26 (m, 2H), 3.73-3.70 (m, 4H), 2.63 (t, 2H).

Step 2. Synthesis of 2-[(pyridin-4-ylmethyl)sulfanyl]ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.120 g, 0.362 mmol), 2-[(pyridin-4-ylmethyl)sulfanyl]ethanol (61.0 mg, 0.398 mmol), EDCI • HCl (0.140 g, 0.725 mmol), DMAP (97.4 mg, 0.797 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 50% ethyl acetate in n-hexane) to give 2-[(pyridin-4-ylmethyl) sulfanyl]ethyl 4-[2-(4-fluorophenyl)-4-oxo-1,3-thiazolidin-3-yl]-3-methylbenzoate (92.2 mg, 53%). $^1$H NMR (CDCl$_3$, 400 MHz) δ 8.55 (dd, 2H), 7.85 (br s, 1H), 7.73 (br s, 1H), 7.33-7.28 (m, 2H), 7.27-7.26 (m, 2H), 6.95 (br t, 2H), 6.08-5.80 (br, 1H), 4.39 (t, 2H), 4.01 (d, 1H), 3.92 (d, 1H), 3.72 (s, 2H), 2.73 (t, 2H), 2.20 (br s, 3H); LC-MS (ESI) m/z 483.5 [M+H]$^+$.

EXAMPLE 420

2-(Pyridin-4-ylsulfanyl)ethyl 4-[2-(4-fluorophenyl)-4-oxo-1,3-thiazolidin-3-yl]-3-methylbenzoate Compound 562

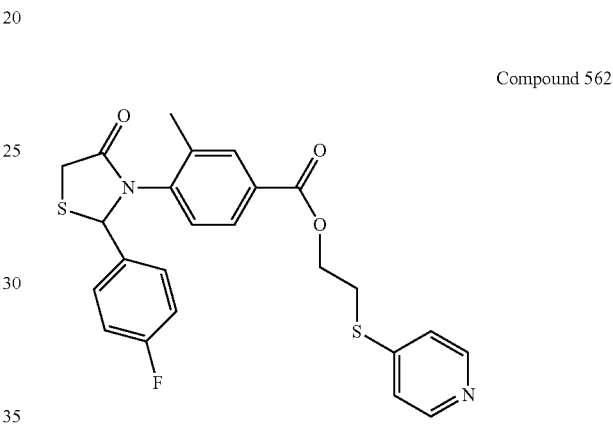

Step 1. Synthesis of 2-(pyridin-4-ylsulfanyl)ethanol

Compound 563

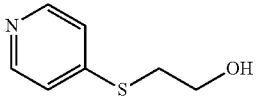

To the solution of 4-mercaptopyridine (0.300 g, 2.70 mmol) in H$_2$O (30.0 mL), 2-chloroethanol (0.200 mL, 2.97 mmol) and sodium hydride (0.300 g, 8.10 mmol) were used to carry out the reaction. After the reaction mixture was stirred at room temperature for 1 h and work-up, the residue was used directly for next step without further purification (0.310 g, curde yield 74%). $^1$H NMR (CDCl$_3$, 400 MHz) δ 8.42-8.38 (m, 2H), 7.17-7.14 (m, 2H), 3.90-3.87 (m, 2H), 3.22-3.19 (m, 2H).

Step 2. Synthesis of 2-(pyridin-4-ylsulfanyl)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 2-(pyridin-4-ylsulfanyl)ethanol (84.0 mg, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 60% ethyl acetate in n-hexane) to give 2-(pyridin-4-ylsulfanyl)ethyl 4-[2-(4-fluorophenyl)-4-oxo-1,3-thiazolidin-3-yl]-3-methylbenzoate (0.180 g, 71%). $^1$H NMR (CDCl$_3$, 400 MHz) δ 8.41 (d, 2H), 7.81 (br s, 1H), 7.68 (br d, 1H), 7.31 (dd, 2H), 7.20 (d, 2H), 6.96 (br t, 2H), 4.53-4.47 (m, 2H), 4.00 (d, 1H), 3.92 (d, 1H), 3.32 (t, 2H), 2.19 (br s, 3H); LC-MS (ESI) m/z 469.6 [M+H]$^+$.

EXAMPLE 421

2-(Pyridin-2-ylsulfanyl)ethyl 4-[2-(4-fluorophenyl)-4-oxo-1,3-thiazolidin-3-yl]-3-methylbenzoate Compound 564

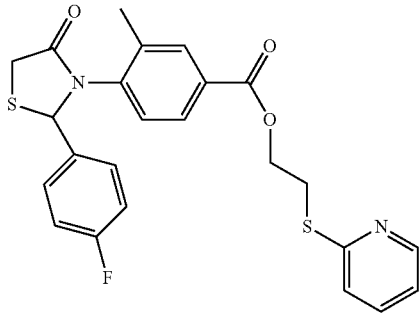

Step 1. Synthesis of 2-(pyridin-2-ylsulfanyl)ethanol

Compound 565

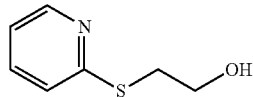

To the solution of 2-mercaptopyridine (0.300 g, 2.70 mmol) in H$_2$O (30.0 mL), 2-chloroethanol (0.200 mL, 2.97 mmol) and sodium hydride (0.300 g, 8.10 mmol) were used to carry out the reaction. After the reaction mixture was stirred at room temperature for 1 h and work-up, the residue was used directly for next step without further purification (0.360 g, crude yield 86%). $^1$H NMR (CDCl$_3$, 400 MHz) δ 8.38-8.37 (m, 1H), 7.51 (t, 1H), 7.29 (d, 1H), 7.04 (dd, 1H), 3.97 (t, 2H), 3.32 (t, 2H).

Step 2. Synthesis of 2-(pyridin-2-ylsulfanyl)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 2-(pyridin-2-ylsulfanyl)ethanol (92.7 mg, 0.598 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give 2-(pyridin-2-ylsulfanyl)ethyl 4-[2-(4-fluorophenyl)-4-oxo-1,3-thiazolidin-3-yl]-3-methylbenzoate (0.120 g, 47%). $^1$H NMR (CDCl$_3$, 400 MHz) δ 8.39 (d, 2H), 7.82 (br s, 1H), 7.70 (br d, 1H), 7.46 (dd, 1H), 7.33-7.28 (m, 2H), 7.22-7.17 (m, 1H), 7.04-6.93 (m, 3H), 5.95 (br s, 1H), 4.50 (t, 2H), 4.00 (d, 1H), 3.93 (d, 1H), 3.54 (t, 2H), 2.20 (br s, 3H); LC-MS (ESI) m/z 469.5 [M+H]$^+$.

EXAMPLE 422

2-(Pyridin-3-ylsulfanyl)ethyl 4-[2-(4-fluorophenyl)-4-oxo-1,3-thiazolidin-3-yl]-3-methylbenzoate Compound 566

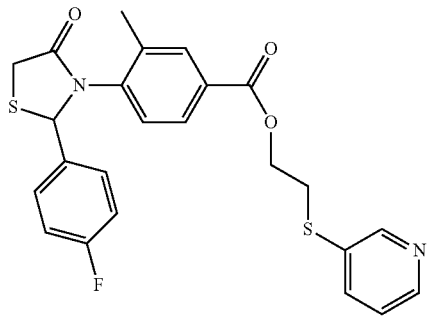

Step. Synthesis of 2-(pyridin-3-ylsulfanyl)ethanol

Compound 567

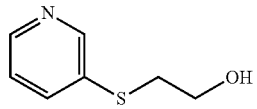

To the solution of 3-mercaptopyridine (39.0 mg, 0.350 mmol) in H$_2$O (5.0 mL), 2-chloroethanol (26.0 μL, 0.386 mmol) and sodium hydride (42.0 mg, 1.05 mmol) were used to carry out the reaction. After the reaction mixture was stirred at room temperature for 1 h and work-up, the residue was used directly for next step without further purification (5.00 mg, crude yield 9%). $^1$H NMR (CDCl$_3$, 400 MHz) δ 8.63 (s, 1H), 8.46 (d, 1H), 7.73 (dd, 1H), 7.25-7.22 (m, 1H), 3.80-3.76 (m, 2H), 3.13 (t, 2H).

Step 2. Synthesis of 2-(pyridin-3-ylsulfanyl)ethyl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (10.7 mg, 0.0320 mmol), 2-(pyridin-3-ylsulfanyl)ethanol (5.00 mg, 0.0320 mmol), EDCI • HCl (12.4 mg, 0.0640 mmol), DMAP (8.70 mg, 0.0710 mmol) and CH$_2$Cl$_2$ (5.0 mL) were used to carry out the reaction. After the reaction mixture was stirred at room temperature for 16 h and work-up, the residue was purified by preparative thin layer chromatography plates (1.0 mm of silica gel on glass support, 30% ethyl acetate in n-hexane) to give 2-(pyridin-3-ylsulfanyl)ethyl 4-[2-(4-fluorophenyl)-4-oxo-1,3-thiazolidin-3-yl]-3-methylbenzoate (15.0 mg, 99%). $^1$H NMR (CDCl$_3$, 400 MHz) δ 8.65 (br s, 1H), 8.42 (br d, 1H), 7.77 (br s, 1H), 7.72 (br d, 1H), 7.67 (br s, 1H), 7.33-7.28 (m, 2H), 7.20-7.17 (m, 1H), 6.98-6.94 (m, 2H), 5.95 (br s, 1H), 4.48-4.42 (m, 2H), 3.99 (d, 1H), 3.92 (d, 1H), 3.28-3.23 (m, 2H), 2.20 (br s, 3H); LC-MS (ESI) m/z 469.1 [M+H]$^+$.

EXAMPLE 423

2-(Pyridin-4-ylamino)ethyl 4-[2-(4-fluorophenyl)-4-oxo-1,3-thiazolidin-3-yl]-3-methylbenzoate Compound 568

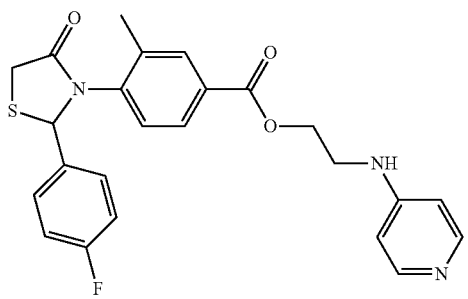

Step 1. Synthesis of tert-butyl (2-hydroxyethyl)pyridin-4-ylcarbamate

Compound 569

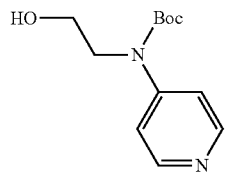

A solution of 2-[(pyridine-4-yl)amino]ethan-1-ol (352 mg, 2.55 mmol) and di-tert-butyl dicarbonate (429 mg, 2.55 mmol) in ethanol (6.0 mL) was stirred at room temperature for 16 h. The solution was concentrated under reduced pressure. The residue was purified by Isco Combi-Flash Companion column chromatography (0-10% methanol in CH$_2$Cl$_2$) to give tert-butyl (2-hydroxyethyl)pyridin-4-ylcarbamate (209 mg, 34%) as a colorless gum. $^1$H NMR (CDCl$_3$, 400 MHz) δ 8.21 (d, 2H), 6.46 (d, 2H), 4.54 (br s, 1H), 4.27 (t, 2H), 3.46 (q, 2H), 1.49 (s, 9H).

Step 2. Synthesis of 2-[(tert-butoxycarbonyl)(pyridin-4-yl)amino]ethyl 4-[2-(4-fluorophenyl)-4-oxo-1,3-thiazolidin-3-yl]-3 methylbenzoate.

Compound 570

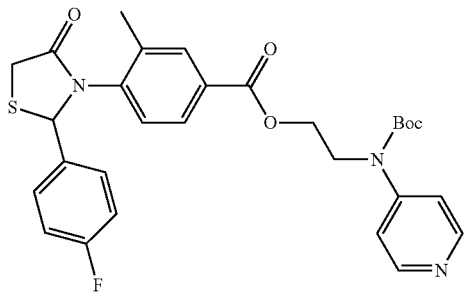

Following standard procedure G, 4-[2-(4-fluorophenyl)-4-oxo-1,3-thiazolidin-3-yl]-3-methylbenzoic acid (163 mg, 0.492 mmol), tert-butyl (2-hydroxyethyl)pyridin-4-ylcarbamate (117 mg, 0.492 mmol), EDCI • HCl (141 mg, 0.738 mmol) and CH$_2$Cl$_2$ (2.0 mL) were used to carry out the reaction. After the reaction mixture was treated with CH$_2$Cl$_2$ and washed with H$_2$O. The organic layer was dried over MgSO$_{4(s)}$, filtered, and concentrated to give 2-[(tert-butoxycarbonyl)(pyridin-4-yl)amino]ethyl 4-[2-(4-fluorophenyl)-4-oxo-1,3-thiazolidin-3-yl]-3-methylbenzoate which was directly used to next step without further purification. $^1$H NMR (CDCl$_3$, 400 MHz) δ 8.38 (d, 2H), 7.22 (dd, 2H), 6.94 (t, 2H), 6.87 (d, 2H), 6.00-5.80 (br, 1H), 4.35 (t, 2H), 4.14 (t, 2H), 3.94 (d, 1H), 3.86 (d, 1H), 2.05 (br s, 3H), 1.41 (s, 9H); LC-MS (ESI) m/z 552.2 [M+H]$^+$.

Step 3. Synthesis of 2-(pyridin-4-ylamino)ethyl 4-[2-(4-fluorophenyl)-4-oxo-1,3-thiazolidin-3-yl]-3-methylbenzoate A solution of 2-[(tert-butoxycarbonyl)(pyridin-4-yl)amino]ethyl 4-[2-(4-fluorophenyl)-4-oxo-1,3-thiazolidin-3-yl]-3-methylbenzoate (0.492 mmol) in trifluoroacetic acid (2.50 mL) and CH$_2$Cl$_2$ (8.0 mL) was stirred at room temperature for 8 h. The solution was concentrated under reduced pressure. The residue was purified by preparative thin layer chromatography plates (1.0 mm of silica gel on glass support, 8% methanol in CH$_2$Cl$_2$) to give 2-(pyridin-4-ylamino)ethyl 4-[2-(4-fluorophenyl)-4-oxo-1,3-thiazolidin-3-yl]-3-methylbenzoate (126 mg, 57% by two steps) as a white solid. $^1$H NMR (CDCl$_3$, 400 MHz) δ 8.19 (d, 2H), 7.83 (br s, 1H), 7.72 (br s, 1H), 7.33-7.29 (m, 2H), 6.96 (br t, 2H), 6.49 (d, 2H), 6.10-5.80 (br, 1H), 4.65 (br s, 1H), 4.48 (t, 2H), 4.00 (d, 1H), 3.92 (d, 1H), 3.55 (q, 2H), 2.19 (br s, 3H); LC-MS (ESI) m/z 452.2 [M+H]$^+$.

EXAMPLE 424

2-(Pyridin-2-ylamino)ethyl 4-[2-(4-fluorophenyl)-4-oxo-1,3-thiazolidin-3-yl]-3-methylbenzoate Compound 571

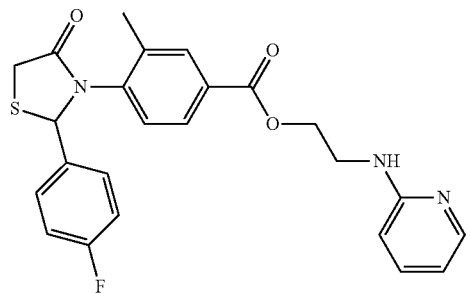

Step 1. Synthesis of tert-butyl (2-hydroxyethyl)pyridin-2-ylcarbamate

Compound 572

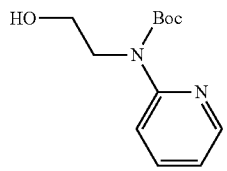

A solution of 2-[(pyridine-2-yl)amino]ethan-1-ol (256 mg, 1.87 mmol), triethylamine (0.260 mL, 1.87 mmol), and di-tert-butyl dicarbonate (556 mg, 1.97 mmol) in CH$_2$Cl$_2$ (10 mL) was stirred at room temperature for 16 h. The solution was diluted with CH$_2$Cl$_2$ and washed with H$_2$O and brine. The organic layer was dried over MgSO$_{4(s)}$, filtered, and concentrated to give tert-butyl (2-hydroxyethyl)pyridin-2-ylcarbamate (347 mg, 78%) as a colorless oil which was directly used to next step without further purification. $^1$H NMR (CDCl$_3$, 400 MHz) δ 8.08 (dd, 1H), 7.42-7.37 (m, 1H), 6.59-6.57 (m, 1H), 6.41 (dd, 1H), 4.74 (br s, 1H), 4.26 (t, 2H), 3.63 (q, 2H), 1.48 (s, 9H).

Step 2. Synthesis of 2-[(tert-butoxycarbonyl)(pyridin-2-yl)amino]ethyl 4-[2-(4-fluorophenyl)-4-oxo-1,3-thiazolidin-3-yl]-3-methylbenzoate Compound 573

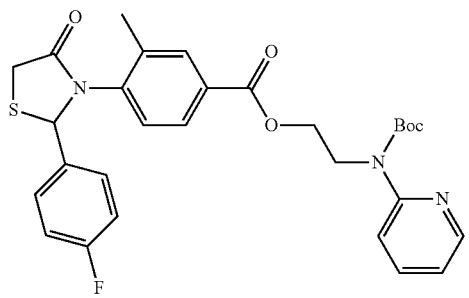

A solution of 4-[2-(4-fluorophenyl)-4-oxo-1,3-thiazolidin-3-yl]-3-methylbenzoic acid (178 mg, 0.537 mmol) in thionyl chloride (2.0 mL) was stirred at 80° C. for 40 min. Thionyl chloride was removed under reduced pressure to afford a acyl chloride intermediate which was directly used to next step without further purification. To a solution of acyl chloride (0.537 mmol) in CH$_2$Cl$_2$ (5.0 mL) was added triethylamine (75.0 μL, 0.537 mmol) and tert-butyl (2-hydroxyethyl)pyridin-2-ylcarbamate (128 mg, 0.537 mmol), and the solution was stirred at room temperature for 8 h. After the reaction mixture was concentrated, the residue was purified by preparative thin layer chromatography plates (1.0 mm of silica gel on glass support, 70% ethyl acetate in n-hexane) to give 2-[(tert-butoxycarbonyl)(pyridin-2-yl)amino]ethyl 4-[2-(4-fluorophenyl)-4-oxo-1,3-thiazolidin-3-yl]-3-methylbenzoate (189 mg, 64% by two steps) as a lightly brown solid. $^1$H NMR (CDCl$_3$, 400 MHz) δ 8.36 (d, 1H), 7.36 (dd, 1H), 7.24-7.20 (m, 4H), 7.03-7.00 (m, 1H), 6.92 (t, 2H), 6.67 (d, 1H), 6.00-5.70 (br, 1H), 4.37-4.31 (m, 4H), 3.94 (d, 1H), 3.86 (d, 1H), 2.04 (br s, 3H), 1.40 (s, 9H).

Step 3. Synthesis of 2-(pyridin-2-ylamino)ethyl 4-[2-(4-fluorophenyl)-4-oxo-1,3-thiazolidin-3-yl]-3-methylbenzoate A solution of 2-[(tert-butoxycarbonyl)(pyridin-2-yl)amino]ethyl 4-[2-(4-fluorophenyl)-4-oxo-1,3-thiazolidin-3-yl]-3-methylbenzoate (189 mg, 0.343 mmol) in trifluoroacetic acid (2.0 mL) and CH$_2$Cl$_2$ (8.0 mL) was stirred at room temperature for 5 h. The solution was concentrated under reduced pressure. The residue was purified by preparative thin layer chromatography plates (1.0 mm of silica gel on glass support, 5% methanol in CH$_2$Cl$_2$) to give 2-(pyridin-2-ylamino)ethyl 4-[2-(4-fluorophenyl)-4-oxo-1, 3-thiazolidin-3-yl]-3-methylbenzoate (132 mg, 85%) as a yellow foam. $^1$H NMR (CDCl$_3$, 400 MHz) δ 8.07 (d, 1H), 7.84 (br s, 1H), 7.74 (br s, 1H), 7.41 (dd, 1H), 7.32-7.29 (m, 2H), 6.96 (br t, 2H), 6.59 (dd, 1H), 6.44 (d, 1H), 6.10-5.80 (br, 1H), 4.86 (br s, 1H), 4.47 (t, 2H), 4.00 (d, 1H), 3.92 (d, 1H), 3.70 (q, 2H), 2.17 (br s, 3H); LC-MS (ESI) m/z 452.2 [M+H]$^+$.

EXAMPLE 425

2-(1-Methyl-1H-imidazol-5-yl)ethyl 4-[2-(4-fluorophenyl)-4-oxo-1,3-thiazolidin-3-yl]-3-methylbenzoate Compound 574

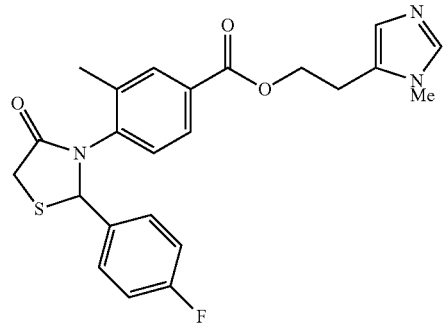

Following standard procedure G, 4-[2-(4-fluorophenyl)-4-oxo-1,3-thiazolidin-3-yl]-3-methylbenzoic acid (147 mg, 0.444 mmol), 2-(1-methyl-1H-imidzol-5-yl)ethan-1-ol (56.0 mg, 0.444 mmol), EDCI • HCl (128 mg, 0.665 mmol), triethylamine (0.124 mL, 0.890 mmol), and CH$_2$Cl$_2$ (5.0 mL) were used to carry out the reaction. After the reaction mixture was stirred at room temperature for 18 h and work-up, the residue was purified by Isco Combi-Flash Companion column chromatography (0-10% MeOH in CH$_2$Cl$_2$) to give 2-(1-methyl-1H-imidazol-5-yl)ethyl 4-[2-(4-fluorophenyl)-4-oxo-1,3-thiazolidin-3-yl]-3-methylbenzoate (74.3 mg, 38%) as a white foam. $^1$H NMR (CDCl$_3$, 400 MHz) δ 7.83 (br s, 1H), 7.72 (br s, 1H), 7.41 (s, 1H), 7.32-7.28 (m, 2H), 6.95 (br t, 2H), 6.89 (s, 1H), 6.10-5.80 (br, 1H), 4.48 (t, 2H), 4.00 (d, 1H), 3.91 (d, 1H), 3.58 (s, 3H), 2.99 (t, 2H), 2.19 (br s, 3H); LC-MS (ESI) m/z 440.2 [M+H]$^+$.

EXAMPLE 426

2-(1-Methyl-1H-imidazol-2-yl)ethyl 4-[2-(4-fluorophenyl)-4-oxo-1,3-thiazolidin-3-yl]-3-methylbenzoate Compound 575

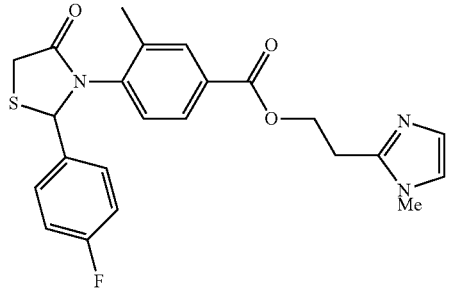

Following standard procedure G, 4-[2-(4-fluorophenyl)-4-oxo-1,3-thiazolidin-3-yl]-3-methylbenzoic acid (158 mg, 0.477 mmol), 2-(1-methyl-1H-imidazol-2-yl)ethan-1-ol (60.2 mg, 0.477 mmol), EDCI • HCl (119 mg, 0.621 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-10% MeOH in CH$_2$Cl$_2$) to give 2-(1-methyl-1H-imidazol-2-yl)ethyl 4-[2-(4-fluorophenyl)-4-oxo-1,3-thiazolidin-3-yl]-3-methylbenzoate (116 mg, 55%) as a yellow solid. $^1$H NMR (CDCl$_3$, 400 MHz) δ 7.84 (br s, 1H), 7.71 (br s, 1H), 7.32-7.28 (m, 2H), 6.97-6.93 (m, 3H), 6.81 (s, 1H), 6.10-5.80 (br, 1H), 4.64 (t, 2H), 4.00 (d, 1H), 3.91 (d, 1H), 3.60 (s, 3H), 3.11 (t, 2H), 2.17 (br s, 3H); LC-MS (ESI) m/z 440.2 [M+H]$^+$.

EXAMPLE 427

Ethyl 4-[2-(3,4-difluorophenyl)-4-oxo-1,3-thiazolidin-3-yl]-3-methylbenzoate

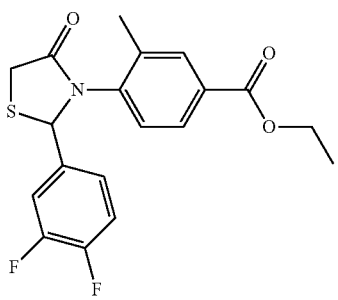

Compound 576

Step 1. Synthesis of ethyl 4-{[(3,4-difluorophenyl)methylidene]amino}-3-methylbenzoate

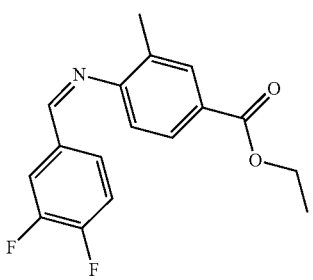

Compound 577

A solution of ethyl 4-amino-3-methylbenzoate (0.706 g, 3.94 mmol) and 3,4-difluorobenzaldehye (1.00 mL, 9.08 mmol) in ethanol (10 mL) was stirred at reflux for 18 h and cooled to room temperature. The crude was washed with diethyl ether/n-hexane (1:20) to give ethyl 4-{[(3,4-difluorophenyl)methylidene]amino}-3-methylbenzoate (0.986 g, 83%) as an orange solid. $^1$H NMR (CDCl$_3$, 400 MHz) δ 8.28 (s, 1H), 7.91-7.81 (m, 3H), 7.62-7.59 (m, 1H), 7.31-7.27 (m, 1H), 6.91 (d, 1H), 4.38 (q, 2H), 2.36 (s, 3H), 1.40 (t, 3H).

Step 2. Synthesis of ethyl 4-[2-(3,4-difluorophenyl)-4-oxo-1,3-thiazolidin-3-yl]-3-methylbenzoate A solution of ethyl 4-{[(3,4-difluorophenyl)methylidene]amino}-3-methylbenzoate (511 mg, 1.68 mmol) and 2-mercaptoacetic acid (0.150 mL, 2.15 mmol) in toluene (15 mL) was stirred at 100° C. for 18 h. The solution was cooled to room temperature and diluted with ethyl acetate. The organic layer was washed with 10% NaOH$_{(aq)}$ and 2N HCl$_{(aq)}$, dried over MgSO$_{4(s)}$, filtered, and concentrated. The residue was purified by Isco Combi-Flash Companion column chromatography (0-40% ethyl acetate in n-hexane) to give ethyl 4-[2-(3,4-difluorophenyl)-4-oxo-1,3-thiazolidin-3-yl]-3-methylbenzoate (137 mg, 22%) as a yellow gum. $^1$HNMR (CDCl$_3$, 400 MHz) δ 7.88 (br s, 1H), 7.77 (br s, 1H), 7.22 (t, 1H), 7.07-6.99 (m, 2H), 6.10-5.80 (br, 1H), 4.33 (q, 2H), 4.01 (d, 1H), 3.92 (d, 1H), 2.20 (br s, 3H), 1.37 (t, 3H); LC-MS (ESI) m/z 378.2 [M+H]$^+$.

EXAMPLE 428

Methyl 4-{2-[4-fluoro-2,3,5,6-d$_4$-phenyl]-4-oxo-1,3-thiazolidin-3-yl}-3-methylbenzoate

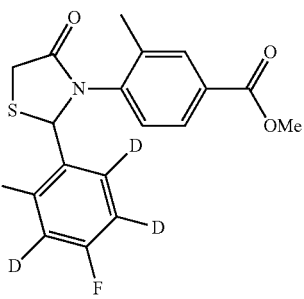

Compound 578

A solution of methyl 4-amino-3-methylbenzoate (0.846 g, 5.12 mmol), Na$_2$SO$_4$ anhydrous (1.46 g, 10.2 mmol), and 4-fluorobenzaldehyde-2,3,5,6-d$_4$ (0.722 g, 5.63 mmol) in toluene (30 mL) was reflux for 24 h. Then 2-mercaptoacetic acid (0.840 mL, 12.0 mmol) was added to the reaction mixture, and it was stirred at 100° C. for 16 h. The reaction mixture was cooled to room temperature and diluted with ethyl acetate. The solution was washed with 10% NaOH$_{(aq)}$ and 3 N HCl$_{(aq)}$. The organic layer was dried over MgSO$_{4(s)}$, filtered, and concentrated. The residue was purified by Isco Combi-Flash Companion column chromatography (0-30% ethyl acetate in n-hexane) to give methyl 4-{2-[4-fluoro-2,3,5,6-d$_4$-phenyl]-4-oxo-1,3-thiazolidin-3-yl}-3-methylbenzoate (0.503 g, 29%) as a white foam. $^1$H NMR (CDCl$_3$, 400 MHz) δ 7.86 (br s, 1H), 7.74 (br d, 1H), 7.10-6.80 (br, 1H), 6.10-5.80 (br, 1H), 4.01 (d, 1H), 3.93 (d, 1H), 3.87 (s, 3H), 2.17 (br s, 3H); LC-MS (ESI) m/z 350.1 [M+H]$^+$.

EXAMPLE 429

4-{2-[4-Fluoro-2,3,5,6-d$_4$-phenyl]-4-oxo-1,3-thiazolidin-3-yl}-3-methylbenzoic acid

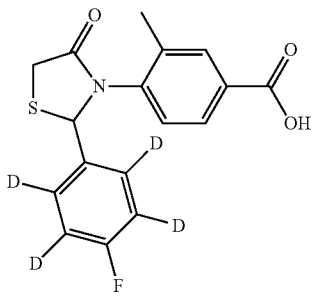

Compound 579

A solution of methyl 4-{2-[4-fluoro-2,3,5,6-d$_4$-phenyl]-4-oxo-1,3-thiazolidin-3-yl}-3-methylbenzoate (0.498 g, 1.43 mmol) in 10% NaOH$_{(aq)}$ (8.0 mL) and methanol (25 mL) was stirred at room temperature for 2 h. Methanol was removed under reduced pressure. The residue was acidified by 2 N HCl$_{(aq)}$ and extracted with ethyl acetate. The combined organic layers were dried over MgSO$_{4(s)}$, filtered, and concentrated give 4-{2-[4-fluoro-2,3,5,6-d$_4$-phenyl]-4-oxo-1,3-thiazolidin-3-yl}-3-methylbenzoic acid (0.407 g, 85%) as a gum. $^1$H NMR (CDCl$_3$, 400 MHz) δ 7.89 (br s, 1H), 7.77 (br s, 1H), 7.10-6.80 (br, 1H), 6.10-5.80 (br, 1H), 4.02 (d, 1H), 3.94 (d, 1H), 2.21 (br s, 3H); LC-MS (ESI) m/z 336.2 [M+H]$^+$.

EXAMPLE 430

Ethyl 4-{2-[4-fluoro-2,3,5,6-d$_4$-phenyl]-4-oxo-1,3-thiazolidin-3-yl}-3-methylbenzoate

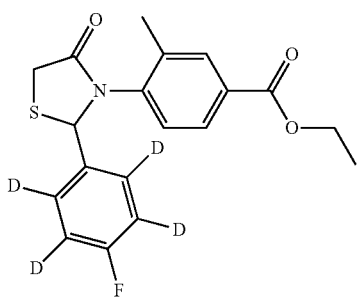

Compound 580

Following standard procedure G, 4-{2-[4-fluoro-2,3,5,6-d$_4$-phenyl]-4-oxo-1,3-thiazolidin-3-yl}-3-methylbenzoic acid (187 mg, 0.558 mmol), ethanol (0.50 mL), DMAP (136 mg, 1.12 mmol), EDCI • HCl (160 mg, 0.836 mmol) and CH$_2$Cl$_2$ (5.0 mL) were used to carry out the reaction. After the reaction mixture was stirred at room temperature for 16 h and concentrated, the residue was purified by preparative thin layer chromatography plates (2.0 mm of silica gel on glass support, 30% ethyl acetate in n-hexane) to give ethyl 4-{2-[4-fluoro-2,3,5,6-d$_4$-phenyl]-4-oxo-1,3-thiazolidin-3-yl}-3-methylbenzoate (153 mg, 75%) as a white foam. $^1$H NMR (CDCl$_3$, 400 MHz) δ 7.86 (br s, 1H), 7.74 (br d, 1H), 7.10-6.70 (br, 1H), 6.10-5.80 (br, 1H), 4.32 (q, 2H), 4.01 (d, 1H), 3.92 (d, 1H), 2.17 (br s, 3H), 1.35 (t, 2H); LC-MS (ESI) m/z 364.2 [M+H]$^+$.

EXAMPLE 431

4-[2-(4-Fluorophenyl)-4-oxo-2-d$_1$-1,3-thiazolidin-3-yl]-3-methylbenzoic acid

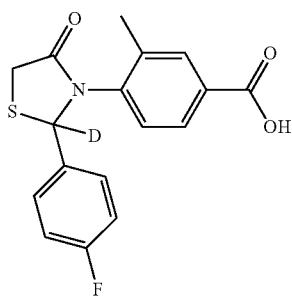

Compound 581

Step 1. Synthesis of methyl 4-[2-(4-fluorophenyl)-4-oxo-2-d1-1,3-thiazolidin-3-yl]-3-methylbenzoate

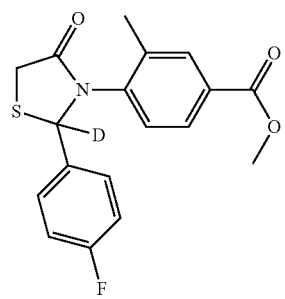

Compound 582

A solution of methyl 4-amino-3-methylbenzoate (390 mg, 2.36 mmol), Na$_2$SO$_4$ anhydrous (503 mg, 3.54 mmol), and 4-fluorobenaldehyde-d$_1$ (325 mg, 2.60 mmol) in toluene (10 mL) was reflux for 18 h. Then 2-mercaptoacetic acid (0.296 mL, 4.24 mmol) was added to the reaction mixture, and it was stirred at 90-100° C. for 18 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by Isco Combi-Flash Companion column chromatography (0-30% ethyl acetate in n-hexane) to give methyl 4-[2-(4-fluorophenyl)-4-oxo-2-d$_1$-1,3-thiazolidin-3-yl]-3-methylbenzoate (152 mg, 19%) as a lightly yellow foam. $^1$H NMR (CDCl$_3$, 400 MHz) δ 7.86 (br s, 1H), 7.73 (br s, 1H), 7.30 (dd, 2H), 6.95 (br t, 2H), 4.00 (d, 1H), 3.92 (d, 1H), 3.87 (s, 3H), 2.19 (br s, 3H); LC-MS (ESI) m/z 347.1 [M+H]$^+$.

Step 2. Synthesis of 4-[2-(4-fluorophenyl)-4-oxo-2-d$_1$-1,3-thiazolidin-3-yl]-3-methylbenzoic acid A solution of methyl 4-[2-(4-fluorophenyl)-4-oxo-2-d$_1$-1,3-thiazolidin-3-yl]-3-methylbenzoate (125 mg, 0.361 mmol) in 10% NaOH$_{(aq)}$ (1.0 mL) and methanol (5.0 mL) was stirred at room temperature for 2 h. Methanol was removed under reduced pressure. The residue was acidified by 2 N HCl$_{(aq)}$ and extracted with ethyl acetate. The combined organic layers were dried over MgSO$_{4(s)}$, filtered, and concentrated. The residue was purified by preparative thin layer chromatography plates (1.0 mm of silica gel on glass support, 100% ethyl acetate) to give 4-[2-(4-fluorophenyl)-4-oxo-2-d$_1$-1,3-thiazolidin-3-yl]-3-methylbenzoic acid (101 mg, 84%) as a white solid. $^1$H NMR (CDCl$_3$, 400 MHz) δ 7.86 (br s, 1H), 7.74 (br s, 1H), 7.30 (dd, 2H), 6.95 (br t, 2H), 4.01 (d, 1H), 3.92 (d, 1H), 2.18 (br s, 3H); LC-MS (ESI) m/z 355.1 [M+Na]$^+$.

EXAMPLE 432

Ethyl 4-[2-(4-fluorophenyl)-4-oxo-2-d$_1$-1,3-thiazolidin-3-yl]-3-methylbenzoate Compound 583

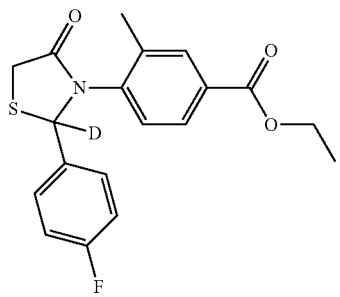

Following standard procedure G, 4-[2-(4-fluorophenyl)-4-oxo-2-d$_1$-1,3-thiazolidin-3-yl]-3-methylbenzoic acid (90.0 mg, 0.271 mmol), ethanol (0.20 mL), DMAP (59.6 mg, 0.488 mmol), EDCI • HCl (77.9 mg, 0.406 mmol) and CH$_2$Cl$_2$ (3.0 mL) were used to carry out the reaction. After the reaction mixture was stirred at room temperature for 8 h and concentrated, the residue was purified by preparative thin layer chromatography plates (1.0 mm of silica gel on glass support, 30% ethyl acetate in n-hexane) to give ethyl 4-[2-(4-fluorophenyl)-4-oxo-2-d$_1$-1,3-thiazolidin-3-yl]-3-methylbenzoate (69.5 mg, 71%) as a white foam. $^1$H NMR (CDCl$_3$, 400 MHz) δ 7.86 (br s, 1H), 7.74 (br s, 1H), 7.32-7.29 (m, 2H), 6.95 (br t, 2H), 4.33 (q, 2H), 4.00 (d, 1H), 3.92 (d, 1H), 2.19 (br s, 3H), 1.35 (t, 3H); LC-MS (ESI) m/z 361.2 [M+H]$^+$.

EXAMPLE 433

6-(Methoxymethyl)pyridin-3-yl 4-[2-(4-fluorophenyl)-4-oxo-1,3-thiazolidin-3-yl]-3-methylbenzoate Compound 584

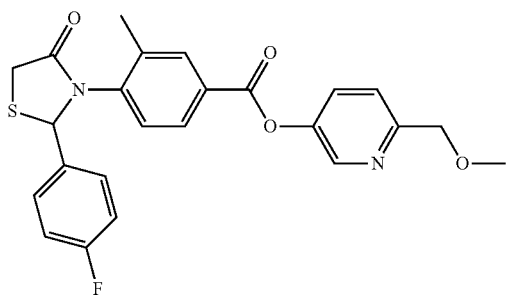

Step 1. Synthesis of 5-(benzyloxy)-2-(methoxymethyl)pyridine

Compound 585

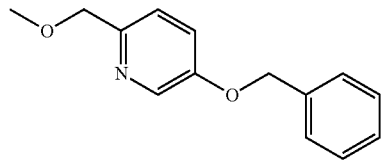

To a solution of (5-(benzyloxy)pyridin-2-yl)methanol (0.300 g, 1.39 mmol) in THF (10.0 mL), sodium hydride (40.0 mg, 1.67 mmol) was added. The reaction mixture was stirred at 0° C. for 3 mins, followed by adding methyl iodide (96.0 μL, 1.53 mmol) and stirred at room temperature for 3 h. The result mixture was extracted with ethyl acetate, dried over MgSO$_{4(s)}$, filtered and concentrated. The residue was purified by Isco Combi-Flash Companion column chromatography (0-40% ethyl acetate in n-hexane) to give 5-(benzyloxy)-2-(methoxymethyl)pyridine (0.270 g, 85%). $^1$H NMR (CDCl$_3$, 400 MHz) δ 8.33 (s, 1H), 7.44-7.31 (m, 6H), 7.27-7.25 (m, 1H), 5.10 (s, 2H), 4.52 (s, 2H), 3.44 (s, 3H).

Step 2. Synthesis of 6-(methoxymethyl)pyridin-3-ol

Compound 586

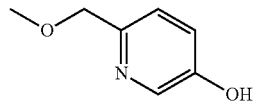

10% palladium on carbon was added to a MeOH (20.0 mL) of 5-(benzyloxy)-2-(methoxymethyl)pyridine (0.270 g), and the mixture was stirred at room temperature for 1 h under hydrogen atmosphere. After reaction, the solution was filtered and concentrated to yield product which was used directly for next step without further purification (0.160 g, crude yield 96%). $^1$H NMR (CDCl$_3$, 400 MHz) δ 8.22 (br s, 1H), 7.34 (d, 1H), 7.27 (d, 1H), 4.53 (s, 2H), 3.44 (s, 3H).

Step 3. Synthesis of 6-(methoxymethyl)pyridin-3-yl 4-[2-(4-fluorophenyl)-4-oxo-1,3-thiazolidin-3-yl]-3-methylbenzoate Following standard procedure G, 4-[2-(4-fluorophenyl)-4-oxo-1,3-thiazolidin-3-yl]-3-methylbenzoic acid (0.180 g, 0.544 mmol), 6-(methoxymethyl)pyridin-3-ol (75.7 mg, 0.544 mmol), EDCI • HCl (0.210 g, 1.09 mmol), DMAP (0.150 g, 1.19 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 6-(methoxymethyl)pyridin-3-yl 4-[2-(4-fluorophenyl)-4-oxo-1,3-thiazolidin-3-yl]-3-methylbenzoate (0.172 g, 70%). $^1$H NMR (CDCl$_3$, 400 MHz) δ 8.43 (s, 1H), 8.03 (br s, 1H), 7.91 (br d, 1H), 7.56 (d, 1H), 7.49 (d, 1H), 7.36-7.32 (m, 2H), 6.98 (br t, 2H), 4.60 (s, 2H), 4.02 (d, 1H), 3.94 (d, 1H), 3.49 (s, 3H), 2.25 (br s, 3H); LC-MS (ESI) m/z 453.2 [M+H]$^+$.

EXAMPLE 434

4-[2-(4-Fluorophenyl)-4-oxo-1,3-thiazolidin-3-yl]-3-methyl-N-(tetrahydro-2H-pyran-2-yloxy)benzamide Compound 587

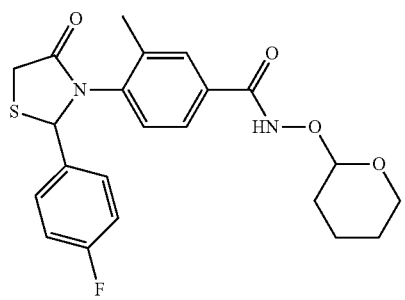

To the solution of 4-[2-(4-fluorophenyl)-4-oxo-1,3-thiazolidin-3-yl]-3-methylbenzoic acid (0.180 g, 0.544 mmol), O-(tetrahydro-2H-pyran-2-yl)hydroxylamine (63.6 mg, 0.544 mmol), EDCI • HCl (0.210 g, 1.09 mmol), DMAP (0.150 g, 1.09 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-60% ethyl acetate in n-hexane) to give 4-[2-(4-fluorophenyl)-4-oxo-1,3-thiazolidin-3-yl]-3-methyl-N-(tetrahydro-2H-pyran-2-yloxy)benzamide (0.210 g, 90%). $^1$H NMR (CDCl$_3$, 400 MHz) δ 8.74 (s, 1H), 7.56 (br s, 1H), 7.43 (br s, 1H), 7.32-7.28 (m, 2H), 6.96 (br t, 2H), 5.93 (br s, 1H), 5.02 (br s, 1H), 4.02-3.89 (m, 4H), 2.20 (br s, 3H), 1.89-1.77 (m, 4H), 1.69-1.59 (m, 2H); LC-MS (ESI) m/z 453.2 [M+Na]$^+$.

EXAMPLE 435

N-ethoxy-4-[2-(4-fluorophenyl)-4-oxo-1,3-thiazolidin-3-yl]-3-methylbenzamide

Compound 588

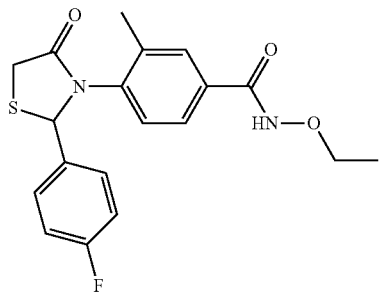

To the solution of 4-[2-(4-fluorophenyl)-4-oxo-1,3-thiazolidin-3-yl]-3-methylbenzoic acid (0.180 g, 0.544 mmol), O-ethylhydroxylamine (53.0 mg, 0.544 mmol), EDCI • HCl (0.210 g, 1.09 mmol), DMAP (0.150 g, 1.09 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-70% ethyl acetate in n-hexane) to give N-ethoxy-4-[2-(4-fluorophenyl)-4-oxo-1,3-thiazolidin-3-yl]-3-methylbenzamide (0.177 g, 87%). $^1$H NMR (CDCl$_3$, 400 MHz) δ 9.13 (br s, 1H), 7.46 (br s, 1H), 7.30-7.27 (m, 3H), 6.94 (br t, 2H), 6.10-5.73 (br, 1H), 4.02-3.97 (m, 3H), 3.90 (d, 1H), 2.15 (br s, 3H), 1.27 (t, 3H); LC-MS (ESI) m/z 375.2 [M+H]$^+$.

EXAMPLE 436

S-Ethyl 4-[2-(4-fluorophenyl)-4-oxo-1,3-thiazolidin-3-yl]-3-methylbenzenecarbothioate Compound 589

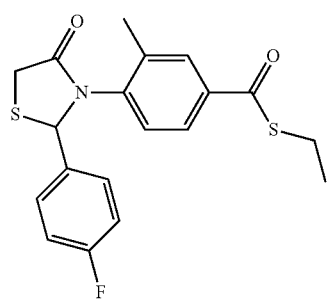

Step 1. Synthesis of 4-[2-(4-fluorophenyl)-4-oxo-1,3-thiazolidin-3-yl]-3-methylbenzoyl chloride Compound 590

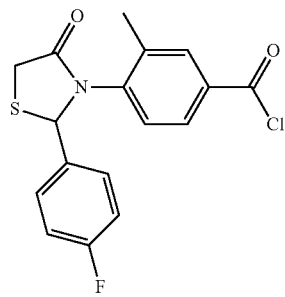

A solution of 4-[2-(4-fluorophenyl)-4-oxo-1,3-thiazolidin-3-yl]-3-methylbenzoic acid (0.200 g) in CH$_2$Cl$_2$ (10.0 mL) and SOCl$_2$ (8.0 mL) were carried out the reaction. After the reaction was stirred at room temperature for 1 h and work-up, the residue was used directly for next step without further purification. (0.210 g, crude yield 99%).

Step 2. Synthesis of S-ethyl 4-[2-(4-fluorophenyl)-4-oxo-1,3-thiazolidin-3-yl]-3-methylbenzenecarbothioate To the solution of 4-[2-(4-fluorophenyl)-4-oxo-1,3-thiazolidin-3-yl]-3-methylbenzoyl chloride (0.210 g, 0.602 mmol), ethanethiol (30.0 μL, 0.401 mmol), 1-methylimidazole (50.0 μL, 0.620 mmol), K$_2$CO$_3$ (0.100 g, 0.720 mmol) and acetonitrile (10.0 mL) were used to carry out the reaction. After the reaction mixture was stirred at room temperature for 16 h and work-up, the residue was purified by Isco Combi-Flash Companion column chromatography (0-30% ethyl acetate in n-hexane) to give S-ethyl 4-[2-(4-fluorophenyl)-4-oxo-1,3-thiazolidin-3-yl]-3-methylbenzenecarbothioate (0.160 g, 71%). $^1$H NMR (CDCl$_3$, 400 MHz)

δ 7.77 (br s, 1H), 7.66 (br d, 1H), 7.31 (dd, 2H), 6.96 (br t, 2H), 5.94 (br s, 1H), 4.01 (d, 1H), 3.92 (d, 1H), 3.03 (q, 2H), 2.21 (br s, 3H), 1.25 (t, 3H); LC-MS (ESI) m/z 376.1 [M+H]+.

EXAMPLE 437

2-(2-Methoxyethoxy)ethyl 4-({4-[2-(4-fluorophenyl)-4-oxo-1,3-thiazolidin-3-yl]-3-methylbenzoyl}sulfamoyl)benzoate

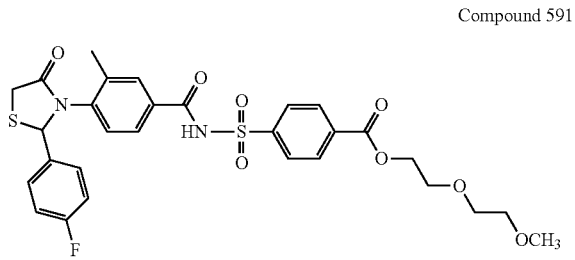 [SMILES: COCCOCCOC(=O)c1ccc(S(=O)(=O)NC(=O)c2ccc(N3C(=O)CSC3c3ccc(F)cc3)c(C)c2)cc1]

Compound 591

Step 1. Synthesis of 2-(2-methoxyethoxy)ethyl 4-sulfamoylbenzoate

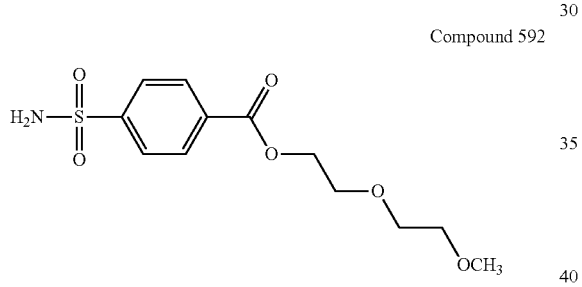

Compound 592

A solution of 4-aminosulfonylbenzoic acid (558 mg, 2.77 mmol) in concentrated $HCl_{(aq)}$ (0.50 mL) and diethylene glycol methyl ether (3.0 mL) was stirred at 100° C. for 20 h and cooled to room temperature. It was diluted with ethyl acetate and washed with water. The organic layer was dried over $MgSO_{4(s)}$, filtered, and concentrated. The residue was purified by Isco Combi-Flash Companion column chromatography (0-80% ethyl acetate in n-hexane) to give 2-(2-methoxyethoxy)ethyl 4-sulfamoylbenzoate (199 mg, 24%) as a colorless gum. $^1$H NMR (CDCl$_3$, 400 MHz) δ 8.18 (d, 2H), 7.99 (d, 2H), 5.01 (s, 2H), 4.52 (dd, 2H), 3.85 (dd, 2H), 3.69 (dd, 2H), 3.58 (dd, 2H), 3.38 (s, 3H).

Step 2. Synthesis of 2-(2-methoxyethoxy)ethyl 4-({4-[2-(4-fluorophenyl)-4-oxo-1,3-thiazolidin-3-yl]-3-methylbenzoyl}sulfamoyl)benzoate Following standard procedure C, 4-[2-(4-fluorophenyl)-4-oxo-1,3-thiazolidin-3-yl]-3-methylbenzoic acid (156 mg, 0.471 mmol), DMAP (115 mg, 0.942 mmol), EDCI • HCl (135 mg, 0.706 mmol), 2-(2-methoxyethoxy)ethyl 4-sulfamoylbenzoate (143 mg, 0.471 mmol), and CH$_2$Cl$_2$ (5.0 mL) were used to carry out the reaction. After the reaction was stirred for 16 h and work-up, the residue was purified by Isco Combi-Flash Companion column chromatography (0-10% MeOH in CH$_2$Cl$_2$) to give 2-(2-methoxyethoxy)ethyl 4-({4-[2-(4-fluorophenyl)-4-oxo-1,3-thiazolidin-3-yl]-3-methylbenzoyl}sulfamoyl)benzoate (228 mg, 79%) as a white solid. $^1$H NMR (CDCl$_3$, 300 MHz) δ 9.50 (br s, 1H), 8.20-8.13 (m, 4H), 7.42 (br, 2H), 7.31-7.28 (m, 2H), 6.91 (br t, 2H), 6.10-5.70 (br, 1H), 4.51 (dd, 2H), 4.10 (br s, 2H), 3.82 (dd, 2H), 3.69-3.66 (m, 2H), 3.57-3.54 (m, 2H), 3.34 (s, 3H), 2.13 (br s, 3H); LC-MS (ESI) m/z 617.2 [M+H]+.

EXAMPLE 438

4-[2-(4-Fluorophenyl)-4-oxo-1,3-thiazolidin-3-yl]-N-[(2-methoxyethyl)sulfonyl]-3-methylbenzamide

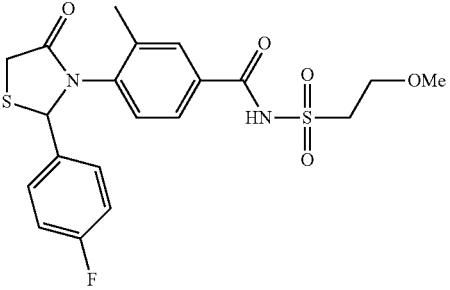

Compound 593

Step 1. Synthesis of sodium 2 methoxyethanesulfonate.

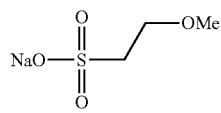

Compound 594

A solution of 2-chloroethyl methyl ether (1.01 g, 10.7 mmol) and Na$_2$SO$_3$ (1.42 g, 11.2 mmol) in H$_2$O (5.0 mL) was stirred at reflux for 20 h. The solution was cooled to room temperature and concentrated to give sodium 2-methoxyethanesulfonate (2.33 g, quantitative yield) as a white solid. $^1$H NMR (DMSO-d$_6$, 400 MHz) δ 3.53 (t, 2H), 3.37 (s, 3H), 2.70 (t, 2H).

Step 2. Synthesis of 2-methoxyethanesulfonyl chloride

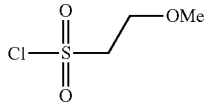

Compound 595

A solution of sodium 2-methoxyethanesulfonate (0.998 g, 2.11 mmol) in POCl$_3$ (3.0 mL) was stirred at 110° C. for 8 h and room temperature for 16 h. The solution was poured into ice warer and extracted with ethyl acetate. The combined organic layers were dried over $MgSO_{4(s)}$, filtered, and concentrated to give 2-methoxyethanesulfonyl chloride (2.13 g, quantitative yield) as a colorless oil. $^1$H NMR (CDCl$_3$, 300 MHz) δ 3.97-3.95 (m, 4H), 3.43 (s, 3H).

Step 3. Synthesis of 2-methoxyethanesulfonamide

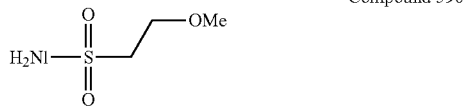

Compound 596

A solution of 2-methoxyethanesulfonyl chloride (2.13 g, 2.11 mmol) in H$_2$O (15 mL) and 28% NH$_{3(aq)}$ (10 mL) was stirred at room temperature for 5 h. The solution was extracted with ethyl acetate. The combined organic layers were dried over MgSO$_{4(s)}$, filtered, and concentrated to give 2-methoxyethanesulfonamide (65.9 mg, 8%) as a yellow oil. $^1$H NMR (CDCl$_3$, 300 MHz) δ 4.89 (br s, 2H), 3.85 (t, 2H), 3.41 (s, 3H), 3.36 (t, 2H).

Step 4. Synthesis of 4-[2-(4-fluorophenyl)-4-oxo-1, 3-thiazolidin-3-yl]-N-[(2-methoxyethyl)sulfonyl]-3-methylbenzamide Following standard procedure C, 4-[2-(4-fluorophenyl)-4-oxo-1,3-thiazolidin-3-yl]-3-methylbenzoic acid (134 mg, 0.405 mmol), DMAP (124 mg, 1.01 mmol), EDCI • HCl (140 mg, 0.729 mmol), 2-methoxyethanesulfonamide (56.4 mg, 0.405 mmol), and CH$_2$Cl$_2$ (5.0 mL) were used to carry out the reaction. After the reaction was stirred for 16 h and work-up, the residue was purified by Isco Combi-Flash Companion column chromatography (0-5% MeOH in CH$_2$Cl$_2$) to give 4-[2-(4-fluorophenyl)-4-oxo-1,3-thiazolidin-3-yl]-N-[(2-methoxyethyl)sulfonyl]-3-methylbenzamide (142 mg, 77%) as a white solid. $^1$H NMR (DMSO-d$_6$, 400 MHz) δ 12.02 (br s, 1H), 7.71 (br s, 1H), 7.59 (br s, 1H), 7.48 (dd, 2H), 7.09 (br t, 2H), 6.60-6.10 (br s, 1H), 4.07 (d, 1H), 3.91 (d, 1H), 3.71 (br s, 4H), 3.10 (s, 3H), 2.13 (br s, 3H); LC-MS (ESI) m/z 475.2 [M+Na]$^+$.

EXAMPLE 439

4-[2-(4-Fluorophenyl)-4-oxo-1, 3-thiazolidin-3-yl]-N-{[2-(2-methoxyethoxy)ethyl]sulfonyl}-3-methylbenzamide Compound 597

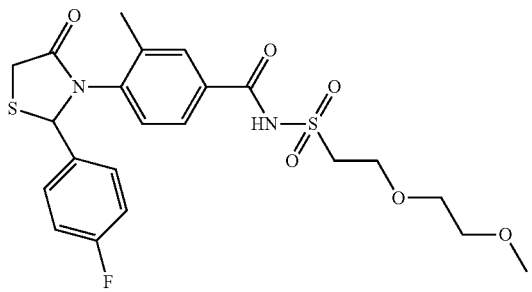

Step 1. Synthesis of 1-bromo-2-(2-methoxyethoxy)ethane

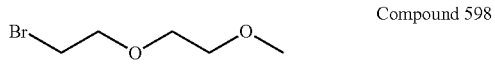

Compound 598

To a solution of diethylene glycol monomethyl ether (0.698 g, 5.81 mmol) in THF (10 mL) was added triphenylphosphine (1.53 g, 5.83 mol) and carbon tetrabromide (1.93 g, 5.81 mol) at 0° C. After the solution was stirred at room temperature for 16 h, it was quenched with saturated NaHCO$_{3(aq)}$ and extracted with CH$_2$Cl$_2$. The combined organic layers were dried over MgSO$_{4(s)}$, filtered, and concentrated. The residue was purified by flash chromatography (20% ethyl acetate in n-hexane) to give 1-bromo-2-(2-methoxyethoxy)ethane as a yellow liquid. $^1$H NMR (CDCl$_3$, 300 MHz) δ 3.81 (t, 2H), 3.68-3.65 (m, 2H), 3.57-3.54 (m, 2H), 3.48 (t, 2H), 3.39 (s, 3H).

Step 2. Synthesis of 2-(2-methoxyethoxy)ethanesulfonamide

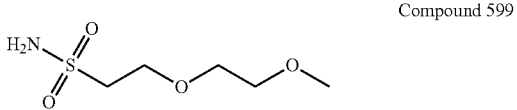

Compound 599

A solution of 1-bromo-2-(2-methoxyethoxy)ethane (0.520 g, 2.86 mmol) and Na$_2$SO$_3$ (360 g, 2.86 mmol) in H$_2$O (3.0 mL) was stirred at reflux for 20 h. The solution was cooled to room temperature and concentrated to give sodium 2-(2-methoxyethoxy)ethanesulfonate as a yellow solid. A solution of sodium 2-(2-methoxyethoxy)ethanesulfonate (0.998 g, 2.11 mmol) in POCl$_3$ (3.0 mL) was stirred at 110° C. for 6 h and room temperature for 16 h. The solution was slowly poured into ice-salt warer and extracted with CH$_2$Cl$_2$. The combined organic layers were dried over MgSO$_{4(s)}$, filtered, and concentrated to give 2-(2-methoxyethoxy)ethanesulfonyl chloride as a brown oil. Then 2-(2-methoxyethoxy)ethanesulfonyl chloride was stirred in H$_2$O (10 mL) and 28% NH$_{3(aq)}$ (10 mL) was at room temperature for 8 h and concentrated. The residue was treated with H$_2$O and extracted with ethyl acetate. The combined organic layers were dried over MgSO$_{4(s)}$, filtered, and concentrated to give 2-(2-methoxyethoxy)ethanesulfonamide (118 mg, 23%) as a brown oil. $^1$H NMR (CDCl$_3$, 400 MHz) δ 5.21 (br s, 2H), 3.97 (dd, 2H), 3.69-3.67 (m, 2H), 3.56-3.54 (m, 2H), 3.38 (s, 3H), 3.34 (dd, 2H).

Step 3. Synthesis of 4-[2-(4-fluorophenyl)-4-oxo-1, 3-thiazolidin-3-yl]-N-{[2-(2-methoxyethoxy)ethyl]sulfonyl}-3-methylbenzamide Following standard procedure C, 4-[2-(4-fluorophenyl)-4-oxo-1,3-thiazolidin-3-yl]-3-methylbenzoic acid (127 mg, 0.383 mmol), DMAP (93.6 mg, 0.766 mmol), EDCI • HCl (117 mg, 0.610 mmol), 2-(2-methoxyethoxy)ethanesulfonamide (70.2 mg, 0.383 mmol), and CH$_2$Cl$_2$ (5.0 mL) were used to carry out the reaction. After the reaction was stirred for 16 h and work-up, the residue was purified by Isco Combi-Flash Companion column chromatography (0-10%

MeOH in CH$_2$Cl$_2$) to give 4-[2-(4-fluorophenyl)-4-oxo-1,3-thiazolidin-3-yl]-N-{[2-(2-methoxyethoxy)ethyl]sulfonyl}-3-methylbenzamide (163 mg, 54%) as a beige solid. $^1$H NMR (CDCl$_3$, 400 MHz) δ 9.90-9.40 (br, 1H), 7.69 (br s, 1H), 7.56 (br s, 1H), 7.32-7.27 (m, 2H), 6.95 (br t, 2H), 6.10-5.80 (br, 1H), 3.99 (d, 1H), 3.94-3.89 (m, 3H), 3.68 (br t, 2H), 3.53 (br t, 2H), 3.32 (br t, 2H), 3.13 (s, 3H), 2.20 (br s, 3H); LC-MS (ESI) m/z 519.2 [M+Na]$^+$.

EXAMPLE 440

2-(4-Fluorophenyl)-3-[2-methyl-4-(2,2,2-trifluoro-1-hydroxyethyl)phenyl]-1,3-thiazolidin-4-one

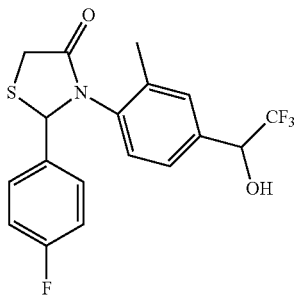

Compound 600

Step 1. Synthesis of 2,2,2-trifluoro-1-(3-methyl-4-nitrophenyl)ethanone

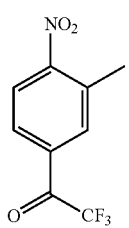

Compound 601

To a solution of ethyl 3-methyl-4-nitrobenzoate (1.58 g, 7.55 mmol) in CH$_2$Cl$_2$ (30 mL) was added (trifluoromethyl)trimethylsilane (1.56 mL, 10.6 mmol) and 1.0 M tetrabutylammonium fluoride (0.22 mL, 0.22 mmol) at −78° C. After the solution was slowly warm to room temperature and stirred for 18 h, it was washed with H$_2$O and brine, dried over MgSO$_{4(s)}$, filtered, and concentrated to give a residue. Then the crude ether was stirred in 1,4-dioxane (6.0 mL) and 12 M HCl$_{(aq)}$ (3.0 mL) for 4 h. The solution was treated with H$_2$O and extracted with ethyl acetate. The combined organic layers were dried over MgSO$_{4(s)}$, filtered, and concentrated. The residue was purified by Isco Combi-Flash Companion column chromatography (0-50% ethyl acetate in n-hexane) to give 2,2,2-trifluoro-1-(3-methyl-4-nitrophenyl)ethanone (0.665 g, 37%) as a yellow solid. $^1$H NMR (CDCl$_3$, 400 MHz) δ 8.05-8.04 (m, 3H), 2.67 (s, 3H).

Step 2. Synthesis of 1-(4-amino-3-methylphenyl)-2,2,2-trifluoroethanone

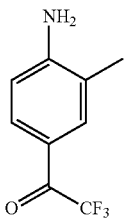

Compound 602

To a solution of 2,2,2-trifluoro-1-(3-methyl-4-nitrophenyl)ethanone (0.647 g, 2.78 mmol) in ethanol (12 mL) was added iron powder (0.775 g, 13.9 mmol) and acetic acid (5.0 mL) at room temperature. After the solution was stirred at reflux for 18 h and cooled to room temperature, the reaction mixture was filtration through celite. The filtrate was concentrated under reduce pressure to afford a residue, The residue was treated with saturated NaHCO$_{3(aq)}$ and extracted with CH$_2$Cl$_2$. The combined organic layers were dried over MgSO$_{4(s)}$, filtered, and concentrated to give 1-(4-amino-3-methylphenyl)-2,2,2-trifluoroethanone (0.447 g, 79%) as a yellow solid. $^1$H NMR (CDCl$_3$, 300 MHz) δ 7.81-7.78 (m, 2H), 6.67 (d, 1H), 4.38 (br s, 2H), 2.20 (s, 3H).

Step 3. Synthesis of 1-(4-amino-3-methylphenyl)-2,2,2-trifluoroethanol

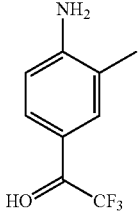

Compound 603

To a solution of 1-(4-amino-3-methylphenyl)-2,2,2-trifluoroethanone (0.200 g, 0.985 mmol) in 2-propanol (3.0 mL) was added sodium borohydride (56.2 mg, 1.49 mmol) at room temperature. After the solution was stirred for 6 h, it was quenched by saturated NaHCO$_{3(aq)}$ and extracted with CH$_2$Cl$_2$. The combined organic layers were dried over MgSO$_{4(s)}$, filtered, and concentrated to give 1-(4-amino-3-methylphenyl)-2,2,2-trifluoroethanol (0.193 g, 96%) as a yellow solid. $^1$H NMR (CDCl$_3$, 400 MHz) δ 7.14-7.11 (m, 2H), 6.68 (d, 1H), 4.87 (q, 1H), 3.73 (br s, 2H), 2.45 (br s, 1H), 2.18 (s, 3H).

Step 4. Synthesis of 2,2,2-trifluoro-1-(4-{[(4-fluorophenyl)methylidene]amino}-3-methylphenyl)ethanol

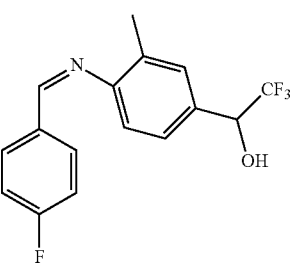

Compound 604

A solution of 1-(4-amino-3-methylphenyl)-2,2,2-trifluoroethanol (0.193 g, 0.941 mmol) and 4-fluorobenzaldehye (0.111 mL, 1.04 mmol) in toluene (6.0 mL) was stirred at reflux for 8 h and then concentrated to give a 2,2,2-trifluoro-1-(4-{[(4-fluorophenyl)methylidene]amino}-3-methylphenyl)ethanol (0.255 g, 87%) as a solid. $^1$H NMR (CDCl$_3$, 400 MHz) δ 8.32 (s, 1H), 7.94-7.90 (m, 2H), 7.32-7.30 (m, 2H), 7.17 (t, 2H), 6.92 (d, 1H), 5.00 (q, 1H), 2.75-2.60 (br, 1H), 2.36 (s, 3H).

Step 5. Synthesis of 2-(4-fluorophenyl)-3-[2-methyl-4-(2,2,2-trifluoro-1-hydroxyethyl)phenyl]-1,3-thiazolidin-4-one A solution of 2,2,2-trifluoro-1-(4-{[(4-fluorophenyl)methylidene]amino}-3-methylphenyl)ethanol (234 mg, 0.752 mmol) and 2-mercaptoacetic acid (68.0 µL, 0.974 mmol) in toluene (10 mL) was stirred at 100° C. for 18 h. The solution was cooled to room temperature and diluted with ethyl acetate. The organic layer was washed with 10% NaOH$_{(aq)}$, dried over MgSO$_{4(s)}$, filtered, and concentrated. The residue was purified by Isco Combi-Flash Companion column chromatography (0-70% ethyl acetate in n-hexane) to give 2-(4-fluorophenyl)-3-[2-methyl-4-(2,2,2-trifluoro-1-hydroxyethyl)phenyl]-1,3-thiazolidin-4-one (48.3 mg, 17%) as a yellow foam. $^1$H NMR (CDCl$_3$, 400 MHz) δ 7.32-7.25 (m, 3H), 7.25-7.00 (br, 1H), 6.97 (br t, 2H), 6.10-5.70 (br, 1H), 4.92-4.89 (m, 1H), 4.02 (d, 1H), 3.91 (d, 1H), 2.70 (br s, 1H), 2.20 (br s, 3H); LC-MS (ESI) m/z 408.1 [M+Na]$^+$.

EXAMPLE 441

Ethyl {4-[2-(4-fluorophenyl)-4-oxo-1,3-thiazolidin-3-yl]-3-methylphenoxy}acetate

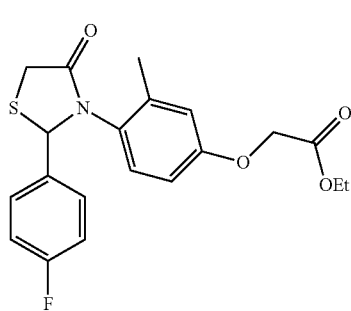

Compound 605

Step 1. Synthesis of ethyl (4-amino-3-methylphenoxy)acetate

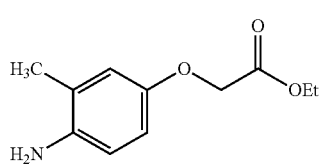

Compound 606

A solution of 4-amino-m-cresol (1.40 g, 11.4 mmol), potassium carbonate (1.73 g, 12.5 mmol), and ethyl bromoacetate (2.09 g, 12.5 mmol) in acetone (20 mL) was stirred at reflux for 3 h and cooled to room temperature. The reaction mixture was concentrated and treated with water. The solution was extracted with CH$_2$Cl$_2$. The combined organic layers were dried over MgSO$_{4(s)}$, filtered, and concentrated under reduced pressure to afford a residue. The residue was purified by combi-flash column chromatography (0-30% ethyl acetate in n-hexane) to give ethyl (4-amino-3-methylphenoxy)acetate (0.256 g, 12%) as a brown oil. $^1$H NMR (CDCl$_3$, 400 MHz) δ 6.70 (d, 1H), 6.65-6.58 (m, 2H), 4.53 (s, 2H), 4.26 (q, 2H), 3.39 (br s, 2H), 2.14 (s, 3H), 1.28 (t, 3H).

Step 2. Synthesis of ethyl {4-[2-(4-fluorophenyl)-4-oxo-1,3-thiazolidin-3-yl]-3-methylphenoxy}acetate Following standard procedure A, ethyl (4-amino-3-methylphenoxy)acetate (0.256 g, 1.33 mmol), 4-fluorobenzaldehyde (0.220 mL, 2.06 mmol), Na$_2$SO$_4$ (0.188 g, 1.33 mmol), 2-mercaptoacetic acid (0.170 mL, 2.44 mmol), and toluene (15 mL) were used to carry out the reaction. It was reflux 4 h for the first step and 18 h for the second step. After work-up, the residue was purified by Isco Combi-Flash Companion column chromatography (0-50% ethyl acetate in n-hexane) to give ethyl {4-[2-(4-fluorophenyl)-4-oxo-1,3-thiazolidin-3-yl]-3-methylphenoxy}acetate (0.201 g, 37%) as a yellow gum. $^1$H NMR (CDCl$_3$, 400 MHz) δ 7.31-7.28 (m, 2H), 6.97 (br s, 2H), 6.90-6.30 (br, 3H), 6.10-5.60 (br, 1H), 4.52 (s, 2H), 4.24 (q, 2H), 4.00 (d, 1H), 3.89 (d, 1H), 2.30-1.80 (br, 3H), 1.26 (t, 3H); LC-MS (ESI) m/z 412.2 [M+Na]$^+$.

EXAMPLE 442

Oxetan-3-yl {4-[2-(4-fluorophenyl)-4-oxo-1,3-thiazolidin-3-yl]-3-methylphenoxy}acetate

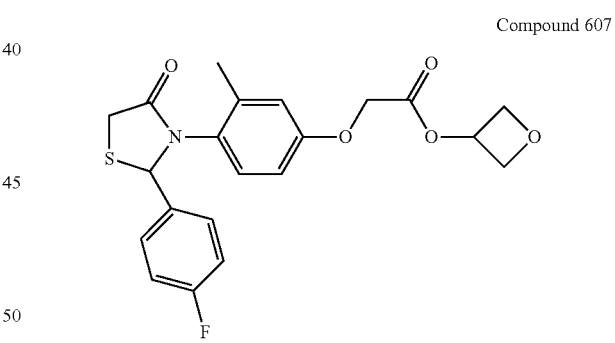

Compound 607

To a solution of {4-[2-(4-fluorophenyl)-4-oxo-1,3-thiazolidin-3-yl]-3-methylphenoxy}acetic acid (139 mg, 0.385 mmol) in CH$_2$Cl$_2$ (5.0 mL) was added DMAP (70.6 mg, 0.578 mmol), 3-hydroxyoxetane (36 µL, 0.578 mmol), and EDCI • HCl (111 mg, 0.578 mmol) at room temperature. After the reaction mixture was stirred for 18 h, it was diluted with CH$_2$Cl$_2$ and washed with 2 N HCl$_{(aq)}$. The organic layer was dried over MgSO$_{4(s)}$, filtered, and concentrated. The residue was purified by preparative thin layer chromatography plates (1.0 mm of silica gel on glass support, 30% ethyl acetate in n-hexane) to give oxetan-3-yl {4-[2-(4-fluorophenyl)-4-oxo-1,3-thiazolidin-3-yl]-3-methylphenoxy}acetate (114 mg, 71%) as a white foam. $^1$H NMR (CDCl$_3$, 400 MHz) δ 7.30 (dd, 2H), 6.97 (br t, 2H), 6.90-6.30 (br, 3H), 6.10-5.60 (br, 1H), 5.53 (quint, 1H), 4.90

(t, 2H), 4.64-4.60 (m, 2H), 4.59 (s, 2H), 4.00 (d, 1H), 3.89 (d, 1H), 2.40-1.80 (br, 3H); LC-MS (ESI) m/z 440.1 [M+Na]⁺.

EXAMPLE 443

2-(Morpholin-4-yl)ethyl {4-[2-(4-fluorophenyl)-4-oxo-1,3-thiazolidin-3-yl]-3-methylphenoxy}acetate Compound 608

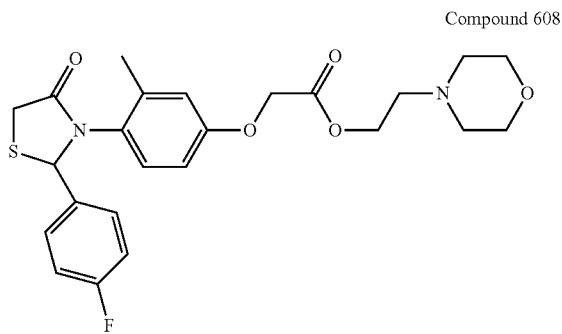 [SMILES: Cc1cc(OCC(=O)OCCN2CCOCC2)ccc1N1C(=O)CSC1c1ccc(F)cc1]

To a solution of {4-[2-(4-fluorophenyl)-4-oxo-1,3-thiazolidin-3-yl]-3-methylphenoxy}acetic acid (135 mg, 0.374 mmol) in CH$_2$Cl$_2$ (5.0 mL) was added DMAP (68.7 mg, 0.563 mmol), 4-(2-hydroxyethyl)morpholine (58.8 mg, 0.448 mmol), and EDCI • HCl (108 mg, 0.563 mmol) at room temperature. After the reaction mixture was stirred for 18 h, it was concentrated to afford a residue. The residue was purified by preparative thin layer chromatography plates (1.0 mm of silica gel on glass support, 8% methanol in CH$_2$Cl$_2$) to give 2-(morpholin-4-yl)ethyl {4-[2-(4-fluorophenyl)-4-oxo-1,3-thiazolidin-3-yl]-3-methylphenoxy}acetate (117 mg, 66%) as a colorless gum. $^1$H NMR (CDCl$_3$, 300 MHz) δ 7.30 (dd, 2H), 6.97 (br t, 2H), 6.90-6.20 (br, 3H), 6.10-5.50 (br, 1H), 4.55 (s, 2H), 4.31 (t, 2H), 4.00 (d, 1H), 3.88 (d, 1H), 3.68-3.62 (m, 4H), 2.61 (t, 2H), 2.46 (dd, 4H), 2.40-1.80 (br, 3H); LC-MS (ESI) m/z 475.2 [M+H]⁺.

EXAMPLE 444

Propan-2-yl {4-[2-(4-fluorophenyl)-4-oxo-1,3-thiazolidin-3-yl]-3-methylphenoxy}acetate Compound 609

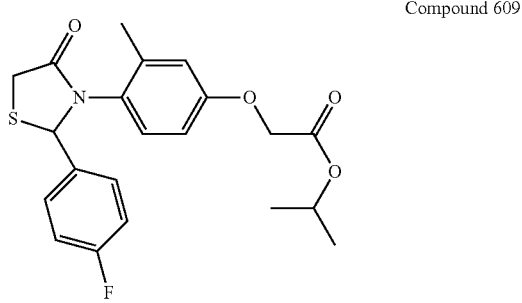 [SMILES: Cc1cc(OCC(=O)OC(C)C)ccc1N1C(=O)CSC1c1ccc(F)cc1]

To a solution of {4-[2-(4-fluorophenyl)-4-oxo-1,3-thiazolidin-3-yl]-3-methylphenoxy}acetic acid (118 mg, 0.327 mmol) in CH$_2$Cl$_2$ (5.0 mL) was added DMAP (59.8 mg, 0.490 mmol), 2-propanol (0.50 mL), and EDCI • HCl (93.9 mg, 0.490 mmol) at room temperature. After the reaction mixture was stirred for 16 h, it was diluted with CH$_2$Cl$_2$ and washed with 2 N HCl$_{(aq)}$. The organic layer was dried over MgSO$_{4(s)}$, filtered, and concentrated. The residue was purified by preparative thin layer chromatography plates (1.0 mm of silica gel on glass support, 40% ethyl acetate in n-hexane) to give propan-2-yl {4-[2-(4-fluorophenyl)-4-oxo-1,3-thiazolidin-3-yl]-3-methylphenoxy}acetate (93.4 mg, 71%) as a colorless gum. $^1$H NMR (CDCl$_3$, 400 MHz) δ 7.31-7.28 (m, 2H), 6.96 (br s, 2H), 6.90-6.30 (br, 3H), 6.10-5.60 (br, 1H), 5.10 (quint, 1H), 4.49 (s, 2H), 4.00 (d, 1H), 3.89 (d, 1H), 2.35-1.80 (br, 3H), 1.24 (d, 6H); LC-MS (ESI) m/z 426.2 [M+Na]⁺.

EXAMPLE 445

Pyridin-3-ylmethyl {4-[2-(4-fluorophenyl)-4-oxo-1,3-thiazolidin-3-yl]-3-methylphenoxy}acetate Compound 610

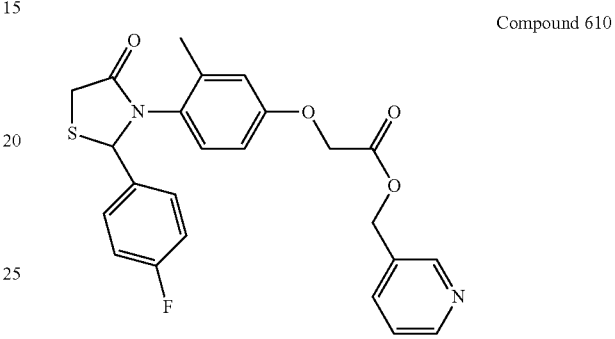

To a solution of {4-[2-(4-fluorophenyl)-4-oxo-1,3-thiazolidin-3-yl]-3-methylphenoxy}acetic acid (128 mg, 0.354 mmol) in CH$_2$Cl$_2$ (5.0 mL) was added DMAP (64.9 mg, 0.531 mmol), 3-(hydroxymethyl)pyridine (38.7 mg, 0.354 mmol), and EDCI • HCl (102 mg, 0.531 mmol) at room temperature. After the reaction mixture was stirred for 16 h, it was diluted with CH$_2$Cl$_2$ and washed with H$_2$O. The organic layer was dried over MgSO$_{4(s)}$, filtered, and concentrated. The residue was purified by preparative thin layer chromatography plates (1.0 mm of silica gel on glass support, 90% ethyl acetate in n-hexane) to give pyridin-3-ylmethyl {4-[2-(4-fluorophenyl)-4-oxo-1,3-thiazolidin-3-yl]-3-methylphenoxy}acetate (112 mg, 70%) as a white foam. $^1$H NMR (CDCl$_3$, 400 MHz) δ 8.60-8.59 (m, 2H), 7.63 (d, 1H), 7.31-7.28 (m, 3H), 6.97 (br s, 2H), 6.90-6.30 (br, 3H), 6.10-5.50 (br, 1H), 5.23 (s, 2H), 4.58 (s, 2H), 4.00 (d, 1H), 3.89 (d, 1H), 2.30-1.80 (br, 3H); LC-MS (ESI) m/z 453.2 [M+H]⁺.

EXAMPLE 446

2-(Dimethylamino)ethyl {4-[2-(4-fluorophenyl)-4-oxo-1,3-thiazolidin-3-yl]-3-methylphenoxy}acetate Compound 611

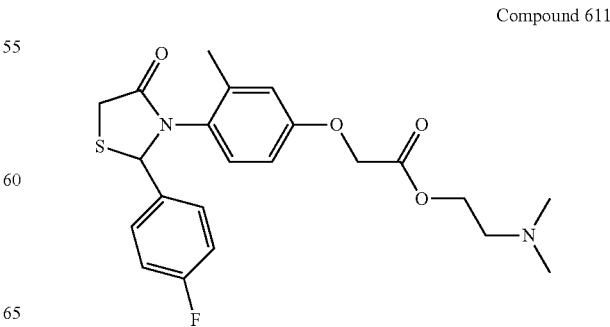

Following standard procedure G, {4-[2-(4-fluorophenyl)-4-oxo-1,3-thiazolidin-3-yl]-3-methylphenoxy}acetic acid (0.180 g, 0.499 mmol), 2-(dimethylamino)ethanol (50.0 µL, 0.499 mmol), EDCI • HCl (0.190 g, 1.00 mmol), DMAP (0.130 g, 1.09 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-20% MeOH in CH$_2$Cl$_2$) to give 2-(dimethylamino)ethyl {4-[2-(4-fluorophenyl)-4-oxo-1,3-thiazolidin-3-yl]-3-methylphenoxy}acetate (24.0 mg, 11%). $^1$H NMR (CDCl$_3$, 300 MHz) δ 7.29 (dd, 2H), 6.96 (br t, 2H), 6.83-6.23 (br, 2H), 6.17-5.51 (br, 1H), 4.55 (s, 2H), 4.27 (t, 2H), 3.99 (d, 1H), 3.87 (d, 1H), 2.55 (t, 2H), 2.40-1.75 (br, 9H); LC-MS (ESI) m/z 433.2 [M+H]$^+$.

EXAMPLE 447

2-(Acetyloxy)ethyl {4-[2-(4-fluorophenyl)-4-oxo-1,3-thiazolidin-3-yl]-3-methylphenoxy}acetate Compound 612

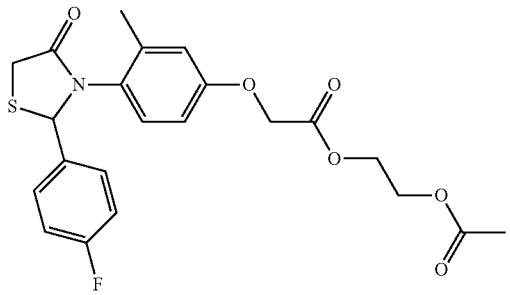

Step 1. Synthesis of 2-hydroxyethyl acetate

Compound 613

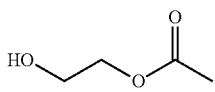

To a solution of acetic acid (0.140 mL, 2.42 mmol), ethylene glycol (0.270 mL, 4.83 mmol) and catalyst of H$_2$SO$_4$ were used to carry out the reaction. After the reaction mixture was stirred at room temperature for 16 h, the residue was extracted with ethyl acetate, dried over MgSO$_{4(s)}$, filtered and concentrated to give 2-hydroxyethyl acetate which was used directly for next step without further purification (0.120 g, crude yield 47%). $^1$H NMR (CDCl$_3$, 400 MHz) δ 4.21-4.19 (m, 2H), 3.82 (br t, 2H), 2.10 (s, 3H).

Step 2. Synthesis of 2-(acetyloxy)ethyl {4-[2-(4-fluorophenyl)-4-oxo-1,3-thiazolidin-3-yl]-3-methylphenoxy}acetate Following standard procedure G, {4-[2-(4-fluorophenyl)-4-oxo-1,3-thiazolidin-3-yl]-3-methylphenoxy}acetic acid (0.370 g, 1.05 mmol), 2-hydroxyethyl acetate (0.120 g, 1.15 mmol), EDCI • HCl (0.390 g, 2.05 mmol), DMAP (0.280 g, 2.25 mmol) and CH$_2$Cl$_2$ (5.0 mL) were used to carry out the reaction. After the reaction mixture was stirred at room temperature for 16 h and work-up, the residue was purified by Isco Combi-Flash Companion column chromatography (0-50% ethyl acetate in n-hexane) to give 2-(acetyloxy)ethyl {4-[2-(4-fluorophenyl)-4-oxo-1,3-thiazolidin-3-yl]-3-methylphenoxy}acetate (0.250 g, 55%). $^1$H NMR (CDCl$_3$, 300 MHz) δ 7.32-7.27 (m, 2H), 6.97 (br t, 2H), 6.91-6.27 (br, 2H), 6.11-5.50 (br, 1H), 4.56 (s, 2H), 4.40-4.31 (m, 2H), 4.29-4.26 (m, 2H), 4.00 (d, 1H), 3.88 (d, 1H), 2.40-1.80 (m, 6H); LC-MS (ESI) m/z 448.3 [M+H]$^+$.

EXAMPLE 448

2-(4-Fluorophenyl)-3-(4-hydroxy-2-methylphenyl)-1,3-thiazolidin-4-one

Compound 614

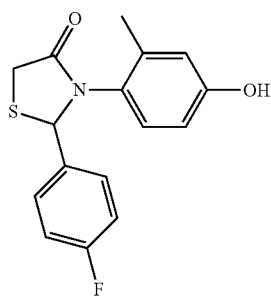

A solution of 4-amino-3-methylphenol (0.658 g, 5.34 mmol), Na$_2$SO$_4$ anhydrous (0.912 g, 6.42 mmol), and 4-fluorobenzaldehyde (0.688 mL, 6.42 mmol) in toluene (20 mL) was stirred at 70° C. for 3 h. Then 2-mercaptoacetic acid (0.670 mL, 9.60 mmol) was added to the reaction mixture, and it was stirred at 90° C. for 16 h. The reaction mixture was cooled to room temperature and diluted with ethyl acetate. The solution was washed with saturated NaHCO$_{3(aq)}$. The organic layer was dried over MgSO$_{4(s)}$, filtered, and concentrated. The residue was purified by Isco Combi-Flash Companion column chromatography (0-60% ethyl acetate in n-hexane) to give 2-(4-fluorophenyl)-3-(4-hydroxy-2-methylphenyl)-1,3-thiazolidin-4-one (0.812 g, 50%) as a lightly brown solid. $^1$H NMR (DMSO-d$_6$, 400 MHz) δ 9.41 (br s, 1H), 7.44 (br s, 2H), 7.10 (br s, 2H), 6.70-6.10 (br, 3H), 5.90-5.80 (br, 1H), 4.03 (d, 1H), 3.82 (d, 1H), 2.20-1.70 (br, 3H); LC-MS (ESI) m/z 304.1 [M+H]$^+$.

EXAMPLE 449

3-(5-Fluoro-4-hydroxy-2-methylphenyl)-2-(4-fluorophenyl)-1,3-thiazolidin-4-one

Compound 615

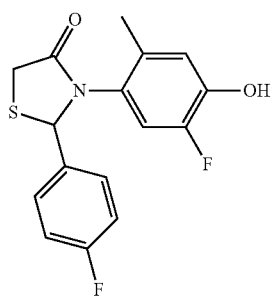

A solution of 4-amino-2-fluoro-5-methylphenol (0.219 g, 1.55 mmol), Na$_2$SO$_4$ anhydrous (0.330 g, 2.33 mmol), and 4-fluorobenzaldehyde (0.183 mL, 1.71 mmol) in toluene (10 mL) was stirred at 70° C. for 3 h. Then 2-mercaptoacetic acid (0.200 mL, 2.87 mmol) was added to the reaction mixture, and it was stirred at 90° C. for 16 h. The reaction mixture was cooled to room temperature and diluted with ethyl acetate. The solution was washed with saturated NaHCO$_{3(aq)}$. The organic layer was dried over MgSO$_{4(s)}$, filtered, and concentrated. The residue was purified by preparative thin layer chromatography plates (2.0 mm of silica gel on glass support, 50% ethyl acetate in n-hexane) to give 3-(5-fluoro-4-hydroxy-2-methylphenyl)-2-(4-fluorophenyl)-1,3-thiazolidin-4-one (0.181 g, 36%) as a white solid. $^1$H NMR (CDCl$_3$, 400 MHz) δ 7.31-7.27 (m, 2H), 6.99 (br s, 2H), 6.69 (br s, 1H), 6.20-5.60 (br, 1H), 5.78 (br s, 1H), 4.00 (d, 1H), 3.90 (d, 1H), 2.20-1.70 (br, 3H); LC-MS (ESI) m/z 322.1 [M+H]$^+$.

EXAMPLE 450

2-(4-Fluorophenyl)-3-[2-methyl-4-(1,3-thiazol-4-ylmethoxy)phenyl]-1,3-thiazolidin-4-one Compound 616

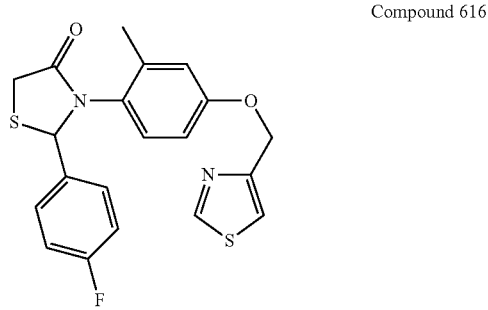 [SMILES: Cc1cc(OCc2cscn2)ccc1N1C(=O)CSC1c1ccc(F)cc1]

To the solution of 2-(4-fluorophenyl)-3-(4-hydroxy-2-methylphenyl)thiazolidin-4-one (80.0 mg, 0.267 mmol) in DMF (5.0 mL), 4-(chloromethyl)thiazole (56.1 mg, 0.267 mmol) and K$_2$CO$_3$ (50.0 mg, 0.290 mmol) were used to carry out the reaction. After the reaction mixture was stirred at 100° C. for 16 h and work-up, the residue was purified by preparative thin layer chromatography plates (1.0 mm of silica gel on glass support, 30% ethyl acetate in n-hexane) to give 2-(4-fluorophenyl)-3-[2-methyl-4-(1,3-thiazol-4-ylmethoxy)phenyl]-1,3-thiazolidin-4-one (34.0 mg, 32%). $^1$H NMR (CDCl$_3$, 400 MHz) δ 8.81 (s, 1H), 7.34 (s, 1H), 7.32-7.28 (m, 2H), 7.17-6.20 (br, 4H), 6.11-5.49 (br, 1H), 5.17 (s, 2H), 4.00 (d, 1H), 3.89 (d, 1H), 2.38-1.80 (br, 3H). LC-MS (ESI) m/z 401.1 [M+H]$^+$.

EXAMPLE 451

Ethyl 4-{4-[2-(4-fluorophenyl)-4-oxo-1,3-thiazolidin-3-yl]-3-methylphenoxy}butanoate Compound 617

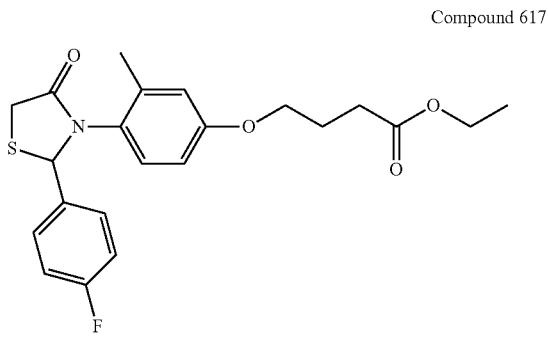 [SMILES: CCOC(=O)CCCOc1ccc(N2C(=O)CSC2c2ccc(F)cc2)c(C)c1]

Following standard procedure L, 2-(4-fluorophenyl)-3-(4-hydroxy-2-methylphenyl)-1,3-thiazolidin-4-one (80.0 mg, 0.264 mmol), ethyl 4-bromobutanoate (31.0 µL, 0.290 mmol) and K$_2$CO$_3$ (40.1 mg, 0.290 mmol) were used to carry out the reaction. After the reaction mixture was stirred at 80° C. for 16 h and work-up, the residue was purified by Isco Combi-Flash Companion column chromatography (0-50% ethyl acetate in n-hexane) to give ethyl 4-{4-[2-(4-fluorophenyl)-4-oxo-1,3-thiazolidin-3-yl]-3-methylphenoxy}butanoate (81.7 mg, 74%). $^1$H NMR (CDCl$_3$, 400 MHz) δ 7.32-7.28 (m, 2H), 6.97 (br s, 2H), 6.79-6.21 (m, 2H), 6.10-5.50 (br, 1H), 4.12 (q, 2H), 3.99 (d, 1H), 3.94-3.86 (m, 3H), 2.45 (t, 2H), 2.30-1.70 (m, 5H), 1.24 (t, 3H); LC-MS (ESI) m/z 418.2 [M+H]$^+$.

EXAMPLE 452

2-(4-Fluorophenyl)-3-{2-methyl-4-[(2-methylprop-2-en-1-yl)oxy]phenyl}-1,3-thiazolidin-4-one Compound 618

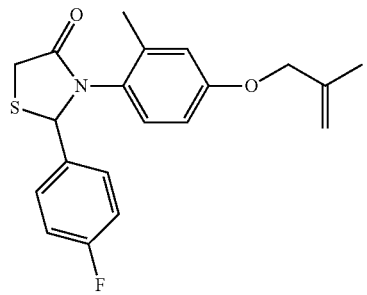

Following standard procedure L, 2-(4-fluorophenyl)-3-(4-hydroxy-2-methylphenyl)-1,3-thiazolidin-4-one (80.0 mg, 0.264 mmol), 3-bromo-2-methylprop-1-ene (32.0 µL, 0.316 mmol) and K$_2$CO$_3$ (40.1 mg, 0.290 mmol) were used to carry out the reaction. After the reaction mixture was stirred at 80° C. for 16 h and work-up, the residue was purified by Isco Combi-Flash Companion column chromatography (0-40% ethyl acetate in n-hexane) to give 2-(4-fluorophenyl)-3-{2-methyl-4-[(2-methylprop-2-en-1-yl)oxy]phenyl}-1,3-thiazolidin-4-one (65.1 mg, 69%). $^1$H NMR (CDCl$_3$, 400 MHz) δ 7.30 (dd, 2H), 6.97 (br s, 2H), 6.82-6.21 (br, 2H), 6.13-5.52 (br, 1H), 5.03 (s, 1H), 4.95 (s, 1H), 4.32 (s, 2H), 4.00 (d, 1H), 3.89 (d, 1H), 2.30-1.58 (m, 6H); LC-MS (ESI) m/z 358.2 [M+H]$^+$.

EXAMPLE 453

2-(4-Fluorophenyl)-3-[2-methyl-4-(pent-2-yn-1-yloxy)phenyl]-1,3-thiazolidin-4-one Compound 619

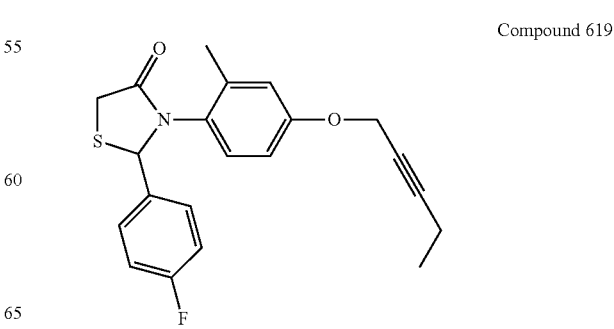

Following standard procedure L, 2-(4-fluorophenyl)-3-(4-hydroxy-2-methylphenyl)-1,3-thiazolidin-4-one (80.0 mg, 0.264 mmol), 1-bromopent-2-yne (32.0 µL, 0.316 mmol) and K₂CO₃ (40.1 mg, 0.290 mmol) were used to carry out the reaction. After the reaction mixture was stirred at 80° C. for 16 h and work-up, the residue was purified by Isco Combi-Flash Companion column chromatography (0-40% ethyl acetate in n-hexane) to give 2-(4-fluorophenyl)-3-[2-methyl-4-(pent-2-yn-1-yloxy)phenyl]-1,3-thiazolidin-4-one (58.9 mg, 61%). ¹H NMR (CDCl₃, 400 MHz) δ 7.30 (dd, 2H), 6.97 (br s, 2H), 6.85-6.22 (br, 3H), 6.18-5.50 (br, 1H), 4.56 (s, 2H), 4.00 (d, 1H), 3.89 (d, 1H), 2.37-1.80 (m, 5H), 1.12 (t, 3H); LC-MS (ESI) m/z 370.2 [M+H]⁺.

EXAMPLE 454

2-(4-Fluorophenyl)-3-{2-methyl-4-[2-(morpholin-4-yl)ethoxy]phenyl}-1,3-thiazolidin-4-one

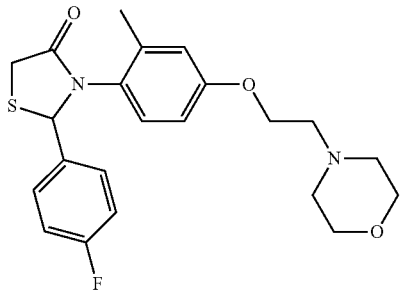

Compound 620

A solution of 2-(4-fluorophenyl)-3-(4-hydroxy-2-methylphenyl)-1,3-thiazolidin-4-one (88.9 mg, 0.293 mmol), 4-(2-chloroethyl)morpholine hydrochloride (60.0 mg, 0.322 mmol), and cesium carbonate (210 mg, 0.645 mmol) in DMF (1.0 mL) was stirred at 50° C. for 20 h. The reaction mixture was cooled to room temperature and concentrated. The residue was purified by preparative thin layer chromatography plates (1.0 mm of silica gel on glass support, 100% ethyl acetate) to give 2-(4-fluorophenyl)-3-{2-methyl-4-[2-(morpholin-4-yl)ethoxy]phenyl}-1,3-thiazolidin-4-one (80.7 mg, 66%) as a white foam. ¹H NMR (CDCl₃, 400 MHz) δ 7.30 (dd, 2H), 7.00 (br s, 2H), 6.80-6.30 (br, 2H), 6.10-5.60 (br, 1H), 4.02-3.98 (m, 3H), 3.89 (d, 1H), 3.71 (dd, 4H), 2.74 (t, 2H), 2.54 (dd, 4H), 2.30-1.80 (br, 3H); LC-MS (ESI) m/z 417.2 [M+H]⁺.

EXAMPLE 455

{4-[2-(4-Fluorophenyl)-4-oxo-1,3-thiazolidin-3-yl]-3-methylphenyl}acetonitrile

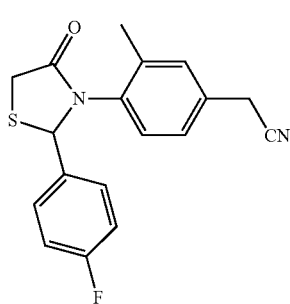

Compound 621

Step 1. Synthesis of (3-methyl-4-nitrophenyl)acetonitrile

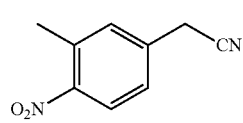

Compound 622

To a solution of ethyl carbonocyanidate (0.470 mL, 7.46 mmol) and potassium hydroxide (0.300 g, 7.46 mmol) in DMSO (1.0 mL) was stirred at room temperature for 1 h, followed by addition of 4-fluoro-2-methyl-1-nitrobenzene (0.690 mL, 5.74 mmol) in one portion. After the reaction mixture was stirred at room temperature for 7 h, a solution of 37% HCl₍ₐq₎ (1.40 mL) and AcOH (1.60 mL) was added and the reaction mixture is heated for 3 h at reflux, then quenched with H₂O, extracted with diethylether. The organic layers are washed with brine, dried over MgSO₄₍s₎, filtered and concentrated to give the residue which was purified by Isco Combi-Flash Companion column chromatography (0-30% ethyl acetate in n-hexane) to yield (3-methyl-4-nitrophenyl)acetonitrile (0.440 g, 57%). ¹H NMR (CDCl₃, 300 MHz) δ 8.00 (d, 1H), 7.34-7.30 (m, 2H), 3.81 (s, 2H), 2.62 (s, 3H).

Step 2. Synthesis of (4-amino-3-methylphenyl)acetonitrile

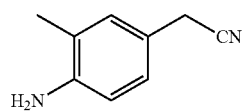

Compound 623

Palladium on carbon was added to a MeOH (20.0 mL) of (3-methyl-4-nitrophenyl)acetonitrile (0.440 g), and the mixture was stirred at room temperature for 2 h under hydrogen atmosphere. After reaction, the solution was filtered and concentrated to yield product which was purified by Isco Combi-Flash Companion column chromatography (0-30% ethyl acetate in n-hexane) to yield (4-amino-3-methylphenyl)acetonitrile (0.315 g, 86%). ¹H NMR (CDCl₃, 400 MHz) δ 7.00 (s, 1H), 6.96 (d, 1H), 6.65 (d, 1H), 3.50 (br s, 1H), 3.61 (s, 2H), 2.16 (s, 3H).

Step 3. Synthesis of 2-(4-(2-(4-fluorophenyl)-4-oxothiazolidin-3-yl)-3-methylphenyl)acetonitrile To a solution of (4-amino-3-methylphenyl)acetonitrile (0.300 g, 2.05 mmol), Na₂SO₄ (0.350 g, 2.46 mmol) and 4-fluorobenzaldehyde (0.330 mL, 3.08 mmol) in toluene (10.0 mL) was stirred at 110° C. for 7 h, followed by addition of thioglycolic acid (0.220 mL, 3.28 mmol) in one portion. The reaction mixture was refluxed overnight, then partitioned between ethyl acetate and H₂O. The organic layer was dried over MgSO₄ (s) and concentrated to give a crude product which was purified by Isco Combi-Flash Companion column chromatography (0-50% ethyl acetate in n-hexane) to give 2-(4-(2-(4-fluorophenyl)-4-oxothiazolidin-3-yl)-3-methylphenyl)acetonitrile (0.130 g, 19%). ¹H NMR (CDCl₃, 300 MHz) δ 7.34-7.28 (m, 2H), 7.16 (br s, 1H), 7.10-6.95 (m, 3H), 4.01 (d, 1H), 3.90 (d, 1H), 3.65 (s, 2H), 2.17 (br s, 3H); LC-MS (ESI) m/z 349.1 [M+Na]⁺.

EXAMPLE 456

2-(4-Fluorophenyl)-3-[2-methyl-4-(1H-tetrazol-5-ylmethyl)phenyl]-1,3-thiazolidin-4-one Compound 624

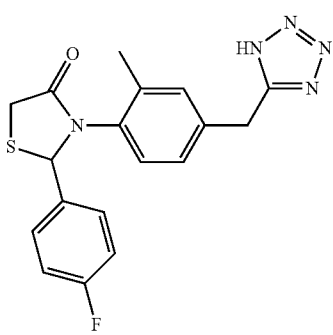

A solution of {4-[2-(4-fluorophenyl)-4-oxo-1,3-thiazolidin-3-yl]-3-methylphenyl}acetonitrile (52.4 mg, 0.161 mmol), sodium azide (15.7 g, 0.241 mmol), and ammonium acetate (18.6 mg, 0.241 mmol) in DMF (1.0 mL) was stirred at 120° C. for 24 h. The reaction mixture was cooled to room temperature and concentrated. The residue was was purified by preparative thin layer chromatography plates (1.0 mm of silica gel on glass support, 10% methanol in CH₂Cl₂) to give 2-(4-fluorophenyl)-3-[2-methyl-4-(1H-tetrazol-5-ylmethyl) phenyl]-1,3-thiazolidin-4-one (13.9 mg, 23%) as a lightly brown solid. ¹H NMR (CDCl₃, 400 MHz) δ 7.38-7.30 (m, 2H), 6.98 (br s, 3H), 6.80-6.30 (br, 2H), 6.20-5.60 (br, 2H), 4.11-4.06 (m, 3H), 3.93 (d, 1H), 2.23 (br s, 3H); LC-MS (ESI) m/z 392.2 [M+Na]⁺.

EXAMPLE 457

2-(4-Fluorophenyl)-3-(pyridin-3-yl)-1,3-thiazolidin-4-one

Compound 625

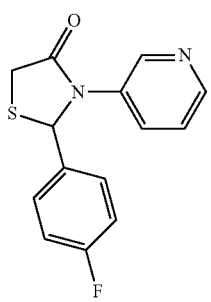

A solution of 3-aminopyridine (0.953 g, 10.1 mmol), Na₂SO₄ anhydrous (1.43 g, 10.1 mmol), and 4-fluorobenzaldehyde (1.26 g, 10.1 mmol) in toluene (20 mL) was stirred at 60° C. for 36 h. Then 2-mercaptoacetic acid (1.27 mL, 18.2 mmol) was added to the reaction mixture, and it was stirred at 90° C. for 16 h. The reaction mixture was cooled to room temperature and diluted with ethyl acetate. The solution was washed with 10% NaOH₍ₐq₎ and brine. The organic layer was dried over MgSO₄₍ₛ₎, filtered, and concentrated. The residue was purified by Isco Combi-Flash Companion column chromatography (0-80% ethyl acetate in n-hexane) to give 2-(4-fluorophenyl)-3-(pyridin-3-yl)-1,3-thiazolidin-4-one (0.985 g, 36%) as a yellow solid. ¹H NMR (CDCl₃, 400 MHz) δ 8.42-8.39 (m, 2H), 7.57-7.54 (m, 1H), 7.31-7.22 (m, 3H), 6.99 (t, 2H), 6.14 (s, 1H), 3.98 (d, 1H), 3.90 (d, 1H); LC-MS (ESI) m/z 275.5 [M+H]⁺.

EXAMPLE 458

2-(4-Fluorophenyl)-3-(pyridin-2-yl)-1,3-thiazolidin-4-one

Compound 626

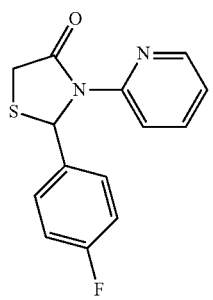

A solution of 2-aminopyridine (0.411 g, 4.54 mmol), Na₂SO₄ anhydrous (0.760 g, 5.35 mmol), and 4-fluorobenzaldehyde (0.579 mL, 5.35 mmol) in toluene (15 mL) was stirred at 60° C. for 16 h. Then 2-mercaptoacetic acid (0.570 mL, 8.17 mmol) was added to the reaction mixture, and it was stirred at 90° C. for 16 h. The reaction mixture was cooled to room temperature and diluted with ethyl acetate. The solution was washed with 10% NaOH₍ₐq₎. The organic layer was dried over MgSO₄₍ₛ₎, filtered, and concentrated. The residue was purified by Isco Combi-Flash Companion column chromatography (0-100% ethyl acetate in n-hexane) to give 2-(4-fluorophenyl)-3-(pyridin-2-yl)-1,3-thiazolidin-4-one (0.484 g, 40%) as a white solid. ¹H NMR (CDCl₃, 400 MHz) δ 8.23 (d, 1H), 8.03 (d, 1H), 7.69 (dd, 1H), 7.31-7.27 (m, 2H), 7.03-7.00 (m, 1H), 6.95 (t, 2H), 6.85 (s, 1H), 4.01 (d, 1H), 3.83 (d, 1H); LC-MS (ESI) m/z 297.1 [M+Na]⁺.

EXAMPLE 459

2-(4-Fluorophenyl)-3-(6-methoxypyridin-3-yl)-1,3-thiazolidin-4-one

Compound 627

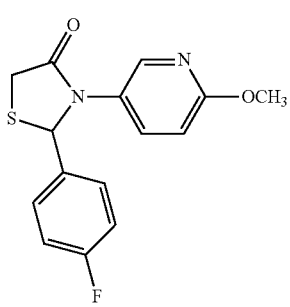

A solution of 5-amino-2-methoxypyridine (0.878 g, 7.07 mmol), Na$_2$SO$_4$ anhydrous (1.00 g, 7.07 mmol), and 4-fluorobenzaldehyde (0.760 mL, 7.09 mmol) in toluene (15 mL) was stirred at 50° C. for 8 h. Then 2-mercaptoacetic acid (0.890 mL, 12.8 mmol) was added to the reaction mixture, and it was stirred at 100° C. for 16 h. The reaction mixture was cooled to room temperature and diluted with ethyl acetate. The solution was washed with 10% NaOH$_{(aq)}$ and brine. The organic layer was dried over MgSO$_{4(s)}$, filtered, and concentrated. The residue was purified by Isco Combi-Flash Companion column chromatography (0-50% ethyl acetate in n-hexane) to give 2-(4-fluorophenyl)-3-(6-methoxypyridin-3-yl)-1,3-thiazolidin-4-one (1.37 g, 64%) as a yellow solid. $^1$H NMR (CDCl$_3$, 400 MHz) δ 7.86 (d, 1H), 7.34-7.28 (m, 3H), 7.00 (t, 2H), 6.66 (d, 1H), 5.97 (s, 1H), 3.97 (d, 1H), 3.89 (d, 1H), 3.86 (s, 3H); LC-MS (ESI) m/z 305.1 [M+H]$^+$.

EXAMPLE 460

2-(4-Fluorophenyl)-3-(6-methylpyridin-3-yl)-1,3-thiazolidin-4-one

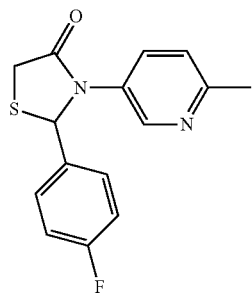

Compound 628

A solution of 5-amino-2-picoline (0.345 g, 3.19 mmol), Na$_2$SO$_4$ anhydrous (0.542 g, 3.82 mmol), and 4-fluorobenzaldehyde (0.410 mL, 3.82 mmol) in toluene (15 mL) was stirred at 60° C. for 6 h. Then 2-mercaptoacetic acid (0.445 mL, 6.38 mmol) was added to the reaction mixture, and it was stirred at 100° C. for 16 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by Isco Combi-Flash Companion column chromatography (0-90% ethyl acetate in n-hexane) to give 2-(4-fluorophenyl)-3-(6-methylpyridin-3-yl)-1,3-thiazolidin-4-one (0.428 g, 47%) as a lightly yellow solid. $^1$H NMR (CDCl$_3$, 300 MHz) δ 8.25 (d, 1H), 7.40 (dd, 1H), 7.29 (dd, 2H), 7.08 (d, 1H), 6.99 (t, 2H), 6.08 (s, 1H), 3.97 (d, 1H), 3.89 (d, 1H), 2.47 (s, 3H); LC-MS (ESI) m/z 289.2 [M+H]$^+$.

EXAMPLE 461

2-(4-Fluorophenyl)-3-(3-methylpyridin-2-yl)-1,3-thiazolidin-4-one

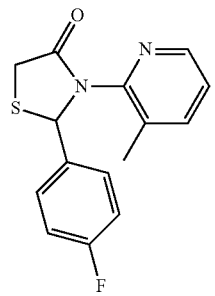

Compound 629

To a solution of 3-methylpyridin-2-amine (0.300 g, 2.77 mmol), Na$_2$SO$_4$ (0.470 g, 3.33 mmol) and 4-fluorobenzaldehyde (0.450 mL, 4.16 mmol) in toluene (5.0 mL) was stirred at 110° C. for 16 h, followed by addition of thioglycolic acid (0.310 mL, 4.44 mmol) in one portion. The reaction mixture was refluxed overnight, then partitioned between ethyl acetate and H$_2$O. The organic layer was dried over MgSO$_{4(s)}$ and concentrated to give a crude product which was purified by Isco Combi-Flash Companion column chromatography (0-50% ethyl acetate in n-hexane) to give 2-(4-fluorophenyl)-3-(3-methylpyridin-2-yl)-1,3-thiazolidin-4-one (0.230 g, 29%). $^1$H NMR (CDCl$_3$, 300 MHz) δ 8.22 (d, 1H), 7.44 (d, 1H), 7.42-7.35 (m, 2H), 7.04 (dd, 1H), 6.89 (t, 2H), 6.59 (s, 1H), 4.00-3.92 (m, 2H), 2.15 (s, 3H); LC-MS (ESI) m/z 289.1 [M+H]$^+$.

EXAMPLE 462

2-(4-Fluorophenyl)-3-(pyrazin-2-yl)-1,3-thiazolidin-4-one

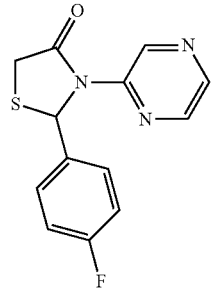

Compound 630

To a solution of pyrazin-2-amine (0.300 g, 3.15 mmol), Na$_2$SO$_4$ (0.540 g, 3.79 mmol) and 4-fluorobenzaldehyde (0.510 mL, 4.73 mmol) in toluene (5.0 mL) was stirred at 110° C. for 16 h, followed by addition of thioglycolic acid (0.350 mL, 5.05 mmol) in one portion. The reaction mixture was refluxed overnight, then partitioned between ethyl acetate and H$_2$O. The organic layer was dried over MgSO$_4$ (s) and concentrated to give a crude product which was purified by Isco Combi-Flash Companion column chromatography (0-40% ethyl acetate in n-hexane) to give 2-(4-fluorophenyl)-3-(pyrazin-2-yl)-1,3-thiazolidin-4-one (0.330 g, 38%). ¹H NMR (CDCl₃, 300 MHz) δ 9.43 (s, 1H), 8.30 (d, 1H), 8.20 (dd, 1H), 7.33-7.25 (m, 2H), 6.97 (t, 2H), 6.71 (s, 1H), 4.04 (d, 1H), 3.84 (d, 1H); LC-MS (ESI) m/z 276.1 [M+H]⁺.

EXAMPLE 463

2-(4-Fluorophenyl)-3-(pyrimidin-2-yl)-1,3-thiazolidin-4-one

Compound 631

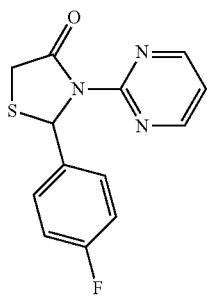

To a solution of pyrimidin-2-amine (0.300 g, 3.15 mmol), Na₂SO₄ (0.540 g, 3.79 mmol) and 4-fluorobenzaldehyde (0.510 mL, 4.73 mmol) in toluene (5.0 mL) was stirred at 110° C. for 16 h, followed by addition of thioglycolic acid (0.350 mL, 5.05 mmol) in one portion. The reaction mixture was refluxed overnight, then partitioned between ethyl acetate and H₂O. The organic layer was dried over MgSO₄ (s) and concentrated to give a crude product which was purified by Isco Combi-Flash Companion column chromatography (0-60% ethyl acetate in n-hexane) to give 2-(4-fluorophenyl)-3-(pyrimidin-2-yl)-1,3-thiazolidin-4-one (24.0 mg, 3%). ¹H NMR (CDCl₃, 400 MHz) δ 8.61 (d, 2H), 7.37-7.32 (m, 2H), 7.03 (t, 1H), 6.95 (t, 2H), 6.66 (s, 1H), 4.00 (d, 1H), 3.85 (d, 1H); LC-MS (ESI) m/z 276.1 [M+H]⁺.

EXAMPLE 464

2-(4-Fluorophenyl)-3-(pyrimidin-4-yl)-1,3-thiazolidin-4-one

Compound 632

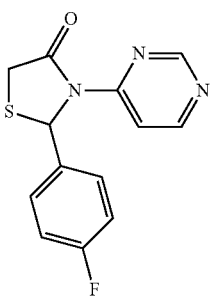

To a solution of pyrimidin-4-amine (0.300 g, 3.15 mmol), Na₂SO₄ (0.540 g, 3.79 mmol) and 4-fluorobenzaldehyde (0.510 mL, 4.73 mmol) in toluene (5.0 mL) was stirred at 110° C. for 7 h, followed by addition of thioglycolic acid (0.350 mL, 5.05 mmol) in one portion. The reaction mixture was refluxed overnight, then partitioned between ethyl acetate and H₂O. The organic layer was dried over MgSO₄₍ₛ₎ and concentrated to give a crude product which was purified by Isco Combi-Flash Companion column chromatography (0-30% ethyl acetate in n-hexane) to give 2-(4-fluorophenyl)-3-(pyrimidin-4-yl)-1,3-thiazolidin-4-one (0.150 g, 18%). ¹H NMR (CDCl₃, 400 MHz) δ 8.81 (s, 1H), 8.65 (d, 1H), 8.33 (d, 1H), 7.27-7.24 (m, 2H), 7.03-6.97 (m, 2H), 6.80 (s, 1H), 4.02 (d, 1H), 3.78 (d, 1H); LC-MS (ESI) m/z 276.1 [M+H]⁺.

EXAMPLE 465

Ethyl 5-[2-(4-fluorophenyl)-4-oxo-1,3-thiazolidin-3-yl]-4-methylpyridine-2-carboxylate Compound 633

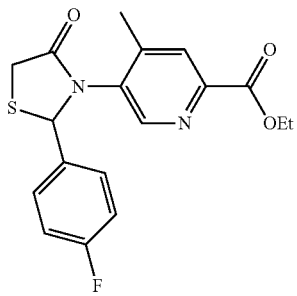

Step 1. Synthesis of ethyl 5-amino-4-methylpyridine-2-carboxylate

Compound 634

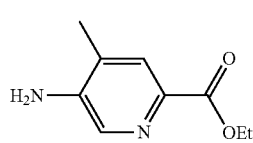

To a solution of ethyl 4-methyl-5-nitropyridine-2-carboxylate (0.665 g, 3.16 mmol) in THF (20 mL) was added palladium on carbon (70 mg) at room temperature under H₂₍g₎ (1 atm). The reaction mixture was stirred at room temperature for 18 h and then filtered through celite and washed with CH₂Cl₂. The filtrate was concentrated and dried under high vacuum to give ethyl 5-amino-4-methylpyridine-2-carboxylate (0.580 g, quantitative yield) as a green solid. ¹H NMR (CDCl₃, 400 MHz) δ 8.08 (s, 1H), 7.86 (s, 1H), 4.42 (q, 2H), 4.04 (br s, 2H), 2.20 (s, 3H), 1.41 (t, 3H).

Step 2. Synthesis of ethyl 5-[2-(4-fluorophenyl)-4-oxo-1,3-thiazolidin-3-yl]-4-methylpyridine-2-carboxylate Following standard procedure A, ethyl 5-amino-4-methylpyridine-2-carboxylate (0.285 g, 1.58 mmol), 4-fluorobenzaldehyde (0.200 mL, 1.87 mmol), Na₂SO₄ (0.336 g, 2.37 mmol), 2-mercaptoacetic acid (0.200 mL, 2.86 mmol), and toluene (5.0 mL) were used to carry out the reaction. It was reflux 24 h for the first step and 18 h for the second step. After work-up, the residue was purified by preparative thin layer chromatography plates (2.0 mm of silica gel on glass support, 70% ethyl acetate in n-hexane) to give ethyl 5-[2-(4-fluorophenyl)-4-oxo-1,3-thiazolidin-3-yl]-4-methylpyridine-2-carboxylate (28.1 mg, 5%) as a red solid. $^1$H NMR (CDCl$_3$, 400 MHz) δ 7.94 (br s, 1H), 7.34-7.31 (m, 2H), 6.97 (t, 2H), 6.10-5.90 (br, 1H), 4.42 (q, 2H), 4.00 (d, 1H), 3.95 (d, 1H), 2.22 (br s, 3H), 1.40 (t, 3H); LC-MS (ESI) m/z 361.2 [M+H]$^+$.

EXAMPLE 466

Ethyl 5-[2-(4-fluorophenyl)-4-oxo-1,3-thiazolidin-3-yl]-6-methylpyridine-2-carboxylate Compound 635

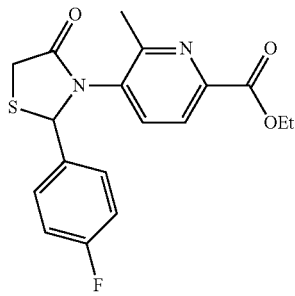

Step 1. Synthesis of 6-methyl-5-nitropyridine-2-carbonitrile

Compound 636

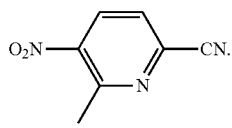

A solution of 6-bromo-2-methyl-3-nitropyridine (2.85 g, 13.1 mmol), zinc cyanide (2.16 g, 18.4 mmol), and Pd(PPh$_3$)$_4$ (0.759 g, 0.607 mmol) in DMF (20 mL) was stirred at 80° C. for 20 h. The reaction mixture was cooled to room temperature, and DMF was removed under reduced pressure. The crude was treated with ethyl acetate and saturated NaHCO$_{3(aq)}$. The organic layer was washed with H$_2$O and brine, dried over MgSO$_{4(s)}$, filtered, and concentrated. The residue was purified by Isco Combi-Flash Companion column chromatography (0-20% ethyl acetate in n-hexane) to give 6-methyl-5-nitropyridine-2-carbonitrile (1.75 g, 82%) as a yellow oil. $^1$H NMR (CDCl$_3$, 400 MHz) δ 8.38 (d, 1H), 7.76 (d, 1H), 2.90 (s, 3H).

Step 2. Synthesis of ethyl 6-methyl-5-nitropyridine-2-carboxylate

Compound 637

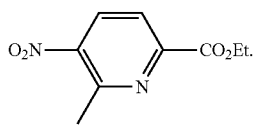

A solution of 6-methyl-5-nitropyridine-2-carbonitrile (0.680 g, 4.17 mmol) in H$_2$O (50 µL) and 1.25 M hydrogen chloride in ethanol solution (6.0 mL) was reflux for 34 h. The reaction mixture was cooled to room temperature and concentrated to give ethyl 6-methyl-5-nitropyridine-2-carboxylate (0.676 g, 77%) as a yellow oil. $^1$H NMR (CDCl$_3$, 400 MHz) δ 8.36 (d, 1H), 8.12 (d, 1H), 4.51 (q, 2H), 2.93 (s, 3H), 1.45 (t, 2H).

Step 3. Synthesis of ethyl 6-Methyl-5-aminopyridine-2-carboxylate

Compound 638

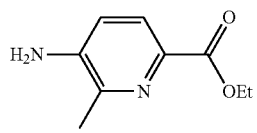

To a solution of ethyl 6-methyl-5-nitropyridine-2-carboxylate (0.676 g, 3.22 mmol) in THF (20 mL) was added palladium on carbon (70 mg) at room temperature under H$_{2(g)}$ (1 atm). The reaction mixture was stirred at room temperature for 18 h and then filtered through celite and washed with CH$_2$Cl$_2$. The filtrate was concentrated and dried under high vacuum to give ethyl 6-methyl-5-aminopyridine-2-carboxylate (0.584 g, quantitative yield) as a yellow solid. $^1$H NMR (CDCl$_3$, 400 MHz) δ 7.86 (d, 1H), 6.93 (d, 1H), 4.42 (q, 2H), 4.04 (br s, 2H), 2.48 (s, 3H), 1.40 (t, 3H),

Step 4. Synthesis of ethyl 5-[2-(4-fluorophenyl)-4-oxo-1,3-thiazolidin-3-yl]-6-methylpyridine-2-carboxylate Following standard procedure A, ethyl 6-methyl-5-aminopyridine-2-carboxylate (0.280 g, 1.55 mmol), 4-fluorobenzaldehyde (0.200 mL, 1.87 mmol), Na$_2$SO$_4$ (0.330 g, 2.33 mmol), 2-mercaptoacetic acid (0.200 mL, 2.86 mmol), and toluene (5.0 mL) were used to carry out the reaction. It was reflux 24 h for the first step and 18 h for the second step. After work-up, the residue was purified by preparative thin layer chromatography plates (2.0 mm of silica gel on glass support, 70% ethyl acetate in n-hexane) to give ethyl 5-[2-(4-fluorophenyl)-4-oxo-1,3-thiazolidin-3-yl]-6-methylpyridine-2-carboxylate (37.3 mg, 7%) as a white solid. $^1$H NMR (CDCl$_3$, 400 MHz) δ 7.84 (d, 1H), 7.32-7.27 (m, 3H), 6.97 (dd, 2H), 5.94 (br s, 1H), 4.43 (q, 2H), 4.01 (d, 1H), 3.93 (d, 1H), 2.52 (br s, 3H), 1.39 (t, 3H); LC-MS (ESI) m/z 361.2 [M+H]$^+$.

EXAMPLE 467

2-(4-Fluorophenyl)-3-(1,3-thiazol-2-yl)-1,3-thiazolidin-4-one

Compound 639

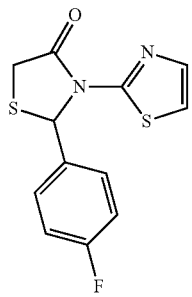

A solution of 2-aminothiazole (0.457 g, 4.56 mmol), Na₂SO₄ anhydrous (0.768 g, 5.41 mmol), and 4-fluorobenzaldehyde (0.580 mL, 5.41 mmol) in toluene (15 mL) was stirred at 60° C. for 16 h. Then 2-mercaptoacetic acid (0.570 mL, 8.17 mmol) was added to the reaction mixture, and it was stirred at 90° C. for 16 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by Isco Combi-Flash Companion column chromatography (0-35% ethyl acetate in n-hexane) to give 2-(4-fluorophenyl)-3-(1,3-thiazol-2-yl)-1,3-thiazolidin-4-one (0.455 g, 36%) as a lightly yellow solid. ¹H NMR (CDCl₃, 400 MHz) δ 7.39 (d, 1H), 7.27-7.24 (m, 2H), 7.03-6.99 (m, 3H), 6.67 (s, 1H), 4.08 (d, 1H), 3.83 (d, 1H); LC-MS (ESI) m/z 303.0 [M+Na]⁺.

EXAMPLE 468

3-(5-tert-Butyl-1,2-oxazol-3-yl)-2-(4-fluorophenyl)-1,3-thiazolidin-4-one

Compound 640

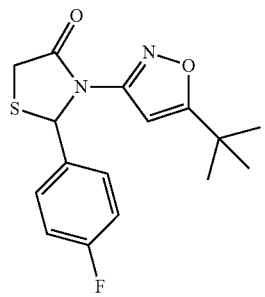

To a solution of 5-(tert-butyl)isoxazol-3-amine (0.300 g, 2.14 mmol), Na₂SO₄ (0.360 g, 2.57 mmol) and 4-fluorobenzaldehyde (0.350 mL, 3.21 mmol) in toluene (5.0 mL) was stirred at 110° C. for 7 h, followed by addition of thioglycolic acid (0.240 mL, 3.42 mmol) in one portion. The reaction mixture was refluxed overnight, then partitioned between ethyl acetate and H₂O. The organic layer was dried over MgSO$_{4(s)}$ and concentrated to give a crude product which was purified by Isco Combi-Flash Companion column chromatography (0-20% ethyl acetate in n-hexane) to give 3-(5-tert-butyl-1,2-oxazol-3-yl)-2-(4-fluorophenyl)-1,3-thiazolidin-4-one (0.620 g, 91%). ¹H NMR (CDCl₃, 400 MHz) δ 7.31-7.27 (m, 2H), 7.05-7.01 (m, 2H), 6.78 (s, 1H), 6.29 (s, 1H), 3.97 (d, 1H), 3.72 (d, 1H), 1.30 (s, 9H); LC-MS (ESI) m/z 321.1 [M+H]⁺.

EXAMPLE 469

2-(4-Fluorophenyl)-3-(1,2-oxazol-3-yl)-1,3-thiazolidin-4-one

Compound 641

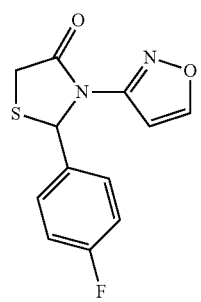

To a solution of 3-aminoisoxazole (0.300 g, 3.57 mmol), Na₂SO₄ (0.610 g, 4.28 mmol) and 4-fluorobenzaldehyde (0.580 mL, 5.35 mmol) in toluene (5.0 mL) was stirred at 110° C. for 7 h, followed by addition of thioglycolic acid (0.400 mL, 5.71 mmol) in one portion. The reaction mixture was refluxed overnight, then partitioned between ethyl acetate and H₂O. The organic layer was dried over MgSO$_{4(s)}$ and concentrated to give a crude product which was purified by Isco Combi-Flash Companion column chromatography (0-30% ethyl acetate in n-hexane) to give 2-(4-fluorophenyl)-3-(1,2-oxazol-3-yl)-1,3-thiazolidin-4-one (0.940 g, 99%). ¹H NMR (CDCl₃, 400 MHz) δ 8.28 (d, 1H), 7.31-7.27 (m, 2H), 7.17 (d, 1H), 7.05-7.00 (m, 2H), 6.34 (s, 1H), 3.99 (d, 1H), 3.76 (d, 1H); LC-MS (ESI) m/z 287.1 [M+Na]⁺.

EXAMPLE 470

2-(4-Fluorophenyl)-3-(5-methyl-1,3,4-thiadiazol-2-yl)-1,3-thiazolidin-4-one

Compound 642

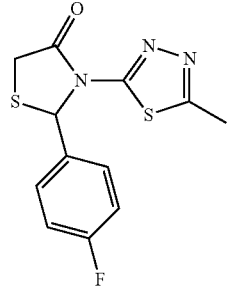

To a solution of 5-methyl-1,3,4-thiadiazol-2-amine (0.300 g, 2.61 mmol), Na₂SO₄ (0.440 g, 3.13 mmol) and 4-fluorobenzaldehyde (0.420 mL, 3.91 mmol) in toluene (5.0 mL) was stirred at 110° C. for 7 h, followed by addition of thioglycolic acid (0.290 mL, 4.17 mmol) in one portion. The reaction mixture was refluxed overnight, then partitioned between ethyl acetate and H₂O. The organic layer was dried over MgSO$_{4(s)}$ and concentrated to give a crude product which was purified by Isco Combi-Flash Companion column chromatography (0-30% ethyl acetate in n-hexane) to give 2-(4-fluorophenyl)-3-(5-methyl-1,3,4-thiadiazol-2-yl)-1,3-thiazolidin-4-one (0.600 g, 78%). ¹H NMR (CDCl₃, 400 MHz) δ 7.33-7.29 (m, 2H), 7.02 (t, 2H), 6.66 (s, 1H), 4.11 (d, 1H), 3.86 (d, 1H), 2.67 (s, 3H); LC-MS (ESI) m/z 318.0 [M+Na]⁺.

EXAMPLE 471

2-(4-Fluorophenyl)-3-(4-methyl-1,3-thiazol-2-yl)-1,3-thiazolidin-4-one

Compound 643

To a solution of 2-amino-4-methylthiazole (0.300 g, 2.63 mmol), Na$_2$SO$_4$ (0.450 g, 3.15 mmol) and 4-fluorobenzaldehyde (0.420 mL, 3.94 mmol) in toluene (10.0 mL) was stirred at 110° C. for 7 h, followed by addition of thioglycolic acid (0.290 mL, 4.20 mmol) in one portion. The reaction mixture was refluxed overnight, then partitioned between ethyl acetate and H$_2$O. The organic layer was dried over MgSO$_{4(s)}$ and concentrated to give a crude product which was purified by Isco Combi-Flash Companion column chromatography (0-20% ethyl acetate in n-hexane) to give 2-(4-fluorophenyl)-3-(4-methyl-1,3-thiazol-2-yl)-1,3-thiazolidin-4-one (0.160 g, 21%). $^1$H NMR (CDCl$_3$, 400 MHz) δ 7.29-7.25 (m, 2H), 7.03-6.97 (m, 2H), 6.66 (s, 1H), 6.55 (s, 1H), 4.06 (d, 1H), 3.81 (d, 1H), 2.22 (s, 3H); LC-MS (ESI) m/z 317.1 [M+Na]$^+$.

EXAMPLE 472

Methyl 3-methyl-4-[4-oxo-2-(pyridin-2-yl)-1,3-thiazolidin-3-yl]benzoate

Compound 644

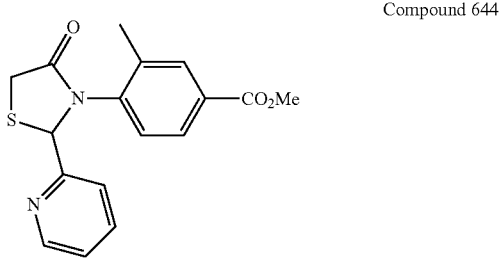 [SMILES: COC(=O)c1ccc(N2C(=O)CSC2c2ccccn2)c(C)c1]

To a solution of methyl 4-amino-3-methylbenzenecarboxylate (0.300 g, 1.82 mmol), Na$_2$SO$_4$ (0.260 g, 1.82 mmol) and pyridine-2-carbaldehyde (0.260 mL, 2.73 mmol) in toluene (10.0 mL) was stirred at 110° C. for 6 h, followed by addition of thioglycolic acid (0.250 mL, 3.63 mmol) in one portion. The reaction mixture was refluxed overnight, then partitioned between ethyl acetate and H$_2$O. The organic layer was dried over MgSO$_4$ (s) and concentrated to give a crude product which was purified by Isco Combi-Flash Companion column chromatography (0-50% ethyl acetate in n-hexane) to give methyl 3-methyl-4-[4-oxo-2-(pyridin-2-yl)-1,3-thiazolidin-3-yl]benzoate (75.0 mg, 13%). $^1$H NMR (CDCl$_3$, 400 MHz) δ 8.56 (br d, 1H), 7.88 (br s, 1H), 7.70 (br d, 1H), 7.61 (t, 1H), 7.22-7.18 (m, 2H), 6.95 (br s, 1H), 5.85 (br s, 1H), 4.19 (d, 1H), 3.85 (s, 3H), 3.79 (d, 1H), 2.30 (br s, 3H); LC-MS (ESI) m/z 329.2 [M+H]$^+$.

EXAMPLE 473

Methyl 3-methyl-4-[4-oxo-2-(pyridin-3-yl)-1,3-thiazolidin-3-yl]benzoate

Compound 645

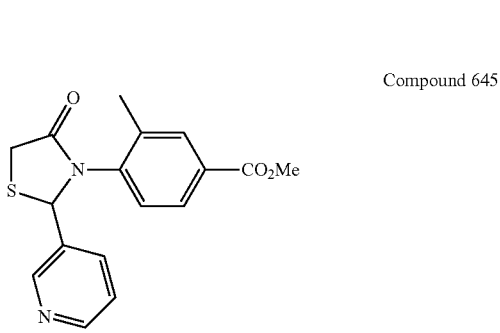 [SMILES: COC(=O)c1ccc(N2C(=O)CSC2c2cccnc2)c(C)c1]

To a solution of methyl 4-amino-3-methylbenzenecarboxylate (0.300 g, 1.82 mmol), Na$_2$SO$_4$ (0.260 g, 1.82 mmol) and nicotinaldehyde (0.290 mL, 2.73 mmol) in toluene (10.0 mL) was stirred at 110° C. for 24 h, followed by addition of thioglycolic acid (0.250 mL, 3.63 mmol) in one portion. The reaction mixture was refluxed overnight, then partitioned between ethyl acetate and H$_2$O. The organic layer was dried over MgSO$_{4(s)}$ and concentrated to give a crude product which was purified by Isco Combi-Flash Companion column chromatography (0-50% ethyl acetate in n-hexane) to give methyl 3-methyl-4-[4-oxo-2-(pyridin-3-yl)-1,3-thiazolidin-3-yl]benzoate (0.115 g, 19%). $^1$H NMR (CDCl$_3$, 400 MHz) δ 8.50 (br d, 1H), 8.45 (s, 1H), 7.84 (br s, 1H), 7.74-7.71 (m, 2H), 7.25-7.21 (m, 1H), 7.18-6.60 (br, 1H), 5.99 (br s, 1H), 4.01 (d, 1H), 3.92 (d, 1H), 3.84 (s, 3H), 2.29-1.85 (br, 3H); LC-MS (ESI) m/z 329.1 [M+H]$^+$.

EXAMPLE 474

Methyl 3-methyl-4-[4-oxo-2-(1,3-thiazol-2-yl)-1,3-thiazolidin-3-yl]benzoate

Compound 646

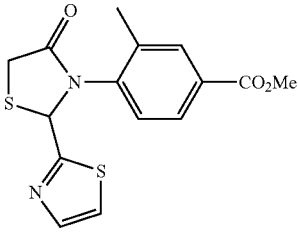

To a solution of methyl 4-amino-3-methylbenzenecarboxylate (0.300 g, 1.82 mmol), Na$_2$SO$_4$ (0.260 g, 1.82 mmol) and thiazole-2-carbaldehyde (0.240 mL, 2.73 mmol) in toluene (5.0 mL) was stirred at 110° C. for 16 h, followed by addition of thioglycolic acid (0.250 mL, 3.63 mmol) in one portion. The reaction mixture was refluxed overnight, then partitioned between ethyl acetate and H$_2$O. The organic layer was dried over MgSO$_4$ (s) and concentrated to give a crude product which was purified by Isco Combi-Flash Companion column chromatography (0-40% ethyl acetate in n-hexane) to give methyl 3-methyl-4-[4-oxo-2-(1,3-thiazol-2-yl)-1,3-thiazolidin-3-yl]benzoate (0.130 g, 21%). $^1$H NMR (CDCl$_3$, 400 MHz) δ 7.92 (br s, 1H), 7.82-7.76 (m, 1H), 7.64 (d, 1H), 7.36 (d, 1H), 7.04 (br s, 1H), 6.23 (br s, 1H), 4.11 (d, 1H), 3.88-3.84 (m, 4H), 2.23 (br s, 3H); LC-MS (ESI) m/z 357.1 [M+Na]$^+$.

EXAMPLE 475

Methyl 4-[2-(1-benzofuran-2-yl)-4-oxo-1,3-thiazolidin-3-yl]-3-methylbenzoate

Compound 647

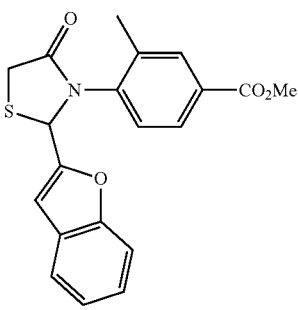

To a solution of methyl 4-amino-3-methylbenzenecarboxylate (0.300 g, 1.82 mmol), Na$_2$SO$_4$ (0.310 g, 2.18 mmol) and benzofuran-2-carbaldehyde (0.330 mL, 2.73 mmol) in toluene (10.0 mL) was stirred at 110° C. for 7 h, followed by addition of thioglycolic acid (0.250 mL, 3.63 mmol) in one portion. The reaction mixture was refluxed overnight, then partitioned between ethyl acetate and H$_2$O. The organic layer was dried over MgSO$_4$ (s) and concentrated to give a crude product which was purified by Isco Combi-Flash Companion column chromatography (0-30% ethyl acetate in n-hexane) to give methyl 4-[2-(1-benzofuran-2-yl)-4-oxo-1,3-thiazolidin-3-yl]-3-methylbenzoate (0.115 g, 17%). $^1$H NMR (CDCl$_3$, 400 MHz) δ 7.91 (br s. 1H), 7.74 (br d, 1H), 7.52-7.46 (m, 2H), 7.33 (t, 1H), 7.24-7.20 (m, 1H), 6.95 (br s, 1H), 6.54 (s, 1H), 5.92 (br s, 1H), 4.23 (d, 1H), 3.93-3.81 (m, 4H), 2.32 (br s, 3H); LC-MS (ESI) m/z 368.2 [M+H]$^+$.

EXAMPLE 476

Methyl 3-methyl-4-[4-oxo-2-(thiophen-3-yl)-1,3-thiazolidin-3-yl]benzoate

Compound 648

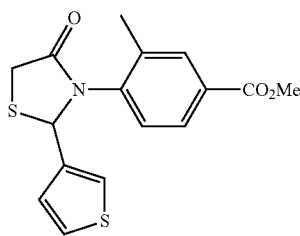

To a solution of methyl 4-amino-3-methylbenzenecarboxylate (0.300 g, 1.82 mmol), Na$_2$SO$_4$ (0.260 g, 1.82 mmol) and thiophene-3-carbaldehyde (0.240 mL, 2.73 mmol) in toluene (5.0 mL) was stirred at 110° C. for 16 h, followed by addition of thioglycolic acid (0.250 mL, 3.63 mmol) in one portion. The reaction mixture was refluxed overnight, then partitioned between ethyl acetate and H$_2$O. The organic layer was dried over MgSO$_4$ (s) and concentrated to give a crude product which was purified by Isco Combi-Flash Companion column chromatography (0-40% ethyl acetate in n-hexane) to give methyl 3-methyl-4-[4-oxo-2-(thiophen-3-yl)-1,3-thiazolidin-3-yl]benzoate (0.134 g, 22%). $^1$H NMR (CDCl$_3$, 300 MHz) δ 7.88 (s, 1H), 7.77 (br d, 1H), 7.26-7.25 (m, 1H), 7.12-7.08 (m, 2H), 6.93 (br s, 1H), 6.03 (br s, 1H), 3.99 (d, 1H), 3.96-3.85 (m, 4H), 2.17 (br s, 3H); LC-MS (ESI) m/z 334.1 [M+H]$^+$.

EXAMPLE 477

3-(4-Fluoro-2-methylphenyl)-2-(thiophen-3-yl)-1,3-thiazolidin-4-one

Compound 650

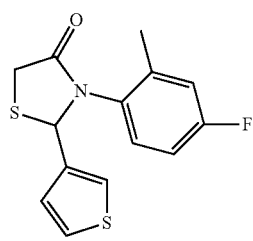

A solution of 4-fluoro-2-methylaniline (259 mg, 2.07 mmol), Na$_2$SO$_4$ anhydrous (441 mg, 3.11 mmol), and thiophene-3-carboxaldehyde (255 mg, 2.28 mmol) in toluene (10 mL) was stirred at 70° C. for 10 h. Then 2-mercaptoacetic acid (0.296 mL, 4.24 mmol) was added to the reaction mixture, and it was stirred at 90° C. for 18 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by preparative thin layer chromatography plates (2.0 mm of silica gel on glass support, 30% ethyl acetate in n-hexane) to give 3-(4-fluoro-2-methylphenyl)-2-(thiophen-3-yl)-1,3-thiazolidin-4-one (136 mg, 22%) as a yellow gum. $^1$H NMR (CDCl$_3$, 400 MHz) δ 7.29 (br s, 1H), 7.11 (br s, 2H), 6.91 (br s, 1H), 6.77 (br s, 1H), 6.70-6.30 (br, 1H), 6.20-5.60 (br, 1H), 3.98 (d, 1H), 3.87 (d, 1H), 2.20-1.80 (br, 3H); LC-MS (ESI) m/z 294.2 [M+H]$^+$.

EXAMPLE 478

3-(5-Fluoro-2-methylphenyl)-2-(thiophen-3-yl)-1,3-thiazolidin-4-one

Compound 650

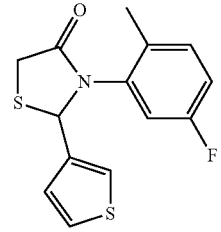

A solution of 5-fluoro-2-methylaniline (218 mg, 1.74 mmol), Na$_2$SO$_4$ anhydrous (371 mg, 2.61 mmol), and thiophene-3-carboxaldehyde (195 mg, 1.74 mmol) in toluene (10 mL) was stirred at 70° C. for 10 h. Then 2-mercaptoacetic acid (0.220 mL, 3.15 mmol) was added to the reaction mixture, and it was stirred at 90° C. for 18 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by preparative thin layer chromatography plates (2.0 mm of silica gel on glass support, 25% ethyl acetate in n-hexane) to give 3-(5-fluoro-2-methylphenyl)-2-(thiophen-3-yl)-1,3-thiazolidin-4-one (63.8 mg, 12%) as a yellow gum. $^1$H NMR (CDCl$_3$, 400 MHz) δ 7.29 (br s, 1H), 7.21-7.11 (m, 3H), 6.92 (ddd, 1H), 6.58 (br s, 1H), 5.96 (br s, 1H), 3.98 (d, 1H), 3.87 (d, 1H), 2.09 (br s, 3H); LC-MS (ESI) m/z 294.4 [M+H]$^+$.

EXAMPLE 479

3-(5-Chloro-2-methylphenyl)-2-(thiophen-3-yl)-1,3-thiazolidin-4-one

Compound 651

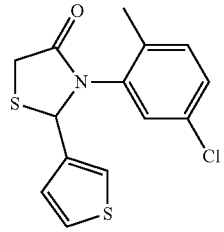

A solution of 5-chloro-2-methylaniline (229 mg, 1.62 mmol), Na₂SO₄ anhydrous (345 mg, 2.43 mmol), and thiophene-3-carboxaldehyde (181 mg, 1.62 mmol) in toluene (10 mL) was stirred at 80° C. for 18 h. Then 2-mercaptoacetic acid (0.200 mL, 2.87 mmol) was added to the reaction mixture, and it was stirred at 90° C. for 20 h. The reaction mixture was cooled to room temperature and diluted with ethyl acetate. The solution was washed with 10% NaOH$_{(aq)}$. The organic layer was dried over MgSO$_{4(s)}$, filtered, and concentrated. The residue was purified by preparative thin layer chromatography plates (2.0 mm of silica gel on glass support, 30% ethyl acetate in n-hexane) to give 3-(5-chloro-2-methylphenyl)-2-(thiophen-3-yl)-1,3-thiazolidin-4-one (48.9 mg, 10%) as a yellow gum. ¹H NMR (CDCl₃, 400 MHz) δ 7.29 (br s, 1H), 7.17-7.11 (m, 4H), 5.97 (br s, 1H), 3.97 (d, 1H), 3.87 (d, 1H), 2.07 (br s, 3H); LC-MS (ESI) m/z 310.1 [M+H]⁺.

EXAMPLE 480

Ethyl {3-methyl-4-[4-oxo-2-(thiophen-3-yl)-1,3-thiazolidin-3-yl]phenoxy}acetate

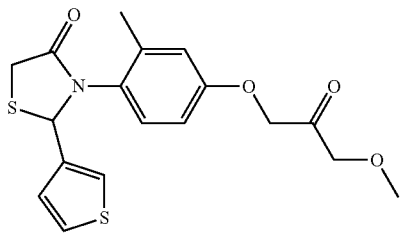

Compound 652

Step 1. Synthesis of ethyl ethyl (4-amino-3-methylphenoxy)acetate

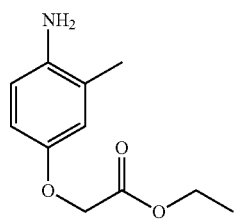

Compound 653

To the solution of 4-amino-3-methylphenol (1.00 g, 8.12 mmol) in acetone (10.0 mL), ethyl 2-chloroacetate (1.04 mL, 9.74 mmol) and K₂CO₃ (1.23 g, 8.93 mmol) were used to carry out the reaction. After the reaction mixture was stirred at 50° C. for 16 h and work-up, the residue was purified by Isco Combi-Flash Companion column chromatography (0-40% ethyl acetate in n-hexane) to give ethyl (4-amino-3-methylphenoxy)acetate (0.480 g, 28%). ¹H NMR (CDCl₃, 400 MHz) δ 6.70 (s, 1H), 6.65-6.58 (m, 2H), 4.53 (s, 2H), 4.25 (q, 2H), 3.39 (br s, 2H), 2.17 (s, 3H), 1.28 (t, 3H).

Step 2. Synthesis of ethyl {3-methyl-4-[4-oxo-2-(thiophen-3-yl)-1,3-thiazolidin-3-yl]phenoxy}acetate To a solution of ethyl (4-amino-3-methylphenoxy)acetate (0.300 g, 1.43 mmol), Na₂SO₄ (0.200 g, 1.43 mmol) and thiophene-3-carbaldehyde (0.190 mL, 2.15 mmol) in toluene (10.0 mL) was stirred at 110° C. for 7 h, followed by addition of thioglycolic acid (0.200 mL, 2.87 mmol) in one portion. The reaction mixture was refluxed overnight, then partitioned between ethyl acetate and H₂O. The organic layer was dried over MgSO₄ (s) and concentrated to give a crude product which was purified by Isco Combi-Flash Companion column chromatography (0-50% ethyl acetate in n-hexane, 0-2% MeOH in CH₂Cl₂) to give ethyl {3-methyl-4-[4-oxo-2-(thiophen-3-yl)-1,3-thiazolidin-3-yl]phenoxy}acetate (0.200 g, 37%). ¹H NMR (CDCl₃, 400 MHz) δ 7.21-7.17 (br, 2H), 7.10 (br s, 2H), 6.83-6.43 (br, 1H), 5.92-5.62 (br, 1H), 4.54 (s, 2H), 4.25 (q, 2H), 3.98 (d, 1H), 3.86 (d, 1H), 2.34-1.72 (br, 3H), 1.28 (t, 3H); LC-MS (ESI) m/z 400.1 [M+Na]⁺.

EXAMPLE 481

3-(4,5-Dimethoxy-2-methylphenyl)-2-(thiophen-3-yl)-1,3-thiazolidin-4-one

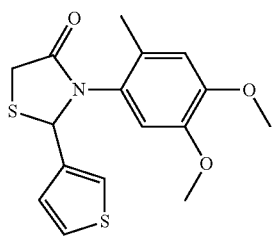

Compound 654

To a solution of 4,5-dimethoxy-2-methylaniline (0.300 g, 1.79 mmol), Na₂SO₄ (0.250 g, 1.79 mmol) and thiophene-3-carbaldehyde (0.240 mL, 2.69 mmol) in toluene (10.0 mL) was stirred at 110° C. for 7 h, followed by addition of thioglycolic acid (0.250 mL, 3.59 mmol) in one portion. The reaction mixture was refluxed overnight, then partitioned between ethyl acetate and H₂O. The organic layer was dried over MgSO$_{4(s)}$ and concentrated to give a crude product which was purified by Isco Combi-Flash Companion column chromatography (0-50% ethyl acetate in n-hexane) to give 3-(4,5-dimethoxy-2-methylphenyl)-2-(thiophen-3-yl)-1,3-thiazolidin-4-one (0.350 g, 58%). ¹H NMR (CDCl₃, 400 MHz) δ 7.52 (br s, 1H), 7.31-7.16 (br, 2H), 6.68 (br s, 1H), 6.00-5.65 (br, 1H), 3.99 (d, 1H), 3.88 (d, 1H), 3.83 (s, 3H), 3.52 (br s, 3H), 2.18 (br s, 3H); LC-MS (ESI) m/z 336.1 [M+H]⁺.

EXAMPLE 482

3-(4-Methoxy-2-methylphenyl)-2-(thiophen-3-yl)-1,3-thiazolidin-4-one

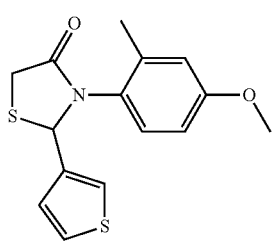

Compound 655

To a solution of 4-methoxy-2-methylaniline (0.280 mL, 2.19 mmol), Na$_2$SO$_4$ (0.310 g, 2.19 mmol) and thiophene-3-carbaldehyde (0.280 mL, 3.28 mmol) in toluene (10.0 mL) was stirred at 110° C. for 7 h, followed by addition of thioglycolic acid (0.250 mL, 3.59 mmol) in one portion. The reaction mixture was refluxed overnight, then partitioned between ethyl acetate and H$_2$O. The organic layer was dried over MgSO$_{4(s)}$ and concentrated to give a crude product which was purified by Isco Combi-Flash Companion column chromatography (0-30% ethyl acetate in n-hexane) to give 3-(4-methoxy-2-methylphenyl)-2-(thiophen-3-yl)-1,3-thiazolidin-4-one (0.420 g, 63%). $^1$H NMR (CDCl$_3$, 400 MHz) δ 7.28 (br s, 1H), 7.10 (br s, 2H), 6.81-6.29 (br, 2H), 6.19-5.64 (br, 1H), 3.98 (d, 1H), 3.86 (d, 1H), 3.73 (s, 3H), 2.30-1.63 (br, 3H); LC-MS (ESI) m/z 328.1 [M+Na]$^+$.

EXAMPLE 483

1-(5-Fluoro-2-methylphenyl)-5-(4-fluorophenyl)pyrrolidin-2-one

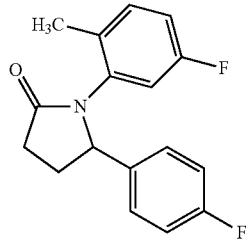

Compound 656

Step 1. Synthesis of N-(5-fluoro-2-methylphenyl)-4-(4-fluorophenyl)-4-oxobutanamide Compound 657

To a solution of 5-fluoro-2-methylaniline (0.701 g, 5.60 mmol), 3-(4-fluorobenzoyl)propionic acid (1.10 g, 5.60 mmol), and DMAP (1.37 g, 11.2 mmol) in CH$_2$Cl$_2$ (20 mL) was added EDCl·HCl (1.93 g, 10.1 mmol) at room temperature. The reaction mixture was stirred for 16 h and diluted with CH$_2$Cl$_2$. The solution was washed with 2 N HCl$_{(aq)}$ and brine. The organic layer was dried over MgSO$_{4(s)}$, filtered, and concentrated. The residue was purified by Isco Combi-Flash Companion column chromatography (0-30% ethyl acetate in n-hexane) to give N-(5-fluoro-2-methylphenyl)-4-(4-fluorophenyl)-4-oxobutanamide (1.06 g, 62%) as a white solid. $^1$H NMR (CDCl$_3$, 300 MHz) δ 8.03 (dd, 2H), 7.82 (br d, 1H), 7.62 (br s, 1H), 7.19-7.07 (m, 3H), 6.74 (br t, 1H), 3.44 (dd, 2H), 2.85 (dd, 2H), 2.27 (s, 3H).

Step 2. Synthesis of 1-(5-fluoro-2-methylphenyl)-5-(4-fluorophenyl)pyrrolidin-2-one To a solution of N-(5-fluoro-2-methylphenyl)-4-(4-fluorophenyl)-4-oxobutanamide (0.282 g, 0.929 mmol) in CH$_3$CN (4.0 mL) was added triethylsilane (0.300 mL, 1.88 mmol) and aluminum triflate (0.441 g, 0.929 mmol) at room temperature, and the reaction mixture was reflux for 3 h. The solution was treated with H$_2$O and extracted with ethyl acetate. The combined organic layers were dried over MgSO$_{4(s)}$, filtered, and concentrated. The residue was purified by Isco Combi-Flash Companion column chromatography (0-100% ethyl acetate in n-hexane) to give 1-(5-fluoro-2-methylphenyl)-5-(4-fluorophenyl)pyrrolidin-2-one (56.8 mg, 21%) as a yellow solid. $^1$H NMR (CDCl$_3$, 300 MHz) δ 7.20-7.16 (m, 2H), 7.11 (dd, 1H), 7.00-6.94 (m, 2H), 6.81 (ddd, 1H), 6.61 (d, 1H), 4.99 (dd, 1H), 2.84-2.63 (m, 3H), 2.23-2.20 (m, 1H), 2.18 (s, 3H); LC-MS (ESI) m/z 288.2 [M+H]$^+$.

EXAMPLE 484

Methyl 4-[2-(4-fluorophenyl)-5-oxopyrrolidin-1-yl]-3-methylbenzoate

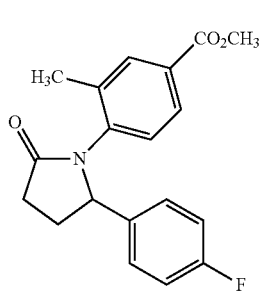

Compound 658

Step 1. Synthesis of methyl 4-{[4-(4-fluorophenyl)-4-oxobutanoyl]amino}-3-methylbenzoate Compound 659

To a solution of methyl 4-amino-3-methylbenzene carboxylate (0.814 g, 4.93 mmol), 3-(4-fluorobenzoyl)propionic acid (0.966 g, 4.93 mmol), and DMAP (1.20 g, 9.86 mmol) in CH$_2$Cl$_2$ (15 mL) was added EDCl·HCl (1.89 g, 9.86 mmol) at room temperature. The reaction mixture was stirred for 16 h and diluted with CH$_2$Cl$_2$. The solution was washed with 2 N HCl$_{(aq)}$. The organic layer was dried over MgSO$_{4(s)}$, filtered, and concentrated. The residue was purified by Isco Combi-Flash Companion column chromatography (0-45% ethyl acetate in n-hexane) to give methyl 4-{[4-(4-fluorophenyl)-4-oxobutanoyl]amino}-3-methylbenzoate (1.08 g, 64%) as a white solid. $^1$H NMR (CDCl$_3$, 300 MHz) δ 8.13 (br d, 1H), 8.04 (dd, 2H), 7.88-7.87 (m, 2H), 7.79 (br s, 1H), 7.15 (t, 2H), 3.88 (s, 3H), 3.45 (dd, 2H), 2.87 (dd, 2H), 2.36 (s, 3H).

Step 2. Synthesis of methyl 4-[2-(4-fluorophenyl)-5-oxopyrrolidin-1-yl]-3-methylbenzoate To a solution of methyl 4-{[4-(4-fluorophenyl)-4-oxobutanoyl]amino}-3-methylbenzoate (0.402 g, 1.17 mmol) in CH₃CN (4.0 mL) was added triethylsilane (0.380 mL, 2.30 mmol) and aluminum triflate (0.554 g, 1.17 mmol) at room temperature, and the reaction mixture was reflux for 5 h. The solution was treated with H₂O and extracted with ethyl acetate. The combined organic layers were dried over $MgSO_{4(s)}$, filtered, and concentrated. The residue was purified by Isco Combi-Flash Companion column chromatography (0-65% ethyl acetate in n-hexane) to give methyl 4-[2-(4-fluorophenyl)-5-oxopyrrolidin-1-yl]-3-methylbenzoate (97.1 mg, 18%) as a yellow gum. $^1$H NMR (CDCl₃, 400 MHz) δ 7.84 (s, 1H), 7.71 (d, 1H), 7.16 (dd, 2H), 6.97-6.92 (m, 3H), 5.07 (dd, 1H), 3.85 (s, 3H), 2.84-2.65 (m, 3H), 2.26 (s, 3H), 2.24-2.17 (m, 1H); LC-MS (ESI) m/z 328.2 [M+H]⁺.

EXAMPLE 485

Synthesis of (−)-Ethyl 4-[2-(4-fluorophenyl)-4-oxo-1,3-thiazolidin-3-yl]-3-methylbenzoate (Compound 660)

Following standard procedure G, (−)-4-[2-(4-fluorophenyl)-4-oxo-1,3-thiazolidin-3-yl]-3-methyl benzoic acid (90.0 mg, 0.272 mmol), ethanol (17.0 μL, 0.299 mmol), EDCI•HCl (0.100 g, 0.544 mmol), DMAP (73.1 mg, 0.598 mmol) and CH₂Cl₂ (5.0 mL) were used to carry out the reaction. After the reaction mixture was stirred at room temperature for 16 h and work-up, the residue was purified by preparative thin layer chromatography plates (1.0 mm of silica gel on glass support, 20% ethyl acetate in n-hexane) to give (−)-ethyl 4-[2-(4-fluorophenyl)-4-oxo-1,3-thiazolidin-3-yl]-3-methylbenzoate (83.4 mg, 85%). $[α]_D^{20}$=−138.50° (c=0.1, CHCl₃).

EXAMPLE 486

Synthesis of (+)-Ethyl 4-[2-(4-fluorophenyl)-4-oxo-1,3-thiazolidin-3-yl]-3-methylbenzoate (Compound 661)

Following standard procedure G, (+)-4-[2-(4-fluorophenyl)-4-oxo-1,3-thiazolidin-3-yl]-3-methyl benzoic acid (90.0 mg, 0.272 mmol), ethanol (17.0 μL, 0.299 mmol), EDCI•HCl (0.100 g, 0.544 mmol), DMAP (73.1 mg, 0.598 mmol) and CH₂Cl₂ (5.0 mL) were used to carry out the reaction. After the reaction mixture was stirred at room temperature for 16 h and work-up, the residue was purified by preparative thin layer chromatography plates (1.0 mm of silica gel on glass support, 20% ethyl acetate in n-hexane) to give (+)-ethyl 4-[2-(4-fluorophenyl)-4-oxo-1,3-thiazolidin-3-yl]-3-methylbenzoate (81.0 mg, 83%). $[α]_D^{20}$=142.20° (c=0.1, CHCl₃).

EXAMPLE 487

Variable-Temperature 1H NMR Spectroscopy Experiment

Chemical shifts of resonances obtained in the NMR spectra are used for structure identification and characterization of organic compounds. The 1H NMR spectrum of thiazolidine derivatives at room temperature showed broadening of signals owing to the restriction of bond rotation. Compound 152 was used to perform and study variable-temperature experiments by NMR spectroscopy. This compound was dissolved in dimethylsulfoxide-d₆ and chemical shifts (δ) were obtained in ppm using the center of the dimethylsulfoxide-d₆ quintet (δ 2.49 ppm) as the internal reference. $^1$H NMR data were acquired at 25-80° C. on a VARIAN VNMRS-700 NMR spectrometer. The chemical shift of the proton of C6' on the benzoate ring was invisible at room temperature. The proton signals of C2, C7', C2', and C6' showed line broadening (FIG. 1a). $^1$H NMR experiments are often recorded at high temperatures to overcome the rotation energy barrier in rigid structures. For compound 152, an improvement on resolution of the 1H NMR spectrum was observed at 80° C. (FIG. 1d). The hydrogen signals at δ 2.16 (s, C7'-H), 6.30 (s, C2-H), and 7.76 (s, C2'-H) became sharper, and the signal for the aromatic hydrogen of C6' at 7.66 ppm appeared as a doublet. The proton peak of C5' was recorded at 7.18 ppm and was broadened. When 1H NMR spectra were measured at 60° C., not all aromatic hydrogen signals could be clearly distinguished.

EXAMPLE 488

The exemplary compounds prepared in Examples 1-486 above were tested for modulating opioid receptor activities.

Cell Culture

Human embryonic kidney 293 (HEK-293) cells constitutively expressing MOR (HEK-MOR) and DOR (HEK-DOR) (kindly provided by Dr. Ping-Yee Law, University of Minnesota, USA) were cultured in high-glucose Dulbecco's modified Eagle's medium (DMEM, GIBCO) supplemented with 400 μg/mL G418 (Sigma), 2 mM L-glutamine and P/S/F (100 units/mL penicillin, 100 μg/mL streptomycin, 10% fetal bovine serum). Chinese hamster ovary (CHO)-K1 cells, stably expressing hMOR and Gα15 (CHO-K1/MOR/Gα15), were cultured in F12 medium (GIBCO) supplemented with 10 μg/mL Hygromycin B (Invivogen), 20 μg/mL Zeocin (Invivogen) P/S/F (100 units/mL penicillin, 100 μg/mL streptomycin, 10% fetal bovine serum). The cultures were incubated at 37° C. in a humidified 5% CO₂ incubator.

FLIPR® Calcium Assay

One day before the assay, CORNING® black with clear flat bottom 96-well assay plates were coated with a 0.1 mg/mL Poly-L-Lysine solution. CHO-K1/MOR/Gα15 cells were suspended in the F12 medium and plated at a density of ~8×10⁴ cells/well in 200 μL medium. Cells were incubated in a humidified atmosphere of 10% CO₂ at 37° C. overnight so as to reach an 80-90% confluent cell monolayer before assay. At the day of assay, 150 μL medium/well was removed from plate. To each well, 50 μL FLIPR® calcium assay reagent dissolved in 1× assay buffer (HBSS: KCl 5 mM, KH₂PO₄ 0.3 mM, NaCl 138 mM, NaHCO₃ 4 mM, Na₂HPO4 0.3 mM, d-glucose 5.6 mM, with additional 20 mM HEPES and 13 mM CaCl₂, pH 7.4), with 2.5 mM probenecid was added and the plate was incubated at 37° C. for 1 h. Compounds and other reagents were dissolved in the assay buffer. Using a FlexStationIII (Molecular Devices Corp.), the $[Ca^{2+}]_i$ fluorescence increases after robotic injections of compounds or other reagents were monitored every 1.52 s interval with excitation wavelength at 485 nm and with emission wavelength at 525 nm. The $[Ca^{2+}]_i$ fluorescence was measured up to 90 s after agonist injection. The fluorescence intensity from 6 to 12 wells of cells were averaged and the relative amount of $[Ca^{2+}]_i$ release was determined by integrating the AUC of the $[Ca^{2+}]_i$ fluorescence averages.

Among the tested compounds, compounds 4-6, 8, 10, 11, 14-16, 20, 37, 38, 44, 46, 47, 49, 52-55, 58-60, 62, 64, 68, 72, 74, 78, 84, 86, 90, 92, 93, 96, 101, 102, 108-110, 112, 113, 122-124, 147, 149, 151, 152, 154, 156, 157, 159, 160, 162, 163, 167, 169, 171, 173-177, 179, 183, 185-190, 192, 194, 196, 198, 200, 202, 204, 206, 208, 210, 211, 213, 215-221, 227-229, 231, 234-236, 239, 258, 261, 263, 266-268, 270, 272, 273, 276, 277, 279-281, 286, 290-292, 294-301, 303, 306, 307, 310, 311, 313, 314, 326, 329, 331, 332, 334, 335, 337, 338, 339-344, 347-351, 353-355, 357, 361, 368, 374-376, 378, 380, 381, 383-388, 579-581, 583, 588, 593, 597, 600, and 648 each showed an $EC_{50}$ value less than 10 μM.

Among the tested compounds, compounds 2, 4-6, 10-12, 14-16, 38, 43, 44, 46, 47, 49, 52-55, 58-60, 62, 64, 68, 74, 78, 84, 86, 90, 92, 93, 96, 101, 102, 108-113, 117, 122, 124, 147, 151, 152, 154, 156, 157, 159, 160, 162, 163, 165, 167, 169, 171, 173-177, 179, 183, 185-190, 192, 194, 196, 198, 200, 202, 204, 206, 208, 210, 211, 213, 215-221, 224, 227-229, 231, 234-236, 238, 253, 258, 261, 263, 266-273, 275-277, 279-281, 286, 290-292, 294-301, 303, 306, 307, 310, 311, 313, 314, 326, 328, 329, 331, 332, 334-344, 347-351, 353-357, 361, 368, 373, 374, 376-378, 380, 381, 383-387, 390, 395, 404, 406, 408, 411, 416, 579-581, 583, 588, 591, 593, 597, 600, 635, 640, and 648 each showed an AUC value more than 5000.

cAMP Assay

Briefly, 2000 HEK-MOR cells or HEK-DOR cells were plated in 10 μL/well of DMEM in 96-well solid bottom white plates and 10 μL/well compound in HBSS in the presence with 1 μM forskolin and 100 μM 3-isobutyl-1-methylxanthine (IBMX). After 30 minutes of incubation at room temperature, 10 μL/well of labeled d2-cAMP and 10 μL/well of anti-cAMP antibody (both diluted in lysis buffer) were added to each well. Two hours later, plates were measured using the FlexStationIII (Molecular Devices Corp.) with excitation at 330 nm and emissions of 620 nm and 665 nm.

Tail-Flick Test

Male wild-type (WT) B6 mice (25-30 g) were kept in a temperature-controlled animal room with a 12-h light/dark cycle. The protocol has been approved by the Institutional Animal Care and Use Committee of the National Health Research Institutes, Taiwan. Animal experiments were carried out in accordance with the Policies on the Use of Animals in Neuroscience Research and the ethical guidelines for investigations of experimental pain in conscious animals, International Association for the Study of Pain. Tail-Flick Analgesia Meter (Columbia Instruments) was used to measure the tail-flick latencies of mice. The cut-off time for each measurement was 10 s to avoid tissue damage. Basal latencies were recorded before treatment and test latencies were recorded 30, 60, 90, 120 and 180 min after an intravenous injection of drugs. A time-response curve was calculated for antinociceptive effects (test latency—basal latency) occurring during 0 to 180 min, and the AUC value was calculated. $ED_{50}$ values were determined by the up-and-down method reported in Crocker et al., *Pharmacol Biochem Behav*, 1984, 21, 133-136.

EXAMPLE 489

Identification of μ-Opioid Receptor Antagonist to Agonist Allosteric Modifiers (AAMs) by Using Calcium Assay System A CHO-K1 cell line, expressing a MOR and Gα15 (GenScript), was used to set up a sensitive high-throughput screen (HTS) system. In a FLIPR® calcium assay using CHO-K1/MOR/Gα15 cells, activation of MOR elicits an intracellular calcium release leading to an increase in the relative fluorescence units (FRU). In this assay, the $EC_{50}$ value of D-ala2-nmephe4-gly-ol-enkephalin (DAMGO), a MOR-specific agonist, was determined to be 0.67 nM. The HTS was performed in the absence or presence of an opioid antagonist, naloxone (25 nM), to identify antagonist to agonist allosteric modifiers (AAM). Compounds 112 and 58 were identified as opioid receptor AAMs. Both compounds 112 and 58 did not show responses on their own, but induced a significant calcium release in the presence of naloxone. Upon co-administrated with naloxone (20 nM), compound 58 induced calcium release in a dose dependent manner, exhibiting an $EC_{50}$ value of 1.3 μM.

Furthermore, concentration-response curves (CRCs) of naloxone in presence of compound 58 at different concentrations were determined by a calcium assay. Magnitudes of the increase in naloxone efficacy produced by each concentration of compound 58 were recorded. It was observed that both $E_{max}$ and potency of naloxone were altered by varying concentrations of compound 58. Similar to naloxone, compound 58 also worked as an AAM of naltrexone, with similar potency but a higher magnitude of efficacy. Probe dependence (effect of allosteric modifier can only be observed when combine with certain ligands) is a unique character in allosteric modifiers. Compared a combination of compounds and naloxone, no activity was observed in CHO-K1/MOR/Gα15 cells treated with a combination of peptide MOR antagonist CTOP (D-Phe-Cys-Tyr-D-Trp-Orn-Thr-Pen-Thr-NH2) and compound 58. Thus, compound showed marked antagonist probe dependence as it produced highly selective AAM property with alkaloid antagonist over peptide antagonist.

To characterize of novel opioid receptor AAMs, the activity and selectivity of compound 58 were tested by inhibiting adenylyl cyclase activity (i.e., cAMP assay).

Opoid receptors inhibit adenylyl cyclase activity through Gi/o family of heterotrimeric G proteins. A cAMP-accumulation assay was performed to determine whether opioid receptor AAMs affect a G protein-dependent signaling pathway. The cAMP-inhibition response produced by an opioid agonist, DAMGO, [D-Pen(2),D-Pen(5)]-enkephalin (DP-DPE) in HEK-MOR or HEK-DOR were 90% and 60% of forskolin-stimulated (1 μM) cAMP assumulation, with $EC_{50}$ values of 5.5 nM and 0.5 nM, respectively. The combination of compound 58 and naloxone (20 nM) significantly inhibited adenylyl cyclase activity in HEK-MOR cells, with an $EC_{50}$ value of 3 μM. By contrast, compound 58 produced no effect in the presence of naloxone (20 nM) in HEK-DOR cells. Thus, compound 58 was determined to be selective for mu-over delta-opioid receptors.

Traditional allosteric modifiers are classified by mode of target protein activity modulated by compounds. Positive allosteric modifiers (PAMs) enhance the binding affinity or efficacy of the orthosteric agonist when they bind to the receptor; negative allosteric modifiers (NAMs) inhibit the binding affinity or efficacy of the orthosteric agonist. Studies were performed to evaluate whether μ-opioid receptor AAMs also showed other properties of traditional allosteric modifiers. Concentration-response curves (CRCs) of morphine, a partial agonist of opioid receptor with high structure similarity of naloxone, were determined by a FLIPR calcium assay in the presence or absence of compound 58 at various concentrations.

It was observed that neither $E_{max}$ nor potency of morphine was significantly altered by compound 58 at any tested concentration. Morphine produced similar $E_{max}$ as compared to the combination of morphine and compound 58 at concentrations of 30, 10, 3.3 μM. These results indicate that compound 58 modulates the action of opiate antagonist without any PAM or NAM effect of mu-opioid receptor.

Naloxone Produced Antinociceptive Effects in Mice Injected with Compound 58

An in vivo study, i.e., tail-flick test, was performed to investigate whether AAMs could change innate character of μ-opioid receptor in the presence of naloxone. Compound 58 alone groups (50, 25, 12.5 and 6.25 nmole; i.t.) didn't exhibit any antinociceptive effects in B6 mice. On the other hand, significant inhibition of the tail-flick response was observed in mice co-injected with both naloxone (10 mg/kg; s.c.) and compound 58 (50, 25, and 12.5 nmole; i.t.), with area under the curve (AUC) values of 649.8±123.3, 560.6±96.5, and 241.5±111.3 (min×s), respectively. In mice injected with naloxone (10 mg/kg; s.c.), the $ED_{50}$ value of compound 58 in inhibition of the tail-flick response was determined to be 23.1±7.1 nmole. In mice injected with saline, no antinociception effect was observed with the highest dose of compound 58 tested (50 nmole; i.t.).

These results indicate that compound 58 worked in vivo as a unique AAM.

EXAMPLE 490

Activation of μ-Opioid Receptor with Compound 58 Combined with a μ-Opioid Receptor Antagonist A CHO-K1 cell line, expressing a MOR and Gα15 (GenScript), was used to set up a sensitive assay system for detecting μ-opioid receptor activation. A FLIPR® calcium assay using CHO-K1/MOR/Gα15 cells, in which activation of MOR elicits intracellular calcium release leading to an increase in the relative fluorescence units (FRU), was conducted and the $EC_{50}$ value of D-ala2-nmephe4-gly-ol-enkephalin (DAMGO), a MOR-specific agonist, was determined to be 0.67 nM. The assay was performed in the presence of an opioid antagonist, i.e., naloxone (25 nM), naltrexone (20 nM), samidorphan (10 nM), naloxonazine dihydrochloride (20 nM), β-funaltrexamine hydrochloride (20 nM), cyprodime hydrochloride (500 nM), or nalmefene (20 nM), in combination with compound 58, an antagonist to agonist allosteric modifier (AAM), to identify activation of the μ-opioid receptor. Compound 58 did not elicit any response on its own, but induced significant calcium release in the presence of an antagonist. Co-administrated with one of the opioid antagonists listed above, compound 58 induced calcium release in a dose dependent manner, exhibiting $EC_{50}$ values and AUC values shown in Table 3 below.

TABLE 3

Effect of compound 58 combined with an opioid antagonist on calcium release

| Opioid antagonist | Concentration (nM) | $EC_{50}$ (μM) | AUC |
|---|---|---|---|
| Naloxonazine dihydrochloride | 20 | 0.642 ± 1.939 | 11819.33 |
| β-Funaltrexamine hydrochloride | 20 | 0.346 ± 0.209 | 8553.5 |
| Cyprodime hydrochloride | 500 | 5.123 ± 2.521 | 7893 |
| Naltrexone | 20 | 0.630 ± 0.217 | 12980.33 |
| Samidorphan | 10 | 5.525 | 13179 |
| Samidorphan | 20 | 5.273 | 14094 |
| Nalmefene | 20 | — | 8506 |

These results indicate that compound 58 combined with an opioid antagonist unexpectedly exhibited high activities in μ-opioid receptor activation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made, screened for their modulating activities to opioid receptor and treating opioid receptor associated conditions. Thus, other embodiments are also within the claims.

What is claimed is:

1. A pharmaceutical composition for treating an opioid receptor-associated condition, the pharmaceutical composition comprising a pharmaceutically acceptable carrier, a compound of Formula (I) below, and a therapeutic agent:

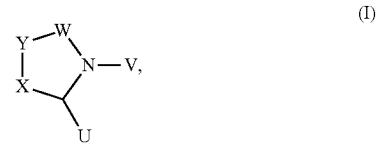

(I)

in which
U is

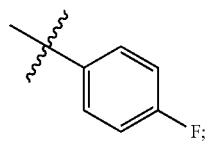 [SMILES: *c1ccc(F)cc1]

V is

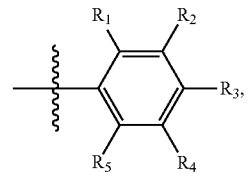

in which $R_1$ is $C_{1-6}$ alkyl; each of $R_2$, $R_4$, and $R_5$, independently, is H; and $R_3$ is —C(O)OR, R being H, acetyl, $C_{1-6}$ alkyl, $C_{1-6}$ multihaloalkyl, $C_{3-8}$ cycloalkyl, $C_{2-8}$ heterocycloalkyl, $C_{6-14}$ aryl, or $C_{1-13}$ heteroaryl;
X is S;
Y is $CH_2$; and
W is —C(O)—.

2. The pharmaceutical composition of claim 1, wherein the therapeutic agent is a mu-opioid receptor antagonist.

3. The pharmaceutical composition of claim 2, wherein the mu-opioid receptor antagonist is naloxone, naltrexone, samidorphan, cyprodime, clocinnamox, β-FNA, naloxonazine, or nalmefene.

4. A method of treating an opioid receptor-associated condition, the method comprising administering to a subject in need thereof a pharmaceutical composition of claim 1 wherein the therapeutic agent is a mu-opioid receptor antagonist.

5. The method of claim 4, wherein the mu-opioid receptor antagonist is naloxone, naltrexone, samidorphan, cyprodime, clocinnamox, β-FNA, naloxonazine, or nalmefene.

6. The method of claim 4, wherein the opioid receptor-associated condition is pain, immune disease, esophageal reflux, diarrhea, anxiety, or heroin addiction.

7. The method of claim 6, wherein the opioid receptor-associated condition is pain.

8. The method of claim 7, wherein the pain is cancer pain, post operative pain, low back pain, rheumatoid arthritis pain, osteoarthritis pain, neuropathic pain, or fibromyalgia pain.

9. The pharmaceutical composition of claim 1, wherein the compound is selected from the group consisting of the following compounds:
   Compound 58: 4-(2-(4-Fluorophenyl)-4-oxothiazolidin-3-yl)-3-methylbenzoic acid,
   Compound 152: 4-[2-(4-Fluoro-phenyl)-4-oxo-thiazolidin-3-yl]-3-methyl-benzoic acid ethyl ester,
   Compound 489: Oxetan-3-yl 4-[2-(4-fluorophenyl)-4-oxo-1,3-thiazolidin-3-yl]-3-methylbenzoate, and
   Compound 660: (-)-Ethyl 4-[2-(4-fluorophenyl)-4-oxo-1,3-thiazolidin-3-yl]-3-methylbenzoate.

10. The pharmaceutical composition of claim 9, wherein the compound is Compound 58: 4-(2-(4-fluorophenyl)-4-oxothiazolidin-3-yl)-3-methylbenzoic acid.

11. The pharmaceutical composition of claim 9, wherein the compound is Compound 152: 4-[2-(4-Fluoro-phenyl)-4-oxo-thiazolidin-3-yl]-3-methyl-benzoic acid ethyl ester.

12. A pharmaceutical composition for treating an opioid receptor-associated condition, the pharmaceutical composition comprising a pharmaceutically acceptable carrier, a compound, and a therapeutic agent, wherein the compound is selected from the group consisting of the following compounds:
   Compound 58: 4-(2-(4-Fluorophenyl)-4-oxothiazolidin-3-yl)-3-methylbenzoic acid,
   Compound 59: Methyl 4-(2-(4-fluorophenyl)-4-oxothiazolidin-3-yl)-3-methylbenzoate,
   Compound 152: 4-[2-(4-Fluoro-phenyl)-4-oxo-thiazolidin-3-yl]-3-methyl-benzoic acid ethyl ester,
   Compound 159: 4-[2-(4-Fluorophenyl)-4-oxo-1,3-thiazolidin-3-yl]-3-methyl-N-(methylsulfonyl)-benzamide,
   Compound 160: 4-[2-(4-Fluorophenyl)-4-oxo-1,3-thiazolidin-3-yl]-3-methyl-N-(propylsulfonyl)-benzamide,
   Compound 162: N-(Ethylsulfonyl)-4-[2-(4-fluorophenyl)-4-oxo-1,3-thiazolidin-3-yl]-3-methylbenzamide,
   Compound 163: N-(Butylsulfonyl)-4-[2-(4-fluorophenyl)-4-oxo-1,3-thiazolidin-3-yl]-3-methylbenzamide,
   Compound 167: 4-[2-(4-Fluorophenyl)-4-oxo-1,3-thiazolidin-3-yl]-3-methyl-N-[(2-methylpropyl)sulfonyl]benzamide,
   Compound 169: N-(Cyclopropylsulfonyl)-4-[2-(4-fluorophenyl)-4-oxo-1,3-thiazolidin-3-yl]-3-methylbenzamide,
   Compound 171: N-(Cyclohexylsulfonyl)-4-[2-(4-fluorophenyl)-4-oxo-1,3-thiazolidin-3-yl]-3-methylbenzamide,
   Compound 173: 4-[2-(4-Fluorophenyl)-4-oxo-1,3-thiazolidin-3-yl]-3-methyl-N-sulfamoylbenzamide,
   Compound 174: N-(Dimethylsulfamoyl)-4-[2-(4-fluorophenyl)-4-oxo-1,3-thiazolidin-3-yl]-3-methylbenzamide,
   Compound 175: 4-[2-(4-Fluorophenyl)-4-oxo-1,3-thiazolidin-3-yl]-3-methyl-N-[(trifluoromethyl)sulfonyl]benzamide,
   Compound 176: N-(Benzylsulfonyl)-4-[2-(4-fluorophenyl)-4-oxo-1,3-thiazolidin-3-yl]-3-methylbenzamide,
   Compound 177: N-[(3-Fluorobenzyl)sulfonyl]-4-[2-(4-fluorophenyl)-4-oxo-1,3-thiazolidin-3-yl]-3-methylbenzamide,
   Compound 179: N-[(3,5-Dimethylbenzyl)sulfonyl]-4-[2-(4-fluorophenyl)-4-oxo-1,3-thiazolidin-3-yl]-3-methylbenzamide,
   Compound 183: 4-[2-(4-Fluorophenyl)-4-oxo-1,3-thiazolidin-3-yl]-3-methyl-N-(phenylsulfonyl)-benzamide,
   Compound 185: 4-[2-(4-Fluorophenyl)-4-oxo-1,3-thiazolidin-3-yl]-3-methyl-N-[(4-methylphenyl)sulfonyl]benzamide,
   Compound 186: N-[(4-Ethylphenyl)sulfonyl]-4-[2-(4-fluorophenyl)-4-oxo-1,3-thiazolidin-3-yl]-3-methylbenzamide,
   Compound 187: N-[(4-Cyanophenyl)sulfonyl]-4-[2-(4-fluorophenyl)-4-oxo-1,3-thiazolidin-3-yl]-3-methylbenzamide,
   Compound 188: 4-[2(4-Fluorophenyl)-4-oxo-1,3-thiazolidin-3-yl]-N-[(4-methoxyphenyl)sulfonyl]-3-methylbenzamide,
   Compound 189: 4-[2-(4-Fluorophenyl)-4-oxo-1,3-thiazolidin-3-yl]-3-methyl-N-{[4-(trifluoromethoxy)phenyl]sulfonyl}benzamide,
   Compound 190: Ethyl 4-({4-[2-(4-fluorophenyl)-4-oxo-1,3-thiazolidin-3-yl]-3-methylbenzoyl}sulfamoyl)benzoate,
   Compound 192: 4-[2-(4-Fluorophenyl)-4-oxo-1,3-thiazolidin-3-yl]-3-methyl-N-[(2,4,6-trimethylphenyl)-sulfonyl]benzamide,
   Compound 194: 4-[2-(4-Fluorophenyl)-4-oxo-1,3-thiazolidin-3-yl]-N-[(3-fluorophenyl)sulfonyl]-3-methylbenzamide,
   Compound 196: 4-[2-(4-Fluorophenyl)-4-oxo-1,3-thiazolidin-3-yl]-N-[(4-fluorophenyl)sulfonyl]-3-methylbenzamide,
   Compound 198: N-[(4-Chlorophenyl)sulfonyl]-4-[2-(4-fluorophenyl)-4-oxo-1,3-thiazolidin-3-yl]-3-methylbenzamide,
   Compound 200: N-[(4-Bromophenyl)sulfonyl]-4-[2-(4-fluorophenyl)-4-oxo-1,3-thiazolidin-3-yl]-3-methylbenzamide,
   Compound 202: N-{[4-(Acetylamino)phenyl]sulfonyl}-4-[2-(4-fluorophenyl)-4-oxo-1,3-thiazolidin-3-yl]-3-methylbenzamide,
   Compound 204: N-[4-Chloro-2-fluorophenyl)sulfonyl]-4-[2-(4-fluorophenyl)-4-oxo-1,3-thiazolidin-3-yl]-3-methylbenzamide,
   Compound 206: N-[(2,4-Difluorophenyl)sulfonyl]-4-[2-(4-fluorophenyl)-4-oxo-1,3-thiazolidin-3-yl]-3- methylbenzamide,
   Compound 208: N-[(4-Chloro-2,5-dimethylphenyl)sulfonyl]-4-[2-(4-fluorophenyl)-4-oxo-1,3-thiazolidin-3-yl]-3-methylbenzamide,
   Compound 210: N-{[5-(Dimethylamino)-1-naphthalenyl]sulfonyl}-4-[2-(4-fluorophenyl)-4-oxo-1,3-thiazolidin-3-yl]-3-methylbenzamide,
   Compound 211: 4-[2-(4-Fluorophenyl)-4-oxo-1,3-thiazolidin-3-yl]-3-methyl-N-(3-pyridinylsulfonyl)-benzamide,
   Compound 213: N-[(3,5-Dimethyl-1,2-oxazol-4-yl)sulfonyl]-4-[2-(4-fluorophenyl)-4-oxo-1,3-thiazolidin-3-yl]-3-methylbenzamide, Compound 215: N-Ethoxy-4-[2-(4-fluorophenyl)-4-oxo-1,3-thiazolidin-3-yl]-3-methylbenzamide,
Compound 216: 4-[2-(4-Fluorophenyl)-4-oxo-1,3-thiazolidin-3-yl]-N-methoxy-3-methylbenzamide,
Compound 217: N-(Benzyloxy)-4-[2-(4-fluorophenyl)-4-oxo-1,3-thiazolidin-3-yl]-3-methylbenzamide,
Compound 218: 4-[2-(4-Fluorophenyl)-4-oxo-1,3-thiazolidin-3-yl]-3-methyl-N-phenoxybenzamide,
Compound 219: 4-[2-(4-Fluorophenyl)-4-oxo-1,3-thiazolidin-3-yl]-N-hydroxy-3-methylbenzamide,
Compound 220: 4-[2-(4-Fluorophenyl)-4-oxo-1,3-thiazolidin-3-yl]-3-methylbenzohydrazide,
Compound 229: 4-[2-(4-Fluoro-phenyl)-4-oxo-thiazolidin-3-yl]-3-methyl-benzoic acid propyl ester,
Compound 231: 4-[2-(4-Fluoro-phenyl)-4-oxo-thiazolidin-3-yl]-3-methyl-benzoic acid isopropyl ester,
Compound 234: 4-[2-(4-Fluoro-phenyl)-4-oxo-thiazolidin-3-yl]-3-methyl-benzoic acid butyl ester,
Compound 235: 2-Methyl-2-propanyl 4-[2-(4-fluorophenyl)-4-oxo-1,3-thiazolidin-3-yl]-3-methylbenzoate,
Compound 236: 1-Methylcyclopropyl 4-[2-(4-fluorophenyl)-4-oxo-1,3-thiazolidin-3-yl]-3-methylbenzoate,
Compound 239: Cyclopentylmethyl 4-[2-(4-fluorophenyl)-4-oxo-1,3-thiazolidin-3-yl]-3-methylbenzoate,
Compound 255: [1-(4-Chlorophenyl)cyclopentyl]methyl 4-[2-(4-fluorophenyl)-4-oxo-1,3-thiazolidin-3-yl]-3-methylbenzoate,
Compound 258: 2-(Benzyloxy)ethyl 4-[2-(4-fluorophenyl)-4-oxo-1,3-thiazolidin-3-yl]-3-methylbenzoate,
Compound 260: 2-(2-Chlorophenoxy)ethyl 4-[2-(4-fluorophenyl)-4-oxo-1,3-thiazolidin-3-yl]-3-methylbenzoate,
Compound 261: 3-Pyridinylmethyl 4-[2-(4-fluorophenyl)-4-oxo-1,3-thiazolidin-3-yl]-3-methylbenzoate,
Compound 263: 3-(2-Pyridinyl)propyl 4-[2-(4-fluorophenyl)-4-oxo-1,3-thiazolidin-3-yl]-3-methylbenzoate,
Compound 264: 2,3-Dihydro-1,4-benzodioxin-2-ylmethyl 4-[2-(4-fluorophenyl)-4-oxo-1,3-thiazolidin-3-yl]-3-methylbenzoate,
Compound 265: 2-(3-Thiophenyl)ethyl 4-[2-(4-fluorophenyl)-4-oxo-1,3-thiazolidin-3-yl]-3-methylbenzoate,
Compound 266: 2-(4-Methyl-1,3-thiazol-5-yl)ethyl 4-[2-(4-fluorophenyl)-4-oxo-1,3-thiazolidin-3-yl]-3-methylbenzoate,
Compound 267: 3-Methoxypropyl 4-[2-(4-fluorophenyl)-4-oxo-1,3-thiazolidin-3-yl]-3-methylbenzoate,
Compound 268: 2-Oxopropyl 4-[2-(4-fluorophenyl)-4-oxo-1,3-thiazolidin-3-yl]-3-methylbenzoate,
Compound 269: 2-Cyanoethyl 4-[2-(4-fluorophenyl)-4-oxo-1,3-thiazolidin-3-yl]-3-methylbenzoate,
Compound 270: 2-(Methylsulfanyl)ethyl 4-[2-(4-fluorophenyl)-4-oxo-1,3-thiazolidin-3-yl]-3-methylbenzoate,
Compound 272: 2-(Acetyloxy)ethyl 4-[2-(4-fluorophenyl)-4-oxo-1,3-thiazolidin-3-yl]-3-methylbenzoate,
Compound 273: [(2,2-Dimethylpropanoyl)oxy]methyl 4-[2-(4-fluorophenyl)-4-oxo-1,3-thiazolidin-3-yl]-3-methylbenzoate,
Compound 276: (2,2-Dimethyl-1,3-dioxolan-4-yl)methyl 4-[2-(4-fluorophenyl)-4-oxo-1,3-thiazolidin-3-yl]-3-methylbenzoate,
Compound 277: 2,2-Dimethyl-1,3-dioxan-5-yl 4-[2-(4-fluorophenyl)-4-oxo-1,3-thiazolidin-3-yl]-3-methylbenzoate,
Compound 279: 1-Methoxy-2-propanyl 4-[2-(4-fluorophenyl)-4-oxo-1,3-thiazolidin-3-yl]-3-methylbenzoate,
Compound 280: 2-(2-Methoxyethoxy)ethyl 4-[2-(4-fluorophenyl)-4-oxo-1,3-thiazolidin-3-yl]-3-methylbenzoate,
Compound 281: 2-Ethoxyethyl 4-[2-(4-fluorophenyl)-4-oxo-1,3-thiazolidin-3-yl]-3-methylbenzoate,
Compound 282: 2-(2-Ethoxyethoxy)ethyl 4-[2-(4-fluorophenyl)-4-oxo-1,3-thiazolidin-3-yl]-3-methylbenzoate,
Compound 286: 2,2,2-Trifluoroethyl 4-[2-(4-fluorophenyl)-4-oxo-1,3-thiazolidin-3-yl]-3-methylbenzoate,
Compound 290: 2-(Dimethylamino)ethyl 4-[2-(4-fluorophenyl)-4-oxo-1,3-thiazolidin-3-yl]-3-methylbenzoate,
Compound 291: 3-(Dimethylamino)propyl 4-[2-(4-fluorophenyl)-4-oxo-1,3-thiazolidin-3-yl]-3-methylbenzoate,
Compound 292: 2-(Diethylamino)ethyl 4-[2-(4-fluorophenyl)-4-oxo-1,3-thiazolidin-3-yl]-3-methylbenzoate,
Compound 294: 2-(1-Pyrrolidinyl)ethyl 4-[2-(4-fluorophenyl)-4-oxo-1,3-thiazolidin-3-yl]-3-methylbenzoate,
Compound 295: 2-(1-Piperidinyl)ethyl 4-[2-(4-fluorophenyl)-4-oxo-1,3-thiazolidin-3-yl]-3-methylbenzoate,
Compound 296: 2-(4-Morpholinyl)ethyl 4-[2-(4-fluorophenyl)-4-oxo-1,3-thiazolidin-3-yl]-3-methylbenzoate,
Compound 297: 3-(4-Morpholinyl)propyl 4-[2-(4-fluorophenyl)-4-oxo-1,3-thiazolidin-3-yl]-3-methylbenzoate,
Compound 298: 3-(1-Piperidinyl)propyl 4-[2-(4-fluorophenyl)-4-oxo-1,3-thiazolidin-3-yl]-3-methylbenzoate,
Compound 299: 2-(1-Acetyl-4-piperidinyl)ethyl 4-[2-(4-fluorophenyl)-4-oxo-1,3-thiazolidin-3-yl]-3-methylbenzoate,
Compound 300: 1-Methyl-3-pyrrolidinyl 4-[2-(4-fluorophenyl)-4-oxo-1,3-thiazolidin-3-yl]-3-methylbenzoate,
Compound 301: 1-Methyl-4-piperidinyl 4-[2-(4-fluorophenyl)-4-oxo-1,3-thiazolidin-3-yl]-3-methylbenzoate,
Compound 303: 2-(2-Aminoethoxy)ethyl 4-[2-(4-fluorophenyl)-4-oxo-1,3-thiazolidin-3-yl]-3-methylbenzoate,
Compound 306: 2-[2-(Dimethylamino)ethoxy]ethyl 4-[2-(4-fluorophenyl)-4-oxo-1,3-thiazolidin-3-yl]-3-methylbenzoate,
Compound 307: 2-[2-(1-Pyrrolidinyl)ethoxy]ethyl 4-[2-(4-fluorophenyl)-4-oxo-1,3-thiazolidin-3-yl]-3-methylbenzoate,
Compound 310: 1,3-Bis(acetyloxy)-2-propanyl 4-[2-(4-fluorophenyl)-4-oxo-1,3-thiazolidin-3-yl]-3-methylbenzoate,
Compound 311: (5-Methyl-2-oxo-1,3-dioxol-4-yl)methyl 4-[2-(4-fluorophenyl)-4-oxo-1,3-thiazolidin-3-yl]-3-methylbenzoate,
Compound 313: 1[(Ethoxycarbonyl)oxy]ethyl 4-[2-(4-fluorophenyl)-4-oxo-1,3-thiazolidin-3-yl]-3-methylbenzoate,
Compound 314: {[(2-Propanyloxy)carbonyl]oxy}methyl 4-[2-(4-fluorophenyl)-4-oxo-1,3-thiazolidin-3-yl]-3-methylbenzoate,
Compound 326: 1-[(3-Pyridinylcarbonyl)amino]-2-propanyl 4-[2-(4-fluorophenyl)-4-oxo-1,3-thiazolidin-3-yl]-3-methylbenzoate,
Compound 329: 4-(2-(4-Fluorophenyl)-4-oxothiazolidin-3-yl)-3-methylbenzamide,
Compound 331: N-Methyl-4-(2-(4-fluorophenyl)-4-oxothiazolidin-3-yl)-3-methylbenzamide,
Compound 332: 4-(2-(4-Fluorophenyl)-4-oxothiazolidin-3-yl)-N,N,3-trimethylbenzamide,
Compound 334: 4-[2-(4-Fluoro-phenyl)-4-oxo-thiazolidin-3-yl]-3-methyl-N-propyl-benzamide,
Compound 335: N-ethyl-4-[2-(4-Fluoro-phenyl)-4-oxothiazolidin-3-yl]-3-methyl-benzamide Compound 337: N-Cyclobutyl-4-[2-(4-fluorophenyl)-4-oxo-1,3-thiazolidin-3-yl]-3-methylbenzamide,
Compound 338: N-Cyclopentyl-4-[2-(4-fluorophenyl)-4-oxo-1,3-thiazolidin-3-yl]-3-methylbenzamide,
Compound 339: N-Cyclohexyl-4-[2-(4-fluorophenyl)-4-oxo-1,3-thiazolidin-3-yl]-3-methylbenzamide,
Compound 340: N-[2-(Dimethylamino)ethyl]-4-[2-(4-fluorophenyl)-4-oxo-1,3-thiazolidin-3-yl]-3-methylbenzamide,
Compound 341: N-(2-(Diethylamino)ethyl)-4-(2-(4-fluorophenyl)-4-oxothiazolidin-3-yl)-3-methylbenzamide,
Compound 342: N-[3-(Dimethylamino)propyl]-4-[2-(4-fluorophenyl)-4-oxo-1,3-thiazolidin-3-yl]-3-methylbenzamide,
Compound 343: 4-[2-(4-Fluorophenyl)-4-oxo-1,3-thiazolidin-3-yl]-N-(3-methoxypropyl)-3-methylbenzamide,
Compound 344: 4-[2-(4-Fluorophenyl)-4-oxo-1,3-thiazolidin-3-yl]-3-methyl-N-[2-(4-morpholinyl)ethyl]benzamide,
Compound 347: 4-[2-(4-Fluorophenyl)-4-oxo-1,3-thiazolidin-3-yl]-3-methyl-N-[3-(4-morpholinyl)propyl]benzamide,
Compound 348: 4-[2-(4-Fluorophenyl)-4-oxo-1,3-thiazolidin-3-yl]-N-[3-(1H-imidazol-1-yl)propyl]-3-methylbenzamide,
Compound 349: 3-(4-{[(3R)-3-(Dimethylamino)-1-pyrrolidinyl]carbonyl}-2-methylphenyl)-2-(4-fluorophenyl)-1,3-thiazolidin-4-one,
Compound 350: 4-({4-[2-(4-fluorophenyl)-4-oxo-1,3-thiazolidin-3-yl]-3-methylbenzoyl }amino)-1-piperidinecarboxylate,
Compound 351: 3-{4-[(3-Amino-1-pyrrolidinyl)carbonyl]-2-methylphenyl}-2-(4-fluorophenyl)-1,3-thiazolidin-4-one,
Compound 353: 2-(4-Fluorophenyl)-3-{4-[(3-hydroxy-1-piperidinyl)carbonyl]-2-methylphenyl }-1,3-thiazolidin-4-one,
Compound 354: 2-(4-Fluorophenyl)-3-{4-[(3-hydroxy-1-azetidinyl)carbonyl]-2-methylphenyl}-1,3-thiazolidin-4-one,
Compound 355: 2-(4-Fluorophenyl)-3-(4-{[(2S)-2-(methoxymethyl)-1-pyrrolidinyl]carbonyl}-2-methylphenyl)-1,3-thiazolidin-4-one,
Compound 357: 3-{4-[(4-Amino-1-piperidinyl)carbonyl]-2-methylphenyl}-2-(4-fluorophenyl)-1,3-thiazolidin-4-one,
Compound 361: 4-[2-(4-Fluorophenyl)-4-oxo-1,3-thiazolidin-3-yl]-3-methyl-N-phenylbenzamide,
Compound 368: 4-[2-(4-Fluorophenyl)-4-oxo-1,3-thiazolidin-3-yl]-N-(3-methoxyphenyl)-3-methylbenzamide,
Compound 374: N-Benzyl-4-[2-(4-fluorophenyl)-4-oxo-1,3-thiazolidin-3-yl] -3-methylbenzamide,
Compound 375: N-(4-Chloro-2-fluorobenzyl)-4-[2-(4-fluorophenyl)-4-oxo-1,3-thiazolidin-3-yl]-3-methylbenzamide,
Compound 376: N-(2,5-Difluorobenzyl)-4-[2-(4-fluorophenyl)-4-oxo-1,3-thiazolidin-3-yl]-3-methylbenzamide,
Compound 378: N-(3,4-Difluorobenzyl)-4-[2-(4-fluorophenyl)-4-oxo-1,3-thiazolidin-3-yl]-3-methylbenzamide,
Compound 380: N-(3,5-Dimethoxybenzyl)-4-[2-(4-fluorophenyl)-4-oxo-1,3-thiazolidin-3-yl]-3-methylbenzamide,
Compound 381: N-(3,5-Difluorobenzyl)-4-[2-(4-fluorophenyl)-4-oxo-1,3-thiazolidin-3-yl]-3-methylbenzamide,
Compound 383: N-[2-(2-Fluorophenyl)ethyl]-4-[2-(4-fluorophenyl)-4-oxo-1,3-thiazolidin-3-yl]-3-methylbenzamide,
Compound 384: N-[2-(2-Chlorophenyl)ethyl]-4-[2-(4-fluorophenyl)-4-oxo-1,3-thiazolidin-3-yl]-3-methylbenzamide,
Compound 385: N-[2-(3-Fluorophenyl)ethyl]-4-[2-(4-fluorophenyl)-4-oxo-1,3-thiazolidin-3-yl]-3-methylbenzamide,
Compound 386: N-[2-(3-Chlorophenyl)ethyl]-4-[2-(4-fluorophenyl)-4-oxo-1,3-thiazolidin-3-yl]-3-methylbenzamide,
Compound 387: N-[2-(4-Fluorophenyl)ethyl]-4-[2-(4-fluorophenyl)-4-oxo-1,3-thiazolidin-3-yl]-3-methylbenzamide,
Compound 388: N-[2-(4-Chlorophenyl)ethyl]-4-[2-(4-fluorophenyl)-4-oxo-1,3-thiazolidin-3-yl]-3-methylbenzamide,
Compound 446: 2-(2-Hydroxyethoxy)ethyl 4-[2-(4-fluorophenyl)-4-oxo-1,3-thiazolidin-3-yl]-3-methylbenzoate,
Compound 449: 2-[2-(Methylamino)ethoxy]ethyl 4-[2-(4-fluorophenyl)-4-oxo-1,3-thiazolidin-3-yl]-3-methylbenzoate,
Compound 453: 2-[2-(Pyridin-2-ylmethoxy)ethoxy]ethyl 4-[2-(4-fluorophenyl)-4-oxo-1,3-thiazolidin-3-yl]-3-methylbenzoate,
Compound 456: 2-[2-(Pyridin-3-ylmethoxy)ethoxy]ethyl 4-[2-(4-fluorophenyl)-4-oxo-1,3-thiazolidin-3-yl]-3-methylbenzoate,
Compound 458: 2-[2-(Pyridin-4-ylmethoxy)ethoxy]ethyl 4-[2-(4-fluorophenyl)-4-oxo-1,3-thiazolidin-3-yl]-3-methylbenzoate,
Compound 460: 2-[2-(2-Methoxyethoxy)ethoxy]ethyl 4-[2-(4-fluorophenyl)-4-oxo-1,3-thiazolidin-3-yl]-3-methylbenzoate,
Compound 461: 2-[2-(Morpholin-4-yl)ethoxy]ethyl 4-[2-(4-fluorophenyl)-4-oxo-1,3-thiazolidin-3-yl]-3-methylbenzoate,
Compound 463: 5-(Morpholin-4-yl)pentyl 4-[2-(4-fluorophenyl)-4-oxo-1,3-thiazolidin-3-yl]-3-methylbenzoate,
Compound 465: 2-[2-(Acetyloxy)ethoxy]ethyl 4-[2-(4-fluorophenyl)-4-oxo-1,3-thiazolidin-3-yl]-3-methylbenzoate,
Compound 467: 2-[2-(Pyrrolidin-2-ylmethoxy)ethoxy]ethyl 4-[2-(4-fluorophenyl)-4-oxo -1,3-thiazolidin-3-yl]-3-methylbenzoate,
Compound 471: 2-[(2-Methoxyethyl)(methyl)amino]ethyl 4-[2-(4-fluorophenyl)-4-oxo-1,3-thiazolidin-3-yl]-3-methylbenzoate,
Compound 474: Octyl 4-[2-(4-fluorophenyl)-4-oxo-1,3-thiazolidin-3-yl]-3-methylbenzoate,
Compound 475: 2-Ethoxy-2-oxoethyl 4-[2-(4-fluorophenyl)-4-oxo-1,3-thiazolidin-3-yl]-3-methylbenzoate,
Compound 476: (2-Methylcyclopropyl)methyl 4-[2-(4-fluorophenyl)-4-oxo-1,3-thiazolidin-3-yl]-3-methylbenzoate,
Compound 477: 3,3-Diethoxypropyl 4-[2-(4-fluorophenyl)-4-oxo-1,3-thiazolidin-3-yl]-3-methylbenzoate,
Compound 478: (1-Methylpiperidin-4-yl)methyl 4-[2-(4-fluorophenyl)-4-oxo-1,3-thiazolidin-3-yl]-3-methylbenzoate,
Compound 479: Tetrahydro-2H-pyran-4-yl 4-[2-(4-fluorophenyl)-4-oxo-1,3-thiazolidin-3-yl]-3-methylbenzoate,
Compound 480: 3-Methoxybutyl 4-[2-(4-fluorophenyl)-4-oxo-1,3-thiazolidin-3-yl]-3-methylbenzoate, Compound 481: (2-Oxo-1,3-dioxolan-4-yl)methyl 4-[2-(4-fluorophenyl)-4-oxo-1,3-thiazolidin-3-yl]-3-methylbenzoate,
Compound 482: 1-Ethoxypropan-2-yl 4-[2-(4-fluorophenyl)-4-oxo-1,3-thiazolidin-3-yl]-3-methylbenzoate,
Compound 483: 1-(Morpholin-4-yl)propan-2-yl 4-[2-(4-fluorophenyl)-4-oxo-1,3-thiazolidin-3-yl]-3-methylbenzoate,
Compound 484: 2-Phenylpropan-2-yl 4-[2-(4-fluorophenyl)-4-oxo-1,3-thiazolidin-3-yl]-3-methylbenzoate,
Compound 485: 4,4-Dimethyl-2-oxotetrahydrofuran-3-yl 4-[2-(4-fluorophenyl)-4-oxo-1,3-thiazolidin-3-yl]-3-methylbenzoate,
Compound 486: Benzyl 4-[2-(4-fluorophenyl)-4-oxo-1,3-thiazolidin-3-yl]-3-methylbenzoate,
Compound 487: 2-Methoxyethyl 4-[2-(4-fluorophenyl)-4-oxo-1,3-thiazolidin-3-yl]-3-methylbenzoate,
Compound 488: 2,3-Dihydroxypropyl 4-[2-(4-fluorophenyl)-4-oxo-1,3-thiazolidin-3-yl]-3-methylbenzoate,
Compound 489: Oxetan-3-yl 4-[2-(4-fluorophenyl)-4-oxo-1,3-thiazolidin-3-yl]-3-methylbenzoate,
Compound 490: (3-Methyloxetan-3-yl)methyl 4-[2-(4-fluorophenyl)-4-oxo-1,3-thiazolidin-3-yl]-3-methylbenzoate,
Compound 491: 3-Hydroxy-2-(hydroxymethyl)-2-methylpropyl 4-[2-(4-fluorophenyl)-4-oxo-1,3-thiazolidin-3-yl]-3-methylbenzoate,
Compound 492: Cyclobutyl 4-[2-(4-fluorophenyl)-4-oxo-1,3-thiazolidin-3-yl]-3-methylbenzoate,
Compound 493: tert-Butyl 4-({4-[2-(4-fluorophenyl)-4-oxo-1,3-thiazolidin-3-yl]-3-methylbenzoyl}oxy)piperidine-1-carboxylate,
Compound 494: Piperidin-4-yl 4-[2-(4-fluorophenyl)-4-oxo-1,3-thiazolidin-3-yl]-3-methylbenzoate,
Compound 495: 2-(4,4-Difluoropiperidin-1-yl)ethyl 4-[2-(4-fluorophenyl)-4-oxo-1,3-thiazolidin-3-yl]-3-methylbenzoate,
Compound 497: 2-(3,3-Difluoropyrrolidin-1-yl)ethyl 4-[2-(4-fluorophenyl)-4-oxo-1,3-thiazolidin-3-yl]-3-methylbenzoate,
Compound 499: tert-Butyl 3-({4-[2-(4-fluorophenyl)-4-oxo-1,3-thiazolidin-3-yl]-3-methylbenzoyl}oxy)azetidine-1-carboxylate,
Compound 500: Azetidin-3-yl 4-[2-(4-fluorophenyl)-4-oxo-1,3-thiazolidin-3-yl]-3-methylbenzoate,
Compound 501: 1-Methylazetidin-3-yl 4-[2-(4-fluorophenyl)-4-oxo-1,3-thiazolidin-3-yl]-3-methylbenzoate,
Compound 504: 1-tert-Butylazetidin-3-yl 4-[2-(4-fluorophenyl)-4-oxo-1,3-thiazolidin-3-yl]-3-methylbenzoate,
Compound 505: 1-(Oxetan-3-yl)azetidin-3-yl 4-[2-(4-fluorophenyl)-4-oxo-1,3-thiazolidin-3-yl]-3-methylbenzoate,
Compound 508: 2-[(3R)-3-Methoxypyrrolidin-1-yl]ethyl 4-[2(4-fluorophenyl)-4-oxo-1,3-thiazolidin-3-yl]-3-methylbenzoate,
Compound 510: 2-[(3S)-3-Methoxypyrrolidin-1-yl]ethyl 4-[2-(4-fluorophenyl)-4-oxo-1,3-thiazolidin-3-yl]-3-methylbenzoate,
Compound 513: 1-(Pyridin-3-yl)ethyl 4-[2-(4-fluorophenyl)-4-oxo-1,3-thiazolidin-3-yl]-3-methylbenzoate,
Compound 514: 1-(Pyridin-4-yl)ethyl 4-[2-(4-fluorophenyl)-4-oxo-1,3-thiazolidin-3-yl]-3-methylbenzoate,
Compound 515: 2-(Pyridin-4-yl)propan-2-yl 4-[2-(4-fluorophenyl)-4-oxo-1,3-thiazolidin-3-yl]-3-methylbenzoate,
Compound 516: Pyridin-3-yl 4-[2-(4-fluorophenyl)-4-oxo-1,3-thiazolidin-3-yl]-3-methylbenzoate,
Compound 517: Pyridin-2-yl 4-[2-(4-fluorophenyl)-4-oxo-1,3-thiazolidin-3-yl]-3-methylbenzoate,
Compound 518: Pyridin-4-yl 4-[2-(4-fluorophenyl)-4-oxo-1,3-thiazolidin-3-yl]-3-methylbenzoate,
Compound 519: 4-Methylpyridin-3-yl 4-[2-(4-fluorophenyl)-4-oxo-1,3-thiazolidin-3-yl]-3-methylbenzoate,
Compound 520: 6-Methylpyridin-3-yl 4-[2-(4-fluorophenyl)-4-oxo-1,3-thiazolidin-3-yl]-3-methylbenzoate,
Compound 521: 5-Methylpyridin-3-yl 4-[2-(4-fluorophenyl)-4-oxo-1,3-thiazolidin-3-yl]-3-methylbenzoate,
Compound 522: 2-Fluoropyridin-3-yl 4-[2-(4-fluorophenyl)-4-oxo-1,3-thiazolidin-3-yl]-3-methylbenzoate,
Compound 523: 6-Fluoropyridin-3-yl 4-[2-(4-fluorophenyl)-4-oxo-1,3-thiazolidin-3-yl]-3-methylbenzoate,
Compound 524: 5-Fluoropyridin-3-yl 4-[2-(4-fluorophenyl)-4-oxo-1,3-thiazolidin-3-yl]-3-methylbenzoate,
Compound 525: 5-Chloropyridin-3-yl 4-[2-(4-fluorophenyl)-4-oxo-1,3-thiazolidin-3-yl]-3-methylbenzoate,
Compound 526: 6-Chloropyridin-3-yl 4-[2-(4-fluorophenyl)-4-oxo-1,3-thiazolidin-3-yl]-3-methylbenzoate,
Compound 527: 2-Chloropyridin-3-yl 4-[2-(4-fluorophenyl)-4-oxo-1,3-thiazolidin-3-yl]-3-methylbenzoate,
Compound 528: 2-(Morpholin-4-ylmethyl)pyridin-3-yl 4-[2-(4-fluorophenyl)-4-oxo-1,3-thiazolidin-3-yl]-3-methylbenzoate,
Compound 530: 5-(Morpholin-4-yl)pyridin-3-yl 4-[2-(4-fluorophenyl)-4-oxo-1,3-thiazolidin-3-yl]-3-methylbenzoate,
Compound 531: 6-(Morpholin-4-yl)pyridin-3-yl 4-[2-(4-fluorophenyl)-4-oxo-1,3-thiazolidin-3-yl]-3-methylbenzoate,
Compound 532: 2-(Pyridin-2-yl)ethyl 4-[2-(4-fluorophenyl)-4-oxo-1,3-thiazolidin-3-yl]-3-methylbenzoate,
Compound 533: 2-({4-[2-(4-Fluorophenyl)-4-oxo-1,3-thiazolidin-3-yl]-3-methylbenzoyl}oxy)ethyl pyridine-3-carboxylate,
Compound 536: 2-({4-[2-(4-Fluorophenyl)-4-oxo-1,3-thiazolidin-3-yl]-3-methylbenzoyl}oxy)ethyl pyridine-4-carboxylate,
Compound 538: 2-({4-[2-(4-Fluorophenyl)-4-oxo-1,3-thiazolidin-3-yl]-3-methylbenzoyl}oxy)ethyl pyridine-2-carboxylate,
Compound 540: 2-(Pyridin-4-ylmethoxy)ethyl 4-[2-(4-fluorophenyl)-4-oxo-1,3-thiazolidin-3-yl]-3-methylbenzoate,
Compound 542: 2-(Pyridin-2-ylmethoxy)ethyl 4-[2-(4-fluorophenyl)-4-oxo-1,3-thiazolidin-3-yl]-3-methylbenzoate,
Compound 544: 2-(Pyridin-3-ylmethoxy)ethyl 4-[2-(4-fluorophenyl)-4-oxo-1,3-thiazolidin-3-yl]-3-methylbenzoate,
Compound 546: 2-(Pyridin-3-yloxy)ethyl 4-[2-(4-fluorophenyl)-4-oxo-1,3-thiazolidin-3-yl]-3-methylbenzoate,
Compound 548: 2-(Pyridin-2-yloxy)ethyl 4-[2-(4-fluorophenyl)-4-oxo-1,3-thiazolidin-3-yl]-3-methylbenzoate,
Compound 550: 2-(Pyridin-4-yloxy)ethyl 4-[2-(4-fluorophenyl)-4-oxo-1,3-thiazolidin-3-yl]-3-methylbenzoate,
Compound 552: 5-(Pyridin-2-ylmethoxy)pentyl 4-[2-(4-fluorophenyl)-4-oxo-1,3-thiazolidin-3-yl]-3-methylbenzoate,
Compound 556: 2-[(Pyridin-3-ylmethyl)sulfanyl]ethyl 4-[2-(4-fluorophenyl)-4-oxo-1,3-thiazolidin-3-yl]-3-methylbenzoate,
Compound 558: 2-[(Pyridin-2-ylmethyl)sulfanyl]ethyl 4-[2-(4-fluorophenyl)-4-oxo-1,3-thiazolidin-3-yl]-3-methylbenzoate, Compound 560: 2-[(Pyridin-4-ylmethyl)sulfanyl]ethyl 4-[2-(4-fluorophenyl)-4-oxo-1,3-thiazolidin-3-yl]-3-methylbenzoate,
Compound 562: 2-(Pyridin-4-ylsulfanyl)ethyl 4-[2-(4-fluorophenyl)-4-oxo-1,3-thiazolidin-3-yl]-3-methylbenzoate,
Compound 564: 2-(Pyridin-2-ylsulfanyl)ethyl 4-[2-(4-fluorophenyl)-4-oxo-1,3-thiazolidin-3-yl]-3-methylbenzoate,
Compound 566: 2-(Pyridin-3-ylsulfanyl)ethyl 4-[2-(4-fluorophenyl)-4-oxo-1,3-thiazolidin-3-yl]-3-methylbenzoate,
Compound 568: 2-(Pyridin-4-ylamino)ethyl 4-[2-(4-fluorophenyl)-4-oxo-1,3-thiazolidin-3-yl]-3-methylbenzoate,
Compound 571: 2-(Pyridin-2-ylamino)ethyl 4-[2-(4-fluorophenyl)-4-oxo-1,3-thiazolidin-3-yl]-3-methylbenzoate,
Compound 574: 2-(1-Methyl-1H-imidazol-5-yl)ethyl 4-[2-(4-fluorophenyl)-4-oxo-1,3-thiazolidin-3-yl]-3-methylbenzoate,
Compound 575: 2-(1-Methyl-1H-imidazol-2-yl)ethyl 4-[2-(4-fluorophenyl)-4-oxo-1,3-thiazolidin-3-yl]-3-methylbenzoate,
Compound 584: 6-(Methoxymethyl)pyridin-3-yl 4-[2-(4-fluorophenyl)-4-oxo-1,3-thiazolidin-3-yl]-3-methylbenzoate,
Compound 587: 4-[2-(4-Fluorophenyl)-4-oxo-1,3-thiazolidin-3-yl]-3-methyl-N-(tetrahydro-2H-pyran-2-yloxy)benzamide,
Compound 588: N-Ethoxy-4-[2-(4-fluorophenyl)-4-oxo-1,3-thiazolidin-3-yl]-3-methylbenzamide,
Compound 591: 2-(2-Methoxyethoxy)ethyl 4-({4-[2-(4-fluorophenyl)-4-oxo-1,3-thiazolidin-3-yl]-3-methylbenzoyl}sulfamoyl)benzoate,
Compound 593: 4-[2-(4-Fluorophenyl)-4-oxo-1,3-thiazolidin-3-yl]-N-[(2-methoxyethyl)sulfonyl]-3-methylbenzamide,
Compound 597: 4-[2-(4-Fluorophenyl)-4-oxo-1,3-thiazolidin-3-yl]-N-{[2-(2-methoxyethoxy)ethyl]sulfonyl}-3-methylbenzamide, and
Compound 660: (-)-Ethyl 4-[2-(4-fluorophenyl)-4-oxo-1,3-thiazolidin-3-yl]-3-methylbenzoate.

13. The pharmaceutical composition of claim 12, wherein the compound is selected from the group consisting of Compounds 58, 152, 160, 169, 174, 175, 187, 196, 204, 236, 239, 255, 258, 260, 263-265, 269, 270, 272, 276, 280, 281, 282, 286, 290, 294, 296, 297, 299, 303, 310, 311, 313, 446, 453, 456, 458, 461, 463, 465, 471, 489, 495, 497, 499, 504, 505, 508, 510, 516, 517, 519, 520, 521, 522, 523, 525, 526, 532, 533, 538, 540, 542, 546, 548, 550, 556, 560, 562, 564, 571, and 660.

14. The pharmaceutical composition of claim 12, wherein the therapeutic agent is a mu-opioid receptor antagonist.

15. The pharmaceutical composition of claim 14, wherein the mu-opioid receptor antagonist is naloxone, naltrexone, samidorphan, cyprodime, clocinnamox, β-FNA, naloxonazine, or nalmefene.

16. A pharmaceutical composition for treating an opioid receptor-associated condition, the pharmaceutical composition comprising a pharmaceutically acceptable carrier, a compound, and a therapeutic agent, wherein the compound is selected from the group consisting of the following compounds:
Compound 12: 4-[2-(4-fluoro-phenyl)-4-oxo-thiazolidin-3-yl]-3-methoxy-benzoic acid,
Compound 54: 3-(2-(4-Fluorophenyl)-4-oxothiazolidin-3-yl)-4-methylbenzoic acid,
Compound 55: 3-(2-(4-Fluorophenyl)-4-oxothiazolidin-3-yl)-4-methylbenzoic acid methyl ester,
Compound 60: 4-(2-(3-Fluorophenyl)-4-oxothiazolidin-3-yl)-3-methylbenzoic acid,
Compound 62: 4-(2-(3,4-Difluorophenyl)-4-oxothiazolidin-3-yl)-3-methylbenzoic acid,
Compound 96: Methyl {4-[2-(4-fluorophenyl)-4-oxo-1,3-thiazolidin-3-yl]-3-methylphenyl}acetate,
Compound 101: {4-[2-(4-Fluorophenyl)-4-oxo-1,3-thiazolidin-3-yl]-3-methylphenyl}acetic acid,
Compound 151: 4-[2-(4-Fluorophenyl)-4-oxo-1,3-thiazolidin-3-yl]-N-hydroxy-3-methylbenzene carboximidamide,
Compound 154: 4-(2-(4-Fluorophenyl)-4-oxothiazolidin-3-yl)-3-methylbenzoic acid,
Compound 156: 3-Ethyl-4-[2-(4-fluoro-phenyl)-4-oxothiazolidin-3-yl]-benzoic acid ethyl ester,
Compound 157: 3-Ethenyl-4-[2-(4-fluorophenyl)-4-oxo-1,3-thiazolidin-3-yl]benzoic acid,
Compound 221: 2-(4-Fluorophenyl)-3-[2-methyl-4-(1H-tetrazol-5-yl)phenyl]-1,3-thiazolidin-4-one,
Compound 576: Ethyl 4-[2-(3,4-difluorophenyl)-4-oxo-1,3-thiazolidin-3-yl]-3-methylbenzoate,
Compound 578: Methyl 4-{2-[4-fluoro-2,3,5,6-d4-phenyl]-4-oxo-1,3-thiazolidin-3-yl}-3-methylbenzoate,
Compound 579: 4-{2-[4-Fluoro-2,3,5,6-d4-phenyl]-4-oxo-1,3-thiazolidin-3-yl}-3-methylbenzoic acid,
Compound 580: Ethyl 4-{2-[4-fluoro-2,3,5,6-d4-phenyl]-4-oxo-1,3-thiazolidin-3-yl}-3-methylbenzoate,
Compound 581: 4-[2-(4-Fluorophenyl)-4-oxo-2-d1-1,3-thiazolidin-3-yl]-3-methylbenzoic acid,
Compound 583: Ethyl 4-[2-(4-fluorophenyl)-4-oxo-2-d1-1,3-thiazolidin-3-yl]-3-methylbenzoate,
Compound 635: Ethyl 5-[2-(4-fluorophenyl)-4-oxo-1,3-thiazolidin-3-yl]-6-methylpyridine-2-carboxylate, and
Compound 648: Methyl 3-methyl-4-[4-oxo-2-(thiophen-3-yl)-1,3-thiazolidin-3-yl]benzoate.

17. The pharmaceutical composition of claim 16, wherein the therapeutic agent is a mu-opioid receptor antagonist.

18. The pharmaceutical composition of claim 17, wherein the mu-opioid receptor antagonist is naloxone, naltrexone, samidorphan, cyprodime, clocinnamox, β-FNA, naloxonazine, or nalmefene.

19. A method of treating an opioid receptor-associated condition, the method comprising administering to a subject in need thereof a pharmaceutical composition of claim 9 wherein the therapeutic agent is a mu-opioid receptor antagonist.

20. A method of treating an opioid receptor-associated condition, the method comprising administering to a subject in need thereof a pharmaceutical composition of claim 10 wherein the therapeutic agent is a mu-opioid receptor antagonist.

21. A method of treating an opioid receptor-associated condition, the method comprising administering to a subject in need thereof a pharmaceutical composition of claim 11 wherein the therapeutic agent is a mu-opioid receptor antagonist.

22. A method of treating an opioid receptor-associated condition, the method comprising administering to a subject in need thereof a pharmaceutical composition of claim 13 wherein the therapeutic agent is a mu-opioid receptor antagonist.

23. A method of treating an opioid receptor-associated condition, the method comprising administering to a subject in need thereof a pharmaceutical composition of claim 12 wherein the therapeutic agent is a mu-opioid receptor antagonist.

\* \* \* \* \*